US008409577B2

(12) United States Patent
Thompson et al.

(10) Patent No.: US 8,409,577 B2
(45) Date of Patent: *Apr. 2, 2013

(54) SINGLE CHAIN MULTIVALENT BINDING PROTEINS WITH EFFECTOR FUNCTION

(75) Inventors: Peter Armstrong Thompson, Bellevue, WA (US); Jeffrey A. Ledbetter, Shoreline, WA (US); Martha Susan Hayden-Ledbetter, Shoreline, WA (US); Laura Sue Grosmaire, Hobart, WA (US); Robert Bader, Seattle, WA (US); William Brady, Bothell, WA (US)

(73) Assignee: Emergent Product Development Seattle, LLC, Seattle, WA (US)

( * ) Notice: Subject to any disclaimer, the term of this patent is extended or adjusted under 35 U.S.C. 154(b) by 284 days.

This patent is subject to a terminal disclaimer.

(21) Appl. No.: 12/304,562

(22) PCT Filed: Jun. 12, 2007

(86) PCT No.: PCT/US2007/071052
§ 371 (c)(1),
(2), (4) Date: Jul. 22, 2010

(87) PCT Pub. No.: WO2007/146968
PCT Pub. Date: Dec. 21, 2007

(65) Prior Publication Data
US 2011/0033483 A1 Feb. 10, 2011
US 2012/0034245 A9 Feb. 9, 2012

Related U.S. Application Data

(60) Provisional application No. 60/813,261, filed on Jun. 12, 2006, provisional application No. 60/853,287, filed on Oct. 20, 2006.

(51) Int. Cl.
C07K 16/46 (2006.01)
C07K 16/22 (2006.01)
C07K 16/24 (2006.01)
C07K 16/28 (2006.01)
C07K 16/30 (2006.01)
A61K 39/395 (2006.01)
A61K 39/00 (2006.01)

(52) U.S. Cl. ............ 424/134.1; 424/135.1; 424/178.1; 530/387.3; 530/391.9

(58) Field of Classification Search .................. None
See application file for complete search history.

(56) References Cited

U.S. PATENT DOCUMENTS

| 3,927,193 A | 12/1975 | Hansen et al. ............ 424/1 |
| 4,179,337 A | 12/1979 | Davis et al. ............ 435/181 |
| 4,301,144 A | 11/1981 | Iwashita et al. ............ 424/78 |
| 4,331,647 A | 5/1982 | Goldenberg ............ 424/1 |
| 4,348,376 A | 9/1982 | Goldenberg ............ 424/1 |
| 4,361,544 A | 11/1982 | Goldenberg ............ 424/1 |
| 4,444,744 A | 4/1984 | Goldenberg ............ 424/1.1 |
| 4,460,459 A | 7/1984 | Shaw et al. ............ 209/9 |
| 4,460,559 A | 7/1984 | Goldenberg ............ 424/1.1 |
| 4,460,561 A | 7/1984 | Goldenberg ............ 424/1.1 |
| 4,468,457 A | 8/1984 | Goldenberg et al. ............ 435/69 |
| 4,496,689 A | 1/1985 | Mitra ............ 525/54.1 |
| 4,624,846 A | 11/1986 | Goldenberg ............ 424/1.1 |
| 4,640,835 A | 2/1987 | Shimizu et al. ............ 424/94 |
| 4,670,417 A | 6/1987 | Iwasaki et al. ............ 514/6 |
| 4,704,692 A | 11/1987 | Ladner ............ 364/496 |
| 4,769,330 A | 9/1988 | Paoletti et al. ............ 435/172.3 |
| 4,782,840 A | 11/1988 | Martin, Jr. et al. ............ 128/654 |
| 4,791,192 A | 12/1988 | Nakagawa et al. ............ 530/399 |
| 4,816,567 A | 3/1989 | Cabilly et al. ............ 530/387 |
| 4,818,709 A | 4/1989 | Primus et al. ............ 436/518 |
| 4,861,579 A | 8/1989 | Meyer, Jr. et al. |
| 4,897,268 A | 1/1990 | Tice et al. ............ 424/422 |
| 4,906,562 A | 3/1990 | Hellstrom et al. ............ 435/7 |
| 4,932,412 A | 6/1990 | Goldenberg ............ 128/654 |
| 4,935,495 A | 6/1990 | Hellström et al. ............ 530/387 |
| 4,946,778 A | 8/1990 | Ladner et al. ............ 435/69.6 |
| 5,017,487 A | 5/1991 | Stunnenberg et al. ...... 435/172.3 |
| 5,075,109 A | 12/1991 | Tice et al. ............ 424/88 |
| 5,091,177 A | 2/1992 | Hellström et al. ............ 424/85.8 |
| 5,098,833 A | 3/1992 | Lasky et al. ............ 435/69.1 |
| 5,141,736 A | 8/1992 | Iwasa et al. ............ 530/387.3 |
| 5,217,713 A | 6/1993 | Iwasa et al. ............ 424/85.91 |
| 5,225,539 A | 7/1993 | Winter ............ 530/387.3 |
| 5,260,203 A | 11/1993 | Ladner et al. ............ 435/172.3 |
| 5,434,131 A | 7/1995 | Linsley et al. ............ 514/2 |
| 5,455,030 A | 10/1995 | Ladner et al. ............ 424/435.1 |

(Continued)

FOREIGN PATENT DOCUMENTS

CA 2 379 586 A1 10/2003
CA 2 414 148 A1 6/2004

(Continued)

OTHER PUBLICATIONS

Catley et al, Pharmacology & Therapeutics 132: 333-351, 2011.*
Amit et al., "Three-dimensional structure of an antigen-antibody complex at 2.8 A resolution," *Science*, 233(4765):747-753, 1986.
Beavil et al., "α-Helical coiled-coil stalks in the low-affinity receptor for IgE (FceRII/CD23) and related C-type lectins," *Proc. Natl. Acad. Sci. USA*, 89:753-757, 1992.
Panka et al., "Variable region framework differences result in decreased or increased affinity of variant anti-digoxin antibodies," *Proc. Natl. Acad. Sci. USA*, 85:3080-3084, 1988.

(Continued)

*Primary Examiner* — Phuong Huynh
(74) *Attorney, Agent, or Firm* — Cooley LLP

(57) ABSTRACT

Multivalent binding peptides, including bi-specific binding peptides, having immunoglobulin effector function are provided, along with encoding nucleic acids, vectors and host cells as well as methods for making such peptides and methods for using such peptides to treat or prevent a variety of diseases, disorders or conditions, as well as to ameliorate at least one symptom associated with such a disease, disorder or condition.

17 Claims, 67 Drawing Sheets

U.S. PATENT DOCUMENTS

| | | | | |
|---|---|---|---|---|
| 5,500,362 | A | 3/1996 | Robinson et al. | 435/7.23 |
| 5,521,288 | A | 5/1996 | Linsley et al. | 530/387.3 |
| 5,530,101 | A | 6/1996 | Queen et al. | 530/387.3 |
| 5,580,756 | A | 12/1996 | Linsley et al. | 435/69.7 |
| 5,585,089 | A | 12/1996 | Queen et al. | 424/133.1 |
| 5,591,828 | A | 1/1997 | Bosslet et al. | 530/387.3 |
| 5,595,721 | A | 1/1997 | Kaminski et al. | |
| 5,597,707 | A | 1/1997 | Marken et al. | 435/69.3 |
| 5,601,819 | A | 2/1997 | Wong et al. | 424/136.1 |
| 5,605,690 | A | 2/1997 | Jacobs et al. | 424/134.1 |
| 5,637,481 | A | 6/1997 | Ledbetter et al. | 435/69.6 |
| 5,645,835 | A | 7/1997 | Fell, Jr. et al. | 424/134.1 |
| 5,677,180 | A | 10/1997 | Robinson et al. | |
| 5,677,425 | A | 10/1997 | Bodmer et al. | 530/387.1 |
| 5,693,762 | A | 12/1997 | Queen et al. | 530/387.3 |
| 5,709,859 | A | 1/1998 | Aruffo et al. | 424/134.1 |
| 5,714,147 | A | 2/1998 | Capon et al. | 424/178.1 |
| 5,721,108 | A | 2/1998 | Robinson et al. | |
| 5,736,137 | A | 4/1998 | Anderson et al. | 424/133.1 |
| 5,770,197 | A | 6/1998 | Linsley et al. | 424/134.1 |
| 5,773,253 | A | 6/1998 | Linsley et al. | 435/69.7 |
| 5,776,456 | A | 7/1998 | Anderson et al. | 424/133.1 |
| 5,795,572 | A | 8/1998 | Diegel et al. | 424/135.1 |
| 5,807,734 | A | 9/1998 | Diegel et al. | 435/252.33 |
| 5,837,243 | A | 11/1998 | Deo et al. | 424/136.1 |
| 5,843,398 | A | 12/1998 | Kaminski et al. | |
| 5,843,439 | A | 12/1998 | Anderson et al. | |
| 5,844,093 | A | 12/1998 | Kettleborough et al. | 530/387.3 |
| 5,844,095 | A | 12/1998 | Linsley et al. | 530/387.3 |
| 5,849,898 | A | 12/1998 | Seed et al. | |
| 5,869,049 | A | 2/1999 | Noelle et al. | 424/154.1 |
| 5,869,620 | A | 2/1999 | Whitlow et al. | 530/387.3 |
| 5,876,718 | A | 3/1999 | Noelle et al. | 424/154.1 |
| 5,876,950 | A | 3/1999 | Siadak et al. | 435/7.23 |
| 5,885,793 | A | 3/1999 | Griffiths et al. | 435/69.1 |
| 5,888,773 | A | 3/1999 | Jost et al. | 435/69.6 |
| 5,892,019 | A | 4/1999 | Schlom et al. | 536/23.53 |
| 5,897,861 | A | 4/1999 | Fanger et al. | 424/136.1 |
| 5,916,560 | A | 6/1999 | Larsen et al. | 424/154.1 |
| 5,922,845 | A | 7/1999 | Deo et al. | 530/387.3 |
| 5,955,315 | A | 9/1999 | Lee et al. | 435/69.52 |
| 5,959,083 | A | 9/1999 | Bosslet et al. | 530/387.3 |
| 5,980,896 | A | 11/1999 | Hellstrom et al. | 424/183.1 |
| 6,015,542 | A | 1/2000 | Kaminski et al. | |
| 6,015,695 | A | 1/2000 | Casterman et al. | 435/69.6 |
| 6,072,035 | A | 6/2000 | Hardman et al. | 530/387.3 |
| 6,074,644 | A | 6/2000 | Pastan et al. | 424/178.1 |
| 6,074,655 | A | 6/2000 | Fowler et al. | |
| 6,087,329 | A | 7/2000 | Armitage et al. | 514/8 |
| 6,090,365 | A | 7/2000 | Kaminski et al. | |
| 6,090,914 | A | 7/2000 | Linsley et al. | 530/350 |
| 6,105,542 | A | 8/2000 | Efford | |
| 6,120,767 | A | 9/2000 | Robinson et al. | 424/133.1 |
| 6,129,914 | A | 10/2000 | Weiner et al. | 424/133.1 |
| 6,132,992 | A | 10/2000 | Ledbetter et al. | 435/69.7 |
| 6,133,426 | A | 10/2000 | Gonzalez et al. | 530/388.23 |
| 6,147,203 | A | 11/2000 | Pastan et al. | 536/23.53 |
| 6,150,584 | A | 11/2000 | Kucherlapati et al. | 800/18 |
| 6,171,586 | B1 | 1/2001 | Lam et al. | |
| 6,180,370 | B1 | 1/2001 | Queen et al. | 435/69.6 |
| 6,193,966 | B1 | 2/2001 | Deo et al. | 424/136.1 |
| 6,194,551 | B1 | 2/2001 | Idusogie et al. | 530/387.1 |
| 6,197,294 | B1 | 3/2001 | Tao et al. | 424/93.21 |
| 6,224,866 | B1 | 5/2001 | Barbera-Guillem | |
| 6,242,195 | B1 | 6/2001 | Idusogie et al. | |
| 6,262,244 | B1 | 7/2001 | Houchins et al. | 536/23.5 |
| 6,264,951 | B1 | 7/2001 | Armitage et al. | 424/184.1 |
| 6,270,765 | B1 | 8/2001 | Deo et al. | 424/136.1 |
| 6,284,536 | B1 | 9/2001 | Morrison et al. | 435/328 |
| 6,287,537 | B1 | 9/2001 | Kaminski et al. | |
| 6,303,755 | B1 | 10/2001 | Deo et al. | 530/387.3 |
| 6,306,393 | B1 | 10/2001 | Goldenberg | 424/141.1 |
| 6,312,692 | B1 | 11/2001 | Noelle et al. | 424/154.1 |
| 6,312,694 | B1 | 11/2001 | Thorpe et al. | 424/178.1 |
| 6,352,694 | B1 | 3/2002 | June et al. | 424/93.71 |
| 6,368,596 | B1 | 4/2002 | Ghetie et al. | |
| 6,376,459 | B1 | 4/2002 | Aruffo et al. | 514/2 |
| 6,379,966 | B2 | 4/2002 | Monahan et al. | 435/455 |
| 6,379,967 | B1 | 4/2002 | Meredith et al. | 435/456 |
| 6,380,169 | B1 | 4/2002 | Adams et al. | 514/44 |
| 6,380,170 | B1 | 4/2002 | Müller et al. | 514/44 |
| 6,380,362 | B1 | 4/2002 | Watson et al. | 530/350 |
| 6,380,369 | B1 | 4/2002 | Adams et al. | 536/23.1 |
| 6,380,371 | B1 | 4/2002 | Sassetti et al. | 536/23.1 |
| 6,380,382 | B1 | 4/2002 | Khodadoust | 536/231 |
| 6,383,138 | B1 | 5/2002 | Sen et al. | 600/365 |
| 6,383,478 | B1 | 5/2002 | Prokop et al. | 424/78.08 |
| 6,383,481 | B1 | 5/2002 | Ikehara et al. | 424/93.1 |
| 6,383,512 | B1 | 5/2002 | Ciccarelli et al. | 424/450 |
| 6,383,522 | B1 | 5/2002 | Dupont | 424/548 |
| 6,383,733 | B1 | 5/2002 | Beug et al. | 435/4 |
| 6,383,737 | B2 | 5/2002 | Olsen et al. | 435/4 |
| 6,383,738 | B1 | 5/2002 | Bruni et al. | 435/5 |
| 6,383,743 | B1 | 5/2002 | Kinzler et al. | 435/6 |
| 6,383,746 | B1 | 5/2002 | Guignard et al. | 435/6 |
| 6,383,753 | B1 | 5/2002 | Thiele et al. | 435/6 |
| 6,383,785 | B1 | 5/2002 | Mueller et al. | 435/91.41 |
| 6,383,794 | B1 | 5/2002 | Mountz et al. | 435/235.1 |
| 6,383,795 | B1 | 5/2002 | Carrión et al. | 435/239 |
| 6,383,811 | B2 | 5/2002 | Wolff et al. | 435/450 |
| 6,383,814 | B1 | 5/2002 | Lee et al. | 435/458 |
| 6,384,018 | B1 | 5/2002 | Content et al. | 514/44 |
| 6,384,198 | B1 | 5/2002 | Diegel et al. | 530/390.1 |
| 6,384,202 | B1 | 5/2002 | Sedlacek et al. | 536/23.1 |
| 6,384,203 | B1 | 5/2002 | Anderson et al. | 536/23.5 |
| 6,384,210 | B1 | 5/2002 | Blanchard | 536/25.3 |
| 6,395,272 | B1 | 5/2002 | Deo et al. | 424/138.1 |
| 6,399,061 | B1 | 6/2002 | Anderson et al. | |
| 6,403,769 | B1 | 6/2002 | Larochelle et al. | 530/387.3 |
| 6,410,319 | B1 | 6/2002 | Raubitschek et al. | 435/343.1 |
| 6,410,391 | B1 | 6/2002 | Zelsacher | |
| 6,410,690 | B1 | 6/2002 | Deo et al. | 530/387.3 |
| 6,444,792 | B1 | 9/2002 | Gray et al. | 530/387.3 |
| 6,455,043 | B1 | 9/2002 | Grillo-Lopez | |
| 6,472,179 | B2 | 10/2002 | Stahl et al. | 435/69.7 |
| 6,472,510 | B1 | 10/2002 | Aruffo et al. | 530/387.3 |
| 6,476,198 | B1 | 11/2002 | Kang | 530/387.3 |
| 6,482,919 | B2 | 11/2002 | Ledbetter et al. | 530/324 |
| 6,515,110 | B1 | 2/2003 | Whitlow et al. | 530/387.3 |
| 6,518,277 | B1 | 2/2003 | Sadhu et al. | |
| 6,528,624 | B1 | 3/2003 | Idusogie et al. | |
| 6,538,124 | B1 | 3/2003 | Idusogie et al. | |
| 6,586,428 | B2 | 7/2003 | Geroni et al. | 514/231.5 |
| 6,589,527 | B1 | 7/2003 | Winter et al. | 424/136.1 |
| 6,623,940 | B1 | 9/2003 | Ledbetter et al. | 435/69.1 |
| 6,641,809 | B1 | 11/2003 | Linsley et al. | 424/134.1 |
| 6,696,290 | B2 | 2/2004 | Fitzpatrick et al. | 435/325 |
| 6,761,889 | B2 | 7/2004 | Lowman et al. | |
| 6,800,620 | B2 | 10/2004 | Sadhu et al. | |
| 6,809,185 | B1 | 10/2004 | Schoonjans et al. | 530/387.3 |
| 6,815,540 | B1 | 11/2004 | Plückthun et al. | 536/23.53 |
| 6,818,213 | B1 | 11/2004 | Thorpe et al. | 424/130.1 |
| 6,881,557 | B2 | 4/2005 | Foote | |
| 6,893,625 | B1 | 5/2005 | Robinson et al. | 424/1.49 |
| 6,896,885 | B2 | 5/2005 | Hanna | |
| 7,052,872 | B1 | 5/2006 | Hansen et al. | 435/69.6 |
| 7,074,403 | B1 | 7/2006 | Goldenberg et al. | 424/130.1 |
| 7,122,646 | B2 | 10/2006 | Holliger et al. | 536/23.1 |
| 7,129,330 | B1 | 10/2006 | Little et al. | 530/387.3 |
| 7,148,321 | B2 | 12/2006 | Gillies et al. | 530/300 |
| 7,166,707 | B2 | 1/2007 | Feige | |
| 7,183,076 | B2 | 2/2007 | Arathoon et al. | 435/69.1 |
| 7,612,181 | B2 | 11/2009 | Wu et al. | 530/387.3 |
| 7,754,208 | B2 | 7/2010 | Ledbetter et al. | 424/133.1 |
| 7,754,209 | B2 | 7/2010 | Ledbetter et al. | 424/133.1 |
| 7,829,056 | B2 * | 11/2010 | Lee | 423/447.2 |
| 7,829,084 | B2 * | 11/2010 | Ledbetter et al. | 424/133.1 |
| 8,106,161 | B2 | 1/2012 | Ledbetter et al. | |
| 8,147,835 | B2 | 4/2012 | Ledbetter et al. | |
| 2001/0044135 | A1 | 11/2001 | Stahi et al. | |
| 2002/0004587 | A1 | 1/2002 | Miller et al. | 530/388.8 |
| 2002/0006404 | A1 | 1/2002 | Hanna et al. | |
| 2002/0009444 | A1 | 1/2002 | Grillo-Lopez | |
| 2002/0012665 | A1 | 1/2002 | Hanna | |
| 2002/0031510 | A1 | 3/2002 | Larsen et al. | 424/131.1 |
| 2002/0039557 | A1 | 4/2002 | White | 424/1.49 |
| 2002/0041847 | A1 | 4/2002 | Goldenberg | |

| Publication No. | Date | Inventor |
|---|---|---|
| 2002/0103345 A1 | 8/2002 | Zhu .................... 530/388.15 |
| 2002/0128448 A1 | 9/2002 | Reff |
| 2002/0128488 A1 | 9/2002 | Yamakawa et al. |
| 2002/0155604 A1 | 10/2002 | Ledbetter et al. ........ 435/372.3 |
| 2002/0192223 A1 | 12/2002 | Hellstrom et al. ........ 424/183.1 |
| 2002/0197255 A1 | 12/2002 | Anderson et al. |
| 2002/0197256 A1 | 12/2002 | Grewal |
| 2003/0021781 A1 | 1/2003 | Anderson et al. |
| 2003/0026780 A1 | 2/2003 | Hood et al. ................. 424/85.5 |
| 2003/0026801 A1 | 2/2003 | Weiner et al. |
| 2003/0031667 A1 | 2/2003 | Deo et al. .................. 424/144.1 |
| 2003/0044423 A1 | 3/2003 | Gillies et al. .............. 424/192.1 |
| 2003/0078385 A1 | 4/2003 | Arathoon et al. .......... 530/388.1 |
| 2003/0088074 A1 | 5/2003 | Hamers et al. ............ 530/387.1 |
| 2003/0115614 A1 | 6/2003 | Kanda et al. ..................... 800/6 |
| 2003/0118592 A1 | 6/2003 | Ledbetter et al. ......... 424/178.1 |
| 2003/0133930 A1 | 7/2003 | Goldenberg et al. ...... 424/141.1 |
| 2003/0133939 A1 | 7/2003 | Ledbetter et al. ......... 424/178.1 |
| 2003/0166868 A1 | 9/2003 | Presta et al. .............. 530/387.1 |
| 2003/0219433 A1 | 11/2003 | Hansen et al. ............ 424/141.1 |
| 2003/0219436 A1 | 11/2003 | Ledbetter et al. ......... 424/144.1 |
| 2003/0219446 A1 | 11/2003 | Linsley et al. ............ 424/178.1 |
| 2003/0219876 A1 | 11/2003 | Ledbetter et al. ........... 435/69.7 |
| 2004/0018557 A1 | 1/2004 | Qu et al. ........................ 435/7.1 |
| 2004/0043029 A1 | 3/2004 | Hellstrom et al. ......... 424/155.1 |
| 2004/0058445 A1 | 3/2004 | Ledbetter et al. ............. 435/372 |
| 2004/0071696 A1 | 4/2004 | Adams et al. .............. 424/143.1 |
| 2004/0191248 A1 | 9/2004 | Goldenberg et al. ...... 424/141.1 |
| 2005/0031617 A1 | 2/2005 | Ma et al. .................... 424/146.1 |
| 2005/0054000 A1 | 3/2005 | Dubel .............................. 435/7.1 |
| 2005/0084933 A1 | 4/2005 | Schilling et al. .............. 435/69.1 |
| 2005/0136049 A1 | 6/2005 | Ledbetter et al. .......... 424/143.1 |
| 2005/0158829 A1 | 7/2005 | Fandl et al. ................... 435/69.1 |
| 2005/0163782 A1 | 7/2005 | Glaser et al. ............... 424/155.1 |
| 2005/0164307 A1 | 7/2005 | Kojima et al. ................. 435/7.2 |
| 2005/0175614 A1 | 8/2005 | Ledbetter et al. .......... 424/145.1 |
| 2005/0180970 A1 | 8/2005 | Ledbetter et al. .......... 424/143.1 |
| 2005/0186203 A1 | 8/2005 | Singh et al. ................. 424/143.1 |
| 2005/0186216 A1 | 8/2005 | Ledbetter et al. .......... 424/155.1 |
| 2005/0202012 A1 | 9/2005 | Ledbetter et al. .......... 424/144.1 |
| 2005/0202023 A1 | 9/2005 | Ledbetter et al. .......... 424/155.1 |
| 2005/0202028 A1 | 9/2005 | Ledbetter et al. .......... 424/178.1 |
| 2005/0202534 A1 | 9/2005 | Ledbetter et al. ............ 435/69.1 |
| 2005/0238646 A1 | 10/2005 | Ledbetter et al. .......... 424/144.1 |
| 2005/0261317 A1 | 11/2005 | Sadhu et al. |
| 2006/0008415 A1 | 1/2006 | Kaisheva et al. .............. 424/1.49 |
| 2006/0051844 A1 | 3/2006 | Heavner et al. |
| 2006/0063715 A1 | 3/2006 | Whitlow et al. ................ 514/12 |
| 2006/0088529 A1 | 4/2006 | Leung et al. ................ 424/143.1 |
| 2006/0099205 A1 | 5/2006 | Adams et al. ............... 424/133.1 |
| 2006/0104971 A1 | 5/2006 | Garber et al. ............... 424/143.1 |
| 2006/0153837 A1 | 7/2006 | Black et al. |
| 2006/0210564 A1 | 9/2006 | Kumagai et al. ............ 424/145.1 |
| 2006/0263367 A1 | 11/2006 | Fey et al. .................... 424/155.1 |
| 2007/0041967 A1 | 2/2007 | Jung et al. ................... 424/133.1 |
| 2007/0059306 A1 | 3/2007 | Grosmaire et al. ......... 424/144.1 |
| 2007/0071675 A1 | 3/2007 | Wu et al. ........................ 424/1.49 |
| 2007/0237779 A1 | 10/2007 | Ledbetter et al. .......... 424/155.1 |
| 2008/0213273 A1 | 9/2008 | Burge .......................... 424/141.1 |
| 2008/0279850 A1 | 11/2008 | Brady et al. ................. 424/133.1 |
| 2009/0041765 A1 | 2/2009 | Espling et al. |
| 2009/0053225 A1 | 2/2009 | Marzari et al. ............. 424/136.1 |
| 2009/0088346 A1 | 4/2009 | Enzelberger et al. ........... 506/17 |
| 2009/0148447 A1 | 6/2009 | Ledbetter et al. .......... 424/134.1 |
| 2009/0162380 A1 | 6/2009 | Glaser et al. |
| 2009/0175867 A1 | 7/2009 | Thompson et al. ......... 424/135.1 |
| 2009/0196870 A1 | 8/2009 | Ledbetter et al. .......... 424/133.1 |
| 2009/0214539 A1 | 8/2009 | Grosmaire et al. ......... 424/135.1 |
| 2009/0252729 A1 | 10/2009 | Farrington et al. ......... 424/135.1 |
| 2009/0274649 A1 | 11/2009 | Qu et al. ........................ 424/85.2 |
| 2009/0274692 A1 | 11/2009 | Tan et al. .................... 424/133.1 |
| 2010/0034820 A1 | 2/2010 | Ledbetter et al. .......... 424/134.1 |
| 2010/0135900 A1 | 6/2010 | Cerveny et al. ............... 424/1.11 |
| 2010/0203052 A1 | 8/2010 | Ledbetter et al. .......... 424/134.1 |
| 2010/0279932 A1 | 11/2010 | Ledbetter et al. ............... 514/7.3 |
| 2011/0033483 A1 | 2/2011 | Thompson et al. ......... 424/179.1 |
| 2011/0091461 A1 | 4/2011 | Ledbetter et al. .......... 424/134.1 |
| 2011/0105729 A1 | 5/2011 | Ledbetter et al. .......... 530/387.3 |
| 2011/0171208 A1 | 7/2011 | Tan et al. |
| 2011/0223164 A1 | 9/2011 | Ledbetter et al. |

FOREIGN PATENT DOCUMENTS

| | | |
|---|---|---|
| EP | 0 274 394 A2 | 7/1988 |
| EP | 0 330 191 A2 | 8/1989 |
| EP | 0 332 865 A2 | 9/1989 |
| EP | 0 555 880 A2 | 8/1993 |
| EP | 0 586 002 A2 | 3/1994 |
| EP | 0 682 039 A1 | 4/1994 |
| EP | 0 330 191 B1 | 10/1996 |
| EP | 0 757 099 A2 | 2/1997 |
| EP | 1 186 300 A1 | 3/2002 |
| EP | 1 654 358 | 2/2005 |
| EP | 0 610 046 B1 | 12/2005 |
| EP | 1 666 500 A1 | 6/2006 |
| EP | 1 746 162 A2 | 1/2007 |
| EP | 1 444 268 B1 | 6/2007 |
| WO | 88/04936 A1 | 7/1988 |
| WO | WO 89/01973 A2 | 3/1989 |
| WO | WO 89/01974 A1 | 3/1989 |
| WO | 89/07142 A1 | 8/1989 |
| WO | WO 90/07936 A1 | 7/1990 |
| WO | 91/00360 A1 | 1/1991 |
| WO | WO 91/02805 A2 | 3/1991 |
| WO | 91/04329 A1 | 4/1991 |
| WO | 91/09967 | 7/1991 |
| WO | 91/11456 A1 | 8/1991 |
| WO | 91/13166 A1 | 9/1991 |
| WO | 92/00092 A1 | 1/1992 |
| WO | 92/08802 A1 | 5/1992 |
| WO | 92/21755 A1 | 12/1992 |
| WO | 93/00431 A1 | 1/1993 |
| WO | WO 93/03709 A1 | 3/1993 |
| WO | WO 93/25234 A1 | 12/1993 |
| WO | WO 93/25698 A1 | 12/1993 |
| WO | WO 94/03622 A1 | 2/1994 |
| WO | 94/04678 A1 | 3/1994 |
| WO | 94/05690 A1 | 3/1994 |
| WO | WO 94/09034 A1 | 4/1994 |
| WO | WO 94/11026 A2 | 5/1994 |
| WO | WO 94/13804 A1 | 6/1994 |
| WO | 94/25591 A1 | 11/1994 |
| WO | WO 95/03770 A1 | 2/1995 |
| WO | 95/08577 A1 | 3/1995 |
| WO | 95/09917 A1 | 4/1995 |
| WO | 95/24220 A1 | 9/1995 |
| WO | 96/34103 A1 | 10/1996 |
| WO | 96/40789 A1 | 12/1996 |
| WO | WO 97/09433 A1 | 3/1997 |
| WO | 98/02462 A1 | 1/1998 |
| WO | 98/02463 A1 | 1/1998 |
| WO | 98/23646 A2 | 6/1998 |
| WO | WO 98/56418 A1 | 12/1998 |
| WO | WO 98/58964 A1 | 12/1998 |
| WO | 99/02711 A2 | 1/1999 |
| WO | WO 99/10494 A2 | 3/1999 |
| WO | WO 99/22764 A1 | 5/1999 |
| WO | 99/37791 A1 | 7/1999 |
| WO | 99/42077 A2 | 8/1999 |
| WO | 99/43713 A1 | 9/1999 |
| WO | WO 99/51642 A1 | 10/1999 |
| WO | 99/57150 A2 | 11/1999 |
| WO | 99/57266 A2 | 11/1999 |
| WO | 00/06605 A2 | 2/2000 |
| WO | WO 00/09160 A1 | 2/2000 |
| WO | WO 00/20864 A1 | 4/2000 |
| WO | 00/27885 A1 | 5/2000 |
| WO | WO 00/27428 A1 | 5/2000 |
| WO | WO 00/27433 A1 | 5/2000 |
| WO | WO 00/42072 A2 | 7/2000 |
| WO | 00/44777 A1 | 8/2000 |
| WO | WO 00/44788 A1 | 8/2000 |
| WO | 00/69913 A1 | 11/2000 |
| WO | WO 00/67795 A1 | 11/2000 |
| WO | WO 00/67796 A1 | 11/2000 |
| WO | WO 00/74718 A1 | 12/2000 |
| WO | WO 00/76542 A1 | 12/2000 |

| | | |
|---|---|---|
| WO | WO 01/03734 A1 | 1/2001 |
| WO | 01/09186 A2 | 2/2001 |
| WO | 01/09187 A2 | 2/2001 |
| WO | 01/09192 A1 | 2/2001 |
| WO | WO 01/10460 A1 | 2/2001 |
| WO | WO 01/10461 A1 | 2/2001 |
| WO | WO 01/10462 A1 | 2/2001 |
| WO | WO 01/13945 A1 | 3/2001 |
| WO | WO 01/72333 A1 | 10/2001 |
| WO | WO 01/74388 A1 | 10/2001 |
| WO | WO 01/77342 A1 | 10/2001 |
| WO | 01/85798 A2 | 11/2001 |
| WO | WO 01/80884 A1 | 11/2001 |
| WO | WO 01/97858 A2 | 12/2001 |
| WO | 02/02773 A2 | 1/2002 |
| WO | WO 02/04021 A1 | 1/2002 |
| WO | WO 02/08773 A2 | 1/2002 |
| WO | WO 02/34790 A1 | 5/2002 |
| WO | WO 02/056910 A1 | 7/2002 |
| WO | 02/064634 A2 | 8/2002 |
| WO | WO 02/060955 A2 | 8/2002 |
| WO | 02/072141 A2 | 9/2002 |
| WO | 02/072605 A2 | 9/2002 |
| WO | WO 02/079255 A1 | 10/2002 |
| WO | 02/100348 A2 | 12/2002 |
| WO | WO 02/096948 A2 | 12/2002 |
| WO | WO 02/102312 A2 | 12/2002 |
| WO | 03/020906 A2 | 3/2003 |
| WO | 03/025018 A2 | 3/2003 |
| WO | 03/026490 A2 | 4/2003 |
| WO | 03/030835 A2 | 4/2003 |
| WO | 03/042231 A2 | 5/2003 |
| WO | 03/048209 A1 | 6/2003 |
| WO | 03/057829 A2 | 7/2003 |
| WO | WO 03/074569 A2 | 9/2003 |
| WO | 03/083069 A2 | 10/2003 |
| WO | WO 03/106622 A2 | 12/2003 |
| WO | 2004/003019 A2 | 1/2004 |
| WO | 2004/016750 A2 | 2/2004 |
| WO | 2004/032857 A2 | 4/2004 |
| WO | 2004/032961 A1 | 4/2004 |
| WO | 2004/035537 A2 | 4/2004 |
| WO | 2004/035607 A2 | 4/2004 |
| WO | 2004/058171 A2 | 7/2004 |
| WO | 2004/058191 A2 | 7/2004 |
| WO | WO 2004/076489 A1 | 9/2004 |
| WO | 2005/004809 A2 | 1/2005 |
| WO | WO 2005/000899 A2 | 1/2005 |
| WO | WO 2005/017148 A1 | 2/2005 |
| WO | 2005/021710 A2 | 3/2005 |
| WO | 2005/037989 A2 | 4/2005 |
| WO | 2005/040220 A1 | 5/2005 |
| WO | 2005/061547 A2 | 7/2005 |
| WO | 2005/063816 A2 | 7/2005 |
| WO | 2005/077981 A2 | 8/2005 |
| WO | 2005/077982 A1 | 8/2005 |
| WO | WO 2005/070966 A2 | 8/2005 |
| WO | 2005/095460 A2 | 10/2005 |
| WO | 2005/103081 A2 | 11/2005 |
| WO | 2006/002438 A2 | 1/2006 |
| WO | 2006/008548 A2 | 1/2006 |
| WO | 2006/020258 A2 | 2/2006 |
| WO | 2006/028936 A2 | 3/2006 |
| WO | 2006/063150 A2 | 6/2006 |
| WO | 2006/074399 A2 | 7/2006 |
| WO | 2006/106905 A1 | 10/2006 |
| WO | WO 2007/011363 A2 | 1/2007 |
| WO | 2007/014238 A2 | 2/2007 |
| WO | 2007/014278 A2 | 2/2007 |
| WO | WO 2007/011363 A3 | 7/2007 |
| WO | WO 2007/095338 A2 | 8/2007 |
| WO | 2007/146968 A2 | 12/2007 |
| WO | WO 2008/052030 A2 | 5/2008 |
| WO | WO 2008/138834 A1 | 11/2008 |
| WO | WO 2008/152387 A1 | 12/2008 |
| WO | WO 2008/152390 A1 | 12/2008 |
| WO | WO 2008/152394 A1 | 12/2008 |
| WO | WO 2008/153636 A1 | 12/2008 |
| WO | 2009/023386 A2 | 2/2009 |
| WO | WO 2009/019312 A2 | 2/2009 |
| WO | WO 2009/036082 A2 | 2/2009 |
| WO | WO 2009/039140 A1 | 3/2009 |
| WO | WO 2009/040552 A2 | 4/2009 |
| WO | WO 2009/042607 A1 | 4/2009 |
| WO | WO 2009/045174 A1 | 4/2009 |
| WO | WO 2009/045175 A1 | 4/2009 |
| WO | WO 2009/046448 A1 | 4/2009 |
| WO | WO 2009/052145 A1 | 4/2009 |
| WO | WO 2009/053715 A1 | 4/2009 |
| WO | WO 2009/053716 A1 | 4/2009 |
| WO | WO 2009/055418 A1 | 4/2009 |
| WO | WO 2009/058361 A1 | 5/2009 |
| WO | WO 2009/059030 A1 | 5/2009 |
| WO | WO 2009/064802 A2 | 5/2009 |
| WO | WO 2009/066084 A1 | 5/2009 |
| WO | WO 2009/068482 A1 | 6/2009 |
| WO | WO 2009/070524 A1 | 6/2009 |
| WO | 2009/126944 A1 | 10/2009 |
| WO | 2010/057047 A1 | 5/2010 |

OTHER PUBLICATIONS

Rudikoff et al., "Single amino acid substitution altering antigen-binding specificity," *Proc. Natl. Acad. Sci. USA*, 79:1979-1983, 1982.

Einfeld, D.A. et al., "Molecular cloning of the human B cell CD20 receptor predicts a hydrophobic protein with multiple transmembrane domains," *The EMBO Journal* 7(3):711-717, 1988.

Engelhard, E.K. et al., "The insect tracheal system: A conduit for the systemic spread of *Autographa californica* M nuclear polyhedrosis virus," *Proc. Natl. Acad. Sci. USA* 91:3224-3227, Apr. 1994.

Felgner, Philip L. et al., "Lipofection: A highly efficient, lipid-mediated DNA-transfection procedure," *Proc. Natl. Acad. Sci. USA* 84:7413-7417, Nov. 1987.

Genbank Accession No. M17953, Liu et al., 2008, 2 pages.

Gilliland, Lisa K. et al., "Elimination of the Immunogenicity of Therapeutic Antibodies," *Journal of Immunology* 162:3663-3671, 1999.

Gluzman, Yakov, "SV40-Transformed Simian Cells Support the Replication of Early SV40 Mutants," *Cell* 23:175-182, Jan. 1981.

Gottdiener, John S. et al., "Cardiac Manifestations in Polymyositis," *American Journal of Cardiology* 41:1141-1149, Jun. 1978.

Graff, Christilyn P. et al., "Directed evolution of an anti-carcinoembryonic antigen scFv with a 4-day monovalent dissociation half-time at 37° C," *Protein Engineering, Design & Selection* 17(4):293-304, 2004.

Griffiths, Andrew D. et al., "Isolation of high affinity human antibodies directly from large synthetic repertoires," *The EMBO Journal* 13(14):3245-3260, 1994.

Hamers-Casterman, C. et al., "Letters to Nature. Naturally occurring antibodies devoid of light chains," *Nature* 363:446-448, Jun. 3, 1993.

Hoogenboom, Hennie R. et al., "By-passing Immunisation. Human Antibodies from Synthetic Repertoires of Germline $V_H$ Gene Segments Rearranged in Vitro," *J. Mol. Biol.* 227:381-388, 1992.

Hudson, Peter J., "Recombinant antibody fragments," *Current Opinion in Biotechnology* 9:395-402, 1998.

Huston, James S. et al., "Protein engineering of antibody binding sites: Recovery of specific activity in an anti-digoxin single-chain Fv analogue produced in *Escherichia coli*," *Proc. Natl. Acad. Sci. USA* 85:5879-5883, Aug. 1988.

International Search Report mailed Apr. 17, 2008 for PCTAN PCT/US2007/071052, 13 pages; and Written Opinion of the International Searching Authority, 18 pages.

Jacquemin, M. et al., "Variable region heavy chain glycosylation determines the anticoagulant activity of a favtor VIII antibody,"*Journal of Thrombosis and Haemostatis* 4:1047-1055, 2006.

Wang, J., et al., "Generation and Characterization of CD20-Specific CD8+ Cytotoxic T Lymphocytes (CTL) Genetically Modified by Introduction of an scFvFc:zeta Chimeric T Cell Receptor Gene: Preclinical Studies Prior to a Phase I Trial of Cellular Immunotherapy of Follicular Lymphoma," Abstract, 44th Annual Meeting of the American Society of Hematology, *Blood* 100(11), Abstract No. 755, Nov. 16, 2002, 1 page.

Coloma, M. Josefina et al., "Design and production of novel tetravalent bispecific antibodies," *Nature Biotechnology* 15:159-163, Feb. 1997.

Lee, H.-S., et al., "Generation and characterization of a novel single-gene-encoded single-chain immunoglobulin molecule with antigen binding activity and effector functions," Mol. Immunol. 36:61-71, 1999.

Lehninger, A.L., et al., Principles of Biochemistry, 2nd Ed., Figure 5-6, Worth Publishers, New York (1993).

Leigh, B.R., et al., "Preclinical evaluation of chimeric L6 antibody for the treatment of Kaposi's sarcoma with radioimmunotherapy," Cancer Biother. Radiopharm. 14(2):113-119, 1999.

Levine, T.D., and Pestronk, A., "IgM antibody-related polyneuropathies: B-cell depletion chemotherapy using Rituximab," Neurology 52:1701-1704, 1999.

Li, S.L., et al., "Single-chain antibodies against human insulin-like growth factor I receptor: expression, purification, and effect on tumor growth," Cancer Immunol. Immunother. 49:243-252, 2000.

Lin, M.C, et al., "Structure-Function Relationships in Glucagon: Properties of Highly Purified Des-His$^1$-, Monoiodo-, and [Des-Asn$^{28}$, Thr$^{29}$](homoserine lactone$^{27}$)-glucagon," Biochemistry 14(8):1559-1563, 1975.

Linsley, P.S., et al., "T-cell antigen CD28 mediates adhesion with B cells by interacting with activation antigen B7/BB-1," Proc. Natl. Acad. Sci. USA 87:5031-5035, 1990.

Liu, A.Y., et al., "Production of a Mouse-Human Chimeric Monoclonal Antibody to CD20 with Potent Fc-Dependent Biologic Activity," J. Immunol. 139(10):3521-3526, 1987.

Maloney, D.G., et al., "Phase I Clinical Trial Using Escalating Single-Dose Infusion of Chimeric Anti-CD20 Monoclonal Antibody (IDEC-C2B8) in Patients With Recurrent B-Cell Lymphoma," Blood 84(8):2457-2466, 1994.

Maloney, D.G., et al., "IDEC-C2B8: results of a phase I multiple-dose trial in patients with relapsed non-Hodgkin's lymphoma," J. Clin. Oncol. 15(10):3266-3274, 1997.

Marsh, J.E., et al., "Targeting the complement system," Curr. Opin. Nephrol. Hypertens. 8:557-562, 1999.

Martens, C.L., et al., "Heavy chain genes of rabbit IgG: Isolation of a cDNA encoding γ heavy chain and identification of two genomic Cγ genes," Proc. Natl. Acad. Sci. USA 79:6018-6022, 1982.

Martin, S., et al., "Efficient Neutralization and Disruption of Rhinovirus by Chimeric ICAM-1/Immunoglobulin Molecules," J. Virol. 67(6):3561-3568, 1993.

Mattu, T.S., et al., "The Glycosylation and Structure of Human Serum IgA1, Fab, and Fc Regions and the Role of N-Glycosylation on Fcα Receptor Interactions," J. Biol. Chem. 273(4):2260-2272, 1998.

Press, O.W., et al., "Treatment of refractory non-Hodgkin's lymphoma with radiolabeled MB-1 (anti-CD37) antibody," J. Clin. Oncol. 7(8):1027-1038, 1989.

Protheroe, A., et al., "Remission of inflammatory arthropathy in association with anti-CD20 therapy for non-Hodgkin's lymphoma," Rheumatology 38:1150-1152, 1999.

PubMed (NCBI) search for "des-leucine" (cited in Office Action dated Dec. 8, 2006 in U.S. Appl. No. 10/627,556, now U.S. Patent No. 7,829,084).

Radaev, S., et al., "The Structure of a Human Type III Fcγ Receptor in Complex with Fc," J. Biol. Chem. 276(19):16469-16477, 2001.

Radaev, S., and Sun, P.D., "Recognition of IgG by Fcγ receptor. The role of Fc glycosylation and the binding of peptide inhibitors," J. Biol. Chem. 276(19):16478-16483, 2001.

Ratanatharathorn, V., et al., "Anti-CD20 Chimeric Monoclonal Treatment of Refractory Immune-Mediated Thrombocytopenia in a Patient with Chronic Graft-versus-Host Disease," Ann. Intern. Med. 133(4):275-279, 2000.

Redpath, S., et al., "The influence of the hinge region length in binding of human IgG to human Fcγ receptors," Hum. Immunol. 59:720-727, 1998.

Reff, M.E., et al., "Depletion of B Cells in Vivo by a Chimeric Mouse Human Monoclonal Antibody to CD20," Blood 83(2):435-445, 1994.

Riechmann, L., "Rearrangement of the former VL interface in the solution structure of a camelised, single antibody VH domain," J. Mol. Biol. 259:957-969, 1996.

Saleh, M.N., et al., A Pilot Study of the Anti-CD20 Monoclonal Antibody Rituximab in Patients With Refractory Immune Thrombocytopenia, Semin. Oncol. 27(6)(Suppl 12):99-103, 2000.

Santos, L., et al., "Role of macrophage migration inhibitory factor (MIF) in murine antigen-induced arthritis: interaction with glucocorticoids," Clin. Exp. Immunol. 123:309-314, 2001.

Scheinberg, D.A., et al., "A phase I toxicity, pharmacology, and dosimetry trial of monoclonal antibody OKB7 in patients with non-Hodgkin's lymphoma: effects of tumor burden and antigen expression," J. Clin. Oncol. 8(5):792-803, 1990.

Schmidt, M., et al., "Suppression of metastasis formation by a recombinant single chain antibody-toxin targeted to full-length and oncogenic variant EGF receptors," Oncogene 18:1711-1721, 1999.

Schwartz, G.P., et al., "A superactive insulin: [B10-aspartic acid]insulin(human)," Proc. Natl. Acad. Sci. USA 84:6408-6411, 1987.

NPL—Search Output from ATCC Website for Hybridomas: 2H7 (pp. 1-2), 1D8 (p. 1), HD37 (p. 1), G28-1 (p. 1), 4.4.220 (p. 1), Fc2-2 (p. 1), UCHL-1 (p. 1), 5B9 (p. 1), L6 (p. 1), 10A8 (p. 1), 2e12 (p. 1). 40.2.36 (p. 1) and G19-4 (p. 1).

Seaver, S.S., "Monoclonal Antibodies in Industry: More Difficult Than Originally Thought," Genet. Eng. News 14(14):10, 21, 1994.

Segal, D.M., et al., "Introduction: bispecific antibodies," J. Immunol. Methods 248:1-6, 2001.

Sensel, M.G., et al., "Engineering novel antibody molecules," Chem. Immunol. 65:129-158, 1997.

Shan, D., et al., "Apoptosis of Malignant Human B Cells by Ligation of CD20 with Monoclonal Antibody," Blood 91(5):1644-1652, 1998.

Shan, D., et al., "Characterization of scFv-Ig Constructs from the Anti-CD20 mAb 1F5 Using Linker Peptides of Varying Lengths," J. Immunol. 162:6589-6595, 1999.

Shankar, S., et al., "Antiepidermal growth factor variant III scFv fragment: effect of radioiodination method on tumor targeting and normal tissue clearance," Nucl. Med. Biol. 33:101-110, 2006.

Shimoni, A., et al., "Autologous T Cells Control B-Chronic Lymphocytic Leukemia Tumor Progression in Human → Mouse Radiation Chimera," Cancer Res. 59:5968-5974, 1999.

Shin, S.-U., et al., "Hybrid antibodies," Int. Rev. Immunol. 10:177-186 (1993).

Shu, L., et al., Secretion of a single-gene-encoded immunoglobulin from myeloma cells, Proc. Natl. Acad. Sci. USA 90:7995-7999, 1993.

Simonds, H.M., and Miles, D., "Adjuvant treatment of breast cancer: impact of monoclonal antibody therapy directed against the HER2 receptor," Expert Opin. Biol. Ther. 7(4):487-491, 2007.

Smellie, W.J.B., et al., "Radioimmunotherapy of breast cancer xenografts with monoclonal antibody ICR12 against c-erbB2 p185: comparison of iodogen and N-succinimidyl 4-methyl-3-(tri-n-butylstannyl)benzoate radioiodination methods," Cancer Res. 55(Suppl):5842s-5846s, 1995.

Smith, K.A., et al., "Isolation and characterization of vascular endothelial growth factor-165 specific scFv fragments by phage display," Int. J. Oncol. 22:333-338, 2003.

Smith-Gill, S.J., et al., "Contributions of immunoglobulin heavy and light chains to antibody specificity for lysozyme and two haptens," J. Immunol. 139:4135-4144, 1987.

Sonderman, P., et al., "The 3.2-Å crystal structure of the human IgG1 Fc fragment-FcγRIII complex," Nature 406:267-273, 2000.

Song, M.-K., et al., "Light chain of natural antibody plays a dominant role in protein antigen binding," Biochem. Biophys. Res. Commun. 268:390-394, 2000.

Souriau, C., and Hudson, P.J., "Recombinant antibodies for cancer diagnosis and therapy," Expert Opin. Biol. Ther. 3(2):305-318, 2003.

Speth, C., et al., "The complement system: Pathophysiology and clinical relevance," Wien. Klin. Wochenschr. 111(10):378-391, 1999.

Spiro, R.G., "Protein glycosylation: nature, distribution, enzymatic formation, and disease implications of glycopeptide bonds," Glycobiology 12(4):43R-56R, 2002.

Sporici, R.A., et al., "ICOS ligand costimulation is required for T-cell encephalitogenicity," Clin. Immunol 100(3):277-288, 2001.

Stamenkovic, I., and Seed, B., "Analysis of Two cDNA Clones Encoding the B Lymphocyte Antigen CD20 (B1, Bp35), A Type III Integral Membrane Protein," J. Exp. Med. 167:1975-1980, 1988.

Stevenson, G.T., et al., "Mechanisms in Removal of Tumor by Antibody," Cell Biophys. 24/25:45-50, 1994.

Stevenson, G.T., et al., "Conjugation of Human Fcγ in Closed-Hinge or Open-Hinge Configuration to Fab'γ and Analogous Ligands," J. Immunol. 158:2242-2250, 1997.

Tamura, H., et al., "B7-H1 costimulation preferentially enhances CD28-independent T-helper cell function," Blood 97(6):1809-1816, 2001.

Tan, L.K., et al., "Influence of the hinge region on complement activation, C1q binding, and segmental flexibility in chimeric human immunoglobulins," Proc. Natl. Acad. Sci. USA 87:162-166, 1990.

Targoff, I.N., "Dermatomyositis and Polymyositis," Curr. Probl. Dermatol., pp. 134-180, Sep./Oct. 1991.

Tedder, T.F., et al., "Cloning of a Complementary DNA Encoding a New Mouse B Lymphocyte Differentiation Antigen, Homologous to the Human B1 (CD20) Antigen, and Localization of the Gene to Chromosome 19," J. Immunol. 141(12):4388-4394, 1988.

Terry, L.A., et al., "The monoclonal antibody, UCHL1, recognizes a 180,000 MW component of the human leucocyte-common antigen, CD45," Immunol. 64:331-336, 1988.

Thommesen, J.E., et al., "Lysine 322 in the human IgG3 C(H)2 domain is crucial for antibody dependent complement activation," Mol. Immunol. 37:995-1004, 2000.

Thompson, P.A., et al., "Single-Chain Multivalent Binding Proteins with Effector Function," Office Action dated May 5, 2011, for U.S. Appl. No. 12/041,590, 8 pages.

Barone, D., et al., "Prolonged Depletion of Circulating B Cells in Cynomolgus Monkeys after a Single Dose of TRU-015, a Novel CD20 Directed Therapeutic," Ann. Rheum. Dis. 64(Suppl. III):159 (Abstract #THU0169), 2005.

Barone, D., et al., "TRU-15, a novel CD20-directed biologic therapy, demonstrates significant anti-tumor activity in human tumor xenograft models," J. Clin. Oncol. 23(16S):178s (Abstract #2549) Jun. 1, 2005.

Calistoga Pharmaceuticals, "Preliminary evidence of clinical activity in a phase 1 study of CAL-101, a potent selective inhibitor of the p110δ isoform of phosphatidylinositol 3-kinase, in patients with B-cell malignancies," European Hematology Association, Jun. 4-7, 2009, Poster Session, 17 pages.

Cambridge, G., et al., "Serologic Changes Following B Lymphocyte Depletion Therapy for Rheumatoid Arthritis," Arthristis Rheum. 48(8):2146-2154, 2003.

Cephalon Oncology, "Treanda Prescribing Information," 6 pages, 2008.

Cheson, B.D., "CLL Response Criteria,"Clin. Adv. Hematol. Oncol. 4(5)(Suppl. 12):4-5, 2006.

Cheson, B.D., et al., "Report of an international working to standardize response criteria for myelodysplastic syndromes," Blood 96:3671-3674, 2000.

Cheson, B.D., et al., "Report of an International Workshop to Standardize Response Criteria for Non-Hodgkin's Lymphomas," J. Clin. Oncol. 17:1244-1253, 1999.

Cheson, B.D., et al., "Revised Recommendations of the International Working Group for Diagnosis, Standardization of Response Criteria, Treatment Outcomes, and Reporting Standards for Therapeutic Trials in Acute Myeloid Leukemia," J. Clin. Oncol. 21(24):4642-4649, 2003.

Classon et al., "The hinge region of the CD8α chain: structure, antigenicity, and utility expression of immunoglobulin superfamily domains," Int. Immunol. 4(2):215-225 (1992).

Cragg, M.S., and Glennie, M.J., "Antibody specificity controls in vivo effector mechanisms of anti-CD20 reagents," Blood 103(7):2738-2743, 2004.

Huret, J.-L., "t(11;14)(q13;q32)," Atlas Genet. Cytogenet. Oncol. Haematol., May 1998. URL: http://atlastgeneticsoncology.org/Anomalies/t1114ID2021.html.

International Non-Hodgkin's Lymphoma Prognostic Factors Project, "A Predictive Model for Aggressive Non-Hodgkin's Lymphoma," New Engl. J. Med. 329:987-994, 1993.

Looney, R.J., et al., "B Cell Depletion as a Novel Treatment for Systemic Lupus Erythematosus," Arthritis Rheum. 50(8):2580-2589, 2004.

Matthews, R., "Medical Heretics," New Scientist, pp. 34-37, Apr. 7, 2001.

McLaughlin, P., et al., "Clinical Status and Optimal Use of Rituximab for B-Cell Lymphomas," Oncology 12(12):1763-1769, 1998; review by Grossbard, M.L., and Multani, P.S., pp. 1769-1770; review by Raubitschek, A., pp. 1775-1776; review by Molina, A., pp. 1776-1777, 1781.

Minsavage, G.D., and Dillman III, J.F., "Bifunctional Alkylating Agent-Induced p53 and Nonclassical Nuclear Factor κB Responses and Cell Death Are Altered by Caffeic Acid Phenethyl Ester: A Potential Role for Antioxidant/Electrophilic Response-Element Signaling," J. Pharmacol. Exp. Ther. 321(1):202-212, 2007.

Moldenhauer, G., "CD37," J. Biol. Regul. Homeost. Agents 14:281-283, 2000.

Monson, N.L., et al., "Effect of Rituximab on the Peripheral Blood and Cerebrospinal Fluid B Cells in Patients with Primary Progressive Multiple Sclerosis," Arch. Neurol. 62:258-264, 2005.

Mukai, Y., et al., "Optimization of anti-tumor necrosis factor-α single chain Fv displayed on phages for creation of functional antibodies," Pharmazie 61:889-890, 2006.

Nguyen, D.T., et al., "IDEC-C2B8 anti-CD20 (Rituximab) immunotherapy in patients with low-grade non-Hodgkin's lymphoma and lymphoproliferative disorders: evaluation of response on 48 patients," Eur. J. Haematol. 62:76-82, 1999.

Oliyai, R., and Stella, V.J., et al., "Prodrugs of Peptides and Proteins for Improved Formulation and Delivery," Annu. Rev. Pharmacol. Toxicol. 32:521-544, 1993.

Brandl et al., "Bispecific antibody fragments with CD20 × CD28 specificity allow effective autologous and allogeneic T-cell activation against malignant cells in peripheral blood and bone marrow cultures from patients with B-cell lineage leukemia and lymphoma," Experimental Hematology, vol. 27: 1264-1270, 1999.

Office Action, Japanese Application Serial No. 2009-515618, mailed Jul. 10, 2012, 7 pages.

Adlersberg, J.B, "The immunoglobulin hinge (interdomain) region," Ric. Clin. Lab. 6:191-205, 1976.

Afanasieva, T.A., et al., "Single-chain antibody and its derivatives directed against vascular endothelial growth factor: application for antiangiogenic gene therapy," Gene Therapy 10:1850-1859, 2003.

Aicher, A., et al., "Characterization of human inducible costimulator ligand expression and function," J. Immunol. 164:4689-4696, 2000.

Anderson, D.R., et al., "Targeting Cytotoxic Immunotherapy. Targeted anti-cancer therapy using rituximab, a chimaeric anti-CD20 antibody (IDEC-C2B8) in the treatment of non-Hodgkin's B-cell lymphoma," Biochem. Soc. Transactions, pp. 705-708, 1997.

Angal, S., et al., "A single amino acid substitution abolishes the heterogeneity of chimeric mouse/human (IgG4) antibody," Mol. Immunol. 30(1):105-108, 1993.

Baum, P.R., et al., "Evaluation of the effect of TRU-016, an anti-CD37 directed SMIP™, in combination with other therapeutic drugs in models of Non-Hodgkin's Lymphoma," 2009 Annual Meeting, American Society of Clinical Oncology (ASCO), J. Clin. Oncol. 27(May 20 Suppl.):15S (Abstract 8571), 2009.

Beiske, K., et al., "Triggering of neoplastic B cells via surface IgM and the cell surface antigens CD20 and CDw40. Responses differ from normal blood B cells and are restricted to certain morphologic subsets," Int. J. Cancer 42:521-528, 1988.

Benoist, C., and Mathis, D., "A revival of the B cell paradigm for rheumatoid arthritis pathogenesis?" Arthritis Res. 2:90-94, 2000.

Berzofsky, J.A., and Berkower, I.J., "Immunogenicity and Antigen Structure," in Fundamental Immunology, Third Edition, William E. Paul, Ed., Chap. 8, pp. 235-282, Raven Press, Ltd., New York, 1993.

Best, W.R., et al., "Development of a Crohn's Disease Activity Index. National Cooperative Crohn's Disease Study," Gastroenterology 70(3)439-444, 1976.

Bloom, J.W., et al., "Intrachain disulfide bond in the core hinge region of human IgG4," Protein Sci. 6:407-415, 1997.

Boehm, M.K., et al., "The Fab and Fc fragments of IgA1 exhibit a different arrangement from that in IgG: a study by X-ray and neutron solution scattering and homology modelling," J. Mol. Biol. 286:1421-1447, 1999.

Braslawsky, G.R., et al., "Adriamycin(hydrazone)-antibody conjugates require internalization and intracellular acid hydrolysis for antitumor activity," Cancer Immunol Immunother. 33:367-374, 1991.

Brekke, O.H., et al., "The structural requirements for complement activation by IgG: does it hinge on the hinge?" Immunol. Today 16(2):85-90, 1995.

Brinkmann, U., et al., "Recombinant immunotoxins containing the VH or VL domain of monoclonal antibody B3 fused to *Pseudomonas* exotoxin," J. Immunol. 150(7):2774-2782, 1993.

Brok, H.P.M., et al., "Prophylactic and therapeutic effects of a humanized monoclonal antibody against the IL-2 receptor (DACLIZUMAB) on collagen-induced arthritis (CIA) in rhesus monkeys," Clin. Exp. Immunol. 124:134-141, 2001.

Brorson, K., et al., "Mutational analysis of avidity and fine specificity of anti-levan antibodies," J. Immunol. 163:6694-6701, 1999.

Brown, R.S., et al., "Intratumoral microdistribution of [$^{131}$I]MB-1 in patients with B-cell lymphoma following radioimmunotherapy," Nucl. Med. Biol. 24:657-663, 1997.

Brown, S.L., et al., "Treatment of B-Cell Lymphomas with Anti-idiotype Antibodies Alone and in Combination with Alpha Interferon," Blood 73(3):651-661, 1989.

Brummell, D.A., et al., "Probing the Combining Site of an Anti-Carbohydrate Antibody by Saturation-Mutagenesis: Role of the Heavy-Chain CDR3 Residues," Biochemistry 32:1180-1187, 1993.

Burgess, W.H., et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111:2129-2138, 1990.

Burke, J.M., et al., "Radioimmunotherapy for acute leukemia," Cancer Control 9(2):106-113, 2002.

Burks, E.A., et al., "In vitro scanning saturation mutagenesis of an antibody binding pocket," Proc. Natl. Acad. Sci. USA 94:412-417, 1997.

Bussel, J.B., "Overview of Idiopathic Thrombocytopenic Purpura: New Approach to Refractory Patients," Semin. Oncol. 27(6) (Suppl 12):91-98, 2000.

Byrd, J.C., et al., "Effect of CD37 small modular immuno-pharmaceutical (SMIP™) on direct apoptosis in chronic lymphocytic leukemia cells via transcriptional up-regulation of the BH3 family member BIM," 2009 Annual Meeting, American Society of Clinical Oncology (ASCO), J. Clin. Oncol. 27(May 20 Suppl.):155 (Abstract 3035), 2009.

Cai, X., and Garen, A., "Comparison of fusion phage libraries displaying VH or single-chain Fv antibody fragments derived from the antibody repertoire of a vaccinated melanoma patient as a source of melanoma-specific targeting molecules," Proc. Natl. Acad. Sci. USA 94:9261-9266, 1997.

Campbell, N.A., et al., Biology, 5th Ed., p. 856, Benjamin-Cummings Publ. Co., Menlo Park, CA (1999).

Carter, P., "Antibody Engineering—IBC's Tenth International Conference, Dec. 6-9, 1999, La Jolla, CA, USA," IDrugs 3(3):259-261, 2000. PubMed Abstract Only, PMID: 16103927.

Carter, P., "Improving the efficacy of antibody-based cancer therapies," Nature Reviews Cancer 1:118-129, 2001.

Casset, F., et al., "A peptide mimetic of an anti-CD4 monoclonal antibody by rational design," Biochem. Biophys. Res. Commun. 307:198-205, 2003.

Chatterjee, M.B., et al., "Idiotypic antibody immunotherapy of cancer," Cancer Immunol. Immunother. 38:75-82, 1994.

Chen, Y., et al., "Selection and Analysis of an Optimized Anti-VEGF Antibody: Crystal Structure of an Affinity-matured Fab in Complex with Antigen," J. Mol. Biol. 293:865-881, 1999.

Chothia, C., et al., "Domain association in immunoglobulin molecules. The packing of variable domains," J. Mol. Biol. 186:651-663, 1985.

Clackson, T., et al., "Making antibody fragments using phage display libraries," Nature 352:624-628, 1991.

Clark, E.A., et al., "Role of the Bp35 cell surface polypeptide in human B-cell activation," Proc. Natl. Acad. Sci. USA 82:1766-1770, 1985.

Clark, E.A., and Einfeld, D, "Human B Cell Surface Molecules Defined by an International Workshop Panel of Monoclonal Antibodies," in Leukocyte Typing II (1986), vol. 2, Reinherz, E.L., et al., Eds., pp. 155-167, Springer-Verlag, New York, 1986.

Clark, E.A., and Ledbetter, J.A., "Activation of human B cells mediated through two distinct cell surface differentiation antigens, Bp35 and Bp50," Proc. Natl. Acad. Sci. USA 83:4494-4498, 1986.

Clark, E.A., and Ledbetter, J.A., "Structure, function, and genetics of human B cell-associated surface molecules," Adv. Cancer Res. 52:81-149, 1989.

Coffin, J.M., et al., Eds., Retroviruses, Cold Spring Harbor Laboratory Press, Plainview, NY, 1997. (Publication details and Table of Contents provided).

Coiffier, B., et al., "Rituximab (Anti-CD-20 Monoclonal Antibody) for the Treatment of Patients With Relapsing or Refractory Aggressive Lymphoma: A Multicenter Phase II Study," Blood 92(6):1927-1932, 1998.

Colman, P.M., "Effects of amino acid sequence changes on antibody-antigen interactions," Res. Immunol. 145:33-36, 1994.

Coloma, M.J., et al., "The hinge as a spacer contributes to covalent assembly and is required for function of IgG," J. Immunol. 158:733-740, 1997.

Cooke, S.P., et al., "A strategy for antitumor vascular therapy by targeting the vascular endothelial growth factor: receptor complex," Cancer Res. 61:3653-3659, 2001.

Cruse, J.M., and Lewis, R.E., Illustrated Dictionary of Immunology, p. 157, CRC Press, Inc., 1995.

Dall'Acqua, W.F., et al., "Modulation of the Effector Functions of a Human IgG1 through Engineering of it Hinge Region," J. Immunol. 177:1129-1138, 2006.

Damle, N.K., et al., "Direct helper T cell-induced B cell differentiation involves interaction between T cell antigen CD28 and B cell activation antigen B7," Eur. J. Immunol. 21:1277-1282, 1991.

Davies, J., and Riechmann, L., "'Camelising' human antibody fragments: NMR studies on VH domains," FEBS Lett. 339:285-290, 1994.

Davies J., and Riechmann, L., "Single antibody domains as small recognition units: design and in vitro antigen selection of camelized, human VH domains with improved protein stability," Protein Eng. 9(6):531-537, 1996.

De Pascalis, R., et al., "Grafting of 'abbreviated' complementarity-determining regions containing specificity-determining residues essential for ligand contact to engineer a less immunogenic humanized monoclonal antibody," J. Immunol. 169:3076-3084, 2002.

Deans, J.P., et al., "Association of tyrosine and serine kinases with the B cell surface antigen CD20. Induction via CD20 of tyrosine phosphorylation and activation of phospholipase C-γ1 and PLC phospholipase C-γ2," J. Immunol. 151(9):4494-4504, 1993.

Dechant, M., et al., "Chimeric IgA antibodies against HLA class II effectively trigger lymphoma cell killing," Blood 100(13):4574-4580, 2002.

Dermer, G.B., "Another Anniversary for the War on Cancer," Bio/Technology 12:320, 1994.

Desmyter, A., et al., "Crystal structure of a camel single-domain VH antibody fragment in complex with lysozyme," Nat. Struct. Biol. 3(9):803-811, 1996.

Dietsch, M.T., et al., "Bispecific receptor globulins, novel tools for the study of cellular interactions. Preparation and characterization of an E-selectin/P-selectin bispecific receptor globulin," J. Immunol. Methods 162:123-132, 1993.

Dietsch, M.T., et al., "Coengagement of CD2 with LFA-1 pr VLA-4 by bispecific ligand fusion proteins primes T cells to respond more effectively to T cell receptor-dependent signals," J. Leukoc. Biol. 56:444-452, 1994.

Dillman, R.O., et al., "Continuous infusion of T101 monoclonal antibody in chronic lymphocytic leukemia and cutaneous T-cell lymphoma," J. Biol. Response Mod. 5(5):394-410, 1986.

Dorai, H., et al., "Role of inter-heavy and light chain disulfide bonds in the effector functions of human immunoglobulin IgG1," Mol. Immunol. 29(12):1487-1491, 1992.

Dorrington, K.J., and Klein, M., "Aspects of immunoglobulin G structure relevant to its interaction with Fc receptors," Arch. Immunol. Ther. Exp. (Warsz.) 29:275-282, 1981.
Dufner, P., et al., "Harnessing phage and ribosome display for antibody optimisation," Trends Biotechnol. 24(11):523-529, 2006.
Duncan, A.R., and Winter, G., "The binding site for C1q on IgG," Nature 332:738-740, 1988.
Durk, F.H., et al., "Prevention of collagen-induced arthritis with an antibody to gp39, the ligand for CD40," Science 261:1328-1330, 1993.
Dyer, M.J., et al., "Effects of CAMPATH-1 antibodies in vivo in patients with lymphoid malignancies: influence of antibody isotype," Blood 73(6):1431-1439, 1989.
Edwards, J.C.W., and Cambridge, G., "Rheumatoid Arthritis: The Predictable Effect of Small Immune Complexes in which Antibody Is Also Antigen," Br. J. Rheumatol. 37:126-130, 1998.
Edwards, J.C.W., et al., "Do self-perpetuating B lymphocytes drive human autoimmune disease?" Immunology 97:188-196, 1999.
Edwards, J.C.W., et al., "B-lymphocyte depletion therapy in rheumatoid arthritis and other autoimmune disorders," Biochem. Soc. Trans. 30(4):824-828, 2002.
Edwards, J.C.W., et al., "Efficacy of B-Cell-Targeted Therapy with Rituximab in Patients with Rheumatoid Arthritis," New Engl. J. Med. 350:2572-2581, 2004.
Faure, P., et al , "Immunohistochmical Profile of Cutaneous B-Cell Lymphoma on Cryostat and Paraffin Sections," Amer. J. Dermatopathol. 12(3):122-133, 1990.
Fell, H.P., et al., "Genetic construction and characterization of a fusion protein consisting of a chimeric F(ab') with specificity for carcinomas and human IL-2," J. Immunol. 146(7):2446-2452, 1991.
Fell, H.P., et al., "Chimeric L6 Anti-tumor Antibody. Genomic construction, expression, and characterization of the antigen binding site," J. Biol. Chem. 267(22):15552-15558, 1992.
Filpula, et al., "Single-chain Fv designs for protein, cell and gene therapeutics," Exp. Opin. Ther. Patents 9(3):231-245, 1999.
Funakoshi, S., et al , "Inhibition of Human B-Cell Lymphoma Growth by CD40 Stimulation," Blood 83(10):2787-2794, 1994.
Funakoshi, S., et al., "Differential in Vitro and in Vivo Antitumor Effects Mediated by Anti-CD40 and Anti-CD20 Monoclonal Antibodies Against Human B-Cell Lymphomas," J. Immunother. 19(2):93-101, 1996.
Genbank Accession No. M17953, Mouse Ig rearranged H-chain V-region mRNA VJ1, Apr. 27, 1993.
Genbank Accession No. M17954, Mouse Ig rearranged kappa-chain mRNA VJ5, Apr. 27, 1993.
Gillies, S.D., and Wesolowski, J.S., "Antigen binding and biological activities of engineered mutant chimeric antibodies with human tumor specificities," Hum. Antibod. Hybridomas 1(1):47-54, 1990.
Gillies, S.D., et al., "Improving the efficacy of antibody-interleukin 2 fusion proteins by reducing their interaction with Fc receptors," Cancer Res. 59:2159-2166, 1999.
Gilliland, L.K., et al., "Rapid and reliable cloning of antibody variable regions and generation of recombinant single chain antibody fragments," Tissue Antigens 47:1-20, 1996.
Gura, T., "Cancer Models. Systems for Identifying New Drugs Are Often Faulty," Science 278:1041-1042, 1997.
Halin, C., et al., "Tumor-targeting properties of antibody-vascular endothelial growth factor fusion proteins," Int. J. Cancer 102:109-116, 2002.
Hayden, M.S., et al., "Single-chain mono- and bispecific antibody derivatives with novel biological properties and antitumour activity from a COS cell transient expression system," Ther. Immunol. 1:3-15, 1994.
Hayden, M.S., et al., "Costimulation by CD28 sFv expressed on the tumor cell surface or as a soluble bispecific molecule targeted to the L6 carcinoma antigen," Tissue Antigens 48:242-254, 1996.
Hayden, M.S., et al., "Antibody engineering," Curr. Opin. Immunol. 9:201-212, 1997.
Hekman, A., et al., "Initial experience with treatment of human B cell lymphoma with anti-CD19 monoclonal antibody," Cancer Immunol. Immunother. 32:364-372, 1991.
Hellström, I., et al., "Monoclonal Mouse Antibodies Raised against Human Lung Carcinoma," Canc. Res. 46:3917-3923, 1986.
Hollenbaugh, D., et al., "The human T cell antigen gp39, a member of the TNF gene family, is a ligand for the CD40 receptor: expression of a soluble form of gp39 with B cell co-stimulatory activity," EMBO J. 11(12):4313-4321, 1992.
Holliger, P., and Hudson, P.J., "Engineered antibody fragments and the rise of single domains," Nat. Biotechnol. 23(9):1126-1136, 2005.
Holm, P., et al., "Functional mapping and single chain construction of the anti-cytokeratin 8 monoclonal antibody TS1," Mol. Immunol. 44:1075-1084, 2007.
Hu, S., et al., "Minibody: a novel engineered anti-carcinoembryonic antigen antibody fragment (single-chain Fv-CH3) which exhibits rapid, high-level targeting of xenografts," Cancer Res. 56:3055-3061, 1996.
Hudson, P.J., "Recombinant antibodies: a novel approach to cancer diagnosis and therapy," Expert Opin. Investig. Drugs 9(6):1231-1242, 2000.
Huls, G., et al., "Antitumor Immune Effector Mechanisms Recruited by Phage Display-derived Fully Human IgG1 and IgA1 Monoclonal Antibodies," Cancer Res. 59:5778-5784, 1999.
Huston, J.S., et al., "Medical applications of single-chain antibodies," Int. Rev. Immunol. 10:195-217, 1993.
Isaacs, J.D., et al., "Therapy with monoclonal antibodies. II. The contribution of Fcγ receptor binding and the influence of CH1 and CH3 domains on in vivo effector function," J. Immunol. 161:3862-3869, 1998.
Isenman, D.E., et al., "Correlation between the exposure of aromatic chromophores at the surface of the Fc domains of immunoglobulin G and their ability to bind complement," Biochemistry 16(2):233-240, 1977.
"IUPAC-IUB commission on biochemical nomenclature rules for naming synthetic modification of natural peptides tentative rules," J. Biol. Chem. 242:555-557, 1967.
Jain, R.K., "Physiological barriers to delivery of monoclonal antibodies and other macromolecules in tumors," Cancer Res. 50(Suppl.):814s-819s, 1990.
Jain, R.K., "Barriers to drug delivery in solid tumors," Scientific American, pp. 58-65, 1994.
Jang, Y.-J., et al., "The structural basis for DNA binding by an anti-DNA autoantibody," Mol. Immunol. 35:1207-1217, 1998.
Joosten, L.A.B., et al., "Protection against cartilage and bone destruction by systemic interleukin-4 treatment in established murine type II collagen-induced arthritis," Arthritis Res. 1(1):81-91, 1999.
Kaminski, M.S., et al., "Imaging, Dosimetry, and Radioimmunotherapy With Iodine 131-Labeled Anti-CD37 Antibody in B-Cell Lymphoma," J. Clin. Oncol. 10(11):1696-1711, 1992.
Kato, K., et al., "A conformational change in the Fc precludes the binding of two Fcγ receptor molecules to one IgG," Immunol. Today 21:310-312, 2000.
Keystone, E., "B cell targeted therapies," Arthritis Res. Ther. 7(Suppl. 3):513-518, 2005.
Kirschfink, M., "Targeting complement in therapy," Immunol. Rev. 180:177-189, 2001.
Klein, M., et al., "Expression of biological effector functions by immunoglobulin G molecules lacking the hinge region," Proc. Natl. Acad. Sci. USA 78(1):524-528, 1981.
Kobayashi, H., et al., "Tryptophan H33 plays an important role in pyrimidine (6-4) pyrimidone photoproduct binding by a high-affinity antibody," Protein Eng. 12(10):879-884, 1999.
Koolwijk, P., et al., "Interaction between hybrid mouse monoclonal antibodies and the human high-affinity IgG FcR, huFc gamma RI, on U937. Involvement of only one of the mIgG heavy chains in receptor binding," J. Immunol. 143(5):1656-1662, 1989.
Kortt, A.A., et al., "Recombinant anti-sialidase single-chain variable fragment antibody. Characterization, formation of dimer and higher-molecular-mass multimers and the solution of the crystal structure of the single-chain variable fragment/sialidase complex," Eur. J. Biochem. 221:151-157, 1994.
Kortt, A.A., et al., "Dimeric and trimeric antibodies: high avidity scFvs for cancer targeting," Biomol. Eng. 18:95-108, 2001.
Kumar, S., et al., "Molecular Cloning and Expression of the Fabs of Human Autoantibodies in *Escherichia coli*," J. Biol. Chem. 275(45):35129-35136, 2000.

Ladetto, M., et al., "Rituximab anti-CD20 monoclonal antibody induces marked but transient reductions of peripheral blood lymphocytes in chronic lymphocytic leukaemia patients," Med. Oncol. 17:203-210, 2000.

Law, C.-L., et al., "Expression and characterization of recombinant soluble human CD3 molecules: presentation of antigenic epitopes defined on the native TCR-CD3 complex," Int. Immunol. 14(4):389-400, 2002.

Layios, N., et al., "Remission of severe cold agglutinin disease after Rituximab therapy," Leukemia, pp. 187-188, 2000.

Lazar, E., et al., "Transforming growth factor α: mutation of aspartic acid 47 and leucine 48 results in different biological activities," Mol. Cell. Biol. 8(3):1247-1252, 1988.

Ledbetter, J.A., et al., "Antibodies to Tp67 and Tp44 Augment and Sustain Proliferative Responses of Activated T Cells," J. Immunol. 135(4):2331-2336, 1985.

Ledbetter, J.A., et al., "Augmentation of normal and malignant B cell proliferation by monoclonal antibody to the B cell-specific antigen BP50 (CDW40)," J. Immunol. 138(3):788-794, 1987.

Ledbetter, J.A., et al., "Monoclonal antibodies to a new gp40-45 (CD37) B-cell-associated cluster group modulate B-cell proliferation," in Leucocyte Typing III: White Cell Differentiation Antigens, A.J. McMichael, Ed., pp. 339-340, Oxford University Press, Oxford (1987).

Lee, E.J., and Kueck, B., "Rituxan in the Treatment of Cold Agglutinin Disease," Blood 92(9):3490-3491, 1998.

McLaughlin, P., et al., "IDEC-C2B8 Anti-CD20 Antibody: Final Report on a Phase III Pivotal Trial in Patients (PTS) with Relapsed Low-Grade or Follicular Lymphoma (LG/F NHL)," Blood 88(10)(Suppl. 1):90a (Abstract 349), 1996.

Merson, A., and Brochier, J., "Phenotypic heterogeneity of B cell chronic lymphocytic leukaemia," Immunol. Lett. 19:269-272, 1988.

Michaelsen, T.E., et al., "Enhancement of complement activation and cytolysis of human IgG3 by deletion of hinge exons," Scand. J. Immunol. 32:517-528, 1990.

Michaelsen, T.E., et al., "Antibody dependent cell-mediated cytotoxicity induced by chimeric mouse-human IgG subclasses and IgG3 antibodies with altered hinge region," Mol. Immunol. 29(3):319-326, 1992.

Michaelsen, T.E., et al., "One disulfide bond in front of the second heavy chain constant region is necessary and sufficient for effector functions of human IgG3 without a genetic hinge," Proc. Natl. Acad. Sci. USA 91:9243-9247, 1994.

Miller, F.W., "Classification and Prognosis of Inflammatory Muscle Disease," Rheum. Dis. Clin. North Amer. 20(4):811-826, 1994.

Miller, F.W., "Inflammatory Myopathies: Polymyositis, Dermatomyositis, and Related Conditions," in Arthritis and Allied Conditions: A Textbook of Rheumatology, 15th ed., Koopman, W.J., and Moreland, L.W., Eds., Chap. 75, pp. 1593-1620, Lippincott Williams & Wilkins, Philadelphia, 2005.

Moore, K., et al., "Use of the Monoclonal Antibody WR17, Identifying the CD37 gp40-45 Kd Antigen Complex, in the Diagnosis of B-Lymphoid Malignancy," J. Pathol. 152:13-21, 1987.

Muñoz, E., et al., "The CH1 domain of IgG is not essential for C3 covalent binding: importance of the other constant domains as targets for C3," Int. Immunol. 10(2):97-106, 1998.

Muyldermans, S., et al., "Sequence and structure of VH domain from naturally occurring camel heavy chain immunoglobulins lacking light chains," Protein Eng. 7(9):1129-1135, 1994.

Muyldermans, S., "Single domain camel antibodies: current status," Rev. Mol. Biotechnol. 74:277-302, 2001.

Nadler, L.M., "B Cell/Leukemia Panel Workshop: Summary and Comments," in Leukocyte Typing II, vol. 2, Reinherz, E.L., et al., Eds., pp. 3-14, 20, 21, Springer Verlag, New York, 1986.

NCBI Reference Sequence NP_001765.1 for Leukocyte Surface Antigen CD37, Oct. 31, 2000.

Neve, R.M., et al., "Biological effects of anti-ErbB2 single chain antibodies selected for internalizing function," Biochem. Biophys. Res. Commun. 280:274-279, 2001.

Nieba, L., et al., "Disrupting the hydrophobic patches at the antibody variable/constant domain interface: improved in vivo folding and physical characterization of an engineered scFv fragment," Protein Eng. 10(4):435-444, 1997.

Nikula, T.K., et al., "Impact of the high tyrosine fraction in complementarity determining regions: measured and predicted effects of radioiodination on IgG immunoreactivity," Mol. Immunol. 32(12):865-872, 1995.

Novak, H., et al., "Selective antibody-mediated targeting of class I MHC to EGFR-expressing tumor cells induces potent antitumor CTL activity in vitro and in vivo," Int. J. Cancer 120:329-336, 2006.

Nuttall, S.D., et al., "Immunoglobulin VH domains and beyond: design and selection of single-domain binding and targeting reagents," Curr. Pharm. Biotechnol. 1:253-263, 2000.

Okazaki, T., et al., "PD-1 immunoreceptor inhibits B cell receptor-mediated signaling by recruiting src homology 2-domain-containing tyrosine phosphatase 2 to phosphotyrosine," Proc. Natl. Acad. Sci. USA 98(24):13866-13871, 2001.

Oki, S., et al., "Augmentation of CTLA-4 expression by wortmannin: involvement of lysosomal sorting properties of CTLA-4," Int. Immunol. 11(9):1563-1571, 1999.

Padlan, E.A., "Anatomy of the Antibody Molecule," Mol. Immunol. 31(3):169-217, 1994.

Pallesen, G., and Hager, H., "The expression of the 40-45 kDa pan-B cluster (CD37) in normal human tissues and in haematopoietic neoplasms as defined by immunohistology," in Leucocyte Typing III: White Cell Differentiation Antigens, A.J. McMichael, Ed., pp. 337-339, Oxford University Press, Oxford (1987).

Park, S.S., et al., "Generation and characterization of a novel tetravalent bispecific antibody that binds to hepatitis B virus surface antigens," Mol. Immunol. 37:1123-1130, 2000.

Pawson, R., et al., "Treatment of T-cell prolymphocytic leukemia with human CD52 antibody," J. Clin. Oncol. 15(7):2667-2672, 1997.

Peter, K. et al., "Construction and functional evaluation of a single-chain antibody fusion protein with fibrin targeting and thrombin inhibition after activation by factor Xa," Circulation 101:1158-1164, 2000.

Pezzutto, A., et al., "CD19 Monoclonal Antibody HD37 Inhibits Anti-Immunoglobulin-Induced B Cell Activation and Proliferation," J. Immunol. 138(9):2793-2799, 1987.

Portolano, S., et al., "Lack of promiscuity in autoantigen-specific H and L chain combinations as revealed by human H and L chain 'roulette'," J. Immunol. 150(3):880-887, 1993.

Press, O.W., et al., "Monoclonal Antibody 1F5 (Anti-CD20) Serotherapy of Human B Cell Lymphomas," Blood 69(2):584-591, 1987.

Treon, S.P., and Anderson, K.C., "The Use of Rituximab in the Treatment of Malignant and Nonmalignant Plasma Cell Disorders," Semin. Oncol. 27(6)(Suppl 12):79-85, 2000.

Vajdos, F.F., et al., "Comprehensive Functional Maps of the Antigen-binding Site of an Anti-ErbB2 Antibody Obtained with Shotgun Scanning Mutagenesis," J. Mol. Biol. 320:415-428, 2002.

Van den Abbeele, A.D., et al., "Antigen-binding site protection during radiolabeling leads to a higher immunoreactive fraction," J. Nucl. Med. 32(1):116-122, 1991.

Van den Beucken, T., et al., "Building novel binding ligands of B7.1 and B7.2 based on human antibody single variable light chain domains," J. Mol. Biol. 310:591-601, 2001.

Vitaliti, A., et al, "Inhibition of tumor angiogenesis by a single-chain antibody directed against vascular endothelial growth factor," Cancer Res. 60:4311-4314, 2000.

Vlasveld, L.T., et al., "Treatment of low-grade non-Hodgkin's lymphoma with continuous infusion of low-dose recombinant interleukin-2 in combination with the B-cell-specific monoclonal antibody CLB-CD19," Cancer Immunol. Immunother. 40:37-47, 1995.

Walker, M.R., et al., "Aglycosylation of human IgG1 and IgG3 monoclonal antibodies can eliminate recognition by human cells expressing Fcγ RI and/or Fcγ RII receptors," Biochem. J. 259:347-353, 1989.

Wang, B., et al., "Human single-chain Fv immunoconjugates targeted to a melanoma-associated chondroitin sulfate proteoglycan mediate specific lysis of human melanoma cells by natural killer cells and complement," Proc. Natl. Acad. Sci. USA 96:1627-1632, 1999.

Ward, E.S., et al., "Binding activities of a repertoire of single immunoglobulin variable domains secreted from *Escherichia coli*," Nature 341:544-546, 1989.

Ward, E.S., and Ghetie, V., "The effector functions of immunoglobulins: implications for therapy," Ther. Immunol. 2:77-94, 1995.

Welschof, M., et al., "The Antigen Binding Domain of Non-idiotypic Human Anti-F(ab')2 Autoantibodies: Study of their Interaction with IgG Hinge Region Epitopes," Hum. Immunol. 60:282-290, 1999.

Weston, K.M., et al., "In vivo binding of mouse IgG via polyreactive surface IgM abrogates progressive lymphocytosis in prolymphocytic leukemia," Leuk. Lymphoma 29:361-373, 1998.

White, M.W., et al., "Activation of Dense Human Tonsilar B Cells. Induction of c-myc Gene Exptession via Two Distinct Signal Transduction," J. Immunol. 146(3):846-853, 1991.

Winberg, G., et al., "Surface Expression of CD28 Single Chain Fv for Costimulation by Tumor Cells," Immunol Rev. 153:209-223, 1996.

Wu, A.M., et al., "Multimerization of a chimeric anti-CD20 single-chain Fv-Fc fusion protein is mediated through variable domain exchange," Protein Eng. 14(12):1025-1033, 2001.

Wu, H., et al., "Humanization of a murine monoclonal antibody by simultaneous optimization of framework and CDR residues," J. Mol. Biol. 294:151-162, 1999.

Wörn, A., and Plückthun, A., "Stability engineering of antibody single-chain Fv fragments," J. Mol. Biol. 305:989-1010, 2001.

Ye, Z., et al., "Gene therapy for cancer using single-chain Fv fragments specific for 4-1BB," Nat. Med. 8(4):343-348, 2002.

Yoshinaga, S.K., et al., "Characterization of a new human B7-related protein: B7RP-1 is the ligand to the co-stimulatory protein ICOS," Int. Immunol. 12(10):1439-1447, 2000.

Zaja, F., et al., "Rituximab for myasthenia gravis developing after bone marrow transplant," Neurology 55:1062-1063, 2000.

Zarling, J.M., et al., "Lysis of Cells Infected with HIV-1 by Human Lymphocytes Targeted with Monoclonal Antibody Heteroconjugates," J. Immunol. 140(8):2609-2613, 1988.

Zhao, X., et al., "Targeting CD37-positive lymphoid malignancies with a novel engineered small modular immunopharmaceutical," Blood 110(7):2569-2577, 2007.

Zhorov, O.V., et al., "Oxidative iodination of rabbit IgG: localization of markers in an Fc-fragment and effects of modification," Biokhimiia 56(5):828-838, 1991 (with PubMed Abstract, PMID: 1747412).

Batra, Janendra K. et al., "Single-Chain Immunotoxins Directed at the Human Transferrin Receptor Containing *Pseudomonas* Exotoxin A or Diphtheria Toxin: Anti-TFR(Fv)-PE40 and DT388-Anti-TFR(Fv)," *Molecular and Cellular Biology* 11(4):2200-2205, Apr. 1991.

Belov, Larissa et al., "Immunophenotyping of Leukemias Using a Cluster of Differentiation Antibody Microarray," *Cancer Research* 61:4483-4489, Jun. 1, 2001.

Better, Marc et al., "*Escherichia coli* Secretion of an Active Chimeric Antibody Fragment," *Science* 240:1041-1043, May 20, 1988.

Bongini, L. et al., "Freezing immunoglobulins to see them move," *PNAS* 101(17):6466-6471, Apr. 27, 2004.

Boussif, Otmane et al., "A versatile vector for gene and oligonucleotide transfer into cells in culture and in vivo: Polyethylenimine," *Proc. Natl. Acad. Sci. USA* 92:7297-7301, Aug. 1995.

Capaldi, Roderick A. et al., "Changes in Order of Migration of Polypeptides in Complex III and Cytochrome c Oxidase under Different Conditions of SDS Polyacrylamide Gel Electrophoresis," *Biochemical and Biophysical Research Communications* 74(2):425-433, 1977.

Capon, Daniel J. et al., "Designing CD4 immunoadhesins for AIDS therapy," *Nature* 337:525-531, Feb. 9, 1989.

Chakraborti, Tapati et al., "Review Article. Complement activation in heart diseases: Role of oxidants," *Cellular Signalling* 12:607-617, 2000.

Chan, Owen T.M. et al., "A Novel Mouse with B Cells but Lacking Serum Antibody Reveals an Antibody-independent Role for B Cells in Murine Lupus," *J. Exp. Med.* 189(10):1639-1647, May 17, 1999.

Chaudhary, Vijay K. et al., "A recombinant immunotoxin consisting of two antibody variable domains fused to *Pseudomonas* exotoxin," *Nature* 339:394-397, Jun. 1, 1989.

Chothia, Cyrus et al., "Conformations of immunoglobulin hypervariable regions," *Nature* 342:877-883, Dec. 21/28, 1989.

Chothia, Cyrus et al., "Canonical Structures for the Hypervariable Regions of Immunoglobulins," *J. Mol. Biol.* 196:901-917, 1987.

Chowdhury, Partha S. et al., "Improving antibody affinity by mimicking somatic hypermutation in vitro," *Nature Biotechnology* 17:568-572, Jun. 1999.

Co, Man Sung et al., "Chimeric and Humanized Antibodies with Specificity for the CD33 Antigen," *Journal of Immunology* 148(4):1149-1154, Feb. 15, 1992.

Co, Man Sung et al., "Genetically Engineered Deglycosylation of the Variable Domain Increases the Affinity of an Anti-CD33 Monoclonal Antibody," *Molecular Immunology* 30(15):1361-1367, 1993.

Co, Man Sung et al., "Humanized antibodies for antiviral therapy," *Proc. Natl. Acad. Sci. USA* 88:2869-2873, Apr. 1991.

Cote, Richard J. et al., "Generation of human monoclonal antibodies reactive with cellular antigens," *Proc. Natl. Acad. Sci. USA* 80:2026-2030, Apr. 1983.

Cotten, Matt et al., "High-efficiency receptor-mediated delivery of small and large (48 kilobase gene constructs using the endosome-disruption activity of defective or chemically inactivated adenovirus particles," Proc. Natl. Acad. Sci. USA 89:6094-6098, Jul. 1992.

Davis, Simon J. et al., "High Level Expression in Chinese Hamster Ovary Cells of Soluble Forms of CD4 T Lymphocyte Glycoprotein Including Glycosylation Variants,"*Journal of Biological Chemistry* 265(18):10410-10418, Jun. 25, 1990.

Jendreyko, Nina et al., "Intradiabodies, Bispecific, Tetravalent Antibodies for the Simultaneous Functional Knockout of Two Cell Surface Receptors," *Journal of Biological Chemistry* 278(48):47812-47819, Nov. 28, 2003.

Jendreyko, Nina et al., "Phenotypic knockout of VEGF-R2 and Tie-2 with an intradiabody reduces tumor growth and angiogenesis in vivo," *PNAS* 102(23):8293-8298, Jun. 7, 2005.

Jermutus, Lutz et al., "Tailoring in vitro evolution for protein affinity or stability," *PNAS* 98(1):75-80, Jan. 2, 2001.

Johnson George et al., "Kabat Database and its applications: 30 years after the first variability plot," *Nucleic Acids Research* 28(1):214-218, 2000.

Jost, Carolina R. et al., "Mammalian Expression and Secretin of Functional Single-chain Fv Molecules," *Journal of Biological Chemistry* 269(42):26267-26273, Oct. 21, 1994.

Kalergis, Alexis M. et al., "Efficient T cell activation requires an optimal dwell-time of interaction between the TCR and the pMHC complex," Nature Immunology 2(3):229-234, Mar. 2001.

Kaminski, Mark S. et al., "Radioimmunotherapy of B-Cell Lymphoma with [131I]Anti-B1 (Anti-CD20) Antibody," *New England Journal of Medicine* 329(7):459-465, Aug. 12, 1993.

Kersh, Ellen Neumeister et al., "Fidelity of T Cell Activation Through Multistep T Cell Recepter ζ Phosphorylation," *Science* 281:572-575, Jul. 24, 1998.

Kiel, C. et al., "Electrostatically optimized Ras-binding Ral guanine dissociation stimulator mutants increase the rate of association by stabilizing the encounter complex," *PNAS* 101(25):9223-9228, Jun. 22, 2004.

Kienberger, Ferry et al., "Scientific Report. Following single antibody binding to purple membranes in real time," *EMBO Reports* 5(6):579-583, 2004.

Knobeloch, Klaus-Peter et al., "Targeted Inactivation of the Tetraspanin CD37 Impairs T-Cell-Dependent B-Cell Response under Suboptimal Costimulatory Conditions," *Molecular and Cellular Biology* 20(15):5363-5369, Aug. 2000.

Köhl, Jörg et al., "On the role of complement and Fc γ-receptors in the Arthus reaction," *Molecular Immunology* 36:893-903, 1999.

Kolls, J. et al., "Prolonged and effective blockade of tumor necrosis factor activity through adenovirus-mediated gene transfer," *Proc. Natl. Acad. Sci. USA* 91:215-219, Jan. 1994.

Kozbor, Danuta et al., "The production of monoclonal antibodies from human lymphocytes," *Immunology Today* 4(3):72-79, 1983.

Kunkel, Thomas A., "Rapid and efficient site-specific mutagenesis without phenotypic selection," *Proc. Natl. Acad. Sci. USA* 82:488-492, Jan. 1985.

Kusumi, Akihiro et al., "Confined Lateral Diffusion of Membrane Receptors as Studied by Single Particle Tracking (Nanovid Microscopy). Effects of Calcium-Induced Differentiation in Cultured Epithelial Cells," *Biophysical Journal* 65:2021-2040, Nov. 1993.

Lazar, Greg A. et al., "Engineered antibody Fc variants with enhanced effector function," *PNAS* 103(11):4005-4010, Mar. 14, 2006.

Leatherbarrow, Robin J. et al., "Effector Functions of a Monoclonal Aglycosylated Mouse IgG2a: Binding and Activation of Complement Componenet C1 and Interaction with Human Monocyte Fc Receptor," *Molecular Immunology* 22(4):407-415, 1985.

Leonard, Paul et al., "Research paper. High throughput ranking of recombinant avian scFv antibody fragments from crude lysates using the Biacore A100," *Journal of Immunological Methods* 323:172-179, 2007.

Li, Qiutang et al., "Assessment of Recombinant Adenoviral Vectors for Hepatic Gene Therapy," *Human Gene Therapy* 4:403-409, 1993.

Link, Michael P. et al., "A Unique Antigen on Mature B Cells Defined by a Monoclonal Antibody,"*Journal of Immunology* 137(9):3013-3018, Nov. 1, 1986.

Lu, Dan et al., "Di-diabody: a novel tetravalent bispecific antibody molecule by design," *Journal of Immunological Methods* 279:219-232, 2003.

Lu, Dan et al., "A Fully Human Recombinant IgG-like Bispecific Antibody to Both the Epidermal Growth Factor Receptor and the Insulin-like Growth Factor Receptor for Enhanced Antitumor Activity," *Journal of Biological Chemistry* 280(20):19665-19672, May 20, 2005.

Lyons, Daniel S. et al., "A TCR Binds to Antagonist Ligands with Lower Affinities and Faster Dissociation Rates than to Agonists," *Immunity* 5:53-61, Jul. 1996.

MacCallum, Robert M. et al., "Antibody-antigen Interactions: Contact Analysis and Binding Site Topography," *J. Mol. Biol.* 262:732-745, 1996.

Maloney, David G. et al., "Rapid Communication. IDEC-C2B8 (Rituximab) Anti-CD20 Monoclonal Antibody Therapy in Patients with Relapsed Low-Grade Non-Hodgkin's Lymphoma," *Blood* 90(6):2188-2195, Sep. 15, 1997.

Marks, James D. et al., "By-passing Immunization. Human Antibodies from V-gene Libraries Displayed on Phage," *J. Mol. Biol.* 222:581-597, 1991.

Marsh, James E. et al., "Targeting the complement system," *Nephrology and Hypertension* 8(5):557-562, Sep. 1999.

Martin, Andrew C.R. et al., "Modeling antibody hypervariable loops: A combined algorithm," *Proc. Natl. Acad. Sci. USA* 86:9268-9272, Dec. 1989.

Marvin, Jonathan S. et al., "Invited Review. Recombinant approaches to IgG-like bispecific antibodies," *Acta Pharmacologica Sinica* 26(6):649-658, Jun. 2005.

Matsui, Kiyoshi et al., "Kinetics of T-cell receptor binding to peptide/I-$E^k$ complexes: Correlation of the dissociation rate with T-cell responsivenesss," *Proc. Natl. Acad. Sci. USA* 91:12862-12866, Dec. 1994.

McLaughlin, P. et al., "Pharmacokinetics (PK) and Pharmacodynamics (PD) of the Anti-CD20 Antibody (MAB) IDEC-C288 in Patients (Pts) with Relapsed Low-Grade or Follicular Lymphoma (LG/F NHL),"*Blood* 88 (Suppl. 1:90a) (abstract), Abstract No. 350, 1 page, 1996.

Miller, A. Dusty et al., "Retrovirus Packaging Cells," *Human Gene Therapy* 1:5-14, 1990.

Mullinax, Rebecca L. et al., "Identification of human antibody fragment clones specific for tetanus toxoid in a bacteriophage λ immunoexpression library," *Proc. Natl. Acad. Sci. USA* 87:8095-8099, Oct. 1990.

Multani, P.S. et al., "Monoclonal antibody-based therapies for hematologic malignancies," *Journal of Clinical Oncology* 16:3691-3710, 1998.

Muraoka, Shizuko et al., "Structural Requirements for IgM Assembly and Cytolytic Activity. Effects of Mutations in the Oligosaccharide Acceptor Site at Asn402," *Journal of Immunology* 142(2):695-701, Jan. 15, 1989.

Nguyen, Viet Khong et al., "Heavy-chain antibodies in *Camelidae*; a case of evolutionary innovation," *Immunogenetics* 54:39-47, 2002.

Nguyen, Viet Khong et al., "Communication. The Specific Variable Domain of Camel Heavy-chain Antibodies is Encoded in the Germline," *J. Mol. Biol.* 275:413-418, 1998.

Nielsen, Ulrik B. et al., "Targeting of Bivalent Anti-ErbB2 Diabody Antibody Fragments to Tumor Cells Is Independent of the Intrinsic Antibody Affinity," *Cancer Research* 60:6434-6440, Nov. 15, 2000.

Ogoshi, Machiko et al., "In Situ Hybridization Analysis of the Expression of Human Telomerase RNA in Normal and Pathologic Conditions of the Skin," *Journal of Investigative Dermatology* 110(5):818-823, May 1998.

Paar, Jodi M. et al., "Bivalent Ligands with Rigid Double-Stranded DNA Spacers Reveal Structural Constraints on Signaling by FcεRI," *Journal of Immunology* 169:856-864, 2002.

Poljak, R.J. et al., "Three-Dimensional Structure of the Fab' Fragment of a Human Immunoglobulin at 2.8-Å Resolution," *Proc. Nat. Acad. Sci. USA* 70(12, Part I):3305-3310, Dec. 1973.

Pollard, Hélène et al., "Polyethylenimine but Not Cationic Lipids Promotes Transgene Delivery to the Nucleus in Mammalian Cells," *Journal of Biological Chemistry* 273(13):7507-7511, Mar. 27, 1998.

Press, Oliver W. et al., "Radiolabeled-Antibody Therapy of B-Cell Lymphoma with Autologous Bone Marrow Support," *New England Journal of Medicine* 329(17):1219-1224, Oct. 21, 1993.

Presta, L.G. et al., "Engineering therapeutic antibodies for improved function," *Biochemical Society Transactions* 30(4):487-490, 2002.

Queen, Cary et al., "A humanized antibody that binds to the interleukin 2 receptor," *Proc. Natl. Acad. Sci. USA* 86:10029-10033, Dec. 1989.

Riechmann, Lutz et al., "Reshaping human antibodies for therapy," *Nature* 332:323-327, Mar. 24, 1988.

Roguska, Michael A. et al., "A comparison of two murine monoclonal antibodies humanized by CDR-grafting and variable domain resurfacing," *Protein Engineering* 9(10):895-904, 1996.

Roux, Kenneth H. et al., "Flexibility of Human IgG Subclasses," *Journal of Immunology* 159:3372-3382, 1997.

Roux, Kenneth H. et al., "Comparisons of the Ability of Human IgG3 Hinge Mutants, IgM, IgE, and IgA2, to Form Small Immune Complexes: A Role for Flexibility and Geometry," *Journal of Immunology* 161:4083-4090, 1998.

Roux, Kenneth H. et al., "Structural analysis of the nurse shark (new) antigen receptor (NAR): Molecular convergence of NAR and unusual mammalian immunoglobulins," *Proc. Natl. Acad. Sci. USA* 95:11804-11809, Sep. 1998.

Saldanha, José W. et al., "A single backmutation in the human kIV framework of a previously unsuccessfully humanized antibody restores the binding activity and increases the secretion in *cos* cells," *Molecular Immunology* 36:709-719, 1999.

Schuster, Manfred et al., "Improved Effector Functions of a Therapeutic Monoclonal Lewis Y-Specific Antibody by Glycoform Engineering," *Cancer Research* 65(17):7934-7941, Sep. 1, 2005.

Schwartz-Albiez, Reinhard et al., "The B Cell-Associated CD37 Antigen (gp40-52) Structure and Subcellular Expression of an Extensively Glycosylated Glycoprotein," *Journal of Immunology* 140(3):905-914, Feb. 1, 1988.

Selzer, Tzvia et al., "Rational design of faster associating and tighter binding protein complexes," *Nature Structural Biology* 7(7):537-541, Jul. 2000.

Shahied, Lillian S. et al., "Bispecific Minibodies Targeting HER2/*neu* and CD16 Exhibit Improved Tumor Lysis When Placed in a Divalent Tumor Antigen Binding Format," *Journal of Biological Chemistry* 279(52): 53907-53914, Dec. 24, 2004.

Shin, Seung-Uon et al., "Genetically-Engineered Antibodies: Tools for the Study of Diverse Properties of the Antibody Molecule," *Immunological Reviews* 130:87-107, 1992.

Shlomchik, Mark J. et al., "The Role of B Cells in *lpr/lpr*-induced Autoimmunity," *J. Exp. Med.* 180:1295-1306, Oct. 1994.

Smith, Gale E. et al., "Molecular Engineering of the *Autographa californica* Nuclear Polyhedrosis Virus Genome: Deletion Mutations Within the Polyhedrin Gene," *Journal of Virology* 46(2):584-593, May 1983.

Steukers, Mieke et al., "Research paper. Rapid kinetic-based screening of human Fab fragments, " *Journal of Immunological Methods* 310:126-135, 2006.

Su, Bin et al., "Research paper. Automated high-throughput purification of antibody fragments to facilitate evaluation in functional and kinetic based assays," *Journal of Immunological Methods* 322:94-103, 2007.

Tao, Mi-Hua et al., "Studies of Aglycosylated Chimeric Mouse-Human IgG. Role of Carbohydrate in the Structure and Effector Functions Mediated by the Human IgG Constant Region," *Journal of Immunology* 143(8):2595-2601, Oct. 15, 1989.

Taylor, Annette K. et al., "Selective Removal of α Heavy-Chain Glycosylation Sites Causes Immunoglobulin A Degradation and Reduced Secretion," *Molecular and Cellular Biology* 8(10):4197-4203, Oct. 1988.

Tempest, Philip R. et al., "Reshaping a Human Monoclonal Antibody to Inhibit Human Respiratory Syncytial Virus Infection In Vivo," *Bio/Technology* 9:266-271, Mar. 1991.

Traunecker, André et al., "Bispecific single chain molecules (Janusins) target cytotoxic lymphocytes on HIV infected cells," *The EMBO Journal* 10(12):3655-3659, 1991.

Vaswani, Surender K. et al., "Review article. Humanized antibodies as potential therapeutic drugs," *Ann. Allergy Asthma Immunol.* 81:105-119, Aug. 1998.

Verhoeyen, Martine et al., "Reshaping Human Antibodies: Grafting an Antilysozyme Activity," *Science* 239:1534-1536, Mar. 25, 1988.

Vincent, Nathalie et al., "Long-term correction of mouse dystrophic degeneration by adenovirus-mediated transfer of a minidystrophin gene," *Nature Genetics* 5:130-134, Oct. 1993.

Walther, Wolfgang et al. (eds.), *Gene therapy of cancer: methods and protocols*, Humana Press, Totowa, N.J., 2000, Table of Contents.

Wang, Chen-Yen et al., "pH-sensitive immunoliposomes mediate target-cell-specific delivery and controlled expression of a foreign gene in mouse," *Proc. Natl. Acad. Sci. USA* 84:7851-7855, Nov. 1987.

Warnock, Dale et al., "In Vitro Galactosylation of Human IgG at 1 kg Scale Using Recombinant Galactosyltransferase," *Biotechnology and Bioengineering* 92(7):831-842, Dec. 30, 2005.

Wu, Catherine H. et al, "Targeting Genes: Delivery and Persistent Expression of a Foreign Gene Driven by Mammalian Regulatory Elements in Vivo," *Journal of Biological Chemistry* 264(29):16985-16987, Oct. 15, 1989.

Xavier, K. Asish et al., "Association and Dissociation Kinetics of Anti-Hen Egg Lysozyme Monoclonal Antibodies HyHEL-5 and HyHel-10," *Biophysical Journal* 74:2036-2045, Apr. 1998.

Yokota, Takashi et al., "Rapid Tumor Penetration of a Single-Chain Fv and Comparison with Other Immunoglobulin Forms," *Cancer Research* 52:3402-3408, Jun. 15, 1992.

Curiel, D.T., et al., "High-efficiency gene transger mediated by adenovirus coupled to DNA-polylysine complexes," Hum. Gene Ther. 3(2):147-154, 1992. PubMed Abstract only, PMID: 1391034.

Genbank Accession No. L07414, *Homo sapiens* CD40 surface protein mRNA, complete cds, Apr. 27, 1993. (date first available in Genbank).

Genbank Accession No. M62541, Mouse CD20 cell surface protein mRNA, complete cds, Jul. 26, 1993. (date first available in Genbank).

Genbank Accession No. M62542, Mouse CD19 gene, complete cds, Apr. 27, 1993. (date first available in Genbank).

Genbank Accession No. M83312, Mouse CD40 mRNA, complete cds, Apr. 27, 1993. (date initial sequence first available in Genbank).

Genbank Accession No. M83312, Mouse CD40 mRNA, complete cds, Sep. 23, 1996. (date updated sequence first available in Genbank).

Genbank Accession No. M84371, Human CD19 gene, complete cds, Apr. 27, 1993. (date initial sequence first available in Genbank).

Genbank Accession No. M84371, Human CD19 gene, complete cds, Jul. 18, 1995. (date updated sequence first available in Genbank).

Genbank Accession No. U15637, *Homo sapiens* CD40 binding protein (CD4OBP) mRNA, complete cds, Dec. 7, 1994. (date first available in Genbank).

Genbank Accession No. X14046, Human mRNA for leukocyte antigen CD37, Apr. 21, 1993. (date first available in Genbank).

Genbank Accession No. X53517, *R. norvegicus* mRNA for antigen CD37, Apr. 21, 1993. (date first available in Genbank).

Genbank Accession No. X65453, *M. musculus* mRNA for CD40 ligand, Apr. 21, 1993. (date initial sequence first available in Genbank).

Genbank Accession No. X65453, *M. musculus* mRNA for CD40 ligand, Apr. 27, 2001. (date updated sequence first available in Genbank).

Genbank Accession No. X67878, *H. sapiens* mRNA for CD40 ligand, Apr. 21, 1993. (date first available in Genbank).

Genbank Accession No. X96710, *H. sapiens* mRNA for CD40 ligand, Apr. 5, 1996. (date first available in Genbank).

Genbank Accession No. Y10507, *H. sapiens* mRNA for CD40 protein, Sep. 9, 1997. (date first available in Genbank).

Kost et al., "Production of a urokinase plasminogen activator-IgG fusion protein (uPA-IgG) in the baculovirus expression system," Gene 190:139-144 (1997).

Vanhove et al., "Selective blockade of CD28 and not CTLA-4 with a single-chain Fv-$\alpha_1$-antitrypsin fusion antibody," Blood 102:564-570 (2003).

Willems et al., "CD3×CD28 cross-interacting bispecific antibodies improve tumor cell dependent T-cell activation," Cancer Immunol. Immunother. 54:1059-1071 (2005).

Afinitor (everolimus) tablets for oral administration, Highlights of Prescribing Information, retrieved from http://www.miochol.org/product/pi/pdf/afinitor.pdf, 2009, 12 pages.

Albrecht, H., et al., "Monospecific bivalent scFv-SH: Effects of linker length and location of an engineered cysteine on production, antigen binding activity and free SH accessibility," J. Immunol. Meth. 310:100-116, 2006.

Andritsos, L., et al., "A phase I trial of TRU-016, an anti-CD37 small modular immunopharmaceutical (SMIP) in relapsed and refractory CLL," 2009 Annual Meeting, American Society of Clinical Oncology (ASCO), J. Clin. Oncol. 27(suppl.):15s (Abstract #3017), 2009.

Anthony, K., Ed., "Selective inhibitors gain traction," Nat. Rev. Cancer 10:160, 2010.

Barone, D., et al., "Efficacy of SMIP-016, a novel CD37-directed biologic therapy, in human NHL tumor xenograft models," J. Clin. Oncol. 24(18S)(Jun. 20 Suppl.):Abstract #2565, 2006.

Barone, D., et al., "Prolonged Depletion of Circulating, B Cells in Cynomolgus Monkeys after a Single Dose of TRU-015, a Novel CD20 Directed Therapeutic," Ann. Rheum. Dis. 64(Suppl. III):159 (Abstract #THU0169), 2005.

Barone, D., et al., "TRU-015, a novel CD20-directed biologic therapy, demonstrates significant anti-tumor activity in human tumor xenograft models," J. Clin. Oncol. 23(16S):178s (Abstract #2549) Jun. 1, 2005.

Bernstein, I.D., et al., "High Dose Radiolabeled Antibody Therapy of Lymphoma," Canc. Res. 50(Suppl.):1017s-1021s, 1990.

Buchsbaum, D.J., et al., "Therapy with Unlabeled and 131I-labeled Pan-B-Cell Monoclonal Antibodies in Nude Mice Bearing Raji Burkitt's Lymphoma Xenografts," Canc. Res. 52:6476-6481, 1992.

Cree, B. et al., "Tolerability and Effects of Rituximab (Anti-CD20 Antibody) in Neuromyelitis Optica (NMO) and Tapidly Worsening Mililiple Sclerosis (MS)," Neurology 62(Suppl 5):A492 (Abstract P06.090), Apr. 2004.

Crunkhorn, S., "Designing selective PI3K inhibitors." Nat. Rev. Drug Discovery 9:105, 2010.

Davies, J., "Hematological malignancies," American Society of Hematology—45th Annual Meeting and Exposition, Dec. 5-9, 2003, San Diego, CA, USA; iDrugs 7(1):1-3, 2004.

De Vita, S., et al., "Efficacy of Selective B Cell Blockade in the Treatment of Rheumatoid Arthritis. Evidence for a Pathogenic Role of B Cells," Arthritis Rheum. 46(8):2029-2033, 2002.

Decker, T., et al., "A pilot trial of the mTOR. (maalian target of rapamycin) inhibitor RAD001 in patients with advanced B-CLL," Ann. Hematol. 88:221-227, 2009.

Dong, H., et al., "B7-H1, a third member of the B7 family, co-stimulates T-cell proliferation and interleukin-10 secretion," Nat. Med. 5(12):1365-1369, 1999.

Edwards, et al., Arthritis Rheum. 46:S197 (Abstract 446), 2002.

Edwards, J.C.W., "Importance of T cells in Rheumatoid Synovitis: Comment on the Review by Firestein and Zvaifler," Arthritis Rheum. 46(11):31105-3106, 2002.

Edwards, J.C.W., and Cambridge, G., "Sustained improvement in rheumatoid arthritis following a protocol designed to deplete B lymphocytes," Rheumatology 40:205-211, 2001.

Elsässer, D., et al., "HLA Class II as Potential Target Antigen on Malignant B Cells for Therapy with Bispecific Antibodies in Combination with Granulocyte Colony-Stimulating Factor," Blood 87(9):3803-3812, 1996.

Endo, K., "Current status of nuclear medicine in Japan," Gan To Kagaku Ryoho 26(6):744-748, 1999. PubMed Abstract only, PMID: 10410141 (Article in Japanese).
Feldman M.E. et al., "Active-Site Inhibitors of mTOR Target Rapamycin-Resistant Outputs of mTORC1 and mTORC2," PLoS Biol. 7(2):0371-0383, 2009.
Felson, D.T, et al., "American College of Rheumatology Preliminary Definition of Improvement in Rheumatoid Arthritis," Arthritis Rheum. 38(6):727-735, 1995.
Fischer, K., et al., "Bendamustirte in Combination with Rituximab (BR) for Patients with Relapsed Chronic Lymphocytic Leukemia (CLL): A Multicentre Phase II Trial of the German CLL Study Group (GCLLSG)," Blood (ASH Annual Meeting Abstracts) 112:Abstract #330, 2008, 2 pages.
Fix, J.A., "Strategies for Delivery of Peptides Utilizing Absorption-Enhancing Agents," J. Pharmaceut. Sci, 85(12):1282-1285, 1996.
Fonseca, R., et al., "Myeloma and the t(11;14)(q13;q32); evidence for a biologically defined unique subset of patients," Blood 99(10):3735-3741, 2002.
Foster, F.M., et al., "The phosphoinositide (PI) 3-kinase family," J. Cell Sci. 116(15):3037-3040, 2003.
Francisco, J.A., et al., "Activity of a Single-Chain Immunotoxin That Selectively Kills Lymphoma and Other B-Lineage Cells Expressing the CD40 Antigen," Canc. Res. 55:3099-3104, 1995.
Gladman, D.D., et al., "Sensitivity to Change of 3 Systemic Lupus Erythematosus Disease Activity Indices: International Validation," J. Rheumatol. 21:1468-1471, 1994.
Grillo-Lopez, A.J., et al., "Response criteria for NHL: Importance of 'normal' lymph node size and correlations with response rates," Ann. Oncol. 11:399-408, 2000.
Grossbard, M.L., et al., "Monoclonal Antibody-Based Therapies of Leukemia and Lymphoma," Blood 80(4):863-878, 1992.
Haritunians, T., et al., "Antiproliferative activity of RAD001 (everolimus) as a single agent and combined with other agents in mantle cell lymphoma," Leukemia 21:333-339, 2007.
Harrison, "Phosphoinositide 3-kinase inhibitors," Nat. Rev. Drug Discovery 8:607, 2009.
Hayden-Ledbetter, M., et al., "Induction of Apoptosis in B Lymphoma Cell Lines by CytoxB37G, a Small Modular ImmunoPharmaceutical (SMIP) That Binds CD37," Blood 102(11):Abstract #1572, 2003, and Poster (18 pages).
Hemler, M.E., "Targeting of tetraspanin proteins—potential benefits and strategies," Nat. Rev. Drug Discovery 7:747-758, 2008.
Higashida, et al., "Treatment of DMARD-Refractory Rheumatoid Arthritis With Rituximab," Annual Scientific Meeting of the American College of Rheumatology (Abstract #LB11), New Orleans, LA (Oct. 2002).
Hinek, A., et al., "The Elastin Receptor: A Galactoside-Binding Protein," Science 239:1539-1541, 1988.
Humphreys et al., "F(ab')$_2$ molecules made from Escherichia coli produced Fab' with hinge sequences conferring increased serum survival in an animal model," J. Immunol. Methods 217:1-10 (1998).
Hwang, W.Y.K., et al., "Use of human germline genes in a CDR homology-based approach to antibody humanization," Methods 36:35-42, 2005.
Janeway, C.A., et al., Eds., Immunobiology: The Immune System in Health and Disease, 4th ed., Chap, 3, p. 92, Elsevier Science Ltd., London, and Garland Publishing, New York, 1999.
Jones, P.T., et al., "Replacing the complementarity-determining regions in a human antibody with those from a mouse," Nature 321:522-525, 1986.
Kiesel, S., et al., "Removal of Cells from a Malignant B-Cell Line from Bone Marrow with Immunomagnetic Beads and with Complement and Immunoglobulin Switch Variant Mediated Cytolysis," Leukemia Res. 11:1119-1125, 1987.
Kurtzke, J.F., "Rating neurologic impairment in multiple sclerosis: An expanded disability status scale (EDSS)," Neurology 33:1444-1452, 1983.
Lamminmäki, U., and Kankare, J. A., "Crystal Structure of a Recombinant Anti-estradiol Fab Fragment in Complex with 17β-Estradiol," J. Biol. Chem. 276(39):36687-36694, 2001.

Leandro, M.J., et al., "An Open Study of B Lymphocyte Depletion in Systemic Lupus Erythematosus," Arthritis Rheum. 46(10):2673-2677, 2002.
Leandro, M.J., et al., "B Lymphocyte Depletion in Rheumatoid Arthritis: Early Evidence for Safety, Efficacy, and Dose Response," Arthritis Rheum. 44(9):S370 (Abstract #1905), 2001.
Leandro, M.J., et al., "Clinical outcome in 22 patients with rheumatoid arthritis treated with B lymphocyte depletion," Ann. Rheum. Dis. 61:883-888, 2002.
Leget, G.A., and Czuczman, M.S., "Use of rituximab, the new FDA-approved antibody," Curr. Opin. Oncol. 10:548-551, 1998.
Levine, T.D., "Rituximab in the Treatment of Dermatomyositis," Arthritis Rheum. 52(2):601-607, 2005.
Li, J.-Y., et al., "Detection of Translocation t(11;14)(q13;q32) in Mantle Cell Lymphoma by Fluorescence in Situ Hybridization," Amer. J. Pathol. 154(5):1449-1452, 1999.
Lin, T.S., et al., "Rituximab in B-Cell Chronic Lymphocytic Leukemia," Sem. Oncol. 30(4):483-492, 2003.
Padlan, E.A., "A Possible Procedure for Reducing the Immunogenicity of Antibody Variable Domains While Preserving Their Ligand-Binding Properties," Mol. Immunol. 28(4/5):489-498, 1991.
Papadakis, K., et al., "Anti-CD20 Chimeric Monoclonal Antibody (Rituximab) Treatment of Immune-Mediated Thrombocytopenia Associated With Crohn's Disease," Gastroenterology 124(2):583, Feb. 2003.
Pelat, T., et al., "Germline Humanization of a Non-human Primate Antibody that Neutralizes the Anthrax Toxin, by in Vitro and in Silico Engineering," J. Mol. Biol. 384:1400-1407, 2008.
Petri, M.A., et al., "Effects of Prasterone on Disease Activity and Symptoms in Women With Active Systemic Lupus Erythematosus. Results of a Multicenter Randomized, Double-Blind, Placebo-Controlled Trial," Arthritis Rheum. 50(9):2858-2868, 2004.
Press, O.W., et al., "High-Dose Radioimmunotherapy of B Cell Lymphomas," in The Present and Future Role of Monoclonal Antibodies in Management of Cancer. Front. Radiat. Ther. Oncol., Vaeth, J.M., and Meyer, J.L., Eds., Karger, Basel, Switzerland, 24:204-213, 225-227 (discussion), 1990.
Press, O.W., et al., "Radiolabeled Antibody Therapy of Human B Cell Lymphomas," in Immunobiology of Proteins and Peptides VI, Atassi, M.Z., Ed., Plenum Press, New York, pp. 91-96, 1991.
Prous, J.R., Ed., "Annual Update 2004/2005—Treatment of Musculoskeletal Disorders," Drugs Fut. 30(2):181-232, 2005.
Rader, C., et al., "A phage display approach for rapid antibody humanization: Designed combinatorial V gene libraries," Proc. Nat. Acad. Sci. USA 95:8910-8915, 1998.
Rai, K.R., et al., "Fludarabine Compared with Chlorambucil as Primary Therapy for Chronic Lymphocytic Leukemia" New Engl. J. Med. 343(24):1750-1757, 2000.
RAPAMUNE (sirolimus) Oral Solution and Tablets, Highlights of Prescribing Information (1 page) and Full Prescribing Information (47 pages), retrieved from http://www.wyeth.com/content/showlabeling.asp?id=139, 2009, 48 pages.
Rastetter, W., et al., "Rituximab: Expanding Role in Therapy for Lymphomas and Autoimmune Diseases," Annu. Rev. Med. 55:477-503, 2004.
Rider, L.G., et al., "International Consensus on Preliminary Definitions of Improvement in Adult and Juvenile Myositis," Arthritis Rheum. 50(7):2281-2290, 2004.
Rothe, C., et al., "The human combinatorial antibody library HuCAL GOLD combines diversification of all six CDRs according to the natural immune system with a novel display method for efficient selection of high-affinity antibodies," J. Mol. Biol. 376:1182-1200, 2008. PubMed Abstract only, PMID: 18191144.
Rudick, R.A., et al., "Impact of interferon beta-1a on neurologic disability in relapsing multiple sclerosis," Neurology 49:358-363, 1997.
Rummel, M.J., "German Experience With Bendamustine Treating Relapsed/Refractory Indolent B-Cell and Mantle Cell Lymphomas," Semin. Hematol. 44:S22-S26, 2007.
Rummel, M.J., et al., "Bendamustine Plus Rituximab Versus CHOP Plus Rituximab in the First-Line Treatment of Patients with Indolent and Mantle Cell Lymphomas—First Interim Results of a Randomized Phase III Study of the StiL (Study Group Indolent Lymphomas, Germany)," Blood (ASH Annual Meeting Abstracts) 110:Abstract #385, 2007.

Shegogue, D., and Trojanowska, M., "Mammalian Target of Rapamycin Positively Regulates Collagen Type I Production via a Phosphatidylinositol 3-Kinase-independent Pathway," J. Biol. Chem. 279(22):23166-23175, 2004.

Simonis B., et al., "Evaluation and Validation of a Crohn's Disease Inflammatory Activity Index Reflecting Pattern of Endoscopic Severity,"Scand. J. Gastroenterol. 33(3):283-288, 1998.

Stasi, R. et al., "Rituximab chimeric anti-CD20 monoclonal antibody treatment for adults with chronic idiopathic thrombocytopenic purpura," Blood 98:952-957, 2001.

Tamburini, J., et al., "Mammalian target of rapamycin (mTOR) inhibition activates phosphatidylinositol 3-kinase/Akt by up-regulating insulin-like growth factor-1 receptor signaling in acute myeloid leukemia: rationale for therapeutic inhibition of both pathways," Blood 111:379-382, 2008.

Tan, E.M., et al., "The 1982 Revised Criteria for the Classification of System Lupus Erythematosus," Arthritis Rheum, 25(11):1271-1277, 1982.

Tan, P., et al., "'Superhumanized' Antibodies: Reduction of Immunogenic Potential by Complementarity-Determining Region Grafting with Human Germline Sequences: Application to an Anti-CD28," J. Immunol. 169:1119-1125, 2002.

Treon, S.P., et al., "CD20-Directed Antibody-Mediated Immunotherapy Induces Responses and Facilitates Hematologic Recovery in Patients With Waldenstrom's Macroglobulinemia," J. Immunother. 24(3):272-279, 2001.

Trubion, "Trubion Pharmaceuticals Announces Upcoming Presentations at the 2006 American Society of Hematology (ASH) Annual Meeting," PR Newswire, Dec. 4, 2006, 2 pages.

Trubion, "Data on Trubion's Drug Candidate TRU-016 Presented at ASCO 2006," Trubion Pharmaceuticals Press Release dated Jun. 4, 2006, 1 page.

Trubion, "Trubion Announces Positive Data for Two Product Candidates at Upcoming American Society of Hematology Meeting; Abstracts to be Published in Nov. 16, 2003 Issue of Blood," PR Newswire, Nov. 20, 2003, 2 pages.

Trubion, "Trubion Announces Presentation of Positive TRU-016 Data at ASCO," PR Newswire, Jun. 2, 2008, 2 pages.

Trubion, "Trubion Announces Upcoming Presentation at the 2007 American Society of Hematology (ASH) Annual Meeting," PR Newswire, Dec. 6, 2007, 2 pages.

Trubion, "Trubion Initiates Phase 1/2 Study of TRU-016 in CLL, Announces Next-Generation Product Candidate for RA and Provides Product Pipeline Update," PR Newswire, Mar. 27, 2008, 3 pages.

Trubion, "Trubion Pharmaceuticals, Inc. Announces Upcoming Presentation at the 2007 ASCO Annual Meeting," PR Newswire, May 31, 2007, 2 pages.

Tuscano, J.M., "Successful Treatment of Infliximab-Refractory Rheumatoid Arthritis with Rituximab," Annual Scientific Meeting of the American College of Rheumatology, New Orleans, LA (Oct. 24-29, 2002), Abstract #LB11, 1 page.

van Spriel, A.B., et al., "A Regulatory Role for CD37 in T Cell Proliferation," J. Immunol. 172:2953-2961, 2004.

White, C.A., et al., "Anti-CD20 monoclonal antibodies as novel treatments for non-Hodgkin's lymphoma," Pharm. Sci. Technol. Today 2(3):95-101, 1999.

Wilson I.A , and Stanfield, R.L., "A Trojan horse with a sweet tooth," Nat. Struct. Biol. 2:433-436, 1995. Abstract only.

Zhao, X.B., et al., "Novel Anti-CD37 Small Modular Immunopharmaceutical (SMIP) Induces B-Cell-Specific, Caspase-Independent Apoptosis in Human CLL: Cells," Blood (ASH Annual Meeting Abstracts) 104:Abstract #2515, 2004, 1 page.

McFarland et al., "Symmetry Recognizing Asymmetry: Analysis of the Interactions between the C-Type Lectin-like Immunoreceptor NKG2D and MHC Class I-like Ligands," Structure, vol. 11:411-422, 2003.

Yokoyama et al., "Immune Functions Encoded by the Natural Killer Gene Complex," Nature Reviews Immunology, vol. 3: 304-316, 2003.

* cited by examiner

FIG. 3
BINDING OF PROTEIN EXPRESSED IN COS SUPERNATANTS TO CELLS EXPRESSING TARGET ANTIGENS
A. BINDING OF COS SUPERNATANTS TO WIL-2S CELLS
2e12 SMIPs vs. 2H7-IgG-2e12 SCORPIONS
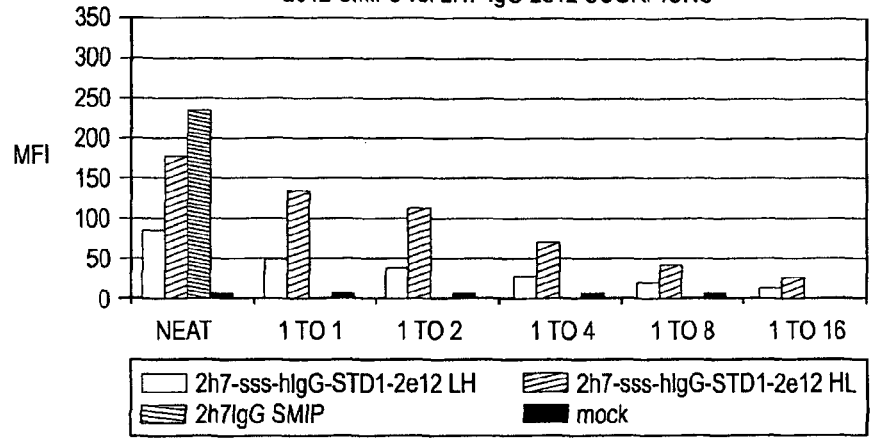
B. BINDING OF COS SUPERNATANTS TO CD28 OHO CELLS
2e12 SMIPs vs. 2H7-2e12 SCORPIONS
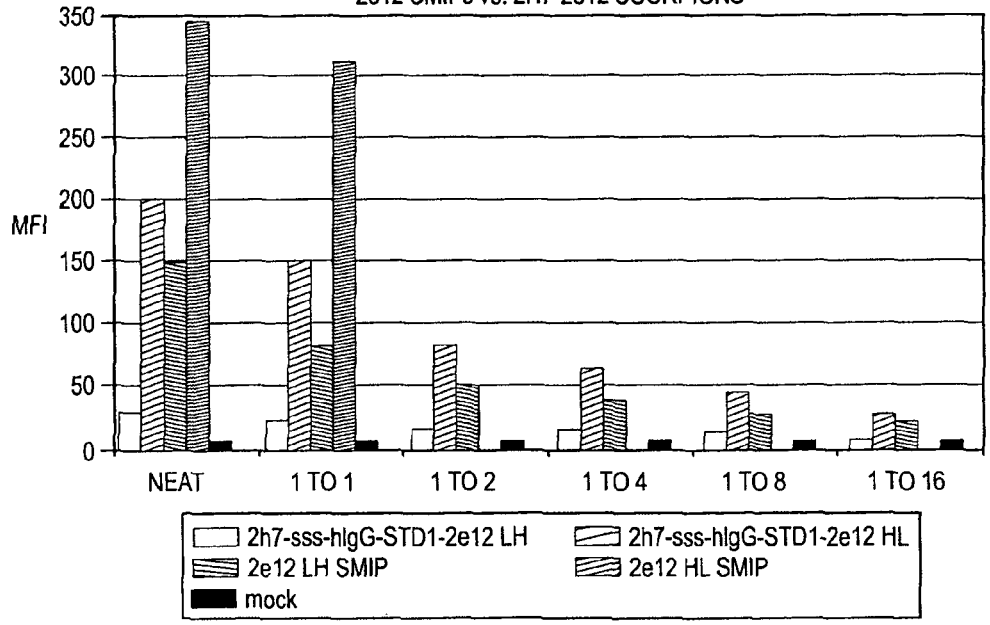

FIG. 6A

TABLE IDENTIFYING FUNCTIONAL ELEMENTS OF MULTISPECIFIC FUSION PROTEINS

[ BD1 ]—[ EFD ]—[ BD2 ]

| BD1 Binding Domain 1 | Linker 1 | EFD Effector Function Domain | Linker 2 ID | Linker Length (aa) Linker Plus R. Site | CH3 COOH | Linker 2 Sequence (- restriction site) | Fusion Junction with BD2 (L2 RS-- QVQ 2e12) | BD2 Binding Domain 2 |
|---|---|---|---|---|---|---|---|---|
| 2H7 $V_L$-$V_H$ | Modified hIgGI hinge ccc->sss | hIgGI-CH2-CH3 | STD | 20 | PGK | NYGGGGSGGGGSGGGGSG | NS QVQ | 2e12 $V_H$-$V_L$ |
| 2H7 $V_L$-$V_H$ | Modified hIgGI hinge ccc->sss | hIgGI-CH2-CH3 | STD2 | 38 | PGK | NYGGGGSGGGGSGGGGSG NYGGGGSGGGGSGGGGSG | NS QVQ | 2e12 $V_H$-$V_L$ |
| 2H7 $V_L$-$V_H$ | Modified hIgGI hinge ccc->sss | hIgGI-CH2-CH3 | H1 L1=2e12 $V_L$-$V_H$ | 2 (RS) | PGK | -- | NS QVQ | 2e12 $V_H$-$V_L$ |
| 2H7 $V_L$-$V_H$ | Modified hIgGI hinge ccc->sss | hIgGI-CH2-CH3 | H2 L2=2e12 $V_L$-$V_H$ | 8 | PGK | GGGGSG | NS QVQ | 2e12 $V_H$-$V_L$ |
| 2H7 $V_L$-$V_H$ | Modified hIgGI hinge ccc->sss | hIgGI-CH2-CH3 | H3 L3=2e12 $V_L$-$V_H$ | 10 | PGK | NYGGGGSG | NS QVQ | 2e12 $V_H$-$V_L$ |
| 2H7 $V_L$-$V_H$ | Modified hIgGI hinge ccc->sss | hIgGI-CH2-CH3 | H4 L4=2e12 $V_L$-$V_H$ | 13 | PGK | GGGGSGGGGSG | NS QVQ | 2e12 $V_H$-$V_L$ |
| 2H7 $V_L$-$V_H$ | Modified hIgGI hinge ccc->sss | hIgGI-CH2-CH3 | H5 L5=2e12 $V_L$-$V_H$ | 15 | PGK | NYGGGGSGGGGSG | NS QVQ | 2e12 $V_H$-$V_L$ |
| 2H7 $V_L$-$V_H$ | Modified hIgGI hinge ccc->sss | hIgGI-CH2-CH3 | H6 L6=2e12 $V_L$-$V_H$ | 18 | PGK | GGGGSGGGGSGGGGSG | NS QVQ | 2e12 $V_H$-$V_L$ |
| 2H7 $V_L$-$V_H$ | Modified hIgGI hinge ccc->sss | hIgGI-CH2-CH3 | H7 | 8 | PGK | GCPPCP | NS QVQ | 2e12 $V_H$-$V_L$ |

FIG. 6B (1 of 5)
Constructs

| Name | BD1 | Hinge | EFD | Linker | BD2 |
|---|---|---|---|---|---|
| 2H7-sss-hIgG-STD1-2e12 LH | 2H7 (VL-VH) | hIgG1-SSS | hIgG or hIgG (P238S/P331S) | STD1 | 2e12 (VL-VH) |
| 2H7-sss-hIgG-STD1-2e12 HL | 2H7 (VL-VH) | hIgG1-SSS | hIgG or hIgG (P238S/P331S) | STD1 | 2e12 (VH-VL) |
| 2H7-sss-hIgG-STD2-2e12 LH | 2H7 (VL-VH) | hIgG1-SSS | hIgG or hIgG (P238S/P331S) | STD2 | 2e12 (VL-VH) |
| 2H7-sss-hIgG-STD2-2e12 HL | 2H7 (VL-VH) | hIgG1-SSS | hIgG or hIgG (P238S/P331S) | STD2 | 2e12 (VH-VL) |
| 2H7-csc-hIgG-STD1-2e12 LH | 2H7 (VL-VH) | hIgG1-csc | hIgG or hIgG (P238S/P331S) | STD1 | 2e12 (VL-VH) |
| 2H7-csc-hIgG-STD2-2e12 LH | 2H7 (VL-VH) | hIgG1-csc | hIgG or hIgG (P238S/P331S) | STD2 | 2e12 (VL-VH) |
| 2H7-csc-hIgG-STD1-2e12 HL | 2H7 (VL-VH) | hIgG1-csc | hIgG or hIgG (P238S/P331S) | STD1 | 2e12 (VL-VH) |
| 2H7-csc-hIgG-STD2-2e12 HL | 2H7 (VL-VH) | hIgG1-csc | hIgG or hIgG (P238S/P331S) | STD2 | 2e12 (VH-VL) |
| 2H7-sss-hIgG-H1-2e12 LH | 2H7 (VL-VH) | hIgG1-SSS | hIgG or hIgG (P238S/P331S) | H1 | 2e12 (VL-VH) |
| 2H7-csc-hIgG-H1-2e12 LH | 2H7 (VL-VH) | hIgG1-csc | hIgG or hIgG (P238S/P331S) | H1 | 2e12 (VL-VH) |
| 2H7-sss-hIgG-H1-2e12 HL | 2H7 (VL-VH) | hIgG1-SSS | hIgG or hIgG (P238S/P331S) | H1 | 2e12 (VH-VL) |
| 2H7-csc-hIgG-H1-2e12 HL | 2H7 (VL-VH) | hIgG1-csc | hIgG or hIgG (P238S/P331S) | H1 | 2e12 (VH-VL) |
| 2H7-sss-hIgG-H2-2e12 LH | 2H7 (VL-VH) | hIgG1-SSS | hIgG or hIgG (P238S/P331S) | H2 | 2e12 (VH-VL) |
| 2H7-csc-hIgG-H2-2e12 LH | 2H7 (VL-VH) | hIgG1-csc | hIgG or hIgG (P238S/P331S) | H2 | 2e12 (VL-VH) |
| 2H7-sss-hIgG-H2-2e12 HL | 2H7 (VL-VH) | hIgG1-SSS | hIgG or hIgG (P238S/P331S) | H2 | 2e12 (VH-VL) |
| 2H7-csc-hIgG-H2-2e12 LH | 2H7 (VL-VH) | hIgG1-csc | hIgG or hIgG (P238S/P331S) | H2 | 2e12 (VH-VL) |
| 2H7-sss-hIgG-H3-2e12 LH | 2H7 (VL-VH) | hIgG1-SSS | hIgG or hIgG (P238S/P331S) | H3 | 2e12 (VL-VH) |
| 2H7-csc-hIgG-H3-2e12 LH | 2H7 (VL-VH) | hIgG1-csc | hIgG or hIgG (P238S/P331S) | H3 | 2e12 (VL-VH) |
| 2H7-sss-hIgG-H3-2e12 HL | 2H7 (VL-VH) | hIgG1-SSS | hIgG or hIgG (P238S/P331S) | H3 | 2e12 (VH-VL) |
| 2H7-csc-hIgG-H3-2e12 LH | 2H7 (VL-VH) | hIgG1-csc | hIgG or hIgG (P238S/P331S) | H3 | 2e12 (VH-VL) |
| 2H7-sss-hIgG-H4-2e12 LH | 2H7 (VL-VH) | hIgG1-SSS | hIgG or hIgG (P238S/P331S) | H4 | 2e12 (VL-VH) |
| 2H7-csc-hIgG-H4-2e12 LH | 2H7 (VL-VH) | hIgG1-csc | hIgG or hIgG (P238S/P331S) | H4 | 2e12 (VL-VH) |
| 2H7-sss-hIgG-H4-2e12 HL | 2H7 (VL-VH) | hIgG1-SSS | hIgG or hIgG (P238S/P331S) | H4 | 2e12 (VH-VL) |
| 2H7-csc-hIgG-H4-2e12 LH | 2H7 (VL-VH) | hIgG1-csc | hIgG or hIgG (P238S/P331S) | H4 | 2e12 (VH-VL) |

FIG. 6B (2 of 5)

| Name | BD1 | Hinge | EFD | Linker | BD2 |
|---|---|---|---|---|---|
| 2H7-sss-hIgG-H5-2e12 LH | 2H7 (VL-VH) | hIgG1-SSS | hIgG or hIgG (P238S/P331S) | H5 | 2e12 (VL-VH) |
| 2H7-csc-hIgG-H5-2e12 LH | 2H7 (VL-VH) | hIgG1-csc | hIgG or hIgG (P238S/P331S) | H5 | 2e12 (VL-VH) |
| 2H7-sss-hIgG-H5-2e12 HL | 2H7 (VL-VH) | hIgG1-SSS | hIgG or hIgG (P238S/P331S) | H5 | 2e12 (VH-VL) |
| 2H7-csc-hIgG-H5-2e12 LH | 2H7 (VL-VH) | hIgG1-csc | hIgG or hIgG (P238S/P331S) | H5 | 2e12 (VH-VL) |
| 2H7-sss-hIgG-H6-2e12 LH | 2H7 (VL-VH) | hIgG1-SSS | hIgG or hIgG (P238S/P331S) | H6 | 2e12 (VL-VH) |
| 2H7-csc-hIgG-H6-2e12 LH | 2H7 (VL-VH) | hIgG1-csc | hIgG or hIgG (P238S/P331S) | H6 | 2e12 (VL-VH) |
| 2H7-sss-hIgG-H6-2e12 HL | 2H7 (VL-VH) | hIgG1-SSS | hIgG or hIgG (P238S/P331S) | H6 | 2e12 (VH-VL) |
| 2H7-csc-hIgG-H6-2e12 LH | 2H7 (VL-VH) | hIgG1-csc | hIgG or hIgG (P238S/P331S) | H6 | 2e12 (VH-VL) |
| 2H7-sss-hIgG-H7-2e12 LH | 2H7 (VL-VH) | hIgG1-SSS | hIgG or hIgG (P238S/P331S) | H7 | 2e12 (VL-VH) |
| 2H7-csc-hIgG-H7-2e12 LH | 2H7 (VL-VH) | hIgG1-csc | hIgG or hIgG (P238S/P331S) | H7 | 2e12 (VL-VH) |
| 2H7-sss-hIgG-H7-2e12 HL | 2H7 (VL-VH) | hIgG1-SSS | hIgG or hIgG (P238S/P331S) | H7 | 2e12 (VH-VL) |
| 2H7-csc-hIgG-H7-2e12 LH | 2H7 (VL-VH) | hIgG1-csc | hIgG or hIgG (P238S/P331S) | H7 | 2e12 (VH-VL) |
| 2H7-sss-hIgG-STD1-G28-1 LH | 2H7 (VL-VH) | hIgG1-SSS | hIgG or hIgG (P238S/P331S) | STD1 | G28-1 (VL-VH) |
| 2H7-sss-hIgG-STD1-G28-1 HL | 2H7 (VL-VH) | hIgG1-SSS | hIgG or hIgG (P238S/P331S) | STD1 | G28-1 (VL-VH) |
| 2H7-sss-hIgG-STD2-G28-1 LH | 2H7 (VL-VH) | hIgG1-SSS | hIgG or hIgG (P238S/P331S) | STD2 | G28-1 (VL-VH) |
| 2H7-sss-hIgG-STD2-G28-1 HL | 2H7 (VL-VH) | hIgG1-SSS | hIgG or hIgG (P238S/P331S) | STD2 | G28-1 (VH-VL) |
| 2H7-csc-hIgG-STD1-G28-1 LH | 2H7 (VL-VH) | hIgG1-csc | hIgG or hIgG (P238S/P331S) | STD1 | G28-1 (VL-VH) |
| 2H7-csc-hIgG-STD2-G28-1 LH | 2H7 (VL-VH) | hIgG1-csc | hIgG or hIgG (P238S/P331S) | STD2 | G28-1 (VH-VL) |
| 2H7-csc-hIgG-STD1-G28-1 HL | 2H7 (VL-VH) | hIgG1-csc | hIgG or hIgG (P238S/P331S) | STD1 | G28-1 (VL-VH) |
| 2H7-csc-hIgG-STD2-G28-1 HL | 2H7 (VL-VH) | hIgG1-csc | hIgG or hIgG (P238S/P331S) | STD2 | G28-1 (VH-VL) |
| 2H7-sss-hIgG-H1-G28-1 LH | 2H7 (VL-VH) | hIgG1-SSS | hIgG or hIgG (P238S/P331S) | H1 | G28-1 (VL-VH) |
| 2H7-csc-hIgG-H1-G28-1 LH | 2H7 (VL-VH) | hIgG1-csc | hIgG or hIgG (P238S/P331S) | H1 | G28-1 (VH-VL) |
| 2H7-sss-hIgG-H1-G28-1 HL | 2H7 (VL-VH) | hIgG1-SSS | hIgG or hIgG (P238S/P331S) | H1 | G28-1 (VL-VH) |
| 2H7-csc-hIgG-H1-G28-1 HL | 2H7 (VL-VH) | hIgG1-csc | hIgG or hIgG (P238S/P331S) | H1 | G28-1 (VH-VL) |
| 2H7-sss-hIgG-H2-G28-1 LH | 2H7 (VL-VH) | hIgG1-SSS | hIgG or hIgG (P238S/P331S) | H2 | G28-1 (VL-VH) |

FIG. 6B (3 of 5)

| Name | BD1 | Hinge | EFD | Linker | BD2 |
|---|---|---|---|---|---|
| 2H7-csc-hIgG-H2-G28-1 LH | 2H7 (VL-VH) | hIgG1-csc | hIgG or hIgG (P238S/P331S) | H2 | G28-1 (VL-VH) |
| 2H7-sss-hIgG-H2-G28-1 HL | 2H7 (VL-VH) | hIgG1-SSS | hIgG or hIgG (P238S/P331S) | H2 | G28-1 (VL-VH) |
| 2H7-csc-hIgG-H2-G28-1 LH | 2H7 (VL-VH) | hIgG1-csc | hIgG or hIgG (P238S/P331S) | H2 | G28-1 (VH-VL) |
| 2H7-sss-hIgG-H3-G28-1 LH | 2H7 (VL-VH) | hIgG1-SSS | hIgG or hIgG (P238S/P331S) | H3 | G28-1 (VL-VH) |
| 2H7-csc-hIgG-H3-G28-1 LH | 2H7 (VL-VH) | hIgG1-csc | hIgG or hIgG (P238S/P331S) | H3 | G28-1 (VH-VL) |
| 2H7-sss-hIgG-H3-G28-1 HL | 2H7 (VL-VH) | hIgG1-SSS | hIgG or hIgG (P238S/P331S) | H3 | G28-1 (VL-VH) |
| 2H7-csc-hIgG-H3-G28-1 LH | 2H7 (VL-VH) | hIgG1-csc | hIgG or hIgG (P238S/P331S) | H3 | G28-1 (VH-VL) |
| 2H7-sss-hIgG-H4-G28-1 LH | 2H7 (VL-VH) | hIgG1-SSS | hIgG or hIgG (P238S/P331S) | H4 | G28-1 (VL-VH) |
| 2H7-csc-hIgG-H4-G28-1 LH | 2H7 (VL-VH) | hIgG1-csc | hIgG or hIgG (P238S/P331S) | H4 | G28-1 (VH-VL) |
| 2H7-sss-hIgG-H4-G28-1 HL | 2H7 (VL-VH) | hIgG1-SSS | hIgG or hIgG (P238S/P331S) | H4 | G28-1 (VL-VH) |
| 2H7-csc-hIgG-H4-G28-1 LH | 2H7 (VL-VH) | hIgG1-csc | hIgG or hIgG (P238S/P331S) | H4 | G28-1 (VH-VL) |
| 2H7-sss-hIgG-H5-G28-1 LH | 2H7 (VL-VH) | hIgG1-SSS | hIgG or hIgG (P238S/P331S) | H5 | G28-1 (VH-VL) |
| 2H7-sss-hIgG-H5-G28-1 LH | 2H7 (VL-VH) | hIgG1-csc | hIgG or hIgG (P238S/P331S) | H5 | G28-1 (VH-VL) |
| 2H7-sss-hIgG-H5-G28-1 LH | 2H7 (VL-VH) | hIgG1-SSS | hIgG or hIgG (P238S/P331S) | H5 | G28-1 (VH-VL) |
| 2H7-csc-hIgG-H5-G28-1 LH | 2H7 (VL-VH) | hIgG1-csc | hIgG or hIgG (P238S/P331S) | H5 | G28-1 (VH-VL) |
| 2H7-sss-hIgG-H6-G28-1 LH | 2H7 (VL-VH) | hIgG1-SSS | hIgG or hIgG (P238S/P331S) | H6 | G28-1 (VL-VH) |
| 2H7-csc-hIgG-H6-G28-1 LH | 2H7 (VL-VH) | hIgG1-csc | hIgG or hIgG (P238S/P331S) | H6 | G28-1 (VL-VH) |
| 2H7-sss-hIgG-H6-G28-1 HL | 2H7 (VL-VH) | hIgG1-SSS | hIgG or hIgG (P238S/P331S) | H6 | G28-1 (VH-VL) |
| 2H7-csc-hIgG-H6-G28-1 LH | 2H7 (VL-VH) | hIgG1-csc | hIgG or hIgG (P238S/P331S) | H6 | G28-1 (VH-VL) |
| 2H7-sss-hIgG-H7-G28-1 LH | 2H7 (VL-VH) | hIgG1-SSS | hIgG or hIgG (P238S/P331S) | H7 | G28-1 (VL-VH) |
| 2H7-csc-hIgG-H7-G28-1 LH | 2H7 (VL-VH) | hIgG1-csc | hIgG or hIgG (P238S/P331S) | H7 | G28-1 (VL-VH) |
| 2H7-sss-hIgG-H7-G28-1 HL | 2H7 (VL-VH) | hIgG1-SSS | hIgG or hIgG (P238S/P331S) | H7 | G28-1 (VH-VL) |
| 2H7-csc-hIgG-H7-G28-1 LH | 2H7 (VL-VH) | hIgG1-csc | hIgG or hIgG (P238S/P331S) | H7 | G28-1 (VH-VL) |
| 2H7-sss-hIgG-STD1-G19-4 LH | 2H7 (VL-VH) | hIgG1-SSS | hIgG or hIgG (P238S/P331S) | STD1 | G19-4 (VL-VH) |
| 2H7-sss-hIgG-STD1-G19-4 HL | 2H7 (VL-VH) | hIgG1-SSS | hIgG or hIgG (P238S/P331S) | STD1 | G19-4 (VH-VL) |

*FIG. 6B (4 of 5)*

| Name | BD1 | Hinge | EFD | Linker | BD2 |
|---|---|---|---|---|---|
| 2H7-sss-hIgG-STD2-G19-4 LH | 2H7 (VL-VH) | hIgG1-SSS | hIgG or hIgG (P238S/P331S) | STD2 | G19-4 (VL-VH) |
| 2H7-sss-hIgG-STD2-G19-4 HL | 2H7 (VL-VH) | hIgG1-SSS | hIgG or hIgG (P238S/P331S) | STD2 | G19-4 (VH-VL) |
| 2H7-csc-hIgG-STD1-G19-4 LH | 2H7 (VL-VH) | hIgG1-csc | hIgG or hIgG (P238S/P331S) | STD1 | G19-4 (VL-VH) |
| 2H7-csc-hIgG-STD2-G19-4 LH | 2H7 (VL-VH) | hIgG1-csc | hIgG or hIgG (P238S/P331S) | STD2 | G19-4 (VH-VL) |
| 2H7-csc-hIgG-STD1-G19-4 HL | 2H7 (VL-VH) | hIgG1-csc | hIgG or hIgG (P238S/P331S) | STD1 | G19-4 (VL-VH) |
| 2H7-csc-hIgG-STD2-G19-4 HL | 2H7 (VL-VH) | hIgG1-csc | hIgG or hIgG (P238S/P331S) | STD2 | G19-4 (VH-VL) |
| 2H7-sss-hIgG-H1-G19-4 LH | 2H7 (VL-VH) | hIgG1-SSS | hIgG or hIgG (P238S/P331S) | H1 | G19-4 (VL-VH) |
| 2H7-csc-hIgG-H1-G19-4 LH | 2H7 (VL-VH) | hIgG1-csc | hIgG or hIgG (P238S/P331S) | H1 | G19-4 (VH-VL) |
| 2H7-sss-hIgG-H1-G19-4 HL | 2H7 (VL-VH) | hIgG1-SSS | hIgG or hIgG (P238S/P331S) | H1 | G19-4 (VL-VH) |
| 2H7-csc-hIgG-H1-G19-4 HL | 2H7 (VL-VH) | hIgG1-csc | hIgG or hIgG (P238S/P331S) | H1 | G19-4 (VH-VL) |
| 2H7-sss-hIgG-H2-G19-4 LH | 2H7 (VL-VH) | hIgG1-SSS | hIgG or hIgG (P238S/P331S) | H2 | G19-4 (VL-VH) |
| 2H7-csc-hIgG-H2-G19-4 LH | 2H7 (VL-VH) | hIgG1-csc | hIgG or hIgG (P238S/P331S) | H2 | G19-4 (VL-VH) |
| 2H7-sss-hIgG-H2-G19-4 HL | 2H7 (VL-VH) | hIgG1-SSS | hIgG or hIgG (P238S/P331S) | H2 | G19-4 (VL-VH) |
| 2H7-csc-hIgG-H2-G19-4 LH | 2H7 (VL-VH) | hIgG1-csc | hIgG or hIgG (P238S/P331S) | H2 | G19-4 (VL-VH) |
| 2H7-sss-hIgG-H3-G19-4 LH | 2H7 (VL-VH) | hIgG1-SSS | hIgG or hIgG (P238S/P331S) | H3 | G19-4 (VL-VH) |
| 2H7-csc-hIgG-H3-G19-4 LH | 2H7 (VL-VH) | hIgG1-csc | hIgG or hIgG (P238S/P331S) | H3 | G19-4 (VH-VL) |
| 2H7-sss-hIgG-H3-G19-4 HL | 2H7 (VL-VH) | hIgG1-SSS | hIgG or hIgG (P238S/P331S) | H3 | G19-4 (VL-VH) |
| 2H7-csc-hIgG-H3-G19-4 LH | 2H7 (VL-VH) | hIgG1-csc | hIgG or hIgG (P238S/P331S) | H3 | G19-4 (VH-VL) |
| 2H7-sss-hIgG-H4-G19-4 LH | 2H7 (VL-VH) | hIgG1-SSS | hIgG or hIgG (P238S/P331S) | H4 | G19-4 (VL-VH) |
| 2H7-csc-hIgG-H4-G19-4 LH | 2H7 (VL-VH) | hIgG1-csc | hIgG or hIgG (P238S/P331S) | H4 | G19-4 (VH-VL) |
| 2H7-sss-hIgG-H4-G19-4 HL | 2H7 (VL-VH) | hIgG1-SSS | hIgG or hIgG (P238S/P331S) | H4 | G19-4 (VL-VH) |
| 2H7-csc-hIgG-H4-G19-4 LH | 2H7 (VL-VH) | hIgG1-csc | hIgG or hIgG (P238S/P331S) | H4 | G19-4 (VH-VL) |
| 2H7-sss-hIgG-H5-G19-4 LH | 2H7 (VL-VH) | hIgG1-SSS | hIgG or hIgG (P238S/P331S) | H5 | G19-4 (VL-VH) |
| 2H7-csc-hIgG-H5-G19-4 LH | 2H7 (VL-VH) | hIgG1-csc | hIgG or hIgG (P238S/P331S) | H5 | G19-4 (VH-VL) |
| 2H7-sss-hIgG-H5-G19-4 HL | 2H7 (VL-VH) | hIgG1-SSS | hIgG or hIgG (P238S/P331S) | H5 | G19-4 (VL-VH) |

FIG. 6B (5 of 5)

| Name | BD1 | Hinge | EFD | Linker | BD2 |
|---|---|---|---|---|---|
| 2H7-csc-hIgG-H5-G19-4 LH | 2H7 (VL-VH) | hIgG1-csc | hIgG or hIgG (P238S/P331S) | H5 | G19-4 (VL-VH) |
| 2H7-sss-hIgG-H6-G19-4 LH | 2H7 (VL-VH) | hIgG1-SSS | hIgG or hIgG (P238S/P331S) | H6 | G19-4 (VL-VH) |
| 2H7-csc-hIgG-H6-G19-4 LH | 2H7 (VL-VH) | hIgG1-csc | hIgG or hIgG (P238S/P331S) | H6 | G19-4 (VL-VH) |
| 2H7-sss-hIgG-H6-G19-4 HL | 2H7 (VL-VH) | hIgG1-SSS | hIgG or hIgG (P238S/P331S) | H6 | G19-4 (VH-VL) |
| 2H7-csc-hIgG-H6-G19-4 LH | 2H7 (VL-VH) | hIgG1-csc | hIgG or hIgG (P238S/P331S) | H6 | G19-4 (VH-VL) |
| 2H7-sss-hIgG-H7-G19-4 LH | 2H7 (VL-VH) | hIgG1-SSS | hIgG or hIgG (P238S/P331S) | H7 | G19-4 (VL-VH) |
| 2H7-csc-hIgG-H7-G19-4 LH | 2H7 (VL-VH) | hIgG1-csc | hIgG or hIgG (P238S/P331S) | H7 | G19-4 (VL-VH) |
| 2H7-sss-hIgG-H7-G19-4 HL | 2H7 (VL-VH) | hIgG1-SSS | hIgG or hIgG (P238S/P331S) | H7 | G19-4 (VH-VL) |
| 2H7-csc-hIgG-H7-G19-4 LH | 2H7 (VL-VH) | hIgG1-csc | hIgG or hIgG (P238S/P331S) | H7 | G19-4 (VH-VL) |

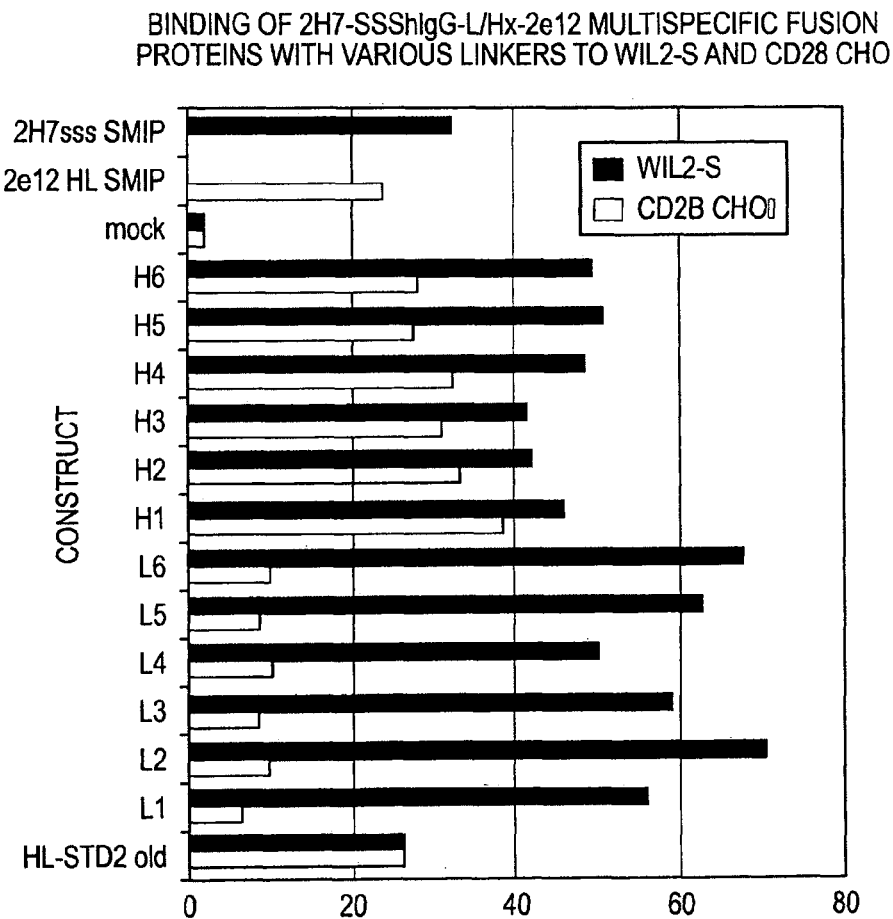

FIG. 9
Western Blots of Multispecific Fusion Proteins With H6 Linker
A. Absence of SMIP or smaller CD28 detectable forms
B. Presence of a SMIP sized form using CD20 anti-id Fab
A. Detection of 2e12 BD2 by CD28-murineIgG
B. Detection of 2H7 CD20 BD1 by Fab: AbyD02429.2
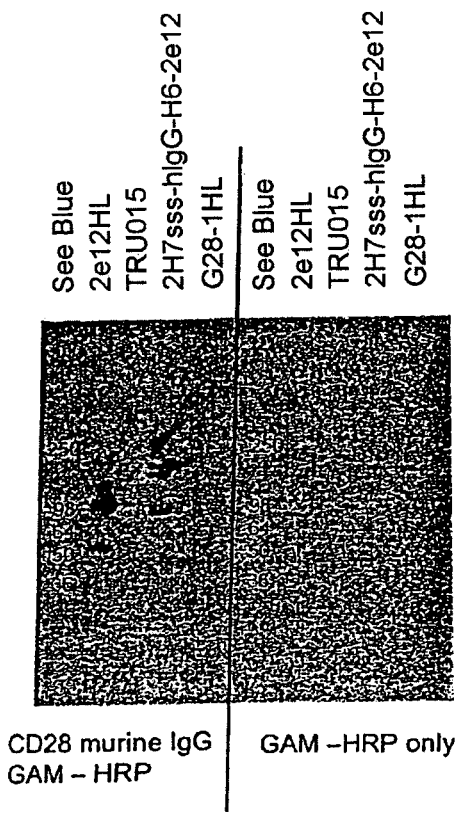
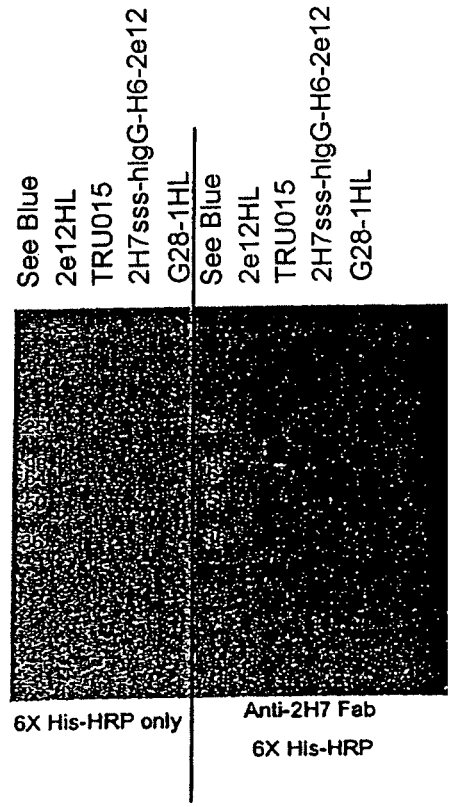

FIG. 10
A. Binding of Multispecific Fusion Proteins With Variant Linkers to WIL-2S Cells
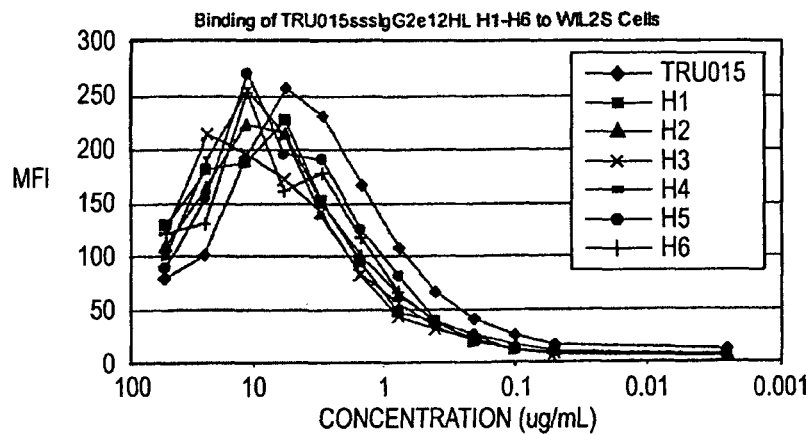
B. Binding of Multispecific Fusion Protein With Variant Linkers to CD28 CHO Cells
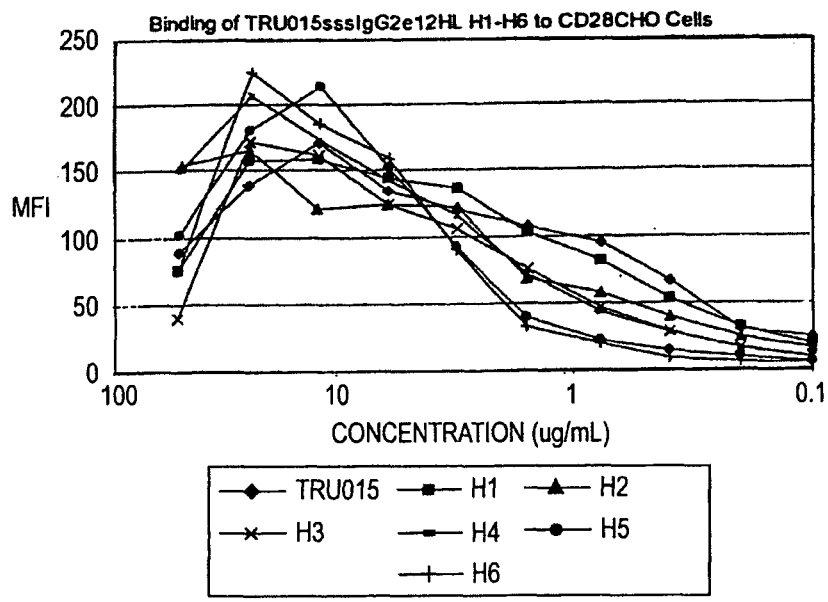

FIG. 11

Summary of SEC Fractionation of 2H7-sssIgG-2e12 HL
Multispecific Fusion Proteins with Variant Linkers

| Linker ID | Retention Time for POI | % POI | % Other Forms | SDS-PAGE Analysis of Cleavage at EFD/BD2 junction |
|---|---|---|---|---|
| H1 | 7.620 | 70.9 | 29.0 | (Yes) |
| H2 | 7.589 | 67.5 | 32.5 | (Yes) |
| H3 | 7.605 | 68.7 | 31.4 | Yes |
| H4 | 7.622 (shoulder) | 68.0 | 32.0 | Yes |
| H5 | 7.933/7.680 (doublet with shoulder) | 32.42/33.94 | 33.63 | YES |
| H6 | 7.901/7.69 (doublet with shoulder) | 34.5/29.3 | 36.1 | YES |
| H7 | 7.788 | 84.2 | 15.8 (HMW) | NO |

FIG. 12
Binding of [2H7-sss-hIgG-H$_x$-2e12 HL] Fusion Proteins with Different Linkers to Cells Expressing Target Antigen for BD1 or BD2
A. WIL-2S Expressing CD20
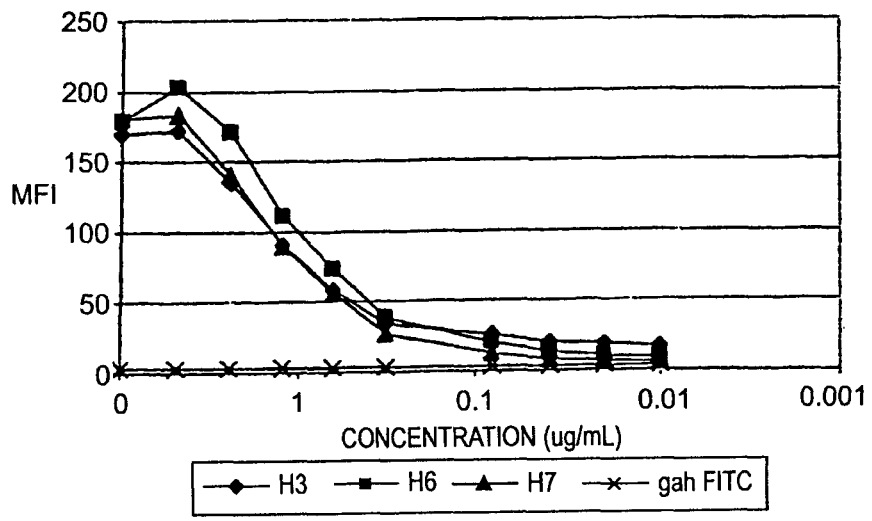
B. CD28 CHO Cells
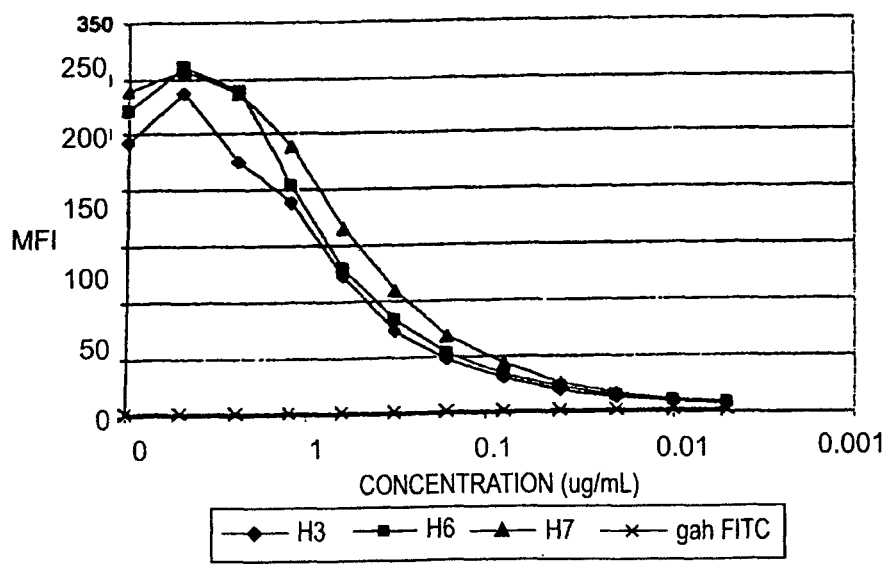

Simultaneous Binding of BD1 and BD2:

Binding of [2H7-sss-hIgG-$H_x$-2e12 HL] Fusion Proteins with H3, H6, and H7 Linkers to WIL-2S Cells can be detected with CD28mIgG + FITC anti-mouse

FIG. 14
A. Blocking of Binding of 2H7-sss-hIgG-H7-G28-1 HL Protein to Ramos Cells by CD20 and/or CD37 Targeted Antibodies
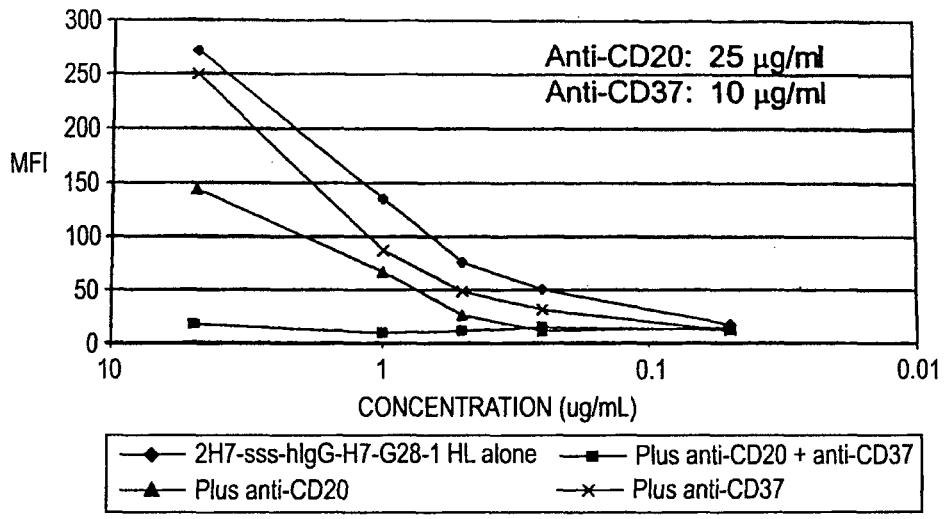
B. Blocking of Binding of 2H7-sss-hIgG-H7-G28-1 HL to BJAB Cells by CD20 and/or CD37 Targeted Antibodies
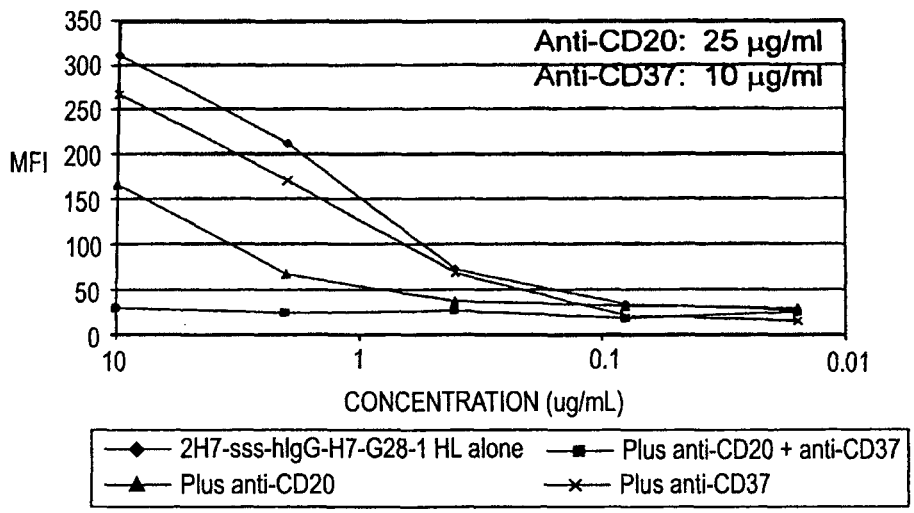

FIG. 16

The Percent CD3, CD19, and CD40 Positive Lymphocytes
Present in Culture after Incubation with TRU-015, G28-1 SMIP,
TRU-015+G28-1 SMIP, or 2H7-sss-hIgG1-H7-G28-1 HL

| 24 Hours | CD3⁺ | CD19⁺ | CD40⁺ |
|---|---|---|---|
| Media | 77% | 8% | 7% |
| TRU015 | 76% | 8.5% | 7.9% |
| G28-1 SMIP | 78% | 8.9% | 7.8% |
| TRU015+G28-1 SMIP | 76.3% | 8.1% | 7.5% |
| 2H7-ssshIgG1-G28-1HL (H7) | 78.4% | 8.9% | 7.9% |

| 72 Hours | CD3⁺ | CD19⁺ | CD40⁺ |
|---|---|---|---|
| Media | 78.5% | 7.9% | 7.7% |
| TRU015 | 85.2% | 2.3% | 2.7% |
| G28-1 SMIP | 86.7% | 2.2% | 2.3% |
| TRU015+G28-1 SMIP | 87.1% | 1.1% | 1.1% |
| 2H7-ssshIgG1-G28-1 HL (H7) | 96.7% | .08% | .77% |

FIG. 17
The Percent Annexin and/or PI Positive B Cells in Culture after 24 Hour Incubation with Single or Multispecific Fusion Proteins.
A. Ramos Cells:
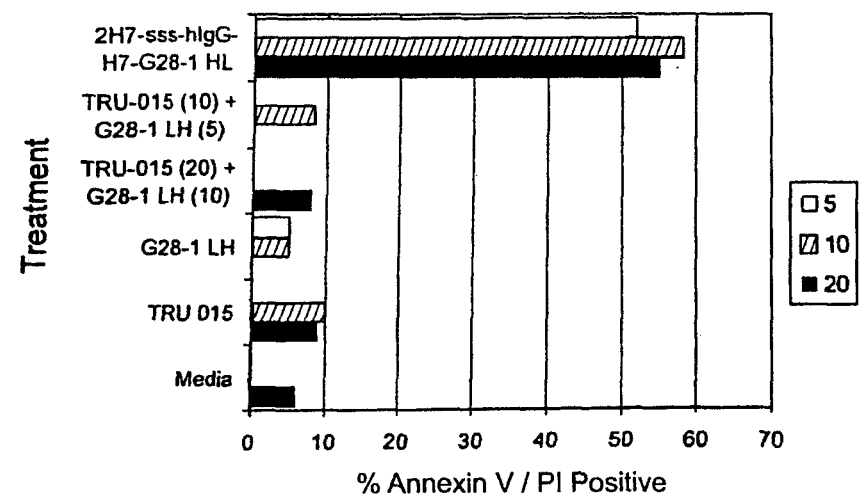
B. Daudi Cells:
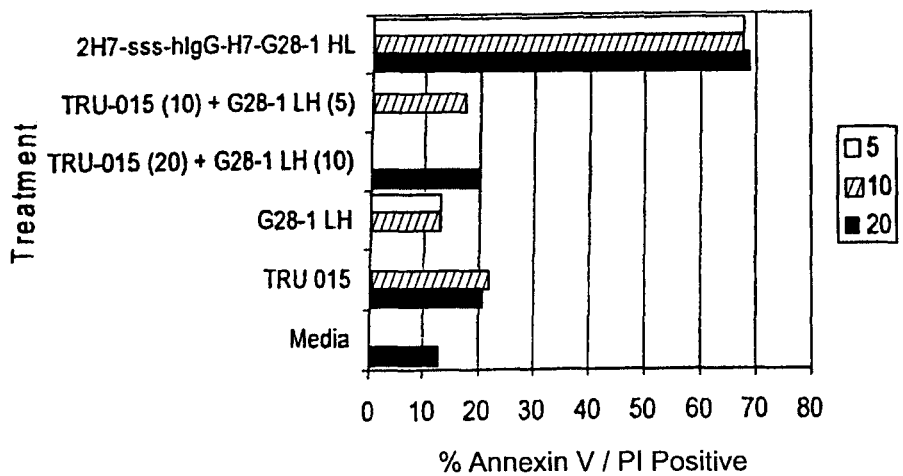

FIG. 18
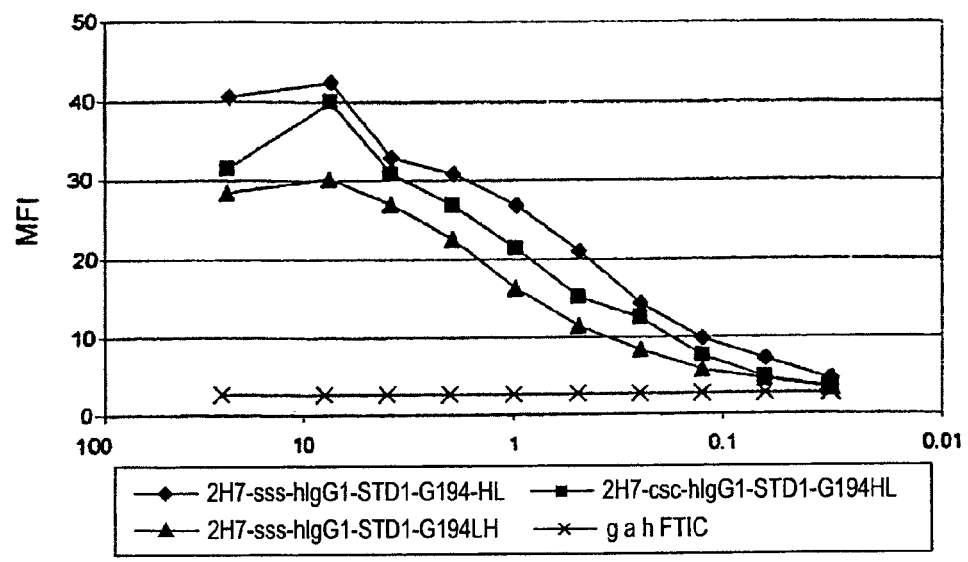
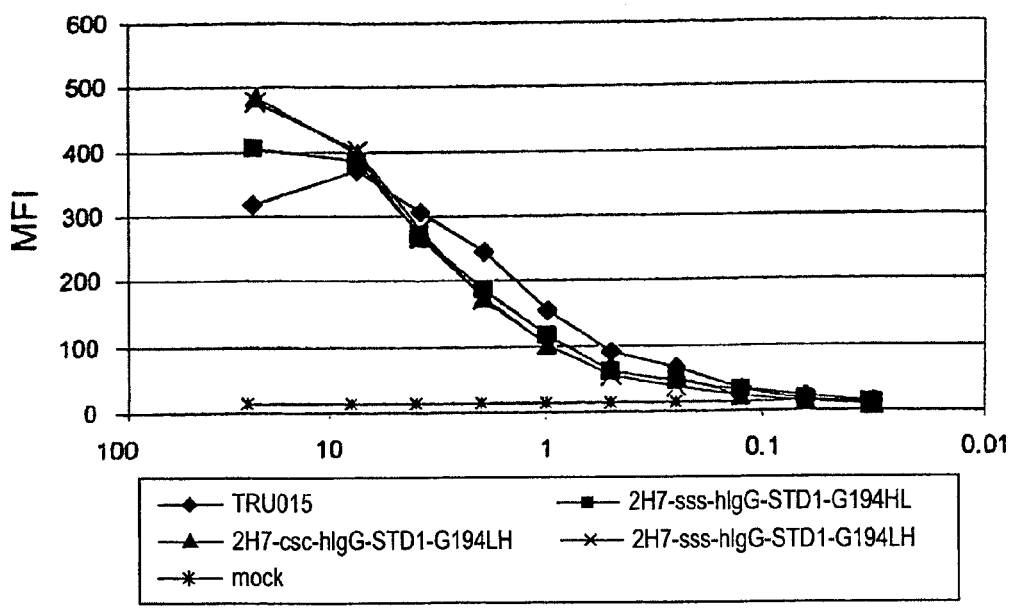

FIG. 19
A. ADCC Activity of 2H7-G19-4 Multispecific Fusion Proteins Against BJAB Targets Using Human PBMC Effectors at 25:1
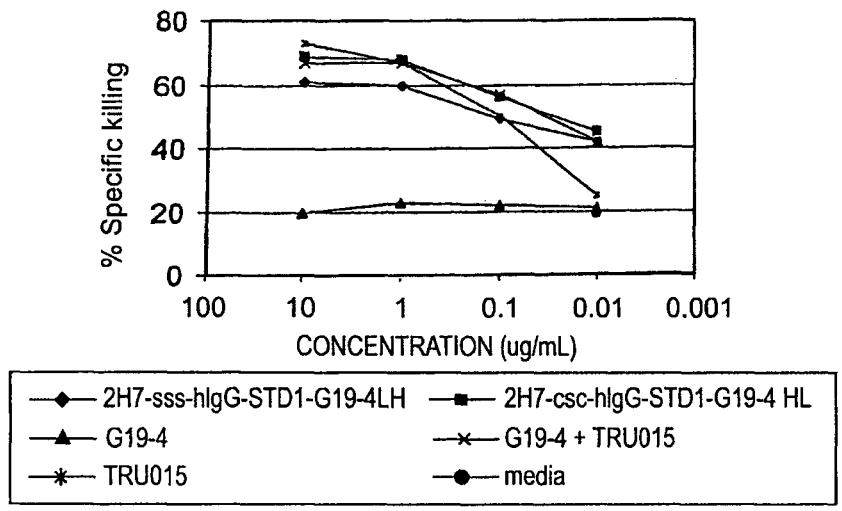
B. ADCC Activity in NK Cell Depleted PBMC Effector Cultures Using BJAB Targets (30:1, E:T) and 2H7-G19-4 Fusion Proteins
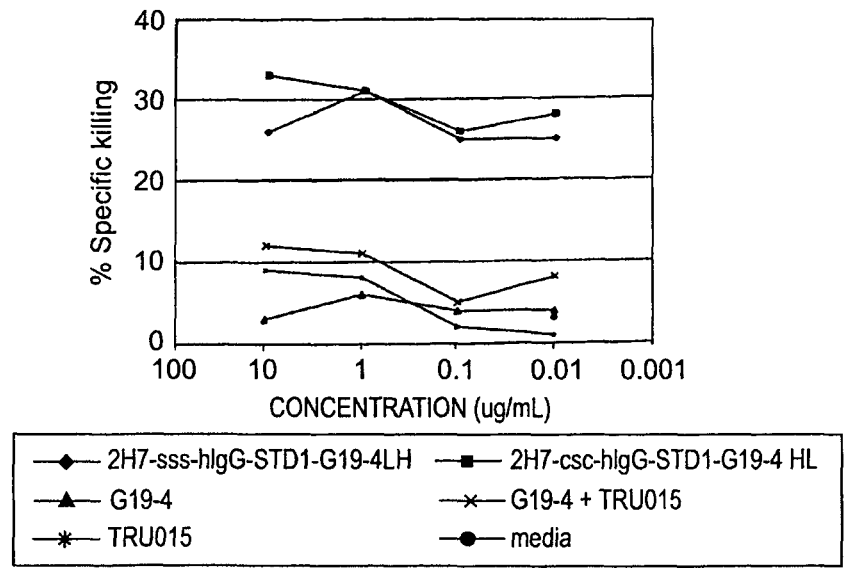

FIG. 29
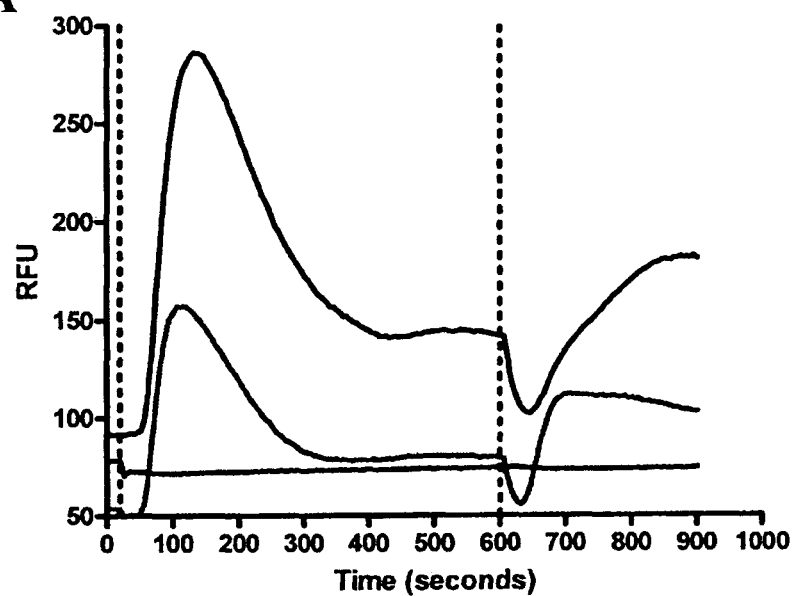
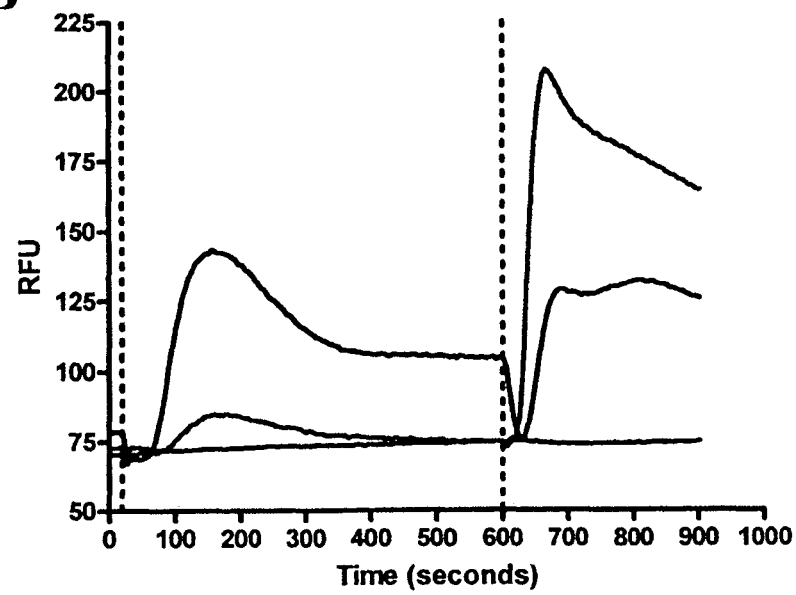

DHL6 Cells Treated with 20x37 Scorpion

SINGLE CHAIN MULTIVALENT BINDING PROTEINS WITH EFFECTOR FUNCTION

FIELD OF THE INVENTION

The invention relates generally to the field of multivalent binding molecules and therapeutic applications thereof.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 910180_406USPC_SEQUENCE_LISTING.txt. The text file is 391 KB, was created on Mar. 4, 2011, and is being submitted electronically via EFS-Web.

BACKGROUND

In a healthy mammal, the immune system protects the body from damage from foreign substances and pathogens. In some instances though, the immune system goes awry, producing traumatic insult and/or disease. For example, B-cells can produce antibodies that recognize self-proteins rather than foreign proteins, leading to the production of the autoantibodies characteristic of autoimmune diseases such as lupus erythematosus, rheumatoid arthritis, and the like. In other instances, the typically beneficial effect of the immune system in combating foreign materials is counterproductive, such as following organ transplantation. The power of the mammalian immune system, and in particular the human immune system, has been recognized and efforts have been made to control the system to avoid or ameliorate the deleterious consequences to health that result either from normal functioning of the immune system in an abnormal environment (e.g., organ transplantation) or from abnormal functioning of the immune system in an otherwise apparently normal environment (e.g., autoimmune disease progression). Additionally, efforts have been made to exploit the immune system to provide a number of target-specific diagnostic and therapeutic methodologies, relying on the capacity of antibodies to specifically recognize and bind antigenic targets with specificity.

One way in which the immune system protects the body is by production of specialized cells called B lymphocytes or B-cells. B-cells produce antibodies that bind to, and in some cases mediate destruction of, a foreign substance or pathogen. In some instances though, the human immune system, and specifically the B lymphocytes of the human immune system, go awry and disease results. There are numerous cancers that involve uncontrolled proliferation of B-cells. There are also numerous autoimmune diseases that involve B-cell production of antibodies that, instead of binding to foreign substances and pathogens, bind to parts of the body. In addition, there are numerous autoimmune and inflammatory diseases that involve B-cells in their pathology, for example, through inappropriate B-cell antigen presentation to T-cells or through other pathways involving B-cells. For example, autoimmune-prone mice deficient in B-cells do not develop autoimmune kidney disease, vasculitis or autoantibodies. (Shlomchik et al., J Exp. Med. 1994, 180:1295-306). Interestingly, these same autoimmune-prone mice which possess B-cells but are deficient in immunoglobulin production, do develop autoimmune diseases when induced experimentally (Chan et al., J Exp. Med. 1999, 189:1639-48), indicating that B-cells play an integral role in development of autoimmune disease.

B-cells can be identified by molecules on their cell surface. CD20 was the first human B-cell lineage-specific surface molecule identified by a monoclonal antibody. It is a non-glycosylated, hydrophobic 35 kDa B-cell transmembrane phosphoprotein that has both its amino and carboxy ends situated inside the cell. Einfeld et al., EMBO J. 1988, 7:711-17. CD20 is expressed by all normal mature B-cells, but is not expressed by precursor B-cells or plasma cells. Natural ligands for CD20 have not been identified, and the function of CD20 in B-cell biology is still incompletely understood.

Another B-cell lineage-specific cell surface molecule is CD37. CD37 is a heavily glycosylated 40-52 kDa protein that belongs to the tetraspanin transmembrane family of cell surface antigens. It traverses the cell membrane four times forming two extracellular loops and exposing its amino and carboxy ends to the cytoplasm. CD37 is highly expressed on normal antibody-producing (sIg+)B-cells, but is not expressed on pre-B-cells or plasma cells. The expression of CD37 on resting and activated T cells, monocytes and granulocytes is low and there is no detectable CD37 expression on NK cells, platelets or erythrocytes. See, Belov et al., Cancer Res., 61(11):4483-4489 (2001); Schwartz-Albiez et al., J. Immunol., 140(3): 905-914 (1988); and Link et al., J. Immunol., 137(9): 3013-3018 (1988). Besides normal B-cells, almost all malignancies of B-cell origin are positive for CD37 expression, including CLL, NHL, and hairy cell leukemia (Moore, et al. 1987; Merson and Brochier 1988; Faure, et al. 1990). CD37 participates in regulation of B-cell function, since mice lacking CD37 were found to have low levels of serum IgG1 and to be impaired in their humoral response to viral antigens and model antigens. It appears to act as a nonclassical costimulatory molecule or by directly influencing antigen presentation via complex formation with MHC class II molecules. See Knobeloch et al., Mol. Cell. Biol., 20(15):5363-5369 (2000).

Research and drug development has occurred based on the concept that B-cell lineage-specific cell surface molecules such as CD37 and CD20 can themselves be targets for antibodies that would bind to, and mediate destruction of, cancerous and autoimmune disease-causing B-cells that have CD37 and CD20 on their surfaces. Termed "immunotherapy," antibodies made (or based on antibodies made) in a non-human animal that bind to CD37 or CD20 were given to a patient to deplete cancerous or autoimmune disease-causing B-cells.

Monoclonal antibody technology and genetic engineering methods have facilitated development of immunoglobulin molecules for diagnosis and treatment of human diseases. The domain structure of immunoglobulins is amenable to engineering, in that the antigen binding domains and the domains conferring effector functions may be exchanged between immunoglobulin classes and subclasses. Immunoglobulin structure and function are reviewed, for example, in Harlow et al., Eds., Antibodies: A Laboratory Manual, Chapter 14, Cold Spring Harbor Laboratory, Cold Spring Harbor (1988). An extensive introduction as well as detailed information about all aspects of recombinant antibody technology can be found in the textbook "Recombinant Antibodies" (John Wiley & Sons, NY, 1999). A comprehensive collection of detailed antibody engineering lab Protocols can be found in R. Kontermann and S. Dübel (eds.), "The Antibody Engineering Lab Manual" (Springer Verlag, Heidelberg/New York, 2000).

An immunoglobulin molecule (abbreviated Ig), is a multimeric protein, typically composed of two identical light chain polypeptides and two identical heavy chain polypeptides ($H_2L_2$) that are joined into a macromolecular complex by interchain disulfide bonds, i.e., covalent bonds between the sulfhydryl groups of neighboring cysteine residues. Five human immunoglobulin classes are defined on the basis of their heavy chain composition, and are named IgG, IgM, IgA, IgE, and IgD. The IgG-class and IgA-class antibodies are further divided into subclasses, namely, IgG1, IgG2, IgG3, and IgG4, and IgA1 and IgA2, respectively. Intrachain disulfide bonds join different areas of the same polypeptide chain, which results in the formation of loops that, along with adjacent amino acids, constitute the immunoglobulin domains. At the amino-terminal portion, each light chain and each heavy chain has a single variable region that shows considerable variation in amino acid composition from one antibody to another. The light chain variable region, $V_L$, has a single antigen-binding domain and associates with the variable region of a heavy chain, $V_H$ (also containing a single antigen-binding domain), to form the antigen binding site of the immunoglobulin, the Fv.

In addition to variable regions, each of the full-length antibody chains has a constant region containing one or more domains. Light chains have a constant region containing a single domain. Thus, light chains have one variable domain and one constant domain. Heavy chains have a constant region containing several domains. The heavy chains in IgG, IgA, and IgD antibodies have three domains, which are designated $C_{H1}$, $C_{H2}$, and $C_{H3}$; the heavy chains in IgM and IgE antibodies have four domains, $C_{H1}$, $C_{H2}$, $C_{H3}$ and $C_{H4}$. Thus, heavy chains have one variable domain and three or four constant domains. Noteworthy is the invariant organization of these domains in all known species, with the constant regions, containing one or more domains, being located at or near the C-terminus of both the light and heavy chains of immunoglobulin molecules, with the variable domains located towards the N-termini of the light and heavy chains. Immunoglobulin structure and function are reviewed, for example, in Harlow et al., Eds., *Antibodies: A Laboratory Manual*, Chapter 14, Cold Spring Harbor Laboratory, Cold Spring Harbor (1988).

The heavy chains of immunoglobulins can also be divided into three functional regions: the Fd region (a fragment comprising $V_H$ and $C_{H1}$, i.e., the two N-terminal domains of the heavy chain), the hinge region, and the Fc region (the "fragment crystallizable" region). The Fc region contains the domains that interact with immunoglobulin receptors on cells and with the initial elements of the complement cascade. Thus, the Fc region or fragment is generally considered responsible for the effector functions of an immunoglobulin, such as ADCC (antibody-dependent cell-mediated cytotoxicity), CDC (complement-dependent cytotoxicity) and complement fixation, binding to Fc receptors, greater half-life in vivo relative to a polypeptide lacking an $F_C$ region, protein A binding, and perhaps even placental transfer. Capon et al., Nature, 337: 525-531, (1989). Further, a polypeptide containing an Fc region allows for dimerization/multimerization of the polypeptide. These terms are also used for analogous regions of the other immunoglobulins.

Although all of the human immunoglobulin isotypes contain a recognizable structure in common, each isotype exhibits a distinct pattern of effector function. IgG, by way of nonexhaustive example, neutralizes toxins and viruses, opsonizes, fixes complement (CDC) and participates in ADCC. IgM, in contrast, neutralizes blood-borne pathogens and participates in opsonization. IgA, when associated with its secretory piece, is secreted and provides a primary defense to microbial infection via the mucosa; it also neutralizes toxins and supports opsonization. IgE mediates inflammatory responses, being centrally involved in the recruitment of other cells needed to mount a full response. IgD is known to provide an immunoregulatory function, controlling the activation of B cells. These characterizations of isotype effector functions provide a non-comprehensive illustration of the differences that can be found among human isotypes.

The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2. The four IgG subclasses also differ from each other with respect to their effector functions. This difference is related to differences in structure, including differences with respect to the interaction between the variable region, Fab fragments, and the constant Fc fragment.

According to crystallographic studies, the immunoglobulin hinge region can be further subdivided functionally into three regions: the upper hinge region, the core region, and the lower hinge region. Shin et al., 1992 *Immunological Reviews* 130:87. The upper hinge region includes amino acids from the carboxyl end of $C_{H1}$ to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. Id. The core hinge region of human IgG1 contains the sequence Cys-Pro-Pro-Cys which, when dimerized by disulfide bond formation, results in a cyclic octapeptide believed to act as a pivot, thus conferring flexibility. The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin.

Conformational changes permitted by the structure and flexibility of the immunoglobulin hinge region polypeptide sequence may also affect the effector functions of the Fc portion of the antibody. Three general categories of effector functions associated with the Fc region include (1) activation of the classical complement cascade, (2) interaction with effector cells, and (3) compartmentalization of immunoglobulins. The different human IgG subclasses vary in the relative efficacies with which they fix complement, or activate and amplify the steps of the complement cascade. See, e.g., Kirschfink, 2001 *Immunol. Rev.* 180:177; Chakraborti et al., 2000 *Cell Signal* 12:607; Kohl et al., 1999 *Mol. Immunol.* 36:893; Marsh et al., 1999 *Curr. Opin. Nephrol. Hypertens.* 8:557; Speth et al., 1999 *Wien Klin. Wochenschr.* 111:378.

Exceptions to the $H_2L_2$ structure of conventional antibodies occur in some isotypes of the immunoglobulins found in camelids (camels, dromedaries and llamas; Hamers-Casterman et al., 1993 *Nature* 363:446; Nguyen et al., 1998 *J. Mol. Biol.* 275:413), nurse sharks (Roux et al., 1998 *Proc. Nat. Acad. Sci. USA* 95:11804), and in the spotted ratfish (Nguyen, et al., 2002 *Immunogenetics* 54(1):39-47). These antibodies can apparently form antigen-binding regions using only heavy chain variable region, i.e., these functional antibodies are homodimers of heavy chains only (referred to as "heavy-chain antibodies" or "HCAbs"). Despite the advantages of antibody technology in disease diagnosis and treatment, there are some disadvantageous aspects of developing whole-antibody technologies as diagnostic and/or therapeutic reagents. Whole antibodies are large protein structures exemplified by the heterotetrameric structure of the IgG isotype, containing two light and two heavy chains. Such large molecules are sterically hindered in certain applications. For example, in treatments of solid tumors, whole antibodies do not readily penetrate the interior of the tumor. Moreover, the relatively large size of whole antibodies presents a challenge to ensure that the in vivo administration of such molecules does not induce an immune response. Further, generation of active antibody molecules typically involves the culturing of recombinant eukaryotic cells capable of providing appropriate post-translational processing of the nascent antibody molecules, and such cells can be difficult to culture and difficult to induce in a manner that provides commercially useful yields of active antibody.

Recently, smaller immunoglobulin molecules have been constructed to overcome problems associated with whole immunoglobulin methodologies. A single-chain variable antibody fragment (scFv) comprises an antibody heavy chain variable domain joined via a short peptide to an antibody light chain variable domain (Huston et al., Proc. Natl. Acad. Sci. USA, 1988, 85: 5879-83). Because of the small size of scFv molecules, they exhibit more effective penetration into tissues than whole immunoglobulin. An anti-tumor scFv showed more rapid tumor penetration and more even distribution through the tumor mass than the corresponding chimeric antibody (Yokota et al., Cancer Res. 1992, 52:3402-08).

Despite the advantages that scFv molecules bring to serotherapy, several drawbacks to this therapeutic approach exist. An scFv is rapidly cleared from the circulation, which may reduce toxic effects in normal cells, but such rapid clearance impedes delivery of a minimum effective dose to the target tissue. Manufacturing adequate amounts of scFv for administration to patients has been challenging due to difficulties in expression and isolation of scFv that adversely affect the yield. During expression, scFv molecules lack stability and often aggregate due to pairing of variable regions from different molecules. Furthermore, production levels of scFv molecules in mammalian expression systems are low, limiting the potential for efficient manufacturing of scFv molecules for therapy (Davis et al, J Biol. Chem. 1990, 265: 10410-18); Traunecker et al., EMBO J 1991, 10: 3655-59). Strategies for improving production have been explored, including addition of glycosylation sites to the variable regions (Jost, C. R. U.S. Pat. No. 5,888,773, Jost et al, J. Biol. Chem. 1994, 69: 26267-73).

Another disadvantage to using scFv for therapy is the lack of effector function. An scFv without a cytolytic function, such as the antibody-dependent cell-mediated cytotoxicity (ADCC) and complement dependent-cytotoxicity (CDC) associated with the constant region of an immunoglobulin, may be ineffective for treating disease. Even though development of scFv technology began over 12 years ago, currently no scFv products are approved for therapy.

Alternatively, it has been proposed that fusion of an scFv to another molecule, such as a toxin, could take advantage of the specific antigen-binding activity and the small size of an scFv to deliver the toxin to a target tissue. Chaudary et al., Nature 1989, 339:394; Batra et al., Mol. Cell. Biol. 1991, 11:2200. Conjugation or fusion of toxins to scFvs has thus been offered as an alternative strategy to provide potent, antigen-specific molecules, but dosing with such conjugates or chimeras can be limited by excessive and/or non-specific toxicity due to the toxin moiety of such preparations. Toxic effects may include supraphysiological elevation of liver enzymes and vascular leak syndrome, and other undesired effects. In addition, immunotoxins are themselves highly immunogenic upon administration to a host, and host antibodies generated against the immunotoxin limit potential usefulness for repeated therapeutic treatments of an individual.

Nonsurgical cancer therapy, such as external irradiation and chemotherapy, can suffer from limited efficacy because of toxic effects on normal tissues and cells, due to the lack of specificity these treatments exhibit towards cancer cells. To overcome this limitation, targeted treatment methodologies have been developed to increase the specificity of the treatment for the cells and tissues in need thereof. An example of such a targeted methodology for in vivo use is the administration of antibody conjugates, with the antibody designed to specifically recognize a marker associated with a cell or tissue in need of treatment, and the antibody being conjugated to a therapeutic agent, such as a toxin in the case of cancer treatment. Antibodies, as systemic agents, circulate to sensitive and undesirable body compartments, such as the bone marrow. In acute radiation injury, destruction of lymphoid and hematopoietic compartments is a major factor in the development of septicemia and subsequent death. Moreover, antibodies are large, globular proteins that can exhibit poor penetration of tissues in need of treatment.

Human patients and non-human subjects suffering from a variety of end-stage disease processes frequently require organ transplantation. Organ transplantation, however, must contend with the untoward immune response of the recipient and guard against immunological rejection of the transplanted organ by depressing the recipient's cellular immune response to the foreign organ with cytotoxic agents which affect the lymphoid and other parts of the hematopoietic system. Graft acceptance is limited by the tolerance of the recipient to these cytotoxic chemicals, many of which are similar to the anticancer (antiproliferative) agents. Likewise, when using cytotoxic antimicrobial agents, particularly antiviral drugs, or when using cytotoxic drugs for autoimmune disease therapy, e.g., in treatment of systemic lupus erythematosis, a serious limitation is the toxic effects of the therapeutic agents on the bone marrow and the hematopoietic cells of the body.

Use of targeted therapies, such as targeted antibody conjugate therapy, is designed to localize a maximum quantity of the therapeutic agent at the site of desired action as possible, and the success of such therapies is revealed by the relatively high signal-to-background ratio of therapeutic agent. Examples of targeted antibodies include diagnostic or therapeutic agent conjugates of antibody or antibody fragments, cell- or tissue-specific peptides, and hormones and other receptor-binding molecules. For example, antibodies against different determinants associated with pathological and normal cells, as well as associated with pathogenic microorganisms, have been used for the detection and treatment of a wide variety of pathological conditions or lesions. In these methods, the targeting antibody is directly conjugated to an appropriate detecting or therapeutic agent as described, for example, in Hansen et al., U.S. Pat. No. 3,927,193 and Goldenberg, U.S. Pat. Nos. 4,331,647, 4,348,376, 4,361,544, 4,468,457, 4,444,744, 4,460,459, 4,460,561, 4,624,846 and 4,818,709.

One problem encountered in direct targeting methods, i.e., in methods wherein the diagnostic or therapeutic agent (the "active agent") is conjugated directly to the targeting moiety, is that a relatively small fraction of the conjugate actually binds to the target site, while the majority of conjugate remains in circulation and compromises in one way or another the function of the targeted conjugate. To ensure maximal localization of the active agent, an excess of the targeted conjugate is typically administered, ensuring that some conjugate will remain unbound and contribute to background levels of the active agent. A diagnostic conjugate, e.g., a radioimmunoscintigraphic or magnetic resonance imaging conjugate that does not bind its target can remain in circulation, thereby increasing background and decreasing resolution of the diagnostic technique. In the case of a therapeutic conjugate having a toxin as an active agent (e.g., a radioisotope, drug or toxic compound) attached to a long-circulating targeting moiety such as an antibody, circulating conjugate can result in unacceptable toxicity to the host, such as marrow toxicity or systemic side effects.

U.S. Pat. No. 4,782,840 discloses a method for reducing the effect of elevated background radiation levels during surgery. The method involves injection of a patient with antibodies specific for neoplastic tissue, with the antibodies labeled with radioisotopes having a suitably long half-life, such as Iodine-125. After injection of the radiolabeled antibody, the surgery is delayed at least 7-10 days, preferably 14-21 days, to allow any unbound radiolabeled antibody to be cleared to a low background level.

U.S. Pat. No. 4,932,412 discloses methods for reducing or correcting for non-specific background radiation during intraoperative detection. The methods include the administration to a patient who has received a radiolabeled primary antibody, of a contrast agent, subtraction agent or second antibody which binds the primary antibody.

Apart from producing the antibodies described above, the immune system includes a variety of cell types that have powerful biological effects. During hematopoiesis, bone marrow-derived stem cells differentiate into either mature cells of the immune system ("B" cells) or into precursors of cells that migrate out of the bone marrow to mature in the thymus ("T" cells).

B cells are central to the humoral component of an immune response. B cells are activated by an appropriate presentation of an antigen to become antibody-secreting plasma cells; antigen presentation also results in clonal expansion of the activated B cell. B cells are primarily responsible for the humoral component of an immune response. A plasma cell typically exhibits about $10^5$ antibody molecules (IgD and IgM) on its surface.

T lymphocytes can be divided into two categories. The cytotoxic T cells, Tc lymphocytes or CTLs (CD8+ T cells), kill cells bearing foreign surface antigen in association with Class I MHC and can kill cells that are harboring intracellular parasites (either bacteria or viruses) as long as the infected cell is displaying a microbial antigen on its surface. Tc cells kill tumor cells and account for the rejection of transplanted cells. Tc cells recognize antigen-Class I MHC complexes on target cells, contact them, and release the contents of granules directly into the target cell membrane, which lyses the cell.

A second category of T cells is the helper T cell or Th lymphocyte (CD4+ T cells), which produces lymphokines that are "helper" factors in the maturation of B cells into antibody-secreting plasma cells. Th cells also produce certain lymphokines that stimulate the differentiation of effector T lymphocytes and the activity of macrophages. Th1 cells recognize antigen on macrophages in association with Class II MHC and become activated (by IL-1) to produce lymphokines, including the IFN-γ that activates macrophages and NK cells. These cells mediate various aspects of the cell-mediated immunity response including delayed-type hypersensitivity reactions. Th2 cells recognize antigen in association with Class II MHC on an antigen presenting cell or APC (e.g., migratory macrophages and dendritic cells) and then produce interleukins and other substances that stimulate specific B-cell and T-cell proliferation and activity.

Beyond serving as APCs that initiate T cell interactions, development, and proliferation, macrophages are involved in expression of cell-mediated immunity because they become activated by IFN-γ produced in a cell-mediated immune response. Activated macrophages have increased phagocytic potential and release soluble substances that cause inflammation and destroy many bacteria and other cells. Natural Killer cells are cytotoxic cells that lyse cells bearing new antigen, regardless of their MHC type, and even lyse some cells that bear no MHC proteins. Natural Killer T cells, or NK cells, are defined by their ability to kill cells displaying a foreign antigen (e.g., tumor cells), regardless of MHC type, and regardless of previous sensitization (exposure) to the antigen. NK cells can be activated by IL-2 and IFN-γ, and lyse cells in the same manner as cytotoxic T lymphocytes. Some NK cells have receptors for the Fc domain of the IgG antibody (e.g, CD16 or $F_C\gamma RIII$) and are thus able to bind to the Fc portion of IgG on the surface of a target cell and release cytolytic components that kill the target cell via antibody-dependent cell-mediated cytotoxicity.

Another group of cells is the granulocytes or polymorphonuclear leukocytes (PMNs). Neutrophils, one type of PMN, kill bacterial invaders and phagocytose the remains. Eosinophils are another type of PMN and contain granules that prove cytotoxic when released upon another cell, such as a foreign cell. Basophils, a third type of PMN, are significant mediators of powerful physiological responses (e.g., inflammation) that exert their effects by releasing a variety of biologically active compounds, such as histamine, serotonin, prostaglandins, and leukotrienes. Common to all of these cell types is the capacity to exert a physiological effect within an organism, frequently by killing, and optionally scavenging, deleterious compositions such as foreign cells.

Although a variety of mammalian cells, including cells of the immune system, are capable of directly exerting a physiological effect (e.g., cell killing, typified by Tc, NK, some PMN, macrophage, and the like), other cells indirectly contribute to a physiological effect. For example, initial presentation of an antigen to a naïve T cell of the immune system requires MHC presentation that mandates cell-cell contact. Further, there often needs to be contact between an activated T cell and an antigen-specific B cell to obtain a particular immunogenic response. A third form of cell-cell contact often seen in immune responses is the contact between an activated B cell and follicular dendritic cells. Each of these cell-cell contact requirements complicates the targeting of a biologically active agent to a given target.

Complement-dependent cytotoxicity (CDC) is believed to be a significant mechanism for clearance of specific target cells such as tumor cells. CDC is a series of events that consists of a collection of enzymes that become activated by each other in a cascade fashion. Complement has an important role in clearing antigen, accomplished by its four major functions: (1) local vasodilation; (2) attraction of immune cells, especially phagocytes (chemotaxis); (3) tagging of foreign organisms for phagocytosis (opsonization); and (4) destruction of invading organisms by the membrane attack complex (MAC attack). The central molecule is the C3 protein. It is an enzyme that is split into two fragments by components of either the classical pathway or the alternative pathway. The classical pathway is induced by antibodies, especially IgG and IgM, while the alternative pathway is nonspecifically stimulated by bacterial products like lipopolysaccharide (LPS). Briefly, the products of the C3 split include a small peptide C3a which is chemotactic for phagocytic immune cells and results in local vasodilation by causing the release of C5a fragment from C5. The other part of C3, C3b, coats antigens on the surface of foreign organisms and acts to opsonize the organism for destruction. C3b also reacts with other components of the complement system to form an MAC consisting of C5b, C6, C7, C8 and C9.

There are problems associated with the use of antibodies in human therapy because the response of the immune system to any antigen, even the simplest, is "polyclonal," i.e., the system manufactures antibodies of a great range of structures both in their binding regions as well as in their effector regions.

Two approaches have been used in an attempt to reduce the problem of immunogenic antibodies. The first is the production of chimeric antibodies in which the antigen-binding part (variable regions) of a mouse monoclonal antibody is fused to the effector part (constant region) of a human antibody. In a second approach, antibodies have been altered through a technique known as complementarity determining region (CDR) grafting or "humanization." This process has been further improved to include changes referred to as "reshaping" (Verhoeyen, et al., 1988 *Science* 239:1534-1536; Riechmann, et al., 1988 *Nature* 332:323-337; Tempest, et al., *Bio/Technol* 1991 9:266-271), "hyperchimerization" (Queen, et al., 1989 *Proc Natl Acad Sci USA* 86:10029-10033; Co, et al., 1991 *Proc Natl Acad Sci USA* 88:2869-2873; Co, et al., 1992 *J Immunol* 148:1149-1154), and "veneering" (Mark, et al., In: Metcalf B W, Dalton B J, eds. Cellular adhesion: molecular definition to therapeutic potential. New York: Plenum Press, 1994:291-312).

An average of less than one therapeutic antibody per year has been introduced to the market beginning in 1986, eleven years after the publication of monoclonal antibodies. Five murine monoclonal antibodies were introduced into human medicine over a ten year period from 1986-1995, including "muromonab-CD3" (OrthoClone OKT3®) for acute rejection of organ transplants; "edrecolomab" (Panorex®) for colorectal cancer; "odulimomab" (Antilfa®) for transplant rejection; and, "ibritumomab" (Zevalin® yiuxetan) for non-Hodgkin's lymphoma. Additionally, a monoclonal Fab, "abciximab" (ReoPro®) has been marketed for preventing coronary artery reocclusion. Three chimeric monoclonal antibodies were also launched: "rituximab" (Rituxan®) for treating B cell lymphomas; "basiliximab" (Simulect®) for transplant rejection; and "infliximab" (Remicade®) for treatment of rheumatoid arthritis and Crohn's disease. Additionally, "abciximab" (ReoPro®), a 47.6 kD Fab fragment of a chimeric human-murine monoclonal antibody is marketed as an adjunct to percutaneous coronary intervention for the prevention of cardiac ischemic complications in patients undergoing percutaneous coronary intervention. Finally, seven "humanized" monoclonal antibodies have been launched. "Daclizumab" (Zenapax®) is used to prevent acute rejection of transplanted kidneys; "palivizumab" (Synagis®) for RSV; "trastuzumab" (Herceptin®) binds HER-2, a growth factor receptor found on breast cancers cells; "gemtuzumab" (Mylotarg®) for acute myelogenous leukemia (AML); and "alemtuzumab" (MabCampath®) for chronic lymphocytic leukemia; "adalimumab" (Humira® (D2E7)) for the treatment of rheumatoid arthritis; and, "omalizumab" (Xolair®), for the treatment of persistent asthma.

Thus, a variety of antibody technologies have received attention in the effort to develop and market more effective therapeutics and palliatives. Unfortunately, problems continue to compromise the promise of each of these therapies. For example, the majority of cancer patients treated with rituximab relapse, generally within about 6-12 months, and fatal infusion reactions within 24 hours of rituximab infusion have been reported. Acute renal failure requiring dialysis with instances of fatal outcome has also been reported in treatments with rituximab, as have severe, occasionally fatal, mucocutaneous reactions. Additionally, high doses of rituximab are required for intravenous injection because the molecule is large, approximately 150 kDa, and diffusion into the lymphoid tissues, where many tumor cells may reside is limited.

Trastuzumab administration can result in the development of ventricular dysfunction, congestive heart failure, and severe hypersensitivity reactions (including anaphylaxis), infusion reactions, and pulmonary events. Daclizumab immunosuppressive therapy poses an increased risk for developing lymphoproliferative disorders and opportunistic infections. Death from liver failure, arising from severe hepatotoxicity, and from veno-occlusive disease (VOD), has been reported in patients who received gemtuzumab.

Hepatotoxicity was also reported in patients receiving alemtuzumab. Serious and, in some rare instances fatal, pancytopenia/marrow hypoplasia, autoimmune idiopathic thrombocytopenia, and autoimmune hemolytic anemia have occurred in patients receiving alemtuzumab therapy. Alemtuzumab can also result in serious infusion reactions as well as opportunistic infections. In patients treated with adalimumab, serious infections and sepsis, including fatalities, have been reported, as has the exacerbation of clinical symptoms and/or radiographic evidence of demyelinating disease, and patients treated with adalimumab in clinical trials had a higher incidence of lymphoma than the expected rate in the general population. Omalizumab reportedly induces malignancies and anaphylaxis.

Cancer includes a broad range of diseases, affecting approximately one in four individuals worldwide. Rapid and unregulated proliferation of malignant cells is a hallmark of many types of cancer, including hematological malignancies. Although patients with a hematologic malignant condition have benefited from advances in cancer therapy in the past two decades, Multani et al., 1998 *J. Clin. Oncology* 16:3691-3710, and remission times have increased, most patients still relapse and succumb to their disease. Barriers to cure with cytotoxic drugs include, for example, tumor cell resistance and the high toxicity of chemotherapy, which prevents optimal dosing in many patients.

Treatment of patients with low grade or follicular B cell lymphoma using a chimeric CD20 monoclonal antibody has been reported to induce partial or complete responses in patients. McLaughlin et al., 1996 *Blood* 88:90a (abstract, suppl. 1); Maloney et al., 1997 *Blood* 90:2188-95. However, as noted above, tumor relapse commonly occurs within six months to one year. Further improvements in serotherapy are needed to induce more durable responses, for example, in low grade B cell lymphoma, and to allow effective treatment of high grade lymphoma and other B cell diseases.

Another approach has been to target radioisotopes to B cell lymphomas using monoclonal antibodies specific for CD20. While the effectiveness of therapy is reportedly increased, associated toxicity from the long in vivo half-life of the radioactive antibody increases, sometimes requiring that the patient undergo stem cell rescue. Press et al., 1993 *N. Eng. J. Med.* 329:1219-1224; Kaminski et al., 1993 *N. Eng. J. Med.* 329:459-65. Monoclonal antibodies to CD20 have also been cleaved with proteases to yield F(ab')$_2$ or Fab fragments prior to attachment of radioisotope. This has been reported to improve penetration of the radioisotope conjugate into the tumor and to shorten the in vivo half-life, thus reducing the toxicity to normal tissues. However, these molecules lack effector functions, including complement fixation and/or ADCC.

Autoimmune diseases include autoimmune thyroid diseases, which include Graves' disease and Hashimoto's thyroiditis. In the United States alone, there are about 20 million people who have some form of autoimmune thyroid disease. Autoimmune thyroid disease results from the production of autoantibodies that either stimulate the thyroid to cause hyperthyroidism (Graves' disease) or destroy the thyroid to cause hypothyroidism (Hashimoto's thyroiditis). Stimulation of the thyroid is caused by autoantibodies that bind and activate the thyroid stimulating hormone (TSH) receptor. Destruction of the thyroid is caused by autoantibodies that react with other thyroid antigens. Current therapy for Graves' disease includes surgery, radioactive iodine, or antithyroid drug therapy. Radioactive iodine is widely used, since antithyroid medications have significant side effects and disease recurrence is high. Surgery is reserved for patients with large goiters or where there is a need for very rapid normalization of thyroid function. There are no therapies that target the production of autoantibodies responsible for stimulating the TSH receptor. Current therapy for Hashimoto's thyroiditis is levothyroxine sodium, and lifetime therapy is expected because of the low likelihood of remission. Suppressive therapy has been shown to shrink goiters in Hashimoto's thyroiditis, but no therapies that reduce autoantibody production to target the disease mechanism are known.

Rheumatoid arthritis (RA) is a chronic disease characterized by inflammation of the joints, leading to swelling, pain, and loss of function. RA affects an estimated 2.5 million people in the United States. RA is caused by a combination of events including an initial infection or injury, an abnormal immune response, and genetic factors. While autoreactive T cells and B cells are present in RA, the detection of high levels of antibodies that collect in the joints, called rheumatoid factor, is used in the diagnosis of RA. Current therapy for RA includes many medications for managing pain and slowing the progression of the disease. No therapy has been found that can cure the disease. Medications include nonsteroidal anti-inflammatory drugs (NSAIDS), and disease modifying antirheumatic drugs (DMARDS). NSAIDS are useful in benign disease, but fail to prevent the progression to joint destruction and debility in severe RA. Both NSAIDS and DMARDS are associated with significant side effects. Only one new DMARD, Leflunomide, has been approved in over 10 years. Leflunomide blocks production of autoantibodies, reduces inflammation, and slows progression of RA. However, this drug also causes severe side effects including nausea, diarrhea, hair loss, rash, and liver injury.

Systemic Lupus Erythematosus (SLE) is an autoimmune disease caused by recurrent injuries to blood vessels in multiple organs, including the kidney, skin, and joints. SLE is estimated to affect over 500,000 people in the United States. In patients with SLE, a faulty interaction between T cells and B cells results in the production of autoantibodies that attack the cell nucleus. These include anti-double stranded DNA and anti-Sm antibodies. Autoantibodies that bind phospholipids are also found in about half of SLE patients, and are responsible for blood vessel damage and low blood counts. Immune complexes accumulate in the kidneys, blood vessels, and joints of SLE patients, where they cause inflammation and tissue damage. No treatment for SLE has been found to cure the disease. NSAIDS and DMARDS are used for therapy depending upon the severity of the disease. Plasmapheresis with plasma exchange to remove autoantibodies can cause temporary improvement in SLE patients. There is general agreement that autoantibodies are responsible for SLE, so new therapies that deplete the B cell lineage, allowing the immune system to reset as new B cells are generated from precursors, would offer hope for long lasting benefit in SLE patients.

Sjogren's syndrome is an autoimmune disease characterized by destruction of the body's moisture-producing glands. Sjogren's syndrome is one of the most prevalent autoimmune disorders, striking up to an estimated 4 million people in the United States. About half of the people stricken with Sjogren's syndrome also have a connective tissue disease, such as RA, while the other half have primary Sjogren's syndrome with no other concurrent autoimmune disease. Autoantibodies, including anti-nuclear antibodies, rheumatoid factor, anti-fodrin, and anti-muscarinic receptor are often present in patients with Sjogren's syndrome. Conventional therapy includes corticosteroids, and additional more effective therapies would be of benefit.

Immune thrombocytopenic purpura (ITP) is caused by autoantibodies that bind to blood platelets and cause their destruction. Some cases of ITP are caused by drugs, and others are associated with infection, pregnancy, or autoimmune disease such as SLE. About half of all cases are classified as being of idiopathic origin. The treatment of ITP is determined by the severity of the symptoms. In some cases, no therapy is needed although in most cases immunosuppressive drugs, including corticosteroids or intravenous infusions of immune globulin to deplete T cells, are provided. Another treatment that usually results in an increased number of platelets is removal of the spleen, the organ that destroys antibody-coated platelets. More potent immunosuppressive drugs, including cyclosporine, cyclophosphamide, or azathioprine are used for patients with severe cases. Removal of autoantibodies by passage of patients' plasma over a Protein A column is used as a second line treatment in patients with severe disease. Additional more effective therapies are needed.

Multiple sclerosis (MS) is also an autoimmune disease. It is characterized by inflammation of the central nervous system and destruction of myelin, which insulates nerve cell fibers in the brain, spinal cord, and body. Although the cause of MS is unknown, it is widely believed that autoimmune T cells are primary contributors to the pathogenesis of the disease. However, high levels of antibodies are present in the cerebrospinal fluid of patients with MS, and some predict that the B cell response leading to antibody production is important for mediating the disease. No B cell depletion therapies have been studied in patients with MS, and there is no cure for MS. Current therapy is corticosteroids, which can reduce the duration and severity of attacks, but do not affect the course of MS over time. New biotechnology interferon (IFN) therapies for MS have recently been approved but additional more effective therapies are required.

Myasthenia Gravis (MG) is a chronic autoimmune neuromuscular disorder that is characterized by weakness of the voluntary muscle groups. MG affects about 40,000 people in the United States. MG is caused by autoantibodies that bind to acetylcholine receptors expressed at neuromuscular junctions. The autoantibodies reduce or block acetylcholine receptors, preventing the transmission of signals from nerves to muscles. There is no known cure for mg. Common treatments include immunosuppression with corticosteroids, cyclosporine, cyclophosphamide, or azathioprine. Surgical removal of the thymus is often used to blunt the autoimmune response. Plasmapheresis, used to reduce autoantibody levels in the blood, is effective in mg, but is short-lived because the production of autoantibodies continues. Plasmapheresis is usually reserved for severe muscle weakness prior to surgery. New and effective therapies would be of benefit.

Psoriasis affects approximately five million people, and is characterized by autoimmune inflammation in the skin. Psoriasis is also associated with arthritis in 30% (psoriatic arthritis). Many treatments, including steroids, uv light retinoids, vitamin D derivatives, cyclosporine, and methotrexate have been used but it is also clear that psoriasis would benefit from new and effective therapies. Scleroderma is a chronic autoimmune disease of the connective tissue that is also known as systemic sclerosis. Scleroderma is characterized by an overproduction of collagen, resulting in a thickening of the skin, and approximately 300,000 people in the United States have scleroderma, which would also benefit from new and effective therapies.

Apparent from the foregoing discussion are needs for improved compositions and methods to treat, ameliorate or prevent a variety of diseases, disorders and conditions, including cancer and autoimmune diseases.

SUMMARY

The invention satisfies at least one of the aforementioned needs in the art by providing proteins containing at least two specific binding domains, wherein those two domains are linked by a constant sub-region derived from an antibody molecule attached at its C-terminus to a linker herein referred to as a scorpion linker, and nucleic acids encoding such proteins, as well as production, diagnostic and therapeutic uses of such proteins and nucleic acids. The constant sub-region comprises a domain derived from an immunoglobulin $C_{H2}$ domain, and preferably a domain derived from an immunoglobulin $C_{H3}$ domain, but does not contain a domain or region derived from, or corresponding to, an immunoglobulin $C_{H1}$ domain. Previously, it had been thought that the placement of a constant region derived from an antibody in the interior of a protein would interfere with antibody function, such as effector function, by analogy to the conventional placement of constant regions of antibodies at the carboxy termini of antibody chains. In addition, placement of a scorpion linker, which may be an immunoglobulin hinge-like peptide, C-terminal to a constant sub-region is an organization that differs from the organization of naturally occurring immunoglobu-lins. Placement of a constant sub-region (with a scorpion linker attached C-terminal to the constant region) in the interior of a polypeptide or protein chain in accordance with the invention, however, resulted in proteins exhibiting effector function and multivalent (mono- or multi-specific) binding capacities relatively unencumbered by steric hindrances. As will be apparent to one of skill in the art upon consideration of this disclosure, such proteins are modular in design and may be constructed by selecting any of a variety of binding domains for binding domain 1 or binding domain 2 (or for any additional binding domains found in a particular protein according to the invention), by selecting a constant sub-region having effector function, and by selecting a scorpion linker, hinge-like or non-hinge like (e.g., type II C-lectin receptor stalk region peptides), with the protein exhibiting a general organization of N-binding domain 1-constant sub-region-scorpion linker-binding domain 2-C. Those of skill will further appreciate that proteins of such structure, and the nucleic acids encoding those proteins, will find a wide variety of applications, including medical and veterinary applications.

One aspect of the invention is drawn to a multivalent single-chain binding protein with effector function, or scorpion (the terms are used interchangeably), comprising a first binding domain derived from an immunoglobulin (e.g., an antibody) or an immunoglobulin-like molecule, a constant sub-region providing an effector function, the constant sub-region located C-terminal to the first binding domain; a scorpion linker located C-terminal to the constant sub-region; and a second binding domain derived from an immunoglobulin (such as an antibody) or immunoglobulin-like molecule, located C-terminal to the constant sub-region; thereby localizing the constant sub-region between the first binding domain and the second binding domain. The single-chain binding protein may be multispecific, e.g., bispecific in that it could bind two or more distinct targets, or it may be monospecific, with two binding sites for the same target. Moreover, all of the domains of the protein are found in a single chain, but the protein may form homo-multimers, e.g., by interchain disulfide bond formation. In some embodiments, the first binding domain and/or the second binding domain is/are derived from variable regions of light and heavy immunoglobulin chains from the same, or different, immunoglobulins (e.g., antibodies). The immunoglobulin(s) may be from any vertebrate, such as a mammal, including a human, and may be chimeric, humanized, fragments, variants or derivatives of naturally occurring immunoglobulins.

The invention contemplates proteins in which the first and second binding domains are derived from the same, or different immunoglobulins (e.g., antibodies), and wherein the first and second binding domains recognize the same, or different, molecular targets (e.g., cell surface markers, such as membrane-bound proteins). Further, the first and second binding domains may recognize the same, or different, epitopes. The first and second molecular targets may be associated with first and second target cells, viruses, carriers and/or objects. In preferred embodiments according to this aspect of the invention, each of the first binding domain, second binding domain, and constant sub-region is derived from a human immunoglobulin, such as an IgG antibody. In yet other embodiments, the multivalent binding protein with effector function has at least one of the first binding domain and the second binding domain that recognizes at least one cell-free molecular target, e.g., a protein unassociated with a cell, such as a deposited protein or a soluble protein. Cell-free molecular targets include, e.g., proteins that were never associated with a cell, e.g., administered compounds such as proteins, as well as proteins that are secreted, cleaved, present in exosomes, or otherwise discharged or separated from a cell.

The target molecules recognized by the first and second binding domains may be found on, or in association with, the same, or different, prokaryotic cells, eukaryotic cells, viruses (including bacteriophage), organic or inorganic target molecule carriers, and foreign objects. Moreover, those target molecules may be on physically distinct cells, viruses, carriers or objects of the same type (e.g., two distinct eukaryotic cells, prokaryotic cells, viruses or carriers) or those target molecules may be on cells, viruses, carriers, or objects that differ in type (e.g., a eukaryotic cell and a virus). Target cells are those cells associated with a target molecule recognized by a binding domain and includes endogenous or autologous cells as well as exogenous or foreign cells (e.g., infectious microbial cells, transplanted mammalian cells including transfused blood cells). The invention comprehends targets for the first and/or second binding domains that are found on the surface of a target cell(s) associated with a disease, disorder or condition of a mammal such as a human. Exemplary target cells include a cancer cell, a cell associated with an autoimmune disease or disorder, and an infectious cell (e.g., an infectious bacterium). A cell of an infectious organism, such as a mammalian parasite, is also contemplated as a target cell. In some embodiments, a protein of the invention is a multivalent (e.g., multispecific) binding protein with effector function wherein at least one of the first binding domain and the second binding domain recognizes a target selected from the group consisting of a tumor antigen, a B-cell target, a TNF receptor superfamily member, a Hedgehog family member, a receptor tyrosine kinase, a proteoglycan-related molecule, a TGF-beta superfamily member, a Wnt-related molecule, a receptor ligand, a T-cell target, a Dendritic cell target, an NK cell target, a monocyte/macrophage cell target and an angiogenesis target.

In some embodiments of the above-described protein, the tumor antigen is selected from the group consisting of SQUAMOUS CELL CARCINOMA ANTIGEN 1 (SCCA-1), (PROTEIN T4-A), SQUAMOUS CELL CARCINOMA ANTIGEN 2 (SCCA-2), Ovarian carcinoma antigen CA125 (1A1-3B) (KIAA0049), MUCIN 1 (TUMOR-ASSOCIATED MUCIN), (CARCINOMA-ASSOCIATED MUCIN), (POLYMORPHIC EPITHELIAL MUCIN), (PEM), (PEMT), (EPISIALIN), (TUMOR-ASSOCIATED EPITHELIAL MEMBRANE ANTIGEN), (EMA), (H23AG), (PEANUT-REACTIVE URINARY MUCIN), (PUM), (BREAST CARCINOMA—ASSOCIATED ANTIGEN DF3), CTCL tumor antigen sel-1, CTCL tumor antigen se14-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, Prostate-specific membrane antigen, 5T4 oncofetal trophoblast glycoprotein, Orf73 Kaposi's sarcoma-associated herpesvirus, MAGE-C1 (cancer/testis antigen CT7), MAGE-B1 ANTIGEN (MAGE-XP ANTIGEN) (DAM10), MAGE-B2 ANTIGEN (DAME), MAGE-2 ANTIGEN, MAGE-4-a antigen, MAGE-4-b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, TUMOR-ASSOCIATED ANTIGEN CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologically defined breast cancer antigen NY-BR-16, Chromogranin A; parathyroid secretory protein 1, DUPAN-2, CA 19-9, CA 72-4, CA 195 and L6.

Embodiments of the above-described method comprise a B cell target selected from the group consisting of CD10, CD19, CD20, CD21, CD22, CD23, CD24, CD37, CD38, CD39, CD40, CD72, CD73, CD74, CDw75, CDw76, CD77, CD78, CD79a/b, CD80, CD81, CD82, CD83, CD84, CD85, CD86, CD89, CD98, CD126, CD127, CDw130, CD138 and CDw150.

In other embodiments of the above-described method, the TNF receptor superfamily member is selected from the group consisting of 4-1BB/TNFRSF9, NGF R/TNFRSF16, BAFF R/TNFRSF13C, Osteoprotegerin/TNFRSF11B, BCMA/TNFRSF17, OX40/TNFRSF4, CD27/TNFRSF7, RANK/TNFRSF11A, CD30/TNFRSF8, RELT/TNFRSF19L, CD40/TNFRSF5, TACI/TNFRSF13B, DcR3/TNFRSF6B, TNF RI/TNFRSF1A, DcTRAIL R1/TNFRSF23, TNF RIFTNFRSF1B, DcTRAIL R2/TNFRSF22, TRAIL R1/TNFRSF10A, DR3/TNFRSF25, TRAIL R2/TNFRSF10B, DR6/TNFRSF21, TRAIL R3/TNFRSF10C, EDAR, TRAIL R4/TNFRSF10D, Fas/TNFRSF6, TROY/TNFRSF19, GITR/TNFRSF18, TWEAK R/TNFRSF12, HVEM/TNFRSF14, XEDAR, Lymphotoxin beta R/TNFRSF3, 4-1BB Ligand/TNFSF9, Lymphotoxin, APRIL/TNFSF13, Lymphotoxin beta/TNFSF3, BAFF/TNFSF13C, OX40 Ligand/TNFSF4, CD27 Ligand/TNFSF7, TL1A/TNFSF15, CD30 Ligand/TNFSF8, TNF-alpha/TNFSF1A, CD40 Ligand/TNFSF5, TNF-beta/TNFSF1B, EDA-A2, TRAIL/TNFSF10, Fas Ligand/TNFSF6, TRANCE/TNFSF11, GITR Ligand/TNFSF18, TWEAK/TNFSF12 and LIGHT/TNFSF14.

The above-described method also includes embodiments in which the Hedgehog family member is selected from the group consisting of Patched and Smoothened. In yet other embodiments, the proteoglycan-related molecule is selected from the group consisting of proteoglycans and regulators thereof.

Additional embodiments of the method are drawn to processes in which the receptor tyrosine kinase is selected from the group consisting of Axl, FGF R4, C1q R1/CD93, FGF R5, DDR1, Flt-3, DDR2, HGF R, Dtk, IGF-I R, EGF R, IGF-II R, Eph, INSRR, EphAl, Insulin R/CD220, EphA2, M-CSF R, EphA3, Mer, EphA4, MSP R/Ron, EphA5, MuSK, EphA6, PDGF R alpha, EphA7, PDGF R beta, EphA8, Ret, EphBl, ROR1, EphB2, ROR2, EphB3, SCF R/c-kit, EphB4, Tie-1, EphB6, Tie-2, ErbB2, TrkA, ErbB3, TrkB, ErbB4, TrkC, FGF R1, VEGF R1/Flt-1, FGF R2, VEGF R2/Flk-1, FGF R3 and VEGF R3/Flt-4.

In other embodiments of the method, the Transforming Growth Factor (TGF)-beta superfamily member is selected from the group consisting of Activin RIA/ALK-2, GFR alpha-1, Activin RIB/ALK-4, GFR alpha-2, Activin RIIA, GFR alpha-3, Activin RIIB, GFR alpha-4, ALK-1, MIS RII, ALK-7, Ret, BMPR-IA/ALK-3, TGF-beta RI/ALK-5, BMPR-IB/ALK-6, TGF-beta RII, BMPR-II, TGF-beta RIIb, Endoglin/CD105 and TGF-beta RIII.

Yet other embodiments of the method comprise a Wnt-related molecule selected from the group consisting of Frizzled-1, Frizzled-8, Frizzled-2, Frizzled-9, Frizzled-3, sFRP-1, Frizzled-4, sFRP-2, Frizzled-5, sFRP-3, Frizzled-6, sFRP-4, Frizzled-7, MFRP, LRP 5, LRP 6, Wnt-1, Wnt-8a, Wnt-3a, Wnt-10b, Wnt-4, Wnt-11, Wnt-5a, Wnt-9a and Wnt-7a.

In other embodiments of the method, the receptor ligand is selected from the group consisting of 4-1BB Ligand/TNFSF9, Lymphotoxin, APRIL/TNFSF13, Lymphotoxin beta/

TNFSF3, BAFF/TNFSF13C, OX40 Ligand/TNFSF4, CD27 Ligand/TNFSF7, TL1A/TNFSF15, CD30 Ligand/TNFSF8, TNF-alpha/TNFSF1A, CD40 Ligand/TNFSF5, TNF-beta/TNFSF1B, EDA-A2, TRAIL/TNFSF10, Fas Ligand/TNFSF6, TRANCE/TNFSF11, GITR Ligand/TNFSF18, TWEAK/TNFSF12, LIGHT/TNFSF14, Amphiregulin, NRG1 isoform GGF2, Betacellulin, NRG1 Isoform SMDF, EGF, NRG1-alpha/HRG1-alpha, Epigen, NRG1-beta 1/HRG1-beta 1, Epiregulin, TGF-alpha, HB-EGF, TMEFF1/Tomoregulin-1, Neuregulin-3, TMEFF2, IGF-I, IGF-II, Insulin, Activin A, Activin B, Activin AB, Activin C, BMP-2, BMP-7, BMP-3, BMP-8, BMP-3b/GDF-10, BMP-9, BMP-4, BMP-15, BMP-5, Decapentaplegic, BMP-6, GDF-1, GDF-8, GDF-3, GDF-9, GDF-5, GDF-11, GDF-6, GDF-15, GDF-7, Artemin, Neurturin, GDNF, Persephin, TGF-beta, TGF-beta 2, TGF-beta 1, TGF-beta 3, LAP (TGF-beta 1), TGF-beta 5, Latent TGF-beta 1, Latent TGF-beta bpl, TGF-beta 1.2, Lefty, Nodal, MIS/AMH, FGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-23, FGF-10, KGF/FGF-7, FGF-11, Neuropilin-1, P1GF, Neuropilin-2, P1GF-2, PDGF, PDGF-A, VEGF, PDGF-B, VEGF-B, PDGF-C, VEGF-C, PDGF-D, VEGF-D and PDGF-AB.

In still other embodiments, the T-cell target is selected from the group consisting of 2B4/SLAMF4, IL-2 R alpha, 4-1BB/TNFRSF9, IL-2 R beta, ALCAM, B7-1/CD80, IL-4 R, B7-H3, BLAME/SLAMF8, BTLA, IL-6 R, CCR3, IL-7 R alpha, CCR4, CXCR1/IL-8 RA, CCR5, CCR6, IL-10 R alpha, CCR7, IL-10 R beta, CCR8, IL-12 R beta 1, CCR9, IL-12 R beta 2, CD2, IL-13 R alpha 1, IL-13, CD3, CD4, ILT2/CD85j, ILT3/CD85k, ILT4/CD85d, ILT5/CD85a, Integrin alpha 4/CD49d, CD5, Integrin alpha E/CD103, CD6, Integrin alpha M/CD11b, CD8, Integrin alpha X/CD11c, Integrin beta 2/CD18, KIR/CD158, CD27/TNFRSF7, KIR2DL1, CD28, KIR2DL3, CD30/TNFRSF8, KIR2DL4/CD158d, CD31/PECAM-1, KIR2DS4, CD40 Ligand/TNFSF5, LAG-3, CD43, LAIR1, CD45, LAIR2, CD83, Leukotriene B4 R1, CD84/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common gamma Chain/IL-2 R gamma, Osteopontin, CRACC/SLAMF7, PD-1, CRTAM, PSGL-1, CTLA-4, RANK/TNFRSF11A, CX3CR1, CX3CL1, L-Selectin, CXCR3, SIRP beta 1, CXCR4, SLAM, CXCR6, TCCR/WSX-1, DNAM-1, Thymopoietin, EMMPRIN/CD147, TIM-1, EphB6, TIM-2, Fas/TNFRSF6, TIM-3, Fas Ligand/TNFSF6, TIM-4, Fc gamma RIII/CD16, TIM-6, GITR/TNFRSF18, TNF RI/TNFRSF1A, Granulysin, TNF RII/TNFRSF1B, HVEM/TNFRSF14, TRAIL R1/TNFRSF10A, ICAM-1/CD54, TRAIL R2/TNFRSF10B, ICAM-2/CD102, TRAIL R3/TNFRSF10C, IFN-gamma R1, TRAIL R4/TNFRSF10D, IFN-gamma R2, TSLP, IL-1 RI and TSLP R.

In other embodiments, the NK cell receptor is selected from the group consisting of 2B4/SLAMF4, KIR2DS4, CD155/PVR, KIR3□L1, CD94, LMIR1/CD300A, CD69, LMIR2/CD300c, CRACC/SLAMF7, LMIR3/CD300LF, DNAM-1, LMIR5/CD300LB, Fc epsilon RII, LMIR6/CD300LE, Fc gamma RI/CD64, MICA, Fc gamma RIIB/CD32b, MICB, Fc gamma RIIC/CD32c, MULT-1, Fc gamma RIIA/CD32a, Nectin-2/CD112, Fc gamma RIII/CD16, NKG2A, FcRH1/IRTA5, NKG2C, FcRH2/IRTA4, NKG2D, FcRH4/IRTA1, NKp30, FcRH5/IRTA2, NKp44, Fc Receptor-like 3/CD16-2, NKp46/NCR1, NKp80/KLRF1, NTB-A/SLAMF6, Rae-1, Rae-1 alpha, Rae-1 beta, Rae-1 delta, H60, Rae-1 epsilon, ILT2/CD85j, Rae-1 gamma, ILT3/CD85k, TREM-1, ILT4/CD85d, TREM-2, ILT5/CD85a, TREM-3, KIR/CD158, TREML1/TLT-1, KIR2DL1, ULBP-1, KIR2DL3, ULBP-2, KIR2DL4/CD158d and ULBP-3.

In other embodiments, the monocyte/macrophage cell target is selected from the group consisting of B7-1/CD80, ILT4/CD85d, B7-H1, ILT5/CD85a, Common beta Chain, Integrin alpha 4/CD49d, BLAME/SLAMF8, Integrin alpha X/CD11c, CCL6/C10, Integrin beta 2/CD18, CD155/PVR, Integrin beta 3/CD61, CD31/PECAM-1, Latexin, CD36/SR-B3, Leukotriene B4 R1, CD40/TNFRSF5, LIMPII/SR-B2, CD43, LMIR1/CD300A, CD45, LMIR2/CD300c, CD68, LMIR3/CD300LF, CD84/SLAMF5, LMIR5/CD300LB, CD97, LMIR6/CD300LE, CD163, LRP-1, CD2F-10/SLAMF9, MARCO, CRACC/SLAMF7, MD-1, ECF-L, MD-2, EMMPRIN/CD147, MGL2, Endoglin/CD105, Osteoactivin/GPNMB, Fc gamma RI/CD64, Osteopontin, Fc gamma RIIB/CD32b, PD-L2, Fc gamma RIIC/CD32c, Siglec-3/CD33, Fc gamma RIIA/CD32a, SIGNR1/CD209, Fc gamma RIII/CD16, SLAM, GM-CSF R alpha, TCCR/WSX-1, ICAM-2/CD102, TLR3, IFN-gamma R1, TLR4, IFN-gamma R2, TREM-1, IL-1 RII, TREM-2, ILT2/CD85j, TREM-3, ILT3/CD85k, TREML1/TLT-1, 2B4/SLAMF4, IL-10 R alpha, ALCAM, IL-10 R beta, Aminopeptidase N/ANPEP, ILT2/CD85j, Common beta Chain, ILT3/CD85k, C1q R1/CD93, ILT4/CD85d, CCR1, ILT5/CD85a, CCR2, Integrin alpha 4/CD49d, CCRS, Integrin alpha M/CD11b, CCR8, Integrin alpha X/CD11c, CD155/PVR, Integrin beta 2/CD18, CD14, Integrin beta 3/CD61, CD36/SR-B3, LAIR1, CD43, LAIR2, CD45, Leukotriene B4 R1, CD68, LIMPII/SR-B2, CD84/SLAMF5, LMIR1/CD300A, CD97, LMIR2/CD300c, CD163, LMIR3/CD300LF, Coagulation Factor III/Tissue Factor, LMIR5/CD300LB, CX3CR1, CX3CL1, LMIR6/CD300LE, CXCR4, LRP-1, CXCR6, M-CSF R, DEP-1/CD148, MD-1, DNAM-1, MD-2, EMMPRIN/CD147, MMR, Endoglin/CD105, NCAM-L1, Fc gamma RI/CD64, PSGL-1, Fc gamma RIII/CD16, RP105, G-CSF R, L-Selectin, GM-CSF R alpha, Siglec-3/CD33, HVEM/TNFRSF14, SLAM, ICAM-1/CD54, TCCR/WSX-1, ICAM-2/CD102, TREM-1, IL-6 R, TREM-2, CXCR1/IL-8 RA, TREM-3 and TREML1/TLT-1.

In yet other embodiments of the method, a Dendritic cell target is selected from the group consisting of CD36/SR-B3, LOX-1/SR-E1, CD68, MARCO, CD163, SR-AI/MSR, CDSL, SREC-I, CL-P1/COLEC12, SREC-II, LIMPII/SR-B2, RP105, TLR4, TLR1, TLRS, TLR2, TLR6, TLR3, TLR9, 4-1BB Ligand/TNFSF9, IL-12/IL-23 p40, 4-Amino-1,8-naphthalimide, ILT2/CD85j, CCL21/6Ckine, ILT3/CD85k, 8-oxo-dG, ILT4/CD85d, 8D6A, ILT5/CD85a, A2B5, Integrin alpha 4/CD49d, Aag, Integrin beta 2/CD18, AMICA, Langerin, B7-2/CD86, Leukotriene B4 R1, B7-H3, LMIR1/CD300A, BLAME/SLAMF8, LMIR2/CD300c, C1q R1/CD93, LMIR3/CD300LF, CCR6, LMIR5/CD300LB, CCR7, LMIR6/CD300LE, CD40/TNFRSF5, MAG/Siglec-4a, CD43, MCAM, CD45, MD-1, CD68, MD-2, CD83, MDL-1/CLEC5A, CD84/SLAMF5, MMR, CD97, NCAM-L1, CD2F-10/SLAMF9, Osteoactivin/GPNMB, Chem 23, PD-L2, CLEC-1, RP105, CLEC-2, Siglec-2/CD22, CRACC/SLAMF7, Siglec-3/CD33, DC-SIGN, Siglec-5, DC-SIGNR/CD299, Siglec-6, DCAR, Siglec-7, DCIR/CLEC4A, Siglec-9, DEC-205, Siglec-10, Dectin-1/CLEC7A, Siglec-F, Dectin-2/CLEC6A, SIGNR1/CD209, DEP-1/CD148, SIGNR4, DLEC, SLAM, EMMPRIN/CD147, TCCR/WSX-1, Fc gamma RI/CD64, TLR3, Fc gamma RIIB/CD32b, TREM-1, Fc gamma RIIC/CD32c, TREM-2, Fc gamma RIIA/CD32a, TREM-3, Fc gamma RIII/CD16, TREML1/TLT-1, ICAM-2/CD102 and Vanilloid R1.

In still other embodiments of the method, the angiogenesis target is selected from the group consisting of Angiopoietin- 1, Angiopoietin-like 2, Angiopoietin-2, Angiopoietin-like 3, Angiopoietin-3, Angiopoietin-like 7/CDT6, Angiopoietin-4, Tie-1, Angiopoietin-like 1, Tie-2, Angiogenin, iNOS, Coagulation Factor III/Tissue Factor, nNOS, CTGF/CCN2, NOV/CCN3, DANCE, OSM, EDG-1, Plfr, EG-VEGF/PK1, Proliferin, Endostatin, ROBO4, Erythropoietin, Thrombospondin-1, Kininostatin, Thrombospondin-2, MFG-E8, Thrombospondin-4, Nitric Oxide, VG5Q, eNOS, EphAl, EphA5, EphA2, EphA6, EphA3, EphA7, EphA4, EphA8, EphBl, EphB4, EphB2, EphB6, EphB3, Ephrin-A1, Ephrin-A4, Ephrin-A2, Ephrin-A5, Ephrin-A3, Ephrin-B1, Ephrin-B3, Ephrin-B2, FGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-23, FGF-10, KGF/FGF-7, FGF-11, FGF R1, FGF R4, FGF R2, FGF R5, FGF R3, Neuropilin-1, Neuropilin-2, Semaphorin 3A, Semaphorin 6B, Semaphorin 3C, Semaphorin 6C, Semaphorin 3E, Semaphorin 6D, Semaphorin 6A, Semaphorin 7A, MMP, MMP-11, MMP-1, MMP-12, MMP-2, MMP-13, MMP-3, MMP-14, MMP-7, MMP-15, MMP-8, MMP-16/MT3-MMP, MMP-9, MMP-24/MT5-MMP, MMP-10, MMP-25/MT6-MMP, TIMP-1, TIMP-3, TIMP-2, TIMP-4, ACE, IL-13 R alpha 1, IL-13, C1q R1/CD93, Integrin alpha 4/CD49d, VE-Cadherin, Integrin beta 2/CD18, CD31/PECAM-1, KLF4, CD36/SR-B3, LYVE-1, CD151, MCAM, CL-P1/COLEC12, Nectin-2/CD112, Coagulation Factor III/Tissue Factor, E-Selectin, D6, P-Selectin, DC-SIGNR/CD299, SLAM, EMMPRIN/CD147, Tie-2, Endoglin/CD105, TNF RI/TNFRSF1A, EPCR, TNF RII/TNFRSF1B, Erythropoietin R, TRAIL R1/TNFRSF10A, ESAM, TRAIL R2/TNFRSF10B, FABP5, VCAM-1, ICAM-1/CD54, VEGF R2/Flk-1, ICAM-2/CD102, VEGF R3/Flt-4, IL-1 RI and VG5Q.

Other embodiments of the method provide multivalent binding proteins wherein at least one of binding domain 1 and binding domain 2 specifically binds a target selected from the group consisting of Prostate-specific Membrane Antigen (Folate Hydrolase 1), Epidermal Growth Factor Receptor (EGFR), Receptor for Advanced Glycation End products (RAGE, also known as Advanced Glycosylation End product Receptor or AGER), IL-17 A, IL-17 F, P19 (IL23A and IL12B), Dickkopf-1 (Dkk1), NOTCH1, NG2 (Chondroitin Sulfate ProteoGlycan 4 or CSPG4), IgE (IgHE or IgH2), IL-22R (IL22RA1), IL-21, Amyloid β oligomers (Ab oligomers), Amyloid β Precursor Protein (APP), NOGO Receptor (RTN4R), Low Density LipoproteinReceptor-Related Protein 5 (LRP5), IL-4, Myostatin (GDF8), Very Late Antigen 4, an alpha 4, beta 1 integrin (VLA4 or ITGA4), an alpha 4, beta 7 integrin found on leukocytes, and IGF-1R. For example, a VLA4 target may be recognized by a multivalent binding protein in which at least one of binding domain 1 and binding domain 2 is a binding domain derived from Natalizumab (Antegren).

In some embodiments, the cancer cell is a transformed, or cancerous, hematopoietic cell. In certain of these embodiments, at least one of the first binding domain and the second binding domain recognizes a target selected from the group consisting of a B-cell target, a monocyte/macrophage target, a dendritic cell target, an NK-cell target and a T-cell target, each as herein defined. Further, at least one of the first binding domain and the second binding domain can recognize a myeloid targets, including but not limited to, CD5, CD10, CD11b, CD11c, CD13, CD14, CD15, CD18, CD19, CD20, CD21, CD22, CD23, CD25, CD27, CD29, CD30, CD31, CD33, CD34, CD35, CD38, CD43, CD45, CD64, CD66, CD68, CD70, CD80, CD86, CD87, CD88, CD89, CD98, CD100, CD103, CD111, CD112, CD114, CD115, CD116, CD117, CD118, CD119, CD120a, CD120b, CDw123, CDw131, CD141, CD162, CD163, CD177, CD312, IRTA1, IRTA2, IRTA3, IRTA4, IRTA5, B-B2, B-B8 and B-cell antigen receptor.

Other embodiments of the invention are drawn to the multivalent binding protein, as described herein, comprising a sequence selected from the group consisting of SEQ ID NOS: 2, 4, 6, 103, 105, 107, 109, 332, 333, 334, and 345. Other embodiments are directed to the multivalent binding protein comprising a sequence selected from the group consisting of SEQ ID NOS: 355, 356, 357, 358, 359, 360, 361, 362, 363, 364 and 365.

In other embodiments, the multivalent and multispecific binding protein with effector function has a first binding domain and a second binding domain that recognize a target pair selected from the group consisting of EPHB4-KDR and TIE-TEK. In such embodiments, the protein has a first binding domain recognizing EPHB4 and a second binding domain recognizing KDR or a first binding domain recognizing KDR and a second binding domain recognizing EPHB4. Analogously, the protein may have a first binding domain recognizing TIE and a second binding domain recognizing TEK, or a first binding domain recognizing TEK and a second binding domain recognizing TIE.

In a related aspect, the invention provides a multivalent binding protein with effector function, wherein the constant sub-region recognizes an effector cell $F_C$ receptor (e.g., $F_C\gamma RI$, $F_C\gamma RII$, $F_C\gamma RIII$, $F_C\alpha R$, and $F_C\epsilon RI$. In particular embodiments, the constant sub-region recognizes an effector cell surface protein selected from the group consisting of CD2, CD3, CD16, CD28, CD32, CD40, CD56, CD64, CD89, $F_C\epsilon RI$, KIR, thrombospondin R, NKG2D, 2B4/NAIL and 41BB. The constant sub-region may comprise a $C_{H2}$ domain and a $C_{H3}$ domain derived from the same, or different, immunoglobulins, antibody isotypes, or allelic variants. In some embodiments, the $C_{H3}$ domain is truncated and comprises a C-terminal sequence selected from the group consisting of SEQ ID NOS: 366, 367, 368, 369, 370 and 371. Preferably, the $C_{H2}$ domain and the scorpion linker are derived from the same class, or from the same sub-class, of immunoglobulin, when the linker is a hinge-like peptide derived from an immunoglobulin.

Some proteins according to the invention are also contemplated as further comprising a scorpion linker of at least about 5 amino acids attached to the constant sub-region and attached to the second binding domain, thereby localizing the scorpion linker between the constant sub-region and the second binding domain. Typically, the scorpion linker peptide length is between 5-45 amino acids. Scorpion linkers include hinge-like peptides derived from immunoglobulin hinge regions, such as IgG1, IgG2, IgG3, IgG4, IgA, and IgE hinge regions. Preferably, a hinge-like scorpion linker will retain at least one cysteine capable of forming an interchain disulfide bond under physiological conditions. Scorpion linkers derived from IgG1 may have 1 cysteine or two cysteines, and will preferably retain the cysteine corresponding to an N-terminal hinge cysteine of IgG1. In some embodiments, the scorpion linker is extended relative to a cognate immunoglobulin hinge region and, in exemplary embodiments, comprises a sequence selected from the group consisting of SEQ ID NOS: 351, 352, 353 and 354. Non-hinge-like peptides are also contemplated as scorpion linkers, provided that such peptides provide sufficient spacing and flexibility to provide a single-chain protein capable of forming two binding domains, one located towards each protein terminus (N and C) relative to a more centrally located constant sub-region domain. Exemplary non-hinge-like scorpion linkers include peptides from the stalk region of type II C-lectins, such as the stalk regions of CD69, CD72, CD94, NKG2A and NKG2D. In some embodiments, the scorpion linker comprises a sequence selected from the group consisting of SEQ ID NOS: 373, 374, 375, 376 and 377.

The proteins may also comprise a linker of at least about 5 amino acids attached to the constant sub-region and attached to the first binding domain, thereby localizing the linker between the constant sub-region and the first binding domain. In some embodiments, linkers are found between the constant sub-region and each of the two binding domains, and those linkers may be of the same or different sequence, and of the same or different lengths.

The constant sub-region of the proteins according to the invention provides at least one effector function. Any effector function known in the art to be associated with an immunoglobulin (e.g., an antibody) is contemplated, such as an effector function selected from the group consisting of antibody-dependent cell-mediated cytotoxicity (ADCC), complement-dependent cytotoxicity (CDC), relatively extended in vivo half-life (relative to the same molecule lacking a constant sub-region), FcR binding, protein A binding, and the like. In some embodiments, the extended half-lives of proteins of the invention are at least 28 hours in a human. Of course, proteins intended for administration to non-human subjects will exhibit relatively extended half-lives in those non-human subjects, and not necessarily in humans.

In general, the proteins (including polypeptides and peptides) of the invention exhibit a binding affinity of less than $10^{-9}$ M, or at least $10^{-6}$ M, for at least one of the first binding domain and the second binding domain.

Another aspect of the invention is drawn to a pharmaceutical composition comprising a protein as described herein and a pharmaceutically acceptable adjuvant, carrier or excipient. Any adjuvant, carrier, or excipient known in the art is useful in the pharmaceutical compositions of the invention.

Yet another aspect of the invention provides a method of producing a protein as described above comprising introducing a nucleic acid encoding the protein into a host cell and incubating the host cell under conditions suitable for expression of the protein, thereby expressing the protein, preferably at a level of at least 1 mg/liter. In some embodiments, the method further comprises isolating the protein by separating it from at least one protein with which it is associated upon intracellular expression. Suitable host cells for expressing the nucleic acids to produce the proteins of the invention include, but are not limited to, a host cell selected from the group consisting of a VERO cell, a HeLa cell, a CHO cell, a COS cell, a W138 cell, a BHK cell, a HepG2 cell, a 3T3 cell, a RIN cell, an MDCK cell, an A549 cell, a PC12 cell, a K562 cell, a HEK293 cell, an N cell, a *Spodoptera frugiperda* cell, a *Saccharomyces cerevisiae* cell, a *Pichia pastoris* cell, any of a variety of fungal cells and any of a variety of bacterial cells (including, but not limited to, *Escherichia coli, Bacillus subtilis, Salmonella typhimurium*, and a Streptomycete).

The invention also provides a method of producing a nucleic acid encoding the protein, as described above, comprising covalently linking the 3' end of a polynucleotide encoding a first binding domain derived from an immunoglobulin variable region to the 5' end of a polynucleotide encoding a constant sub-region, covalently linking the 5' end of a polynucleotide encoding a scorpion linker to the 3' end of the polynucleotide encoding the constant sub-region, and covalently linking the 5' end of a polynucleotide encoding a second binding domain derived from an immunoglobulin variable region to the 3' end of the polynucleotide encoding the scorpion linker, thereby generating a nucleic acid encoding a multivalent binding protein with effector function. Each of these coding regions may be separated by a coding region for a linker or hinge-like peptide as part of a single-chain structure according to the invention. In some embodiments, the method produces a polynucleotide encoding a first binding domain that comprises a sequence selected from the group consisting of SEQ ID NO: 2 (anti-CD20 variable region, oriented $V_L$-$V_H$), SEQ ID NO: 4 (anti-CD28 variable region, oriented $V_L$-$V_H$) and SEQ ID NO: 6 (anti-CD28 variable region, oriented $V_H$-$V_L$) in single-chain form, rather than requiring assembly from separately encoded polypeptides as must occur for heteromultimeric proteins, including natural antibodies. Exemplary polynucleotide sequences encoding first binding domains are polynucleotides comprising any of SEQ ID NOS: 1, 3 or 5.

This aspect of the invention also provides methods for producing encoding nucleic acids that further comprise a linker polynucleotide inserted between the polynucleotide encoding a first binding domain and the polynucleotide encoding a constant sub-region, the linker polynucleotide encoding a peptide linker of at least 5 amino acids. Additionally, these methods produce nucleic acids that further comprise a linker polynucleotide inserted between the polynucleotide encoding a constant sub-region and the polynucleotide encoding a second binding domain, the linker polynucleotide encoding a peptide linker of at least 5 amino acids. Preferably, the encoded peptide linkers are between 5 and 45 amino acids.

The identity of the linker regions present either between BD1 and EFD or EFD and BD2 may be derived from other sequences identified from homologous -Ig superfamily members. In developing novel linkers derived from existing sequences present in homologous members of the -Ig superfamily, it may be preferable to avoid sequence stretches similar to those located between the end of a C-like domain and the transmembrane domain, since such sequences are often substrates for protease cleavage of surface receptors from the cell to create soluble forms. Sequence comparisons between different members of the -Ig superfamily and subfamilies can be compared for similarities between molecules in the linker sequences that join multiple V-like domains or between the V and C like domains. From this analysis, conserved, naturally occurring sequence patterns may emerge; these sequences when used as the linkers between subdomains of the multivalent fusion proteins should be more protease resistant, might facilitate proper folding between Ig loop regions, and would not be immunogenic since they occur in the extracellular domains of endogenous cell surface molecules.

The nucleic acids themselves comprise another aspect of the invention. Contemplated are nucleic acids encoding any of the proteins of the invention described herein. As such, the nucleic acids of the invention comprise, in 5' to 3' order, a coding region for a first binding domain, a constant sub-region sequence, and a coding region for a second binding domain. Also contemplated are nucleic acids that encode protein variants wherein the two binding domains and the constant sub-region sequences are collectively at least 80%, and preferably at least 85%, 90%, 95%, or 99% identical in amino acid sequence to the combined sequences of a known immunoglobulin variable region sequence and a known constant sub-region sequence. Alternatively, the protein variants of the invention are encoded by nucleic acids that hybridize to a nucleic acid encoding a non-variant protein of the invention under stringent hybridization conditions of 0.015 M sodium chloride, 0.0015 M sodium citrate at 65-68° C. or 0.015 M sodium chloride, 0.0015 M sodium citrate, and 50% formamide at 42° C. Variant nucleic acids of the invention exhibit the capacity to hybridize under the conditions defined immediately above, or exhibit 90%, 95%, 99%, or 99.9% sequence identity to a nucleic acid encoding a non-variant protein according to the invention.

In related aspects, the invention provides a vector comprising a nucleic acid as described above, as well as host cells comprising a vector or a nucleic acid as described herein. Any vector known in the art may be used (e.g., plasmids, phagemids, phasmids, cosmids, viruses, artificial chromosomes, shuttle vectors and the like) and those of skill in the art will recognize which vectors are particularly suited for a given purpose. For example, in methods of producing a protein according to the invention, an expression vector operable in the host cell of choice is selected. In like manner, any host cell capable of being genetically transformed with a nucleic acid or vector of the invention is contemplated. Preferred host cells are higher eukaryotic host cells, although lower eukaryotic (e.g., yeast) and prokaryotic (bacterial) host cells are contemplated.

Another aspect of the invention is drawn to a method of inducing damage to a target cell comprising contacting a target cell with a therapeutically effective amount of a protein as described herein. In some embodiments, the target cell is contacted in vivo by administration of the protein, or an encoding nucleic acid, to an organism in need. Contemplated within this aspect of the invention are methods wherein the multivalent single-chain binding protein induces an additive amount of damage to the target cell, which is that amount of damage expected from the sum of the damage attributable to separate antibodies comprising one or the other of the binding domains. Also contemplated are methods wherein the multivalent single-chain binding protein induces a synergistic amount of damage to the target cell compared to the sum of the damage induced by a first antibody comprising the first binding domain but not the second binding domain and a second antibody comprising the second binding domain but not the first binding domain. In some embodiments, the multivalent single-chain binding protein is multispecific and comprises a binding domain pair specifically recognizing a pair of antigens selected from the group consisting of CD19/CD20, CD20/CD21, CD20/CD22, CD20/CD40, CD20/CD79a, CD20/CD79b, CD20/CD81, CD21/CD79b, CD37/CD79b, CD79b/CD81, CD19/CL II (i.e., MHC class II), CD20/CL II, CD30/CL II, CD37/CL II, CD72/CL II, and CD79b/CL II.

This aspect of the invention also comprehends methods wherein the multispecific, multivalent single-chain binding protein induces an inhibited amount of damage to the target cell compared to the sum of the damage induced by a first antibody comprising the first binding domain but not the second binding domain and a second antibody comprising the second binding domain but not the first binding domain. Exemplary embodiments include methods wherein the multispecific, multivalent single-chain binding protein comprises a binding domain pair specifically recognizing a pair of antigens selected from the group consisting of CD20/CL II, CD21/CD79b, CD22/CD79b, CD40/CD79b, CD70/CD79b, CD72/CD79b, CD79a/CD79b, CD79b/CD80, CD79b/CD86, CD21/CL II, CD22/CL II, CD23/CL II, CD40/CL II, CD70/CL II, CD80/CL II, CD86/CL II, CD19/CD22, CD20/CD22, CD21/CD22, CD22/CD23, CD22/CD30, CD22/CD37, CD22/CD40, CD22/CD70, CD22/CD72, CD22/79a, CD22/79b, CD22/CD80, CD22/CD86 and CD22/CL II.

In a related aspect, the invention provides a method of treating a cell proliferation disorder, e.g., cancer, comprising administering a therapeutically effective amount of a protein (as described herein), or an encoding nucleic acid, to an organism in need. Those of skill in the art, including medical and veterinary professionals, are proficient at identifying organisms in need of treatment. Disorders contemplated by the invention as amenable to treatment include a disorder selected from the group consisting of a cancer, an autoimmune disorder, Rous Sarcoma Virus infection and inflammation. In some embodiments, the protein is administered by in vivo expression of a nucleic acid encoding the protein as described herein. The invention also comprehends administering the protein by a route selected from the group consisting of intravenous injection, intraarterial injection, intramuscular injection, subcutaneous injection, intraperitoneal injection and direct tissue injection.

Another aspect of the invention is directed to a method of ameliorating a symptom associated with a cell proliferation disorder comprising administering a therapeutically effective amount of a protein, as described herein, to an organism in need. Those of skill in the art are also proficient at identifying those disorders, or diseases or conditions, exhibiting symptoms amenable to amelioration. In some embodiments, the symptom is selected from the group consisting of pain, heat, swelling and joint stiffness.

Yet another aspect of the invention is drawn to a method of treating an infection associated with an infectious agent comprising administering a therapeutically effective amount of a protein according to the invention to a patient in need, wherein the protein comprises a binding domain that specifically binds a target molecule of the infectious agent. Infectious agents amenable to treatment according to this aspect of the invention include prokaryotic and eukaryotic cells, viruses (including bacteriophage), foreign objects, and infectious organisms such as parasites (e.g., mammalian parasites).

A related aspect of the invention is directed to a method of ameliorating a symptom of an infection associated with an infectious agent comprising administering an effective amount of a protein according to the invention to a patient in need, wherein the protein comprises a binding domain that specifically binds a target molecule of the infectious agent. Those of skill in the medical and veterinary arts will be able to determine an effective amount of a protein on a case-by-case basis, using routine experimentation.

Yet another related aspect of the invention is a method of reducing the risk of infection attributable to an infectious agent comprising administering a prophylactically effective amount of a protein according to the invention to a patient at risk of developing the infection, wherein the protein comprises a binding domain that specifically binds a target molecule of the infectious agent. Those of skill in the relevant arts will be able to determine a prophylactically effective amount of a protein on a case-by-case basis, using routine experimentation.

Another aspect of the invention is drawn to the above-described multivalent single-chain binding protein wherein at least one of the first binding domain and the second binding domain specifically binds an antigen selected from the group consisting of CD19, CD20, CD21, CD22, CD23, CD30, CD37, CD40, CD70, CD72, CD79a, CD79b, CD80, CD81, CD86, and a major histocompatibility complex class II peptide.

In certain embodiments, one of the first binding domain and the second binding domain specifically binds CD20, and in some of these embodiments, the other binding domain specifically binds an antigen selected from the group consisting of CD19, CD20, CD21, CD22, CD23, CD30, CD37, CD40, CD70, CD72, CD79a, CD79b, CD80, CD81, CD86, and a major histocompatibility complex class II peptide. For example, in one embodiment, the first binding domain is capable of specifically binding CD20 while the second binding domain is capable of specifically binding, e.g., CD19. In another embodiment, the first binding domain binds CD19 while the second binding domain binds CD20. An embodiment in which both binding domains bind CD20 is also contemplated.

In certain other embodiments according to this aspect of the invention, one of the first binding domain and the second binding domain specifically binds CD79b, and in some of these embodiments, the other binding domain specifically binds an antigen selected from the group consisting of CD19, CD20, CD21, CD22, CD23, CD30, CD37, CD40, CD70, CD72, CD79a, CD79b, CD80, CD81, CD86, and a major histocompatibility complex class II peptide. Exemplary embodiments include distinct multi-specific, multivalent single-chain binding proteins in which a first binding domain: second binding domain specifically binds CD79b:CD19 or CD19:CD79b. A multivalent binding protein having first and second binding domains recognizing CD79b is also comprehended.

In still other certain embodiments, one of the first binding domain and the second binding domain specifically binds a major histocompatibility complex class II peptide, and in some of these embodiments, the other binding domain specifically binds an antigen selected from the group consisting of CD19, CD20, CD21, CD22, CD23, CD30, CD37, CD40, CD70, CD72, CD79a, CD79b, CD80, CD81, CD86, and a major histocompatibility complex class II peptide. For example, in one embodiment, the first binding domain is capable of specifically binding a major histocompatibility complex class II peptide while the second binding domain is capable of specifically binding, e.g., CD19. In another embodiment, the first binding domain binds CD19 while the second binding domain binds a major histocompatibility complex class II peptide. An embodiment in which both binding domains bind a major histocompatibility complex class II peptide is also contemplated.

In yet other embodiments according to this aspect of the invention, one of the first binding domain and the second binding domain specifically binds CD22, and in some of these embodiments, the other binding domain specifically binds an antigen selected from the group consisting of CD19, CD20, CD21, CD22, CD23, CD30, CD37, CD40, CD70, CD72, CD79a, CD79b, CD80, CD81, CD86, and a major histocompatibility complex class II peptide. Exemplary embodiments include distinct multi-specific, multivalent single-chain binding proteins in which a first binding domain:second binding domain specifically binds CD22:CD19 or CD19:CD22. A multivalent binding protein having first and second binding domains recognizing CD22 is also comprehended.

A related aspect of the invention is directed to the above-described multivalent single-chain binding protein wherein the protein has a synergistic effect on a target cell behavior relative to the sum of the effects of each of the binding domains. In some embodiments, the protein comprises a binding domain pair specifically recognizing a pair of antigens selected from the group consisting of CD20-CD19, CD20-CD21, CD20-CD22, CD20-CD40, CD20-CD79a, CD20-CD79b and CD20-CD81.

The invention further comprehends a multivalent single-chain binding protein as described above wherein the protein has an additive effect on a target cell behavior relative to the sum of the effects of each of the binding domains. Embodiments according to this aspect of the invention include multi-specific proteins comprising a binding domain pair specifically recognizing a pair of antigens selected from the group consisting of CD20-CD23, CD20-CD30, CD20-CD37, CD20-CD70, CD20-CD80, CD20-CD86, CD79b-CD37, CD79b-CD81, major histocompatibility complex class II peptide-CD30, and major histocompatibility complex class II peptide-CD72.

Yet another related aspect of the invention is a multivalent single-chain binding protein as described above wherein the protein has an inhibitory effect on a target cell behavior relative to the sum of the effects of each of the binding domains. In some embodiments, the protein is multispecific and comprises a binding domain pair specifically recognizing a pair of antigens selected from the group consisting of CD20-major histocompatibility complex class II peptide, CD79b-CD19, CD79b-CD20, CD79b-CD21, CD79b-CD22, CD79b-CD23, CD79b-CD30, CD79b-CD40, CD79b-CD70, CD79b-CD72, CD79b-CD79a, CD79b-CD80, CD79b-CD86, CD79b-major histocompatibility complex class II peptide, major histocompatibility complex class II peptide-CD19, major histocompatibility complex class II peptide-CD20, major histocompatibility complex class II peptide-CD21, major histocompatibility complex class II peptide-CD22, major histocompatibility complex class II peptide-CD23, major histocompatibility complex class II peptide-CD37, major histocompatibility complex class II peptide-CD40, major histocompatibility complex class II peptide-CD70, major histocompatibility complex class II peptide-CD79a, major histocompatibility complex class II peptide-CD79b, major histocompatibility complex class II peptide-CD80, major histocompatibility complex class II peptide-CD81, major histocompatibility complex class II peptide-CD86, CD22-CD19, CD22-CD40, CD22-CD79b, CD22-CD86 and CD22-major histocompatibility complex class II peptide.

Another aspect of the invention is a method of identifying at least one of the binding domains of the multivalent binding molecule, such as a multispecific binding molecule, described above comprising: (a) contacting an anti-isotypic antibody with an antibody specifically recognizing a first antigen and an antibody specifically recognizing a second antigen; (b) further contacting a target comprising at least one of said antigens with the composition of step (a); and (c) measuring an activity of the target, wherein the activity is used to identify at least one of the binding domains of the multivalent binding molecule. In some embodiments, the target is a diseased cell, such as a cancer cell (e.g., a cancerous B-cell) or an auto-antibody-producing B-cell.

In each of the foregoing methods of the invention, it is contemplated that the method may further comprise a plurality of multivalent single-chain binding proteins. In some embodiments, a binding domain of a first multivalent single-chain binding protein and a binding domain of a second multivalent single-chain binding protein induce a synergistic, additive, or inhibitory effect on a target cell, such as a synergistic, additive, or inhibitory amount of damage to the target cell. The synergistic, additive or inhibitory effects of a plurality of multivalent single-chain binding proteins is determined by comparing the effect of such a plurality of proteins to the combined effect of an antibody comprising one of the binding domains and an antibody comprising the other binding domain.

A related aspect of the invention is directed to a composition comprising a plurality of multivalent single-chain binding proteins as described above. In some embodiments, the composition comprises a plurality of multivalent single-chain binding proteins wherein a binding domain of a first multivalent single-chain binding protein and a binding domain of a second multivalent single-chain binding protein are capable of inducing a synergistic, additive, or inhibitory effect on a target cell, such as a synergistic, additive or inhibitory amount of damage to the target cell.

The invention further extends to a pharmaceutical composition comprising the composition described above and a pharmaceutically acceptable carrier, diluent or excipient. In addition, the invention comprehends a kit comprising the composition as described herein and a set of instructions for administering said composition to exert an effect on a target cell, such as to damage the target cell.

Finally, the invention also comprehends a kit comprising the protein as described herein and a set of instructions for administering the protein to treat a cell proliferation disorder or to ameliorate a symptom of the cell proliferation disorder.

Other features and advantages of the present invention will be better understood by reference to the following detailed description, including the examples.

BRIEF DESCRIPTION OF THE DRAWING

FIG. 3 shows two columnar graphs illustrating the binding properties of the 2H7-sssIgG (P238S/P331S)-STD1-2e12 LH and HL derivatives expressed from COS cells. These experiments were performed with crude culture supernatants rather than purified proteins. Serial dilutions from undiluted to 16× of the culture supernatants were incubated with either CD20 expressing cells (WIL-25) or CD28 expressing cells (CD28 CHO). Binding activity in the supernatants was compared to control samples testing binding of the relevant single specificity SMIP, such as TRU-015, or 2e12 VLVH, or 2e12VHVL SMIPs. Binding in each sample was detected using fluorescein isothyocyanate (FITC) conjugated goat anti-human IgG at a dilution of 1:100.

FIG. 6 A) shows a table which identifies the linkers joining the constant sub-region and binding domain 2. The linkers are identified by name, sequence, sequence identifier, sequence length, and the sequence of the fusion with binding domain 2. B) shows a table identifying a variety of constructs identifying elements of exemplified molecules according to the invention. In addition to identifying the multivalent binding molecules by name, the elements of those molecules are disclosed in terms of binding domain 1 (BD1), the constant sub-region (hinge and effector domain or EFD), a linker (see FIG. 6A for additional information regarding the linkers), and binding domain 2 (BD2). The sequences of a number of exemplified multivalent binding proteins are provided, and are identified in the figure by a sequence identifier. Other multivalent binding proteins have altered elements, or element orders, with predictable alterations in sequence from the disclosed sequences.

FIG. 7 shows a composite columnar graph illustrating the binding of purified proteins at a single, fixed concentration to CD20 expressing WIL-2S cells and to CHO cells expressing CD28. "H1-H6" refers to the 2H7-sss-hIgG-Hx-2e12 molecules with the H1-H6 linkers and the 2e12 V regions in the orientation of $V_H$-$V_L$. "L1-L6" refers to the 2H7-sss-hIgG-Lx-2e12 molecules with the L1-L6 linkers and the 2e12 V regions in the orientation of $V_L$-$V_H$. All the molecules were tested at a concentration of 0.72 µg/ml, and the binding detected using FITC conjugated goat anti-human IgG at 1:100. The mean fluorescence intensity for each sample was then plotted as paired bar graphs for the two target cell types tested versus each of the multivalent constructs being tested, L1-L6, or H1-H6.

FIG. 9 shows Western Blots of the [2H7-sss-hIgG-H6-2e12] fusion proteins and the relevant single specificity SMIPs probed with either (a) CD28mIgG or with (b) a Fab reactive with the 2H7 specificity. The results show that the presence of the H6 linker results in the generation of cleaved forms of the multivalent constructs which are missing the CD28 binding specificity.

FIG. 10 shows binding curves of the different linker variants for the [TRU015-sss-IgG-Hx-2e12 HL] H1-H6 linker forms. The first panel shows the binding curves for binding to CD20 expressing WIL-2S cells. The second panel shows the binding curves for binding of the different forms to CD28 CHO cells. These binding curves were generated with serial dilutions of protein A purified fusion protein, and binding detected using FITC conjugated goat anti-human IgG at 1:100.

FIG. 11 shows a table summarizing the results of SEC fractionation of 2H7-sss-IgG-2e12 HL multispecific fusion proteins with variant linkers H1-H7. Each row in the table lists a different linker variant of the [2H7-sss-IgG-Hx-2e12-HL] fusion proteins. The retention time of the peak of interest (POI), and the percentage of the fusion protein present in POI, and the percentage of protein found in other forms is also tabulated. The cleavage of the molecules is also listed, with the degree of cleavage indicated in a qualitative way, with (Yes), Yes, and YES, or No being the four possible choices.

FIG. 12 shows two graphs with binding curves for [2H7-sss-hIgG-Hx-2e12] multispecific fusion proteins with variant linkers H3, H6, and H7 linkers to cells expressing CD20 or CD28. Serial dilutions of the protein A purified fusion proteins from 10 µg/ml down to 0.005 µg/ml were incubated with either CD20 expressing WIL-2S cells or CD28 CHO cells. Binding was detected using FITC conjugated goat anti-human IgG at 1:100. Panel A shows the binding to WIL-25 cells, and panel B shows the binding to CD28 CHO cells.

FIG. 14 shows results obtained using another multispecific fusion construct variant. In this case, modifications were made in the specificity for BD2, so that the V regions for the G28-1 antibody were used to create a CD37 specific binding domain. Shown are two graphs which illustrate the relative ability of CD20 and/or CD37 antibodies to block the binding of the [2H7-sss-IgG-Hx-G28-1] multispecific fusion protein to Ramos or BJAB cells expressing the CD20 and CD37 targets. Each cell type was preincubated with either the CD20 specific antibody (25 µg/ml) or the CD37 specific antibody (10 µg/ml) or both reagents (these are mouse anti-human reagents) prior to incubation with the multispecific fusion protein. Binding of the multispecific fusion protein was then detected with a FITC goat anti-human IgG reagent at 1:100, (preadsorbed to mouse to eliminate cross-reactivity).

FIG. 16 shows a table tabulating the results of a co-culture experiment where PBMC were cultured in the presence of TRU 015, G28-1 SMIP, both molecules together, or the [2H7-sss-IgG-H7-G28-1HL] variant. The fusion proteins were used at 20 µg/ml, and incubated for 24 hours or 72 hours. Samples were then stained with CD3 antibodies conjugated to FITC, and either CD19 or CD40 specific antibodies conjugated to PE, then subjected to flow cytometry. The percentage of cells in each gate was then tabulated.

FIG. 17 shows two columnar graphs of the effects on B cell line apoptosis after 24 hour incubation with the [2H7-sss-hIgG-H7-G28-1 HL] molecule or control single CD20 and/or CD37 specificity SMIPs alone or in combination. The percentage of annexin V-propidium iodide positive cells is plotted as a function of the type of test reagent used for the coincubation experiments. Panel A shows the results obtained using Ramos cells, and panel B shows those for Daudi cells. Each single CD20 or CD37 directed SMIP is shown at the concentrations indicated; in addition, where combinations of the two reagents were used, the relative amount of each reagent is shown in parentheses. For the multispecific CD20-CD37 fusion protein, concentrations of 5, 10, and 20 µg/ml were tested.

FIG. 18 shows two graphs of the [2H7-hIgG-G19-4] molecule variants and their binding to either CD3 expressing cells (Jurkats) or CD20 expressing cells (WIL-2S). The molecules include [2H7-sss-hIgG-STD1-G19-4 HL], LH, and [2H7-csc-hIgG-STD1-G19-4 HL]. Protein A purified fusion proteins were titrated from 20 µg/ml down to 0.05 µg/ml, and the binding detected using FITC goat anti-human IgG at 1:100. MFI (mean fluorescence intensity) is plotted as a function of protein concentration.

FIG. 19 shows the results of ADCC assays performed with the [2H7-hIgG-STD1-G19-4 HL] molecule variants with either an SSS hinge or a CSC hinge, BJAB target cells, and either total human PBMC as effector cells or NK cell depleted PBMC as effector cells. Killing was scored as a function of concentration of the multispecific fusion proteins. The killing observed with these molecules was compared to that seen using G19-4, TRU 015, or a combination of these two reagents. Each data series plots a different test reagent, with the percent specific killing plotted as a function of protein concentration.

FIG. 29 presents graphs of data establishing that treatment of lymphoma cells with scorpions resulted in increased signaling capacity compared to free SMIPs, as measured by calcium ion flux.

DETAILED DESCRIPTION

Figure 1:
FIG. 1 shows a schematic representation of the multivalent single-chain molecules envisioned by the invention. Individual subdomains of the fusion protein expression cassette are indicated by separate shapes/blocks on the figure. BD1 refers to binding domain 1, linker 1 refers to any potential linker or hinge like peptide between BD1 and the "effector function domain", indicated as EFD. This subdomain is usually an engineered form of the Fc domain of human IgG1, but may include other subdomains with one or more effector functions as defined herein. Linker 2 refers to the linker sequence, if any, present between the carboxy terminus of the EFD and the binding domain 2, BD2.

The present invention provides compositions of relatively small peptides having at least two binding regions or domains, which may provide one or more binding specificities, derived from variable binding domains of immunoglobulins, such as antibodies, disposed terminally relative to an effector domain comprising at least part of an immunoglobulin constant region (i.e., a source from which a constant sub-region, as defined herein, may be derived), as well as nucleic acids, vectors and host cells involved in the recombinant production of such peptides and methods of using the peptide compositions in a variety of diagnostic and therapeutic applications, including the treatment of a disorder as well as the amelioration of at least one symptom of such a disorder. The peptide compositions advantageously arrange a second binding domain C-terminal to the effector domain, an arrangement that unexpectedly provides sterically unhindered or less hindered binding by at least two binding domains of the peptide, while retaining an effector function or functions of the centrally disposed effector domain.

The first and second binding domains of the multivalent peptides according to the invention may be the same (i.e., have identical or substantially identical amino acid sequences and be monospecific) or different (and be multispecific). Although different in terms of primary structure, the first and second binding domains may recognize and bind to the same epitope of a target molecule and would therefore be monospecific. In many instances, however, the binding domains will differ structurally and will bind to different binding sites, resulting in a multivalent, multispecific protein. Those different binding sites may exist on a single target molecule or on different target molecules. In the case of the two binding molecules recognizing different target molecules, those target molecules may exist, e.g., on or in the same structure (e.g., the surface of the same cell), or those target molecules may exist on or in separate structures or locales. For example, a multispecific binding protein according to the invention may have binding domains that specifically bind to target molecule on the surfaces of distinct cell types. Alternatively, one binding domain may specifically bind to a target on a cell surface and the other binding domain may specifically bind to a target not found associated with a cell, such as an extracellular structural (matrix) protein or a free (e.g., soluble or stromal) protein.

The first and second binding domains are derived from one or more regions of the same, or different, immunoglobulin protein structures such as antibody molecules. The first and/or second binding domain may exhibit a sequence identical to the sequence of a region of an immunoglobulin, or may be a modification of such a sequence to provide, e.g., altered binding properties or altered stability. Such modifications are known in the art and include alterations in amino acid sequence that contribute directly to the altered property such as altered binding, for example by leading to an altered secondary or higher order structure for the peptide. Also contemplated are modified amino acid sequences resulting from the incorporation of non-native amino acids, such as non-native conventional amino acids, unconventional amino acids and imino acids. In some embodiments, the altered sequence results in altered post-translational processing, for example leading to an altered glycosylation pattern.

Any of a wide variety of binding domains derived from an immunoglobulin or immunoglobulin-like polypeptide (e.g., receptor) are contemplated for use in scorpions. Binding domains derived from antibodies comprise the CDR regions of a $V_L$ and a $V_H$ domain, seen, e.g., in the context of using a binding domain from a humanized antibody. Binding domains comprising complete $V_L$ and $V_H$ domains derived from an antibody may be organized in either orientation. A scorpion according to the invention may have any of the binding domains herein described. For scorpions having at least one binding domain recognizing a B-cell, exemplary scorpions have at least one binding domain derived from CD3, CD10, CD19, CD20, CD21, CD22, CD23, CD24, CD37, CD38, CD39, CD40, CD72, CD73, CD74, CDw75, CDw76, CD77, CD78, CD79a/b, CD80, CD81, CD82, CD83, CD84, CD85, CD86, CD89, CD98, CD126, CD127, CDw130, CD138 or CDw150. In some embodiments, the scorpion is a multivalent binding protein comprising at least one binding domain having a sequence selected from the group consisting of SEQ ID NOS: 2, 4, 6, 103, 105, 107 and 109. In some embodiments, a scorpion comprises a binding domain comprising a sequence selected from the group consisting of any of SEQ ID NOS: 332-345. In some embodiments, a scorpion comprises a binding domain comprising a sequence derived from immunoglobulin $V_L$ and $V_H$ domains, wherein the sequence is selected from the group consisting of any of SEQ ID NOS: 355-365. The invention further contemplates scorpions comprising a binding domain that has the opposite orientation of $V_L$ and $V_H$ having sequences deducible from any of SEQ ID NOS:355-365.

For embodiments in which either, or both, of the binding domains are derived from more than one region of an immunoglobulin (e.g., an Ig $V_L$ region and an Ig $V_H$ region), the plurality of regions may be joined by a linker peptide. Moreover, a linker may be used to join the first binding domain to a constant sub-region. Joinder of the constant sub-region to a second binding domain (i.e., binding domain 2 disposed towards the C-terminus of a scorpion) is accomplished by a scorpion linker. These scorpion linkers are preferably between about 2-45 amino acids, or 2-38 amino acids, or 5-45 amino acids. For example, the H1 linker is 2 amino acids in length and the STD2 linker is 38 amino acids in length. Beyond general length considerations, a scorpion linker region suitable for use in the scorpions according to the invention includes an antibody hinge region selected from the group consisting of IgG, IgA, IgD and IgE hinges and variants thereof. For example, the scorpion linker may be an antibody hinge region selected from the group consisting of human IgG1, human IgG2, human IgG3, and human IgG4, and variants thereof. In some embodiments, the scorpion linker region has a single cysteine residue for formation of an interchain disulfide bond. In other embodiments, the scorpion linker has two cysteine residues for formation of interchain disulfide bonds. In some embodiments, a scorpion linker region is derived from an immunoglobulin hinge region or a C-lectin stalk region and comprises a sequence selected from the group consisting of SEQ ID NOS:111, 113, 115, 117, 119, 121, 123, 125, 127, 129, 131, 133, 135, 149, 151, 153, 155, 157, 159, 161, 163, 165, 167, 169, 231, 233, 235, 237, 239, 241, 243, 245, 247, 249, 251, 253, 255, 257, 259, 261, 263, 265, 267, 269, 271, 273, 275, 277, 279, 281, 287, 289, 297, 305, 307, 309, 310, 311, 313, 314, 315, 316, 317, 318, 319, 320, 321, 322, 323, 324, 325, 326, 327, 328, 329, 330, 331, 346, 351, 352, 353, 354, 373, 374, 375, 376 and 377. More generally, any sequence of amino acids identified in the sequence listing as providing a sequence derived from a hinge region is contemplated for use as a scorpion linker in the scorpion molecules according to the invention. In addition, a scorpion linker derived from an Ig hinge is a hinge-like peptide domain having at least one free cysteine capable of participating in an interchain disulfide bond. Preferably, a scorpion linker derived from an Ig hinge peptide retains a cysteine that corresponds to the hinge cysteine disposed towards the N-terminus of that hinge. Preferably, a scorpion linker derived from an IgG1 hinge has one cysteine or has two cysteines corresponding to hinge cysteines. Additionally, a scorpion linker is a stalk region of a Type II C-lectin molecule. In some embodiments, a scorpion comprises a scorpion linker having a sequence selected from the group consisting of SEQ ID NOS:373-377.

The centrally disposed constant sub-region is derived from a constant region of an immunoglobulin protein. The constant sub-region generally is derived from a $C_{H2}$ portion of a $C_H$ region of an immunoglobulin in the abstract, although it may be derived from a $C_{H2}$-$C_{H3}$ portion. Optionally, the constant sub-region may be derived from a hinge-$C_{H2}$ or hinge-$C_{H2}$—$C_{H3}$ portion of an immunoglobulin, placing a peptide corresponding to an Ig hinge region N-terminal to the constant sub-region and disposed between the constant sub-region and binding domain 1. Also, portions of the constant sub-region may be derived from the $C_H$ regions of different immunoglobulins. Further, the peptide corresponding to an Ig CH3 may be truncated, leaving a C-terminal amino acid sequence selected from the group consisting of SEQ ID NOS:366-371. It is preferred, however, that in embodiments in which a scorpion hinge is a hinge-like peptide derived from an immunoglobulin hinge, that the scorpion linker and the constant sub-region be derived from the same type of immunoglobulin. The constant sub-region provides at least one activity associated with a $C_H$ region of an immunoglobulin, such as antibody-dependent cell-mediated cytotoxicity (ADCC), complement-dependent cytotoxicity (CDC), protein A binding, binding to at least one $F_C$ receptor, reproducibly detectable stability relative to a protein according to the invention except for the absence of a constant sub-region, and perhaps placental transfer where generational transfer of a molecule according to the invention would be advantageous, as recognized by one of skill in the art. As with the above-described binding domains, the constant sub-region is derived from at least one immunoglobulin molecule and exhibits an identical or substantially identical amino acid sequence to a region or regions of at least one immunoglobulin. In some embodiments, the constant sub-region is modified from the sequence or sequences of at least one immunoglobulin (by substitution of one or more non-native conventional or unconventional, e.g., synthetic, amino acids or imino acids), resulting in a primary structure that may yield an altered secondary or higher order structure with altered properties associated therewith, or may lead to alterations in post-translational processing, such as glycosylation.

For those binding domains and constant sub-regions exhibiting an identical or substantially identical amino acid sequence to one or more immunoglobulin polypeptides, the post-translational modifications of the molecule according to the invention may result in a molecule modified relative to the immunoglobulin(s) serving as a basis for modification. For example, using techniques known in the art, a host cell may be modified, e.g. a CHO cell, in a manner that leads to an altered polypeptide glycosylation pattern relative to that polypeptide in an unmodified (e.g., CHO) host cell.

Provided with such molecules, and the methods of recombinantly producing them in vivo, new avenues of targeted diagnostics and therapeutics have been opened to allow, e.g., for the targeted recruitment of effector cells of the immune system (e.g., cytotoxic T lymphocytes, natural killer cells, and the like) to cells, tissues, agents and foreign objects to be destroyed or sequestered, such as cancer cells and infectious agents. In addition to localizing therapeutic cells to a site of treatment, the peptides are useful in localizing therapeutic compounds, such as radiolabeled proteins. Further, the peptides are also useful in scavenging deleterious compositions, for example by associating a deleterious composition, such as a toxin, with a cell capable of destroying or eliminating that toxin (e.g., a macrophage). The molecules of the invention are useful in modulating the activity of binding partner molecules, such as cell surface receptors. This is shown in FIG. 17 where apoptotic signaling through CD20 and/or CD37 is markedly enhanced by a molecule of the present invention. The effect of this signaling is the death of the targeted cell. Diseases and conditions where the elimination of defined cell populations is beneficial would include infectious and parasitic diseases, inflammatory and autoimmune conditions, malignancies, and the like. One skilled in the art would recognize that there is no limitation of the approach to the enhancement of apoptotic signaling. Mitotic signaling and signaling leading to differentiation, activation, or inactivation of defined cell populations can be induced by molecules of the present invention through the appropriate selection of binding partner molecules. Further consideration of the disclosure of the invention will be facilitated by a consideration of the following express definitions of terms used herein.

A "single-chain binding protein" is a single contiguous arrangement of covalently linked amino acids, with the chain capable of specifically binding to one or more binding partners sharing sufficient determinants of a binding site to be detectably bound by the single-chain binding protein. Exemplary binding partners include proteins, carbohydrates, lipids and small molecules.

For ease of exposition, "derivatives" and "variants" of proteins, polypeptides, and peptides according to the invention are described in terms of differences from proteins and/or polypeptides and/or peptides according to the invention, meaning that the derivatives and variants, which are proteins/polypeptides/peptides according to the invention, differ from underivatized or non-variant proteins, polypeptides or peptides of the invention in the manner defined. One of skill in the art would understand that the derivatives and variants themselves are proteins, polypeptides and peptides according to the invention.

An "antibody" is given the broadest definition consistent with its meaning in the art, and includes proteins, polypeptides and peptides capable of binding to at least one binding partner, such as a proteinaceous or non-proteinaceous antigen. An "antibody" as used herein includes members of the immunoglobulin superfamily of proteins, of any species, of single- or multiple-chain composition, and variants, analogs, derivatives and fragments of such molecules. Specifically, an "antibody" includes any form of antibody known in the art, including but not limited to, monoclonal and polyclonal antibodies, chimeric antibodies, CDR-grafted antibodies, humanized antibodies, single-chain variable fragments, bi-specific antibodies, diabodies, antibody fusions, and the like.

A "binding domain" is a peptide region, such as a fragment of a polypeptide derived from an immunoglobulin (e.g., an antibody), that specifically binds one or more specific binding partners. If a plurality of binding partners exists, those partners share binding determinants sufficient to detectably bind to the binding domain. Preferably, the binding domain is a contiguous sequence of amino acids.

An "epitope" is given its ordinary meaning herein of a single antigenic site, i.e., an antigenic determinant, on a substance (e.g., a protein) with which an antibody specifically interacts, for example by binding. Other terms that have acquired well-settled meanings in the immunoglobulin (e.g., antibody) art, such as a "variable light region," variable heavy region," "constant light region," constant heavy region," "antibody hinge region," "complementarity determining region," "framework region," "antibody isotype," "$F_C$ region," "single-chain variable fragment" or "scFv," "diabody," "chimera," "CDR-grafted antibody," "humanized antibody," "shaped antibody," "antibody fusion," and the like, are each given those well-settled meanings known in the art, unless otherwise expressly noted herein.

Terms understood by those in the art as referring to antibody technology are each given the meaning acquired in the art, unless expressly defined herein. Examples of such terms are "$V_L$" and "$V_H$", referring to the variable binding region derived from an antibody light and heavy chain, respectively; and $C_L$ and $C_H$, referring to an "immunoglobulin constant region," i.e., a constant region derived from an antibody light or heavy chain, respectively, with the latter region understood to be further divisible into $C_{H1}$, $C_{H2}$, $C_{H3}$ and $C_{H4}$ constant region domains, depending on the antibody isotype (IgA, IgD, IgE, IgG, IgM) from which the region was derived. CDR means "complementarity determining region." A "hinge region" is derived from the amino acid sequence interposed between, and connecting, the $C_{H1}$ and $C_{H2}$ regions of a single chain of an antibody, which is known in the art as providing flexibility, in the form of a "hinge," to whole antibodies.

A "constant sub-region" is a term defined herein to refer to a peptide, polypeptide, or protein sequence that corresponds to, or is derived from, one or more constant region domains of an antibody. Thus, a constant sub-region may include any or all of the following domains: a $C_{H1}$ domain, a hinge region, a $C_{H2}$ domain, a $C_{H3}$ domain (IgA, IgD, IgG, IgE, and IgM), and a $C_{H4}$ domain (IgE, IgM). A constant sub-region as defined herein, therefore, can refer to a polypeptide region corresponding to an entire constant region of an antibody, or a portion thereof. Typically, a constant sub-region of a polypeptide, or encoding nucleic acid, of the invention has a hinge, $C_{H2}$ domain, and $C_{H3}$ domain.

An "effector function" is a function associated with or provided by a constant region of an antibody. Exemplary effector functions include antibody-dependent cell-mediated cytotoxicity (ADCC), complement activation and complement-dependent cytotoxicity (CDC), $F_C$ receptor binding, and increased plasma half-life, as well as placental transfer. An effector function of a composition according to the invention is detectable; preferably, the specific activity of the composition according to the invention for that function is about the same as the specific activity of a wild-type antibody with respect to that effector function, i.e., the constant sub-region of the multivalent binding molecule preferably has not lost any effector function relative to a wild-type antibody]

A "linker" is a peptide, or polynucleotide, that joins or links other peptides or polynucleotides. Typically, a peptide linker is an oligopeptide of from about 2-50 amino acids, with typical polynucleotide linkers encoding such a peptide linker and, thus, being about 6-150 nucleotides in length. Linkers join the first binding domain to a constant sub-region domain. An exemplary peptide linker is $(Gly_4Ser)_3$. A scorpion linker is used to join the C-terminal end of a constant sub-region to a second binding domain. The scorpion linker may be derived from an immunoglobulin hinge region or from the stalk region of a type II C-lectin, as described in greater detail below.

A "target" is given more than one meaning, with the context of usage defining an unambiguous meaning in each instance. In its narrowest sense, a "target" is a binding site, i.e., the binding domain of a binding partner for a peptide composition according to the invention. In a broader sense, "target" or "molecular target" refers to the entire binding partner (e.g., a protein), which necessarily exhibits the binding site. Specific targets, such as "CD20," "CD37," and the like, are each given the ordinary meaning the term has acquired in the art. A "target cell" is any prokaryotic or eukaryotic cell, whether healthy or diseased, that is associated with a target molecule according to the invention. Of course, target molecules are also found unassociated with any cell (i.e., a cell-free target) or in association with other compositions such as viruses (including bacteriophage), organic or inorganic target molecule carriers, and foreign objects.

Examples of materials with which a target molecule may be associated include autologous cells (e.g., cancer cells or other diseased cells), infectious agents (e.g., infectious cells and infectious viruses), and the like. A target molecule may be associated with an enucleated cell, a cell membrane, a liposome, a sponge, a gel, a capsule, a tablet, and the like, which may be used to deliver, transport or localize a target molecule, regardless of intended use (e.g., for medical treatment, as a result of benign or unintentional provision, or to further a bioterrorist threat). "Cell-free," "virus-free," "carrier-free," "object-free," and the like refer to target molecules that are not associated with the specified composition or material.

"Binding affinity" refers to the strength of non-covalent binding of the peptide compositions of the invention and their binding partners. Preferably, binding affinity refers to a quantitative measure of the attraction between members of a binding pair.

An "adjuvant" is a substance that increases or aids the functional effect of a compound with which it is in association, such as in the form of a pharmaceutical composition comprising an active agent and an adjuvant. An "excipient" is an inert substance used as a diluent in formulating a pharmaceutical composition. A "carrier" is a typically inert substance used to provide a vehicle for delivering a pharmaceutical composition.

"Host cell" refers to any cell, prokaryotic or eukaryotic, in which is found a polynucleotide, protein or peptide according to the invention.

"Introducing" a nucleic acid or polynucleotide into a host cell means providing for entry of the nucleic acid or polynucleotide into that cell by any means known in the art, including but not limited to, in vitro salt-mediated precipitations and other forms of transformation of naked nucleic acid/polynucleotide or vector-borne nucleic acid/polynucleotide, virus-mediated infection and optionally transduction, with or without a "helper" molecule, ballistic projectile delivery, conjugation, and the like.

"Incubating" a host cell means maintaining that cell under environmental conditions known in the art to be suitable for a given purpose, such as gene expression. Such conditions, including temperature, ionic strength, oxygen tension, carbon dioxide concentration, nutrient composition, and the like, are well known in the art.

"Isolating" a compound, such as a protein or peptide according to the invention, means separating that compound from at least one distinct compound with which it is found associated in nature, such as in a host cell expressing the compound to be isolated, e.g. by isolating spent culture medium containing the compound from the host cells grown in that medium.

An "organism in need" is any organism at risk of, or suffering from, any disease, disorder or condition that is amenable to treatment or amelioration with a composition according to the invention, including but not limited to any of various forms of cancer, any of a number of autoimmune diseases, radiation poisoning due to radiolabeled proteins, peptides and like compounds, ingested or internally produced toxins, and the like, as will become apparent upon review of the entire disclosure. Preferably, an organism in need is a human patient.

"Ameliorating" a symptom of a disease means detectably reducing the severity of that symptom of disease, as would be known in the art. Exemplary symptoms include pain, heat, swelling and joint stiffness.

Unless clear from context, the terms "protein," "peptide," and "polypeptide" are used interchangeably herein, with each referring to at least one contiguous chain of amino acids. Analogously, the terms "polynucleotide," "nucleic acid," and "nucleic acid molecule" are used interchangeably unless it is clear from context that a particular, and non-interchangeable, meaning is intended.

"Pharmaceutically acceptable salt" refers to salts of the compounds of the present invention derived from the combination of such compounds and an organic or inorganic acid (acid addition salts) or an organic or inorganic base (base addition salts).

Using the terms as defined above, a general description of the various aspects of the invention is provided below. Following the general description, working examples are presented to provide supplementary evidence of the operability and usefulness of the invention disclosed herein.

Proteins and Polypeptides

In certain embodiments of the invention, there are provided any of the herein-described multivalent binding proteins with effector function, including binding domain-immunoglobulin fusion proteins, wherein the multivalent binding protein or peptide with effector function comprises two or more binding domain polypeptide sequences. Each of the binding domain polypeptide sequences is capable of binding or specifically binding to a target(s), such as an antigen(s), which target(s) or antigen(s) may be the same or may be different. The binding domain polypeptide sequence may be derived from an antigen variable region or it may be derived from immunoglobulin-like molecules, e.g., receptors that fold in ways that mimic immunoglobulin molecules. The antibodies from which the binding domains are derived may be antibodies that are polyclonal, including monospecific polyclonal, monoclonal (mAbs), recombinant, chimeric, humanized (such as CDR-grafted), human, single-chain, catalytic, and any other form of antibody known in the art, as well as fragments, variants or derivatives thereof. In some embodiments, each of the binding domains of the protein according to the invention is derived from a complete variable region of an immunoglobulin. In preferred embodiments, the binding domains are each based on a human Ig variable region. In other embodiments, the protein is derived from a fragment of an Ig variable region. In such embodiments, it is preferred that each binding domain polypeptide sequence correspond to the sequences of each of the complementarity determining regions of a given Ig variable region. Also contemplated within the invention are binding domains that correspond to fewer than all CDRs of a given Ig variable region, provided that such binding domains retain the capacity to specifically bind to at least one target.

The multivalent binding protein with effector function also has a constant sub-region sequence derived from an immunoglobulin constant region, preferably an antibody heavy chain constant region, covalently juxtaposed between the two binding domains in the multivalent binding protein with effector function.

The multivalent binding protein with effector function also has a scorpion linker that joins the C-terminal end of the constant sub-region to the N-terminal end of binding domain 2. The scorpion linker is not a helical peptide and may be derived from an antibody hinge region, from a region connecting binding domains of an immunoglobulin, or from the stalk region of type II C-lectins. The scorpion linker may be derived from a wild-type hinge region of an immunoglobulin, such as an IgG1, IgG2, IgG3, IgG4, IgA, IgD or an IgE hinge region. In other embodiments, the invention provides multivalent binding proteins with altered hinges. One category of altered hinge regions suitable for inclusion in the multivalent binding proteins is the category of hinges with an altered number of Cysteine residues, particularly those Cys residues known in the art to be involved in interchain disulfide bond formation in immunoglobulin counterpart molecules having wild-type hinges. Thus, proteins may have an IgG1 hinge in which one of the three Cys residues capable of participating in interchain disulfide bond formations is missing. To indicate the Cysteine sub-structure of altered hinges, the Cys subsequence is presented from N- to C-terminus. Using this identification system, the multivalent binding proteins with altered IgG hinges include hinge structures characterized as cxc, xxc, ccx, xxc, xcx, cxx, and xxx. The Cys residue may be either deleted or substituted by an amino acid that results in a conservative substitution or a non-conservative substitution. In some embodiments, the Cysteine is replaced by a Serine. For proteins with scorpion linkers comprising IgG1 hinges, the number of cysteines corresponding to hinge cysteines is reduced to 1 or 2, preferably with one of those cysteines corresponding to the hinge cysteine disposed closest to the N-terminus of the hinge.

For proteins with scorpion linkers comprising IgG2 hinges, there may be 0, 1, 2, 3, or 4 Cys residues. Forscorpion linkers comprising altered IgG2 hinges containing 1, 2 or 3 Cys residues, all possible subsets of Cys residues are contemplated. Thus, for such linkers having one Cys, the multivalent binding proteins may have the following Cys motif in the hinge region: cxxx, xcxx, xxcx, or xxxc. For scorpion linkers comprising IgG2 hinge variants having 2 or 3 Cys residues, all possible combinations of retained and substituted (or deleted) Cys residues are contemplated. For multivalent binding proteins with scorpion linkers comprising altered IgG3 or altered IgG4 hinge regions, a reduction in Cys residues from 1 to one less than the complete number of Cys residues in the hinge region is contemplated, regardless of whether the loss is through deletion or substitution by conservative or non-conservative amino acids (e.g., Serine). In like manner, multivalent binding proteins having a scorpion linker comprising a wild-type IgA, IgD or IgE hinge are contemplated, as are corresponding altered hinge regions having a reduced number of Cys residues extending from 0 to one less than the total number of Cys residues found in the corresponding wild-type hinge. In some embodiments having an IgG1 hinge, the first, or N-terminal, Cys residue of the hinge is retained. For proteins with either wild-type or altered hinge regions, it is contemplated that the multivalent binding proteins will be single-chain molecules capable of forming homo-multimers, such as dimers, e.g., by disulfide bond formation. Further, proteins with altered hinges may have alterations at the termini of the hinge region, e.g., loss or substitution of one or more amino acid residues at the N-terminus, C-terminus or both termini of a given region or domain, such as a hinge domain, as disclosed herein.

In another exemplary embodiment, the constant sub-region is derived from a constant region that comprises a native, or an engineered, IgD hinge region. The wild-type human IgD hinge has one cysteine that forms a disulfide bond with the light chain in the native IgD structure. In some embodiments, this IgD hinge cysteine is mutated (e.g., deleted) to generate an altered hinge for use as a connecting region between binding domains of, for example, a bispecific molecule. Other amino acid changes or deletions or alterations in an IgD hinge that do not result in undesired hinge inflexibility are within the scope of the invention. Native or engineered IgD hinge regions from other species are also within the scope of the invention, as are humanized native or engineered IgD hinges from non-human species, and (other non IgD) hinge regions from other human, or non-human, antibody isotypes, (such as the llama IgG2 hinge).

The invention further comprehends constant sub-regions attached to scorpion linkers that may be derived from hinges that correspond to a known hinge region, such as an IgG1 hinge or an IgD hinge, as noted above. The constant sub-region may contain a modified or altered (relative to wild-type) hinge region in which at least one cysteine residue known to participate in inter-chain disulfide bond linkage is replaced by another amino acid in a conservative substitution (e.g., Ser for Cys) or a non-conservative substitution. The constant sub-region does not include a peptide region or domain that corresponds to an immunoglobulin $C_{H1}$ domain.

Alternative hinge and linker sequences that can be used as connecting regions are from portions of cell surface receptors that connect immunoglobulin V-like or immunoglobulin C-like domains. Regions between Ig V-like domains where the cell surface receptor contains multiple Ig V-like domains in tandem, and between Ig C-like domains where the cell surface receptor contains multiple tandem Ig C-like regions are also contemplated as connecting regions. Hinge and linker sequences are typically from 5 to 60 amino acids long, and may be primarily flexible, but may also provide more rigid characteristics. In addition, linkers frequently provide spacing that facilitates minimization of steric hindrance between the binding domains. Preferably, these hinge and linker peptides are primarily a helical in structure, with minimal β sheet structure. The preferred sequences are stable in plasma and serum and are resistant to proteolytic cleavage. The preferred sequences may contain a naturally occurring or added motif such as the CPPC motif that confers a disulfide bond to stabilize dimer formation. The preferred sequences may contain one or more glycosylation sites. Examples of preferred hinge and linker sequences include, but are not limited to, the interdomain regions between the Ig V-like and Ig C-like regions of CD2, CD4, CD22, CD33, CD48, CD58, CD66, CD80, CD86, CD150, CD166, and CD244.

The constant sub-region may be derived from a camelid constant region, such as either a llama or camel IgG2 or IgG3.

Specifically contemplated is a constant sub-region having the $C_{H2}$-$C_{H3}$ region from any Ig class, or from any IgG subclass, such as IgG1 (e.g., human IgG1). In preferred embodiments, the constant sub-region and the scorpion linker derived from an immunoglobulin hinge are both derived from the same Ig class. In other preferred embodiments, the constant sub-region and the scorpion linker derived from an immunoglobulin hinge are both derived from the same Ig sub-class. The constant sub-region also may be a CH3 domain from any Ig class or subclass, such as IgG1 (e.g., human IgG1), provided that it is associated with at least one immunoglobulin effector function.

The constant sub-region does not correspond to a complete immunoglobulin constant region (i.e., $C_{H1}$-hinge-$C_{H2}$-$C_{H3}$) of the IgG class. The constant sub-region may correspond to a complete immunoglobulin constant region of other classes, IgA constant domains, such as an IgA1 hinge, an IgA2 hinge, an IgA $C_{H2}$ and an IgA $C_{H3}$ domains with a mutated or missing tailpiece are also contemplated as constant sub-regions. Further, any light chain constant domain may function as a constant sub-region, e.g., $C_K$ or any $C_L$. The constant sub-region may also include JH or JK, with or without a hinge. The constant sub-region may also correspond to engineered antibodies in which, e.g., a loop graft has been constructed by making selected amino acid substitutions using an IgG framework to generate a binding site for a receptor other than a natural $F_CR$(CD16, CD32, CD64, $F_C\epsilon R1$), as would be understood in the art. An exemplary constant sub-region of this type is an IgG $C_{H2}$-$C_{H3}$ region modified to have a CD89 binding site.

This aspect of the invention provides a multivalent binding protein or peptide having effector function, comprising, consisting essentially of, or consisting of (a) an N-terminally disposed binding domain polypeptide sequence derived from an immunoglobulin that is fused or otherwise connected to (b) a constant sub-region polypeptide sequence derived from an immunoglobulin constant region, which preferably includes a hinge region sequence, wherein the hinge region polypeptide may be as described herein, and may comprise, consist essentially of, or consist of, for example, an alternative hinge region polypeptide sequence, in turn fused or otherwise connected to (c) a C-terminally disposed second native or engineered binding domain polypeptide sequence derived from an immunoglobulin.

The centrally disposed constant sub-region polypeptide sequence derived from an immunoglobulin constant region is capable of at least one immunological activity selected from the group consisting of antibody dependent cell-mediated cytotoxicity, CDC, complement fixation, and $F_C$ receptor binding, and the binding domain polypeptides are each capable of binding or specifically binding to a target, such as an antigen, wherein the targets may be the same or different, and may be found in effectively the same physiological environment (e.g., the surface of the same cell) or in different environments (e.g., different cell surfaces, a cell surface and a cell-free location, such as in solution).

This aspect of the invention also comprehends variant proteins or polypeptides exhibiting an effector function that are at least 80%, and preferably 85%, 90%, 95% or 99% identical to a multivalent protein with effector function of specific sequence as disclosed herein.

Polynucleotides

The invention also provides polynucleotides (isolated or purified or pure polynucleotides) encoding the proteins or peptides according to the invention, vectors (including cloning vectors and expression vectors) comprising such polynucleotides, and cells (e.g., host cells) transformed or transfected with a polynucleotide or vector according to the invention. In encoding the proteins or polypeptides of the invention, the polynucleotides encode a first binding domain, a second binding domain and an $F_C$ domain, all derived from immunoglobulins, preferably human immunoglobulins. Each binding domain may contain a sequence corresponding to a full-length variable region sequence (either heavy chain and/or light chain), or to a partial sequence thereof, provided that each such binding domain retains the capacity to specifically bind. The $F_C$ domain may have a sequence that corresponds to a full-length immunoglobulin $F_C$ domain sequence or to a partial sequence thereof, provided that the $F_C$ domain exhibits at least one effector function as defined herein. In addition, each of the binding domains may be joined to the $F_C$ domain via a linker peptide that typically is at least 8, and preferably at least 13, amino acids in length. A preferred linker sequence is a sequence based on the $Gly_4Ser$ motif, such as $(Gly_4Ser)_3$.

Variants of the multivalent binding protein with effector function are also comprehended by the invention. Variant polynucleotides are at least 90%, and preferably 95%, 99%, or 99.9% identical to one of the polynucleotides of defined sequence as described herein, or that hybridizes to one of those polynucleotides of defined sequence under stringent hybridization conditions of 0.015 M sodium chloride, 0.0015 M sodium citrate at 65-68° C. or 0.015 M sodium chloride, 0.0015M sodium citrate, and 50% formamide at 42° C. The polynucleotide variants retain the capacity to encode a multivalent binding protein with effector function.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., Molecular Cloning: A Laboratory Manual, 2nd Ed., Cold Spring Harbor Laboratory, (Cold Spring Harbor, N.Y. 1989).

More stringent conditions (such as higher temperature, lower ionic strength, higher formamide, or other denaturing agent) may also be used; however, the rate of hybridization will be affected. In instances wherein hybridization of deoxyoligonucleotides is concerned, additional exemplary stringent hybridization conditions include washing in 6×SSC, 0.05% sodium pyrophosphate at 37° C. (for 14-base oligonucleotides), 48° C. (for 17-base oligonucleotides), 55° C. (for 20-base oligonucleotides), and 60° C. (for 23-base oligonucleotides).

In a related aspect of the invention, there is provided a method of producing a polypeptide or protein or other construct of the invention, for example, including a multivalent binding protein or peptide having effector function, comprising the steps of (a) culturing a host cell as described or provided for herein under conditions that permit expression of the construct; and (b) isolating the expression product, for example, the multivalent binding protein or peptide with effector function from the host cell or host cell culture.

Constructs

The present invention also relates to vectors, and to constructs prepared from known vectors, that each include a polynucleotide or nucleic acid of the invention, and in particular to recombinant expression constructs, including any of various known constructs, including delivery constructs, useful for gene therapy, that include any nucleic acids encoding multivalent, for example, multispecific, including bi-specific, binding proteins and polypeptides with effector function, as provided herein; to host cells which are genetically engineered with vectors and/or other constructs of the invention and to methods of administering expression or other constructs comprising nucleic acid sequences encoding multivalent, for example, multispecific, including bi-specific, binding proteins with effector function, or fragments or variants thereof, by recombinant techniques.

Various constructs of the invention including multivalent, for example, multispecific binding proteins with effector function, can be expressed in virtually any host cell, including in vivo host cells in the case of use for gene therapy, under the control of appropriate promoters, depending on the nature of the construct (e.g., type of promoter, as described above), and on the nature of the desired host cell (e.g., postmitotic terminally differentiated or actively dividing; e.g., maintenance of an expressible construct as an episome or integrated into the host cell genome).

Appropriate cloning and expression vectors for use with prokaryotic and eukaryotic hosts are described, for example, in Sambrook, et al., *Molecular Cloning: A Laboratory Manual*, Second Edition, Cold Spring Harbor, N.Y., (1989). Exemplary cloning/expression vectors include, but are not limited to, cloning vectors, shuttle vectors, and expression constructs, that may be based on plasmids, phagemids, phasmids, cosmids, viruses, artificial chromosomes, or any nucleic acid vehicle suitable for amplification, transfer, and/or expression of a polynucleotide contained therein that is known in the art. As noted herein, in preferred embodiments of the invention, recombinant expression is conducted in mammalian cells that have been transfected, transformed or transduced with a nucleic acid according to the invention. See also, for example, Machida, Calif., "Viral Vectors for Gene Therapy: Methods and Protocols"; Wolff, J A, "Gene Therapeutics: Methods and Applications of Direct Gene Transfer" (Birkhauser 1994); Stein, U and Walther, W (eds., "Gene Therapy of Cancer: Methods and Protocols" (Humana Press 2000); Robbins, P D (ed.), "Gene Therapy Protocols" (Humana Press 1997); Morgan, J R (ed.), "Gene Therapy Protocols" (Humana Press 2002); Meager, A (ed.), "Gene Therapy Technologies, Applications and Regulations: From Laboratory to Clinic" (John Wiley & Sons Inc. 1999); MacHida, Calif. and Constant, J G, "Viral Vectors for Gene Therapy: Methods and Protocols" (Humana Press 2002); "New Methods Of Gene Therapy For Genetic Metabolic Diseases NIH Guide," Volume 22, Number 35, Oct. 1, 1993. See also U.S. Pat. Nos. 6,384,210; 6,384,203; 6,384,202; 6,384,018; 6,383,814; 6,383,811; 6,383,795; 6,383,794; 6,383,785; 6,383,753; 6,383,746; 6,383,743; 6,383,738; 6,383,737; 6,383,733; 6,383,522; 6,383,512; 6,383,481; 6,383,478; 6,383,138; 6,380,382; 6,380,371; 6,380,369; 6,380,362; 6,380,170; 6,380,169; 6,379,967; and 6,379,966.

Typically, expression constructs are derived from plasmid vectors. One preferred construct is a modified pNASS vector (Clontech, Palo Alto, Calif.), which has nucleic acid sequences encoding an ampicillin resistance gene, a polyadenylation signal and a T7 promoter site. Other suitable mammalian expression vectors are well known (see, e.g., Ausubel et al., 1995; Sambrook et al., supra; see also, e.g., catalogues from Invitrogen, San Diego, Calif.; Novagen, Madison, Wis.; Pharmacia, Piscataway, N.J.). Presently preferred constructs may be prepared that include a dihydrofolate reductase (DHFR)-encoding sequence under suitable regulatory control, for promoting enhanced production levels of the multivalent binding protein with effector function, which levels result from gene amplification following application of an appropriate selection agent (e.g., methotrexate).

Generally, recombinant expression vectors will include origins of replication and selectable markers permitting transformation of the host cell, and a promoter derived from a highly-expressed gene to direct transcription of a downstream structural sequence, as described above. A vector in operable linkage with a polynucleotide according to the invention yields a cloning or expression construct. Exemplary cloning/expression constructs contain at least one expression control element, e.g., a promoter, operably linked to a polynucleotide of the invention. Additional expression control elements, such as enhancers, factor-specific binding sites, terminators, and ribosome binding sites are also contemplated in the vectors and cloning/expression constructs according to the invention. The heterologous structural sequence of the polynucleotide according to the invention is assembled in appropriate phase with translation initiation and termination sequences. Thus, for example, the multivalent binding protein-encoding nucleic acids as provided herein may be included in any one of a variety of expression vector constructs as a recombinant expression construct for expressing such a protein in a host cell. In certain preferred embodiments the constructs, are included in formulations that are administered in vivo. Such vectors and constructs include chromosomal, nonchromosomal and synthetic DNA sequences, e.g., derivatives of SV40; bacterial plasmids; phage DNA; yeast plasmids; vectors derived from combinations of plasmids and phage DNA, viral DNA, such as vaccinia, adenovirus, fowl pox virus, and pseudorabies, or replication deficient retroviruses as described below. However, any other vector may be used for preparation of a recombinant expression construct, and in preferred embodiments such a vector will be replicable and viable in the host.

The appropriate DNA sequence(s) may be inserted into a vector, for example, by a variety of procedures. In general, a DNA sequence is inserted into an appropriate restriction endonuclease cleavage site(s) by procedures known in the art. Standard techniques for cloning, DNA isolation, amplification and purification, for enzymatic reactions involving DNA ligase, DNA polymerase, restriction endonucleases and the like, and various separation techniques are contemplated. A number of standard techniques are described, for example, in Ausubel et al. (1993 *Current Protocols in Molecular Biology*, Greene Publ. Assoc. Inc. & John Wiley & Sons, Inc., Boston, Mass.); Sambrook et al. (1989 *Molecular Cloning*, Second Ed., Cold Spring Harbor Laboratory, Plainview, N.Y.); Maniatis et al. (1982 Molecular Cloning, Cold Spring Harbor Laboratory, Plainview, N.Y.); Glover (Ed.) (1985 *DNA Cloning Vol. I and II*, IRL Press, Oxford, UK); Hames and Higgins (Eds.), (1985 *Nucleic Acid Hybridization*, IRL Press, Oxford, UK); and elsewhere.

The DNA sequence in the expression vector is operatively linked to at least one appropriate expression control sequence (e.g., a constitutive promoter or a regulated promoter) to direct mRNA synthesis. Representative examples of such expression control sequences include promoters of eukaryotic cells or their viruses, as described above. Promoter regions can be selected from any desired gene using CAT (chloramphenicol transferase) vectors or other vectors with selectable markers. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a nucleic acid encoding a protein or polypeptide according to the invention is described herein.

Transcription of the DNA encoding proteins and polypeptides of the invention by higher eukaryotes may be increased by inserting an enhancer sequence into the vector. Examples include the SV40 enhancer on the late side of the replication origin by 100 to 270, a cytomegalovirus early promoter enhancer, the polyoma enhancer on the late side of the replication origin, and adenovirus enhancers.

Gene therapies using the nucleic acids of the invention are also contemplated, comprising strategies to replace defective genes or add new genes to cells and/or tissues, and is being developed for application in the treatment of cancer, the correction of metabolic disorders and in the field of immunotherapy. Gene therapies of the invention include the use of various constructs of the invention, with or without a separate carrier or delivery vehicle or constructs, for treatment of the diseases, disorders, and/or conditions noted herein. Such constructs may also be used as vaccines for treatment or prevention of the diseases, disorders, and/or conditions noted herein. DNA vaccines, for example, make use of polynucleotides encoding immunogenic protein and nucleic acid determinants to stimulate the immune system against pathogens or tumor cells. Such strategies can stimulate either acquired or innate immunity or can involve the modification of immune function through cytokine expression. In vivo gene therapy involves the direct injection of genetic material into a patient or animal, typically to treat, prevent or ameliorate a disease or symptoms associated with a disease. Vaccines and immune modulation are systemic therapies. With tissue-specific in vivo therapies, such as those that aim to treat cancer, localized gene delivery and/or expression/targeting systems are preferred. Diverse gene therapy vectors that target specific tissues are known in the art, and procedures have been developed to physically target specific tissues, for example, using catheter-based technologies, all of which are contemplated herein.

Ex vivo approaches to gene therapy are also contemplated herein and involve the removal, genetic modification, expansion and re-administration of a subject's, e.g., human patient's, own cells. Examples include bone marrow transplantation for cancer treatment or the genetic modification of lymphoid progenitor cells. Ex vivo gene therapy is preferably applied to the treatment of cells that are easily accessible and can survive in culture during the gene transfer process (such as blood or skin cells).

Useful gene therapy vectors include adenoviral vectors, lentiviral vectors, Adeno-associated virus (AAV) vectors, Herpes Simplex Virus (HSV) vectors, and retroviral vectors. Gene therapies may also be carried out using "naked DNA," liposome-based delivery, lipid-based delivery (including DNA attached to positively charged lipids), electroporation, and ballistic projection.

In certain embodiments, including but not limited to gene therapy embodiments, the vector may be a viral vector such as, for example, a retroviral vector. Miller et al., 1989 *BioTechniques* 7:980; Coffin and Varmus, 1996 Retroviruses, *Cold Spring Harbor Laboratory Press*, NY. For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

Retroviruses are RNA viruses which can replicate and integrate into the genome of a host cell via a DNA intermediate. This DNA intermediate, or provirus, may be stably integrated into the host cell DNA. According to certain embodiments of the present invention, an expression construct may comprise a retrovirus into which a foreign gene that encodes a foreign protein is incorporated in place of normal retroviral RNA. When retroviral RNA enters a host cell coincident with infection, the foreign gene is also introduced into the cell, and may then be integrated into host cell DNA as if it were part of the retroviral genome. Expression of this foreign gene within the host results in expression of the foreign protein.

Most retroviral vector systems that have been developed for gene therapy are based on murine retroviruses. Such retroviruses exist in two forms, as free viral particles referred to as virions, or as proviruses integrated into host cell DNA. The virion form of the virus contains the structural and enzymatic proteins of the retrovirus (including the enzyme reverse transcriptase), two RNA copies of the viral genome, and portions of the source cell plasma membrane containing viral envelope glycoprotein. The retroviral genome is organized into four main regions: the Long Terminal Repeat (LTR), which contains cis-acting elements necessary for the initiation and termination of transcription and is situated both 5' and 3' to the coding genes, and the three genes encoding gag, pol, and env. These three genes, gag, pol, and env, encode, respectively, internal viral structures, enzymatic proteins (such as integrase), and the envelope glycoprotein (designated gp70 and p15e) which confers infectivity and host range specificity of the virus, as well as the "R" peptide of undetermined function.

Separate packaging cell lines and vector-producing cell lines have been developed because of safety concerns regarding the uses of retroviruses, including uses in expression constructs. Briefly, this methodology employs the use of two components, a retroviral vector and a packaging cell line (PCL). The retroviral vector contains long terminal repeats (LTRs), the foreign DNA to be transferred and a packaging sequence (y). This retroviral vector will not reproduce by itself because the genes which encode structural and envelope proteins are not included within the vector genome. The PCL contains genes encoding the gag, pol, and env proteins, but does not contain the packaging signal "y." Thus, a PCL can only form empty virion particles by itself Within this general method, the retroviral vector is introduced into the PCL, thereby creating a vector-producing cell line (VCL). This VCL manufactures virion particles containing only the foreign genome of the retroviral vector, and therefore has previously been considered to be a safe retrovirus vector for therapeutic use.

A "retroviral vector construct" refers to an assembly which is, within preferred embodiments of the invention, capable of directing the expression of a sequence(s) or gene(s) of interest, such as multivalent binding protein-encoding nucleic acid sequences. Briefly, the retroviral vector construct must include a 5' LTR, a tRNA binding site, a packaging signal, an origin of second strand DNA synthesis and a 3' LTR. A wide variety of heterologous sequences may be included within the vector construct including, for example, sequences which encode a protein (e.g., cytotoxic protein, disease-associated antigen, immune accessory molecule, or replacement gene), or which are useful as a molecule itself (e.g., as a ribozyme or antisense sequence).

Retroviral vector constructs of the present invention may be readily constructed from a wide variety of retroviruses, including for example, B, C, and D type retroviruses as well as spumaviruses and lentiviruses (see, e.g., RNA Tumor Viruses, Second Edition, Cold Spring Harbor Laboratory, 1985). Such retroviruses may be readily obtained from depositories or collections such as the American Type Culture Collection ("ATCC"; Rockville, Md.), or isolated from known sources using commonly available techniques. Any of the above retroviruses may be readily utilized in order to assemble or construct retroviral vector constructs, packaging cells, or producer cells of the invention, given the disclosure provided herein and standard recombinant techniques (e.g., Sambrook et al, *Molecular Cloning: A Laboratory Manual*, 2d ed., Cold Spring Harbor Laboratory Press, 1989; Kunkle, 1985 *Proc. Natl. Acad. Sci.* (USA) 82:488).

Suitable promoters for use in viral vectors generally may include, but are not limited to, the retroviral LTR; the SV40 promoter; and the human cytomegalovirus (CMV) promoter described in Miller, et al., 1989 *Biotechniques* 7:980-990, or any other promoter (e.g., cellular promoters such as eukaryotic cellular promoters including, but not limited to, the histone, pol III, and β-actin promoters). Other viral promoters that may be employed include, but are not limited to, adenovirus promoters, thymidine kinase (TK) promoters, and B19 parvovirus promoters. The selection of a suitable promoter will be apparent to those skilled in the art from the teachings contained herein, and may be from among either regulated promoters or promoters as described above.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, 1:5-14 (1990). The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the multivalent binding proteins with effector function. Such retroviral vector particles then may be employed to transduce eukaryotic cells, either in vitro or in vivo. The transduced eukaryotic cells will express the nucleic acid sequence(s) encoding the protein or polypeptide. Eukaryotic cells that may be transduced include, but are not limited to, embryonic stem cells, as well as hematopoietic stem cells, hepatocytes, fibroblasts, circulating peripheral blood mononuclear and polymorphonuclear cells including myelomonocytic cells, lymphocytes, myoblasts, tissue macrophages, dendritic cells, Kupffer cells, lymphoid and reticuloendothelial cells of the lymph nodes and spleen, keratinocytes, endothelial cells, and bronchial epithelial cells.

Host Cells

A further aspect of the invention provides a host cell transformed or transfected with, or otherwise containing, any of the polynucleotides or cloning/expression constructs of the invention. The polynucleotides and cloning/expression constructs are introduced into suitable cells using any method known in the art, including transformation, transfection and transduction. Host cells include the cells of a subject undergoing ex vivo cell therapy including, for example, ex vivo gene therapy. Eukaryotic host cells contemplated as an aspect of the invention when harboring a polynucleotide, vector, or protein according to the invention include, in addition to a subject's own cells (e.g., a human patient's own cells), VERO cells, HeLa cells, Chinese hamster ovary (CHO) cell lines (including modified CHO cells capable of modifying the glycosylation pattern of expressed multivalent binding molecules, see Published US Patent Application No. 2003/0115614 A1), incorporated herein by reference, COS cells (such as COS-7), W138, BHK, HepG2, 3T3, RIN, MDCK, A549, PC12, K562, HEK293 cells, HepG2 cells, N cells, 3T3 cells, *Spodoptera frugiperda* cells (e.g., Sf9 cells), *Saccharomyces cerevisiae* cells, and any other eukaryotic cell known in the art to be useful in expressing, and optionally isolating, a protein or peptide according to the invention. Also contemplated are prokaryotic cells, including but not limited to, *Escherichia coli, Bacillus subtilis, Salmonella typhimurium*, a Streptomycete, or any prokaryotic cell known in the art to be suitable for expressing, and optionally isolating, a protein or peptide according to the invention. In isolating protein or peptide from prokaryotic cells, in particular, it is contemplated that techniques known in the art for extracting protein from inclusion bodies may be used. The selection of an appropriate host is within the scope of those skilled in the art from the teachings herein.

The engineered host cells can be cultured in a conventional nutrient medium modified as appropriate for activating promoters, selecting transformants, or amplifying particular genes. The culture conditions for particular host cells selected for expression, such as temperature, pH and the like, will be readily apparent to the ordinarily skilled artisan. Various mammalian cell culture systems can also be employed to express recombinant protein. Examples of mammalian expression systems include the COS-7 lines of monkey kidney fibroblasts, described by Gluzman, 1981 *Cell* 23:175, and other cell lines capable of expressing a compatible vector, for example, the C127, 3T3, CHO, HeLa and BHK cell lines. Mammalian expression vectors will comprise an origin of replication, a suitable promoter and, optionally, enhancer, and also any necessary ribosome binding sites, polyadenylation site, splice donor and acceptor sites, transcriptional termination sequences, and 5' flanking nontranscribed sequences, for example as described herein regarding the preparation of multivalent binding protein expression constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, calcium phosphate transfection, DEAE-Dextran-mediated transfection, or electroporation (Davis et al., 1986 *Basic Methods in Molecular Biology*).

In one embodiment, a host cell is transduced by a recombinant viral construct directing the expression of a protein or polypeptide according to the invention. The transduced host cell produces viral particles containing expressed protein or polypeptide derived from portions of a host cell membrane incorporated by the viral particles during viral budding.

Pharmaceutical Compositions

In some embodiments, the compositions of the invention, such as a multivalent binding protein or a composition comprising a polynucleotide encoding such a protein as described herein, are suitable to be administered under conditions and for a time sufficient to permit expression of the encoded protein in a host cell in vivo or in vitro, for gene therapy, and the like. Such compositions may be formulated into pharmaceutical compositions for administration according to well known methodologies. Pharmaceutical compositions generally comprise one or more recombinant expression constructs, and/or expression products of such constructs, in combination with a pharmaceutically acceptable carrier, excipient or diluent. Such carriers will be nontoxic to recipients at the dosages and concentrations employed. For nucleic acid-based formulations, or for formulations comprising expression products according to the invention, about 0.01 µg/kg to about 100 mg/kg body weight will be administered, for example, by the intradermal, subcutaneous, intramuscular or intravenous route, or by any route known in the art to be suitable under a given set of circumstances. A preferred dosage, for example, is about 1 µg/kg to about 1 mg/kg, with about 5 µg/kg to about 200 µg/kg particularly preferred.

It will be evident to those skilled in the art that the number and frequency of administration will be dependent upon the response of the host. Pharmaceutically acceptable carriers for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and the like may be provided in the pharmaceutical composition. For example, sodium benzoate, sorbic acid and esters of p-hydroxybenzoic acid may be added as preservatives. Id. at 1449. In addition, antioxidants and suspending agents may be used. Id. The compounds of the present invention may be used in either the free base or salt forms, with both forms being considered as being within the scope of the present invention.

The pharmaceutical compositions that contain one or more nucleic acid constructs of the invention, or the proteins corresponding to the products encoded by such nucleic acid constructs, may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavernous, intrathecal, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain, in addition to one or more binding domain-immunoglobulin fusion construct or expressed product, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following adjuvants:

sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

It may also be desirable to include other components in the preparation, such as delivery vehicles including, but not limited to, aluminum salts, water-in-oil emulsions, biodegradable oil vehicles, oil-in-water emulsions, biodegradable microcapsules, and liposomes. Examples of immunostimulatory substances (adjuvants) for use in such vehicles include N-acetylmuramyl-L-alanine-D-isoglutamine (MDP), lipopolysaccharides (LPS), glucan, IL-12, GM-CSF, gamma interferon and IL-15.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. In this regard, it is preferable that the microsphere be larger than approximately 25 microns.

Pharmaceutical compositions may also contain diluents such as buffers, antioxidants such as ascorbic acid, low molecular weight (less than about 10 residues) polypeptides, proteins, amino acids, carbohydrates (e.g., glucose, sucrose or dextrins), chelating agents (e.g., EDTA), glutathione and other stabilizers and excipients. Neutral buffered saline or saline mixed with nonspecific serum albumin are exemplary appropriate diluents. Preferably, product is formulated as a lyophilizate using appropriate excipient solutions (e.g., sucrose) as diluents.

The pharmaceutical compositions according to the invention also include stabilized proteins and stable liquid pharmaceutical formulations in accordance with technology known in the art, including the technology disclosed in Published US Patent Application No. 2006/0008415 A1, incorporated herein by reference. Such technologies include derivatization of a protein, wherein the protein comprises a thiol group coupled to N-acetyl-L-cysteine, N-ethyl-maleimide, or cysteine.

As described above, the subject invention includes compositions capable of delivering nucleic acid molecules encoding multivalent binding proteins with effector function. Such compositions include recombinant viral vectors, e.g., retroviruses (see WO 90/07936, WO 91/02805, WO 93/25234, WO 93/25698, and WO 94/03622), adenovirus (see Berkner, 1988 *Biotechniques* 6:616-627; Li et al., 1993 *Hum. Gene Ther.* 4:403-409; Vincent et al., *Nat. Genet.* 5:130-134; and Kolls et al., 1994 *Proc. Natl. Acad. Sci. USA* 91:215-219), pox virus (see U.S. Pat. No. 4,769,330; U.S. Pat. No. 5,017,487; and WO 89/01973)), recombinant expression construct nucleic acid molecules complexed to a polycationic molecule (see WO 93/03709), and nucleic acids associated with liposomes (see Wang et al., 1987 *Proc. Natl. Acad. Sci. USA* 84:7851). In certain embodiments, the DNA may be linked to killed or inactivated adenovirus (*see Curiel et al.,* 1992 *Hum. Gene Ther.* 3:147-154; Cotton et al., 1992 *Proc. Natl. Acad. Sci. USA* 89:6094). Other suitable compositions include DNA-ligand (see Wu et al., 1989 *J. Biol. Chem.* 264:16985-16987) and lipid-DNA combinations (see Felgner et al., 1989 *Proc. Natl. Acad. Sci. USA* 84:7413-7417).

In addition to direct in vivo procedures, ex vivo procedures may be used in which cells are removed from a host (e.g., a subject, such as a human patient), modified, and placed into the same or another host animal. It will be evident that one can utilize any of the compositions noted above for introduction of constructs of the invention, either the proteins/polypeptides or the nucleic acids encoding them into tissue cells in an ex vivo context. Protocols for viral, physical and chemical methods of uptake are well known in the art.

Generation of Antibodies

Polyclonal antibodies directed toward an antigen polypeptide generally are produced in animals (e.g., rabbits, hamsters, goats, sheep, horses, pigs, rats, gerbils, guinea pigs, mice, or any other suitable mammal, as well as other nonmammal species) by means of multiple subcutaneous or intraperitoneal injections of antigen polypeptide or a fragment thereof and an adjuvant. Adjuvants include, but are not limited to, complete or incomplete Freund's adjuvant, mineral gels such as aluminum hydroxide, and surface active substances such as lysolecithin, pluronic polyols, polyanions, peptides, oil emulsions, and dinitrophenol. BCG (bacilli Calmette-Guerin) and *Corynebacterium parvum* are also potentially useful adjuvants. It may be useful to conjugate an antigen polypeptide to a carrier protein that is immunogenic in the species to be immunized; typical carriers include keyhole limpet hemocyanin, serum albumin, bovine thyroglobulin, or soybean trypsin inhibitor. Also, aggregating agents such as alum are used to enhance the immune response. After immunization, the animals are bled and the serum is assayed for anti-antigen polypeptide antibody titer using conventional techniques. Polyclonal antibodies may be utilized in the sera from which they were detected, or may be purified from the sera using, e.g., antigen affinity chromatography.

Monoclonal antibodies directed toward antigen polypeptides are produced using any method which provides for the production of antibody molecules by continuous cell lines in culture. For example, monoclonal antibodies may be made by the hybridoma method as described in Kohler et al., Nature 256:495 [1975]; the human B-cell hybridoma technique (Kosbor et al., Immunol Today 4:72, 1983; Cote et al., Proc Natl Acad Sci 80: 2026-2030, 1983) and the EBV-hybridoma technique (Cole et al., Monoclonal Antibodies and Cancer Therapy, Alan R Liss Inc, New York N.Y., pp 77-96, (1985).

When the hybridoma technique is employed, myeloma cell lines may be used. Cell lines suited for use in hybridoma-producing fusion procedures preferably do not produce endogenous antibody, have high fusion efficiency, and exhibit enzyme deficiencies that render them incapable of growing in certain selective media which support the growth of only the desired fused cells (hybridomas). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

In an alternative embodiment, human antibodies can be produced from phage-display libraries (Hoogenboom et al., J. Mol. Biol. 227: 381 [1991]; Marks et al., J. Mol. Biol. 222: 581, see also U.S. Pat. No. 5,885,793).). These processes mimic immune selection through the display of antibody repertoires on the surface of filamentous bacteriophage, and subsequent selection of phage by their binding to an antigen of choice. One such technique is described in PCT Application No. PCT/US98/17364, filed in the name of Adams et al., which describes the isolation of high affinity and functional agonistic antibodies for MPL- and msk-receptors using such an approach. In this approach, a complete repertoire of human antibody genes can be created by cloning naturally rearranged human V genes from peripheral blood lymphocytes as previously described (Mullinax, et al., Proc. Natl. Acad. Sci. (USA) 87: 8095-8099 [1990]).

Alternatively, an entirely synthetic human heavy chain repertoire can be created from unrearranged V gene segments by assembling each human VH segment with D segments of random nucleotides together with a human J segment (Hoogenboom, et al., J. Mol. Biol. 227:381-388 [1992]). Likewise, a light chain repertoire can be constructed by combining each human V segment with a J segment (Griffiths, et al, EMBO J. 13:3245-3260 [1994]). Nucleotides encoding the complete antibody (i.e., both heavy and light chains) are linked as a single-chain Fv fragment and this polynucleotide is ligated to a nucleotide encoding a filamentous phage minor coat protein. When this fusion protein is expressed on the surface of the phage, a polynucleotide encoding a specific antibody can be identified by selection using an immobilized antigen.

Beyond the classic methods of generating polyclonal and monoclonal antibodies, any method for generating any known antibody form is contemplated. In addition to polyclonals and monoclonals, antibody forms include chimerized antibodies, humanized antibodies, CDR-grafted antibodies, and antibody fragments and variants.

Variants and Derivatives of Specific Binding Agents

In one example, insertion variants are provided wherein one or more amino acid residues supplement a specific binding agent amino acid sequence. Insertions may be located at either or both termini of the protein, or may be positioned within internal regions of the specific binding agent amino acid sequence. Variant products of the invention also include mature specific binding agent products, i.e., specific binding agent products wherein leader or signal sequences are removed, and the resulting protein having additional amino terminal residues. The additional amino terminal residues may be derived from another protein, or may include one or more residues that are not identifiable as being derived from a specific protein. Polypeptides with an additional methionine residue at position −1 (e.g., Met-1-multivalent binding peptides with effector function) are contemplated, as are polypeptides of the invention with additional methionine and lysine residues at positions −2 and −1 (Met-2-Lys-1-multivalent binding proteins with effector function). Variants of the polypeptides of the invention having additional Met, Met-Lys, or Lys residues (or one or more basic residues in general) are particularly useful for enhanced recombinant protein production in bacterial host cells.

The invention also embraces specific polypeptides of the invention having additional amino acid residues which arise from use of specific expression systems. For example, use of commercially available vectors that express a desired polypeptide as part of a glutathione-S-transferase (GST) fusion product provides the desired polypeptide having an additional glycine residue at position −1 after cleavage of the GST component from the desired polypeptide. Variants which result from expression in other vector systems are also contemplated, including those wherein histidine tags are incorporated into the amino acid sequence, generally at the carboxy and/or amino terminus of the sequence.

In another aspect, the invention provides deletion variants wherein one or more amino acid residues in a polypeptide of the invention are removed. Deletions can be effected at one or both termini of the polypeptide, or from removal of one or more residues within the amino acid sequence. Deletion variants necessarily include all fragments of a polypeptide according to the invention.

Antibody fragments refer to polypeptides having a sequence corresponding to at least part of an immunoglobulin variable region sequence. Fragments may be generated, for example, by enzymatic or chemical cleavage of polypeptides corresponding to full-length antibodies. Other binding fragments include those generated by synthetic techniques or by recombinant DNA techniques, such as the expression of recombinant plasmids containing nucleic acid sequences encoding partial antibody variable regions. Preferred polypeptide fragments display immunological properties unique to, or specific for, a target as described herein. Fragments of the invention having the desired immunological properties can be prepared by any of the methods well known and routinely practiced in the art.

In still another aspect, the invention provides substitution variants of multivalent binding polypeptides having effector function. Substitution variants include those polypeptides wherein one or more amino acid residues in an amino acid sequence are removed and replaced with alternative residues. In some embodiments, the substitutions are conservative in nature; however, the invention embraces substitutions that ore also non-conservative. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table A (see WO 97/09433, page 10, published Mar. 13, 1997 (PCT/GB96/02197, filed Sep. 6, 1996), immediately below.

TABLE A

| Conservative Substitutions I | | |
|---|---|---|
| SIDE CHAIN | CHARACTERISTIC | AMINO ACID |
| Aliphatic | Non-polar | G A P I L V |
|  | Polar-uncharged | S T M N Q |
|  | Polar-charged | D E K R |
| Aromatic |  | H F W Y |
| Other |  | N Q D E |

Alternatively, conservative amino acids can be grouped as described in Lehninger, [Biochemistry, Second Edition; Worth Publishers, Inc. NY:NY (1975), pp. 71-77] as set out in Table B, immediately below.

TABLE B

| Conservative Substitutions II | | |
|---|---|---|
| SIDE CHAIN | CHARACTERISTIC | AMINO ACID |
| Non-polar (hydrophobic) | A. Aliphatic: | A L I V P |
|  | B. Aromatic | F W |

TABLE B-continued

| | | |
|---|---|---|
| | C. Sulfur-containing | M |
| | D. Borderline | G |
| Uncharged-polar | A. Hydroxyl | S T Y |
| | B. Amides | N Q |
| | C. Sulfhydryl | C |
| | D. Borderline | G |
| Positively Charged (Basic) | | K R H |
| Negatively Charged (Acidic) | | D E |

| Conservative Substitutions II | | |
|---|---|---|
| SIDE CHAIN | CHARACTERISTIC | AMINO ACID |
| Non-polar (hydrophobic) | A. Aliphatic: | A L I V P |
| | B. Aromatic: | F W |
| | C. Sulfur-containing: | M |
| | D. Borderline: | G |
| Uncharged-polar | A. Hydroxyl: | S T Y |
| | B. Amides: | N Q |
| | C. Sulfhydryl: | C |
| | D. Borderline: | G |
| Positively Charged (Basic) | | K R H |
| Negatively Charged (Acidic) | | D E |

The invention also provides derivatives of specific binding agent polypeptides. Derivatives include specific binding agent polypeptides bearing modifications other than insertion, deletion, or substitution of amino acid residues. Preferably, the modifications are covalent in nature, and include for example, chemical bonding with polymers, lipids, other organic, and inorganic moieties. Derivatives of the invention may be prepared to increase circulating half-life of a specific binding agent polypeptide, or may be designed to improve targeting capacity for the polypeptide to desired cells, tissues, or organs.

The invention further embraces multivalent binding proteins with effector function that are covalently modified or derivatized to include one or more water-soluble polymer attachments such as polyethylene glycol, polyoxyethylene glycol, or polypropylene glycol, as described U.S. Pat. Nos. 4,640,835, 4,496,689, 4,301,144, 4,670,417, 4,791,192 and 4,179,337. Still other useful polymers known in the art include monomethoxy-polyethylene glycol, dextran, cellulose, and other carbohydrate-based polymers, poly-(N-vinyl pyrrolidone)-polyethylene glycol, propylene glycol homopolymers, a polypropylene oxide/ethylene oxide copolymer, polyoxyethylated polyols (e.g., glycerol) and polyvinyl alcohol, as well as mixtures of these polymers. Particularly preferred are polyethylene glycol (PEG)—derivatized proteins. Water-soluble polymers may be bonded at specific positions, for example at the amino terminus of the proteins and polypeptides according to the invention, or randomly attached to one or more side chains of the polypeptide. The use of PEG for improving therapeutic capacities is described in U.S. Pat. No. 6,133,426 to Gonzales, et al.

Target Sites for Immunoglobulin Mutagenesis

Certain strategies are available to manipulate inherent properties of an antigen-specific immunoglobulin (e.g., an antibody) that are not available to non-immunoglobulin-based binding molecules. A good example of the strategies favoring, e.g., antibody-based molecules, over these alternatives is the in vivo modulation of the affinity of an antibody for its target through affinity maturation, which takes advantage of the somatic hypermutation of immunoglobulin genes to yield antibodies of increasing affinity as an immune response progresses. Additionally, recombinant technologies have been developed to alter the structure of immunoglobulins and immunoglobulin regions and domains. Thus, polypeptides derived from antibodies may be produced that exhibit altered affinity for a given antigen, and a number of purification protocols and monitoring screens are known in the art for identifying and purifying or isolating these polypeptides. Using these known techniques, polypeptides comprising antibody-derived binding domains can be obtained that exhibit decreased or increased affinity for an antigen. Strategies for generating the polypeptide variants exhibiting altered affinity include the use of site-specific or random mutagenesis of the DNA encoding the antibody to change the amino acids present in the protein, followed by a screening step designed to recover antibody variants that exhibit the desired change, e.g., increased or decreased affinity relative to the unmodified parent or referent antibody.

The amino acid residues most commonly targeted in mutagenic strategies to alter affinity are those in the complementarity-determining region (CDR) or hyper-variable region of the light and the heavy chain variable regions of an antibody. These regions contain the residues that physicochemically interact with an antigen, as well as other amino acids that affect the spatial arrangement of these residues. However, amino acids in the framework regions of the variable domains outside the CDR regions have also been shown to make substantial contributions to the antigen-binding properties of an antibody, and can be targeted to manipulate such properties. See Hudson, P. J. Curr. Opin. Biotech., 9: 395-402 (1999) and references therein.

Smaller and more effectively screened libraries of antibody variants can be produced by restricting random or site-directed mutagenesis to sites in the CDRs that correspond to areas prone to "hyper-mutation" during the somatic affinity maturation process. See Chowdhury, et al., Nature Biotech., 17: 568-572 (1999) and references therein. The types of DNA elements known to define hyper-mutation sites in this manner include direct and inverted repeats, certain consensus sequences, secondary structures, and palindromes. The consensus DNA sequences include the tetrabase sequence Purine-G-Pyrimidine-A/T (i.e., A or G-G-C or T-A or T) and the serine codon AGY (wherein Y can be C or T).

Thus, another aspect of the invention is a set of mutagenic strategies for modifying the affinity of an antibody for its target. These strategies include mutagenesis of the entire variable region of a heavy and/or light chain, mutagenesis of the CDR regions only, mutagenesis of the consensus hyper-mutation sites within the CDRs, mutagenesis of framework regions, or any combination of these approaches ("mutagenesis" in this context could be random or site-directed). Definitive delineation of the CDR regions and identification of residues comprising the binding site of an antibody can be accomplished though solving the structure of the antibody in question, and the antibody:ligand complex, through techniques known to those skilled in the art, such as X-ray crystallography. Various methods based on analysis and characterization of such antibody crystal structures are known to those of skill in the art and can be employed to approximate the CDR regions. Examples of such commonly used methods include the Kabat, Chothia, AbM and contact definitions.

The Kabat definition is based on sequence variability and is the most commonly used definition to predict CDR regions. Johnson, et al., Nucleic Acids Research, 28: 214-8 (2000). The Chothia definition is based on the location of the structural loop regions. (Chothia et al., J. Mol. Biol., 196: 901-17 [1986]; Chothia et al., Nature, 342: 877-83 [1989].) The AbM definition is a compromise between the Kabat and Chothia definitions. AbM is an integral suite of programs for antibody structure modeling produced by the Oxford Molecular Group (Martin, et al., Proc. Natl. Acad. Sci. (USA) 86:9268-9272 [1989]; Rees, et al., ABMTM, a computer program for modeling variable regions of antibodies, Oxford, UK; Oxford Molecular, Ltd.). The AbM suite models the tertiary structure of an antibody from primary sequence using a combination of knowledge databases and ab initio methods An additional definition, known as the contact definition, has been recently introduced. See MacCallum et al., J. Mol. Biol., 5:732-45 (1996). This definition is based on an analysis of the available complex crystal structures.

By convention, the CDR domains in the heavy chain are typically referred to as H1, H2 and H3, and are numbered sequentially in order moving from the amino terminus to the carboxy terminus. The CDR regions in the light chain are typically referred to as L1, L2 and L3, and are numbered sequentially in order moving from the amino terminus to the carboxy terminus.

The CDR-H1 is approximately 10 to 12 residues in length and typically starts 4 residues after a Cys according to the Chothia and AbM definitions, or typically 5 residues later according to the Kabat definition. The H1 is typically followed by a Trp, typically Trp-Val, but also Trp-Ile, or Trp-Ala. The length of H1 is approximately 10 to 12 residues according to the AbM definition, while the Chothia definition excludes the last 4 residues.

The CDR-H2 typically starts 15 residues after the end of H1 according to the Kabat and AbM definitions. The residues preceding H2 are typically Leu-Glu-Trp-Ile-Gly but there are a number of variations. H2 is typically followed by the amino acid sequence Lys/Arg-Leu/Ile/Val/Phe/Thr/Ala-Thr/Ser/Ile/Ala. According to the Kabat definition, the length of H2 is approximately 16 to 19 residues, where the AbM definition predicts the length to be typically 9 to 12 residues.

The CDR-H3 typically starts 33 residues after the end of H2 and is typically preceded by the amino acid sequence Cys-Ala-Arg. H3 is typically followed by the amino acid Gly. The length of H3 ranges from 3 to 25 residues The CDR-L1 typically starts at approximately residue 24 and will typically follow a Cys. The residue after the CDR-L1 is always Trp and will typically begin one of the following sequences: Trp-Tyr-Gln, Trp-Leu-Gln, Trp-Phe-Gln, or Trp-Tyr-Leu. The length of CDR-L1 is approximately 10 to 17 residues.

The CDR-L2 starts approximately 16 residues after the end of L1. It will generally follow residues Ile-Tyr, Val-Tyr, Ile-Lys or Ile-Phe. The length of CDR-L2 is approximately 7 residues.

The CDR-L3 typically starts 33 residues after the end of L2 and typically follows a Cys. L3 is typically followed by the amino acid sequence Phe-Gly-XXX-Gly. The length of L3 is approximately 7 to 11 residues.

Various methods for modifying antibodies have been described in the art, including, e.g., methods of producing humanized antibodies wherein the sequence of the humanized immunoglobulin heavy chain variable region framework is 65% to 95% identical to the sequence of the donor immunoglobulin heavy chain variable region framework. Each humanized immunoglobulin chain will usually comprise, in addition to the CDRs, amino acids from the donor immunoglobulin framework that are, e.g., capable of interacting with the CDRs to effect binding affinity, such as one or more amino acids that are immediately adjacent to a CDR in the donor immunoglobulin or those within about 3 angstroms, as predicted by molecular modeling. The heavy and light chains may each be designed by using any one or all of various position criteria. When combined into an intact antibody, humanized immunoglobulins are substantially non-immunogenic in humans and retain substantially the same affinity as the donor immunoglobulin to the antigen, such as a protein or other compound containing an epitope.

In one example, methods for the production of antibodies, and antibody fragments, are described that have binding specificity similar to a parent antibody, but which have increased human characteristics. Humanized antibodies are obtained by chain shuffling using, for example, phage display technology and a polypeptide comprising the heavy or light chain variable region of a non-human antibody specific for an antigen of interest, which is then combined with a repertoire of human complementary (light or heavy) chain variable regions. Hybrid pairings which are specific for the antigen of interest are identified and human chains from the selected pairings are combined with a repertoire of human complementary variable domains (heavy or light). In another embodiment, a component of a CDR from a non-human antibody is combined with a repertoire of component parts of CDRs from human antibodies. From the resulting library of antibody polypeptide dimers, hybrids are selected and may used in a second humanizing shuffling step; alternatively, this second step is eliminated if the hybrid is already of sufficient human character to be of therapeutic value. Methods of modification to increase human character are known in the art.

Another example is a method for making humanized antibodies by substituting a CDR amino acid sequence for the corresponding human CDR amino acid sequence and/or substituting a FR amino acid sequence for the corresponding human FR amino acid sequences.

Yet another example provides methods for identifying the amino acid residues of an antibody variable domain that may be modified without diminishing the native affinity of the antigen binding domain while reducing its immunogenicity with respect to a heterologous species and methods for preparing these modified antibody variable regions as useful for administration to heterologous species.

Modification of an immunoglobulin such as an antibody by any of the methods known in the art is designed to achieve increased or decreased binding affinity for an antigen and/or to reduce immunogenicity of the antibody in the recipient and/or to modulate effector activity levels. In one approach, humanized antibodies can be modified to eliminate glycosylation sites in order to increase affinity of the antibody for its cognate antigen (Co, et al., Mol. Immunol. 30:1361-1367 [1993]). Techniques such as "reshaping," hyperchimerization," and "veneering/resurfacing" have produced humanized antibodies with greater therapeutic potential. Vaswami, et al., Annals of Allergy, Asthma, & Immunol 81:105 (1998); Roguska, et al., Prot. Engineer. 9:895-904 (1996)]. See also U.S. Pat. No. 6,072,035, which describes methods for reshaping antibodies. While these techniques diminish antibody immunogenicity by reducing the number of foreign residues, they do not prevent anti-idiotypic and anti-allotypic responses following repeated administration of the antibodies. Alternatives to these methods for reducing immunogenicity are described in Gilliland et al., J. Immunol. 62(6): 3663-71 (1999).

In many instances, humanizing antibodies results in a loss of antigen binding capacity. It is therefore preferable to "back mutate" the humanized antibody to include one or more of the amino acid residues found in the original (most often rodent) antibody in an attempt to restore binding affinity of the antibody. See, for example, Saldanha et al., Mol. Immunol. 36:709-19 (1999).

Glycosylation of immunoglobulins has been shown to affect effector functions, structural stability, and the rate of secretion from antibody-producing cells (see Leatherbarrow et al., Mol. Immunol. 22:407 (1985), incorporated herein by reference). The carbohydrate groups responsible for these properties are generally attached to the constant regions of antibodies. For example, glycosylation of IgG at Asn 297 in the $C_{H2}$ domain facilitates full capacity of the IgG to activate complement-dependent cytolysis (Tao et al., J. Immunol. 143:2595 (1989)). Glycosylation of IgM at Asn 402 in the $C_{H3}$ domain, for example, facilitates proper assembly and cytolytic activity of the antibody (Muraoka et al., J. Immunol. 142:695 (1989)). Removal of glycosylation sites at positions 162 and 419 in the $C_{H1}$ and $C_{H3}$ domains of an IgA antibody led to intracellular degradation and at least 90% inhibition of secretion (Taylor et al., Wall, Mol. Cell. Biol. 8:4197 (1988)). Accordingly, the molecules of the invention include mutationally altered immunoglobulins exhibiting altered glycosylation patterns by mutation of specific residues in, e.g., a constant sub-region to alter effector function. See Co et al., Mol. Immunol. 30:1361-1367 (1993), Jacquemon et al., J. Thromb. Haemost. 4:1047-1055 (2006), Schuster et al., Cancer Res. 65:7934-7941 (2005), and Warnock et al., Biotechnol Bioeng. 92:831-842 (2005), each incorporated herein by reference.

The invention also includes multivalent binding molecules having at least one binding domain that is at least 80%, preferably 90% or 95% or 99% identical in sequence to a known immunoglobulin variable region sequence and which has at least one residue that differs from such immunoglobulin variable region, wherein the changed residue adds a glycosylation site, changes the location of one or more glycosylation site(s), or preferably removes a glycosylation site relative to the immunoglobulin variable region. In some embodiments, the change removes an N-linked glycosylation site in a an immunoglobulin variable region framework, or removes an N-linked glycosylation site that occurs in the immunoglobulin heavy chain variable region framework in the region spanning about amino acid residue 65 to about amino acid residue 85, using the numbering convention of Co et al., J. Immunol. 148: 1149, (1992).

Any method known in the art is contemplated for producing the multivalent binding molecules exhibiting altered glycosylation patterns relative to an immunoglobulin referent sequence. For example, any of a variety of genetic techniques may be employed to alter one or more particular residues. Alternatively, the host cells used for production may be engineered to produce the altered glycosylation pattern. One method known in the art, for example, provides altered glycosylation in the form of bisected, non-fucosylated variants that increase ADCC. The variants result from expression in a host cell containing an oligosaccharide-modifying enzyme. Alternatively, the Potelligent technology of BioWa/Kyowa Hakko is contemplated to reduce the fucose content of glycosylated molecules according to the invention. In one known method, a CHO host cell for recombinant immunoglobulin production is provided that modifies the glycosylation pattern of the immunoglobulin $F_C$ region, through production of GDP-fucose. This technology is available to modify the glycosylation pattern of a constant sub-region of a multivalent binding molecule according to the invention.

In addition to modifying the binding properties of binding domains, such as the binding domains of immunoglobulins, and in addition to such modifications as humanization, the invention comprehends the modulation of effector function by changing or mutating residues contributing to effector function, such as the effector function of a constant sub-region. These modifications can be effected using any technique known in the art, such as the approach disclosed in Presta et al., Biochem. Soc. Trans. 30:487-490 (2001), incorporated herein by reference. Exemplary approaches would include the use of the protocol disclosed in Presta et al. to modify specific residues known to affect binding in one or more constant sub-regions corresponding to FCγRI, FCγRII, FCγRIII, FCαR, and FCεR.

In another approach, the Xencor XmAb technology is available to engineer constant sub-regions corresponding to $F_C$ domains to enhance cell killing effector function. See Lazar et al., Proc. Natl. Acad. Sci. (USA) 103(11):4005-4010 (2006), incorporated herein by reference. Using this approach, for example, one can generate constant sub-regions optimized for $F_C\gamma R$ specificity and binding, thereby enhancing cell killing effector function.

Production of Multivalent Binding Proteins with Effector Function

A variety of expression vector/host systems may be utilized to contain and express the multivalent binding protein (with effector function) of the invention. These systems include but are not limited to microorganisms such as bacteria transformed with recombinant bacteriophage, plasmid, cosmid, or other expression vectors; yeast transformed with yeast expression or shuttle vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant multivalent binding protein productions include, but are not limited to, VERO cells, HeLa cells, Chinese hamster ovary (CHO) cell lines, COS cells (such as COS-7), W138, BHK, HepG2, 3T3, RIN, MDCK, A549, PC12, K562 and HEK293 cells. Exemplary protocols for the recombinant expression of the multivalent binding protein are described herein below.

An expression vector can comprise a transcriptional unit comprising an assembly of (1) a genetic element or elements having a regulatory role in gene expression, for example, a promoter, enhancer, or factor-specific binding site, (2) a structural or sequence that encodes the binding agent which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant multivalent binding protein is expressed without a leader or transport sequence, it may include an amino terminal methionine residue. This residue may or may not be subsequently cleaved from the expressed recombinant protein to provide a final multivalent binding protein.

For example, the multivalent binding proteins may be recombinantly expressed in yeast using a commercially available expression system, e.g., the *Pichia* Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol. The secreted multivalent binding peptide may be purified from the yeast growth medium by, e.g., the methods used to purify the peptide from bacterial and mammalian cell supernatants.

Alternatively, the cDNA encoding the multivalent binding peptide may be cloned into the baculovirus expression vector pVL1393 (PharMingen, San Diego, Calif.). This vector can be used according to the manufacturer's directions (PharMingen) to infect *Spodoptera frugiperda* cells in SF9 protein-free medium and to produce recombinant protein. The multivalent binding protein can be purified and concentrated from the medium using a heparin-Sepharose column (Pharmacia, Piscataway, N.J.). Insect systems for protein expression, such as the SF9 system, are well known to those of skill in the art. In one such system, *Autographa californica* nuclear polyhedrosis virus (AcNPV) can be used as a vector to express foreign genes in the *Spodoptera frugiperda* cells or in *Trichoplusia larvae*. The multivalent binding peptide coding sequence can be cloned into a nonessential region of the virus, such as the polyhedrin gene, and placed under control of the polyhedrin promoter. Successful insertion of the multivalent binding peptide will render the polyhedrin gene inactive and produce recombinant virus lacking coat protein. The recombinant viruses can be used to infect *S. frugiperda* cells or *Trichoplusia larvae* in which peptide is expressed (Smith et al., J Virol 46: 584, 1983; Engelhard et al., Proc Nat Acad Sci (USA) 91: 3224-7, 1994).

In another example, the DNA sequence encoding the multivalent binding peptide can be amplified by PCR and cloned into an appropriate vector, for example, pGEX-3× (Pharmacia, Piscataway, N.J.). The pGEX vector is designed to produce a fusion protein comprising glutathione-S-transferase (GST), encoded by the vector, and a multivalent binding protein encoded by a DNA fragment inserted into the cloning site of the vector. The primers for the PCR can be generated to include for example, an appropriate cleavage site. Where the multivalent binding protein fusion moiety is used solely to facilitate expression or is otherwise not desirable as an attachment to the peptide of interest, the recombinant multivalent binding protein fusion may then be cleaved from the GST portion of the fusion protein. The pGEX-3×/multivalent binding peptide construct is transformed into *E. coli* XL-1 Blue cells (Stratagene, La Jolla Calif.), and individual transformants isolated and grown. Plasmid DNA from individual transformants is purified and may be partially sequenced using an automated sequencer to confirm the presence of the desired multivalent binding protein-encoding nucleic acid insert in the proper orientation.

The fused multivalent binding protein, which may be produced as an insoluble inclusion body in the bacteria, can be purified as follows. Host cells can be harvested by centrifugation; washed in 0.15 M NaCl, 10 mM Tris, pH 8, 1 mM EDTA; and treated with 0.1 mg/ml lysozyme (Sigma Chemical Co.) for 15 minutes at room temperature. The lysate can be cleared by sonication, and cell debris can be pelleted by centrifugation for 10 minutes at 12,000×g. The multivalent binding protein fusion-containing pellet can be resuspended in 50 mM Tris, pH 8, and 10 mM EDTA, layered over 50% glycerol, and centrifuged for 30 minutes at 6000 g. The pellet can be resuspended in standard phosphate buffered saline solution (PBS) free of $Mg^{++}$ and $Ca^{++}$. The multivalent binding protein fusion can be further purified by fractionating the resuspended pellet in a denaturing SDS polyacrylamide gel (Sambrook et al.). The gel is soaked in 0.4 M KCl to visualize the protein, which is excised and electroeluted in gel-running buffer lacking SDS. If the GST/multivalent binding peptide fusion protein is produced in bacteria as a soluble protein, it can be purified using the GST Purification Module (Pharmacia Biotech).

The multivalent binding protein fusion is preferably subjected to digestion to cleave the GST from the multivalent binding peptide of the invention. The digestion reaction (20-40 µg fusion protein, 20-30 units human thrombin (4000 U/mg (Sigma) in 0.5 ml PBS) can be incubated 16-48 hours at room temperature and loaded on a denaturing SDS-PAGE gel to fractionate the reaction products. The gel can be soaked in 0.4 M KCl to visualize the protein bands. The identity of the protein band corresponding to the expected molecular weight of the multivalent binding peptide can be confirmed by amino acid sequence analysis using an automated sequencer (Applied Biosystems Model 473A, Foster City, Calif.). Alternatively, the identity can be confirmed by performing HPLC and/or mass spectrometry of the peptides.

Alternatively, a DNA sequence encoding the multivalent binding peptide can be cloned into a plasmid containing a desired promoter and, optionally, a leader sequence (see, e.g., Better et al., Science, 240:1041-43, 1988). The sequence of this construct can be confirmed by automated sequencing. The plasmid can then be transformed into a suitable *E. coli* strain, such as strain MC1061, using standard procedures employing $CaCl_2$ incubation and heat shock treatment of the bacteria (Sambrook et al.). The transformed bacteria can be grown in LB medium supplemented with carbenicillin or another suitable form of selection as would be known in the art, and production of the expressed protein can be induced by growth in a suitable medium. If present, the leader sequence can effect secretion of the multivalent binding peptide and be cleaved during secretion. The secreted recombinant protein can be purified from the bacterial culture medium by the methods described herein below.

Mammalian host systems for the expression of the recombinant protein are well known to those of skill in the art and are preferred systems. Host cell strains can be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Different host cells such as CHO, HeLa, MDCK, 293, WI38, and the like, have specific cellular machinery and characteristic mechanisms for such post-translational activities and can be chosen to ensure the correct modification and processing of the foreign protein.

It is preferable that the transformed cells be used for long-term, high-yield protein production and, as such, stable expression is desirable. Once such cells are transformed with vectors that preferably contain at least one selectable marker along with the desired expression cassette, the cells are grown for 1-2 days in an enriched medium before being switched to selective medium. The selectable marker is designed to confer resistance to selection and its presence allows growth and recovery of cells that successfully express the foreign protein. Resistant clumps of stably transformed cells can be proliferated using tissue culture techniques appropriate to the cell.

A number of selection systems can be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, which confers resistance to methotrexate; gpt, which confers resistance to mycophenolic acid; neo, which confers resistance to the aminoglycoside G418 and confers resistance to chlorsulfuron; and hygro, which confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, β-glucuronidase and its substrate, GUS, and luciferase and its substrate, luciferin.

Purification of Proteins

Protein purification techniques are well known to those of skill in the art. These techniques involve, at one level, the crude fractionation of the polypeptide and non-polypeptide fractions. Having separated the multivalent binding polypeptide from at least one other protein, the polypeptide of interest is purified, but further purification using chromatographic and electrophoretic techniques to achieve partial or complete purification (or purification to homogeneity) is frequently desired. Analytical methods particularly suited to the preparation of a pure multivalent binding peptide are ion-exchange chromatography, exclusion chromatography; polyacrylamide gel electrophoresis; and isoelectric focusing. Particularly efficient methods of purifying peptides are fast protein liquid chromatography and HPLC.

Certain aspects of the present invention concern the purification, and in particular embodiments, the substantial purification, of an encoded multivalent binding protein or peptide. The term "purified multivalent binding protein or peptide" as used herein, is intended to refer to a composition, isolatable from other components, wherein the multivalent binding protein or peptide is purified to any degree relative to its naturally obtainable state. A purified multivalent binding protein or peptide therefore also refers to a multivalent binding protein or peptide, free from the environment in which it may naturally occur.

Generally, "purified" will refer to a multivalent binding protein composition that has been subjected to fractionation to remove various other components, and which composition substantially retains its expressed biological activity. Where the term "substantially purified" is used, this designation refers to a multivalent binding protein composition in which the multivalent binding protein or peptide forms the major component of the composition, such as constituting about 50%, about 60%, about 70%, about 80%, about 90%, about 95%, about 99% or more of the protein, by weight, in the composition.

Various methods for quantifying the degree of purification of the multivalent binding protein will be known to those of skill in the art in light of the present disclosure. These include, for example, determining the specific binding activity of an active fraction, or assessing the amount of multivalent binding polypeptides within a fraction by SDS/PAGE analysis. A preferred method for assessing the purity of a multivalent binding protein fraction is to calculate the binding activity of the fraction, to compare it to the binding activity of the initial extract, and to thus calculate the degree of purification, herein assessed by a "—fold purification number." The actual units used to represent the amount of binding activity will, of course, be dependent upon the particular assay technique chosen to follow the purification and whether or not the expressed multivalent binding protein or peptide exhibits a detectable binding activity.

Various techniques suitable for use in multivalent binding protein purification are well known to those of skill in the art. These include, for example, precipitation with ammonium sulfate, PEG, antibodies and the like, or by heat denaturation, followed by centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified multivalent binding protein.

There is no general requirement that the multivalent binding protein always be provided in its most purified state. Indeed, it is contemplated that less substantially multivalent binding proteins will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in greater purification than the same technique utilizing a low pressure chromatography system. Methods exhibiting a lower degree of relative purification may have advantages in total recovery of multivalent binding protein product, or in maintaining binding activity of an expressed multivalent binding protein.

It is known that the migration of a polypeptide can vary, sometimes significantly, with different conditions of SDS/PAGE (Capaldi et al., Biochem. Biophys. Res. Comm., 76:425, 1977). It will therefore be appreciated that under differing electrophoresis conditions, the apparent molecular weights of purified or partially purified multivalent binding protein expression products may vary.

Effector Cells

Effector cells for inducing, e.g., ADCC, ADCP (antibody-dependent cellular phagocytosis), and the like, against a target cell include human leukocytes, macrophages, monocytes, activated neutrophils, activated natural killer (NK) cells, and eosinophils. Effector cells express $F_c\alpha R(CD89)$, Fc$\gamma$RI, Fc$\gamma$RII, Fc$\gamma$RIII, and/or $F_c\epsilon RI$ and include, for example, monocytes and activated neutrophils. Expression of Fc$\gamma$RI, e.g., has been found to be up-regulated by interferon gamma (IFN-$\gamma$). This enhanced expression increases the cytotoxic activity of monocytes and neutrophils against target cells. Accordingly, effector cells may be activated with (IFN-$\gamma$) or other cytokines (e.g., TNF-$\alpha$ or $\beta$, colony stimulating factor, IL-2) to increase the presence of Fc$\gamma$RI on the surface of the cells prior to being contacted with a multivalent protein of the invention.

The multivalent proteins of the invention provide an antibody effector function, such as antibody-dependent effector cell-mediated cytotoxicity (ADCC), for use against a target cell. Multivalent proteins with effector function are administered alone, as taught herein, or after being coupled to an effector cell, thereby forming an "activated effector cell." An "activated effector cell" is an effector cell, as defined herein, linked to a multivalent protein with effector function, also as defined herein, such that the effector cell is effectively provided with a targeting function prior to administration.

Activated effector cells are administered in vivo as a suspension of cells in a physiologically acceptable solution. The number of cells administered is on the order of $10^8$-$10^9$, but will vary depending on the therapeutic purpose. In general, the amount will be sufficient to obtain localization of the effector cell at the target cell, and to provide a desired level of effector cell function in that locale, such as cell killing by ADCC and/or phagocytosis. The term physiologically acceptable solution, as used herein, is intended to include any carrier solution which stabilizes the targeted effector cells for administration in vivo including, for example, saline and aqueous buffer solutions, solvents, antibacterial and antifungal agents, isotonic agents, and the like.

Accordingly, another aspect of the invention provides a method of inducing a specific antibody effector function, such as ADCC, against a cell in a subject, comprising administering to the subject a multivalent protein (or encoding nucleic acid) or activated effector cell in a physiologically acceptable medium. Routes of administration can vary and suitable administration routes will be determined by those of skill in the art based on a consideration of case-specific variables and routine procedures, as is known in the art.

Cell-Free Effects

Cell-free effects are also provided by the multivalent molecules of the invention, e.g., by providing a CDC functionality. The complement system is a biochemical cascade of the immune system that helps clear foreign matter such as pathogens from an organism. It is derived from many small plasma proteins that work together in inducing cytolysis of a target cell by disrupting the target cell's plasma membrane. The complement system consists of more than 35 soluble and cell-bound proteins, 12 of which are directly involved in the complement pathways. The proteins are active in three biochemical pathways leading to the activation of the complement system: the classical complement pathway, the alternate complement pathway, and the mannose-binding lectin pathway. Antibodies, in particular the IgG1 class, can also "fix" complement. A detailed understanding of these pathways has been achieved in the art and will not be repeated here, but it is worth noting that complement-dependent cytotoxicity is not dependent on the interaction of a binding molecule with a cell, e.g., a B cell, of the immune system. Also worth noting is that the complement system is regulated by complement regulating proteins. These proteins are present at higher concentrations in the blood plasma than the complement proteins. The complement regulating proteins are found on the surfaces of self-cells, providing a mechanism to prevent self-cells from being targeted by complement proteins. It is expected that the complement system plays a role in several diseases with an immune component, such as Barraquer-Simons Syndrome, Alzheimer's disease, asthma, lupus erythematosus, various forms of arthritis, autoimmune heart disease, and multiple sclerosis. Deficiencies in the terminal pathway predispose an individual to both autoimmune disease and infections (particularly meningitis).

Diseases, Disorders and Conditions

The invention provides a multivalent binding proteins with effector function, and variant and derivative thereof, that bind to one or more binding partners and those binding events are useful in the treatment, prevention, or amelioration of a symptom associated with a disease, disorder or pathological condition, preferably one afflicting humans. In preferred embodiments of these methods, the multivalent (and multispecific) binding protein with effector function associates a cell bearing a target, such as a tumor-specific cell-surface marker, with an effector cell, such as a cell of the immune system exhibiting cytotoxic activity. In other embodiments, the multispecific, multivalent binding protein with effector function specifically binds two different disease-, disorder- or condition-specific cell-surface markers to ensure that the correct target is associated with an effector cell, such as a cytotoxic cell of the immune system. Additionally, the multivalent binding protein with effector function can be used to induce or increase antigen activity, or to inhibit antigen activity. The multivalent binding proteins with effector function are also suitable for combination therapies and palliative regimes.

In one aspect, the present invention provides compositions and methods useful for treating or preventing diseases and conditions characterized by aberrant levels of antigen activity associated with a cell. These diseases include cancers and other hyperproliferative conditions, such as hyperplasia, psoriasis, contact dermatitis, immunological disorders, and infertility. A wide variety of cancers, including solid tumors and leukemias are amenable to the compositions and methods disclosed herein. Types of cancer that may be treated include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include, but are not limited to, angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia. The invention further provides compositions and methods useful in the treatment of other conditions in which cells have become immortalized or hyperproliferative due to abnormally high expression of antigen.

Exemplifying the variety of hyperproliferative disorders amenable to the compositions and methods of the invention are B-cell cancers, including B-cell lymphomas (such as various forms of Hodgkin's disease, non-Hodgkins lymphoma (NHL) or central nervous system lymphomas), leukemias (such as acute lymphoblastic leukemia (ALL), chronic lymphocytic leukemia (CLL), Hairy cell leukemia and chronic myoblastic leukemia) and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder.

Disorders characterized by autoantibody production are often considered autoimmune diseases. Autoimmune diseases include, but are not limited to: arthritis, rheumatoid arthritis, juvenile rheumatoid arthritis, osteoarthritis, polychondritis, psoriatic arthritis, psoriasis, dermatitis, polymyositis/dermatomyositis, inclusion body myositis, inflammatory myositis, toxic epidermal necrolysis, systemic scleroderma and sclerosis, CREST syndrome, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitis/angiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, myasthenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), bullous pemphigoid, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant) vs NSIP, Guillain-BarréSyndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, familial Mediterranean fever, microscopic polyangiitis, Cogan's syndrome, Whiskott-Aldrich syndrome and thromboangiitis obliterans.

Rheumatoid arthritis (RA) is a chronic disease characterized by inflammation of the joints, leading to swelling, pain, and loss of function. Patients having RA for an extended period usually exhibit progressive joint destruction, deformity, disability and even premature death. Beyond RA, inflammatory diseases, disorders and conditions in general are amenable to treatment, prevention or amelioration of symptoms (e.g., heat, pain, swelling, redness) associated with the process of inflammation, and the compositions and methods of the invention are beneficial in treating, preventing or ameliorating aberrant or abnormal inflammatory processes, including RA.

Crohn's disease and a related disease, ulcerative colitis, are the two main disease categories that belong to a group of illnesses called inflammatory bowel disease (IBD). Crohn's disease is a chronic disorder that causes inflammation of the digestive or gastrointestinal (GI) tract. Although it can involve any area of the GI tract from the mouth to the anus, it most commonly affects the small intestine and/or colon. In ulcerative colitis, the GI involvement is limited to the colon. Crohn's disease may be characterized by antibodies against neutrophil antigens, i.e., the "perinuclear anti-neutrophil antibody" (pANCA), and *Saccharomyces cervisiae*, i.e. the "anti-*Saccharomyces cerevisiae* antibody" (ASCA). Many patients with ulcerative colitis have the pANCA antibody in their blood, but not the ASCA antibody, while many Crohn's patients exhibit ASCA antibodies, and not pANCA antibodies. One method of evaluating Crohn's disease is using the Crohn's disease Activity Index (CDAI), based on 18 predictor variables scores collected by physicians. CDAI values of 150 and below are associated with quiescent disease; values above that indicate active disease, and values above 450 are seen with extremely severe disease [Best et al., "Development of a Crohn's disease activity index." Gastroenterology 70:439-444 (1976)]. However, since the original study, some researchers use a 'subjective value' of 200 to 250 as an healthy score.

Systemic Lupus Erythematosus (SLE) is an autoimmune disease caused by recurrent injuries to blood vessels in multiple organs, including the kidney, skin, and joints. In patients with SLE, a faulty interaction between T cells and B-cells results in the production of autoantibodies that attack the cell nucleus. There is general agreement that autoantibodies are responsible for SLE, so new therapies that deplete the B-cell lineage, allowing the immune system to reset as new B-cells are generated from precursors, would offer hope for long lasting benefit in SLE patients.

Multiple sclerosis (MS) is also an autoimmune disease. It is characterized by inflammation of the central nervous system and destruction of myelin, which insulates nerve cell fibers in the brain, spinal cord, and body. Although the cause of MS is unknown, it is widely believed that autoimmune T cells are primary contributors to the pathogenesis of the disease. However, high levels of antibodies are present in the cerebral spinal fluid of patients with MS, and some theories predict that the B-cell response leading to antibody production is important for mediating the disease.

Autoimmune thyroid disease results from the production of autoantibodies that either stimulate the thyroid to cause hyperthyroidism (Graves' disease) or destroy the thyroid to cause hypothyroidism (Hashimoto's thyroiditis). Stimulation of the thyroid is caused by autoantibodies that bind and activate the thyroid stimulating hormone (TSH) receptor. Destruction of the thyroid is caused by autoantibodies that react with other thyroid antigens.

Additional diseases, disorders, and conditions amenable to the benefits provided by the compositions and methods of the invention include Sjogren's syndrome is an autoimmune disease characterized by destruction of the body's moisture-producing glands. Further, immune thrombocytopenic purpura (ITP) is caused by autoantibodies that bind to blood platelets and cause their destruction, and this condition is suitable for application of the materials and methods of the invention. Myasthenia Gravis (MG), a chronic autoimmune neuromuscular disorder characterized by autoantibodies that bind to acetylcholine receptors expressed at neuromuscular junctions leading to weakness of the voluntary muscle groups, is a disease having symptoms that are treatable using the composition and methods of the invention, and it is expected that the invention will be beneficial in treating and/or preventing MG. Still further, Rous Sarcoma Virus infections are expected to be amenable to treatment, or amelioration of at least one symptom, with the compositions and methods of the invention.

Another aspect of the present invention is using the materials and methods of the invention to prevent and/or treat any hyperproliferative condition of the skin including psoriasis and contact dermatitis or other hyperproliferative disease. Psoriasis, is characterized by autoimmune inflammation in the skin and is also associated with arthritis in 30% of cases, as well as scleroderma, inflammatory bowel disease, including Crohn's disease and ulcerative colitis. It has been demonstrated that patients with psoriasis and contact dermatitis have elevated antigen activity within these lesions (Ogoshi et al., J. Inv. Dermatol., 110:818-23 [1998]). The multispecific, multivalent binding proteins can deliver a cytotoxic cell of the immune system, for example, directly to cells within the lesions expressing high levels of antigen. The multivalent, e.g., multispecific, binding proteins can be administered subcutaneously in the vicinity of the lesions, or by using any of the various routes of administration described herein and others which are well known to those of skill in the art.

Also contemplated is the treatment of idiopathic inflammatory myopathy (IIM), including dermatomyositis (DM) and polymyositis (PM). Inflammatory myopathies have been categorized using a number of classification schemes. Miller's classification schema (Miller, Rheum Dis Clin North Am. 20:811-826, 1994) identifies 2 idiopathic inflammatory myopathies (IIM), polymyositis (PM) and dermatomyositis (DM).

Polymyositis and dermatomyositis are chronic, debilitating inflammatory diseases that involve muscle and, in the case of DM, skin. These disorders are rare, with a reported annual incidence of approximately 5 to 10 cases per million adults and 0.6 to 3.2 cases per million children per year in the United States (Targoff, Curr Probl Dermatol. 1991, 3:131-180). Idiopathic inflammatory myopathy is associated with significant morbidity and mortality, with up to half of affected adults noted to have suffered significant impairment (Gottdiener et al., Am J Cardiol. 1978, 41:1141-49). Miller (Rheum Dis Clin North Am. 1994, 20:811-826 and Arthritis and Allied Conditions, Ch. 75, Eds. Koopman and Moreland, Lippincott Williams and Wilkins, 2005) sets out five groups of criteria used to diagnose IIM, i.e., Idiopathic Inflammatory Myopathy Criteria (IIMC) assessment, including muscle weakness, muscle biopsy evidence of degeneration, elevation of serum levels of muscle-associated enzymes, electromagnetic triad of myopathy, evidence of rashes in dermatomyositis, and also includes evidence of autoantibodies as a secondary criteria.

IIM associated factors, including muscle-associated enzymes and autoantibodies include, but are not limited to, creatine kinase (CK), lactate dehydrogenase, aldolase, C-reactive protein, aspartate aminotransferase (AST), alanine aminotransferase (ALT), and antinuclear autoantibody (ANA), myositis-specific antibodies (MSA), and antibody to extractable nuclear antigens.

Preferred autoimmune diseases amenable to the methods of the invention include Crohn's disease, Guillain-Barré syndrome (GBS; also known as acute inflammatory demyelinating polyneuropathy, acute idiopathic polyradiculoneuritis, acute idiopathic polyneuritis and Landry's ascending paralysis), lupus erythematosus, multiple sclerosis, myasthenia gravis, optic neuritis, psoriasis, rheumatoid arthritis, hyperthyroidism (e.g., Graves' disease), hypothyroidism (e.g., Hashimoto's disease), Ord's thyroiditis (a thyroiditis similar to Hashimoto's disease), diabetes mellitus (type 1), aplastic anemia, Reiter's syndrome, autoimmune hepatitis, primary biliary cirrhosis, antiphospholipid antibody syndrome (APS), opsoclonus myoclonus syndrome (OMS), temporal arteritis (also known as "giant cell arteritis"), acute disseminated encephalomyelitis (ADEM), Goodpasture's syndrome, Wegener's granulomatosis, coeliac disease, pemphigus, canine polyarthritis, warm autoimmune hemolytic anemia. In addition, the invention contemplates methods for the treatment, or amelioration of a symptom associated with, the following diseases, endometriosis, interstitial cystitis, neuromyotonia, scleroderma, vitiligo, vulvodynia, Chagas' disease leading to Chagasic cardiopathy (cardiomegaly), sarcoidosis, chronic fatigue syndrome, and dysautonomia.

The complement system is believed to play a role in many diseases with an immune component, such as Alzheimer's disease, asthma, lupus erythematosus, various forms of arthritis, autoimmune heart disease and multiple sclerosis, all of which are contemplated as diseases, disorders or conditions amenable to treatment or symptom amelioration using the methods according to the invention.

Certain constant sub-regions are preferred, depending on the particular effector function or functions to be exhibited by a multivalent single-chain binding molecule. For example, IgG (IgG1, 2, or 3) and IgM are preferred for complement activation, IgG of any subtype is preferred for opsonization and toxin neutralization; IgA is preferred for pathogen binding; and IgE for binding of such parasites as worms.

By way of example, $F_c$Rs recognizing the constant region of IgG antibodies have been found on human leukocytes as three distinct types of Fcγ receptors, which are distinguishable by structural and functional properties, as well as by antigenic structures detected by CD monoclonal antibodies. They are known as FcγRI, FcγRII, and FcγRIII, and are differentially expressed on (overlapping) subsets of leukocytes.

FcgRI (CD64), a high-affinity receptor expressed on monocytes, macrophages, neutrophils, myeloid precursors and dendritic cells, comprised isoforms 1a and 1b. FcgRI has a high affinity for monomeric human IgG1 and IgG3. Its affinity for IgG4 is about 10 times lower, while it does not bind IgG2. FcgRI does not show genetic polymorphism.

FcγRII (CD32), comprised of isoforms lla, llb1, llb2, llb3 and llc, is the most widely distributed human FcγR type, being expressed on most types of blood leukocytes, as well as on Langerhans cells, dendritic cells and platelets. FcγRII is a low-affinity receptor that only binds aggregated IgG. It is the only FcγR class able to bind IgG2. FcγRIIa shows genetics polymorphism, resulting in two distinct allotypes, FcγRlla-H131 and FcγRlla-R131, respectively. This functional polymorphism is attributable to a single amino acid difference: a histidine (H) or an arginine (R) residue at position 131, which is critical for IgG binding. FcγRlla readily binds human IgG and IgG3 and appears not to bind IgG4. The FcγRlla-H131 has a much higher affinity for complexed IgG2 than the FcγR-lla-R131 allotype.

FcγRIII (CD16) has two isoforms or allelotypes, both of which are able to bind IgG1 and IgG3. The FcγRIIa, with an intermediate affinity for IgG, is expressed on macrophages, monocytes, natural killer (NK) cells and subsets of T cells. FcγRIIIb is a low-affinity receptor for IgG, selectively expressed on neutrophils. It is a highly mobile receptor with efficient collaboration with other membrane receptors. Studies with myeloma IgG dimers have shown that only IgG1 and IgG3 bind to FcγRIIIb (with low affinity), while no binding of IgG2 and IgG4 has been found. The FcγRIIIb bears a co-dominant, bi-allelic polymorphism, the allotypes being designated NA1 (Neutrophil Antigen) and NA2.

Yet another aspect of the invention is use of the materials and methods of the invention to combat, by treating, preventing or mitigating the effects of, infection, resulting from any of a wide variety of infectious agents. The multivalent, multispecific binding molecules of the invention are designed to efficiently and effectively recruit the host organism's immune system to resist infection arising from a foreign organism, a foreign cell, a foreign virus or a foreign inanimate object. For example, a multispecific binding molecule may have one binding domain that specifically binds to a target on an infectious agent and another binding domain that specifically binds to a target on an Antigen Presenting Cell, such as CD40, CD80, CD86, DC-SIGN, DEC-205, CD83, and the like). Alternatively, each binding domain of a multivalent binding molecule may specifically bind to an infectious agent, thereby more effectively neutralizing the agent. In addition, the invention contemplates multispecific, multivalent binding molecules that specifically bind to a target on an infectious agent and to a non-cell-associated binding partner, which may be effective in conjunction with an effector function of the multispecific binding molecule in treating or preventing infection arising from an infectious agent.

Infectious cells contemplated by the invention include any known infectious cell, including but not limited to any of a variety of bacteria (e.g., pathogenic $E.\ coli$, $S.\ typhimurium$, $P.\ aeruginosa$, $B.\ anthracis$, $C.\ botulinum$, $C.\ difficile$, $C.\ perfringens$, $H.\ pylori$, $V.\ cholerae$, and the like), mycobacteria, mycoplasma, fungi (including yeast and molds), and parasites (including any known parasitic member of the Protozoa, Trematoda, Cestoda and Nematoda). Infectious viruses include, but are not limited to, eukaryotic viruses (e.g., adenovirus, bunyavirus, herpesvirus, papovavirus, paramyxovirus, picornavirus, poxvirus, reovirus, retroviruses, and the like) as well as bacteriophage. Foreign objects include objects entering an organism, preferably a human, regardless of mode of entry and regardless of whether harm is intended. In view of the increasing prevalence of multi-drug-resistant infectious agents (e.g., bacteria), particularly as the causative agents of nosocomial infection, the materials and methods of the invention, providing an approach to treatment that avoids the difficulties imposed by increasing antibiotic resistance.

Diseases, conditions or disorders associated with infectious agents and amenable to treatment (prophylactic or therapeutic) with the materials and methods disclosed herein include, but are not limited to, anthrax, aspergillosis, bacterial meningitis, bacterial $pneumoniae$ (e.g., $chlamydia\ pneumoniae$), blastomycosis, botulism, brucellosis, candidiasis, cholera, ciccidioidomycosis, cryptococcosis, diahhreagenic, enterohemorrhagic or enterotoxigenic $E.\ coli$, diphtheria, glanders, histoplasmosis, legionellosis, leprosy, listeriosis, nocardiosis, pertussis, salmonellosis, scarlet fever, sporotrichosis, strep throat, toxic shock syndrome, traveler's diarrhea, and typhoid fever.

Additional aspects and details of the invention will be apparent from the following examples, which are intended to be illustrative rather than limiting. Example 1 describes recombinant cloning of immunoglobulin heavy and light chain variable regions. Example 2 describes the construction of Small Modular ImmunoPharmaceuticals. Example 3 describes the construction of a prototype cassette for a multivalent binding protein with effector function. Example 4 describes binding and expression studies with this initial prototype molecule. Example 5 describes construction of alternative constructs derived from this initial prototype molecule where the sequence of the linker region between the EFD and BD2 was changed in both length and sequence. In addition, it describes alternative forms where the orientation of V regions in binding domain 2 were also altered. Example 6 describes subsequent binding and functional studies on these alternative constructs with variant linker forms, identifying a cleavage in the linker region in several of these derivative forms, and the new sequence variants developed to address this problem. Example 7 describes the construction of an alternative preferred embodiment of the multispecific, multivalent fusion proteins, where both BD1 and BD2 bind to antigens on the same cell type (CD20 and CD37), or another multispecific fusion protein where the antigen binding specificity for BD2 has been changed to human CD3 instead of CD28. Example 8 describes the binding and functional studies performed with the CD20-hIgG-CD37 multispecific constructs. Example 9 describes the binding and functional studies with the CD20-hIgG-CD3 multivalent fusion protein constructs. Example 10 discloses multivalent binding molecules having linkers based on specific regions of the extracellular domains of members of the immunoglobulin superfamily. Example 11 discloses assays for identifying binding domains expected to be effective in multivalent binding molecules in achieving at least one beneficial effect identified as being associated with such molecules (e.g., disease treatment).

EXAMPLE 1

Cloning of Immunoglobulin Heavy and Light Chain Variable Regions

Any methods known in the art can be used to elicit antibodies to a given antigenic target. Further, any methods known in the art can be used to clone the immunoglobulin light and/or heavy chain variable regions, as well as the constant sub-region of an antibody or antibodies. The following method provides an exemplary cloning method.

A. Isolation of Total RNA

To clone the immunoglobulin heavy and light chain variable regions, or the constant sub-region, total RNA is isolated from hybridoma cells secreting the appropriate antibody. Cells ($2 \times 10^7$) from the hybridoma cell line are washed with 1×PBS and pelleted via centrifugation in a 12×75 mm round bottom polypropylene tube (Falcon no. 2059). TRIzol™ Total RNA Isolation Reagent (Gibco BRL, Life Technologies, Cat no. 15596-018) is added (8 ml) to each tube and the cells are lysed via repeated pipetting. The lysate is incubated for 5 minutes at room temperature prior to the addition of 1.6 ml (0.2× volume) of chloroform and vigorous shaking for 15 seconds. After standing 3 minutes at room temperature, the lysates are centrifuged at 9,000 rpm for 15 minutes in a 4° C. pre-chilled Beckman JA-17 rotor in order to separate the aqueous and organic phases. The top aqueous phase (about 4.8 ml) is transferred into a new tube and mixed gently with 4 ml of isopropanol. After a 10 minute incubation at room temperature, the RNA is precipitated by centrifugation at 9,000 rpm in a 4° C. JA-17 rotor for 11 minutes. The RNA pellet is washed with 8 ml of ice-cold 75% ethanol and re-pelleting by centrifugation at 7,000× rpm for 7 minutes in a JA-17 rotor at 4° C. The ethanol wash is decanted and the RNA pellets are air-dried for 10 minutes. The RNA pellets are resuspended in 150 µl of diethylpyrocarbonate (DEPC)-treated ddH$_2$O containing 1 µl of RNase Inhibitor (Catalog No. 799017; Boehringer Mannheim/Roche) per 1 ml of DEPC-treated ddH$_2$O. The pellets are resuspended by gentle pipetting and are incubated for 20 minutes at 55° C. RNA samples are quantitated by measuring the OD$_{260\,nm}$ of diluted aliquots (1.0 OD$_{260\,nm}$ unit=40 µg/ml RNA).

B. Rapid Amplification of cDNA Ends

5' RACE is carried out to amplify the ends of the heavy and light chain variable regions, or the constant sub-region. The 5' RACE System for Rapid Amplification of cDNA Ends Kit version 2.0 (Life Technologies, cat. no. 18374-058) is used according to the manufacturer's instructions. Degenerate 5' RACE oligonucleotide primers are designed to match, e.g., the constant regions of two common classes of mouse immunoglobulin heavy chains (IgG1 and IgG2b) using the oligonucleotide design program Oligo version 5.1 (Molecular Biology Insights, Cascade Colo.). Primers are also designed to match the constant region of the mouse IgG kappa light chain. This is the only class of immunoglobulin light chain, so no degeneracy is needed in the primer design. The sequences of the primers are as follows:

| Name Sequence | SEQ ID NO |
|---|---|
| Heavy Chain GSP1<br>5'AGGTGCTGGAGGGGACAGTCACTGAGCTGC3' | 7 |
| Nested Heavy Chain<br>5'GTCACWGTCACTGRCTCAGGGAARTAGC3'<br>(W = A or T; R = A or G) | 8 |
| Light Chain GSP1<br>5'GGGTGCTGCTCATGCTGTAGGTGCTGTCTTTGC3' | 9 |
| Nested Light Chain<br>5'CAAGAAGCACACGACTGAGGCACCTCCAGATG3' | 10 |
| 5' Race Abridged Anchor Primer<br>5'GGCCACGCGTCGACTAGTACGGGNNGGGNNGGGNNG3' | 11 |

To amplify the mouse immunoglobulin heavy chain component, the reverse transcriptase reaction is carried in a 0.2 ml thin-walled PCR tube containing 2.5 pmoles of heavy chain GSP1 primer (SEQ ID NO: 7), 4 µg of total RNA isolated from a suitable hybridoma clone (e.g., either clone 4A5 or clone 4B5), and 12 µl of DEPC treated ddH2O. Likewise, for the mouse light chain component, the reverse transcriptase reaction is carried out in a 0.2 ml thin-walled PCR tube containing 2.5 pmoles of a light chain GSP1 primer (SEQ ID NO: 9), 4 µg of total RNA from a suitable hybridoma clone (e.g., either clone 4A5 or clone 4B5), and 12 µl of DEPC treated ddH2O.

The reactions are carried out in a PTC-100 programmable thermal cycler (MJ research Inc., Waltham, Mass.). The mixture is incubated at 70° C. for 10 minutes to denature the RNA and then chilled on wet ice for 1 minute. The tubes are centrifuged briefly in order to collect moisture from the lids of the tubes. Subsequently, the following components are added to the reaction: 2.5 µl of 10×PCR buffer (200 mM Tris-HCl, pH 8.4, 500 mM KCl), 2.5 µl of 25 mM MgCl$_2$, 1 µl of 10 mM dNTP mix, and 2.5 µl of 0.1 M DTT. After mixing each tube by gentle pipetting, the tubes are placed in a PTC-100 thermocycler at 42° C. for 1 minute to pre-warm the mix. Subsequently, 1 µl (200 units) of SuperScript™ II Reverse Transcriptase (Gibco-BRL; cat no. 18089-011) is added to each tube, gently mixed by pipetting, and incubated for 45 minutes at 42° C. The reactions are cycled to 70° C. for 15 minutes to terminate the reaction, and then cycled to 37° C. RNase mix (1 µl) is then added to each reaction tube, gently mixed, and incubated at 37° C. for 30 minutes.

The first-strand cDNA generated by the reverse transcriptase reaction is purified with the GlassMAX DNA Isolation Spin Cartridge (Gibco-BRL) according to the manufacturer's instructions. To each first-strand reaction, 120 µl of 6 M NaI binding solution is added. The cDNA/NaI solution is then transferred into a GlassMAX spin cartridge and centrifuged for 20 seconds at 13,000×g. The cartridge inserts are carefully removed and the flow-through is discarded from the tubes. The spin cartridges are then placed back into the empty tubes and 0.4 ml of cold (4° C.) 1× wash buffer is added to each spin cartridge. The tubes are centrifuged at 13,000×g for 20 seconds and the flow-through is discarded. This wash step is repeated three additional times. The GlassMAX cartridges are then washed 4 times with 0.4 ml of cold (4° C.) 70% ethanol. After the flow-through from the final 70% ethanol wash is discarded, the cartridges are placed back in the tubes and centrifuged at 13,000×g for an additional 1 minute in order to completely dry the cartridges. The spin cartridge inserts are then transferred to a fresh sample recovery tube where 50 µl of 65° C. (pre-heated) DEPC-treated ddH$_2$O is quickly added to each spin cartridge. The cartridges are centrifuged at 13,000×g for 30 seconds to elute the cDNA.

C. Terminal Deoxynucleotidyl Transferase (TdT) Tailing

For each first-strand cDNA sample, the following components are added to a 0.2 ml thin-walled PCR tube: 6.5 µl of DEPC-treated ddH$_2$O, 5.0 µl of 5× tailing buffer, 2.5 µl of 2 mM dCTP, and 10 µl of the appropriate GlassMAX-purified cDNA sample. Each 24 µl reaction is incubated 2-3 minutes in a thermal cycler at 94° C. to denature the DNA, and chilled on wet ice for 1 minute. The contents of the tube are collected by brief centrifugation. Subsequently, 1 µl of terminal deoxynucleotidyl transferase (TdT) is added to each tube. The tubes are mixed via gentle pipetting and incubated for 10 minutes at 37° C. in a PTC-100 thermal cycler. Following this 10 minute incubation, the TdT is heat inactivated by cycling to 65° C. for 10 minutes. The reactions are cooled on ice and the TdT-tailed first-strand cDNA is stored at −20° C.

D. PCR of dC-Tailed First-Strand cDNA

Duplicate PCR amplifications (two independent PCR reactions for each dC-tailed first-strand cDNA sample) are performed in a 50 µl volume containing 200 µM dNTPs, 0.4 µM of 5' RACE Abridged Anchor Primer (SEQ ID NO: 11), and 0.4 µM of either Nested Heavy Chain GSP2 (SEQ ID NO: 8) or Nested Light Chain GSP2 (SEQ ID NO: 10), 10 mM Tris-HCl (pH 8.3), 1.5 mM MgCl$_2$, 50 mM KCl, 5 µl of dC-tailed cDNA, and 5 units of Expand™ Hi-Fi DNA polymerase (Roche/Boehringer Mannheim GmbH, Germany). The PCR reactions are amplified using a "Touch-down/Touch-up" annealing temperature protocol in a PTC-100 programmable thermal cycler (MJ Research Inc.) with the following conditions: initial denaturation of 95° C. for 40 seconds, 5 cycles at 94° C. for 20 seconds, 61° C.-2° C./cycle for 20 seconds, 72° C. for 40 seconds+1 second/cycle, followed by 5 cycles at 94° C. for 25 seconds, 53° C.+1° C./cycle for 20 seconds, 72° C. for 46 seconds+1 second/cycle, followed by 20 cycles at 94° C. for 25 seconds, 55° C. for 20 seconds, 72° C. for 51 seconds+1 second/cycle, and a final incubation of 72° C. for 5 minutes.

E. TOPO TA-Cloning

The resulting PCR products are gel-purified from a 1.0% agarose gel using the QIAQuick Gel purification system (QIAGEN Inc., Chatsworth, Calif.), TA-cloned into pCR2.1 using the TOPO TA Cloning® kit (Invitrogen, San Diego, Calif., cat. no. K4550-40), and transformed into *E. coli* TOP10F' cells (Invitrogen), according to manufacturers' instructions. Clones with inserts are identified by blue/white screening according to the manufacturer's instructions, where white clones are considered positive clones. Cultures of 3.5 ml liquid Luria Broth (LB) containing 50 µg/ml ampicillin are inoculated with white colonies and grown at 37° C. overnight (about 16 hours) with shaking at 225 rpm.

The QIAGEN Plasmid Miniprep Kit (QIAGEN Inc., cat. no. 12125) is used to purify plasmid DNA from the cultures according to the manufacturer's instructions. The plasmid DNA is suspended in 34 µl of 1×TE buffer (pH 8.0) and then positive clones sequenced as previously described by fluorescent dideoxy nucleotide sequencing and automated detection using ABI Big Dye Terminator 3.1 reagents at 1:4-1:8 dilutions and analyzed using an ABI 3100 DNA sequencer. Sequencing primers used include T7 (5'GTAATACGACT-CACTATAGG3'; SEQ ID NO: 12) and M13 Reverse (5'CAG-GAAACAGCTATGACC3'; SEQ ID NO: 13) primers. Sequencing results will confirm that the clones correspond to mouse IgG sequences.

F. De Novo Gene Synthesis Using Overlapping Oligonucleotide Extension PCR

This method involves the use of overlapping oligonucleotide primers and PCR using either a high fidelity DNA polymerase or a mix of polymerases to synthesize an immunoglobulin V-region or other gene. Starting at the middle of the V-region sequence, 40-50 base primers are designed such that the growing chain is extended by 20-30 bases, in either direction, and contiguous primers overlap by a minimum of 20 bases. Each PCR step requires two primers, one priming on the anti-sense strand (forward or sense primer) and one priming on the sense strand (reverse or anti-sense primer) to create a growing double-stranded PCR product. During primer design, changes can be made in the nucleotide sequence of the final product to create restriction enzyme sites, destroy existing restriction enzyme sites, add flexible linkers, change, delete or insert bases that alter the amino acid sequence, optimize the overall DNA sequence to enhance primer synthesis and conform to codon usage rules for the organism contemplated for use in expressing the synthetic gene.

Primer pairs are combined and diluted such that the first pair are at 5 µM an each subsequent pair has a 2-fold greater concentration up to 80 µM. One µL, from each of these primer mixes is amplified in a 50 µL, PCR reaction using Platinum PCR SuperMix-High Fidelity (Invitrogen, San Diego, Calif., cat. no. 12532-016). After a 2-minute initial denaturation at 94° C., 30 cycles of PCR are performed using a cycling profile of 94° C. for 20 seconds, 60° C. for 10 seconds; and 68° C. for 15 seconds. PCR products are purified using Qiaquick PCR Purification columns (Qiagen Inc., cat. no. 28704) to remove excess primers and enzyme. This PCR product is then reamplified with the next set of similarly diluted primer pairs using PCR conditions exactly as described above, but increasing the extension time of each cycle to 68° C. for 30 seconds. The resultant PCR product is again purified from primers and enzymes as described above and TOPO-TA cloned and sequenced exactly as described in section E above.

EXAMPLE 2

Construction of Small Modular ImmunoPharmaceuticals (SMIPs)

A multispecific, multivalent binding protein with effector function was constructed that contained a binding domain 1 in the form of a single-chain recombinant (murine/human) scFv designated 2H7 (VL-linker-VH). The scFv 2H7 is a small modular immunopharmacaceutical (SMIP) that specifically recognizes CD20. The binding domain was based on a publicly available human CD20 antibody sequence GenBank Accession Numbers, M17953 for VH, and M17954 for VL. CD20-specific SMIPs are described in co-owned US Patent Publications 2003/133939, 2003/0118592 and 2005/0136049, incorporated herein in their entireties by reference. The peptide linker separating VL and VH was a 15-amino acid linker encoding the sequence: Asp-Gly$_3$Ser-(Gly$_4$Ser)$_2$. Binding domain 1 was located at the N-terminus of the multispecific binding protein, with the C-terminus of that domain linked directly to the N-terminus of a constant sub-region containing a hinge, $C_{H2}$ and $C_{H3}$ domains (in amino-to-carboxy orientation). The constant sub-region was derived from an IgG1 antibody, which was isolated by PCR amplification of human IgG1 from human PBMCs. The hinge region was modified by substituting three Ser residues in place of the three Cys residues present in the wild type version of the human IgG1 hinge domain, encoded by the 15 amino acid sequence: EPKSCDKTHTCPPCP (SEQ ID NO: 14; the three Cys residues replaced by Ser residues are indicated in bold). In alternative embodiments, the hinge region was modified at one or more of the cysteines, so that SSS and CSC type hinges were generated. In addition, the final proline was sometimes substituted with a serine as well as the cysteine substitutions.

The C-terminal end of the $C_{H3}$ domain was covalently attached to a series of alternative linker domains juxtaposed between the constant sub-region C-terminus and the amino terminus of binding domain 2. Preferred multivalent binding proteins with effector function will have one of these linkers to space the constant sub-region from binding domain 2, although the linker is not an essential component of the compositions according to the invention, depending on the folding properties of BD2. For some specific multivalent molecules, the linker might be important for separation of domains, while for others it may be less important. The linker was attached to the N-terminal end of scFv 2E12 (($V_H$-linker-$V_L$), which specifically recognizes CD28. The linker separating the VH and VL domains of the scFv 2E12 part of the multivalent binding molecule was a 20-amino acid linker (Gly$_4$Ser)$_4$, rather than the standard (Gy$_4$Ser)$_3$ linker usually inserted between V domains of an scFv. The longer linker was observed to improve the binding properties of the 2e12 scFv in the VH-VL orientation.

The multispecific, multivalent binding molecule as constructed contained a binding domain 1, which comprises the 2E12 leader peptide sequence from amino acids 1-23 of SEQ ID NO: 171; the 2H7 murine anti-human CD20 light chain variable region, which is reflected at position 24 in SEQ ID NO: 171; an Asp-Gly$_3$-Ser-(Gly$_4$Ser)$_2$ linker, beginning at residue 130 in SEQ ID NO: 171, the 2H7 murine anti-human CD20 heavy chain variable region with a leucine to serine (VHL11S) amino acid substitution at residue 11 in the variable domain for VH, and which has a single serine residue at the end of the heavy chain region (i.e., VTVS where a canonical sequence would be VTVSS) (Genbank Acc. No. M17953), and interposed between the two binding domains BD1 (2H7) and BD2 (2E12) is a human IgG1 constant sub-region, including a modified hinge region comprising a "CSC" or an "SSS" sequence, and wild-type $C_{H2}$ and $C_{H3}$ domains. The nucleotide and amino acid sequences of the multivalent binding protein with effector function are set out in SEQ ID NOS: 228 and 229 for the CSC forms, respectively and SEQ ID NOS: 170 and 171, for the SSS forms.

Stably expressing cell lines were created by transfection via electroporation of either uncut or linearized, recombinant expression plasmid into Chinese hamster ovary cells (CHO DG44 cells) followed by selection in methotrexate containing medium. Bulk cultures and master wells producing the highest level of multivalent binding protein were amplified in increasing levels of methotrexate, and adapted cultures were subsequently cloned by limiting dilution. Transfected CHO cells producing the multivalent binding protein were cultured in bioreactors or wave bags using serum-free medium obtained from JRH Biosciences (Excell 302, cat. no. 14324-1000M, supplemented with 4 mM glutamine (Invitrogen, 25030-081), sodium pyruvate (Invitrogen 11360-070, diluted to 1×), non-essential amino acids (Invitrogen, 11140-050, final dilution to 1×), penicillin-streptromycin 100 IU/ml (Invitrogen, 15140-122), and recombulin insulin at 1 µg/ml (Invitrogen, 97-503311). Other serum free CHO basal medias may also be used for production, such as CD-CHO, and the like.

Fusion protein was purified from spent CHO culture supernatants by Protein A affinity chromatography. The multivalent binding protein was purified using a series of chromatography and filtration steps, including a virus reduction filter. Cell culture supernatants were filtered, then subjected to protein A Sepharose affinity chromatography over a GE Healthcare XK 16/40 column. After binding of protein to the column, the column was washed in dPBS, then 1.0 M NaCl, 20 mM sodium phosphate pH 6.0, and then 25 mM NaCl, 25 mN NaOAc, pH 5.0 to remove nonspecific binding proteins. Bound protein was eluted from the column in 100 mM Glycine (Sigma), pH 3.5, and brought to pH 5.0 with 0.5 M 2-(N-Morpholino) ethanesulfonic acid (MES), pH 6.0. Protein samples were concentrated to 25 mg/ml in preparation for GPC purification. Size exclusion chromatography was performed on a GE Healthcare AKTA Explorer 100 Air apparatus, using a GE healthcare XK column and Superdex 200 preparative grade (GE healthcare).

The material was then concentrated and formulated with 20 mM sodium phosphate and 240 mM sucrose, with a resulting pH of 6.0. The composition was filtered before filling into sterile vials at various concentrations, depending on the amount of material recovered.

EXAMPLE 3

Construction of Scorpion Expression Cassette

A nucleic acid containing the synthetic 2H7 scFv (anti-CD20; SEQ ID NO: 1) linked to a constant sub-region as described in Example 2 has been designated TRU-015. TRU-015 nucleic acid, as well as synthetic scFv 2E12 (anti-CD28 VL-VH; SEQ ID NO: 3) and synthetic scFv 2E12 (anti-CD28 VH-VL; SEQ ID NO: 5) nucleic acids encoding small modular immunopharmaceuticals, were used as templates for PCR amplification of the various components of the scorpion cassettes The template, or scaffold, for binding domain 1 and the constant sub-region was provided by TRU-015 (the nucleic acid encoding scFv 2H7 (anti-CD20) linked to the constant sub-region) and this template was constructed in the expression vector pD18. The above-noted nucleic acids containing scFv 2E12 in either of two orientations ($V_L$-$V_H$ and $V_H$-$V_L$) provided the coding region for binding domain 2.

TRU 015 SSS hinge $C_{H2}C_{H3}$ for BD2/Linker Insertion

A version of the synthetic 2H7 scFv IgG1 containing the SSS hinge was used to create a scorpion cassette by serving as the template for addition of an EcoRI site to replace the existing stop codon and XbaI site. This molecule was amplified by PCR using primer 9 (SEQ ID NO: 23; see Table 1) and primer 87 (SEQ ID NO: 40; see Table 1) as well as a Platinum PCR High Fidelity mix (Invitrogen). The resultant 1.5 Kbp fragment was purified and cloned into the vector pCR2.1-TOPO (Invitrogen), transformed into *E. coli* strain TOP10 (Invitrogen), and the DNA sequence verified.

TABLE 1

Table 1. Oligonucleotide primers used to construct CD20-CD28 scorpion cassette. Primers are separated into 2 groups, PCR and Sequencing. PCR primers were used to construct the cassette and sequencing primers were used to confirm the DNA sequence of all intermediates and final constructs.

| No. Name | Sequence 5'-3' | SEQ ID NO. |
|---|---|---|
| PCR Primers | | |
| 1 hVK3L-F3H3 | GCGATAAAGCTTGCCGCCATGGAAGCACCAGCGCAGCTTCTCTTCC | 15 |
| 2 hVK3L-F2 | ACCAGCGCAGCTTCTCTTCCTCCTGCTACTCTGGCTCCCAGATACCACCG | 16 |
| 3 hVK3L-F1-2H7VL | GGCTCCCAGATACCACCGGTCAAATTGTTCTCTCCCAGTCTCCAG | 17 |
| 4 2H7VH-NheF | GCGATAGCTAGCCAGGCTTATCTACAGCAGTCTGG | 18 |
| 5 G4S-NheR | GCGATAGCTAGCCCCACCTCCTCCAGATCCACCACCGCCCGAG | 19 |
| 6 015VH-XhoR | GCGTACTCGAGGAGACGGTGACCGTGGTCCCTGTG | 20 |
| 7 G1H-C-XHO | GCAGTCTCGAGCGAGCCCAAATCTTGTGACAAAACTC | 21 |
| 8 G1H-S-XHO | GCAGTCTCGAGCGAGCCCAAATCTTCTGACAAAACTC | 22 |
| 9 CH3R-EcoR1 | GCGTGAGAATTCTTACCCGGAGACAGGGAGAGGCTC | 23 |
| 10 G1-XBA-R | GCGACGTCTAGAGTCATTTACCCGGAGACAGG | 24 |
| 11 G4SLinkR1-S | AATTATGGTGGCGGTGGCTCGGGCGGTGGTGGATCTGGAGGAGGTGGGAGTGGG | 25 |

TABLE 1-continued

Table 1. Oligonucleotide primers used to construct CD20-CD28 scorpion cassette. Primers are separated into 2 groups, PCR and Sequencing. PCR primers were used to construct the cassette and sequencing primers were used to confirm the DNA sequence of all intermediates and final constructs.

| No. | Name | Sequence 5'-3' | SEQ ID NO. |
|---|---|---|---|
| 12 | G4SLinkR1-AS | AATTCCCACTCCCACCTCCTCCAGATCCA CCACCGCCCGAGCCACCGCCACCAT | 26 |
| 13 | 2E12VLXbaR | GCGTGTCTAGATTAACGTTTGATTTCCAG CTTGGTG | 27 |
| 14 | 2E12VLR1F | GCGATGAATTCTGACATTGTGCTCACCCA ATCTCC | 28 |
| 15 | 2E12VHR1F | GCGATGAATTCTCAGGTGCAGCTGAAGGA GTCAG | 29 |
| 16 | 2E12VHXbaR | GCGAGTCTAGATTAAGAGGAGACGGTGAC TGAGGTTC | 30 |
| 17 | 2e12VHdXbaF1 | GGGTCTGGAGTGGCTGGGAATGATATG | 31 |
| 18 | 2e12VHdXbaR1 | ATTCCCAGCCACTCCAGACCCTTTCCTG | 32 |
| 19 | IgBsrG1F | GAGAACCACAGGTGTACACCCTG | 33 |
| 20 | IgBsrG1R | GCAGGGTGTACACCTGTGGTTCTCG | 34 |

| | | Sequencing Primers | |
|---|---|---|---|
| 82 | M13R | CAGGAAACAGCTATGAC | 35 |
| 83 | M13F | GTAAAACGACGGCCAGTG | 36 |
| 84 | T7 | GTAATACGACTCACTATAGG | 37 |
| 85 | pD18F-17 | AACTAGAGAACCCACTG | 38 |
| 86 | pD18F-20 | GCTAACTAGAGAACCCACTG | 39 |
| 87 | pD18F-1 | ATACGACTCACTATAGGG | 40 |
| 88 | pD18R-s | GCTCTAGCATTTAGGTGAC | 41 |
| 89 | CH3seqF1 | CATGAGGCTCTGCACAAC | 42 |
| 90 | CH3seqF2 | CCTCTACAGCAAGCTCAC | 43 |
| 91 | CH3seqR1 | GGTTCTTGGTCAGCTCATC | 44 |
| 92 | CH3seqR2 | GTGAGCTTGCTGTAGAGG | 45 | n2H7 $V_K$ and Human $V_{K3}$ Leader Sequence Fusion

Oligonucleotide-directed PCR mutagenesis was used to introduce an AgeI (ACCGGT) restriction site at the 5' end of the coding region for TRU 015 VK and an Nhe I (GCTAGC) restriction site at the 3' end of the coding region for the (G4S)3 linker using primers 3 and 5 from Table 1. Since primer 3 also encodes the last 6 amino acids of the human VK3 leader (gb:X01668), overlapping PCR was used to sequentially add the N-terminal sequences of the leader including a consensus Kozak box and HinDIII (AAGCTT) restriction site using primers 1, 2 and 5 from Table 1.

n2H7 IgG1 SSS Hinge-$C_{H2}C_{H3}$ Construction

Primers 4 and 6 (SEQ ID NOS: 18 and 20, respectively; Table 1) were used to re-amplify the TRU-015 $V_H$ with an NheI site 5' to fuse with the $V_K$ for TRU-015 and an Xho I (5'-CTCGAG-3') site at the 3' end junction with the IgG1 hinge-$C_{H2}C_{H3}$ domains. Likewise, the IgG1 hinge-$C_{H2}$-$C_{H3}$ region was amplified using primers 8 and 9 from Table 1, introducing a 5' Xho I site and replacing the existing 3' end with an EcoRI (5'-GAATTC-3') site for cloning, and destroying the stop codon to allow translation of Binding Domain 2 attached downstream of the CH3 domain. This version of the scorpion cassette is distinguished from the previously described cassette by the prefix "n."

In addition to the multivalent binding protein described above, a protein according to the invention may have a binding domain, either binding domain 1 or 2 or both, that corresponds to a single variable region of an immunoglobulin. Exemplary embodiments of this aspect of the invention would include binding domains corresponding to the $V_H$ domain of a camelid antibody, or a single modified or unmodified V region of another species antibody capable of binding to the target antigen, although any single variable domain is contemplated as useful in the proteins of the invention.

2E12 VL-VH and VH-VL Constructions

In order to make the 2E12 scFvs compatible with the cassette, an internal Xba I (5'-TCTAGA-3') site had to be destroyed using overlapping oligonucleotide primers 17 and 18 from Table 1. These two primers in combination with primer pairs 14/16 (VL-VH) or 13/15 (VH-VL) were used to amplify the two oppositely oriented binding domains such that they both carried EcoRI and XbaI sites at their 5' and 3' ends, respectively. Primers 13 and 16 also encode a stop codon (TAA) immediately in front of the Xba I site.

2H7 SSS IgG12e12 LH/HL Construction

Effector Domain-Binding Domain 2 Linker Addition. (Std Linkers—STD1 and STD2)

Complementary primers 11 and 12 from Table 1 were combined, heated to 70° C. and slow-cooled to room temperature to allow annealing of the two strands. 5' phosphate groups were added using T4 polynucleotide kinase (Roche) in 1× Ligation buffer with 1 mM ATP (Roche) using the manufacturer's protocol. The resulting double-stranded linker was then ligated into the EcoRI site between the coding regions for the IgG1 $C_{H3}$ terminus and the beginning of Binding Domain 2 using T4 DNA ligase (Roche). The resultant DNA constructs were screened for the presence of an EcoRI site at the linker-BD2 junction and the nucleotide sequence GAATTA at the $C_{H3}$-linker junction. The correct STD 1 linker construct was then re-digested with EcoRI and the linker ligation repeated to produce a molecule that had a linker composed of two (STD 2) identical iterations of the Lx 1 sequence. DNA constructs were again screened as above.

EXAMPLE 4

Expression Studies

Expression studies were performed on the nucleic acids described above that encode multivalent binding proteins with effector function. Nucleic acids encoding multivalent binding proteins were transiently transfected into COS cells and the transfected cells were maintained under well known conditions permissive for heterologous gene expression in these cells. DNA was transiently transfected into COS cells using PEI or DEAE-Dextran as previously described (PEI=Boussif O. et al., PNAS 92: 7297-7301, (1995), incorporated herein by reference; Pollard H. et al., JBC 273: 7507-7511, (1998), incorporated herein by reference). Multiple independent transfections of each new molecule were performed in order to determine the average expression level for each new form. For transfection by PEI, COS cells were plated onto 60 mm tissue culture plates in DMEM/10% FBS medium and incubated overnight so that they would be approximately 90% confluent on the day of transfection. Medium was changed to serum free DMEM containing no antibiotics and incubated for 4 hours. Transfection medium (4 ml/plate) contained serum free DMEM with 50 μg PEI and 10-20 ug DNA plasmid of interest. Transfection medium was mixed by vortexing, incubated at room temperature for 15 minutes, and added to plates after aspirating the existing medium. Cultures were incubated for 3-7 days prior to collection of supernatants. Culture supernatants were assayed for protein expression by SDS-PAGE, Western blotting, binding verified by flow cytometry, and function assayed using a variety of assays including ADCC, CDC, and coculture experiments.

SDS-PAGE Analysis and Western Blotting Analysis

Samples were prepared either from crude culture supernatants (usually 30 μl/well) or purified protein aliquots, containing 8 ug protein per well, and 2× Tris-Glycine SDS Buffer (Invitrogen) was added to a 1× final concentration. Ten (10) μl SeeBlue Marker (Invitrogen, Carlsbad, Calif.) were run to provide MW size standards. The multivalent binding (fusion) protein variants were subjected to SDS-PAGE analysis on 4-20% Novex Tris-glycine gels (Invitrogen, San Diego, Calif.). Samples were loaded using Novex Tris-glycine SDS sample buffer (2×) under reducing or non-reducing conditions after heating at 95° C. for 3 minutes, followed by electrophoresis at 175V for 60 minutes. Electrophoresis was performed using 1× Novex Tris-Glycine SDS Running Buffer (Invitrogen).

Figure 2:
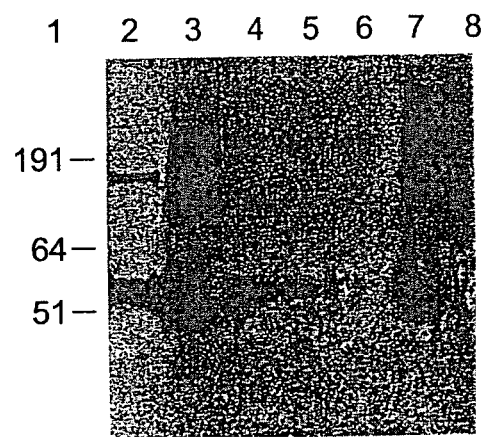
FIG. 2 shows a Western blot of non-reduced proteins expressed in COS cells. Protein was secreted into the culture medium, and culture supernatants isolated after 48-72 hours from transiently transfected cells by centrifugation. Thirty microliters, 30 µl of crude supernatant were loaded into each well of the gel. Lane identifications: 1-molecular weight markers, with numerals indicating kilodaltons; 2-2H7-IgG-STD1-2E12 LH; 3-2H7-IgG-STD1-2E12 HL, 4-2H7-IgG-STD2-2E12 LH; 5-2H7-IgG-STD2-2E12 HL; 6-2E12 LH SMIP; 7-2E12 HL SMIP; 8-2H7 SMIP. "2H7" refers to a single-chain construct, where BD1 encodes the CD20 specific binding domain (2H7) in the VLVH orientation; "2E12" refers to a binding domain specific for CD28; -IgG-refers to a single-chain construct, with a hinge encoding a sequence where all C are mutated to S (sss), and the CH2 and CH3 domains of IgG1 contain mutations which eliminate both ADCC and CDC effector functions (P238S and P331 S), "STD 1 refers to a 20-amino-acid linker (identified in FIG. 7 as "STD1=20aa") inserted adjacent to the BD2 in the VL-VH orientation, or 2E12 ($V_L$-$V_H$). "STD1-HL" refers to a similar construct as just described, but with the BD2 V regions in the VH-VL orientation as follows: 2H7-sssIgG (P238/331S)-20-amino-acid linker-2E12 ($V_H$-$V_L$). "STD2-LH" refers to 2H7-sssIgG (P238/331S)-38-amino-acid linker-2E12 ($V_L$-$V_H$); "STD2-LH" refers to 2H7-sssIgG (P238/331SS)-38-amino-acid linker-2E12 ($V_H$-$V_L$); "SMIP" refers to small modular immunopharmaceutical; and "H" generally refers to $V_H$, while "L" generally refers to $V_L$. Unless otherwise indicated, all protein orientations are N-terminal to C-terminal orientations.
Figure 5:
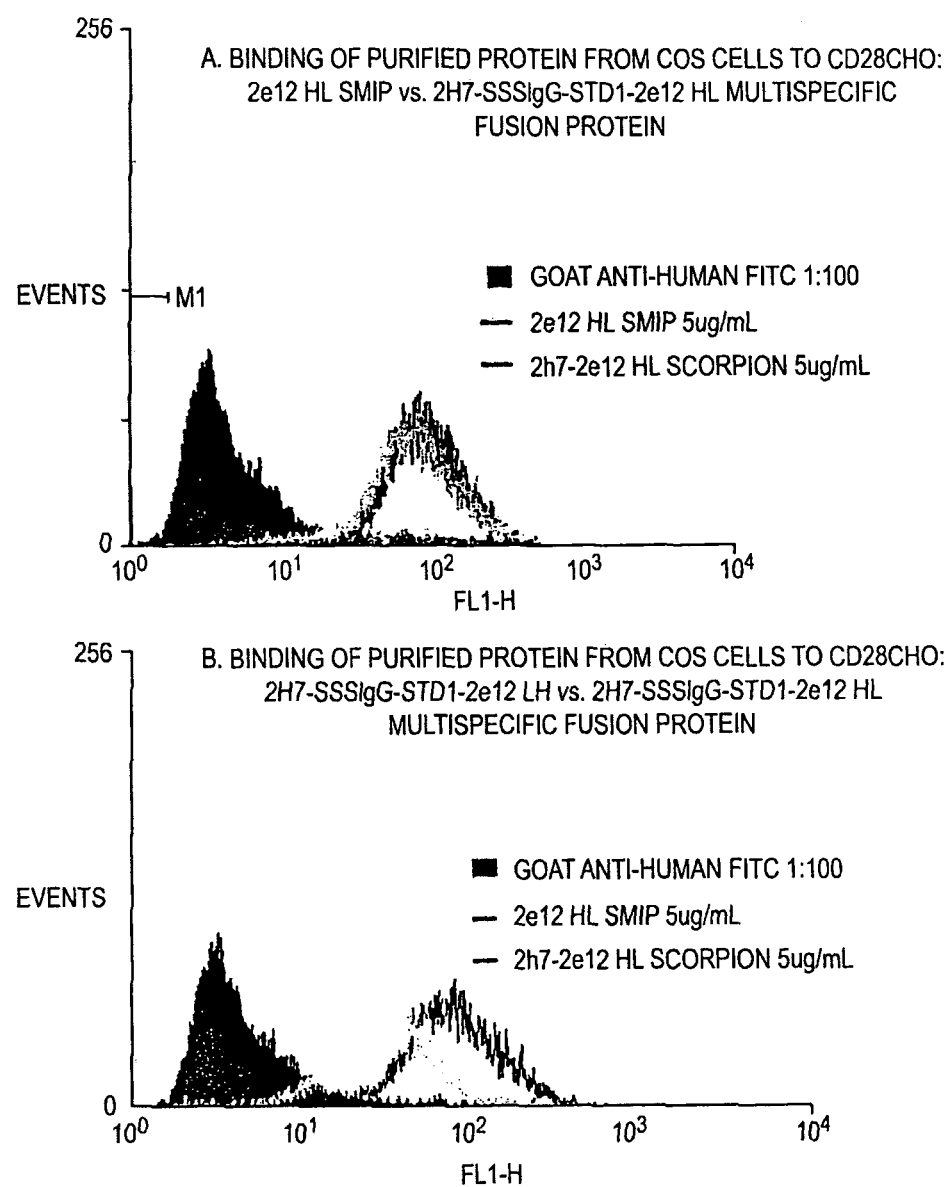
FIG. 5 shows two histograms illustrating the binding by protein A purified multispecific binding proteins with effector function to CHO cells expressing CD28. "2H7-2E12 LH" has binding domain 2, specific for CD28, in $V_L$-$V_H$ orientation; "2H7-2E12 HL" has binding domain 2, specific for CD28, in $V_H$-$V_L$ orientation. Each of the proteins was tested for binding at 5 µg/ml, and binding was detected with FITC goat anti-human IgG at 1:100. See the descriptions in FIG. 2 for a more complete description of the molecules tested.

After electrophoresis, proteins were transferred to PVDF membranes using a semi-dry electroblotter apparatus (Ellard, Seattle, Wash.) for 1 hour at 100 mAmp. Western transfer buffers included the following three buffers present on saturated Whatman filter paper, and stacked in succession: no. 1 contains 36.34 g/liter Tris, pH 10.4, and 20% methanol; no. 2 contains 3.02 g/liter Tris, pH 10.4, and 20% methanol; and no. 3 contains 3.03 g/liter Tris, pH 9.4, 5.25 g/liter ε-amino caproic acid, and 20% methanol. Membranes were blocked in BLOTTO=5% nonfat milk in PBS overnight with agitation. Membranes were incubated with HRP conjugated goat anti-human IgG (Fc specific, Caltag) at 5 ug/ml in BLOTTO for one hour, then washed 3 times for 15 minutes each in PBS-0.5% Tween 20. Wet membranes were incubated with ECL solution for 1 minute, followed by exposure to X-omat film for 20 seconds. FIG. 2 shows a Western Blot of proteins expressed in COS cell culture supernatant (30 μl/well) electrophoresed under non-reducing conditions. Lanes are indicated with markers 1-9 and contain the following samples: Lane 1 (cut off=See Blue Markers, kDa are indicated to the side of the blot. Lane 2=2H7-sssIgG P238S/P331S-STD1-2e12 VLVH; lane 3=2H7-sssIgG P238S/P331S-STD1-2e12 VHVL, Lane 4=2H7-sssIgG P238S/P331S-STD2-2e12 VLVH; Lane 5=2H7-sssIgG P238S/P331S-STD2-2e12 VHVL; Lane 6=2e12 VLVH SMIP; Lane 7=2e12 VHVL SMIP; Lane 8=2H7 SMIP. 2H7 in these constructs is always in the $V_L V_H$ orientation, sssIgG indicates the identity of the hinge/linker located at linker position 1 as shown in FIG. 5, P238S/P331S indicates the version of human IgG1 with mutations from wild type (first aa listed) to mutant (second aa listed) and the amino acid position at which they occur in wild type human IgG1 $C_{H2}$ and CH3 domains, STD1 indicates the 20-amino-acid (18+ restriction site) linker located in linker position 2 as shown in FIG. 5, and STD2 indicates the 38 amino acid (36+ restriction site) linker located in linker position 2 as shown in FIG. 6.

Binding Studies

Binding studies were performed to assess the bispecific binding properties of the CD20/CD28 multispecific, multivalent binding peptides. Initially, WIL2-S cells were added to 96 well plates and centrifuged to pellet cells. To the seeded plates, CD20/CD28 purified protein was added, using two-fold titrations across the plate from 20 μg/ml down to 0.16 μg/ml. A two-fold dilution series of TRU-015 (source of binding domain 1) purified protein was also added to seeded plate wells, the concentration of TRU-015 extending from 20 μg/ml down to 0.16 μg/ml. One well containing no protein served as a background control.

Seeded plates containing the proteins were incubated on ice for one hour. Subsequently, the wells were washed once with 200 μl 1% FBS in PBS. Goat anti-human antibody labeled with FITC (Fc Sp) at 1:100 was then added to each well, and the plates were again incubated on ice for one hour. The plates were then washed once with 200 μl 1% FBS in PBS and the cells were re-suspended in 200 μl 1% FBS and analyzed by FACS.

To assess the binding properties of the anti-CD28 peptide 2E12 $V_H V_L$, CD28-expressing CHO cells were plated by seeding in individual wells of a culture plate. The CD20/CD28 purified protein was then added to individual wells using a two-fold dilution scheme, extending from 20 μg/ml down to 0.16 μg/ml. The 2E12IgG-VHVL SMIP purified protein was added to individual seeded wells, again using a two-fold dilution scheme, i.e., from 20 μg/ml down to 0.16 μg/ml. One well received no protein to provide a background control. The plates were then incubated on ice for one hour, washed once with 200 μl 1% FBS in PBS, and goat anti-human antibody labeled with FITC (Fc Sp, CalTag, Burlingame, Calif.) at 1:100 was added to each well. The plates were again incubated on ice for one hour and subsequently washed once with 200 μl 1% FBS in PBS. Following re-suspension of the cells in 200 μl 1% FBS, FACS analysis was performed. The results showed that multivalent binding proteins with the N-terminal CD20 binding domain 1 bound CD20; those proteins having the C-terminal CD28 binding domain 2 in the N-$V_H$-$V_L$-C orientation also bound CD28.

The expressed proteins were shown to bind to CD20 presented on WIL-2S cells (see FIG. 3) and to CD28 presented on CHO cells (refer to FIG. 3) by flow cytometry (FACS), thereby demonstrating that either BD1 or BD2 could function to bind the specific target antigen. Each data set on the graphs in FIG. 3 shows the binding of serial dilutions of the different multivalent binding (fusion) proteins over the titration ranges indicated. The data obtained using these initial constructs indicate that multivalent binding (fusion) proteins with the binding domain 2 version using 2e12 in the VHVL orientation express better and bind better to CD28 than the form in the VLVH orientation at equivalent concentrations.

Figure 4:
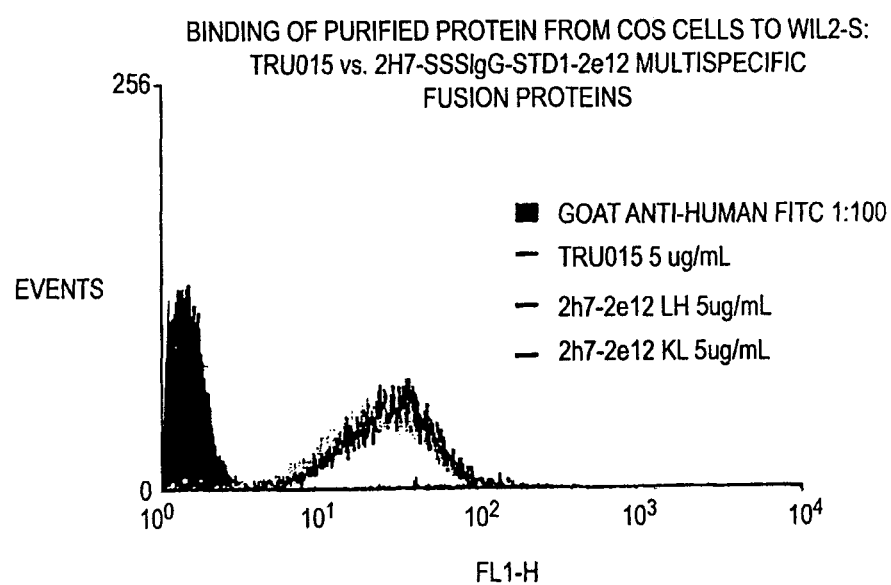
FIG. 4 is a histogram showing the binding pattern of protein A purified versions of the proteins tested in FIG. 3 to WIL2-S cells. "TRU015" is a SMIP specific for CD20. Two multispecific binding proteins with effector function were also analyzed: "2H7-2E12 LH" has binding domain 2, specific for CD28, in $V_L$-$V_H$ orientation; "2H7-2E12 HL" has binding domain 2, specific for CD28, in $V_H$-$V_L$ orientation. Each of the proteins was tested for binding at 5 µg/ml, and binding detected with FITC goat anti-human IgG at 1:100. See the description for FIG. 2 above for more complete descriptions of the molecules tested.

FIG. 4 shows a graphical presentation of the results of binding studies performed with purified proteins from each of these transfections/constructs. The figure shows binding profiles of the proteins to CD20 expressing WIL-2S cells, demonstrating that the multivalent molecule binds to CD20 as well as the single specificity SMIP at the same concentration. The top and bottom panels for FIG. 5 show the binding profiles of the BD2 specificity (2e12=CD28) to CD28 CHO cells. For binding of binding domain 2 to CD28, the orientation of the V regions affected binding of the 2e12. 2H7-sss-hIgG-STD1-2e12 multivalent binding proteins with the 2e12 in the VH-VL (HL) orientation showed binding at a level equivalent to the single specificity SMIP, while the 2e12 LH molecule showed less efficient binding at the same concentration.

EXAMPLE 5

Construction of Various Linker Forms of the Multivalent Fusion Proteins

This example describes the construction of the different linker forms listed in the table shown in FIG. 6.

Construction of $C_{H3}$-BD2 Linkers H1 Through H7

To explore the effect of $C_{H3}$-BD2 linker length and composition on expression and binding of the scorpion molecules, an experiment was designed to compare the existing molecule 2H7sssIgG1-Lx1-2e12HL to a larger set of similar constructs with different linkers. Using 2H7sssIgG1-Lx1-2e12HL as template, a series of PCR reactions were performed using the primers listed in Oligonucleotide Table 2, which created linkers that varied in length form 0 to 16 amino acids. These linkers were constructed as nucleic acid fragments that spanned the coding region for $C_{H3}$ at the BsrGI site to the end of the nucleic acid encoding the linker-BD2 junction at the EcoRI site.

TABLE 2

Table 2. Sequences of primers used to generate CH3-BD2 linker variants.

| No. | Name | Sequence 5'-3' | SEQ ID NO. |
|---|---|---|---|
| | | PCR Primers | |
| 1 | L1-11R | GCGATAGAATTCCCAGATCCACCACCGCCCGA GCCACCGCCACCATAATTC | 46 |
| 2 | L1-6R | GCGATAGAATTCCCAGAGCCACCGCCACCATA ATTC | 47 |
| 3 | L3R | GCGTATGAATTCCCCGAGCCACCGCCACCCTT ACCCGGAGACAGG | 48 |
| 4 | L4R | GCGTATGAATTCCCAGATCCACCACCGCCCGA GCCACCGCCACCCTTAC | 49 |
| 5 | L5R | GCGTATGAATTCCCGCTGCCTCCTCCCCCAGA TCCACCACCGCC | 50 |
| 6 | IgBsrG1F | GAGAACCACAGGTGTACACCCTG | 51 |
| 7 | L-CPPCPR | GCGATAGAATTCGGACAAGGTGGACACCCCTT ACCCGGAGACAGGGAGAG | 52 |

FIG. 6 diagrams the schematic structure of a multivalent binding (fusion) protein and shows the orientation of the V regions for each binding domain, the sequence present at linker position 1 (only the Cys residues are listed), and the sequence and identifier for the linker(s) located at linker position 2 of the molecules.

EXAMPLE 6

Binding and Functional Studies With Variant Linker Forms of the 2H7-IgG-2e12 Prototype Multivalent Fusion Proteins This example shows the results of a series of expression and binding studies on the "prototype" 2H7-sssIgG-Hx-2e12 VHVL construct with various linkers (H1-H7) present in the linker position 2. Each of these proteins was expressed by large-scale COS transient transfection and purification of the molecules using protein A affinity chromatography, as described in the previous examples. Purified proteins were then subjected to analyses including SDS-PAGE, Western blotting, binding studies analyzed by flow cytometry, and functional assays for biological activity.

Binding Studies Comparing the Different BD2 Orientations

Figure 13:
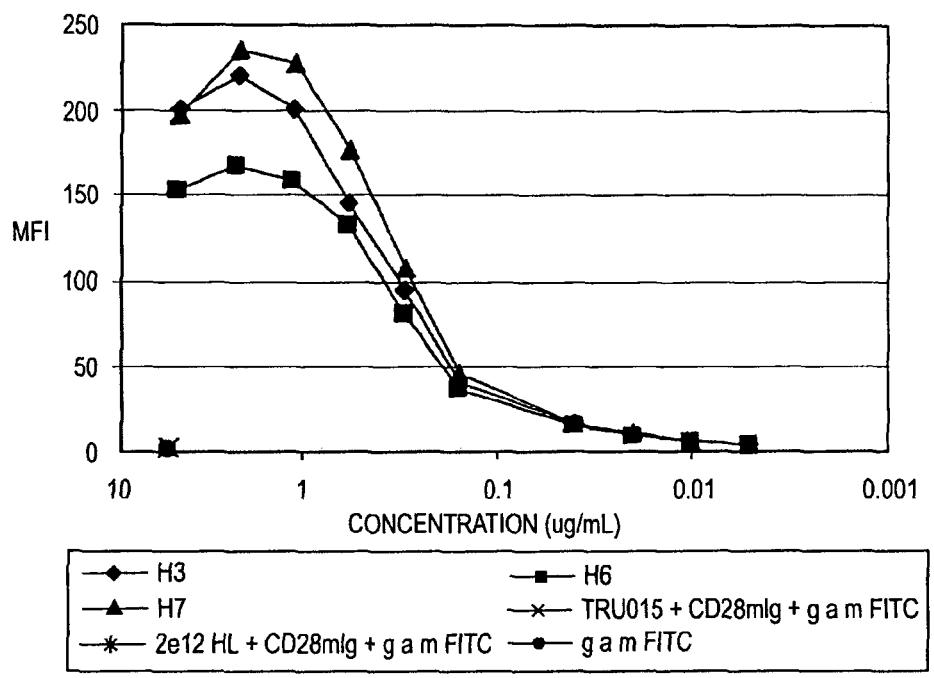
FIG. 13 shows the results of an alternative binding assay generated by the molecules used for FIG. 12. In this case, the fusion proteins were first bound to WIL-2S CD20 expressing cells, and binding was then detected with CD28mIgG (5 µg/ml) and FITC anti-mouse reagent at 1:100. These results demonstrate the simultaneous binding to both CD20 and CD28 in the same molecule.

Binding studies were performed as described in the previous examples, except that protein A-purified material was used, and a constant amount of binding (fusion) protein was used for each variant studied, i.e., 0.72 ug/ml. FIG. 7 shows a columnar graph comparing the binding properties of each linker variant and 2e12 orientation variant to both CD20 and CD28 target cells. H1-H6 refer to constructs with the H1-H6 linkers and 2e12 in the VH-VL orientation. L1-L6 refer to constructs with the H1-H6 linkers and 2e12 in the VL-VH orientation. The data demonstrate that the binding domain 2 specificity for 2e12 binds much more efficiently when present in the HL orientation (samples H1-H6) than when in the LH orientation (samples L1-L6). The effect of linker length is complicated by the discovery, as shown in the next set of figures, that molecules with the longer linkers contain some single-specificity cleaved molecules which are missing the CD28 binding specificity at the carboxy terminus. Other experiments were performed which address the binding of selected linkers, with the results shown in FIGS. 10, 12, and 13.

SDS-PAGE Analysis of Purified H1-H7 Linker Variants

Figure 8:
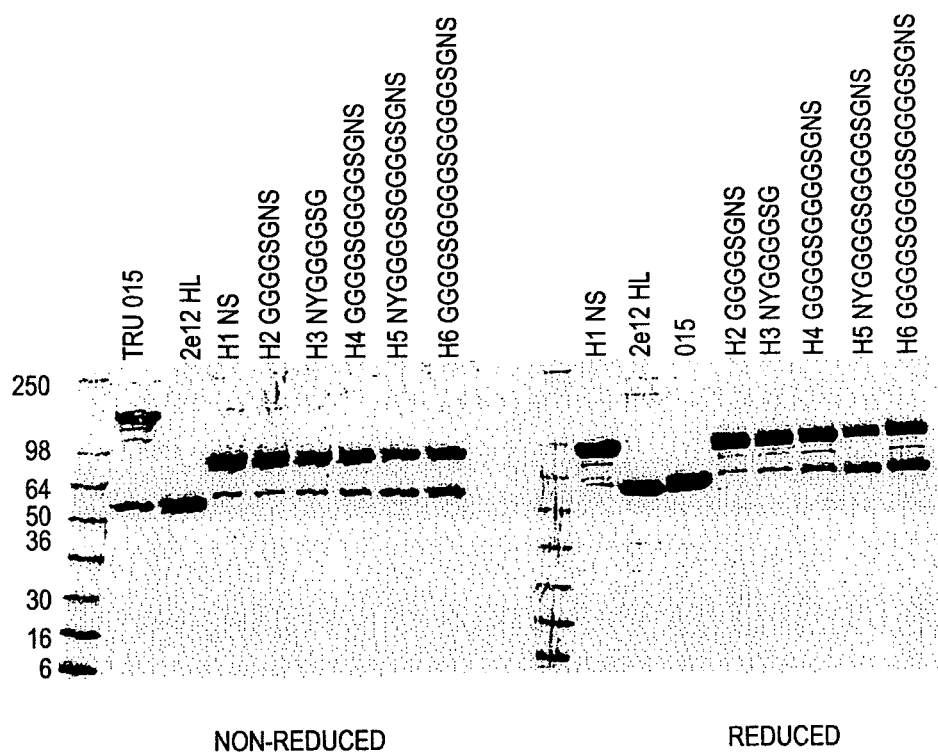
FIG. 8 shows photographs of Coomassie stained non-reducing and reducing SDS-PAGE gels. These gels show the effect of the variant linker sequence/length on the 2H7-sss-hIgG-Hx-2e12 HL protein on the amounts of the two predominate protein bands visualized on the gel.

Samples were prepared from purified protein aliquots, containing 8 μg protein per well, and 2× Tris-Glycine SDS Buffer (Invitrogen) was added to a 1× final concentration. For reduced samples/gels, 10× reducing buffer was added to 1× to samples plus Tris-Glycine SDS buffer. Ten (10) μl SeeBlue Marker (Invitrogen, Carlsbad, Calif.) was run to provide MW size standards. The multivalent binding (fusion) protein variants were subjected to SDS-PAGE analyses on 4-20% Novex Tris-glycine gels (Invitrogen, San Diego, Calif.). Samples were loaded using Novex Tris-glycine SDS sample buffer (2×) under reducing or non-reducing conditions after heating at 95° C. for 3 minutes, followed by electrophoresis at 175V for 60 minutes. Electrophoresis was performed using 1× Novex Tris-Glycine SDS Running Buffer (Invitrogen). Gels were stained after electrophoresis in Coomassie SDS PAGE R-250 stain for 30 minutes with agitation, and destained for at least one hour. FIG. 8 shows the nonreduced and reduced Coomassie stained gels of the [2H7-sss-hIgG P238S/P331S-Hx-2e12 VHVL] multivalent binding (fusion) protein variants, along with TRU-015 and 2e12 HLSMIP as control samples. As the linker length is increased, the amount of protein running at approximately SMIP size (or 52 kDa) increases. The increase in the amount of protein in this band corresponds with a decrease in the amount of protein in the upper band running at about 90 kDa. The gel data indicate that the full-length molecule is being cleaved at or near the linker, to generate a molecule which is missing the BD2 region. A smaller BD2 fragment is not present, indicating (1) that the nucleotide sequence within the linker sequence may be creating a cryptic splice site that removes the smaller fragment from the spliced RNA transcript, or (2) that the protein is proteolytically cleaved after translation of the full-size polypeptide, and that the smaller BD2 fragment is unstable, i.e., susceptible to proteolytic processing. Western blotting of some of these molecules indicates that the proteins all contain the CD20 BD 1 sequence, but the smaller band is missing the CD28 BD2 reactivity. No smaller band migrating at "bare" scFv size (25-27 kDa) was observed on any gels or blots, indicating that this smaller peptide fragment is not present in the samples.

Western Blot Binding of BD1 and BD2 by 2H7 Specific Fab or CD28mIg

FIG. 9 shows the results of Western blotting of the 2H7-sss-hIgG-H6 multivalent binding (fusion) proteins compared to each single-specificity SMIP.

Electrophoresis was performed under non-reducing conditions, and without boiling samples prior to loading. After electrophoresis, proteins were transferred to PVDF membranes using a semi-dry electroblotter apparatus (Ellard, Seattle, Wash.) for 1 hour at 100 mAmp. Membranes were blocked in BLOTTO (5% nonfat milk in PBS) overnight with agitation. FIG. 9A: Membranes were incubated with the AbyD02429.2, a Fab directed to the 2H7 antibody, at 5 µg/ml in BLOTTO for one hour, then washed 3 times for 5 minutes each in PBS-0.5% Tween 20. Membranes were then incubated in 6×His-HRP for one hour at a concentration of 0.5 µg/ml. Blots were washed three times for 15 minutes each in PBST. Wet membranes were incubated with ECL solution for 1 minute, followed by exposure to X-omat film for 20 seconds.

FIG. 9B: Membranes were incubated with CD28Ig (Ancell, Bayport, Minn.) at 10 µg/ml in BLOTTO, then washed three times for 15 minutes each in PBS-0.5% Tween 20. Membranes were then incubated in goat anti-mouse HRP conjugate (CalTag, Burlingame, Calif.) at 1:3000 in BLOTTO. Membranes were washed three times, for 15 minutes each, then incubated in ECL solution for 1 minute, followed by exposure to X-omat film for 20 seconds. The results from the Western blots indicated that the CD28 binding domain was present in the multivalent "monomer" fraction migrating at approximately 90 kDa, and in higher order forms. No band was detectable migrating at the position expected for a single SMIP or bare scFv size fragment. When the CD20 anti-idiotype Fab was used, a SMIP-sized fragment was detected, indicating the presence of a peptide fragment containing (2H7-sss-hIgG), and missing the CD28 scFv BD2 portion of the fusion protein.

Binding Studies on Selected Linkers

FIG. 10 shows the results of binding studies performed on the purified 2H7-sss-hIgG-Hx-2e12 fusion proteins. Binding studies were performed to assess the bispecific binding properties of the CD20/CD28 multispecific binding peptides. Initially, WIL2-S cells were plated using conventional techniques. To the seeded plates, CD20/CD28 purified protein was added, using two-fold titrations across the plate from 20 µg/ml down to 0.16 µg/ml. A two-fold dilution series of TRU-015 (source of binding domain 1) purified protein was also added to seeded plate wells, the concentration of TRU-015 extending from 20 µg/ml down to 0.16 µg/ml. One well containing no protein served as a background control.

Seeded plates containing the proteins were incubated on ice for one hour. Subsequently, the wells were washed once with 200 µl 1% FBS in PBS. Goat anti-human antibody labeled with FITC (Fc Sp) at 1:100 was then added to each well, and the plates were again incubated on ice for one hour. The plates were then washed once with 200 µl 1% FBS in PBS and the cells were re-suspended in 200 µl 1% FBS and analyzed by FACS.

To assess the binding properties of the anti-CD28 peptide 2E12 $V_H V_L$, CD28-expressing CHO cells were plated by seeding in individual wells of a culture plate. The CD20/CD28 purified protein was then added to individual wells using a two-fold dilution scheme, extending from 20 µg/ml down to 0.16 µg/ml. The 2E12IgGvHvL SMIP purified protein was added to individual seeded wells, again using a two-fold dilution scheme, i.e., from 20 µg/ml down to 0.16 µg/ml. One well received no protein to provide a background control. The plates were then incubated on ice for one hour, washed once with 200 µl 1% FBS in PBS, and goat anti-human antibody labeled with FITC (Fc Sp) at 1:100 was added to each well. The plates were again incubated on ice for one hour and subsequently washed once with 200 µl 1% FBS in PBS. Following re-suspension of the cells in 200 µl 1% FBS, FACS analysis was performed. The expressed proteins were shown to bind to CD20 presented on WIL-2S cells (see FIG. 10A) and to CD28 presented on CHO cells (refer to FIG. 10B) by flow cytometry (FACS), thereby demonstrating that either BD1 or BD2 could function to bind the specific target antigen. In addition, the linker used (H1-H6) was not found to significantly affect binding avidity to target antigen.

SEC Fractionation of Multivalent Binding (Fusion) Proteins. The binding (fusion) protein was purified from cell culture supernatants by protein A Sepharose affinity chromatography over a GE Healthcare XK 16/40 column. After binding of protein to the column, the column was washed in dPBS, then 1.0 M NaCl, 20 mM sodium phosphate pH 6.0, and then 25 mM NaCl, 25 mN NaOAc, pH 5.0, to remove nonspecific binding proteins. Bound protein was eluted from the column in 100 mM Glycine (Sigma), pH 3.5, and brought to pH 5.0 with 0.5 M 2-(N-Morpholino) ethanesulfonic acid (MES), pH 6.0. Protein samples were concentrated to 25 mg/ml using conventional techniques in preparation for GPC purification. Size exclusion chromatography (SEC) was performed on a GE Healthcare AKTA Explorer 100 Air apparatus, using a GE healthcare XK column and Superdex 200, preparative grade (GE healthcare).

FIG. 12 shows a table summarizing the results of SEC fractionation of the different binding (fusion) proteins. With increasing linker length, the complexity of the molecules in solution also increases, making it difficult to isolate peak of interest, or POI from higher order forms by HPLC. The H7 linker seems to resolve much of this complexity into a more homogeneous form in solution, so that the soluble forms migrate mostly as a single POI at approximately 172 kDa.

Additional Binding Studies

A second series of experiments was performed (see FIGS. 12 and 13) with a smaller subset of multivalent binding (fusion) proteins, this time comparing linkers H3, H6, and H7. The data demonstrate that the binding level drops more significantly for CD28 than for CD20 binding, but both drop slightly as linker length increases. Further, the data showed that the H7 linker exhibited the highest level of binding to both antigens. These data were obtained using protein A-purified multivalent binding (fusion) proteins, but were not further purified by SEC, so multiple forms of the molecules may have been present in solution. The results also indicated that the truncated form may have been less stable than the true multivalent polypeptide, since the binding curves do not appear to fully reflect the significant amount of single specificity form present in solution for linker H6.

Demonstration of Multispecific Binding from a Single Molecule

An alternative binding assay was performed (see FIG. 13), where binding to CD20 on the surface of WIL-2S cells was detected with a reagent specific for the CD28 BD2, thereby demonstrating that simultaneous binding may occur to both target antigens, engaging both BD1 and BD2 on the same multispecific binding (fusion) protein (refer to FIG. 12) This assay demonstrates the multispecific binding property of the proteins.

EXAMPLE 7

Construction of Multispecific Binding (Fusion) Proteins with Alternative Specificities in BD2

In addition to the prototype CD20-CD28 multispecific binding molecule, two other forms were made with alternative binding domain 2 regions, including CD37 and CD3 binding domains. The molecules were also made with several of the linker domains described for the [2H7-sss-IgG-Hx/STDx-2e12 HL] multispecific binding (fusion) proteins. The construction of these additional multispecific binding (fusion) molecules are described below.

Anti-CD37 Binding Domain Construction

TABLE 3

Table 3. Oligonucleotide primers used to generate G28-1 anti-CD37 binding domains for both SMIP molecules and scorpions.

| No. | Name | Sequence | SEQ ID NO. |
|---|---|---|---|
| 23 | G281LH-NheR | ACTGCTGCAGCTGGACCGCGCT AGCTCCGCCGCCACCCGAC | 53 |
| 24 | G281LH-NheF | GGCGGAGCTAGCGCGGTCCAGC TGCAGCAGTCTGGACCTG | 54 |
| 25 | G281-LH-LPinF | GCGATCACCGGTGACATCCAGAT GACTCAGTCTCCAG | 55 |
| 26 | G281-LH-HXhoR | GCGATACTCGAGGAGACGGTGAC TGAGGTTCCTTGAC | 56 |
| 27 | G281-LH-LEcoF | GCGATCGAATTCAGACATCCAGAT GACTCAGTCTCCAG | 57 |
| 28 | G281-LH-HXbaR | GCGATTCTAGATTAGGAAGAGACG GTGACTGAGGTTCCTTGAC | 58 |
| 29 | G281-HL-HF | GCGATAACCGGTGCGGTCCAGCTG CAGCAGTCTGGAC | 59 |
| 30 | G281-HL-HR3 | GACCCACCACCGCCCGAGCCACCG CCACCAGAAGAGACGGTGACTGAGG TTC | 60 |
| 31 | G281-HL-HR2 | ACTCCCGCCTCCTCCTGATCCGCCG CCACCCGACCCACCACCGCCCGAG | 61 |
| 32 | G281-HL-HNheR | GAGTCATCTGGATGTCGCTAGCACTC CCGCCTCCTCCTGATC | 62 |
| 33 | G281-HL-LNheF | ATCAGGAGGAGGCGGGAGTGCTAGC GACATCCAGATGACTCAGTC | 63 |
| 34 | G281-HL-LXhoR | GCGATACTCGAGCCTTTGATCTCCAG TTCGGTGCCTC | 64 |
| 35 | G281-HL-LXbaR | GCGATATCTAGACTCAACCTTTGATCT CCAGTTCGGTGCCTC | 65 |

TABLE 3-continued

Table 3. Oligonucleotide primers used to generate G28-1 anti-CD37 binding domains for both SMIP molecules and scorpions.

| No. | Name | Sequence | SEQ ID NO. |
|---|---|---|---|
| 36 | G281-HL-EcoF | GCGATAGAATTCGCGGTCCAGCTGCA GCAGTCTGGAC | 66 |

The G28-1 scFv (SEQ ID NO:102) was converted to the G28-1 LH SMIP by PCR using the primers in Table X above. Combining primers 23 and 25 with 10 ng G28-1 scFv, the VK was amplified for 30 cycles of 94 C, 20 seconds, 58 C, 15 seconds, 68 C, 15 seconds using Platinum PCR Supermix Hi-Fidelity PCR mix (Invitrogen, Carlsbad, Calif.) in an ABI 9700 Thermalcycler. The product of this PCR had the restriction sites PinAI (AgeI) at the 5' end of the VK and NheI at the end of the scFv (G4S)3 linker. The VH was similarly altered by combining primers 24 and 26 with 10 ng G28-1 scFv in a PCR run under the identical conditions as with the VK above. This PCR product had the restriction sites NheI at the 5' end of the VH and XhoI at the 3' end. Because significant sequence identity overlap was engineered into primers 23 and 24, the VK and VH were diluted 5-fold, then added at a 1:1 ratio to a PCR using the flanking primers 25 and 26 and a full-length scFv was amplified as above by lengthening the 68 C extension time from 15 seconds to 45 seconds. This PCR product represented the entire G28-1 scFv as a PinAI-XhoI fragment and was purified by MinElute column (Qiagen,) purification to remove excess primers, enzymes and salts. The eluate was digested to completion with PinAI (Invitrogen) and XhoI (Roche) in 1×H buffer (Roche,) at 37 C for 4 hours in a volume of 50 µL. The digested PCR product was then electrophoresed in a 1% agarose gel, the fragment was removed from the gel and re-purified on a MinElute column using buffer QG and incubating the gel-buffer mix at 50 C for 10 minutes with intermittent mixing to dissolve the agarose after which the purification on the column was identical for primer removal post-PCR. 3 µL PinAI-XhoI digested G28-1 LH was combined with 1 µL PinAI-XhoI digested pD18-n2H7sssIgG1 SMIP in a 10 µL reaction with 5 µL 2× LigaFast Ligation Buffer (Promega, Madison, Wis.) and 1 µL T4 DNA ligase (Roche), mixed well and incubated at room temperature for 10 minutes. 3 µL of this ligation was then transformed into competent TOP 10 (Invitrogen) using the manufacturer's protocol. These transformants were plated on LB agar plates with 100 µg/ml carbenicillin (Teknova,) and incubated overnight at 37 C. After 18 hours of growth, colonies were picked and inoculated into 1 ml T-Broth (Teknova,) containing 100 µg/ml carbenicillin in a deep well 96-well plate and grown overnight in a 37 C shaking incubator. After 18-24 hours of growth, DNA was isolated from each overnight culture using the QIAprep 96 Turbo Kit (Qiagen) on the BioRobot8000 (Qiagen). 10 µL from each clone was then digested with both HindIII and XhoI restriction enzymes in 1×B buffer in a 15 µL reaction volume. The digested DNA was electrophoresed on 1% agarose E-gels (Invitrogen, CA) for restriction site analysis. Clones that contained a HindIII-XhoI fragment of the correct size were sequence verified. The G28-1 HL SMIP was constructed in a similar manner by placing a PinAI site on the 5' end and a (G4S)4 linker ending in an Nhe I site of the G28-1 VH using primers 29, 30 31 and 32 from Table X above. The VK was altered by PCR using primers 33 and 34 from Table X such that an NheI site was introduced at the 5' end of the VK and XhoI at the 3' end. These PCRs were then combined as above and amplified with the flanking primers 29 and 34 to yield an intact G28-1 scFv DNA in the VH-VL orientation which was cloned into PinAI-XhoI digested pD18-(n2H7) sssIgG1 SMIP exactly as with the G28-1 LH SMIP.

2H7sssIgG1-STD1-G28-1 LH/HL Construction

Using the G28-1 LH and G28-1 HL SMIPs as templates, the LH and HL anti-CD37 binding domains were altered by PCR such that their flanking restriction sites were compatible with the scorpion cassette. An EcoRI site was introduced at the 5' end of each scFv using either primer 27 (LH) or 36 (HL) and a stop codon/XbaI site at the 3' end using either primer 28 (LH) or 35 (HL). The resulting DNAs were cloned into EcoRI-XbaI digested pD18-2H7sssIgG-STD1.

2H7sssIgG1-Hx-G28-1 HL Construction

2H7sssIgG1-Hx-2e12 HL DNAs were digested with BsrGI and EcoRI and the 325 bp fragment consisting of the C-terminal end of the IgG1 and linker. These were substituted for the equivalent region in 2H7sssIgG1-STD1-G19-4 HL by removal of the STD1 linker using BsrGI-EcoRI and replacing it with the corresponding linkers from the 2H7sssIgG1-Hx-2e12 HL clones.

Anti-CD3 Binding Domain Construction

TABLE 4

Table 4. Oligonucleotides used to generate anti-CD3 binding domain from the G19-4 scFv sequence.

| No. | Name | Sequence | SEQ ID NO. |
|---|---|---|---|
| 37 | 194-LH-LF1 | GCGTATGAACCGGTGACATCCAGATGACACAGACTACATC | 67 |
| 38 | 194-LF2 | ATCCAGATGACACAGACTACATCCTCCCTGTCTGCCTCTCTGGGAGACAG | 68 |
| 39 | 194-LF3 | GTCTGCCTCTCTGGGAGACAGAGTCACCATCAGTTGCAGGGCAAGTCAGGAC | 69 |
| 40 | 194-LF4 | GTTGCAGGGCAAGTCAGGACATTCGCAATTATTTAAACTGGTATCAGCAG | 70 |
| 41 | 194-LF5 | ATTTAAACTGGTATCAGCAGAAACCAGATGGAACTGTTAAACTCCTGATC | 71 |
| 42 | 194-LF6 | GAACTGTTAAACTCCTGATCTACTACACATCAAGATTACACTCAGGAGTC | 72 |
| 43 | 194-LF7 | CAAGATTACACTCAGGAGTCCCATCAAGGTTCAGTGGCAGTGGGTCTGGAAC | 73 |
| 44 | 194-LR7 | CAGGTTGGCAATGGTGAGAGAATAATCTGTTCCAGACCCACTGCCACTGAAC | 74 |
| 45 | 194-LR6 | GCAAAAGTAAGTGGCAATATCTTCTGGTTGCAGGTTGGCAATGGTGAGAG | 75 |
| 46 | 194-LR5 | GAACGTCCACGGAAGCGTATTACCCTGTTGGCAAAAGTAAGTGGCAATATC | 76 |
| 47 | 194-LR4 | CGTTTGGTTACCAGTTTGGTGCCTCCACCGAACGTCCACGGAAGCGTATTAC | 77 |
| 48 | 194-LR3 | ACCACCGCCCGAGCCACCGCCACCCCGTTTGGTTACCAGTTTGGTG | 78 |
| 49 | 194-LR2 | GCTAGCGCTCCCACCTCCTCCAGATCCACCACCGCCCGAGCCACCGCCAC | 79 |
| 50 | 194-LH-LR1 | GTTGCAGCTGGACCTCGCTAGCGCTCCCACCTCCTCCAGATC | 80 |

TABLE 4-continued

Table 4. Oligonucleotides used to generate anti-CD3 binding domain from the G19-4 scFv sequence.

| No. | Name | Sequence | SEQ ID NO. |
|---|---|---|---|
| 51 | 194-LH-HF1 | GATCTGGAGGAGGTGGGAGCGCTAGCGAGGTCCAGCTGCAACAGTCTGGACCTG | 81 |
| 52 | 194-HF2 | AGCTGCAACAGTCTGGACCTGAACTGGTGAAGCCTGGAGCTTCAATGAAG | 82 |
| 53 | 194-HF3 | AGCCTGGAGCTTCAATGAAGATTTCCTGCAAGGCCTCTGGTTACTCATTC | 83 |
| 54 | 194-HF4 | GCAAGGCCTCTGGTTACTCATTCACTGGCTACATCGTGAACTGGCTGAAGCAG | 84 |
| 55 | 194-HF5 | ATCGTGAACTGGCTGAAGCAGAGCCATGGAAAGAACCTTGAGTGGATTGGAC | 85 |
| 56 | 194-HF6 | GAACCTTGAGTGGATTGGACTTATTAATCCATACAAAGGTCTTACTACCTAC | 86 |
| 57 | 194-HR6 | AATGTGGCCTTGCCCTTGAATTTCTGGTTGTAGGTAGTAAGACCTTTGTATG | 87 |
| 58 | 194-HR5 | CATGTAGGCTGTGCTGGATGACTTGTCTACAGTTAATGTGGCCTTGCCCTTG | 88 |
| 59 | 194-HR4 | ACTGCAGAGTCTTCAGATGTCAGACTGAGGAGCTCCATGTAGGCTGTGCTGGATG | 89 |
| 60 | 194-HR3 | ACCATAGTACCCAGATCTTGCACAGTAATAGACTGCAGAGTCTTCAGATGTC | 90 |
| 61 | 194-HR2 | GCGCCCAGACATCGAAGTACCAGTCCGAGTCACCATAGTACCCAGATCTTG | 91 |
| 62 | 194-LH-HR1 | GCGAATACTCGAGGAGACGGTGACCGTGGTCCCTGCGCCCCAGACATCGAAG | 92 |
| 63 | 194-HL-HF1 | GCGTATGAACCGGTGAGGTCCAGCTGCAACAGTCTGGACCTG | 93 |
| 64 | 194-HL-HR1 | ACCGCCACCAGAGGAGACGGTGACCGTGGTCCCTGCGCCCCAGACATCGAAGTAC | 94 |
| 65 | 194-HL-HR0 | ACCTCCTCCAGATCCACCACCGCCCGAGCCACCGCCACCAGAGGAGACGGTG | 95 |
| 66 | 194-HL-LF1 | GCGGGGGAGGTGGCAGTGCTAGCGACATCCAGATGACACAGACTACATC | 96 |
| 67 | 194-HL-LR3Xho | GCGAATACTCGAGCGTTTGGTTACCAGTTTGGTG | 97 |
| 68 | 194-HL-LR3Xba | GCGATATCTAGATTACCGTTTGGTTACCAGTTTGGTG | 98 |
| 69 | 194-HL-HF1R1 | GCGTATGAGAATTCAGAGGTCCAGCTGCAACAGTCTGGACCTG | 99 |
| 70 | 194-LH-LF1R1 | GCGTATGAGAATTCTGACATCCAGATGACACAGACTACATC | 100 |
| 71 | 194-LH-HR1Xba | GCGTATCTAGATTAGGAGACGGTGACCGTGGTCCCTGCGCCCCAGACATCGAAG | 101 |

The G19-4 binding domain was synthesized by extension of overlapping oligonucleotide primers as described previously. The light chain PCR was done in two steps, beginning by combining primers 43/44, 42/45, 41/46 and 40/47 at concentrations of 5 uM, 10 μM, 20 μM and 40 μM, respectively, in Platinum PCR Supermix Hi-Fidelity for 30 cycles of 94° C., 20 seconds, 60° C., 10 seconds, 68° C., 15 seconds. 1 μL of the resultant PCR product was reamplified using a primer mix of 39/48 (10 μM), 38/49 (20 μM) and 37/50 (40 μM) for the LH or 66/67 (40 μM) for the HL orientation, using the same PCR conditions with the exception of the 68 C extension which was increased to 25 seconds. The VK in the LH orientation was bounded by PinAI at the 5' end and NheI at the 3' end, while the HL orientation had NheI at the 5' end and XhoI at the 3' end.

To synthesize the heavy chain, primer mixes with the same concentrations as above were prepared by combining primers 56/57, 55/58, 54/59 and 53/60 for the first PCR step. In the second PCR, primers 52/61 (20 μM) and 51/62 (50 μM) were amplified with 1 μl from the first PCR using the same PCR conditions as with the second PCR of the light chain to make the LH orientation with NheI at the 5' end and XhoI at the 3' end. Primers 52/61 (10 μM), 63/64 (20 μM), 63 (20 μM)/65 (40 μM) and 63 (20 μM)/5 (80 μM) were combined in a second PCR with 1uL from the previous PCR to create the heavy chain in the HL orientation with PinAI at the 5' end and NheI at the 3' end. As with previous constructs, sufficient overlap was designed into the primers centered around the NheI site such that the G19-4 LH was synthesized by combining the heavy and light chain PCRs in the LH orientation and reamplifying with the flanking primers, 37 and 62 and the G19-4 HL was synthesized by combining the HL PCRs and re-amplifying with primers 63 and 67.

Full-length G19-4 LH/HL PCR products were separated by agarose gel electrophoresis, excised from the gel and purified with Qiagen MinElute columns as described earlier. These DNAs were then TOPO-cloned into pCR2.1 (Invitrogen), transformed into TOP10 and colonies screened first by EcoRI fragment size, then by DNA sequencing. G19-4 LH/HL were then cloned into pD18-IgG1 via PinAI-XhoI for expression in mammalian cells.

2H7sssIgG1-STD1-G19-4 LH/HL Construction

Using the G19-4 LH and G19-4 HL SMIPs as templates, the LH and HL anti-CD3 binding domains were altered by PCR such that their flanking restriction sites were compatible with the scorpion cassette. An EcoRI site was introduced at the 5' end of each scFv using either primer 27 (LH) or 36 (HL) and a stop codon/XbaI site at the 3' end using either primer 28 (LH) or 35 (HL). The resulting DNAs were cloned into EcoRI-XbaI digested pD18-2H7sssIgG-STD1.

2H7sssIgG1-Hx-G19-4 HL Construction

2H7sssIgG1-Hx-2e12 HL DNAs were digested with BsrGI and EcoRI and the 325 bp fragment consisting of the C-terminal end of the IgG1 and linker. These were substituted for the equivalent region in 2H7sssIgG1-STD1-G19-4 HL by removal of the STD 1 linker using BsrGI-EcoRI and replacing it with the corresponding linkers from the 2H7sssIgG1-Hx-2e12 HL clones.

Apparent from a consideration of the variety of multivalent binding proteins disclosed herein are features of the molecules that are amenable to combination in forming the molecules of the invention. Those features include binding domain 1, a constant sub-region, including a hinge or hinge-like domain, a linker domain, and a binding domain 2. The intrinsic modularity in the design of these novel binding proteins makes it straightforward for one skilled in the art to manipulate the DNA sequence at the N-terminal and/or C-terminal ends of any desirable module such that it can be inserted at almost any position to create a new molecule exhibiting altered or enhanced functionality compared to the parental molecule(s) from which it was derived. For example, any binding domain derived from a member of the immunoglobulin superfamily is contemplated as either binding domain 1 or binding domain 2 of the molecules according to the invention. The derived binding domains include domains having amino acid sequences, and even encoding polynucleotide sequences, that have a one-to-one correspondence with the sequence of a member of the immunoglobulin superfamily, as well as variants and derivatives that preferably share 80%, 90%, 95%, 99%, or 99.5% sequence identity with a member of the immunoglobulin superfamily. These binding domains (1 and 2) are preferably linked to other modules of the molecules according to the invention through linkers that may vary in sequence and length as described elsewhere herein, provided that the linkers are sufficient to provide any spacing and flexibility necessary for the molecule to achieve a functional tertiary structure. Another module of the multivalent binding proteins is the hinge region, which may correspond to the hinge region of a member of the immunoglobulin superfamily, but may be a variant thereof, such as the "CSC" or "SSS" hinge regions described herein. Also, the constant sub-region comprises a module of the proteins according to the invention that may correspond to a sub-region of a constant region of an immunoglobulin superfamily member, as is typified by the structure of a hinge-$C_{H2}$-$C_{H3}$ constant sub-region. Variants and derivatives of constant sub-regions are also contemplated, preferably having amino acid sequences that share 80%, 90%, 95%, 99%, or 99.5% sequence identity with a member of the immunoglobulin superfamily.

Exemplary primary structures of the features of such molecules are presented in Table 5, which discloses the polynucleotide and cognate amino acid sequence of illustrative binding domains 1 and 2, as well as the primary structure of a constant sub-region, including a hinge or hinge-like domain, and a linker that may be interposed, e.g., between the C-terminal end of a constant sub-region and the N-terminal end of a binding domain 2 region of a multivalent binding protein. Additional exemplars of the molecules according to the invention include the above-described features wherein, e.g., either or both of binding domains 1 and 2 comprise a domain derived from a $V_L$ or $V_L$-like domain of a member of the immunoglobulin superfamily and a $V_H$ or $V_H$-like domain derived from the same or a different member of the immunoglobulin superfamily, with these domains separated by a linker typified by any of the linkers disclosed herein. Contemplated are molecules in which the orientation of these domains is $V_L$-$V_H$ or $V_H$-$V_L$ for BD1 and/or BD2. A more complete presentation of the primary structures of the various features of the multivalent binding molecules according to the invention is found in the table appended at the end of this disclosure. The invention further comprehends polynucleotides encoding such molecules.

TABLE 5

Table 5. Primary structures (polynucoleotide and cognate amino acid sequences) of exemplary features of multivalent binding molecules.

| Binding Domain | Nucleotide Sequence | Amino Acid Sequence | SEQ ID NOS. (amino acid sequence) |
|---|---|---|---|
| 2H7 LH | atggattttcaagtgcagattttcag cttcctgctaatcagtgcttcagtca | mdfqvqifsfllisasvimsrgqivls qspailsaspgekvtmtcrasssysym | 1 (2) |

TABLE 5-continued

Table 5. Primary structures (polynucoleotide and cognate amino acid sequences) of exemplary features of multivalent binding molecules.

| | | | |
|---|---|---|---|
| | taatgtccagaggacaaattgttctc<br>tcccagtctccagcaatcctgtctgc<br>atctccaggggagaaggtcacaatga<br>cttgcagggccagctcaagtgtaagt<br>tacatgcactggtaccagcagaagcc<br>aggatcctcccccaaaccctggattt<br>atgccccatccaacctggcttctgga<br>gtccctgctcgcttcagtggcagtgg<br>gtctgggacctcttactctctcacaa<br>tcagcagagtggaggctgaagatgct<br>gccacttattactgccagcagtggag<br>ttttaacccacccacgttcggtgctg<br>ggaccaagctggagctgaaagatggc<br>ggtggctcgggcggtggtggatctgg<br>aggaggtgggagctctcaggcttatc<br>tacagcagtctggggctgagtcggtg<br>aggcctggggcctcagtgaagatgtc<br>ctgcaaggcttctggctacacattta<br>ccagttacaatatgcactgggtaaag<br>cagacacctagacagggcctggaatg<br>gattggagctatttatccaggaaatg<br>gtgatacttcctacaatcagaagttc<br>aagggcaaggccacactgactgtaga<br>caaatcctccagcacagcctacatgc<br>agctcagcagcctgacatctgaagac<br>tctgcggtctatttctgtgcaagagt<br>ggtgtactatagtaactcttactggt<br>acttcgatgtctggggcacagggacc<br>acggtcaccgtctct | hwyqqkpgsspkpwiyapsnlasgvpa<br>rfsgsgsgtsysltisrveaedaatyy<br>cqqwsfnpptfgagtklelkdgggsgg<br>ggsggggssqaylqqsgaesvrpgasv<br>kmsckasgytftsynmhwvkqtprqgl<br>ewigaiypgngdtsynqkfkgkatltv<br>dkssstaymqlssltsedsavyfcarv<br>vyysnsywyfdvwgtgttvtvs | | |
| 2e12 LH | atggattttcaagtgcagatttcag<br>cttcctgctaatcagtgcttcagtca<br>taatgtccagaggagtcgacattgtg<br>ctcacccaatctccagcttctttggc<br>tgtgtctctaggtcagagagccacca<br>tctcctgcagagccagtgaaagtgtt<br>gaatattatgtcacaagtttaatgca<br>gtggtaccaacagaaaccaggacagc<br>cacccaaactcctcatctctgctgct<br>agcaacgtagaatctggggtccctgc<br>caggtttagtggcagtgggtctggga<br>cagactttagcctcaacatccatcct<br>gtggaggaggatgatattgcaatgta<br>tttctgtcagcaaagtaggaaggttc<br>catggacgttcggtggaggcaccaag<br>ctggaaatcaaacggggtggcggtgg<br>atccggcggaggtgggtcgggtggcg<br>gcggatctcaggtgcagctgaaggag<br>tcaggacctggcctggtggcgccctc<br>acagagcctgtccatcacatgcaccg<br>tctcagggttctcattaaccggctat<br>ggtgtaaactgggttcgccagcctcc<br>aggaaagggtctggagtggctgggaa<br>tgatatgggtgatggaagcacagac<br>tataattcagctctcaaatccagact<br>atcgatcaccaaggacaactccaaga<br>gccaagttttcttaaaaatgaacagt<br>ctgcaaactgatgacacagccagata<br>ctactgtgcccgagatggttatagta<br>actttcattactatgttatggactac<br>tggggtcaaggaacctcagtcaccgt<br>ctcctct | MDFQVQIFSFLLISASVIMSRGVDIVL<br>TQSPASLAVSLGQRATISCRASESVEY<br>YVTSLMQWYQQKPGQPPKLLISAASNV<br>ESGVPARFSGSGSGTDFSLNIHPVEED<br>DIAMYFCQQSRKVPWTFGGGTKLEIKR<br>GGGGSGGGGSGGGGSQVQLKESGPGLV<br>APSQSLSITCTVSGFSLTGYGVNWVRQ<br>PPGKGLEWLGMIWGDGSTDYNSALKSR<br>LSITKDNSKSQVFLKMNSLQTDDTARY<br>YCARDGYSNFHYYVMDYWGQGTSVTVS<br>S | 3 | (4) |
| 2e12 HL | atggattttcaagtgcagatttcag<br>cttcctgctaatcagtgcttcagtca<br>taatgtccagaggagtccaggtgcag<br>ctgaaggagtcaggacctggcctggt<br>ggcgccctcacagagcctgtccatca<br>catgcaccgtctcagggttctcatta<br>accggctatggtgtaaactgggttcg<br>ccagcctccaggaaagggtctggagt<br>ggctgggaatgatatggggtgatgga<br>agcacagactataattcagctctcaa<br>atccagactatcgatcaccaaggaca<br>actccaagagccaagttttcttaaaa<br>atgaacagtctgcaaactgatgacac<br>agccagatactactgtgcccgagatg | MDFQVQIFSFLLISASVIMSRGVQVQL<br>KESGPGLVAPSQSLSITCTVSGFSLTG<br>YGVNWVRQPPGKGLEWLGMIWGDSTD<br>YNSALKSRLSITKDNSKSQVFLKMNSL<br>QTDDTARYYCARDGYSNFHYYVMDYWG<br>QGTSVTVSSGGGGSGGGGSGGGGSGGG<br>GSDIVLTQSPASLAVSLGQRATISCRA<br>SESVEYYVTSLMQWYQQKPGQPPKLLI<br>SAASNVESGVPARFSGSGSGTDFSLNI<br>HPVEEDDIAMYFCQQSRKVPWTFGGGT<br>KLEIKR | 5 | (6) |

TABLE 5-continued

Table 5. Primary structures (polynucoleotide and cognate amino acid sequences) of exemplary features of multivalent binding molecules.

```
         gttatagtaactttcattactatgtt
         atggactactggggtcaaggaacctc
         agtcaccgtctcctctggggtggag
         gctctggtggcggtggatccggcgga
         ggtgggtcggtggcggcggatctga
         cattgtgctcacccaatctccagctt
         ctttggctgtgtctcaggtcagaga
         gccaccatctcctgcagagccagtga
         aagtgttgaatattatgtcacaagtt
         taatgcagtggtaccaacagaaacca
         ggacagccacccaaactcctcatctc
         tgctgctagcaacgtagaatctgggg
         tccctgccaggtttagtggcagtggg
         tctgggacagactttagcctcaacat
         ccatcctgtggaggaggatgatattg
         caatgtatttctgtcagcaaagtagg
         aaggttccatggacgttcggtggagg
         caccaagctggaaatcaaacgt
```

G28-1 LH  accggtgacatccagatgactcagtc  DIQMTQSPASLSASVGETVTITCRTSE  102 (103)
         tccagcctccctatctgcatctgtgg  NVYSYLAWYQQKQGKSPQLLVSFAKTL
         gagagactgtcaccatcacatgtcga  AEGVPSRFSGSGSGTQFSLKISSLQPE
         acaagtgaaaatgtttacagttattt  DSGSYFCQHHSDNPWTFGGGTELEIKG
         ggcttggtatcagcagaaacaggaa   GGGSGGGGSGGGGSASAVQLQQSGPEL
         aatctcctcagctcctggtctctttt  EKPGASVKISCKASGYSFTGYNMNWVK
         gcaaaaaccttagcagaaggtgtgcc  QNNGKSLEWIGNIDPYYGGTTYNRKFK
         atcaaggttcagtggcagtggatcag  GKATLTVDKSSSTAYMQLKSLTSEDSA
         gcacacagttttctctgaagatcagc  VYYCARSVGPMDYWGQGTSVTVS
         agcctgcagcctgaagattctggaag
         ttatttctgtcaacatcattccgata
         atccgtggacgttcggtggaggcacc
         gaactggagatcaaaggtggcggtgg
         ctcgggcggtggtgggtcgggtggcg
         gcggatctgctagcgcagtccagctg
         cagcagtctggacctgagctggaaaa
         gcctggcgcttcagtgaagatttcct
         gcaaggcttctggttactcattcact
         ggctacaatatgaactgggtgaagca
         gaataatgaaagagccttgagtgga
         ttggaaatattgatccttattatggt
         ggtactacctacaaccggaagttcaa
         gggcaaggccacattgactgtagaca
         aatcctccagcacagcctacatgcag
         ctcaagagtctgacatctgaggactc
         tgcagtctattactgtgcaagatcgg
         tcggccctatggactactggggtcaa
         ggaacctcagtcaccgtctcgag
```

G28-1 HL  accggtgaggtccagctgcaacagtc  EVQLQQSGPELVKPGASMKISCKASGY  104 (105)
         tggacctgaactggtgaagcctggag  SFTGYIVNWLKQSHGKNLEWIGLINPY
         cttcaatgaagatttcctgcaaggcc  KGLTTYNQKFKGKATLTVDKSSSTAYM
         tctggttactcattcactggctacat  ELLSLTSEDSAVYYCARSGYYGDSDWY
         cgtgaactggctgaagcagagccatg  FDVWGAGTTVTVSSGGGGSGGGGSGGG
         gaaagaaccttgagtggattggactt  GSGGGGSASDIQMTQTTSSLSASLGDR
         attaatccatacaaaggtcttactac  VTISCRASQDIRNYLNWYQQKPDGTVK
         ctacaaccagaaattcaagggcaagg  LLIYYTSRLHSGVPSRFSGSGSGTDYS
         ccacattaactgtagacaagtcatcc  LTIANLQPEDIATYFCQQGNTLPWTFG
         agcacagcctacatggagctcctcag  GGTKLVTKRS
         tctgacatctgaagactctgcagtct
         attactgtgcaagatctgggtactat
         ggtgactcggactggtacttcgatgt
         ctggggcgcagggaccacggtcaccg
         tctcctctggtggcggtggctcgggc
         ggtggtggatctggaggaggtgggag
         cggggggaggtggcagtgctagcgaca
         tccagatgacacagactacatcctcc
         ctgtctgcctctctgggagacagagt
         caccatcagttgcagggcaagtcagg
         acattcgcaattatttaaactggtat
         cagcagaaaccagatggaactgttaa
         actcctgatctactacacatcaagat
         tacactcaggagtcccatcaaggttc
         agtggcagtgggtctggaacagatta
         ttctctcaccattgccaacctgcaac
         cagaagatattgccacttacttttgc
```

TABLE 5-continued

Table 5. Primary structures (polynucoleotide and cognate amino acid sequences) of exemplary features of multivalent binding molecules.

```
        caacagggtaatacgcttccgtggac
        gttcggtggaggcaccaaactggtaa
        ccaaacgctcgag
```

| | | | |
|---|---|---|---|
| G19-4 LH | accggtgacatccagatgacacagac<br>tacatcctccctgtctgcctctctgg<br>gagacagagtcaccatcagttgcagg<br>gcaagtcaggacattcgcaattattt<br>aaactggtatcagcagaaaccagatg<br>gaactgttaaactcctgatctactac<br>acatcaagattacactcaggagtccc<br>atcaaggttcagtggcagtgggtctg<br>gaacagattattctctcaccattgcc<br>aacctgcaaccagaagatattgccac<br>ttacttttgccaacagggtaatacgc<br>ttccgtggacgttcggtggaggcacc<br>aaactggtaaccaaacggggtggcgg<br>tggctcgggcggtggtggatctggag<br>gaggtgggagcgctagcgaggtccag<br>ctgcaacagtctggacctgaactggt<br>gaagcctggagcttcaatgaagattt<br>cctgcaaggcctctggttactcattc<br>actggctacatcgtgaactggctgaa<br>gcagagccatggaaagaaccttgagt<br>ggattggacttattaatccatacaaa<br>ggtcttactacctacaaccagaaatt<br>caagggcaaggccacattaactgtag<br>acaagtcatccagcacagcctacatg<br>gagctcctcagtctgacatctgaaga<br>ctctgcagtctattactgtgcaagat<br>ctgggtactatggtgactcggactgg<br>tacttcgatgtctggggcgcaggga c<br>cacggtcaccgtctcctcgag | DIQMTQTTSSLSASLGDRVTISCRASQ<br>DIRNYLNWYQQKPDGTVKLLIYYTSRL<br>HSGVPSRFSGSGSGTDYSLTIANLQPE<br>DIATYFCQQGNTLPWTFGGGTKLVTKR<br>GGGGSGGGGSGGGGSASEVQLQQSGPE<br>LVKPGASMKISCKASGYSFTGYIVNWL<br>KQSHGKNLEWIGLINPYKGLTTYNQKF<br>KGKATLTVDKSSTAYMELLSLTSEDS<br>AVYYCARSGYYGDSDWYFDVWGAGTTV<br>TVSS | 106 (107) |

| | | | |
|---|---|---|---|
| G19-4 HL | accggtgaggtccagctgcaacagtc<br>tggacctgaactggtgaagcctggag<br>cttcaatgaagatttcctgcaaggcc<br>tctggttactcattcactggctacat<br>cgtgaactggctgaagcagagccatg<br>gaaagaaccttgagtggattggactt<br>attaatccatacaaaggtcttactac<br>ctacaaccagaaattcaagggcaagg<br>ccacattaactgtagacaagtcatcc<br>agcacagcctacatggagctcctcag<br>tctgacatctgaagactctgcagtct<br>attactgtgcaagatctgggtactat<br>ggtgactcggactggtacttcgatgt<br>ctggggcgcagggaccacggtcaccg<br>tctcctctggtggcggtggctcgggc<br>ggtggtggatctggaggaggtgggag<br>cgctagcgacatccagatgacacaga<br>ctacatcctccctgtctgcctctctg<br>ggagacagagtcaccatcagttgcag<br>ggcaagtcaggacattcgcaattatt<br>taaactggtatcagcagaaaccagat<br>ggaactgttaaactcctgatctacta<br>cacatcaagattacactcaggagtcc<br>catcaaggttcagtggcagtgggtct<br>ggaacagattattctctcaccattgc<br>caacctgcaaccagaagatattgcca<br>cttacttttgccaacagggtaatacg<br>cttccgtggacgttcggtggaggcac<br>caaactggtaaccaaacgctcgag | EVQLQQSGPELVKPGASMKISCKASGY<br>SFTGYIVNWLKQSHGKNLEWIGLINPY<br>KGLTTYNQKFKGKATLTVDKSSSTAYM<br>ELLSLTSEDSAVYYCARSGYYGDSDWY<br>FDVWGAGTTVTVSSGGGGSGGGGSGGG<br>GSASDIQMTQTTSSLSASLGDRVTISC<br>RASQDIRNYLNWYQQKPDGTVKLLIYY<br>TSRLHSGVPSRFSGSGSGTDYSLTIAN<br>LQPEDIATYFCQQGNTLPWTFGGGTKL<br>VTKRS | 108 (109) |

| Hinge<br>Region | Nucleotide Sequence | Amino Acid Sequence | SEQ ID NO.<br>(amino acid<br>sequence) |
|---|---|---|---|
| sss(s)-<br>hIgG1 | gagcccaaatcttctgacaaaact<br>cacacatctccaccgagctca | EPKSSDKTHTSPPSS | 230 (231) |
| csc(s)-<br>hIgG1 | gagcccaaatcttgtgacaaaact<br>cacacatctccaccgtgctca | EPKSCDKTHTSPPCS | 232 (233) |
| ssc(s)-<br>hIgG1 | gagcccaaatcttctgacaaaact<br>cacacatctccaccgtgctca | EPKSSDKTHTSPPCS | 110 (111) |

TABLE 5-continued

Table 5. Primary structures (polynucoleotide and cognate amino acid sequences) of exemplary features of multivalent binding molecules.

| | Nucleotide Sequence | Amino acid Sequence | Sequence Identifier (amino acid sequence) |
|---|---|---|---|
| scc(s)-hIgG1 | gagcccaaatcttctgacaaaact cacacatgtccaccgtgctca | EPKSSDKTHTCPPCS | 112 (113) |
| css(s)-hIgG1 | gagcccaaatcttgtgacaaaact cacacatctccaccgagctca | EPKSCDKTHTSPPSS | 114 (115) |
| scs(s)-hIgG1 | gagcccaaatcttgtgacaaaact cacacatgtccaccgagctca | EPKSSDKTHTCPPSS | 116 (117) |
| ccc(s)-hIgG1 | gagcccaaatcttgtgacaaaact cacacatgtccaccgtgctca | EPKSCDKTHTSPPCS | 118 (119) |
| ccc(p)-hIgG1 | gagcccaaatcttgtgacaaaact cacacatgtccaccgtgctca | EPKSCDKTHTSPPCP | 120 (121) |
| sss(p)-hIgG1 | gagcccaaatcttctgacaaaact cacacatctccaccgagctca | EPKSSDKTHTSPPSP | 122 (123) |
| csc(p)-hIgG1 | gagcccaaatcttgtgacaaaact cacacatctccaccgagctca | EPKSCDKTHTSPPCP | 124 (125) |
| ssc(p)-hIgG1 | gagcccaaatcttctgacaaaact cacacatctccaccgtgctca | EPKSSDKTHTSPPCP | 126 (127) |
| scc(p)-hIgG1 | gagcccaaatcttctgacaaaact cacacatgtccaccgtgctca | EPKSSDKTHTCPPCP | 128 (129) |
| css(p)-hIgG1 | gagcccaaatcttgtgacaaaact cacacatctccaccgagctca | EPKSCDKTHTSPPSP | 130 (131) |
| scs(p)-hIgG1 | gagcccaaatcttgtgacaaaact cacacatgtccaccgagccca | EPKSSDKTHTCPPSP | 132 (133) |
| scppcp | agttgtccaccgtgccca | SCPPCP | 134 (135) |

| EFD | Nucleotide Sequence | Amino acid Sequence | Sequence Identifier (amino acid sequence) |
|---|---|---|---|
| hIgG1 (P238S) $C_{H2}C_{H3}$ | gcacctgaactcctgggtggatcg tcagtcttcctcttccccccaaaa cccaaggacaccctcatgatctcc cggacccctgaggtcacatgcgtg gtggtggacgtgagccacgaagac cctgaggtcaagttcaactggtac gtggacggcgtggaggtgcataat gccaagacaaagccgcgggaggag cagtacaacagcacgtaccgtgtg gtcagcgtcctcaccgtcctgcac caggactggctgaatggcaaggag tacaagtgcaaggtctccaacaaa gccctcccagcccccatcgagaaa acaatctccaaagccaaagggcag ccccgagaaccacaggtgtacacc ctgcccccatcccgggatgagctg accaagaaccaggtcagcctgacc tgcctggtcaaaggcttctatccc agcgacatcgccgtggagtgggag agcaatgggcagccggagaacaac tacaagaccacgcctcccgtgctg gactccgacggctccttcttcctc tacagcaagctcaccgtggacaag agcaggtggcagcaggggaacgtc ttctcatgctccgtgatgcatgag gctctgcacaaccactacacgcag aagagcctctcc tgtctccgggtaaatga | APELLGGSSVFLFPPKPKDTLMIS RTPEVTCVVVDVSHEDPEVKFNWY VDGVEVHNAKTKPREEQYNSTYRV VSVLTVLHQDWLNGKEYKCKVSNK ALPAPIEKTISKAKGQPREPQVYT LPPSRDELTKNQVSLTCLVKGFYP SDIAVEWESNGQPENNYKTTPPVL DSDGSFFLYSKLTVDKSRWQQGNV FSCSVMHEALHNHYTQKSLSLSPG K | 142 (143) |
| hIgG1 (P331S) $C_{H2}C_{H3}$ | gcacctgaactcctgggtggaccg tcagtcttcctcttccccccaaaa cccaaggacaccctcatgatctcc cggacccctgaggtcacatgcgtg gtggtggacgtgagccacgaagac cctgaggtcaagttcaactggtac gtggacggcgtggaggtgcataat gccaagacaaagccgcgggaggag | APELLGGPSVFLFPPKPKDTLMIS RTPEVTCVVVDVSHEDPEVKFNWY VDGVEVHNAKTKPREEQYNSTYRV VSVLTVLHQDWLNGKEYKCKVSNK ALPASIEKTISKAKGQPREPQVYT LPPSRDELTKNQVSLTCLVKGFYP SDIAVEWESNGQPENNYKTTPPVL DSDGSFFLYSKLTVDKSRWQQGNV | 144 (145) |

TABLE 5-continued

Table 5. Primary structures (polynucoleotide and cognate amino acid sequences) of exemplary features of multivalent binding molecules.

| | | | |
|---|---|---|---|
| | cagtacaacagcacgtaccgtgtg gtcagcgtcctcaccgtcctgcac caggactggctgaatggcaagga tacaagtgcaaggtctccaacaaa gccctcccagcctccatcgagaaa acaatctccaaagccaaagggcag ccccgagaaccacaggtgtacacc ctgcccccatcccgggatgagctg accaagaaccaggtcagcctgacc tgcctggtcaaaggcttctatccc agcgacatcgccgtggagtgggag agcaatgggcagccggagaacaac tacaagaccacgcctcccgtgctg gactccgacggctccttcttcctc tacagcaagctcaccgtggacaag agcaggtggcagcaggggaacgtc ttctcatgctccgtgatgcatgag gctctgcacaaccactacacgcag aagagcctctccc tgtctccgggtaaatga | FSCSVMHEALHNHYTQKSLSLSPG K | | |
| hIgG1 (P238S/ P331S) $C_{H2}C_{H3}$ | gcacctgaactcctggggtggatcg tcagtcttcctcttccccccaaaa cccaaggacaccctcatgatctcc cggacccctgaggtcacatgcgtg gtggtggacgtgagccacgaagac cctgaggtcaagttcaactggtac gtggacggcgtggaggtgcataat gccaagacaaagccgcgggaggag cagtacaacagcacgtaccgtgtg gtcagcgtcctcaccgtcctgcac caggactggctgaatggcaagga tacaagtgcaaggtctccaacaaa gccctcccagcctccatcgagaaa acaatctccaaagccaaagggcag ccccgagaaccacaggtgtacacc ctgcccccatcccgggatgagctg accaagaaccaggtcagcctgacc tgcctggtcaaaggcttctatccc agcgacatcgccgtggagtgggag agcaatgggcagccggagaacaac tacaagaccacgcctcccgtgctg gactccgacggctccttcttcctc tacagcaagctcaccgtggacaag agcaggtggcagcaggggaacgtc ttctcatgctccgtgatgcatgag gctctgcacaaccactacacgcag aagagcctctccctgtctccgggt aaatga | APELLGGSSVFLFPPKPKDTLMIS RTPEVTCVVVDVSHEDPEVKFNWY VDGVEVHNAKTKPREEQYNSTYRV VSVLTVLHQDWLNGKEYKCKVSNK ALPASIEKTISKAKGQPREPQVYT LPPSRDELTKNQVSLTCLVKGFYP SDIAVEWESNGQPENNYKTTPPVL DSDGSFFLYSKLTVDKSRWQQGNV FSCSVMHEALHNHYTQKSLSLSPG K | 146 (147) |

| Linker | Nucleotide Sequence | Amino Acid Sequence | Sequence Identifier |
|---|---|---|---|
| STD1 | aattatggtggcggtggctcgggc ggtggtggatctggaggaggtggg agtgggaattct | NYGGGGSGGGGSGGGGSGNS | 148 (149) |
| STD2 | aattatggtggcggtggctcgggc ggtggtggatctggaggaggtggg agtgggaattatggtggcggtggc tcgggcggtggtggatctggagga ggtgggagtgggaattct | NYGGGGSGGGGSGGGGSGNYGGGG SGGGGSGGGGSGNS | 150 (151) |
| H1 | aattct | NS | 152 (153) |
| H2 | ggtggcggtggctcggggaattct | GGGGSGNS | 154 (155) |
| H3 | aattatggtggcggtggctctggg aattct | NYGGGGSGNS | 156 (157) |
| H4 | ggtggcggtggctcgggcggtggt ggatctgggaattct | GGGGSGGGGSGNS | 158 (159) |
| H5 | aattatggtggcggtggctcgggc ggtggtggatctgggaattct | NYGGGGSGGGGSGNS | 160 (161) |

TABLE 5-continued

Table 5. Primary structures (polynucoleotide and cognate amino acid sequences) of exemplary features of multivalent binding molecules.

| | | | |
|---|---|---|---|
| H6 | ggtggcggtggctcgggcggtggt ggatctgggggaggaggcagcggg aattct | GGGGSGGGGSGGGGSGNS | 162 (163) |
| H7 | gggtgtccaccttgtccgaattct | GCPPCPNS | 164 (165) |
| (G4S)3 | ggtggcggtggatccggcggaggt gggtcgggtggcggcggatct | GGGSGGGSGGGS | 166 (167) |
| (G4S)4 | ggtggcggtggctcgggcggtggt ggatctggaggaggtgggagcggg ggaggtggcagt | GGGSGGGSGGGSGGGGS | 168 (169) |

EXAMPLE 8

Binding and Functional Studies with Alternative Multispecific Fusion Proteins

Experiments that parallel the experiments described above for the prototypical CD20-IgG-CD28 multispecific binding (fusion) molecule were conducted for each of the additional multivalent binding molecules described above. In general, the data obtained for these additional molecules parallel the results observed for the prototype molecule. Some of the salient results of these experiments are disclosed below. FIG. 14 shows results of blocking studies performed on one of the new molecules where both BD1 and BD2 bind to target antigens on the same cell or cell type, in this case, CD20 and CD37. This multispecific, multivalent binding (fusion) protein was designed with binding domain 1 binding CD20 (2H7; VLVH orientation), and binding domain 2 binding CD37, G28-1 VL-VH (LH) or VH-VL (HL). The experiment was performed in order to demonstrate the multispecific properties of the protein.

Blocking Studies: Ramos or BJAB B lymphoblastoid cells ($2.5 \times 10^5$) were pre-incubated in 96-well V-bottom plates in staining medium (PBS with 2% mouse sera) with murine anti-CD20 (25 µg/ml) antibody, or murine anti-CD37 (10 µg/ml) antibody, both together or staining medium alone for 45 minutes on ice in the dark. Blocking antibodies were pre-incubated with cells for 10 minutes at room temperature prior to addition of the multispecific binding (fusion) protein at the concentration ranges indicated, usually from 0.02 µg/ml to 10 µg/ml, and incubated for a further 45 minutes on ice in the dark. Cells were washed 2 times in staining medium, and incubated for one hour on ice with Caltag (Burlingame, Calif.) FITC goat anti-human IgG (1:100) in staining medium, to detect binding of the multispecific binding (fusion) proteins to the cells. The cells were then washed 2 times with PBS and fixed with 1% paraformaldehyde (cat. no. 19943, USB, Cleveland, Ohio). The cells were analyzed by flow cytometry using a FACsCalibur instrument and CellQuest software (BD Biosciences, San Jose, Calif.). Each data series plots the binding of the 2H7-sss-hIgG-STD1-G28-1 HL fusion protein in the presence of CD20, CD37, or both CD20 and CD37 blocking antibodies. Even though this experiment used one of the cleaved linkers, only the presence of both blocking antibodies completely eliminates binding by the multispecific binding (fusion) protein, demonstrating that the bulk of the molecules possess binding function for both CD20 and CD37. The data were similar for two cell lines tested in panels A and B, Ramos and BJAB, where the CD20 blocking antibody was more effective than the CD37 blocking antibody at reducing the level of binding observed by the multispecific binding (fusion) protein.

ADCC Assays

Figure 15:
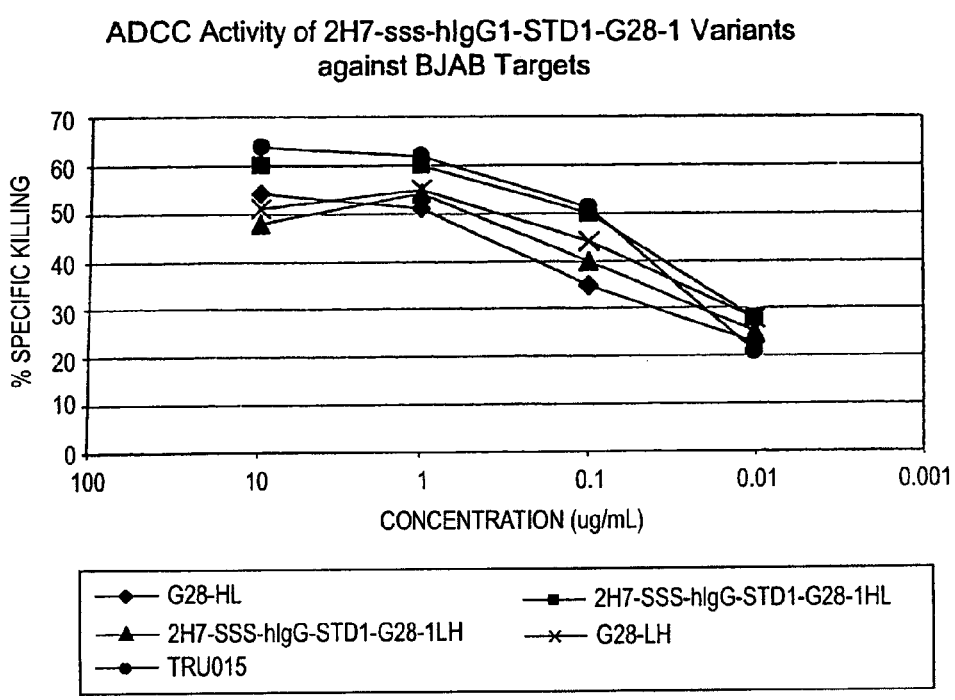
FIG. 15 shows the results of an ADCC assay performed with BJAB target cells, PBMC effector cells, and with the CD20-hIgG-CD37 specific fusion protein as the test reagent. For a full description of the procedure see the appropriate example. The graph plots the concentration of fusion protein versus the % specific killing at each dosage tested for the single specificity SMIP reagents, and for the [2H7-sss-hIgG-STD1-G28-1] LH and HL variants. Each data series plots the dose-response effects for one of these single specificity or multispecific single-chain fusion proteins.

FIG. 15 shows the results of ADCC assays performed on the CD20-CD37 multispecific binding (fusion) proteins. ADCC assays were performed using BJAB lymphoblastoid B cells as targets and human PBMC as effector cells. BJAB cells were labeled with 500 µCi/ml $^{51}$Cr sodium chromate (250 µCi/µg) for 2 hours at 37° C. in IMDM/10% FBS. The labeled cells were washed three times in RPMI.10% FBS and resuspended at $4 \times 10^5$ cells/ml in RPMI. Heparinized, human whole blood was obtained from anonymous, in-house donors and PBMC isolated by fractionation over Lymphocyte Separation Media (LSM, ICN Biomedical) gradients. Buffy coats were harvested and washed twice in RPMI/10% FBS prior to resuspension in RPMI/10% FBS at a final concentration of $5 \times 10^6$ cells/ml. Cells were counted by trypan blue exclusion using a hemacytometer prior to use in subsequent assays. Reagent samples were added to RPMI medium with 10% FBS at 4 times the final concentration and three 10 fold serial dilutions for each reagent were prepared. These reagents were then added to 96-well U-bottom plates at 50 µl/well for the indicated final concentrations. The $^{51}$Cr-labeled BJAB cells were added to the plates at 50 µl/well ($2 \times 10^4$ cells/well). The PBMCs were then added to the plates at 100 µl/well ($5 \times 10^5$ cells/well) for a final ratio of 25:1 effector (PBMC):target (BJAB). Effectors and targets were added to medium alone to measure background killing. The $^{51}$Cr-labeled cells were added to medium alone to measure spontaneous release of $^{51}$Cr and to medium with 5% NP40 (cat. no. 28324, Pierce, Rockford, Ill.) to measure maximal release of $^{51}$Cr. Reactions were set up in triplicate wells of a 96-well plate. Multispecific binding (fusion) proteins were added to wells at a final concentration ranging from 0.01 µg/ml to 10 µg/ml, as indicated on the graphs. Each data series plots a different multispecific binding (fusion) protein or the corresponding single specificity SMIPs at the titration ranges described. Reactions were allowed to proceed for 6 hours at 37° C. in 5% $CO_2$ prior to harvesting and counting. Twenty-five µl of the supernatant from each well were then transferred to a Luma Plate 96 (cat. no. 6006633, Perkin Elmer, Boston, Mass.) and dried overnight at room temperature. CPM released was measured on a Packard TopCounNXT. Percent specific killing was calculated by subtracting (cpm {mean of triplicate samples} of sample–cpm spontaneous release)/(cpm maximal release–cpm spontaneous release)×100. Data are plotted as % specific killing versus protein concentration. The data demonstrate that the multispecific binding (fusion) protein is able to mediate ADCC activity against cells expressing the target antigen (s) as well as the single specificity SMIPs for CD20 and/or CD37, but does not show augmentation in the level of this effector function.

Co-Culture Experiments

FIG. 16 shows the results of experiments designed to look at other properties of this type of multispecific binding (fusion) protein, where having two binding domains against targets expressed on the same cell or cell type might result in synergistic effects by signaling/binding through the two surface receptors bound. The co-culture experiments were performed using PBMC isolated as described for the ADCC assays above. These PBMC were resuspended in culture medium at $2 \times 10^6$ cells/ml in a final volume of 500 µl/well, and cultured alone or incubated with single specificity SMIPs for CD20, CD37, CD20+CD37, or the multispecific binding (fusion) protein using the H7 linker, [2H7-sss-IgG-H7-G28-1 HL]. Each of the test reagents was added at a final concentration of 20 µg/ml. After 24 hours of culture, no real differences were seen in the % of B cells in culture; however, when the cells were subjected to flow cytometry, cell clumping was visible in the FWD X 90 staining pattern for the cultures containing the multispecific binding (fusion) protein, indicating that the B cells expressing the two target antigens were engaged in homotypic adhesion. After 72 hours in culture, the multispecific binding (fusion) protein resulted in the death of almost all the B cells present. The combination of the two single-specificity SMIPs also drastically decreased the percentage of B cells, but not to the level seen with the multispecific binding molecule. These data suggest that engaging both binding domains for CD20 and CD37 on the same multispecific molecule, results in homotypic adhesion between B cells and may also result in binding of both CD20 and CD37 antigens on the same cell. Without wishing to be bound by theory, the synergistic effect in eliminating target cells may be due (1) to the binding through binding domains 1 and 2 on the same cell types, and/or (2) to interactions of the effector function domain (constant sub-region) of the multivalent binding molecules with monocytes or other cell types in the PBMC culture that result in delayed killing. The kinetics of this killing effect are not rapid, taking more than 24 hours to be achieved, indicating that it is may be a secondary effect, requiring production of cytokines or other molecules prior to the effects being observed.

Apoptosis Assays

FIG. 17 shows the results of experiments designed to explore the induction of apoptosis after treatment of B cell lines with either the [2H7-sss-hIgG-H7-G28-1 HL] multispecific, multivalent binding (fusion) proteins or the single specificity CD20 and/or CD37 SMIPS, alone and in combination with one another. Ramos cells (panel A; ATCC No. CRL-1596), and Daudi cells (panel B; ATCC No. CCL-213) were incubated overnight (24 hours) at 37° C. in 5% $CO_2$ in Iscoves (Gibco) complete medium with 10% FBS at $3 \times 10^5$ cells/ml and 5, 10, or 20 µg/ml fusion proteins. For combination experiments with the single specificity SMIPs, the proteins were used at the following concentrations: TRU-015 (CD20 directed SMIP)=10 µg/ml, with 5 µg/ml G28-1 LH(CD37 directed SMIP). Alternatively, TRU-015=20 µg/ml was combined with G28-1 LH at 10 µg/ml. Cells were then stained with Annexin V-FITC and propidium iodide using the BD Pharmingen Apoptosis Detection Kit I cat. no. 556547), and processed according to kit instructions. The cells were gently vortexed, incubated in the dark at room temperature for 15 minutes, and diluted in 400 µl binding buffer prior to analysis. Samples were analyzed by flow cytometry on a FACsCalibur (Becton Dickinson) instrument using Cell Quest software (Becton Dickinson). The data are presented as columnar graphs plotting the percentage of Annexin V/propidium iodide positive cells versus type of treatment. Clearly, the multispecific binding (fusion) protein is able to induce a significantly higher level of apoptotic death in both cell lines than the single specificity reagents, even when used together. This increased functional activity reflects an interaction of the coordinate binding of BD1 and BD2 (specific for CD20 and CD37) receptors on the target cells.

EXAMPLE 9

Binding and Functional Properties of 2H7-hIgG-G19-4 Multispecific Binding (Fusion) Proteins This example describes the binding and functional properties of the 2H7-hIgG-G19-4 multispecific fusion proteins. The construction of these molecules is described in Example 7. Expression and purification are as described in previous Examples.

Binding experiments were performed as described for previous molecules, except that the target cells used to measure CD3 binding were Jurkat cells expressing CD3 on their surface. Refer to FIG. 18, where the top graph shows binding curves obtained for binding of the CD20-CD3 multispecific molecules to Jurkat cells using purified proteins serially diluted from 20 to 0.05 µg/ml. The HL orientation of the G19-4 specificity seems to bind better to the CD3 antigen than does the LH orientation. The lower panel shows the binding curves obtained for the BD1, the binding domain recognizing CD20. All of the molecules bind well, and at a level nearly equivalent to a single specificity SMIP for CD20.

ADCC Assays

For the data presented in FIG. 19, ADCC assays were performed as described in the previous Example. In this case, the fusion proteins were all 2H7-hIgG-G19-4 variants or combinations of the single-specificity SMIPs (2H7, specific for CD20) or antibodies (G19-4, specific for CD3). In addition, for the data presented in the lower panel of FIG. 19, NK cells were depleted from PBMC prior to use, by magnetic bead depletion using a MACS (Miltenyi Biotec, Auburn, Calif.) column separation apparatus and NK cell-specific CD16 magnetic microbeads (cat no.: 130-045-701). The data presented in the two panels demonstrate that all of the CD20-hIgG-CD3 multispecific molecules mediate ADCC, regardless of whether NK cells are depleted or total PBMC are used in the assay. For the TRU 015 or combinations of G19-4 and TRU015, only cultures containing NK cells could mediate ADCC. G19-4 did not work well in either assay against BJAB targets, which do not express CD3, although G19-4 may have bound to CD3 expressing NK T cells and activated these cells in the first assay shown. The killing observed in the lower panel for the multispecific binding (fusion) proteins is probably mediated through activation of cytotoxicity in the T cell population by binding CD3, against the BJAB targets expressing the CD20 antigen. This killing activity appears to be relatively insensitive to the dosage of the molecules over the concentration ranges used, and is still significantly different from the other molecules tested, even at a concentration of 0.01 ug/ml.

EXAMPLE 10

Multivalent Binding Molecules

Other embodiments include linker domains derived from immunoglobulins. More specifically, the source sequences for these linkers are sequences obtained by comparing regions present between the V-like domains or the V- and C-like domains of other members of the immunoglobulin superfamily. Because these sequences are usually expressed as part of the extracellular domain of cell surface receptors, they are expected to be more stable to proteolytic cleavage, and should also not be immunogenic. One type of sequence that is not expected to be as useful in the role of a linker for the multivalent binding (fusion) proteins is the type of sequence expressed on surface-expressed members of the -Ig superfamily, but that occur in the intervening region between the C-like domain and the transmembrane domain. Many of these molecules have been observed in soluble form, and are cleaved in these intervening regions close to the cell membrane, indicating that the sequences are more susceptible to cleavage than the rest of the molecule.

The linkers described above are inserted into either a single specificity SMIP, between the binding domain and the effector function domain, or are inserted into one of the two possible linker positions in a multivalent binding (fusion) protein, as described herein.

A complete listing of the sequences disclosed in this application is appended, and is incorporated herein by reference in its entirety. The color coding indicating the sequence of various regions or domains of the particular polynucleotides and polypeptides are useful in identifying a corresponding region or domain in the sequence of any of the molecules disclosed herein.

EXAMPLE 11

Screening Matrix for Scorpion Candidates Targeting B-Cells
Introduction

As a means of identifying combinations of paired monoclonal antibody binding domains that would most likely yield useful and potent multivalent binding molecules, or scorpions, against a target population, a series of monoclonal antibodies against B cell antigens was tested in a combination matrix against B cell lines representing various non Hodgkin's lymphomas. To ensure that all possible pairwise comparisons of antibodies known or expected to bind to the cell of interest are assayed, a two-dimensional matrix of antibodies may be used to guide the design of studies using a given cell type. Monoclonal antibodies against numerous B cell antigens known by their cluster designations (CDs) are recorded in the left column. Some of these antibodies (designated by the antigen(s) to which they specifically bind), i.e., CD19, CD20, CD21, CD22, CD23, CD30, CD37, CD40, CD70, CD72, CD79a, CD79b, CD80, CD81, CD86, and CL II (MHC Class II), were incubated, alone or in combination with other members of this monoclonal antibody set, with antigen-positive target cells. The variable domains of these antibodies are contemplated as binding domains in exemplary embodiments of the multivalent binding molecules. Using the knowledge in the art and routine procedures, those of skill in the art are able to identify suitable antibody sequences (nucleic acid encoding sequences as well as amino acid sequences), for example in publicly available databases, to generate a suitable antibody or fragment thereof (e.g., by hybridization-based cloning, PCR, peptide synthesis, and the like), and to construct multivalent binding molecules using such compounds. Sources of exemplary antibodies from which binding domains were obtained as described herein are provided in Table 6. Typically, a cloning or synthesis strategy that realizes the CDR regions of an antibody chain will be used, although any antibody, fragment thereof, or derivative thereof that retains the capacity to specifically bind to a target antigen is contemplated.

Stated in more detail, the cloning of heavy and/or light chain variable regions of antibodies from hybridomas is standard in the art. There is no requirement that the sequence of the variable region of interest be known in order to obtain that region using conventional cloning techniques. See, e.g., Gilliland et al., Tissue Antigens 47(1):1-20 (1996). To prepare single-chain polypeptides comprising a variable region recognizing a murine or human leukocyte antigen, a method was devised for rapid cloning and expression that yielded functional protein within two to three weeks of RNA isolation from hybridoma cells. Variable regions were cloned by poly-G tailing the first-strand cDNA followed by anchor PCT with a forward poly-C anchor primer and a reverse primer specific for the constant region sequence. Both primers contain flanking restriction endonuclease sites for insertion into pUC19. Sets of PCR primers for isolation of murine, hamster and rat $V_L$ and $V_H$ genes were generated. Following determination of consensus sequences for a specific $V_L$ and $V_H$ pair, the $V_L$ and $V_H$ genes were linked by DNA encoding an intervening peptide linker (typically encoding $(Gly_4Ser)_3$) and the $V_L$-linker-$V_H$ gene cassettes were transferred into the pCDM8 mammalian expression vector. The constructs were transfected into COS cells and sFvs were recovered from conditioned culture medium supernatant. This method has been successfully used to generate functional sFv to human CD2, CD3, CD4, CD8, CD28, CD40, CD45 and to murine CD3 and gp39, from hybridomas producing murine, rat, or hamster antibodies. Initially, the sFvs were expressed as fusion proteins with the hinge-$C_{H2}$-$C_{H3}$ domains of human IgG1 to facilitate rapid characterization and purification using goat anti-human IgG reagents or protein A. Active sFv could also be expressed with a small peptide, e.g., a tag, or in a tailless form. Expression of CD3 (G19-4) sFv tailless forms demonstrated increased cellular signaling activity and revealed that sFvs have potential for activating receptors.

Alternatively, identification of the primary amino acid sequence of the variable domains of monoclonal antibodies can be achieved directly, e.g., by limited proteolysis of the antibody followed by N-terminal peptide sequencing using, e.g., the Edman degradation method or by fragmentation mass spectroscopy. N-terminal sequencing methods are well known in the art. Following determination of the primary amino acid sequence, the variable domains, a cDNA encoding this sequence is assembled by synthetic nucleic acid synthesis methods (e.g., PCR) followed by scFv generation. The necessary or preferred nucleic acid manipulation methods are standard in the art.

Fragments, derivatives and analogs of antibodies, as described above, are also contemplated as suitable binding domains. Further, any of the constant sub-regions described above are contemplated, including constant sub-regions comprising any of the above-described hinge regions. Additionally, the multivalent single-chain binding molecules described in this example may include any or all of the linkers described herein.

Monoclonal antibodies were initially exposed to cells and then cross-linked using a goat anti-mouse second-step antibody ($2^{nd}$ step). Optionally, one could cross-link the antibodies prior to contacting cells with the antibodies, e.g., by cross-linking the antibodies in solution. As another alternative, monoclonal antibodies could be cross-linked in a solid phase by adsorbing onto the plastic bottom of tissue culture wells or "trapped" on this plastic by means of goat anti-mouse antibody adsorbed to the plastic, followed by plate-based assays to evaluate, e.g., growth arrest or cell viability.

Inversion of phosphatidylserine from the cytosolic side of the cell membrane to the exterior cell surface of that plasma membrane is an accepted indicator of pro-apoptotic events. Progression to apoptosis leads to loss of cell membrane integrity, which can be detected by entry of a cell-impermeant intercalating dye, e.g., propidium iodide (PI). Following cell exposure to monoclonal antibodies alone or in combination, a dual, pro-apoptotic assay was performed and treated cell populations were scored for cell surface-positive annexin V (ANN) and/or PI inclusion.

Annexin V Binding/Propidium Iodide Internalization Analysis

Cells and cell culture conditions. Experiments were performed to examine the effect of cross-linking two different monoclonal antibodies against targets expressed on four human B-cell lines. Effects on cell lines were measured by determining levels of ANN and/or PI staining following exposure. The human B cell lines BJAB, Ramos (ATCC#CRL-1596), Daudi (ATCC#CCL-213), and DHL-4 (DSMZ#ACC495) were incubated for 24 hours at 37° C. in 5% $CO_2$ in Iscoves (Gibco) complete medium with 10% FBS. Cells were maintained at a density between $2-8\times10^5$ cells/ml and a viability typically>95% prior to study.

Experiments were conducted at a cell density of $2\times10^5$ cells/ml and 2 µg/ml of each comparative monoclonal antibody from a matrix against B-cell antigens. Each comparator monoclonal antibody was added at 2 µg/ml alone or individually when combined with each matrix monoclonal antibody, also at 2 µg/ml. Table 6 lists the catalog number and sources of monoclonal antibodies used in these experiments. For cross-linking these monoclonal antibodies in solution, goat anti-mouse IgG (Jackson Labs catalog no. 115-001-008) was added to each well at a concentration ratio of 2:1 (goat anti-mouse: each monoclonal antibody), e.g., a well with only one monoclonal antibody at 2 µg/ml would have goat anti-mouse added to a final concentration of 4 µg/ml, while wells with both comparator monoclonal antibody (2 µg/ml) and a monoclonal antibody from the matrix (2 µg/ml) would have 8 µg/ml of goat anti-mouse antibody added to the well.

After 24 hours of incubation at 37° C. in 5% $CO_2$, cells were stained with Annexin V-FITC and propidium iodide using the BD Pharmingen Annexin V-FITC Apoptosis Detection Kit I (#556547). Briefly, cells were washed twice with cold PBS and resuspended in "binding buffer" at $1\times10^6$ cells/ml. One hundred microliters of the cells in binding buffer were then stained with 5 µl of Annexin V-FITC and 5 µl of propidium iodide. The cells were gently mixed and incubated in the dark at room temperature for 15 minutes. Four hundred microliters of binding buffer were then added to each sample. The samples were then read on a FACsCalibur (Becton Dickinson) and analyzed using Cell Quest software (Becton Dickinson).

TABLE 6

Antibodies against B cell antigens used in this study and their sources.

| Name | Catalog number | Commercial supplier |
| --- | --- | --- |
| Anti-CD19 | #C2269-74 | US Biological (Swampscott, MA) |
| Anti-CD20 | #169-820 | Ancell Corp (Bayport, MN) |
| Anti-CD21 | #170-820 | Ancell Corp (Bayport, MN) |
| Anti-CD22 | #171-820 | Ancell Corp (Bayport, MN) |
| Anti-CD23 | #172-820 | Ancell Corp (Bayport, MN) |
| Anti-CD30 | #179-820 | Ancell Corp (Bayport, MN) |
| Anti-CD37 | #186-820 | Ancell Corp (Bayport, MN) |
| Anti-CD40 | #300-820 | Ancell Corp (Bayport, MN) |
| Anti-CD70 | #222-820 | Ancell Corp (Bayport, MN) |
| Anti-CD72 | #C2428-41B1 | US Biological (Swampscott, MA) |
| Anti-CD79a | #235-820 | Ancell Corp (Bayport, MN) |
| Anti-CD79b | #301-820 | Ancell Corp (Bayport, MN) |
| Anti-CD80 | #110-820 | Ancell Corp (Bayport, MN) |
| Anti-CD81 | #302-820 | Ancell Corp (Bayport, MN) |

TABLE 6-continued

Antibodies against B cell antigens used in this study and their sources.

| Name | Catalog number | Commercial supplier |
| --- | --- | --- |
| Anti-CD86 | #307-820 | Ancell Corp (Bayport, MN) |
| Anti-CL II DR, DQ, DP | #131-820 | Ancell Corp (Bayport, MN) |

Addition of the cross-linking antibody (e.g., goat anti-mouse antibody) to monoclonal antibody A alone resulted in increased cell sensitivity, suggesting that a multivalent binding molecule, or scorpion, constructed with two binding domains recognizing the same antigen would be effective at increasing cell sensitivity. Without wishing to be bound by theory, this increased sensitivity could be due to antigen clustering and altered signaling. TNF receptor family members, for example, require homo-multimerization for signal transduction and scorpions with equivalent binding domains on each end of the molecule could facilitate this interaction. The clustering and subsequent signaling by CD40 is an example of this phenomenon in the B cell system.

Figure 20:
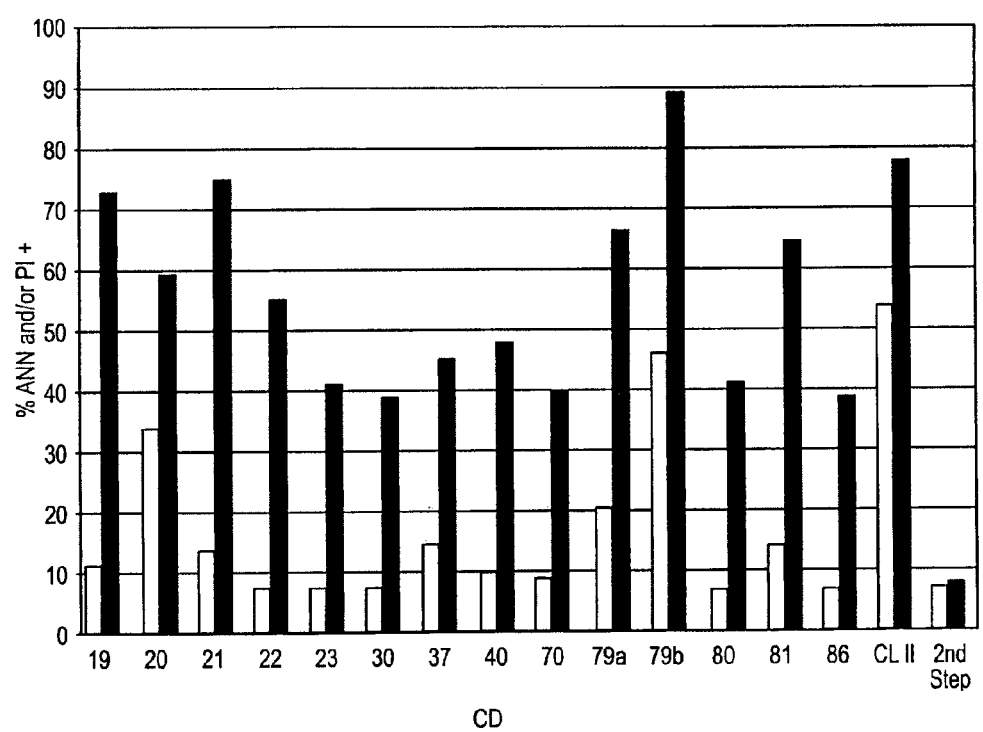
FIG. 20 shows the percentage of Ramos B-cells that stained positive with Annexin V (Ann) and/or propidium iodide (PI) after overnight incubation with each member of a matrix panel of B-cell antibodies (2 µg/ml) in the presence, or absence, of an anti-CD20 antibody (present at 2 µg/ml where added). Goat-anti-mouse secondary antibody was always present at a two-fold concentration ratio relative to other antibodies (either matrix antibody alone, or matrix antibody and anti-CD20 antibody). Vertically striped bars—matrix antibody (2 µg/ml) denoted on X-axis and goat anti-mouse antibody (4 µg/ml). Horizontally striped bars—matrix antibody (2 µg/ml) denoted on X-axis, anti-CD20 antibody (2 µg/ml), and goat anti-mouse antibody (4 µg/ml). The "$2^{nd}$ step" condition served as a control and involved the addition of goat anti-mouse antibody at 4 µg/ml (vertically striped bar) or 8 µg/ml (horizontally striped bar), without a matrix antibody or anti-CD20 antibody. "CL II" (MHC class II) in the figures refers to a monoclonal antibody cross-reactive to HLA DR, DQ and DP, i.e., to MHC Class II antigens.
Figure 21:
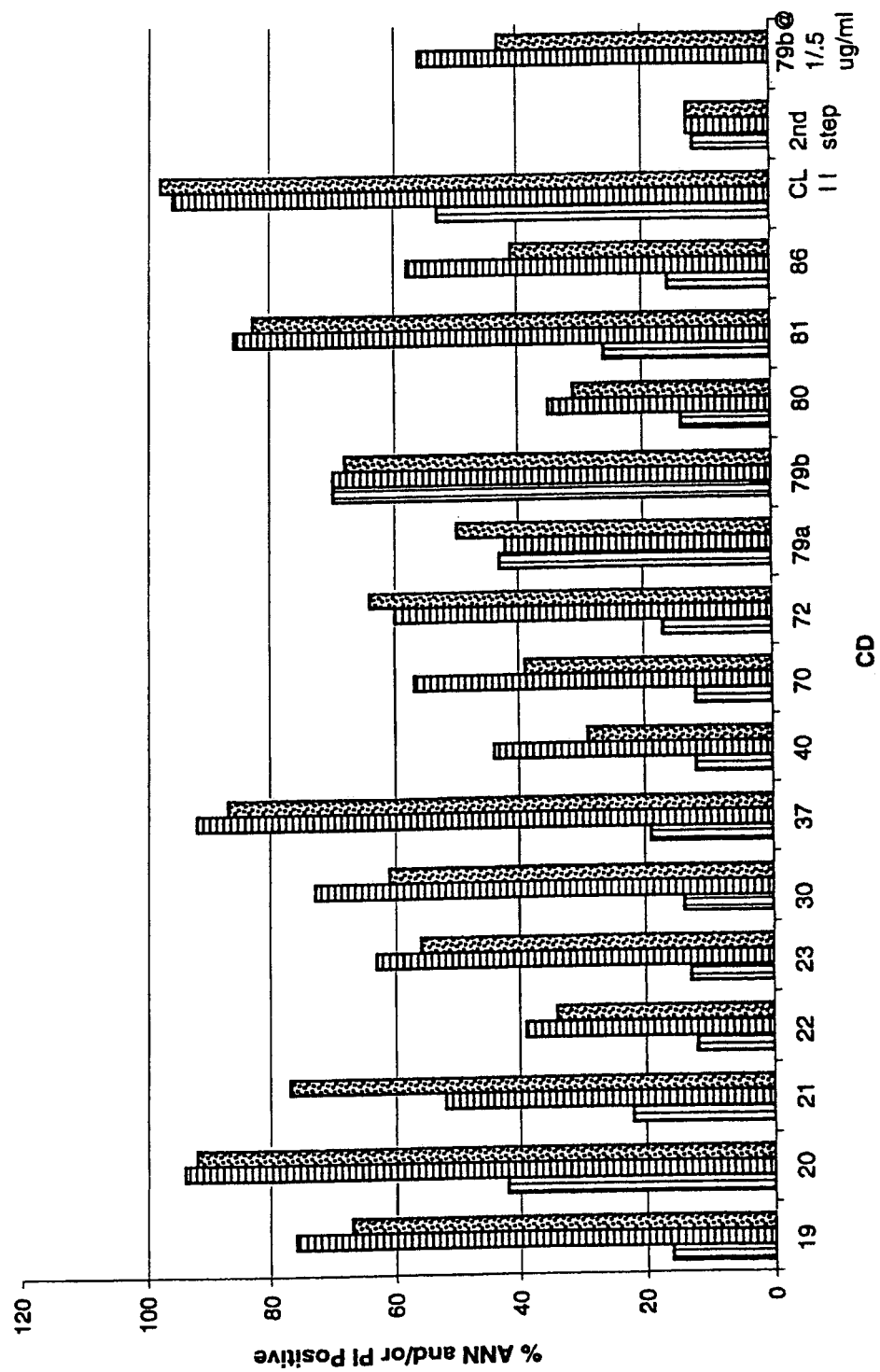
FIG. 21 shows the percentage of Ramos B-cells that stained positive with Annexin V (Ann) and/or propidium iodide (PI) after overnight incubation with each member of a matrix panel of B-cell antibodies (2 µg/ml) in the presence, or absence, of an anti-CD79b antibody (present at either 0.5 or 1.0 µg/ml where added). See the description of FIG. 20 for identification of "CL II" and "$2^{nd}$ step" samples. Vertically striped bars—matrix antibody (2 µg/ml) and goat anti-mouse antibody (4 µg/ml); horizontally striped bars—matrix antibody (2 µg/ml), anti-CD79b antibody (1.0 µg/ml) and goat anti-mouse antibody (6 µg/ml); stippled bars—matrix antibody (2 µg/ml), anti-CD79b antibody (0.5 µg/ml) and goat anti-mouse antibody (5 µg/ml).
Figure 22:
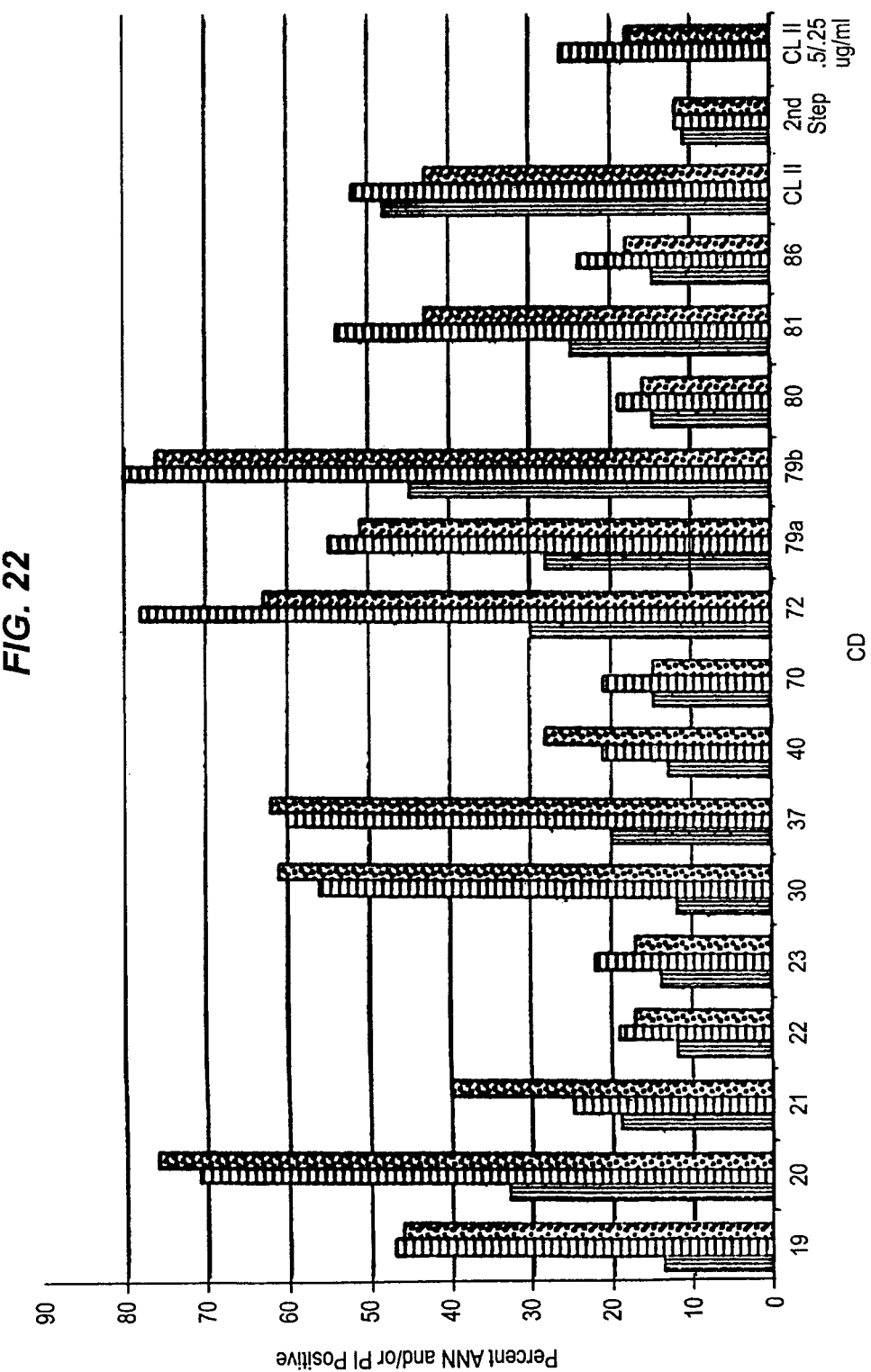
FIG. 22 shows the percentage of Ramos B-cells that stained positive with Annexin V (Ann) and/or propidium iodide (PI) after overnight incubation with each member of a matrix panel of B-cell antibodies (2 µg/ml) in the presence, or absence, of an anti-CL II antibody (present at either 0.25 or 0.5 µg/ml where added). See the description of FIG. 20 for identification of "CL II" and "$2^{nd}$ step" samples. Vertically striped bars—matrix antibody (2 µg/ml) and goat anti-mouse antibody (4 µg/ml); horizontally striped bars—matrix antibody (2 µg/ml), anti-CL II antibody (0.5 µg/ml) and goat anti-mouse antibody (5 µg/ml); stippled bars—matrix antibody (2 µg/ml), anti-CL II antibody (0.25 µg/ml) and goat anti-mouse antibody (4.5 µg/ml).

As shown in FIGS. 20, 21 and 22, the addition of monoclonal antibody A and monoclonal antibody B against different antigens will produce additive or in some combinations greater than additive (i.e., synergistic) pro-apoptotic effects on treated cells. In FIG. 20, for example, the combination of anti-CD20 with monoclonal antibodies against other B cell antigens all resulted, to varying extents, in increased cell sensitivity. Some combinations, such as anti-CD20 combined with anti-CD19 or anti-CD20 combined with anti-CD21, however, produced greater than additive pro-apoptotic effects, indicating that multivalent binding molecules or scorpions composed of these binding domains should be particularly effective at eliminating transformed B cells. Referring to FIG. 20, the percentage of cells exhibiting pro-apoptotic activities when exposed to anti-CD 20 antibody alone is about 33% (vertically striped bar corresponding to "20," i.e., the anti-CD20 antibody); the percentage of pro-apoptotic cells upon exposure to anti-CD19 antibody is about 12% (vertically striped bar in FIG. 20 corresponding to "19," i.e., the anti-CD19 antibody); and the percentage of pro-apoptotic cells upon exposure to both anti-CD20 and anti-CD19 antibodies is about 73% (horizontally striped bar in FIG. 20 corresponding to "19"). The 73% of pro-apoptotic cells following exposure to both antibodies is significantly greater than the 45% (33%+12%) sum of the effects attributable to each individual antibody, indicating a synergistic effect attributable to the anti-CD19 and anti-CD 20 antibody pair. Useful multivalent binding molecules include molecules in which the two binding domains lead to an additive effect on B-cell behavior as well as multivalent binding molecules in which the two binding domains lead to synergistic effects on B-cell behavior. In some embodiments, one binding domain will have no detectable effect on the measured parameter of cell behavior, with each of the paired binding domains contributing to distinct aspects of the activities of the multivalent binding molecule, such as a multispecific, multivalent binding molecule (e.g., binding domain A binds to a target cell and promotes apoptosis while binding domain B binds to a soluble therapeutic such as a cytotoxin). Depending on the design of a multivalent binding molecule, the issue of the type of combined effect (additive, synergistic, or inhibitory) of the two binding domains on a target cell may not be relevant because one of the binding domains is specific for a non-cellular (e.g., soluble) binding partner or is specific for a cell-associated binding partner, but on a different cell type.

Exemplary binding domain pairings producing additive, synergistic or inhibitory effects, as shown in FIGS. 20-23, are apparent from Tables 7 and 8. Table 7 provides quantitative data extracted from each of FIGS. 20-23 in terms of the percentage of cells staining positive for ANN and/or PI. Table 8 provides calculations using the data of Table 7 that provided a basis for determining whether the interaction of a given pair of antibodies yielded an additive, synergistic, or inhibitory effect, again as assessed by the percentage of cells staining positive for ANN and/or PI.

TABLE 7

| Name | Anti-CD20 | Anti-CD79b | Anti-CL II | Anti-CD22 |
|---|---|---|---|---|
| Anti-CD19 | 13/73* | 18/76/66 | 14/47/46 | 12/11 |
| Anti-CD20 | 33/NA | 42/94/92 | 33/71/76 | 28/33 |
| Anti-CD21 | 14/75 | 22/50/76 | 18/24/40 | 11/11 |
| Anti-CD22 | 8/55 | 12/39/33 | 12/19/17 | 10/12 |
| Anti-CD23 | 8/41 | 12/63/55 | 14/22/17 | 10/12 |
| Anti-CD30 | 8/38 | 14/72/61 | 12/56/61 | 10/11 |
| Anti-CD37 | 15/45 | 19/92/86 | 20/60/62 | 19/20 |
| Anti-CD40 | 10/48 | 12/44/30 | 13/21/28 | 14/13 |
| Anti-CD70 | 9/40 | 12/56/39 | 15/21/15 | 10/10 |
| Anti-CD72 | NA | 16/60/64 | 30/78/63 | 17/17 |
| Anti-CD79a | 21/66 | 43/42/50 | 28/55/51 | 14/14 |
| Anti-CD79b | 46/88 | 70/70/68 | 45/80/76 | 26/16 |
| Anti-CD80 | 7/41 | 14/35/30 | 15/19/17 | 11/11 |
| Anti-CD81 | 14/65 | 25/86/83 | 25/54/43 | 19/20 |
| Anti-CD86 | 7/38 | 16/58/42 | 15/24/18 | 14/11 |
| Anti- CL II | 53/77 | 52/96/98 | 47/52/43 | 72/57 |

*In columns 2-4 of Table 7, the numerical values reflect the heights of histogram bars in FIGS. 20-22, respectively, with the first number in each cell denoting the height of a vertically striped bar, the second number denoting the height of a horizontally striped bar and, where present, the third number reflecting the height of a stippled bar. In column 5, the first number reflects the height of a solid bars and the second number reflects the height of a slant-striped bar in FIG. 23.

Figure 23:
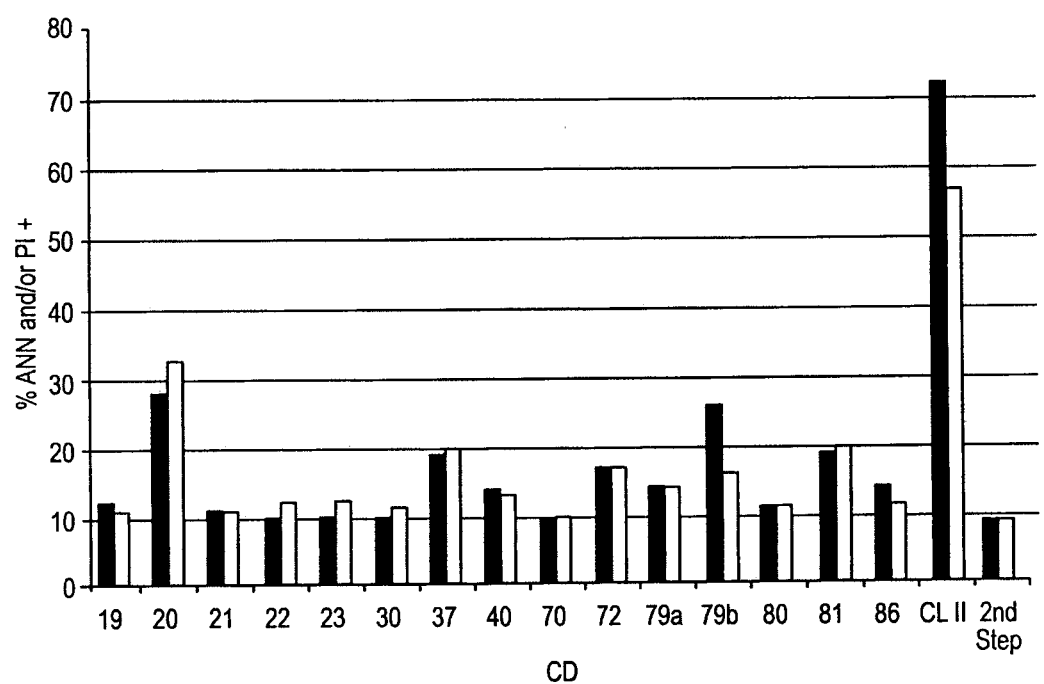
FIG. 23 shows the percentage of DHL-4 B-cells that stained positive with Annexin V (Ann) and/or propidium iodide (PI) after overnight incubation with each member of a matrix panel of B-cell antibodies (2 µg/ml) in the presence, or absence, of an anti-CD22 antibody (present at 2 µg/ml where added). See the description of FIG. 20 for identification of "CL II" and "$2^{nd}$ step" samples. Solid bars—matrix antibody (2 µg/ml) and goat anti-mouse antibody (4 µg/ml); slant-striped bars—matrix antibody (2 µg/ml), anti-CD22 antibody (2 µg/ml) and goat anti-mouse antibody (8 µg/ml).

In some embodiments, the two binding domains interact in an inhibitory, additive or synergistic manner in sensitizing (or de-sensitizing) a target cell such as a B cell. FIG. 23 shows the protective, or inhibitory, effects resulting from combining anti-CD22 antibody with strongly pro-apoptotic monoclonal antibodies such as the anti-CD79b antibody or anti-MHC class II (i.e., anti-CL II) antibody. For example, FIG. 23 and Table 7 show that anti-CD22 antibody alone induces no more than about 10% of cells to exhibit pro-apoptotic behavior (solid bar corresponding to "22" in FIG. 23) and anti-CD79b induces about 26% pro-apoptotic cells (solid bar corresponding to "CD79b" in FIG. 23). In combination, however, anti-CD22 and anti-CD79b induce only about 16% pro-apoptotic cells (slant-striped bar corresponding to "79b" in FIG. 23). Thus, the combined antibodies induce 16% pro-apoptotic cells, which is less than the 38% sum of the individual effects attributable to anti-CD22 (12%) and anti-CD79b (26%). Using this approach, an inspection of FIG. 23 and/or Tables 7-8 reveals that anti-CD22 antibody, and by extension a multispecific, multivalent binding molecule comprising an anti-CD22 binding domain, when used in separate combination with each of the following antibodies (or corresponding binding domains): anti-CD19, anti-CD20, anti-CD21, anti-CD23, anti-CD30, anti-CD37, anti-CD40, anti-CD70, anti-CD72, anti-CD79a, anti-CD79b, anti-CD80, anti-CD81, anti-CD86 and anti-MHC class II antibodies/binding domains, will result in an inhibited overall effect.

Without wishing to be bound by theory, the data can be interpreted as indicating that anti-CD22 antibody, or a mul-

TABLE 8

| Name | Anti-CD20 | Anti-CD79b | Anti-CL II | Anti-CD22 |
|---|---|---|---|---|
| Anti-CD19 | S: 13 + 33 = 46* | A: 18 + 56 = 74<br>A: 18 + 43 = 61 | S: 14 + 26 = 40<br>S: 14 + 18 = 32 | I: 12 + 10 = 22 |
| Anti-CD20 | NA | A: 42 + 56 = 98<br>A: 42 + 43 = 85 | S: 33 + 26 = 59<br>S: 33 + 18 = 51 | A/I: 28 + 10 = 38 |
| Anti-CD21 | S: 14 + 33 = 47 | I: 22 + 56 = 78<br>S: 22 + 43 = 65 | I: 18 + 26 = 44<br>A: 18 + 18 = 36 | I: 11 + 10 = 21 |
| Anti-CD22 | S: 8 + 33 = 41 | I: 12 + 56 = 68<br>I: 12 + 43 = 55 | I: 12 + 26 = 38<br>I: 12 + 18 = 30 | NA |
| Anti-CD23 | A: 8 + 33 = 41 | A: 12 + 56 = 68<br>A: 12 + 43 = 55 | I: 14 + 26 = 40<br>I: 14 + 18 = 32 | I: 10 + 10 = 20 |
| Anti-CD30 | A: 8 + 33 = 41 | A: 14 + 56 = 70<br>A: 14 + 43 = 57 | S: 12 + 26 = 38<br>S: 12 + 18 = 30 | I: 10 + 10 = 20 |
| Anti-CD37 | A: 15 + 33 = 48 | S: 19 + 56 = 75<br>S: 19 + 43 = 62 | S: 20 + 26 = 46<br>S: 20 + 18 = 38 | I: 19 + 10 = 29 |
| Anti-CD40 | A/S: 10 + 33 = 43 | I: 12 + 56 = 68<br>I: 12 + 43 = 55 | I: 13 + 26 = 39<br>A: 13 + 18 = 31 | I: 14 + 10 = 24 |
| Anti-CD70 | A: 9 + 33 = 42 | I: 12 + 56 = 68<br>I: 12 + 43 = 55 | I: 15 + 26 = 41<br>I: 15 + 18 = 33 | I: 10 + 10 = 20 |
| Anti-CD72 | NA | I: 16 + 56 = 72<br>A: 16 + 43 = 59 | S: 30 + 26 = 56<br>S: 30 + 18 = 48 | I: 17 + 10 = 27 |
| Anti-CD79a | S: 21+ 33 = 54 | I: 43 + 56 = 99<br>I: 43 + 43 = 86 | A: 28 + 26 = 54<br>A: 28 + 18 = 46 | I: 14 + 10 = 24 |
| Anti-CD79b | S: 46 + 33 = 79 | NA | S: 45 + 26 = 71<br>S: 45 + 18 = 63 | I: 26 + 10 = 36 |
| Anti-CD80 | A: 7 + 33 = 40 | I: 14 + 56 = 70<br>I: 14 + 43 = 57 | I: 15 + 26 = 41<br>I: 15 + 18 = 33 | I: 11 + 10 = 21 |
| Anti-CD81 | S: 14 + 33 = 47 | A: 25 + 56 = 81<br>S: 25 + 43 = 68 | A: 25 + 26 = 51<br>A: 25 + 18 = 43 | I: 19 + 10 = 29 |
| Anti-CD86 | A: 7 + 33 = 40 | I: 16 + 56 = 72<br>I: 16 + 43 = 59 | I: 15 + 26 = 41<br>I: 15 + 18 = 33 | I: 14 + 11 = 25 |
| Anti- CL II | I: 53 + 33 = 86 | A: 52 + 56 = 108<br>A: 52 + 43 = 95 | NA | I: 72 + 10 = 82 |

"A" means an "additive" effect was observed
"S" means a "synergistic" effect was observed
"I" means an "inhibitory" effect was observed
*Equation schematic: A + B = C, where "A" is the percent ANN and/or PI positive cells due to matrix antibody alone, "B" is the percent ANN and/or PI positive cells due to the common antibody (anti-CD20 for FIG. 20, anti-CD79b for FIG. 21, anti-CLII for FIG. 22, and anti-CD22 for FIG. 23), and "C" is the expected additive effect. (See Table 7, above, for the quantitative data corresponding to FIGS. 20-23.) Where two equations are present in a cell, the upper equation reflects results use of the higher indicated concentration of common antibody; the lower equation reflects use of the lower indicated concentration of common antibody.

tispecific, multivalent binding molecule comprising an anti-CD22 binding domain, will protect against, or mitigate an effect of, any of the antibodies listed immediately above. More generally, a multispecific, multivalent binding molecule comprising an anti-CD22 binding domain will inhibit the effect arising from interaction with any of CD19, CD20, CD21, CD23, CD30, CD37, CD40, CD70, CD72, CD 79a, CD79b, CD80, CD81, CD86, and MHC class II molecules. It can be seen in FIG. 23 and Table 8 that anti-CD22 antibody, and by extension a binding domain comprising an anti-CD22 binding domain, will function as an inhibitor or mitigator of the activity of any antibody/binding domain recognizing a B-cell surface marker such as a CD antigen. Multivalent binding molecules, including multispecific, multivalent binding molecules, are expected to be useful in refining treatment regimens for a variety of diseases wherein the activity of a binding domain needs to be attenuated or controlled.

In addition to the inhibitory, additive or synergistic combined effect of two binding domains interacting with a target cell, typically through the binding of cell-surface ligands, the experimental results disclosed herein establish that a given pair of binding domains may provide a different type of combined effect depending on the relative concentrations of the two binding domains, thereby increasing the versatility of the invention. For example, Table 8 discloses that anti-CD21 and anti-CD79b interact in an inhibitory manner at the higher tested concentration of anti-CD79b, but these two antibodies interact in a synergistic manner at the lower tested concentration of anti-CD79b. Although some embodiments will use a single type of multivalent binding molecule, i.e., a monospecific, multivalent binding molecule, comprising, e.g., a single CD21 binding domain and a single CD79b binding domain, the invention comprehends mixtures of multivalent binding molecules that will allow adjustments of relative binding domain concentrations to achieve a desired effect, such as an inhibitory, additive or synergistic effect. Moreover, the methods of the invention encompass use of a single multivalent binding molecule in combination with another binding molecule, such as a conventional antibody molecule, to adjust or optimize the relative concentrations of binding domains. Those of skill in the art will be able to determine useful relative concentrations of binding domains using standard techniques (e.g., by designing experimental matrices of two dilution series, one for each binding domain).

Without wishing to be bound by theory, it is recognized that the binding of one ligand may induce or modulate the surface appearance of a second ligand on the same cell type, or it may alter the surface context of the second ligand so as to alter its sensitivity to binding by a specific binding molecule such as an antibody or a multivalent binding molecule.

Although exemplified herein using B cell lines and antigens, these methods to determine optimally effective multivalent binding molecules (i.e., scorpions) are applicable to other disease settings and target cell populations, including other normal cells, their aberrant cell counterparts including chronically stimulated hematopoietic cells, carcinoma cells and infected cells.

Other signaling phenotypes such as $Ca^{2+}$ mobilization; tyrosine phosphoregulation; caspase activation; NF-κB activation; cytokine, growth factor or chemokine elaboration; or gene expression (e.g., in reporter systems) are also amenable to use in methods of screening for the direct effects of monoclonal antibody combinations.

As an alternative to using a secondary antibody to cross-link the primary antibodies and mimic the multivalent binding molecule or scorpion structure, other molecules that bind the Fc portion of antibodies, including soluble Fc receptors, protein A, complement components including C1q, mannose binding lectin, beads or matrices containing reactive or cross-linking agents, bifunctional chemical cross-linking agents, and adsorption to plastic, could be used to cross-link multiple monoclonal antibodies against the same or different antigens.

EXAMPLE 12

Multivalent Binding Protein with Effector Function, or Scorpion, Structures

The general schematic structure of a scorpion polypeptide is H2N-binding domain 1-scorpion linker-constant sub-region-binding domain 2. scorpions may also have a hinge-like region, typically a peptide region derived from an antibody hinge, disposed N-terminal to binding domain 1. In some scorpion embodiments, binding domain 1 and binding domain 2 are each derived from an immunoglobulin binding domain, e.g., derived from a $V_L$ and a $V_H$. The $V_L$ and a $V_H$ are typically joined by a linker. Experiments have been conducted to demonstrate that scorpion polypeptides may have binding domains that differ from an immunoglobulin binding domain, including an Ig binding domain from which the scorpion binding domain was derived, by amino acid sequence differences that result in a sequence divergence of typically less than 5%, and preferably less than 1%, relative to the source Ig binding domain.

Frequently, the sequence differences result in single amino acid changes, such as substitutions. A preferred location for such amino acid changes is in one or more regions of a scorpion binding domain that correspond, or exhibit at least 80% and preferably 85% or 90%, sequence identity to an Ig complementarity determining region (CDR) of an Ig binding domain from which the scorpion binding domain was derived. Further guidance is provided by comparing models of peptides binding the same target, such as CD20. With respect to CD20, epitope mapping has revealed that the 2H7 antibody, which binds CD20, recognizes the Ala-Asn-Pro-Ser (ANPS) motif of CD20 and it is expected that CD20-binding scorpions will also recognize this motif. Amino acid sequence changes that result in the ANPS motif being deeply embedded in a pocket formed of scorpion binding domain regions corresponding to Ig CDRs are expected to be functional binders of CD20. Modeling studies have also revealed that scorpion regions corresponding to CDR3 ($V_L$), CDR1-3 ($V_H$) contact CD20 and changes that maintain or facilitate these contacts are expected to yield scorpions that bind CD20.

In addition to facilitating interaction of a scorpion with its target, changes to the sequences of scorpion binding domains (relative to cognate Ig binding domain sequences) that promote interaction between scorpion binding domain regions that correspond to Ig $V_L$ and $V_H$ domains are contemplated. For example, in a CD20-binding scorpion region corresponding to $V_L$, the sequence SYIV may be changed by substituting an amino acid for Val (V33), such as His, resulting in the sequence SYIH. This change is expected to improve interaction between scorpion regions corresponding to $V_L$ and $V_H$ domains. Further, it is expected that the addition of a residue at the N-terminus of a scorpion region corresponding to $V_H$-CDR3 will alter the orientation of that scorpion region, likely affecting its binding characteristics, because the N-terminal Ser of $V_H$-CDR3 makes contact with CD20. Routine assays will reveal those orientations that produce desirable changes in binding characteristics. It is also contemplated that mutations in scorpion regions corresponding to $V_H$-CDR2 and/or $V_H$-CDR3 will create potential new contacts with a target, such as CD20. For example, based on modeling studies, it is expected that substitutions of either Y105 and W106 (found in the sequence NSYW) in a region corresponding to $V_H$-CDR3 will alter the binding characteristics of a scorpion in a manner amenable to routine assay for identifying scorpions with modified binding characteristics. By way of additional example, it is expected that an alteration in the sequence of a CDR3Y105D. Due to expected synergistic effects of combining some of theses mutations, 11 mutants were designed, combining different mutations as shown in Table 9 (residues introduced by mutation are bolded and underscored).

TABLE 9

| V$_L$ CDR1 | V$_L$ CDR3 | V$_H$ CDR2 | V$_H$ CDR3 |
|---|---|---|---|
| RASSSVSYIH | QQWSFNPPT | AIYPGNGDTSYNQK-FKG | SVYYSNYWYFDL |
| (SEQ ID NO: 332) | (SEQ ID NO: 334) | (SEQ ID NO: 336) | (SEQ ID NO: 338) |
| RASSSVSYIH | QQWSFNPPT | AIYPGNGDTSYNQK-FKG | SVYYGGYWYFDL |
| (SEQ ID NO: 332) | (SEQ ID NO: 334) | (SEQ ID NO: 336) | (SEQ ID NO: 339) |
| RASSSVSYIH | QQWSFNPPT | AIYPGNGDTSYNQK-FKG | SYYSNSDWYFDL |
| (SEQ ID NO: 332) | (SEQ ID NO: 334) | (SEQ ID NO: 336) | (SEQ ID NO: 340) |
| RASSSVSYIH | QQWSFNPPT | AIYPGNGDTSYNQK-FKG | SYYSGGDWYFDL |
| (SEQ ID NO: 332) | (SEQ ID NO: 334) | (SEQ ID NO: 336) | (SEQ ID NO: 341) |
| RASSSVSYIV | QQWSFNPPT | AIYPGNGDTSYNQK-FKG | SYKSNSYWYFDL |
| (SEQ ID NO: 333) | (SEQ ID NO: 334) | (SEQ ID NO: 336) | (SEQ ID NO: 342) |
| RASSSVSYIV | QQWSFNPPT | AIYPGNGETSYNQKFKG | SYYSNSYWYFDL |
| (SEQ ID NO: 333) | (SEQ ID NO: 334) | (SEQ ID NO: 337) | (SEQ ID NO: 343) |
| RASSSVSYIV | QQYSFNPPT | AIYPGNGDTSYNQK-FKG | SYYSNSYWYFDL |
| (SEQ ID NO: 333) | (SEQ ID NO: 335) | (SEQ ID NO: 336) | (SEQ ID NO: 343) |
| RASSSVSYIH | QQWSFNPPT | AIYPGNGDTSYNQK-FKG | SYKSNSDWYFDL |
| (SEQ ID NO: 332) | (SEQ ID NO: 334) | (SEQ ID NO: 336) | (SEQ ID NO: 344) |
| RASSSVSYIH | QQWSFNPPT | AIYPGNGETSYNQKFKG | SYYSNSDWYFDL |
| (SEQ ID NO: 332) | (SEQ ID NO: 334) | (SEQ ID NO: 337) | (SEQ ID NO: 340) |
| RASSSVSYIH | QQYSFNPPT | AIYPGNGDTSYNQK-FKG | SYYSNSDWYFDL |
| (SEQ ID NO: 332) | (SEQ ID NO: 335) | (SEQ ID NO: 336) | (SEQ ID NO: 340) |
| RASSSVSYIH | QQYSFNPPT | AIYPGNGETSYNQKFKG | SYKSGGDWYFDL |
| (SEQ ID NO: 332) | (SEQ ID NO: 335) | (SEQ ID NO: 337) | (SEQ ID NO: 345) | scorpion binding domain corresponding to an Ig VL-CDR3, such as the Trp (W) in the sequence CQQW, will affect binding. Typically, alterations in a scorpion region corresponding to an Ig CDR will be screened for those scorpions exhibiting an increase in affinity for the target.

Based on the model structure of the humanized CD20 scFv binding domain 20-4, on the published information relating to the CD20 extracellular loop structure (Du, et al., J Biol. Chem. 282(20):15073-80 (2007)), and on the CD20 binding epitope recognized by the mouse 2H7 antibody (which was the source of CDRs for the humanized 20-4 scFv binding domain), mutations were engineered in the CDR regions of the 2Lm20-4×2Lm20-4 scorpion with the aim of improving the affinity of its binding to CD20. First, the mutations were design to influence the 20-4 CDR conformation and to promote more efficient binding to the CD20 extracellular loop. Second, the introduced changes were designed to provide new intermolecular interactions between the 2Lm20-4×2Lm20-4 scorpion and its target. These mutations include: VL CDR1V33H i.e., a substitution of His for Val at position 33 of CDR1 in the VL region), VL CDR3W90Y, VH CDR2D57E, VH CDR3 insertion of V after residue S99, VH CDR3Y101K, VH CDR3N103G, VH CDR3N104G, and VH Mutations were introduced into binding domains of the CD20×CD20 scorpion (2Lm20-4×2Lm20-4) by PCR mutagenesis using primers encoding the altered sequence region. After sequence confirmation, DNA fragments encoding the 2Lm20-4 scFv fragments with corresponding mutations were cloned into a conventional expression vector containing a coding region for the constant sub-region of a scorpion, resulting in a polynucleotide containing the complete DNA sequence of new versions of the 2Lm20-4×2Lm20-4 scorpion. The variants of the 2Lm20-4×2Lm20-4 scorpion with CDR mutations were produced by expression in a transient COS cell system and purified through Protein A and size-exclusion (SEC) chromatography. The binding properties of 2Lm20-4×2Lm20-4 scorpion variants were evaluated by FACS analysis using primary B-cells and the WIL2-S B-lymphoma cell line.

Other mutants have also been generated using a similar approach to optimize CD20 binding domains. The CD20 SMIP designated TRU015 served as a substrate for generating mutants and, unless noted to the contrary, all domains were human domains. The following mutants were found to contain useful and functional CD20 binding domains. The 018008 molecule contained a substitution of Q (single-letter amino acid code) for S at position 27 of CDR1 in VL, a substitution of S for T at position 28 in CDR1 of VH and a substitution of L for V at position 102 in CDR3 of VH. The following partial scorpion linker sequences, corresponding to the CCCP sequence in an IgG1 hinge, were separately combined with the mutated VL and VH: CSCS, SCCS and SCCP, consistent with the modular design of scorpions. The 018009 molecule contained a substitution of Q for S at position 27 of CDR1 of VL, a substitution of S for T at position 28 of CDR1 of VH and substitutions of S for V at position 96, L for V at position 102 and deletion of the V at position 95, all in CDR3 of VH. The same scorpion linkers sub-sequences described above as being found in the scorpion linkers used in 018008 were used in 018009. The 018010 molecule contained substitutions of a Q for S at position 27, an I for M at position 33 and a V for H at position 34, all in CDR1 of VL, along with an S for T substitution at position 28 of CDR1 of VH and an L for V substitution at position 102 in CDR3 of VH. Scorpion linkers defined by the CSCS and SCCS sub-sequences were used with 018010. 018011 contained the same mutations in CDR1 of VL and in CDR1 of VH as described for 018010, along with deletion of V at position 95, substitution of S for V at position 96 and substitution of L for V at postion 102, all in CDR3 of VH. Scorpion linkers defined by the CSCS, SCCS and SCCP sub-sequences were used in 018011 molecules. The 018014 VL was an unmutated mouse VL, with a human VH containing the S for T change at 28 in CDR1 and the L for V change at 102 in CDR3. 018015 also contained an unmutated mouse VL along with a human VH containing an S for T change at 28 of CDR1 and, in CDR3, a deletion of V at 95, substitution of S for V at 96, and substitution of L for V at 102. The 2Lm5 molecule had a Q for S at 27 in CDR1 of VL, an F for Y at 27 and an S for T at 30, both in CDR1 of VH, as well as deletion of the V at 95, S for V at 96 and L for V at 102, all in CDR3 of VH. Scorpion linkers defined by the CSCS, SCCS and SCCP were separately used in each of 018014 and 018015. 2Lm5-1 was the same as 2Lm5 except 2Lm5-1 had no mutations in CDR1 of VH, and only a scorpion linker defined by the CSSS sub-sequence was used. 2Lm6-1 had the mutations of 2Lm5 and a substitution of T for S at 92 and S for F at 93 in CDR3 of VL, and only the scorpion linker defined by the CSSS sub-sequence was used. The only mutations in 2Lm16 were the mutations in CDR3 of VH listed above for 2Lm5-1. Scorpion linkers defined by the sub-sequences CSCS, SCCS, and SCCP were separately used in 2Lm16. 2Lm16-1 substituted Q for S at 27 in CDR1 of VL and substituted T for S at 92, and S for F at 93, both in CDR3 of VL, and, in CDR3 of VH, deleted V at 95, substituted S for V at 96 and substituted L for V at 102; only the scorpion linker defined by the CSSS sub-sequence was used. 2Lm19-3 substituted Q for S at 27, I for M at 33, and V for H at 34, all in CDR1 of VL, along with the mutations in CDR3 of VH listed for 2Lm16-1. Scorpion linkers defined by the sub-sequences CSCS, SCCS, and SCCP were separately used in 2Lm19-3. The 2Lm20-4 molecule contained an I for M at 33 and a V for H at 34, both in CDR1 of VL, along with the mutations in CDR3 of VH listed for 2Lm16-1. For 2Lm5-1, 2Lm6-1, 2Lm16, 2Lm16-1, 2Lm19-3, and 2Lm20-4, there also was an S for L substitution at position 11 in the framework region of VH. Scorpion linkers defined by the CSCS, SCCS and SCCP sub-sequences were separately used in 2Lm20-4. Finally, the substitution of S for P at position 331 was present in the following mutants: 018008 with the scorpion linker defined by CSCS, 018009 with each of scorpion linkers defined by CSCS and SCCP, 018010 with the scorpion linker defined by CSCS, 018011 with the scorpion linker defined by SCCP, 018014 with the scorpion linker defined by CSCS, 018015 with the scorpion linker defined by CSCS, 2Lm16 with scorpion linkers defined by any of CSCS, SCCS, and SCCP, 2Lm19-3 with a scorpion linker defined by CSCS or SCCP, and 2Lm20-4 with a scorpion linker defined by CSCS or SCCP.

In addition, changes in the length of a linker joining two regions of a binding domain, such as regions of a scorpion binding domain that correspond to an Ig $V_L$ and $V_H$, are contemplated. For example, removal of a C-terminal Asp in interdomain linkers where it is found is expected to affect the binding characteristics of a scorpion, as is a substitution of Gly for Asp.

Also contemplated are scorpions that have a scorpion linker (interposed C-terminal to the constant sub-region and N-terminal to binding domain 2) that is lengthened relative to a hinge region of an Ig, with amino acid residues being added C-terminal to any cysteine in the scorpion that corresponds to an Ig hinge cysteine, with the scorpion cysteine being capable of forming an interchain disulfide bond. Scorpions containing these features have been constructed and are characterized below.

Efforts were undertaken to improve the expression, stability and therapeutic potency of scorpions through the optimization of the scorpion linker covalently joining the constant sub-region and the C-terminally disposed binding domain 2. The prototypical scorpion used for optimization studies contained an anti-CD20 scFV (binding domain 1) fused N-terminal to the constant sub-region derived from IgG1 $C_{H2}$ and $C_{H3}$, with a second anti-CD20 scFv fused C-terminal to that constant sub-region. This scorpion, like immunoglobulin molecules, is expected to associate through the constant region (or sub-region) to form a homodimeric complex with peptide chains linked by disulfide bonds. To obtain high level of expression of a stable, tetravalent molecule with high affinity for its CD20 target, the scorpion linker between the constant sub-region and the second binding domain must accommodate the following considerations. First, steric hindrance between the homologous binding domains carried by the two scFv fragments (one scFv fragment on each of two scorpion monomers) should be minimized to facilitate maintenance of the native conformations of each binding domain. Second, the configurations and orientations of binding domains should allow productive association of domains and high-affinity binding of each binding domain to its target. Third, the scorpion linker itself should be relatively protease-resistant and non-immunogenic.

In the exemplary CD20×CD20 scorpion construct S0129, the C-terminus of $C_{H3}$ and the second anti-CD20 scFV domain were linked by the 2H7 scorpion linker, a peptide derived from, and corresponding to, a fragment of a natural human hinge sequence of IgG1. The 2H7 scorpion linker served as a base for design efforts using computer-assisted modeling that were aimed at improving the expression of scorpions and improving the binding characteristics of the expressed molecules.

To analyze the 2H7 scorpion linker, the 3-dimensional structure of a dimeric form of the human IgG1 hinge was modeled using Insight II software. The crystal structure of anti-CD20 scFV in the $V_H$-$V_L$ orientation was chosen as a reference structure for the 20-4 binding domains (RCSB Protein Data Bank entry code: 1A14). In intact IgG1, the hinge connects the C-terminus of the $C_{H1}$ domain to the N-terminus of the $C_{H2}$ domain, with the configuration of each domain being such that hinge cysteine residues can pair to form a homodimer. In the exemplary scorpion molecule, the hinge-derived 2H7 linker connected the C-terminal end of the scorpion domain derived from the IgG1 $C_{H3}$ domain to the N-terminal end of that portion of scorpion binding domain 2 derived from an IgG1 $V_{H2}$ domain. Using a 3-D modeled structure of the $V_H$-$V_L$ scFV, expectations of the optimal distance between the C-terminal ends of the 2H7 linkers was influenced by three considerations. First, hinge stability must be maintained, and stability is aided by dimerization, e.g., homodimerization, which means that the hinge cysteines must be able to pair in the presence of the two folded binding domains. Second, two binding domains, e.g., scFVs, must accommodate the 2H7 linker C-termini without steric interference in order to allow for proper protein folding. Third, the CDRs of each binding domain should be able to face the same direction, as in a native antibody, because each binding domain of the prototypical scorpion can bind adjacent receptors (CD20) on the same cell surface. Given these considerations, the distance between the two N-terminal ends of scFvs is expected to be approximately 28 Å. The distance between the C-terminal ends of the theoretically designed 2H7 linkers in dimeric scorpion forms is expected to be about 16 Å. To accommodate the distances expected to be needed for optimizing the performance of a scorpion, the C-terminus of the 2H7 linker was extended by at least 3 amino acids. Such an extension is expected to allow for the formation of disulfide bonds between 2H7 linker cysteine residues, to allow for proper folding of the C-terminal binding domain 2, and to facilitate a correct orientation of the CDRs. In addition, in intact IgG1, due to the presence of the $C_{H1}$ and $V_{L1}$ domains between the hinge and binding domains, the distance between the binding domains carried by the two chains is further increased and is expected to further favor the cross-linking of adjacent receptors on the same cell surface. In view of the considerations described above, a set of linkers with different lengths was designed (Table 10). To minimize immunogenicity, natural residues present at the N-terminal end of the $C_{H2}$ domain (Ala-Pro-Glu-Leu or APEL) were used to lengthen the 2H7 scorpion linker by sequence addition to the C-terminus of the scorpion linker. The longer constructs contained one or multiple (Gly4Ser) linker units known to be protease-resistant and flexible.

The CD20×CD20 scorpion constructs containing extended scorpion linkers between the $C_{H3}$ domain of the constant sub-region and the C-terminal scFv binding domain were constructed using PCR mutagenesis and subcloned into a conventional mammalian expression vector. The effect of linker length on CD20×CD20 scorpion expression could be analyzed be comparing the yield of secreted protein in transient expression experiments using COS or HEK293 cells, or by analysis of protein synthesis and accumulation in the cells by Western blot analyses or pulse-chase studies with $^{35}$S-labeled methionine/cysteine.

TABLE 10

| Construct Number | Scorpion linker core (2H7) sequence | Extension sequence | Extended scorpion linker sequence |
|---|---|---|---|
| 1 | GCPPCPNS (SEQ ID NO: 346) | APEL (SEQ ID NO: 347) | GCPPCPNSAPEL (SEQ ID NO: 351) |
| 2 | GCPPCPNS (SEQ ID NO: 346) | APELGGGGS (SEQ ID NO: 348) | GCPPCPNSAPELGGGGS (SEQ ID NO: 352) |
| 3 | GCPPCPNS (SEQ ID NO: 346) | APELGGGGSGGGGS (SEQ ID NO: 349) | GCPPCPNSAPELGGGGSGGGGS (SEQ ID NO: 353) |
| 4 | GCPPCPNS (SEQ ID NO: 346) | APELGGGGSGGGGSGGGGS (SEQ ID NO: 350) | GCPPCPNSAPELGGGGSGGGGSGGGGS (SEQ ID NO: 354) |

Glycosylated scorpions are also contemplated and, in this context, it is contemplated that host cells expressing a scorpion may be cultured in the presence of a carbohydrate modifier, which is defined herein as a small organic compound, preferably of molecular weight less than 1000 daltons, that inhibits the activity of an enzyme involved in the addition, removal, or modification of sugars that are part of a carbohydrate attached to a polypeptide, such as occurs during N-linked carbohydrate maturation of a protein. Glycosylation is a complex process that takes place in the endoplasmic reticulum ("core glycosylation") and in the Golgi bodies ("terminal glycosylation"). A variety of glycosidase and/or mannosidase inhibitors provide one or more of desired effects of increasing ADCC activity, increasing Fc receptor binding, and altering glycosylation pattern. Exemplary inhibitors include, but are not limited to, castanospermine and kifunensine. The effects of expressing scorpions in the presence of at least one such inhibitor are disclosed in the following example.

EXAMPLE 13

Scorpion Protein Expression Levels and Characterization

Scorpion protein expression levels were determined and the expressed proteins were characterized to demonstrate that the protein design led to products having practical benefits. A monospecific CD20×CD20 scorpion and a bispecific CD20×CD37 scorpion were expressed in CHO DG44 cells in culture using conventional techniques.

Basal level, stable expression of the CD20×CD20 scorpion S0129 (21 m20-4×21 m20-4) in CHO DG44 cells cultured in the presence of various feed supplements was observed as shown in FIG. 34. All culture media contained 50 nM methotrexate, a concentration that maintained copy number of the scorpion-encoding polynucleotide. The polynucleotide contained a coding region for the scorpion protein that was not codon-optimized for expression in CHO DG44 cells. The polynucleotide was introduced into cells using the pD18 vector Apparent from FIG. 34, expression levels of about 7-46 μg/ml were obtained. Expression levels following amplification of the polynucleotide encoding a bispecific CD20×CD37 scorpion were also determined. The pD18 vector was used to clone the CD20×CD37 scorpion coding region and the plasmid was introduced into CHO DG44 cells. Amplification of the encoding polynucleotide was achieved using the dhfr-methotrexate technique known in the art, where increasing concentrations of MTX are used to select for increased copy number of the Dihydrofolate Reductase gene (dhfr), which leads to co-amplification of the tightly linked polynucleotide of interest. FIG. 35 shows that stable expression levels of about 22-118 μg/ml of the bispecific CD20×CD37 scorpion were typically observed. Variability in yield was seen under different conditions, including methotrexate concentration used for amplification, but these variables are amenable to optimization by those of skill in the art. A variety of other scorpion molecules described herein were also subjected to expression analyses in CHO and/or COS cells, with the results provided in Table 11, below. These results demonstrate that significant yields of scorpion proteins can be obtained using conventional techniques and routine optimization of the amplification technique.

Figure 36:
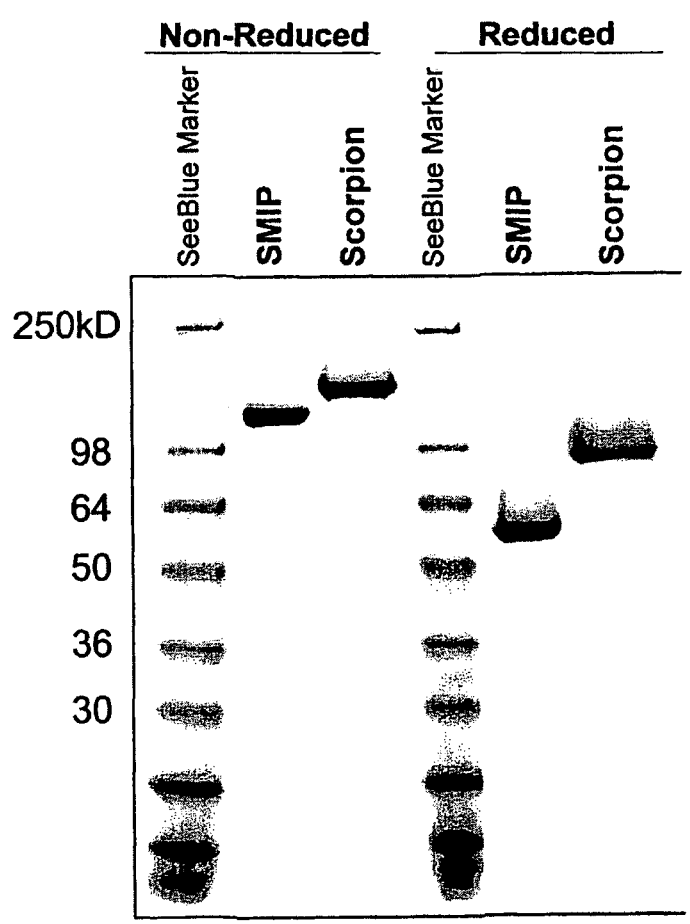
FIG. 36 presents SDS-PAGE gels (under reducing and non-reducing conditions) of a SMIP and a scorpion.

Expressed proteins were also characterized by SDS-PAGE analysis to assess the degrees of homogeneity and integrity of the expressed proteins and to confirm molecular weight of monomeric peptides. The denaturing polyacrylamide gels (4-20% Tris Glycine) were run under reducing and non-reducing conditions. The results presented in FIG. 36 reveal single protein bands for each of a 2Lm20-4 SCC SMIP and S1000 (CD20(21 m20-4)×CD20(21 m20-4) monospecific scorpion. S0126) of the expected monomeric molecular weights under reducing conditions. These data establish that SMIPs and scorpions are amenable to purification in an intact form. Under non-reducing conditions, a trace amount of a peptide consistent with the expected size of a monomeric SMIP was seen, with the vast majority of the protein appearing in a single well-defined band consistent with a dimeric structure. Under these non-reducing conditions, the monospecific scorpion protein showed a single well-defined band of a molecular weight consistent with a dimeric structure. The dimeric structures for both the SMIP and the scorpion are consistent with their monomeric structures, each of which contains a hinge-like scorpion linker containing at least one Cysteine capable of participating in disulfide bond formation.

The effect of scorpion linkers on the expression and integrity of scorpions was also assessed, and results are shown in Table 12. This table lists scorpion linker variants of the monospecific CD20×CD20 (2Lm20-4×2Lm20-4) S0129 scorpion and the CD20×CD28 S0033 scorpion (2H7sccpIgG1-H7-2e12), their integrity as single chain molecules, and their transient expression levels in COS cells relative to the parent scorpion S0129 or S0033, as appropriate, with an H7 linker (set as 100%). Table 13 provides data resulting from an evaluation of scorpion linker variants incorporated into the CD20×CD20 scorpion, along with analogous data for the CD20×CD28 scorpion. Table 13 provides data resulting from an evaluation of S0129 variants containing scorpion linkers that are not hinge-like linkers containing at least one Cysteine capable of disulfide bond formation; rather, the scorpion linkers in these molecules are derived from Type II C-lectin stalks. Apparent from the data presented in Table 13 is that hinge-like scorpion linkers may be associated with scorpions expressed at higher or lower levels than an unmodified parent scorpion linker in transient expression assays. Further, some of the linker variants exhibit greater resistance to proteolytic cleavage than the unmodified parent linker, a concern for all or almost all expressed proteins. The data of Table 13 show that non-hinge-like linkers such as linkers derived from the stalk region of Type II C-lectins are found in scorpions that exhibit binding characteristics that vary slightly from scorpions containing hinge-like scorpion linkers. Additionally, the scorpion containing a non-hinge-like scorpion linker exhibits effector function (ADCC) that either equals or exceeds the ADCC associated with scorpions having hinge-like scorpion linkers.

TABLE 11

| Linker Name | Upstream (CH3) Sequence | S0129 (2Lm20-4 × 2Lm20-4) linker variants-aa seq[1] | based on | # AAs | Expression COS[2] | Cleavage[3] | Expression CHO[2] |
|---|---|---|---|---|---|---|---|
| H7 | QKSLSLSPGK | GCPPCPNS | H7 | 18 | 100 | – | 100 |
| H16 | QKSLSLSPGK | LSVKADFLTPSIGNS | CD80 | 25 | 174 | + | |
| H18 | QKSLSLSPGK | LSVLANFSQPEIGNS | CD86 | 25 | 165 | ++ | |
| H19 | QKSLSLSPGK | LSVLANFSQPEISCPPCPNS | CD86 + H7 | 30 | 161 | + | 108 |
| H26 | QKSLSLSPGK | RIHQMNSELSVLANS | CD86 | 25 | 170 | ++ | |
| H32 | QKSLSLSPGK | RIHLNVSERPFPPNS | CD22 | 25 | 184 | ++ | |
| H47 | QKSLSLSPG | LSVKADFLTPSIGNS | H16 | 24 | 141 | – | 206 |
| H48 | QKSLSLSPG | KADFLTPSIGNS | H16 | 21 | 137 | – | |
| H50 | Q | LSVLANFSQPEIGNS | H18 | 16 | 21 | – | |
| H51 | QKS | LSVLANFSQPEIGNS | H18 | 18 | 110 | – | |
| H52 | QKSLSLSPG | SQPEIVPISNS | H18 | 20 | 95 | – | |
| H53 | QKSLSL | SQPEIVPISCPPCPNS | H19 | 26 | 95 | – | |
| H54 | Q | SVLANFSQPEISCPPCPNS | H19 | 21 | 72 | +/– | |
| H55 | QKSLSLSPG | RIHQMNSELSVLANS | H26 | 24 | 118 | + | |
| H56 | QKSLSLSPG | QMNSELSVLANS | H26 | 21 | 130 | – | 163 |
| H57 | QKSLSLSPG | VSERPFPPNS | H32 | 19 | 118 | – | |

TABLE 11-continued

| Linker Name | Upstream (CH3) Sequence | S0129 (2Lm20-4 x 2Lm20-4) linker variants-aa seq[1] | based on | # AAs | Expression COS[2] | Cleavage[3] | Expression CHO[2] |
|---|---|---|---|---|---|---|---|
| H58 | QKSLSLSPG | KPFFTCGSADTCPNS | CD72 | 24 | 103 | − | |
| H59 | QKSLS | KPFFTCGSADTCPNS | CD72 | 20 | 94 | − | |

[1]NFS is a glycosylation consensus motif
[2]Transient expression in COS (6W plates), or CHO (single flask) relative to S0129-H7 (%)
[3]Cleavage product(s) observed by SDS-PAGE/silver stain: − = none, + = faint band, ++ = major band(s), +++ > 50% cleaved

TABLE 12

| Linker Name | S0129 (2Lm20-4 x 2Lm20-4) linker variants-aa seq | Changes in CH3?[1] | Linker seq. based on | 20 x 20 Expression[2] | 20 x 20 Cleavage[3] |
|---|---|---|---|---|---|
| H7 | GCPPCPNS | N | H7 | 100 | − |
| H8 | GSPPSPNS | N | H7 | 107 | + |
| H9 | GSPPSPNS | Y | H7 | 142 | − |
| H10 | EPKSTDKTHTCPPCPNS | N | IgG1 | 98 | − |
| H11 | EPKSTDKTHTSPPSPNS | N | IgG1 | 126 | + |
| H16 | LSVKADFLTPSIGNS | N | CD80 | 174 | + |
| H17 | LSVKADFLTPSISCPPCPNS | N | CD80 + H7 | 113 | + |
| H18 | LSVLANFSQPEIGNS | N | CD86 | 165 | ++ |
| H19 | LSVLANFSQPEISCPPCPNS | N | CD86 + H7 | 161 | + |
| H20 | LKIQERVSKPKISNS | N | CD2 | 115 | +++ |
| H21 | LKIQERVSKPKISCPPCPNS | N | CD2 + H7 | 90 | +++ |
| H22 | LNVSERPFPPHIQNS | N | CD22 | 149 | ++ |
| H23 | LDVSERPFPPHIQSCPPCPNS | N | CD22 + H7 | 121 | ++ |
| H24 | REQLAEVTLSLKANS | N | CD80 | 145 | ++ |
| H25 | REQLAEVTLSLKACPPCPNS | N | CD80 + H7 | 98 | + |
| H26 | RIHQMNSELSVLANS | N | CD86 | 170 | ++ |
| H27 | RIHQMNSELSVLACPPCPNS | N | CD86 + H7 | 154 | ++ |
| H28 | DTKGKNVLEKIFSNS | N | CD2 | 153 | + |
| H30 | LPPETQESQEVTLNS | N | CD22 | 78 | + |
| H32 | RIHLNVSERPFPPNS | N | CD22 | 184 | ++ |
| H33 | RIHLNVSERPFPPCPPCPNS | N | CD22 + H7 | 74 | + |
| H36 | GCPPCPGGGSNS | N | H7 | 110 | + |
| H40 | GCPPCPANS | Y | H7 | 110 | + |
| H41 | GCPPCPANS | Y | H7 | 102 | − |
| H42 | GCPPCPNS | Y | H7 | 99 | − |
| H44 | GGGASCPPCPGNS | Y | H7 | 108 | + |
| H45 | GGGASCPPCAGNS | Y | H7 | 107 | − |
| H46 | GGGASCPPCANS | Y | H7 | 98 | − |
| H47 | LSVKADFLTPSIGNS | Y | CD80 | 141 | − |
| H48 | ADFLTPSIGNS | N | CD80 | 137 | − |

TABLE 12-continued

| Linker Name | S0129 (2Lm20-4 × 2Lm20-4) linker variants-aa seq | Changes in CH3?[1] | Linker seq. based on | 20 × 20 Expression[2] | 20 × 20 Cleavage[3] |
|---|---|---|---|---|---|
| H50 | LSVLANFSQPEIGNS | Y | CD86 | 21 | - |
| H51 | LSVLANFSQPEIGNS | Y | CD86 | 110 | - |
| H52 | SQPEIVPISNS | Y | CD86 | 95 | - |
| H53 | SQPEIVPISCPPCPNS | Y | CD86 + H7 | 95 | - |
| H54 | SVLANFSQPEISCPPCPNS | Y | CD86 + H7 | 72 | +/- |
| H55 | RIHQMNSELSVLANS | Y | CD86 | 118 | + |
| H56 | QMNSELSVLANS | Y | CD86 | 130 | - |
| H57 | VSERPFPPNS | Y | CD22 | 118 | - |
| H58 | KPFFTCGSADTCPNS | Y | CD72 | 103 | - |
| H59 | KPFFTCGSADTCPNS | Y | CD72 | 94 | - |
| H60 | QYNCPGQYTFSMNS | Y | CD69 | >100[5] | - |
| H61 | EPAFTPGPNIELQKDSDCNS | Y | CD94 | >100 | - |
| H62 | QRHNNSSLNTRTQKARHCNS | Y | NKG2A | >100 | - |
| H63 | NSLFNQEVQIPLTESYCNS | Y | NKG2D | >100 | - |

[1]Additional changes to the end of CH3 such as 1-9 aa deletion and/or codon optimization
[2]Transient expression in COS (6W plates), relative to S0129-H7 parent (%)
[3]Cleavage product(s) observed by SDS-PAGE/silver stain: - = none, + = faint band, ++ = major band(s), +++>50% cleaved
[5]H60-H63 variants compared by estimation of recovery of protein purified from COS spent media.

TABLE 13

| Proteins | Description | Production Yield (ug protein purified/ml sup) | % POI (M. wt in Kd by MALS) | Improvement over S0129wt POI | Binding to Ramos | ADCC assay | Sequence of scorpion linker |
|---|---|---|---|---|---|---|---|
| S0129wt | H7 linker | 1.6 | 67 (167 ) | — | — | — | GCPPC |
| S0129-CD69 | CD69 stalk | 2.9 | 66 (167) | 1.8 | Weaker than S0129 wt | *Slightly better than S0129wt POI | QYNCPGQYTFSM |
| S0129-CD72 | CD72 truncated stalk | 2.0 | 69 (165) | 1.2 | Similar to S0129wt | *Slightly better than S0129wt POI | PFFTCGSADTC |
| S0129-CD94 | CD94 stalk | 2.9 | 67 (171) | 1.8 | Similar to S0129wt | *Slightly better than S0129wt POI | EPAFTPGPNIELQKDSDC |
| S0129-NKG2A | NKG2A stalk | 2.5 | 93 (170) | 2.2 | Slightly better than S0129wt | Similar to S0129wt POI | QRHNNSSLNTRTQKARHC |
| S0129-NKG2D | NKG2D stalk | 1.9 | 70 (166) | 1.2 | Similar to S0129wt | *Slightly better than S0129wt POI | NSLFNQEVQIPLTESYC |

As noted in the preceding example, production by expression of scorpions in cultures containing a carbohydrate modifier is contemplated. In exemplary embodiments, castanospermine (MW 189.21) is added to the culture medium to a final concentration of about 200 μM (corresponding to about 37.8 μg/mL), or concentration ranges greater than about 10, 20, 30, 40, 50, 60, 70, 80, 90, 100, 110, 120, 130, 140, or 150 μM, and up to about 300, 275, 250, 225, 200, 175, 150, 125, 100, 75, 60, or 50 μg/mL. For example, ranges of 10-50, or 50-200, or 50-300, or 100-300, or 150-250 μM are contemplated. In other exemplary embodiments, DMJ, for example DMJ-HCl (MW 199.6) is added to the culture medium to a final concentration of about 200 μM (corresponding to about 32.6 μg DMJ/mL), or concentration ranges greater than about 10, 20, 30, 40, 50, 60, 70, 80, 90, 100, 110, 120, 130, 140, or 150 μM, and up to about 300, 275, 250, 225, 200, 175, 150, 125, 100, 75, 60, or 50 μg/mL. For example, ranges of 10-50, or 50-200, or 50-300, or 100-300, or 150-250 μM are contemplated. In other exemplary embodiments, kifunensine (MW 232.2) is added to the culture medium to a final concentration of about 10 μM (corresponding to about 2.3 μg/mL), or concentration ranges greater than about 0.5, 1, 2, 3, 4, 5, 6, 7, 8, 9 or 10 μM, and up to about 50, 45, 40, 35, 30, 25, 20, 19, 18, 17, 16, 15, 14, 13, 12, or 11 μM. For example, ranges of 1-10, or 1-25, or 1-50, or 5-10, or 5-25, or 5-15 μM are contemplated.

Figure 42:
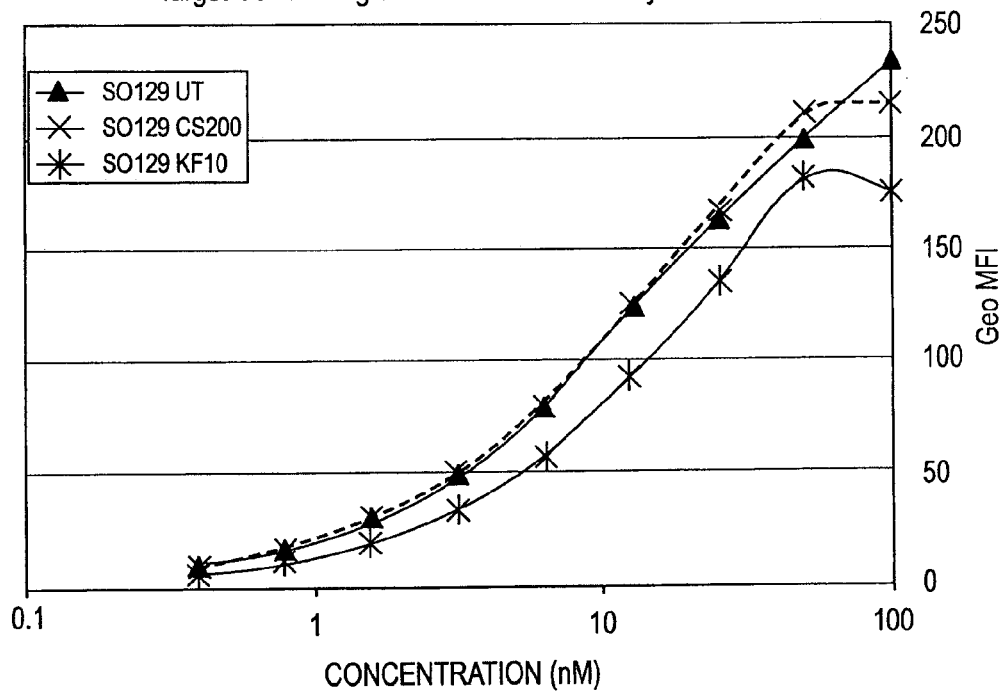
FIG. 42 shows target B-cell binding by a monospecific CD20×CD20 scorpion (S0129) and glycovariants.

In one experiment, a monospecific CD20×CD20 scorpion (S0129) was expressed in cells cultured in 200 μM castanospermine (S0129 CS200) or 10 μM (excess) kifunensine (S0129 KF 10) and the binding, or staining, of WIL2S cells by the expressed scorpion was measured, as shown in FIG. 42. In comparative binding studies, moreover, a glycosylated S0129 scorpion bound CD16 (FCγRIII) approximately three times better than the unglycosylated S0129 scorpion.

Figure 43:
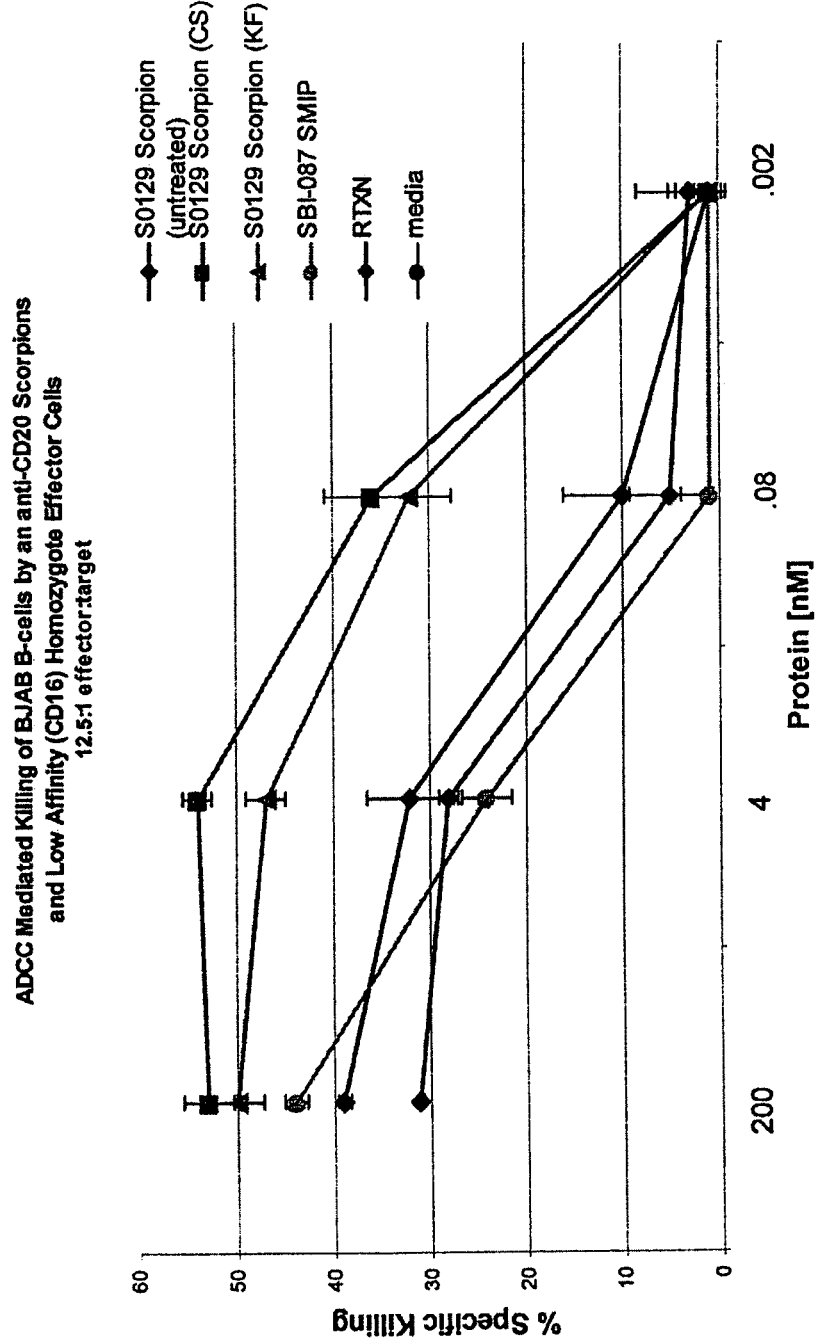
FIG. 43 provides graphs illustrating CD20×CD20 scorpions (parent and glycovariants) inducing ADCC-mediated killing of BJAB B-cells.

In another study, the ADCC-mediated killing of BJAB B-cells by humanized CD20×CD20 scorpion (S0129) was explored. The results shown in FIG. 43 establish that the scorpion, when expressed in cells being cultured in the presence of either castanospermine or kifunensine, led to significantly more potent ADCC-mediatd BJAB B-cell death for a given concentration of scorpion exposure.

EXAMPLE 14

Scorpion Binding
a. Domain Spacing

Bispecific scorpions are capable of binding at least two targets simultaneously, utilizing the pairs of binding domains at the N- and C-terminus of the molecule. In so doing, for cell-surface targets, the composition can cross-link or cause the physical co-approximation of the targets. It will be appreciated by those skilled in the art that many receptor systems are activated upon such cross-linking, resulting in signal induction causing changes in cellular phenotype. The design of the compositions disclosed herein was intended, in part, to maximize such signaling and to control the resultant phenotype.

Approximate dimensions of domains of the scorpion compositions, as well as expectations of interdomain flexibility in terms of ranges of interdomain angles, are known and were considered in designing the scorpion architecture. For scorpions using scFv binding domains for binding domains 1 and 2 (BD1 and BD2), an IgG1 N-terminal hinge (H1), and the H7 PIMS linker described herein, the binding domain at the N-terminus and the binding domain at the C-terminus may be maximally about 150-180A apart and minimally about 20-30A apart. Binding domains at the N-terminus may be maximally about 90-100A apart and minimally about 10-20A apart (Deisenhofer, et al., 1976, Hoppe-Seyler's Z. Physiol. Chem. Bd. 357, S. 435-445; Gregory, et al., 1987, Mol. Immunol. 24(8):821-9; Poljak, et al., 1973, Proc. Natl. Acad. Sci., 1973, 70: 3305-3310; Bongini, et al., 2004, Proc. Natl. Acad. Sci. 101: 6466-6471; Kienberger, et al., 2004, EMBO Reports, 5: 579-583, each incorporated herein by reference). The choice of these dimensions was done in part to allow for receptor-receptor distances of less than about 50 Å in receptor complexes bound by the scorpion as distances less than this may be optimal for maximal signaling of certain receptor oligomers (Paar, et al., 2002, J. Immunol., 169: 856-864, incorporated herein by reference) while allowing for the incorporation of $F_C$ structures required for effector function.

The binding domains at the N- and C-terminus of scorpions were designed to be flexible structures to facilitate target binding and to allow for a range of geometries of the bound targets. It will also be appreciated by those skilled in the art that flexibility between the N- or C-terminal binding domains (BD1 and BD2, respectively) and between the binding domains and the $F_C$ domain of the molecule, as well as the maximal and minimal distances between receptors bound by BD1 and/or BD2, can be modified, for example by choice of N-terminal hinge domain (H1) and, by structural analogy, the more C-terminally located scorpion linker domain (H2). For example hinge domains from IgG1, IgG2, IgG3, IgG4, IgE, IgA2, synthetic hinges and the hinge-like $C_{H2}$ domain of IgM show different degrees of flexibility, as well as different lengths. Those skilled in the art will understand that the optimal choice of H1 and scorpion linker (H2) will depend upon the receptor system(s) the scorpion is designed to interact with as well as the desired signaling phenotype induced by scorpion binding.

Figure 44:
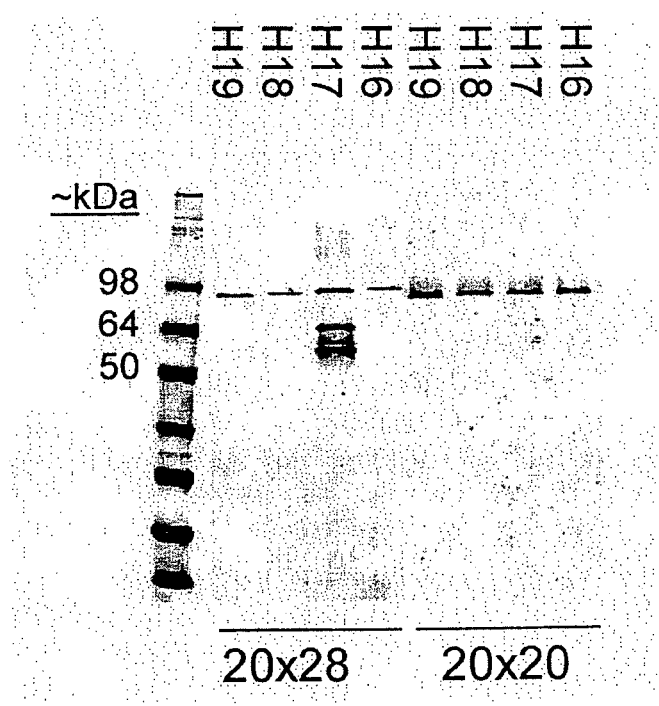
FIG. 44 shows a gel revealing the effects on scorpion stability arising from changes in the scorpion linker, including changing the sequence of that linker and extending the linker by adding an H7 sequence to the linker, indicated by a "+" in the H7 line under the gel.
Figure 45:
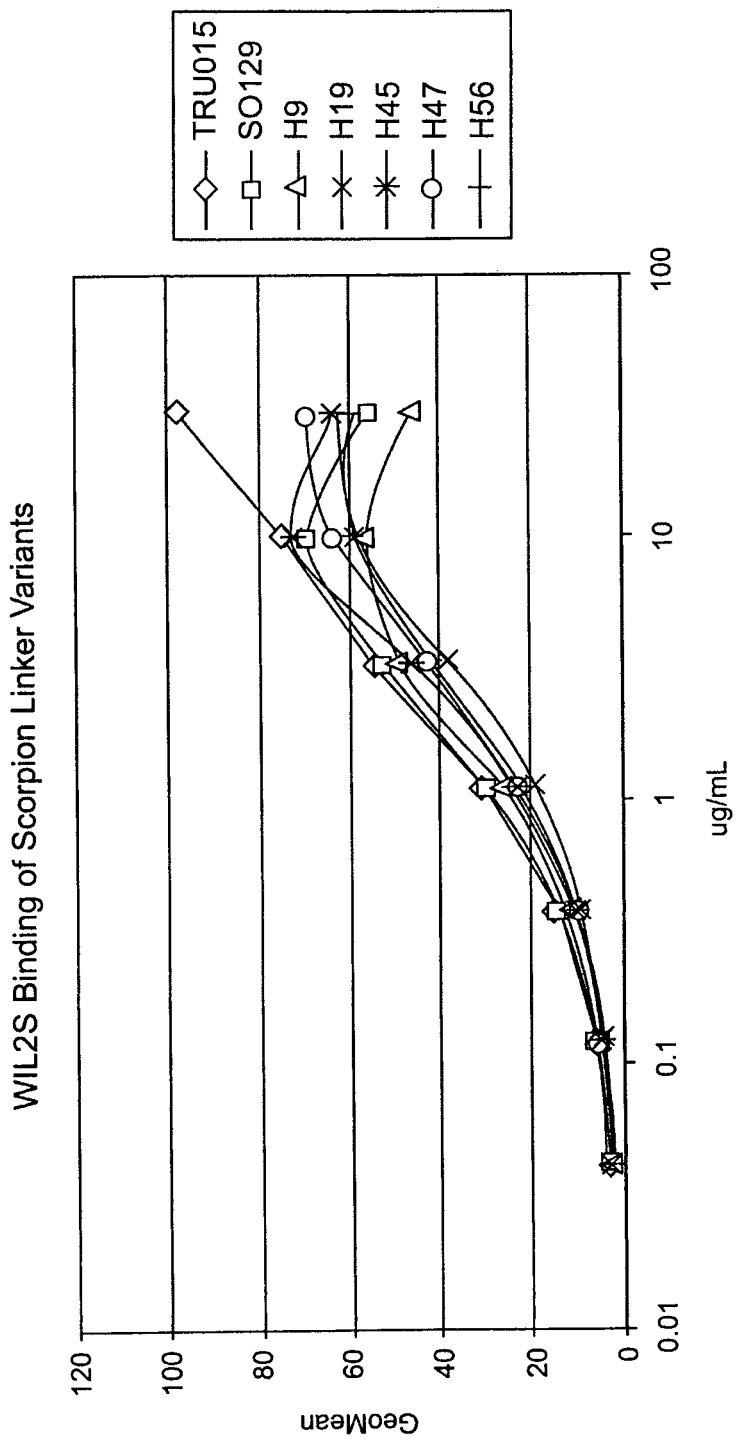
FIG. 45 shows the binding to WIL2S cells of a CD20×CD20 scorpion (S0129) and scorpion linker variants thereof.

In some embodiments, scorpions have a scorpion linker (H2) that is a hinge-like linker corresponding to an Ig hinge, such as an IgG1 hinge. These embodiments include scorpions having an amino acid sequence of the scorpion hinge that is an N-terminally extended sequence relative to, e.g., the H7 sequence or the wild-type IgG1 hinge sequence. Exemplary scorpion linkers of this type would have the sequence of the H7 hinge N-termanally extended by $H_2N\text{-}APEL(x)_y\text{-}CO_2H$, where x is a unit of the $Gly_4Ser$ linker and y is a number between 0 and 3. Exemplifying the influence of the scorpion linker on scorpion stability is a study done using two scorpions, a bispecific CD20×CD28 scorpion and a monospecific CD20×CD20 scorpion. For each of these two scorpion designs, a variety of scorpion linkers were inserted. In particular, scorpion linkers H16 and H17, which primarily differ in that H17 has the sequence of H16 with the sequence of H7 appended at the C-terminus, and scorpion linkers H18 and 19, in which analogously the sequence of H7 is appended at the C-terminus of H18 in generating H19. For each of the two scorpion backbones (20×28 and 20×20), each of the four above-described scorpion linkers were inserted at the appropriate location. Transient expression of these constructs was obtained in COS cells and the scorpion proteins found in the culture supernatants were purified on protein A/G-coated wells (Pierce SEIZE IP kit). Purified proteins were fractionated on SDS-PAGE gels and visualized by silver stain. Inspection of FIG. 44 reveals that the additional H7 sequence in the scorpion linker adds to the stability of each type of scorpion linker and each type of scorpion protein. In other words, appending H7 to the C-terminus of either H16 or H18 added to the stability of the scorpion molecule, and this observation held regardless of whether the scorpion was CD20×CD28 or CD20×CD20. In terms of target binding, the scorpion proteins having the CD20×CD20 architecture exhibited similar binding properties to the parent monospecific humanized CD20×CD20 scorpion S0129, as shown in FIG. 45.

Beyond the preceding embodiments, however, it may be desirable to prevent bound receptors from approaching within about 50 Å of each other to intentionally create submaximal signals (Paar, et al., J. Immunol., 169: 856-864). In such a case, choices of H1 and Scorpion linker (H2) that are shorter and less flexible than those described above would be expected to be appropriate.

Figure 38:
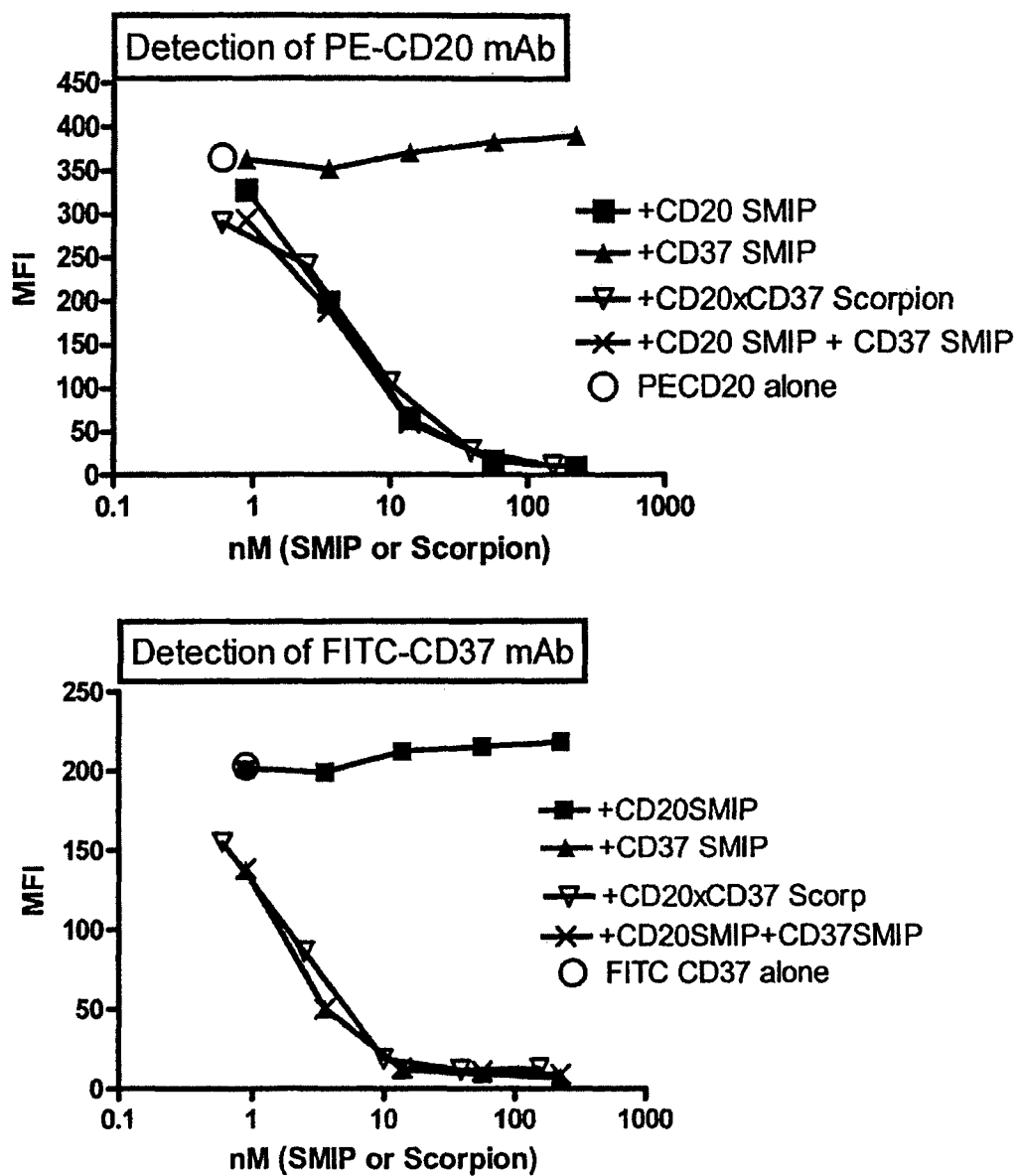
FIG. 38 contains graphs showing the results of competitive binding assays establishing that both N- and C-terminal scorpion binding domains participate in target cell binding.

The same spacing considerations apply to scorpion linkers that are not hinge-like. These scorpion linkers are exemplified by the class of peptides having the amino acid sequence of a stalk region of a C-lectin. Exemplary scorpion hinges comprising a C-lectin stalk region are scorpion hinges derived from the CD72 stalk region, the CD94 stalk region, and the NKG2A stalk region. Scorpions containing such scorpion hinges were constructed and characterized in terms of expression, susceptibility to cleavage, and amenability to purification. The data are presented in Table 14.

to theconcentrations indicated in FIG. 38. The diluted compounds were added to the plated cells in addition to media alone for control wells. The cells were incubated for 10 minutes with the compounds and then FITC anti-CD37 antibody (#186-040, Ancell, Bayport, Minn.) at 5 µg/ml and PE anti-CD20 antibody (#555623, BD Pharmingen, San Jose, Calif.) at 3 µg/ml (neet) were added together to the wells in 25 µl staining media. The cells were incubated on ice in the dark for 45 minutes and then washed 2.5 times with PBS. Cells were fixed with 1% paraformaldehyde (#19943 1 LT, USB Corp, Cleveland, Ohio) and then run on a FACs Calibur (BD Biosciences, San Jose, Calif.). The data were analyzed with Cell Quest software (BD Biosciences, San Jose, Calif.). The results shown in FIG. 38 establish that all SMIPs, SMIP combinations and scorpions containing a CD20 binding site successfully competed with PE-labeled anti-CD 20 antibody for binding to Ramos B-cells (upper panel); all SMIPs, SMIP combinations and scorpions containing a CD37 binding site successfully competed with FITC-labeled anti-CD 37 anti-

TABLE 14

| Linker Name | G$_4$S Codon optimization[1] | End of CH3 | S0129 Scorpion Linker variants amino acid seq | Linker seq. based on | Expression (% S0129)[2] | Cleavage[3] | Bench-top purification % POI |
|---|---|---|---|---|---|---|---|
| H7 | N | K | GCPPCPNS | H7 | 100 | — | 70 |
| H60 | Y(17) | K | GCPPCPNS | H7 | 114 | — | ND |
| H61 | Y(15) | K | GCPPCPNS | H7 | 90 | — | 66 |
| H62 | N | G | QRHNNSSLNTRTQKARHCPNS | NKG2A stalk | 129 | — | 89 |
| H63 | Y(17) | G | QRHNNSSLNTRTQKARHCPNS | NKG2A stalk | 100 | — | 85 |
| H64 | Y(15) | G | QRHNNSSLNTRTQKARHCPNS | NKG2A stalk | 81 | — | 83 |
| H65 | N | G | EPAFTPGPNIELQKDSDCPNS | CD94 stalk | 133 | — | 66 |
| H66 | Y(17) | G | EPAFTPGPNIELQKDSDCPNS | CD94 stalk | 200 | — | 64 |
| H67 | Y(15) | G | EPAFTPGPNIELQKDSDCPNS | CD94 stalk | 129 | — | 65 |
| H68 | N | G | RTRYLQVSQQLQQTNRVLEVTNSSLRQQLRLKITQLGQSAEDLQGSRRELAQSQEALQVEQRAHQAAEGQLQACQADRQKTKETLQSEEQQRRALEQKLSNMENRLKPFFTCGSADTC | CD72 full stalk | 110 | — | 75 |

[1]Codon optimization of Gly$_4$Ser linker, with (17) or without (15) restriction site
[2]Estimate of expression in COS based on recovery of protein in benchtop purification
[3]Cleavage product(s) observed by SDS-PAGE/Coomassie Blue stain of purified protein b. Binding of N- and C-Terminal Binding Domains Both N- and C-Terminal Domains Participate in Target Cell Binding The target cell binding abilities of a CD20 SMIP (TRU015), a CD37 SMIP (SMIP016), a combination of CD20 and CD37 SMIPS (TRU015+SMIP016), and the CD20×CD37 bispecific scorpion (015×016), were assessed by measuring the capacity of each of these molecules to block the binding of an antibody specifically competing for binding to the relevant target, either CD37 or CD20. The competing antibodies were FITC-labeled monoclonal anti-CD37 antibody or PE-labeled monoclonal anti-CD20 antibody, as appropriate. Ramos B-cells provided the targets.

Ramos B-cells at 1.2×10$^7$/ml in PBS with 5% mouse sera (#100-113, Gemini Bio-Products, West Sacramento, Calif.) (staining media) were added to 96-well V-bottom plates (25 µl/well). The various SMIPs and scorpions were diluted to 75 µg/ml in staining media and 4-fold dilutions were performed body for binding to Ramos B-cells (lower panel). The bispecific CD20×CD37 scorpion, therefore, was shown to have operable N- and C-terminal binding sites for targets on B-cells.

c. Cell-Surface Persistence

Figure 37:
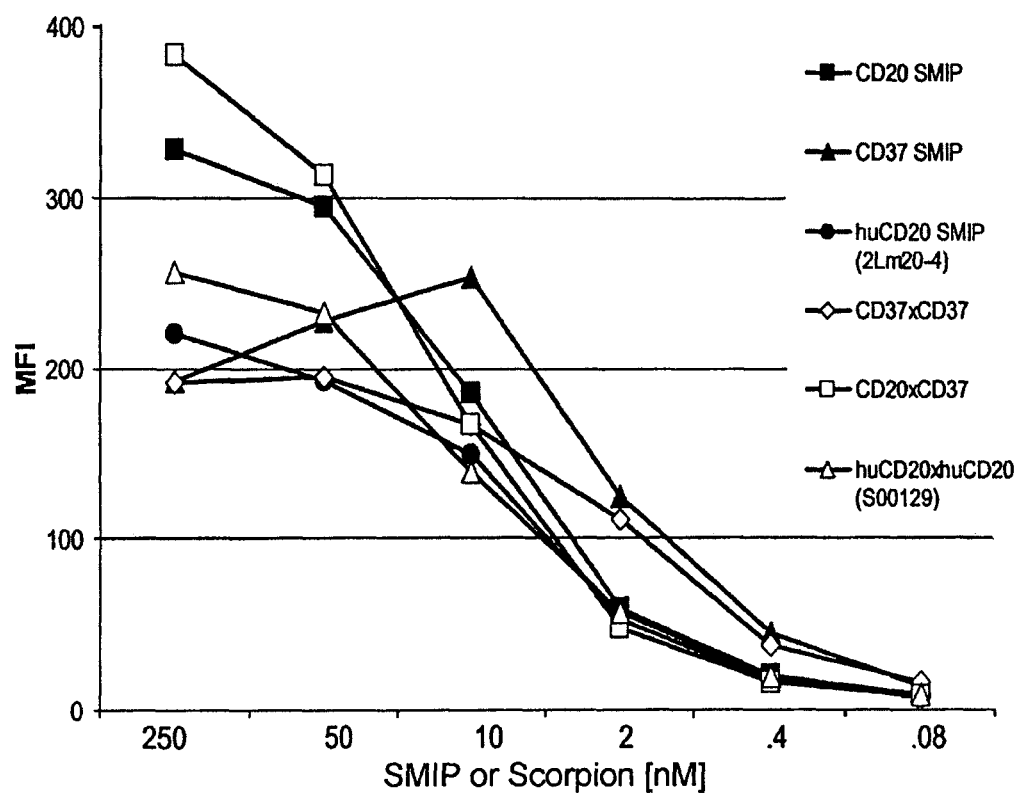
FIG. 37 provides a graph showing that scorpions retain the capacity to bind to target cells. Filled squares: CD20 SMIP; filled triangles: CD37 SMIP; filled circles: humanized CD20 (2Lm20-4) SMIP; open diamond: CD37×CD37 monospecific scorpion; open squares: CD20×CD37 bi-specific scorpion; and open triangles: humanized CD20 (2Lm20-4)×humanized CD20 (2Lm20-4) scorpion.

An investigation of the cell-surface persistence of bound SMIPs and scorpions (monospecific and bispecific) on the surface of B-cells revealed that scorpions exhibited greater cell-surface persistence than SMIPs. Ramos B-cells at 6×10$^6$/ml (3×10$^5$/well) in staining media (2.5% goat sera, 2.5% mouse sera in PBS) were added to 96-well V-bottom plates. Test reagents were prepared at two-fold the final concentration in staining media by making a 5-fold serial dilution of a 500 nM initial stock and then were added 1:1 to the Ramos B-cells. In addition, media controls were also plated. The cells were incubated in the dark, on ice, for 45 minutes. The plates were then washed 3.5 times with cold PBS. The secondary reagent, FITC goat anti-human IgG (#H10501, Caltag/Invitrogen, Carlsbad, Calif.) was then added at a 1:100 dilution in staining media. The cells were incubated for 30 minutes in the dark, on ice. Cells were then washed 2.5 times by centrifugation with cold PBS, fixed with a 1% paraformaldehyde solution (#19943 1 LT, USB Corp, Cleveland, Ohio) and then run on a FACs Calibur (BD Biosciences, San Jose, Calif.). The data were analyzed with CellQuest software (BD Biosciences, San Jose, Calif.). Results of the data analysis are presented in FIG. 37, which shows the binding of several SMIPs, a monospecific CD20×CD20 scorpion and a bispecific CD20×CD37 scorpion to their targets on Ramos B cells.

Two tubes of Ramos B-cells ($7 \times 10^5$/ml) were incubated for 30 minutes on ice with each of the two compounds being investigated, i.e., a humanized CD20 (2Lm20-4) SMIP and a humanized CD20×CD20 (2Lm20-4×2Lm20-4) scorpion, each at 25 µg/ml in Iscoves media with 10% FBS. At the end of the incubation period, both tubes were washed 3 times by centrifugation. One tube of cells was then plated into 96-well flat-bottom plates at $2 \times 10^5$ cells/well in 150 µl of Iscoves media with one plate then going into the 37° C. incubator and the other plate incubated on ice. The second tube of each set was resuspended in cold PBS with 2% mouse serum and 1% sodium azide (staining media) and plated into a 96-well V-bottom plate at $2 \times 10^5$ cells/well for immediate staining with the secondary antibody, i.e., FITC goat anti-human IgG (#H10501, Caltag/Invitrogen, Carlsbad, Calif.). The secondary antibody was added at a 1:100 final dilution in staining media and the cells were stained on ice, in the dark, for 30 minutes. Cells were then washed 2.5 times with cold PBS, and fixed with 1% paraformaldehyde (#19943 1 LT, USB Corp, Cleveland, Ohio).

Figure 39:
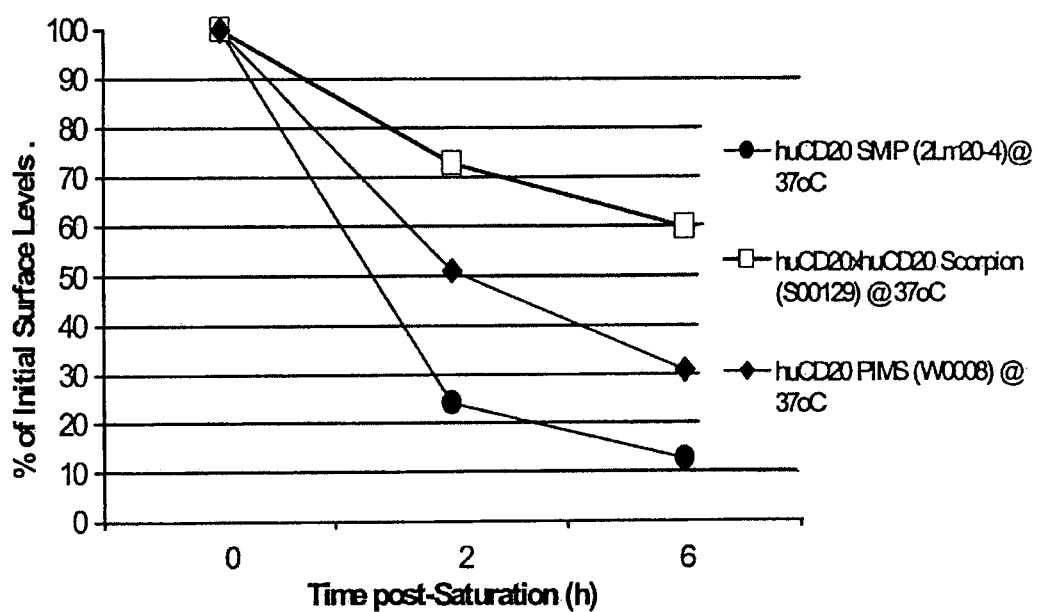
FIG. 39 presents data in the form of graphs showing that scorpions have lower off-rates than SMIPs.

At the time points designated in FIG. 39, samples were harvested from the 96-well flat-bottom plates, incubated at either 37° C. or on ice, and placed into 96-well V-bottom plates ($2 \times 10^5$ cells/well). The cells were washed once with cold staining media, resuspended, and the secondary antibody was added at a final dilution of 1:100 in staining media. These cells were incubated on ice, in the dark, for 30 minutes. The cells were then washed 2.5 times by centrifugation in cold PBS, and subsequently fixed with 1% paraformaldehyde. The samples were run on a FACS Calibur (BD Biosciences, San Jose, Calif.) and the data was analyzed with CellQuest software (BD Biosciences, San Jose, Calif.). Results presented in FIG. 39 demonstrate that the binding of a SMIP and a scorpion to the surface of B-cells persists for at least six hours, with the monospecific hu CD20×CD20 (2Lm20-4×2Lm20-4) scorpion persisting to a greater extent than the hu CD20 (2Lm20-4) SMIP.

EXAMPLE 15

Direct Cell Killing by Monospecific and Bispecific Scorpions

Experiments were conducted to assess the capacity of monospecific and bispecific scorpion molecules to directly kill lymphoma cells, i.e., to kill these cells without involvement of ADCC or CDC. In particular, the Su-DHL-6 and DoHH2 lymphoma cell lines were separately subjected to a monospecific scorpion, i.e., a CD20×CD20 scorpion or a CD37×CD37 scorpion, or to a bispecific CD20×CD37 scorpion.

Cultures of Su-DHL-6, DoHH2, Rec-1, and WSU-NHL lymphoma cells were established using conventional techniques and some of these cultures were then individually exposed to a monospecific CD20 SMIP, a monospecific scorpion (CD20×CD20 or CD37×CD37), or a bispecific scorpion (CD20×CD37 or CD19×CD37). The exposure of cells to SMIPs or scorpions was conducted under conditions that did not result in cross-linking. The cells remained in contact with the molecules for 96 hours, after which growth was measured by detection of ATP, as would be known in the art. The cell killing attributable to the CD20 SMIP and the CD20×CD20 monospecific scorpion are apparent in FIG. 24 and Table 15. The cell killing capacity of the CD37×CD37 monospecific scorpion is apparent from FIG. 25 and Table 15, the ability of the CD20×CD37 bispecific scorpion to kill lymphoma cells is apparent from FIG. 26 and Table 15, and the capacity of the CD19×CD37 bispecific scorpion to kill lymphoma cells is evident from FIG. 27 and Table 15. Data were pooled from three independent experiments and points represent the mean±SEM. $IC_{50}$ values in Table 15 were determined from the curves in FIGS. 24, 25, and 26, as noted in the legend to Table 15, and are defined as the concentration resulting in 50% inhibition compared to untreated cultures. The data in the figures and table demonstrate that scorpions are greater than 10-fold more potent in killing these cell lines than the free SMIP using the same binding domains.

TABLE 15

|  | Cell Line | | |
| --- | --- | --- | --- |
| $IC_{50}$ (nM) | SU-DHL-6 | DoHH2 | WSU-NHL |
| CD20 SMIP* | >100 | 60 | NA |
| CD20 × CD20 scorpion* | 0.3 | 4.0 | NA |
| CD37 SMIP** | >100 | >100 | NA |
| CD37 × CD37 scorpion** | 10 | 1.2 | NA |
| CD20 SMIP and CD37 SMIP*** | 6 | 2 | NA |
| CD20 × CD37 scorpion*** | 0.05 | 0.05 | NA |
| CD19 SMIP and CD37 SMIP**** | 0.16 | NA | 0.40 |
| CD19 × CD37 scorpion**** | 0.005 | NA | 0.04 |

Figure 24:
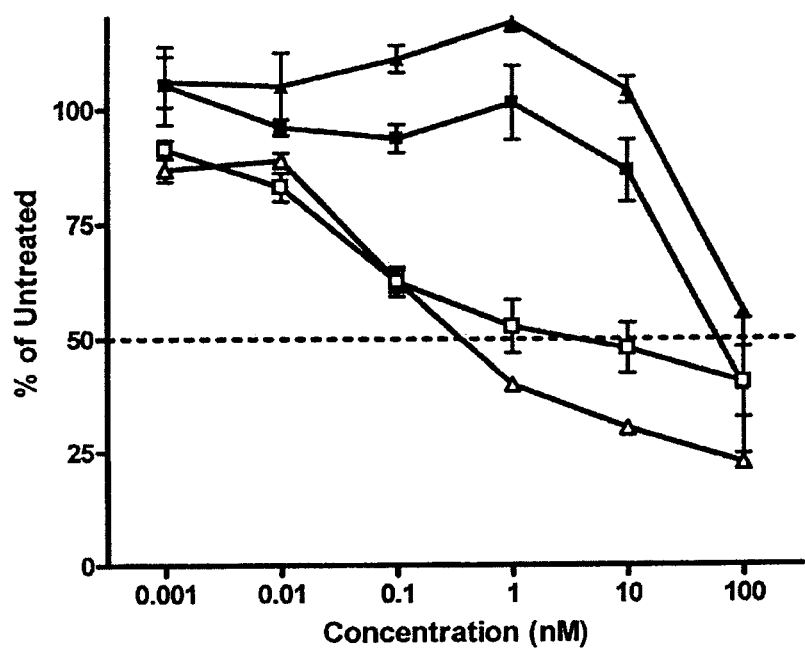
FIG. 24 provides a graph demonstrating direct growth inhibition of lymphoma cell lines Su-DHL6 (triangles) and DoHH2 (squares) by free CD20 SMIP (closed symbols) or monospecific CD20×CD20 scorpion (open symbols).
Figure 25:
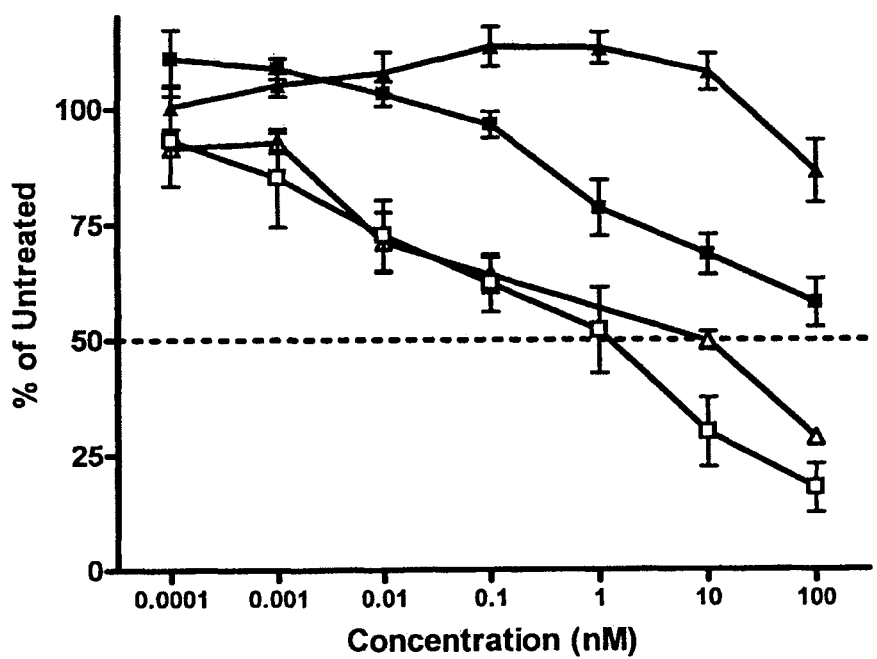
FIG. 25 is a graph showing direct growth inhibition of lymphoma cell lines Su-DHL-6 (triangles) and DoHH2 (squares) by free anti-CD37 SMIP (closed symbols) or monospecific anti-CD37 scorpion (open symbols).
Figure 26:
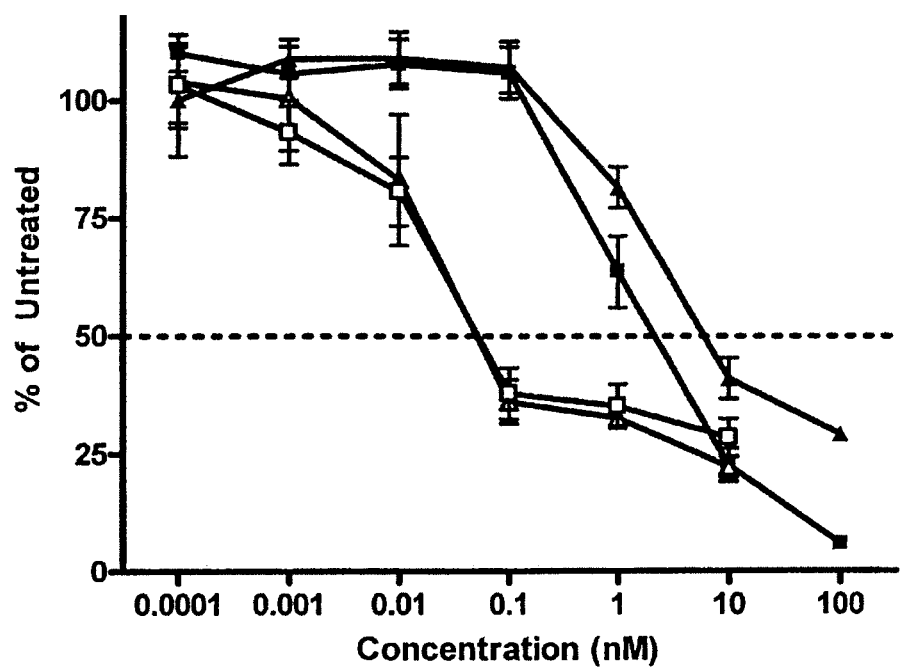
FIG. 26 presents a graph showing direct growth inhibition of lymphoma cell lines Su-DHL-6 (triangles) and DoHH2 (squares) by a combination of two different monospecific SMIPs (closed symbols) or by a bispecific CD20-CD37 scorpion (open symbols).
Figure 27:
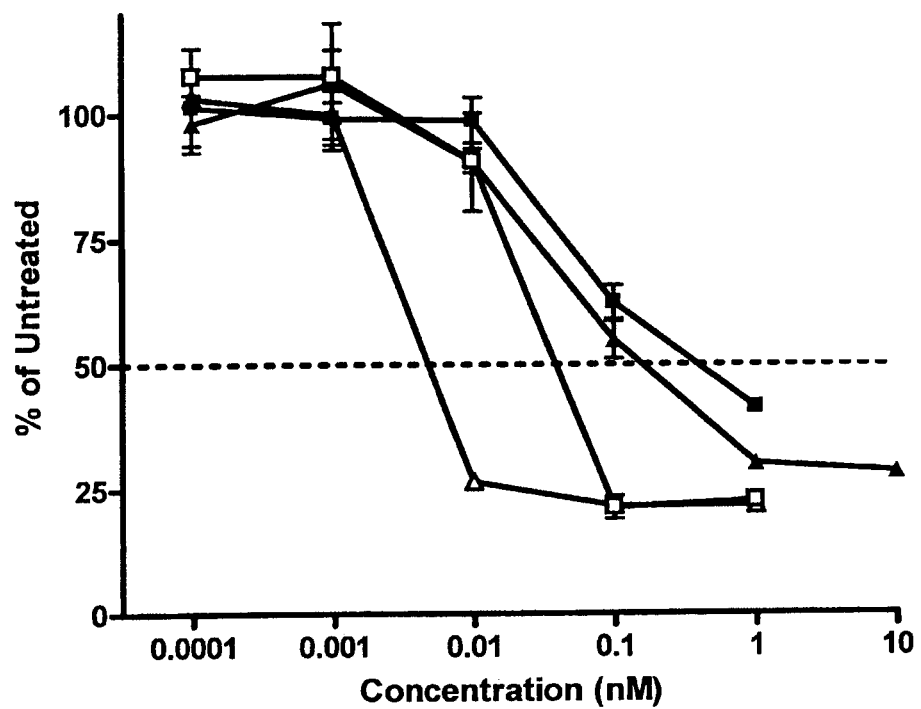
FIG. 27 is a graph revealing direct growth inhibition of lymphoma cell lines Su-DHL-6 (triangles) and WSU-NHL (squares) by free CD20 SMIP and CD37 SMIPcombination (closed symbols) or bispecific CD20×CD37 scorpion (open symbols).

*Data derived from FIG. 24.
**Data derived from FIG. 25.
***Data derived from FIG. 26.
****Data derived from FIG. 27.

Figure 46:
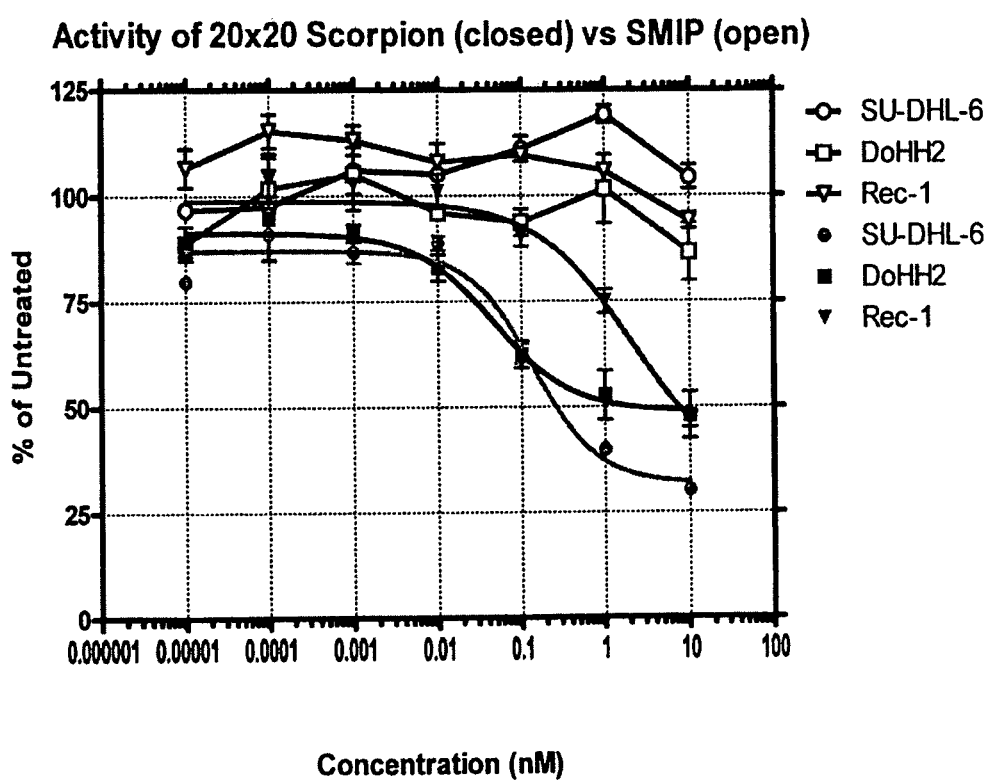
FIG. 46 shows the direct cell killing of a variety of B-cells by a CD20×CD20 scorpion and by a CD20 SMIP.
Figure 47:
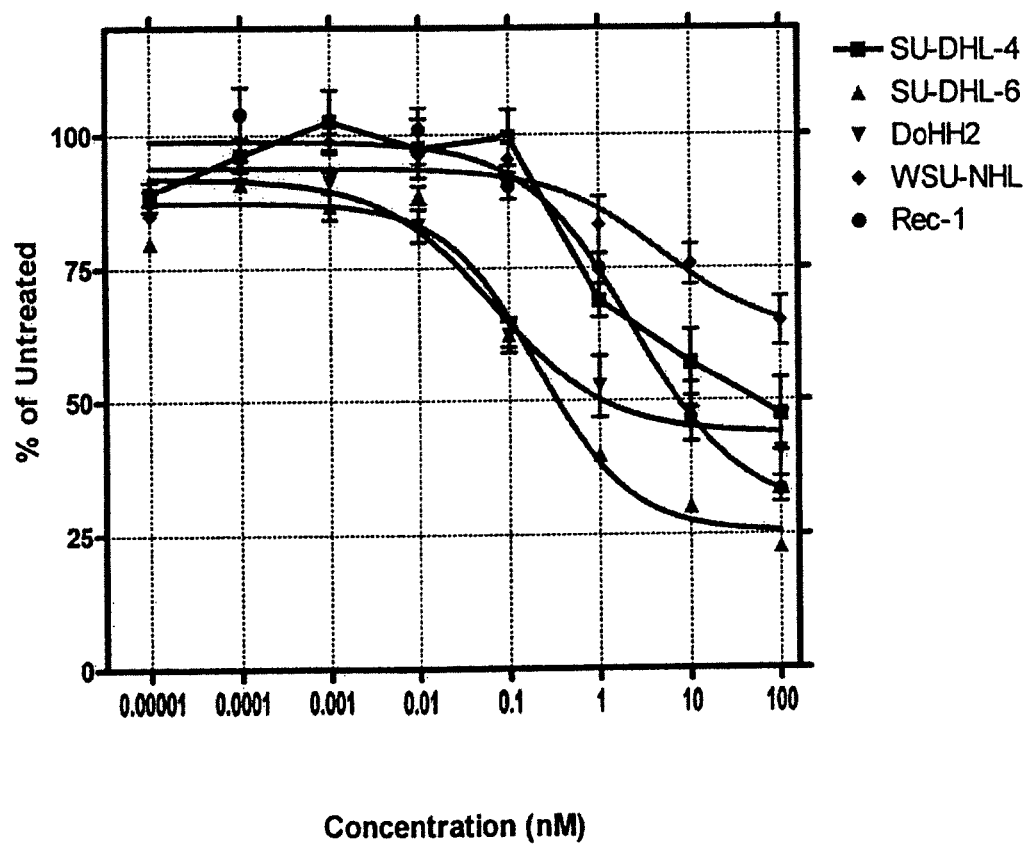
FIG. 47 reveals the direct cell killing of additional B-cell lines by a monospecific CD20×CD20 scorpion.

Additional experiments with the humanized CD20×CD20 scorpion S0129 were conducted in Su-DHL-4, Su-DHL-6, DoHH2, Rec-1, and WSU-NHL cells. The results are presented in FIG. 46 and FIG. 47. The data provided in these figures extends the findings discussed above in showing that scorpions have the capacity to directly kill a variety of cell lines.

Figure 48:
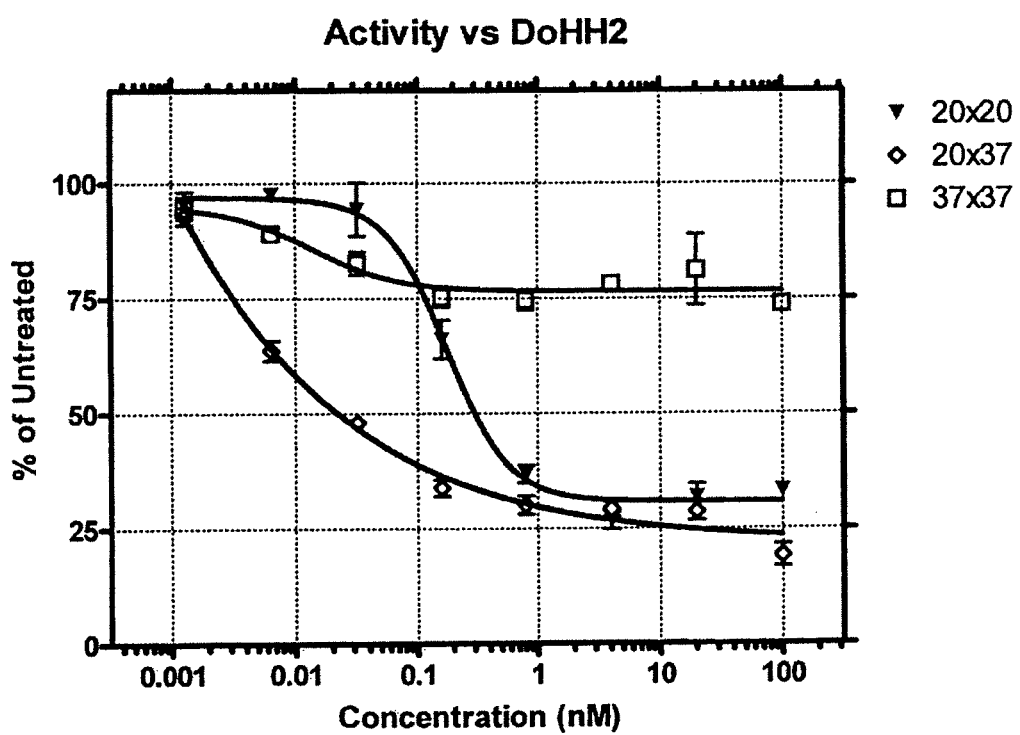
FIG. 48 shows the direct cell killing capacities of each of two monospecific scorpions, i.e., CD20×CD20 and CD37×CD37, and a bispecific CD20×CD37 scorpion, the latter exhibiting a different form of kill curve.

The above findings were extended to other monospecific and bispecific scorpions, with each scorpion demonstrating capacity to directly kill B cells. DoHH2 B-cells were exposed in vitro to the monospecific CD20×CD20 scorpion, a monospecific CD37×CD37 scorpion, or a bispecific CD20×CD37 scorpion. The results presented in FIG. 48 demonstrate that bispecific scorpions have kill curves that are different in form from monospecific scorpions.

Figure 49:
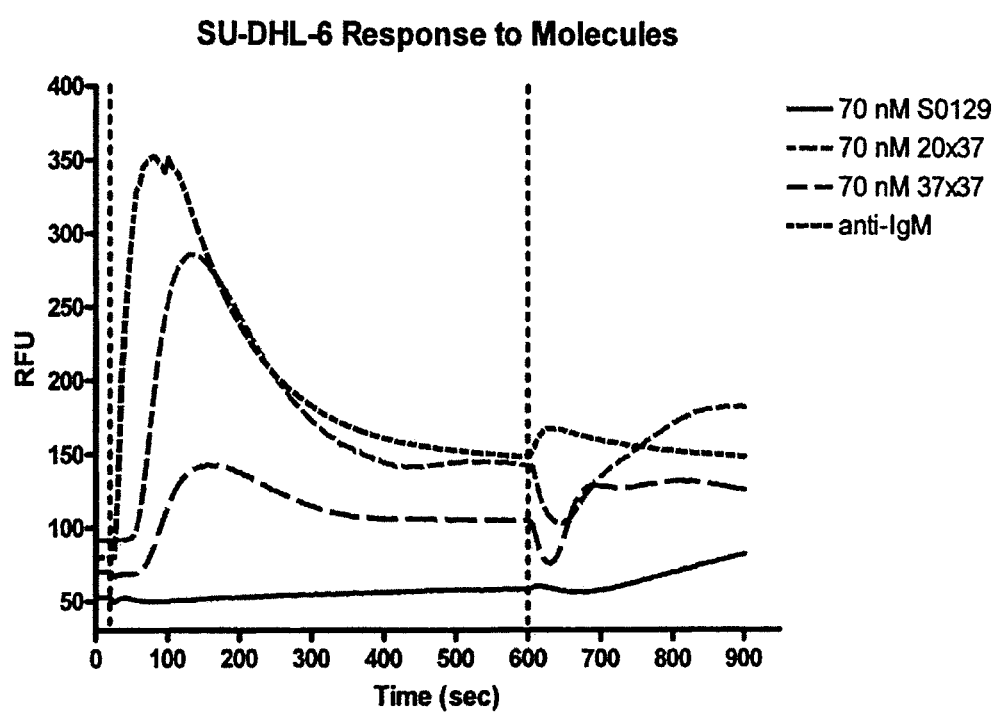
FIG. 49 graphically depicts the response of Su-DHL-6 B-cells to each of a CD20×CD20 (S0129), a CD37×CD37, and a CD20×CD37 scorpion.
Figure 50:
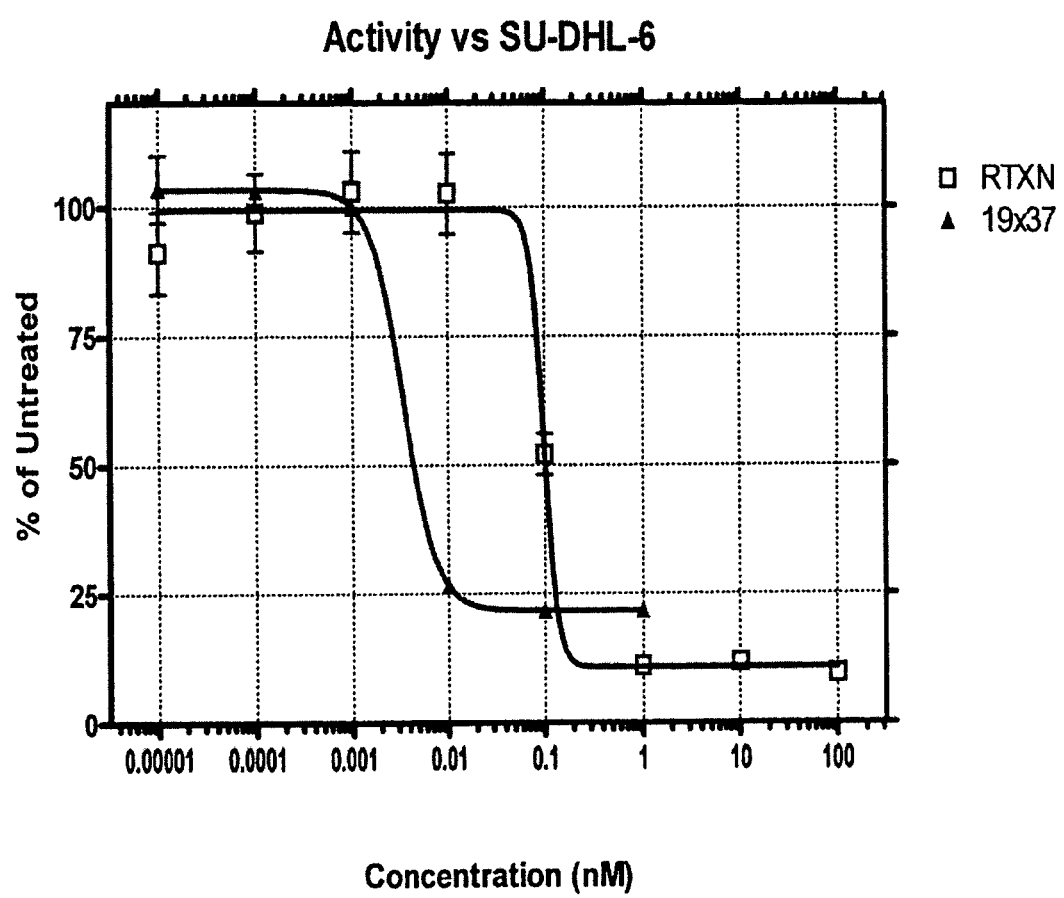
FIG. 50 shows the capacity of a bispecific CD19×CD37 scorpion and Rituxan® to directly kill Su-DHL-6 B-cells.

Culturing Su-DHL-6 cells in the presence of 70 nM CD20× CD20 scorpion (S0129), CD20×CD37 scorpion, or CD37× CD37 scorpion also led to direct B-cell killing in an in vitro environment (FIG. 49). Consistently, Su-DHL-6 cells exposed to either a bispecific CD19×CD37 scorpion or to Rituxan® led to direct cell killing, with the bispecific scorpion exhibiting lethality at lower doses, as revealed in FIG. 50.

Figure 51:
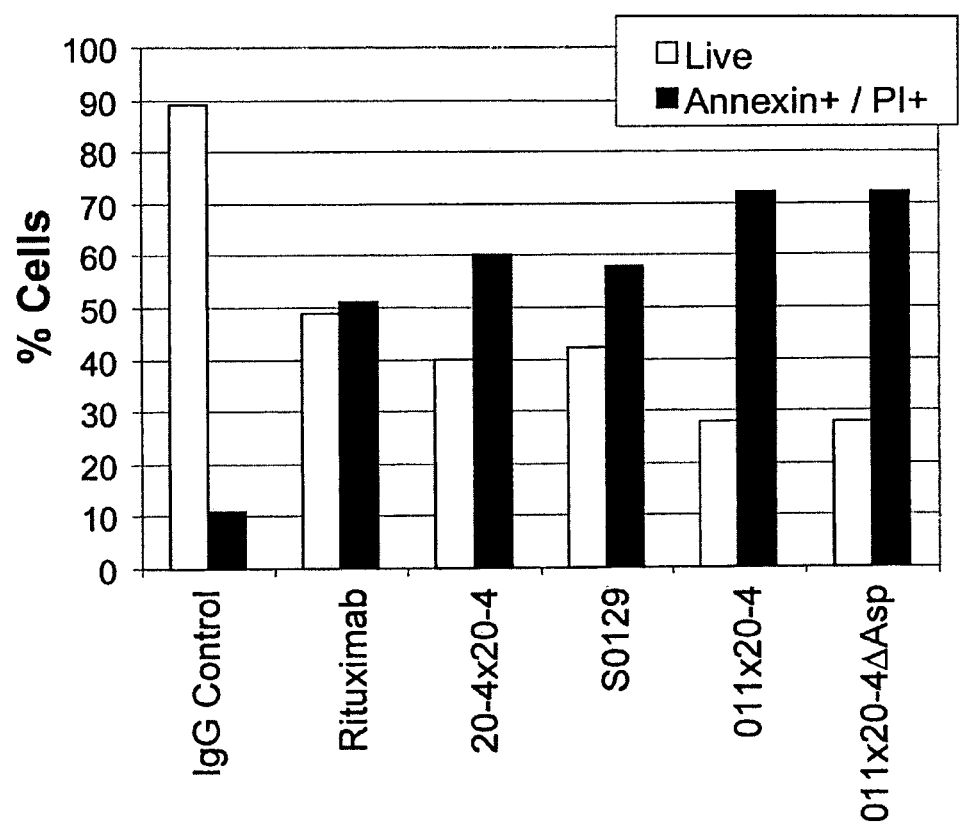
FIG. 51 provides histograms showing the direct killing of DHL-4 B-cells by a variety of CD20-binding scorpions and SMIPs, as well as by Rituxan®, as indicated in the figure. Open bars: live cells; solid bars on the right of each pair: Annexin+/PI+.
Figure 52:
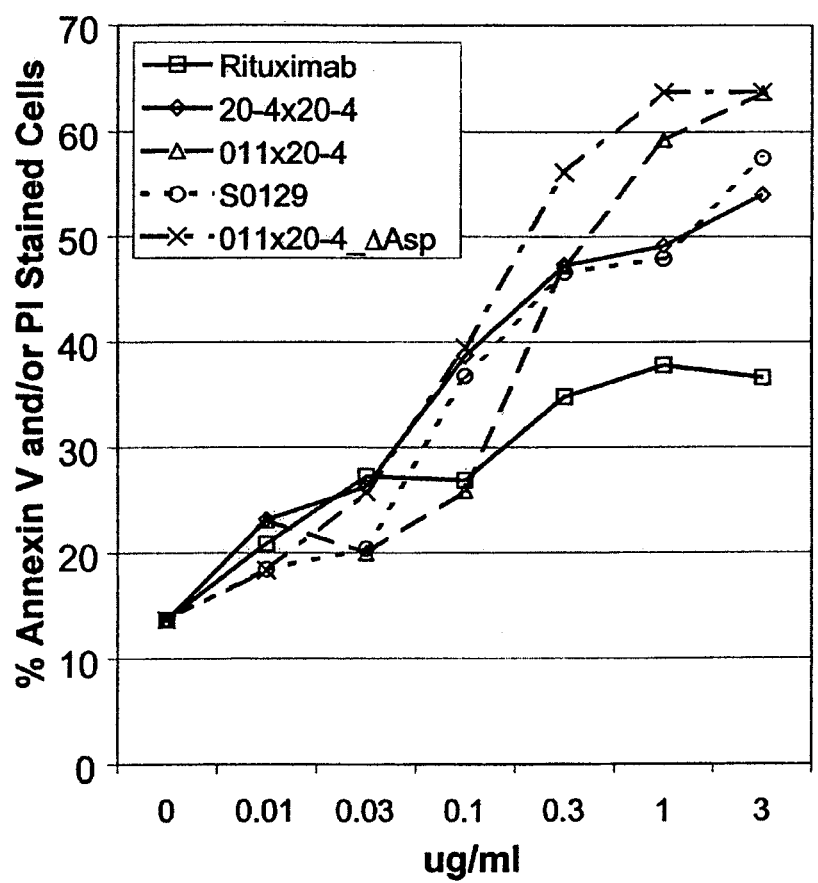
FIG. 52 provides a graphic depiction of the direct cell killing of various CD20-binding scorpions and SMIPs, as well as by Rituxan®, as indicated in the figure.

Another demonstration of direct cell killing was provided by exposing DHL-4 cells to four independent monospecific scorpions recognizing CD20. Two versions of CD20×CD20 scorpion were designed to incorporate two 20-4 binding domains (20-4×20-4 and S0129) and the second two incorporate a hybrid of the 011 and 20-4 binding domains. All four of the independently constructed and purified versions of the two CD20×CD20 scorpion designs, (20-4×20-4 and S0129) and hybrid (011×20-4 and 011×20-4ΔAsp), efficiently killed the DHL-4 cells in a direct manner. For this study, DHL-4 cells were treated in vitro with 1 μg/ml of the indicated proteins for 24 hours. Cells were then stained with Annexin V and Propidium Iodide, early and late markers of cell death, respectively, and cell populations were quantified by FACS. The results presented in FIG. 51 establish the direct killing capacity of each of the CD20×CD20 constructs as evidenced by increased staining shown in black bars. In addition, the results demonstrate that the hybrid 011×20-4 proteins exhibited a slight increase in direct cell killing relative to 20-4×20-4-based scorpions, despite the fact that each of these scorpions monospecifically recognized CD20. In a separate set of experiments, the dose-response of the four independent scorpion constructs was determined by FACS analysis of Annexin V- and Propidium Iodide-stained cell populations. The results, shown in FIG. 52, demonstrate dose-responsive increases in cell death resulting from treatment of the DHL-4 cells with each of the independent scorpion constructs.

EXAMPLE 16

Accessory Functions Mediated by Scorpions (ADCC & CDC)

a. Scorpion-Dependent Cellular Cytotoxicity

Experiments were conducted to determine whether scorpions would mediate the killing of BJAB B lymphoma cells. BJAB B lymphoma cells were observed to be killed with CD20 and/or CD37 scorpions.

Initially, $1\times10^7$/ml BJAB B-cells were labeled with 500 μCi/ml $^{51}$Cr sodium chromate (#CJS1, Amersham Biosciences, Piscataway, N.J.) for 2 hours at 37° C. in Iscoves media with 10% FBS. The $^{51}$Cr-loaded BJAB B cells were then washed 3 times in RPMI media with 10% FBS and resuspended at $4\times10^5$/ml in RPMI. Peripheral blood mononuclear cells (PBMC) from in-house donors were isolated from heparinized whole blood via centrifugation over Lymphocyte Separation Medium (#50494, MP Biomedicals, Aurora, Ohio), washed 2 times with RPMI media and resuspended at $5\times10^6$/ml in RPMI with 10% FBS. Reagent samples were added to RPMI media with 10% FBS at 4 times the final concentration and three 10-fold serial dilutions for each reagent were prepared. These reagents were then added to 96-well U-bottom plates at 50 μl/well to the indicated final concentrations. The $^{51}$Cr-labeled BJAB were then added to the plates at 50 μl/well ($2\times10^4$/well). The PBMC were then added to the plates at 100 μl/well ($5\times10^5$/well) for a final ratio of 25:1 effectors (PBMC):target (BJAB). Effectors and targets were added to media alone to measure background killing. The $^{51}$Cr-labeled BJAB were added to media alone to measure spontaneous release of $^{51}$Cr and to media with 5% NP40 (#28324, Pierce, Rockford, Ill.) to measure maximal release of $^{51}$Cr. The plates were incubated for 6 hours at 37° C. in 5% $CO_2$. Fifty μl (25 μl would also be suitable) of the supernatant from each well were then transferred to a Luma-Plate-96 (#6006633, Perkin Elmer, Boston, Mass.) and dried overnight at room temperature.

Figure 30:
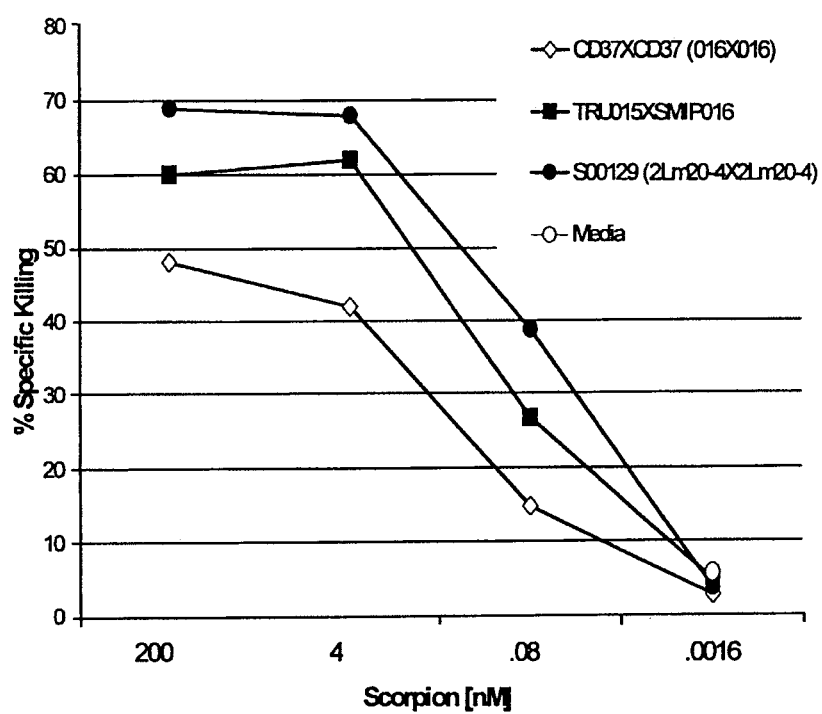
FIG. 30 provides graphs demonstrating scorpion-dependent cellular cytotoxicity

After drying, radioactive emissions were quantitated as cpm on a Packard TopCount-NXT. Sample values were the mean of triplicate samples. Percent specific killing was calculated using the following equation: % Kill=((sample−spontaneous release)/(maximal release−spontaneous release))× 100. The plots in FIG. 30 show that BJAB B cells were killed by monospecific scorpions CD20×CD20 and CD37×CD37. The combination of CD20 SMIP and CD37 SMIP also killed BJAB B cells. These results demonstrate that scorpions exhibit scorpion-dependent cellular cytotoxicity and it is expected that this functionality is provided by the constant sub-region of the scorpion, providing ADCC activity.

b. Scorpion Role in Complement-Dependent Cytotoxicity

Figure 31:
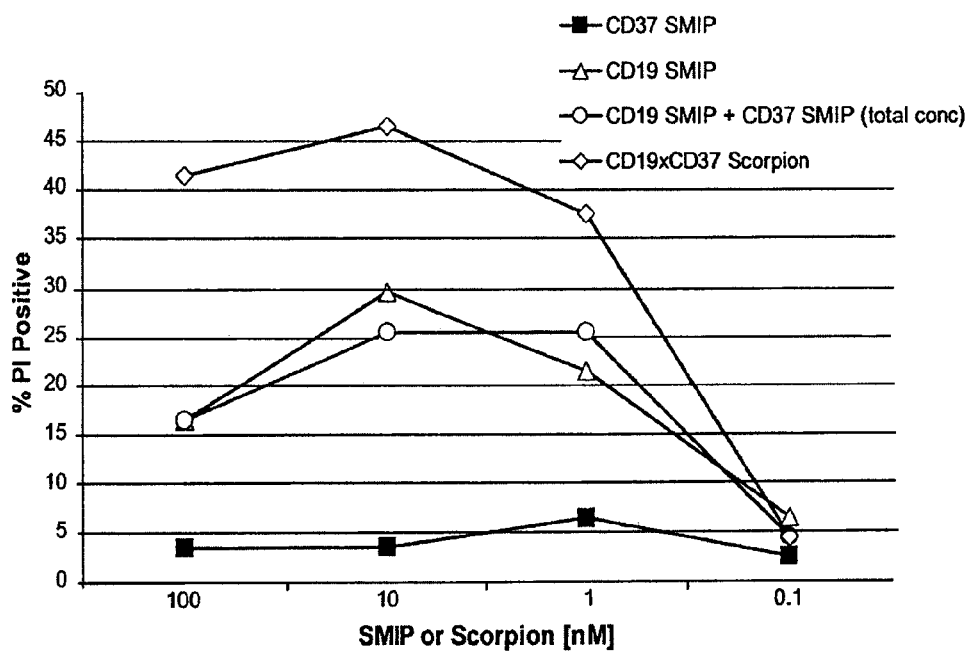
FIG. 31 shows graphs of data indicating that scorpions mediate Complement Dependent Cytotoxicity.

Experiments also demonstrated that scorpions have Complement-Dependent Cytotoxicity (CDC) activity. The experiment involved exposure of Ramos B-cells to CD19 and/or CD37 SMIPs and scorpions, as described below and as shown in FIG. 31.

The experiment was initiated by adding from 5 to $2.5\times10^5$ Ramos B-cells to wells of 96-well V-bottomed plates in 50 μl of Iscoves media (no FBS). The test compounds in Iscoves, (or Iscoves alone) were added to the wells in 50 μl at twice the indicated final concentration. The cells and reagents were incubated for 45 minutes at 37° C. The cells were washed 2.5 times in Iscoves with no FBS and resuspended in Iscoves with human serum (# A113, Quidel, San Diego, Calif.) in 96-well plates at the indicated concentrations. The cells were then incubated for 90 minutes at 37° C. The cells were washed by centrifugation and resuspended in 125 μl cold PBS. Cells were then transferred to FACs cluster tubes (#4410, CoStar, Corning, N.Y.) and 125 μl PBS with propidium iodide (# P-16063, Molecular Probes, Eugene, Oreg.) at 5 μg/ml was added. The cells were incubated with the propidium iodide for 15 minutes at room temperature in the dark and then placed on ice, quantitated, and analyzed on a FACsCalibur with CellQuest software (Becton Dickinson). The results presented in FIG. 31 establish that the CD19 SMIP, but not the CD37 SMIP, exhibits CDC activity, with a combination of the two SMIPs exhibiting approximately the same level of CDC activity as CD19 SMIP alone. The CD19×CD37 scorpion, however, exhibited significantly greater CDC activity than either SMIP alone or in combination, establishing that the scorpion architecture provides a greater level of Complement-dependent Cytotoxicity than other molecular designs.

c. ADCC/CDC Activity of CD20×CD20 Monospecific Scorpions

Figure 53:
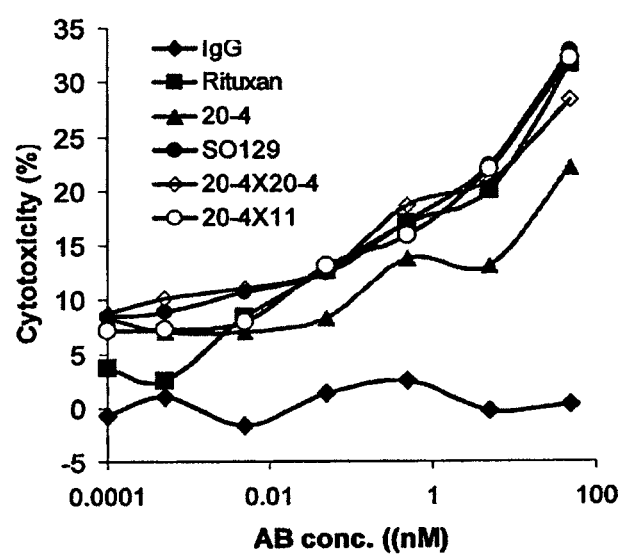
FIG. 53 provides graphs of the ADCC activity induced by various CD20-binding scorpions and SMIPs, as indicated in the figure, as well as by Rituxan®.

Three distinct CD20×CD20 monospecific scorpions were examined for ADCC and CDC functionality, along with appropriate controls. ADCC was assayed using conventional techniques, and the results are presented in FIG. 53. Apparent from the Figure is the appreciable, but not identical, ADCC activity associated with each of the tested CD20×CD20 monospecific scorpions.

Figure 54:
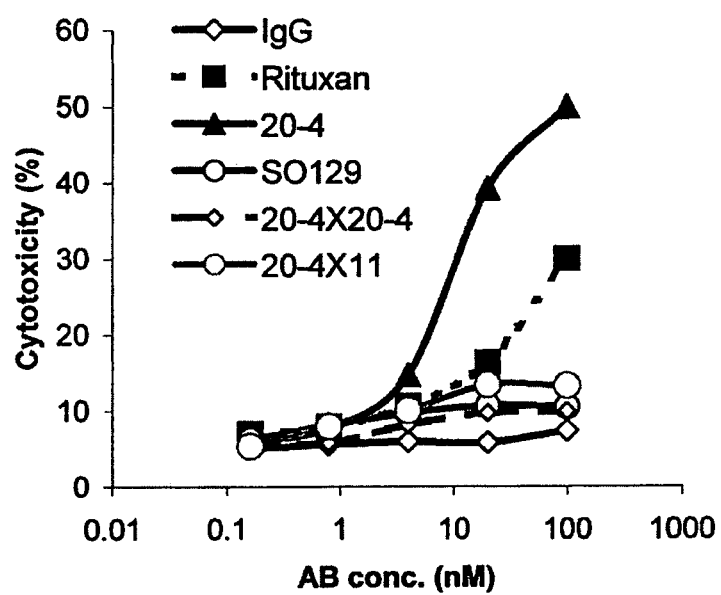
FIG. 54 provides graphs of the CDC activity induced by vawrious CD20-binding scorpions and SMIPs, as indicated in the figure, as well as by Rituxan®.
Figure 55:
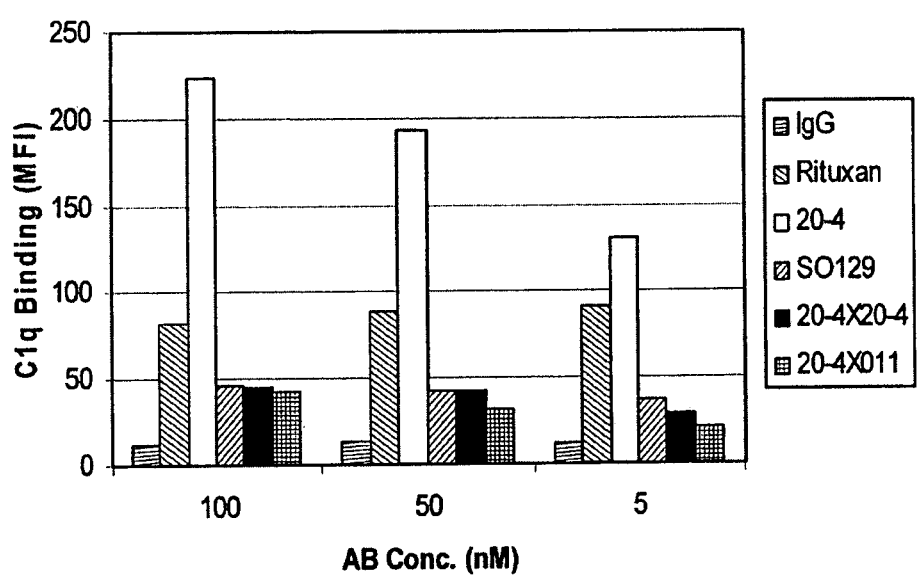
FIG. 55 provides histograms showing the levels of C1q binding to CD20-binding scorpions bound to Ramos B-cells.

To assess CDC, Ramos B-cell samples ($4\times10^5$) were incubated with each of the CD20×CD20 scorpions (0, 0.5, 5, 50 and 500 nM) and serum (10%) for 3.5 hour at 37° C. Cell death was assessed by 7-AAD staining and FACS analysis. The results are presented in FIG. 54, which reveals that the scorpions exhibit some CDC activity. In a similar experiment, Ramos B-cell samples ($4\times10^5$) were incubated with CD20× CD20 scorpion protein (5, 50, 100 nM) and serum (10%) for 2 hour at 37° C. Cells were washed 2× and incubated with anti-human C1q FITC antibody. Bound C1q was assessed by FACS analysis and the results are presented in FIG. 55. These results are consistent with the results presented in FIG. 54 that each of the CD20×CD20 monospecific scorpions was associated with some CDC activity, although less activity than was associated with a CD20 SMIP.

d. Interactions of Scorpions with $F_C\gamma RIII$

Figure 32A:
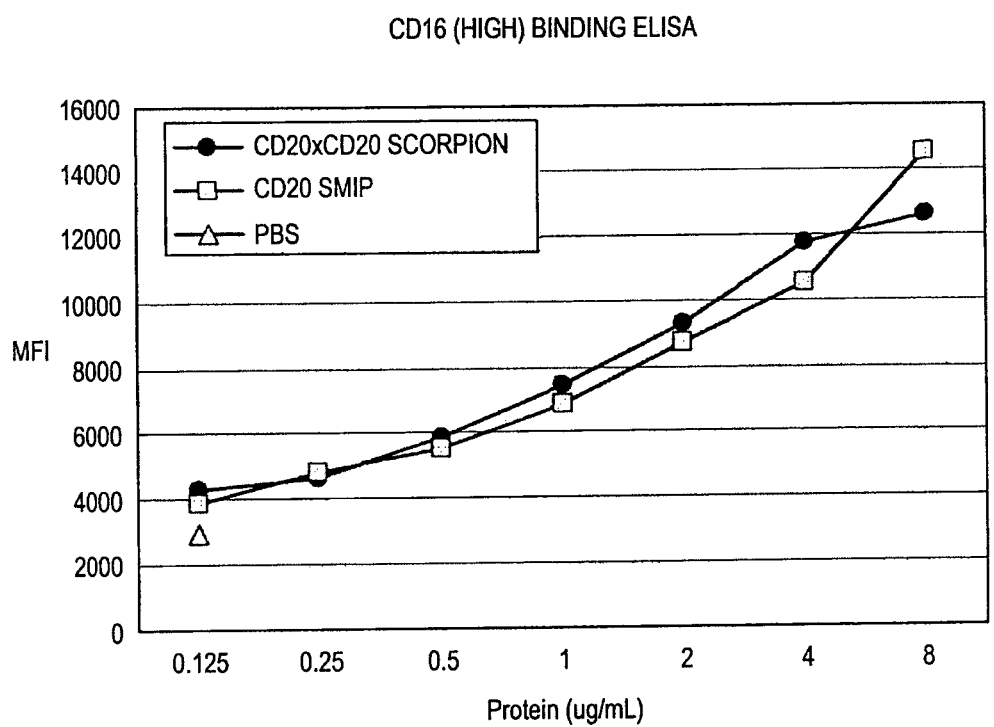
FIG. 32 provides data in graphical form showing comparative ELISA binding of a SMIP and a scorpion to low-(B) and high-affinity (A) isoforms of FcγRIII (CD16).
Figure 32B:
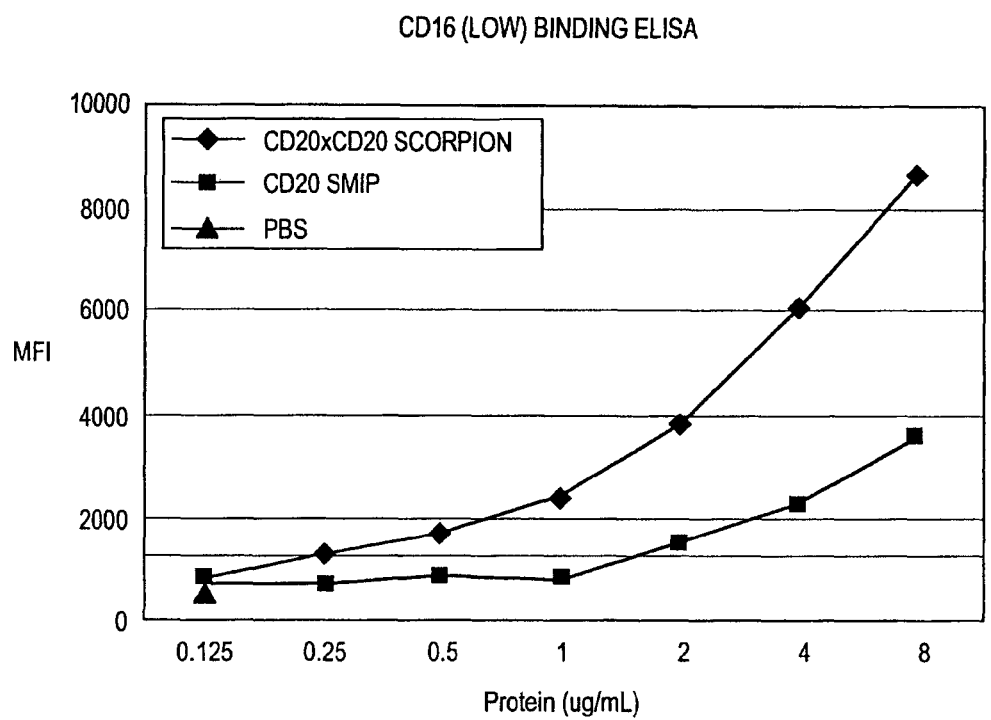

ELISA studies showed that scorpions bound to FcγRIII (CD16) low (a low affinity isoform or allelotype) at increased levels in the absence of target cells. ELISA plates were initially coated with either low- or high-affinity CD16mIgG using conventional techniques. The ability of this immobilized fusion protein to capture either a CD20 SMIP or a CD20×CD20 monospecific scorpion was assessed. Bound SMIPs and scorpions were detected with goat anti-human IgG (HRP) secondary antibody and mean fluorescence intensity (MFI) was determined. PBS alone (negative control) is shown as a single point. The results are presented in FIG. 32A (capture by CD16 high affinity isoform fusion) and 32B (capture by CD16 low affinity isoform fusion). Apparent from a consideration of FIGS. 32A and 32B is that both CD20 SMIP and CD20×CD20 monospecific scorpion showed increased binding to both the high- and low-affinity CD16 isoform fusions, with the CD20×CD20 scorpion showing a dramatic increase in binding to the low affinity isoform fusion with increasing protein concentration.

The binding of scorpions to the FcγRIII isoforms in the presence of target cells was also assessed. The data show the increased binding of scorpions to both FcγRIII (CD16) low- and high-affinity isoforms or allelotypes in the presence of target cells with increasing protein concentration.

Figure 33:
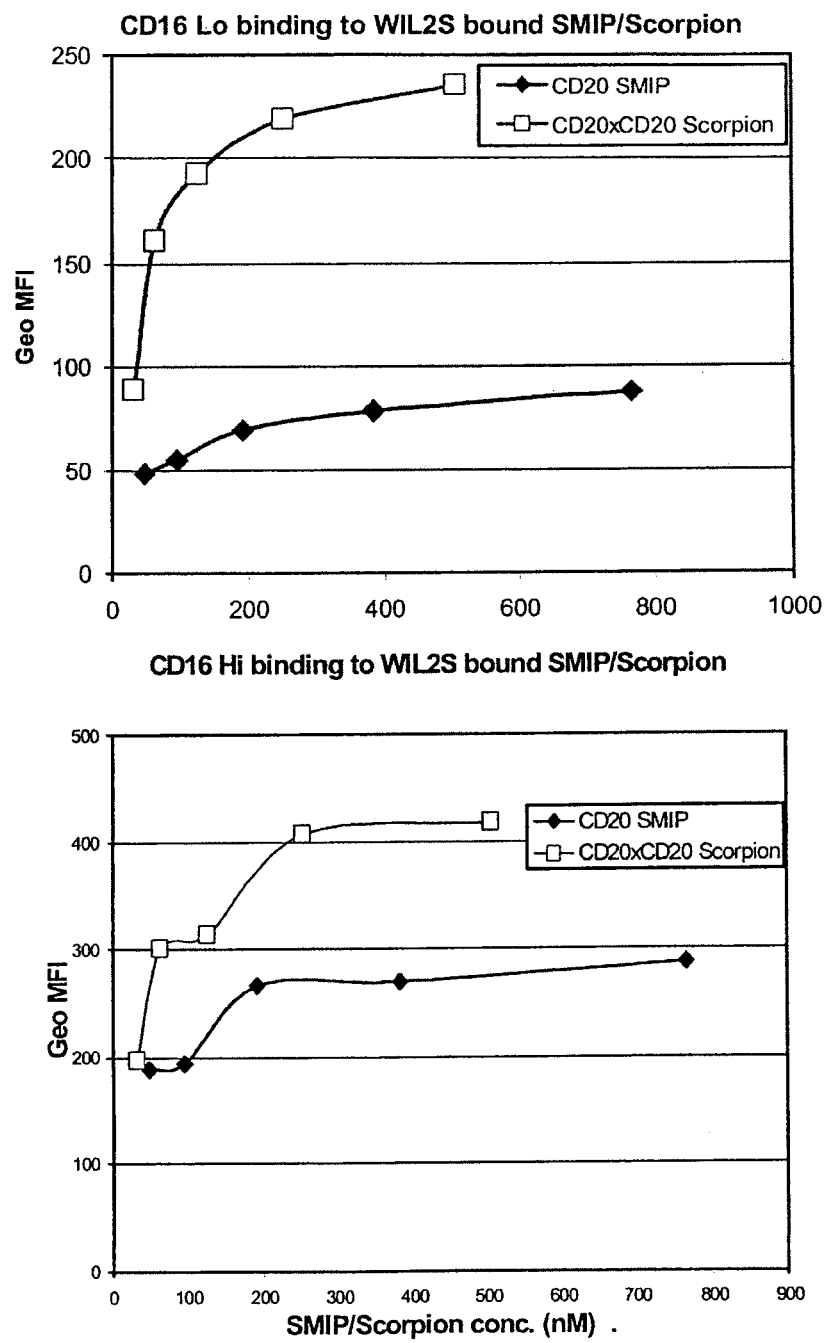
FIG. 33 presents graphs establishing the binding of a SMIP and a scorpion to low (A)- and high (B)-affinity allelotypes of FcγRIII (CD16) in the presence of target cells.
Figure 34:
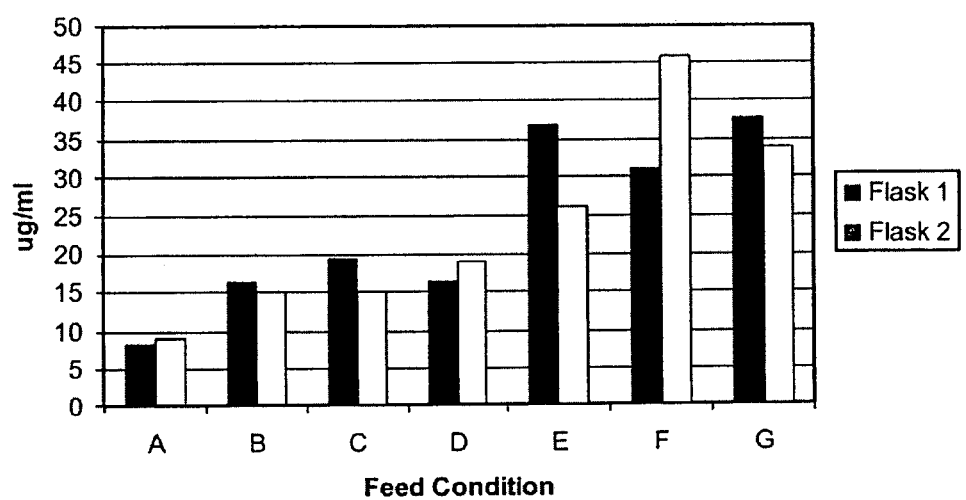
FIG. 34 is a histogram showing the expression level of a CD20×CD20 scorpion in two experiments (flask 1 and flask 2) under six different culturing conditions. Solid black bars: flask 1; striped bars: flask 2.
Figure 35:
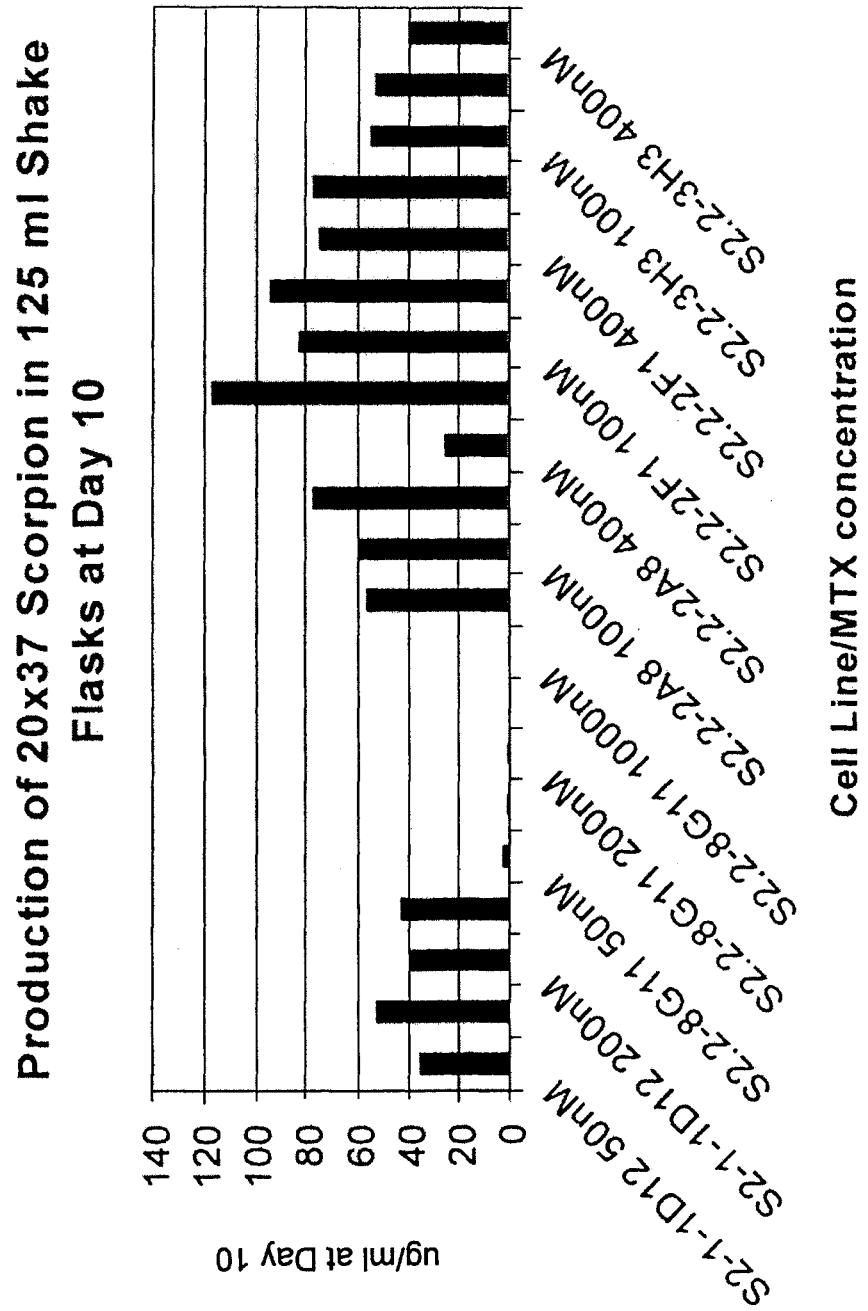
FIG. 35 provides a histogram showing the production yield of a CD20×CD37 scorpion.

In conducting the experiment, CD20-positive target cells were exposed to CD20 SMIPs or CD20×CD20 monospecific scorpions under conditions that allowed the binding of the SMIP or scorpion to the CD20-positive target cell. Subsequently, the SMIP- or scorpion-bearing target cell was exposed to either CD16 high- or low-affinity isoform tagged with mouse IgFc. A labeled goat anti-mouse Fc was then added as a secondary antibody to label the immobilized CD16 tagged with the mouse IgFc. Cells were then detected using flow cytometry on a FACs Calibur (BD Biosciences, San Jose, Calif.) and analyzed with Cell Quest software (BD Biosciences, San Jose, Calif.). As shown in FIG. 33, increased concentrations of each of the CD20 SMIP and the CD20× CD20 monospecific scorpion led to increased binding to the CD16 isoforms in the presence of target cells, with the increase in binding of the CD20×CD20 scorpion being more significant than the increased binding seen with the CD20 SMIP.

EXAMPLE 17

Cell-Cycle Effects of Scorpions on Target Lymphoma Cells

Figure 28:
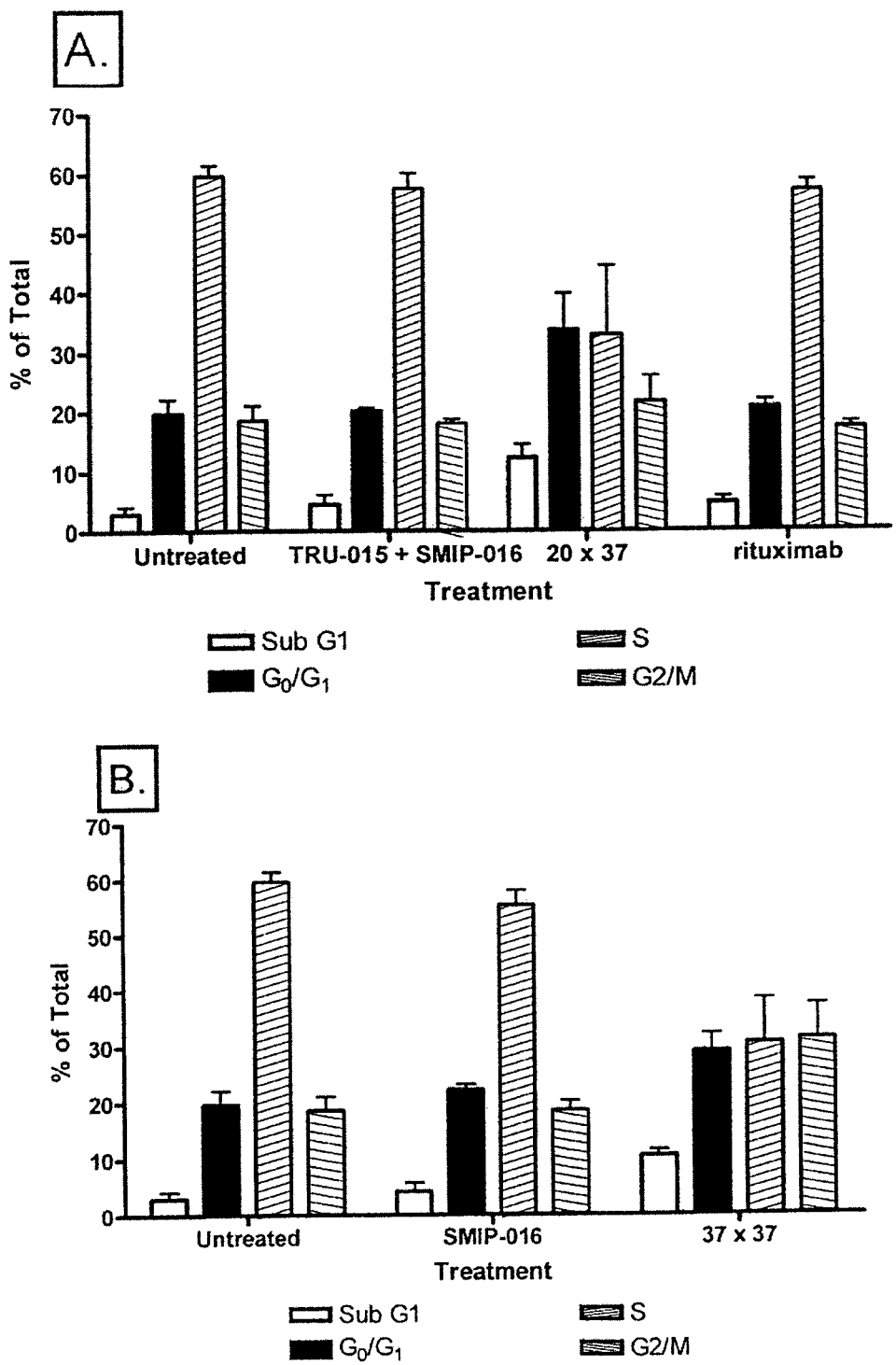
FIG. 28 provides histograms showing the cell-cycle effects of scorpions. Samples of DoHH2 lymphoma cells were separately left untreated, treated with SMIP 016 or treated with the monospecific CD37×CD37 scorpion. Open bars: sub-$G_1$ phase of the cell Gyle; black bars: $G_0/G_1$ phase; shaded: S phase; and striped: $G_2/M$ phase.

The cell-cycle effects of scorpions were assessed by exposing lymphoma cells to SMIPs, monospecific scorpions and bispecific scorpions. More particularly, DoHH2 lymphoma cells ($0.5 \times 10^6$) were treated for 24 hours with 0.4 nM rituximab, CD20×CD37 scorpion, TRU-015 (CD20 SMIP)+ SMIP-016 combination (0.2 nM each), 100 nM SMIP-016 or 100 nM CD37×CD37 scorpion. These concentrations represent about 10-fold more than the IC50 value of the scorpion in a 96-hour growth inhibition assay (see FIGS. 24-27). Cultures were labeled for 20 minutes at 37° C. with 10 μM BrdU (bromodeoxyuridine). Following fixation, cells were stained with anti-BrdU-FITC antibody and counterstained with propidium iodide. Values in FIG. 28 are the mean+/−SD of 4 replicate cultures from 2-3 independent experiments. All sample data were analyzed at the same time and pooled for presentation using both the BrdU and PI incorporation dot plots. Plots demonstrate that a major effect of scorpion treatment is a depletion of cells in S-phase, as well as an increase in the $G_0/G_1$ compartment.

EXAMPLE 18

Physiological Effects of Scorpions
a. Mitochondrial Potential

CD20×CD20 scorpions induced loss of mitochondrial membrane potential in DHL4 B-cells, as revealed in a JC-1 assay. JC-1 is a cationic carbocyanine dye that exhibits potential-dependent accumulation in the mitochondria (Mitoprobe® JC-1 Assay Kit for Flow Cytometry from Molecular Probes). JC-1 is more specific to the mitochondrial membrane than the plasma membrane and is used to determine changes in mitochondrial membrane potential. Accumulation in mitochondria is indicated by a fluorescence shift from green (529 nm) to red (590 nm).

Figure 56:
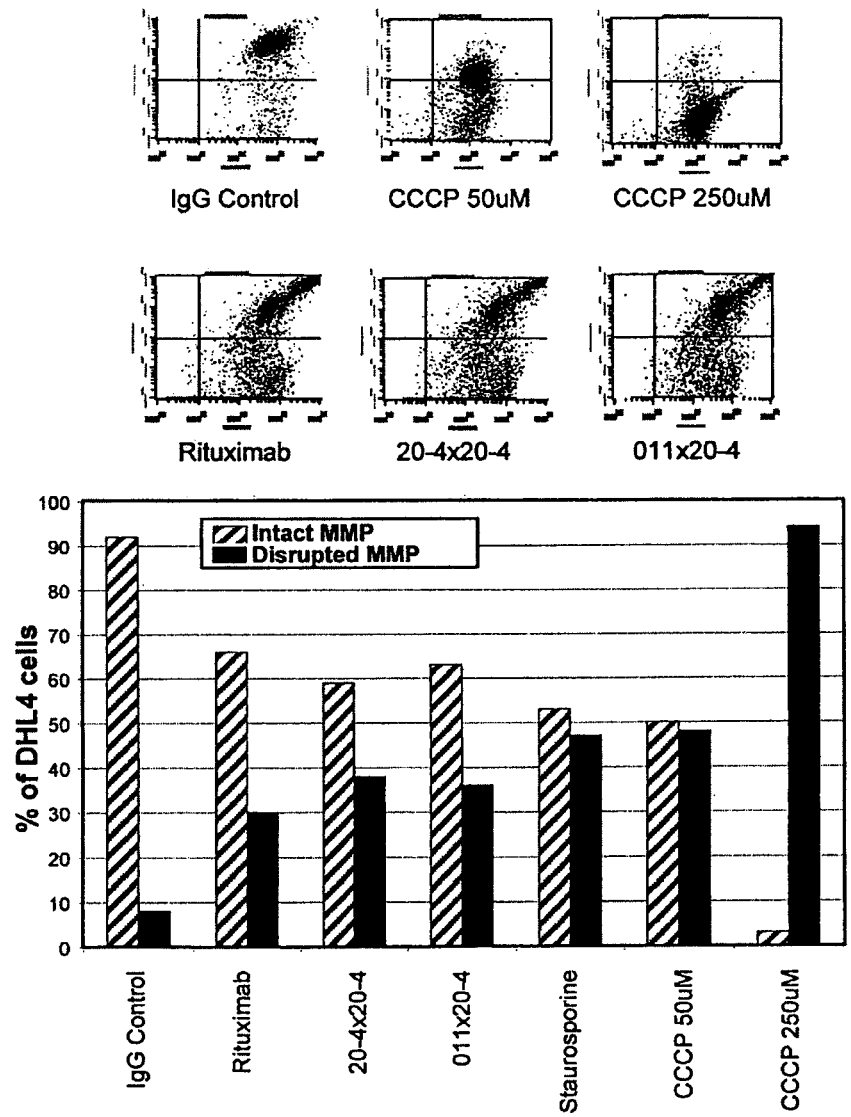
FIG. 56 provides scatter plots of FACS analyses showing the loss of mitochondrial membrane potential attributable to CD20-binding scorpions (2Lm20–4×2Lm20-4 and 011× 2Lm20-4) and Rituxan®, relative to controls (upper panel); histograms of the percentage of cells with disrupted mitochondrial membrane potential (disrupted MMP: black bars) are shown in the lower panel.

In conducting the experiment, DHL-4 B-cells ($5 \times 10^5$ cells/ml) were initially cultured in 24-well plates and treated for 24 hours with 1 μg/ml CD20×CD20 scorpion, Rituximab, IgG control antibody, or 5 μM staurosporine at 37° C., 5% $CO_2$, in a standard tissue-culture incubator. JC-1 dye (10 μl/ml, 2 μM final concentration) was added and cells were incubated for another 30 minutes at 37° C. Cells were harvested by centrifugation (5 minutes at 1200 rpm), washed with 1 ml PBS, and resuspended in 500 μl PBS. Cells were analyzed by flow cytometry (FACSCalibur, BD) with 488 nM excitation and 530 nM and 585 nM emission filters. For the representative scatter plots shown in FIG. 56, red fluorescence was measured on the Y-axis and green fluorescence was measured on the X-axis. Depolarization of the mitochondrial membrane was measured as a decrease in red fluorescence, as seen in the positive control CCCP (carbonyl cyanide 3-chlorophenylhydrazone), a known mitochondrial membrane potential disrupter. To confirm that JC-1 was responsive to changes in membrane potential, DHL-4 B-cells were treated with two concentrations of CCCP (500 μM and 250 μM) for 5 minutes at 37° C., 5% $CO_2$. An additional positive control was cells treated with the broad-spectrum kinase inhibitor staurosporine to induce apoptosis. The results shown in FIG. 56 are dot-plot graphs of 10,000 counts, with red fluorescence plotted on the Y-axis and green fluorescence plotted on the X-axis. A summary histogram of the percentage of cells with disrupted mitochondrial membrane potential (disrupted MMP: black bars) is shown in FIG. 56. These results demonstrate that treatment with either the 20-4×20-4 scorpion or the 011× 20-4 scorpion generated a decrease in the mitochondrial membrane potential associated with cell death.

b. Calcium Flux

Scorpion molecules were analyzed for influences on cell signaling pathways, using $Ca^{++}$ mobilization, a common feature of cell signaling, as a measure therefor. SU-DHL-6 lymphoma cells were labeled with Calcium 4 dye and treated with the test molecules identified below. Cells were read for 20 seconds to determine background fluorescence, and then SMIPs/scorpions were added (first dashed line in FIG. 28) and fluorescence was measured out to 600 seconds. At 600 seconds, an 8-fold excess of cross-linked goat-anti-human F(ab)'2 was added and fluorescence was measured for a further 300 seconds. Panel (A) of FIG. 28 shows the results obtained with a combination of CD20 SMIP and CD37 SMIP (red line); or obtained with a CD20×CD37 bispecific scorpion (black line), compared with unstimulated cells (blue line). In panel B of FIG. 28, the results of treating cells with CD20 SMIP alone (red line) resulted in $Ca^{++}$ mobilization, but this was not as robust as the signal generated by the monospecific CD20×CD20 scorpion (black line). The $Ca^{++}$ mobilization plots of FIG. 28 represent the fluorescence from triplicate wells treated with equimolar amounts of scorpion and SMIP/SMIP combinations.

c. Caspases 3, 7 and 9

The ability of CD20-binding scorpions to directly kill B-cells as evidenced by increased Annexin V and Propidium Iodide staining and the loss of mitochondrial membrane potential led to an further investigation of additional apoptosis-related effects of CD20-binding scorpions in B-cells. The approach taken was to perform Apol assays on DHL-4 B-cells exposed to CD20×CD20 scorpions or appropriate controls. The Apol assay is based on a synthetic peptide substrate for caspase 3 and 7. The assay components are available from Promega (Apo-ONE® Homogeneuous Caspase-3/7 Assay). Caspase-mediated cleavage of the labeled peptide Z-DEVD-Rhodamine 110 releases the fluorescent rhodamine 110 label, which is measured using 485 nm excitation and 530 nm detection.

Figure 57:
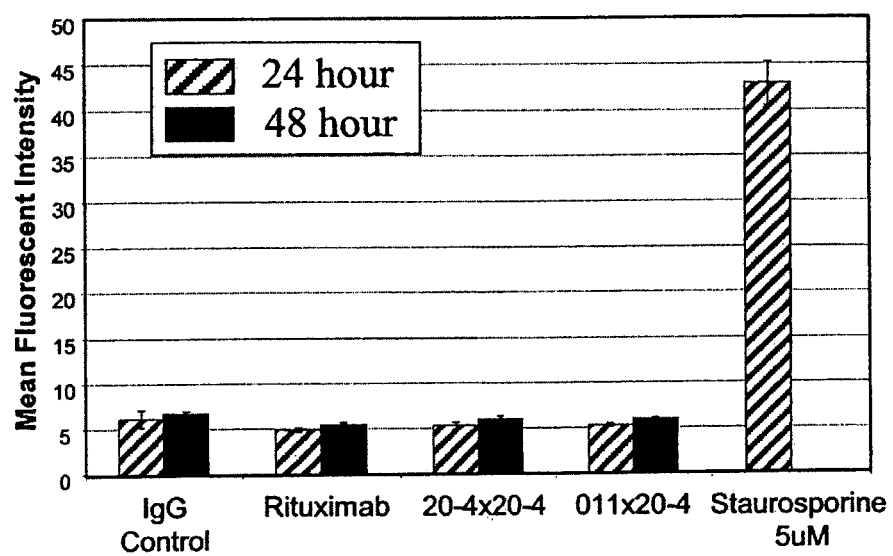
FIG. 57 provides histograms showing the relative lack of caspase 3 activation by CD20-binding scorpions (2Lm20-4× 2Lm20-4 and 011×2Lm20-4), Rituximab, CD95, and controls.

In the experiment, 100 µl DHL-4 B-cells (1×10$^6$ cells/ml) were plated in black 96-well flat-bottom tissue culture plates and treated for 24 or 48 hours with 1 µg/ml CD20×CD20 scorpion, Rituximab, an IgG control antibody, or 5 µM staurosporine at 37° C., 5% $CO_2$ in a standard tissue-culture incubator. (Staurosporine is a small-molecule, broad-spectrum protein kinase inhibitor that is known in the art as a potent inducer of classical apoptosis in a wide variety of cell types.) After 24 or 48 hours, 100 µl of the 100-fold diluted substrate was added to each well, gently mixed for one minute on a plate shaker (300 rpm) and incubated at room temperature for two hours. Fluorescence was measured using 485 nM excitation and 527 nM emission filter (Fluoroskan Ascent FL, Thermo Labsystems). Graphs showing average fluorescent intensity of triplicate treatments plus/minus standard deviation after 24 hours and 48 hours (24 hours only for staurosporine) are presented in FIG. 57. These results establish that CD20-binding scorpions do not directly kill B-cells by an apoptotic pathway involving activation of caspase 3/7.

Figure 58:
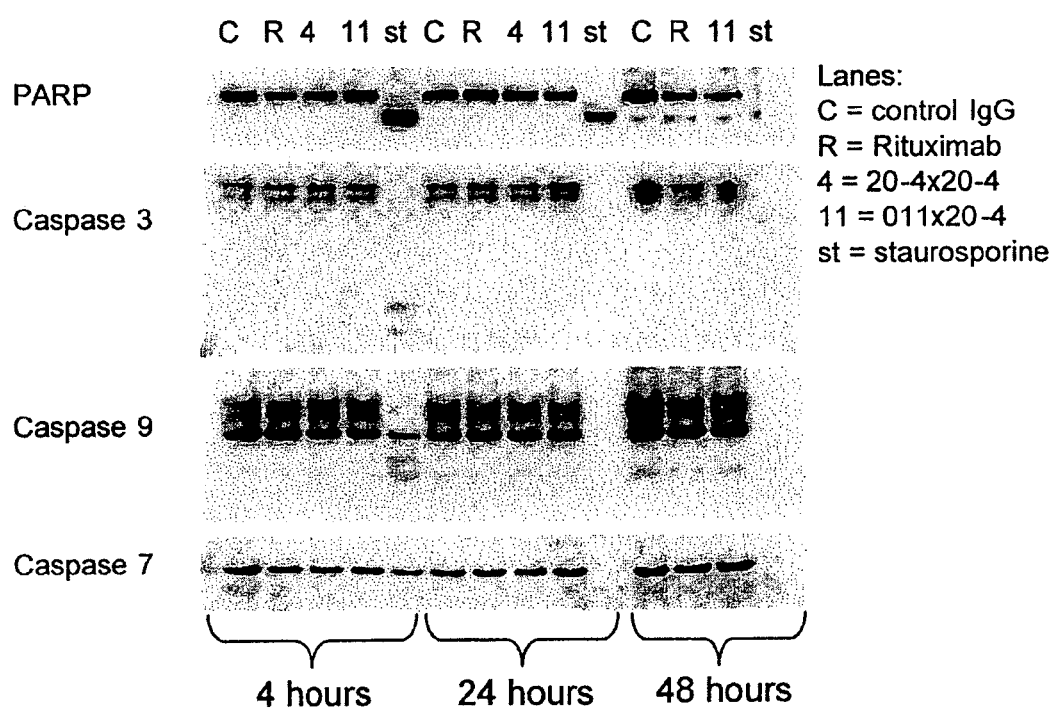
FIG. 58 provides a composite of four Western blot analyses of Poly (ADP-ribose) Polymerase and caspases 3, 7, and 9 from B-cells showing little degradation of any of these proteins attributable to CD20-binding scorpions binding to the cells.

The results obtained in the Apo-1 assay were confirmed by Western blot analyses designed to detect pro-caspase cleavage resulting in activated caspase or to detect cleavage of PARP (Poly (ADP-Ribose) Polymerase), a protein known to be cleaved by activated caspase 3. DHL-4 B-cells were exposed to a CD20 binding scorpion or a control for 4, 24, or 48 hours and cell lysates were fractionated on SDS-PAGE and blotted for Western analyses using conventional techniques. FIG. 58 presents the results in the form of a collection of Western blots. The bottom three Westerns utilized anti-caspase antibodies to detect shifts in molecular weight of the caspase enzyme, reflecting proteolytic activation. For caspases 3, 7, and 9, there was no evidence of caspase activation by any of the CD20-binding molecules. Staurosporine served as a positive control for the assay, and induced pro-caspase cleavage to active caspase for each of caspases 3, 7 and 9. The fourth Western blot shown in FIG. 58 reveals that PARP, a known substrate of activated caspase 3, was not cleaved, consistent with a failure of CD20-binding scorpions to activate caspase 3. The results of all of these experiments are consistent in showing that caspase 3 activation is not a significant feature of the direct cell killing of DHL-4 B-cells induced by CD20 binding scorpions.

In addition, a time series study was conducted to determine the effect of CD20 binding proteins, including a CD20×CD20 scorpion, on Caspase 3. DoHH2 or Su-DHL-6 B-cells were incubated with 10 nM CD20 binding protein (S0129 scorpion, 2 Lm20-4 SMIP, or Rituxan®)+/−soluble CD16 Ig (40 nM), soluble CD16 Ig alone, or media. The cells were cultured in complete RPMI with 10% FBS at 3×10$^5$/well/300 µl and harvested at 4 hours, 24 hours or 72 hours. The 72-hour time-point samples were plated in 500 µl of the test agent. Cells were washed with PBS and then stained for intracellular active caspase-3 using the BD Pharmingen Caspase 3, Active Form, mAB Apoptosis Kit:FITC (cat no. 55048, BD Pharmingen, San Jose, Calif.). Briefly, after 2 additional washes in cold PBS, the cells were suspended in cold cytofix/cytoperm solution and incubated on ice for 20 minutes. Cells were then washed by centrifugation, aspirated, and washed two times with Perm/Wash buffer at room temperature. The samples were then stained with 20 µl FITC-anti-caspase 3 in 100 µl of Perm-Wash buffer at room temperature in the dark for thirty minutes. The samples were then washed two times with Perm-Wash buffer, and resuspended in 500 µl of Perm-Wash buffer. Washed cells were then transferred to FACs tubes and run on a FACs Calibur (BD Biosciences, San Jose, Calif.) and analyzed with Cell Quest software (BD Biosciences, San Jose, Calif.). The results are shown in Table 16.

TABLE 16

| Molecule (10 nM) | Percentage Caspase-3 positive cells | | | Percentage in live gate | | |
|---|---|---|---|---|---|---|
| | 4 hours | 24 hours | 48 hours | 4 hours | 24 hours | 48 hours |
| RTXN | 7 | 25 | 7 | 75 | 53 | 56 |
| and CD16 hi (4×) | 27 | 47 | 21 | 79 | 60 | 43 |
| CD20 SMIP (2Lm20-4) | 5 | 5 | 10 | 89 | 85 | 81 |
| and CD16 hi | 28 | 54 | 21 | 61 | 60 | 41 |
| Humanized CD20 × CD20 scorpion (S00129) | 7 | 13 | 14 | 69 | 68 | 61 |
| and CD16 hi | 30 | 31 | 15 | 67 | 75 | 72 |
| Media | 7 | 5 | 9 | 89 | 82 | 80 |
| and CD16 hi | 6 | 5 | 9 | 91 | 83 | 80 |

The results of all of these experiments are consistent in showing that there is limited activation of caspase 3 in the absence of CD16, which does not implicate caspase 3 activation as a significant feature of the direct cell killing induced by CD20 binding scorpions.

d. DNA Fragmentation

Figure 59:
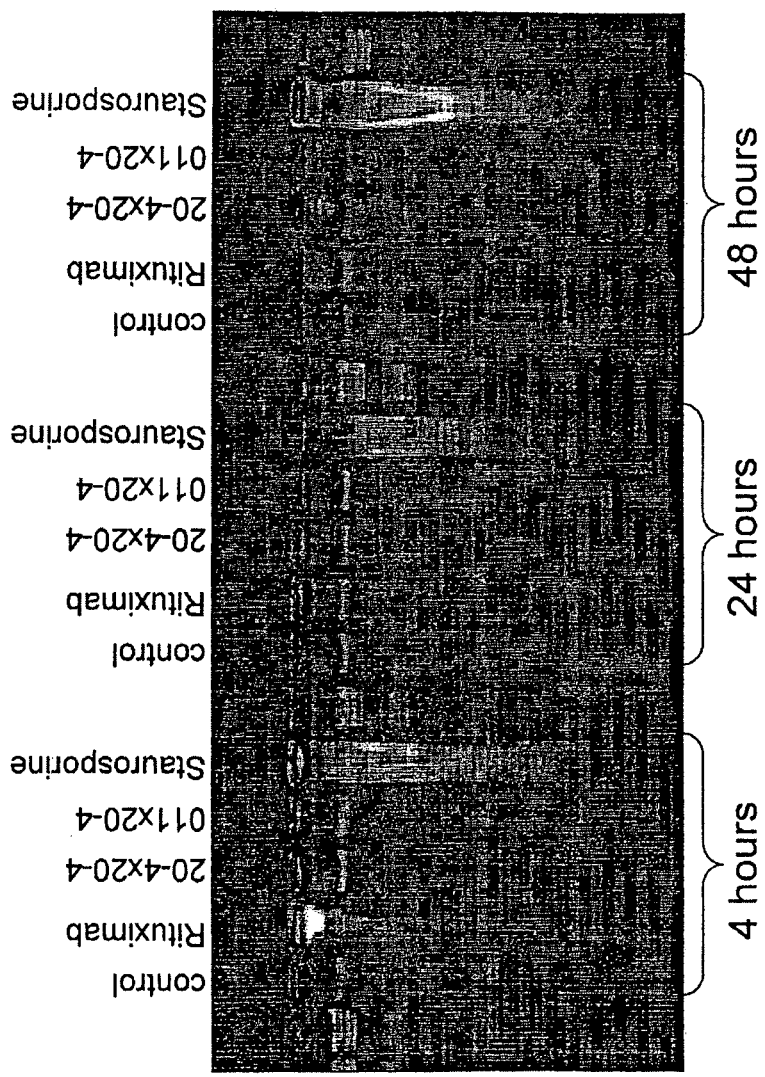
FIG. 59 is a gel electrophoretogram of B-cell chromosomal DNAs showing the degree of fragmentation attributable to CD20-binding scorpions binding to the cells.

Induction of classical apoptotic signaling pathways ultimately results in condensation and fragmented degradation of chromosomal DNA. To determine whether CD20-binding scorpions directly killed B-cells through a classical apoptotic mechanism, the state of B-cell chromosomal DNA was examined following exposure of the cells to CD20-binding scorpions, or controls. Initially, DHL-4 B-cells were treated in vitro for 4, 24 or 48 hours with a CD20-binding molecule, i.e., the monospecific CD20×CD20 (2Lm20-4×2Lm20-4) scorpion, the CD20×CD20 (011×2Lm20-4) scorpion, or Rituximab, or with a control. Subsequently, cells were lysed and chromosomal DNA was purified using conventional techniques. The chromosomal DNA was then size-fractionated by gel electrophoresis. The gel electrophoretogram shown in FIG. 59 reveals a lack of DNA fragmentation that demonstrated that the cell death generated by CD20-binding scorpions was not mediated by a classical apoptotic pathway. Staurosporine-treated cells were used as positive control in these assays.

e. SYK Phosphorylation

SYK is a phospho-regulated protein with several phosphorylation sites that functions as a transcriptional repressor. SYK is localized to the cell nucleus, but is capable of rapid relocation to the membrane upon activation. For activation, SYK must retain its nuclear localization sequence. Activated SYK has a role in suppressing breast cancer tumors and SYK is activated by pro-apoptotic signals such as ionizing radiation, BCR ligation and MHC class II cross-linking Further, SYK has been shown to affect the PLC-γ and $Ca^{++}$ pathways. Given these observations, the capacity of CD20-binding scorpions to affect SYK was investigated.

Figure 60:
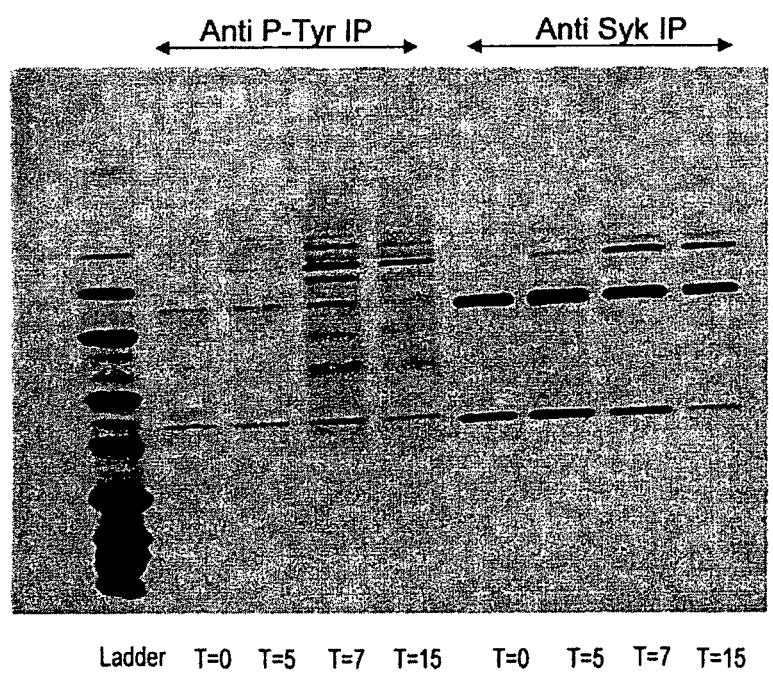
FIG. 60 is a gel electrophoretogram of immunoprecipitates obtained with each of an anti-phosphotyrosine antibody and an anti-SYK antibody. The immunoprecipitates were obtained from lysates of B-cells contacted with CD20-binding scorpions, as indicated in the figure.

DHL-6 B-cells were exposed to a bispecific CD20×CD37 scorpion for 0, 5, 7 or 15 hours and the cells were lysed. Lysates were immunoprecipitated with either an anti-phosphotyrosine antibody or with an anti-SYK antibody. Immunoprecipitates were fractionated by gel electrophoresis and the results are shown in FIG. 60. Apparent from an inspection of FIG. 60 is the failure of the bispecific CD20×CD37 scorpion to induce phosphorylation of SYK, thereby activating it. Consistent with the above-described studies on caspase activation and chromosomal DNA fragmentation, it does not appear that CD20-binding scorpions directly kill B-cells using a classic apoptotic pathway, such as the caspase-dependent pathway. While not wishing to be bound by theory, it is expected that the CD20-binding scorpions directly kill B-cells through a caspase-, and SYK-, independent pathway that does not prominently feature chromosomal DNA fragmentation, at least not on the same time frame as fragmentation occurs during caspase-dependent apoptosis.

EXAMPLE 19

Scorpion Applications a. In Vivo Activity of Scorpions

Figure 40:
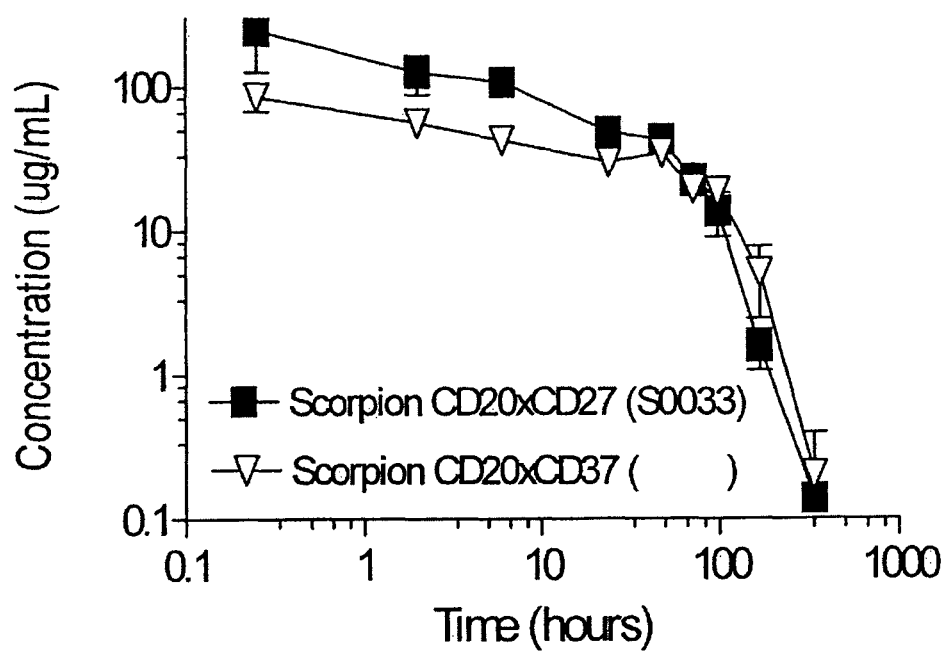
FIG. 40 shows a graph establishing that scorpions are stable in serum in vivo, characterized by a reproducible, sustained circulating half-life for the scorpion.

The activity of scorpions was also assessed using a mouse model. Measurements of scorpion activity in vivo involved administration of 10-300 µg scorpion and subsequent time-series determinations of serum concentrations of that scorpion. Results of these studies, presented as serum concentration curves for each of two bispecific scorpions (i.e., S0033, a CD20×CD27 scorpion and a CD20×CD37 scorpion) from three-week pharmacokinetic studies in mice are presented in FIG. 40. The data in FIG. 40 show that it took at least 500 hours after administration before the serum levels of each of the two bispecific scorpions fell back to baseline levels. Thus, scorpions show serum stability and reproducible, sustained circulating half-lives in vivo.

Figure 41:
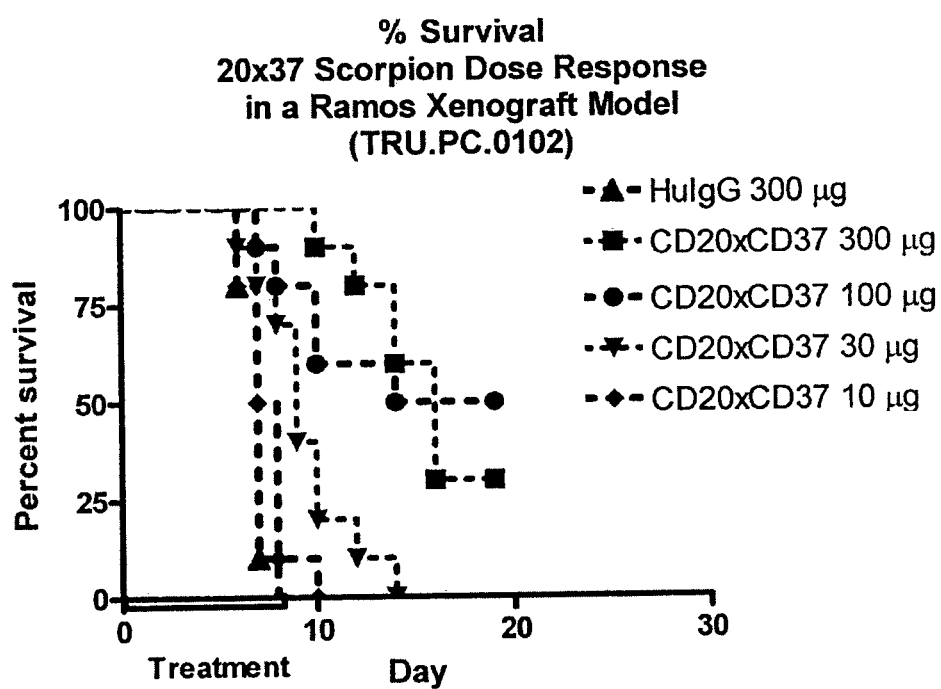
FIG. 41 provides a dose-response graph for a CD20×CD37 bispecific scorpion, demonstrating the in vivo efficacy of scorpion administration.

The in vivo efficacy of scorpions was also assessed. An aggressive Ramos xenograft model was used in parallel experiments with SMIPs versus historical immunoglobulin controls. The survival curves provided in FIG. 41 reveal that administration of 10 µg bispecific scorpion had negligible influence on survival, but administration of 100-300 µg had significant positive effect on the survival of mice bearing Ramos xenografts.

b. Combination Therapies

It is contemplated that scorpions will find application in the prevention, treatment or amelioration of a symptom of, a wide variety of conditions affecting man, other mammals and other organisms. For example, CD20-binding scorpions are expected to be useful in treating or preventing a variety of diseases associated with excessive or aberrant B-cells. In fact, any disease amenable to a treatment involving the depletion of B-cells would be amenable to treatment with a CD20-binding scorpion. In addition, scorpions, e.g., CD20-binding scorpions, may be used in combination therapies with other therapeutics. To illustrate the feasibility of a wide variety of combination therapies, the monospecific CD20×CD20 scorpion (S0129) was administered to Su-DHL-6 B-cells in combination with doxorubicin, vincristine or rapamycin. Doxorubicin is a topoisomerase II poison that interferes with DNA biochemistry and belongs to a class of drugs contemplated for anti-cancer treatment. Rapamycin (Sirolimus) is a macrolide antibiotic that inhibits the initiation of protein synthesis and suppresses the immune system, finding application in organ transplantation and as an anti-proliferative used with coronary stents to inhibit or prevent restenosis. Vincristine is a vinca alkaloid that inhibits tubule formation and has been used to treat cancer.

Figure 61:
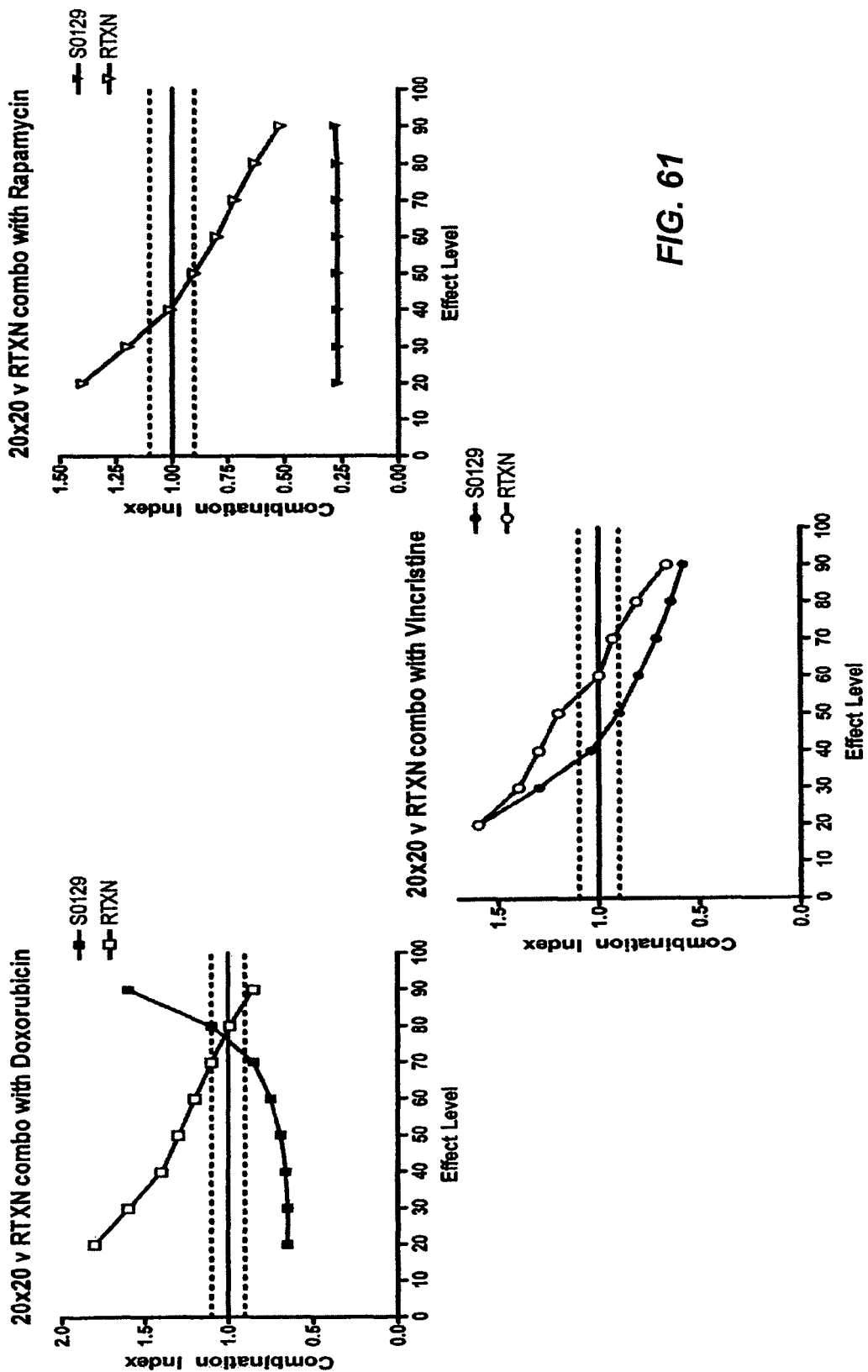
FIG. 61 provides combination index plots of CD20-binding scorpions in combination therapies with each of doxorubicin, vincristine and rapamycin.

The experimental results shown in FIG. 61 are presented as Combination Index values for each combination over a range of effect levels. The interactions of the monospecific CD20× CD20 scorpion S0129 are different for each drug class, while with Rituxan® (RTXN) the plots forms are similar. The effect seen with doxorubicin at high concentrations may reflect a shift towards monovalent binding. The data establish that CD20-binding scorpions may be used in combination with a variety of other therapeutics and such combinations would be apparent to one of skill in the art in view of the present disclosure.

Variations on the structural themes for multivalent binding molecules with effector function, or scorpions, will be apparent to those of skill in the art upon review of the present disclosure, and such variant structures are within the scope of the invention.

What is claimed is:

1. A single-chain multispecific binding protein comprising from amino-terminus to carboxy-terminus:
   (a) a first binding domain comprising variable regions from an immunoglobulin;
   (b) a first linker peptide;
   (c) a constant sub-region comprising an immunoglobulin $C_{H2}$ domain and a $C_{H3}$ domain;
   (d) a second linker peptide, wherein said second linker peptide comprises the sequence of SEQ ID NO: 165; and
   (e) a second binding domain comprising variable regions from an immunoglobulin.

2. The protein according to claim 1 wherein the first and second binding domains specifically bind different target molecules located on the same cell.

3. The protein according to claim 1 wherein the first and second binding domains specifically bind different target molecules located on physically distinct cells.

4. The protein according to claim 1 wherein at least one binding domain specifically binds a cell-free molecular target.

5. The protein according to claim 1 wherein at least one binding domain is an ssFv comprising a sequence selected from SEQ ID NO:2, 4, 6, 103, 105, 107, and 109.

6. The protein according to claim 1 wherein the first and second binding domains comprise chimeric, humanized, or human immunoglobulin variable domains.

7. The protein according to claim 1 wherein the constant sub-region comprises IgG1 immunoglobulin $C_{H2}$ and $C_{H3}$ domains.

8. The protein according to claim 1 wherein the constant sub-region is a human immunoglobulin constant sub-region.

9. The protein according to claim 1 wherein at least one binding domain specifically binds a target selected from the group consisting of a tumor antigen, a B-cell target, a TNF receptor superfamily member, a Hedgehog family member, a receptor tyrosine kinase, a proteoglycan-related molecule, a TGF-beta superfamily member, a Wnt-related molecule, a receptor ligand, a T-cell target, a Dendritic cell target, an NK cell target, a monocyte/macrophage cell target and an angiogenesis target.

10. The protein according to claim 1 wherein one of the two binding domains specifically binds a target selected from the group consisting of CD3, CD20, CD37, CD79b, CD80, CD86, IRTA1, IRTA2, IRTA3, IRTA4, IRTA5, TNFRI/TNFRSF1A, TNFRII/TNFRSF1B, Fas/TNFRSF6, TRAILR/TNFRSF10, RANK/TNFRSF11A, Osteoprotegerin/TNFRSF11B, TWEAKR/TNFRSF12, HVEM/TNFRSF14, GITR/TNFRSF18, TNF-α/TNFSF1A, TNF-β/TNFSF1B, TRAIL/TNFSF10, Fas Ligand/TNFSF6, TWEAK/TNFSF12, APRIL/TNFSF13, LIGHT/TNFSF14, GITRL/TNFSF18, FGFR, Flt-3, HGFR, IGF-IR, IGF-IIR, MSPR/Ron, PDGFRα, PDGFRβ, EGFR, ErbB2, ErbB3, VEGFR1/Flt-1, VEGFR2/Flt-1, VEGFR3/Flt-4, TGF-βRI/ALK-5, TGF-βRII, TGF, βRIIb, TGF-α, IGF-I, IGF-II, BMP, TGF-β, FGF, PlGF, PDGF-A, PDGF-B, PDGF-C, PDGF-D, VEGF, VEGF-B, VEGF-C, VEGF-D, IL-2R , IL-2Rβ, IL-4R, B7-H3, IL-6R, IL-10Rα, IL-10β, IL-12Rβ, IL-12Rβ2, IL-13RαI, Osteopontin, PD-1, CTLA-4, IFN-γR1, IFN-γR2, Receptor for Advanced Glycation End products (RAGE), IL-13, IL-22R, IL-21, and IL-4.

11. The protein according to claim 1 wherein the protein comprises a binding domain pair specifically recognizing a pair of antigens selected from the group consisting of CD19/CD20, CD19/CD22, CD19/CL II, CD20/CD21, CD20/CD22, CD20/CD40, CD20/CD79a, CD20/CD79b, CD20/CD81, CD20/CL II, CD21/CD22, CD21/CD79b, CD21/CL II, CD22/CD23, CD22/CD30, CD22/CD37, CD22/CD40, CD22/CD70, CD22/CD72, CD22/CD79a, CD22/CD79b, CD22/CD80, CD22/CD86, CD22/CL II, CD23/CL II, CD30/CL II, CD37/CD79b, CD37/CL II, CD40/CD79b, CD40/CL II, CD70/CD79b, CD70/CL II, CD72/CD79b, CD72/CL II, CD79a/CD79b, CD79b/CD80, CD79b/CD81, CD79b/CD86, CD79b/CL II, CD80/CL II, and CD86/CL II.

12. A composition comprising the protein according to claim 1 and a pharmaceutically acceptable adjuvant, carrier or excipient.

13. The protein according to claim 10, wherein one of the two binding domains specifically binds to IL-13.

14. The protein according to claim 10, wherein one of the two binding domains specifically binds to IL-4.

15. The protein according to claim 1, wherein the first linker peptide is at least five amino acids in length.

16. The composition of claim 12, wherein the composition comprises a plurality of said protein.

17. A protein dimer comprising two single-chain multispecific binding proteins according to claim 1.

* * * * *

SEQUENCE LISTING

```
<160> NUMBER OF SEQ ID NOS: 379

<210> SEQ ID NO 1
<211> LENGTH: 795
<212> TYPE: DNA
<213> ORGANISM: Artificial sequence
<220> FEATURE:
<223> OTHER INFORMATION: Synthetic polynucleotide - anti-CD20 (2H7) LH
      (DNA)

<400> SEQUENCE: 1
atggattttc aagtgcagat tttcagcttc ctgctaatca gtgcttcagt cataatgtcc        60
agaggacaaa ttgttctctc ccagtctcca gcaatcctgt ctgcatctcc aggggagaag       120
gtcacaatga cttgcagggc cagctcaagt gtaagttaca tgcactggta ccagcagaag       180
ccaggatcct cccccaaacc ctggatttat gccccatcca acctggcttc tggagtccct       240
gctcgcttca gtggcagtgg gtctgggacc tcttactctc tcacaatcag cagagtggag       300
```

```
gctgaagatg ctgccactta ttactgccag cagtggagtt ttaacccacc cacgttcggt    360
gctgggacca agctggagct gaaagatggc ggtggctcgg gcggtggtgg atctggagga    420
ggtgggagct ctcaggctta tctacagcag tctggggctg agtcggtgag gcctggggcc    480
tcagtgaaga tgtcctgcaa ggcttctggc tacacattta ccagttacaa tatgcactgg    540
gtaaagcaga cacctagaca gggcctggaa tggattggag ctatttatcc aggaaatggt    600
gatacttcct acaatcagaa gttcaagggc aaggccacac tgactgtaga caaatcctcc    660
agcacagcct acatgcagct cagcagcctg acatctgaag actctgcggt ctatttctgt    720
gcaagagtgg tgtactatag taactcttac tggtacttcg atgtctgggg cacagggacc    780
acggtcaccg tctct                                                    795
```

```
<210> SEQ ID NO 2
<211> LENGTH: 265
<212> TYPE: PRT
<213> ORGANISM: Artificial sequence
<220> FEATURE:
<223> OTHER INFORMATION: Synthetic polypeptide - anti-CD20 (2H7) LH (AA)
<220> FEATURE:
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (23)..(128)
<223> OTHER INFORMATION: VL
<220> FEATURE:
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH
```

<400> SEQUENCE: 2

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Gly Ser Gly Gly Gly Gly Ser Ser
    130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

-continued

```
Gly Ala Ile Tyr Pro Gly Asn Gly Asp Thr Ser Tyr Asn Gln Lys Phe
            195                 200                 205
Lys Gly Lys Ala Thr Leu Thr Val Asp Lys Ser Ser Thr Ala Tyr
    210                 215                 220
Met Gln Leu Ser Ser Leu Thr Ser Glu Asp Ser Ala Val Tyr Phe Cys
225                 230                 235                 240
Ala Arg Val Val Tyr Tyr Ser Asn Ser Tyr Trp Tyr Phe Asp Val Trp
                245                 250                 255
Gly Thr Gly Thr Thr Val Thr Val Ser
            260                 265

<210> SEQ ID NO 3
<211> LENGTH: 813
<212> TYPE: DNA
<213> ORGANISM: Artificial sequence
<220> FEATURE:
<223> OTHER INFORMATION: Synthetic polynucleotide - anti-CD28 (2e12) LH
      (DNA)

<400> SEQUENCE: 3
atggattttc aagtgcagat tttcagcttc ctgctaatca gtgcttcagt cataatgtcc      60
agaggagtcg acattgtgct cacccaatct ccagcttctt tggctgtgtc tctaggtcag     120
agagccacca tctcctgcag agccagtgaa agtgttgaat attatgtcac aagtttaatg     180
cagtggtacc aacagaaacc aggacagcca cccaaactcc tcatctctgc tgctagcaac     240
gtagaatctg ggtccctgc caggtttagt ggcagtgggt ctgggacaga ctttagcctc     300
aacatccatc ctgtggagga ggatgatatt gcaatgtatt tctgtcagca aagtaggaag     360
gttccatgga cgttcggtgg aggcaccaag ctggaaatca acggggtgg cggtggatcc     420 ggcggaggtg ggtcgggtgg cggcggatct caggtgcagc tgaaggagtc aggacctggc     480
ctggtggcgc cctcacagag cctgtccatc acatgcaccg tctcagggtt ctcattaacc     540
ggctatggtg taaactgggt tcgccagcct ccaggaaagg gtctggagtg gctgggaatg     600
atatggggtg atggaagcac agactataat tcagctctca aatccagact atcgatcacc     660
aaggacaact ccaagagcca gtttttctta aaaatgaaca gtctgcaaac tgatgacaca     720
gccagatact actgtgcccg agatggttat agtaactttc attactatgt tatggactac     780
tggggtcaag gaacctcagt caccgtctcc tct                                  813

<210> SEQ ID NO 4
<211> LENGTH: 271
<212> TYPE: PRT
<213> ORGANISM: Artificial sequence
<220> FEATURE:
<223> OTHER INFORMATION: Synthetic polypeptide - anti-CD28 (2e12) LH
      (AA)
<220> FEATURE:
<221> NAME/KEY: misc_feature
<222> LOCATION: (1)..(23)
<223> OTHER INFORMATION: Leader
<220> FEATURE:
<221> NAME/KEY: misc_feature
<222> LOCATION: (24)..(135)
<223> OTHER INFORMATION: VL
<220> FEATURE:
<221> NAME/KEY: misc_feature
<222> LOCATION: (136)..(150)
<223> OTHER INFORMATION: Linker
<220> FEATURE:
<221> NAME/KEY: misc_feature
<222> LOCATION: (151)..(271)
<223> OTHER INFORMATION: VH
```

-continued

<400> SEQUENCE: 4

```
Met Asp Phe Gln Val Gln Ile Phe Ser Phe Leu Leu Ile Ser Ala Ser
1               5                   10                  15

Val Ile Met Ser Arg Gly Val Asp Ile Val Leu Thr Gln Ser Pro Ala
            20                  25                  30

Ser Leu Ala Val Ser Leu Gly Gln Arg Ala Thr Ile Ser Cys Arg Ala
        35                  40                  45

Ser Glu Ser Val Glu Tyr Tyr Val Thr Ser Leu Met Gln Trp Tyr Gln
    50                  55                  60

Gln Lys Pro Gly Gln Pro Pro Lys Leu Leu Ile Ser Ala Ala Ser Asn
65                  70                  75                  80

Val Glu Ser Gly Val Pro Ala Arg Phe Ser Gly Ser Gly Ser Gly Thr
                85                  90                  95

Asp Phe Ser Leu Asn Ile His Pro Val Glu Glu Asp Ile Ala Met
            100                 105                 110

Tyr Phe Cys Gln Gln Ser Arg Lys Val Pro Trp Thr Phe Gly Gly Gly
        115                 120                 125

Thr Lys Leu Glu Ile Lys Arg Gly Gly Gly Ser Gly Gly Gly Gly
    130                 135                 140

Ser Gly Gly Gly Gly Ser Gln Val Gln Leu Lys Glu Ser Gly Pro Gly
145                 150                 155                 160

Leu Val Ala Pro Ser Gln Ser Leu Ser Ile Thr Cys Thr Val Ser Gly
                165                 170                 175

Phe Ser Leu Thr Gly Tyr Gly Val Asn Trp Val Arg Gln Pro Pro Gly
            180                 185                 190

Lys Gly Leu Glu Trp Leu Gly Met Ile Trp Gly Asp Gly Ser Thr Asp
        195                 200                 205

Tyr Asn Ser Ala Leu Lys Ser Arg Leu Ser Ile Thr Lys Asp Asn Ser
    210                 215                 220

Lys Ser Gln Val Phe Leu Lys Met Asn Ser Leu Gln Thr Asp Asp Thr
225                 230                 235                 240

Ala Arg Tyr Tyr Cys Ala Arg Asp Gly Tyr Ser Asn Phe His Tyr Tyr
                245                 250                 255

Val Met Asp Tyr Trp Gly Gln Gly Thr Ser Val Thr Val Ser Ser
            260                 265                 270
```

<210> SEQ ID NO 5
<211> LENGTH: 828
<212> TYPE: DNA
<213> ORGANISM: Artificial sequence
<220> FEATURE:
<223> OTHER INFORMATION: Synthetic polynucleotide - anti-CD28 (2e12) HL
      (DNA)

<400> SEQUENCE: 5

```
atggatttc aagtgcagat ttcagcttc ctgctaatca gtgcttcagt cataatgtcc        60
agaggagtcc aggtgcagct gaaggagtca ggacctggcc tggtggcgcc ctcacagagc     120
ctgtccatca catgaccgt ctcagggttc tcattaaccg gctatggtgt aaactgggtt      180
cgccagcctc caggaaaggg tctggagtgg ctgggaatga tatggggtga tggaagcaca    240
gactataatt cagctctcaa atccagacta tcgatcacca aggacaactc caagagccaa    300
gttttcttaa aaatgaacag tctgcaaact gatgacacag ccagatacta ctgtgcccga    360
gatggttata gtaactttca ttactatgtt atggactact ggggtcaagg aacctcagtc    420
accgtctcct ctggggggtgg aggctctggt ggcggtggat ccggcggagg tgggtcgggt    480
```

-continued

```
ggcggcggat ctgacattgt gctcacccaa tctccagctt ctttggctgt gtctctaggt      540
cagagagcca ccatctcctg cagagccagt gaaagtgttg aatattatgt cacaagttta      600
atgcagtggt accaacagaa accaggacag ccacccaaac tcctcatctc tgctgctagc      660
aacgtagaat ctggggtccc tgccaggttt agtggcagtg ggtctgggac agactttagc      720
ctcaacatcc atcctgtgga ggaggatgat attgcaatgt atttctgtca gcaaagtagg      780
aaggttccat ggacgttcgg tggaggcacc aagctggaaa tcaaacgt                   828
```

<210> SEQ ID NO 6
<211> LENGTH: 276
<212> TYPE: PRT
<213> ORGANISM: Artificial sequence
<220> FEATURE:
<223> OTHER INFORMATION: Synthetic polypeptide - anti-CD28 (2e12) HL (AA)
<220> FEATURE:
<221> NAME/KEY: misc_feature
<222> LOCATION: (1)..(23)
<223> OTHER INFORMATION: Leader
<220> FEATURE:
<221> NAME/KEY: misc_feature
<222> LOCATION: (24)..(144)
<223> OTHER INFORMATION: VH
<220> FEATURE:
<221> NAME/KEY: misc_feature
<222> LOCATION: (145)..(164)
<223> OTHER INFORMATION: Linker
<220> FEATURE:
<221> NAME/KEY: misc_feature
<222> LOCATION: (165)..(276)
<223> OTHER INFORMATION: VL

<400> SEQUENCE: 6

```
Met Asp Phe Gln Val Gln Ile Phe Ser Phe Leu Leu Ile Ser Ala Ser
1               5                   10                  15

Val Ile Met Ser Arg Gly Val Gln Val Gln Leu Lys Glu Ser Gly Pro
            20                  25                  30

Gly Leu Val Ala Pro Ser Gln Ser Leu Ser Ile Thr Cys Thr Val Ser
        35                  40                  45

Gly Phe Ser Leu Thr Gly Tyr Gly Val Asn Trp Val Arg Gln Pro Pro
    50                  55                  60

Gly Lys Gly Leu Glu Trp Leu Gly Met Ile Trp Gly Asp Gly Ser Thr
65                  70                  75                  80

Asp Tyr Asn Ser Ala Leu Lys Ser Arg Leu Ser Ile Thr Lys Asp Asn
                85                  90                  95

Ser Lys Ser Gln Val Phe Leu Lys Met Asn Ser Leu Gln Thr Asp Asp
            100                 105                 110

Thr Ala Arg Tyr Tyr Cys Ala Arg Asp Gly Tyr Ser Asn Phe His Tyr
        115                 120                 125

Tyr Val Met Asp Tyr Trp Gly Gln Gly Thr Ser Val Thr Val Ser Ser
    130                 135                 140

Gly Gly Gly Gly Ser Gly Gly Gly Ser Gly Gly Gly Ser Gly
145                 150                 155                 160

Gly Gly Gly Ser Asp Ile Val Leu Thr Gln Ser Pro Ala Ser Leu Ala
                165                 170                 175

Val Ser Leu Gly Gln Arg Ala Thr Ile Ser Cys Arg Ala Ser Glu Ser
            180                 185                 190

Val Glu Tyr Tyr Val Thr Ser Leu Met Gln Trp Tyr Gln Gln Lys Pro
        195                 200                 205

Gly Gln Pro Pro Lys Leu Leu Ile Ser Ala Ala Ser Asn Val Glu Ser
    210                 215                 220
```

```
Gly Val Pro Ala Arg Phe Ser Gly Ser Gly Ser Gly Thr Asp Phe Ser
225                 230                 235                 240

Leu Asn Ile His Pro Val Glu Glu Asp Asp Ile Ala Met Tyr Phe Cys
            245                 250                 255

Gln Gln Ser Arg Lys Val Pro Trp Thr Phe Gly Gly Gly Thr Lys Leu
        260                 265                 270

Glu Ile Lys Arg
        275

<210> SEQ ID NO 7
<211> LENGTH: 30
<212> TYPE: DNA
<213> ORGANISM: Artificial sequence
<220> FEATURE:
<223> OTHER INFORMATION: Synthetic primer - Heavy Chain GSP1

<400> SEQUENCE: 7
aggtgctgga ggggacagtc actgagctgc                                          30

<210> SEQ ID NO 8
<211> LENGTH: 28
<212> TYPE: DNA
<213> ORGANISM: Artificial sequence
<220> FEATURE:
<223> OTHER INFORMATION: Synthetic primer - Nested Heavy Chain

<400> SEQUENCE: 8
gtcacwgtca ctgrctcagg gaartagc                                            28

<210> SEQ ID NO 9
<211> LENGTH: 33
<212> TYPE: DNA
<213> ORGANISM: Artificial sequence
<220> FEATURE:
<223> OTHER INFORMATION: Synthetic primer - Light Chain GSP1

<400> SEQUENCE: 9
gggtgctgct catgctgtag gtgctgtctt tgc                                      33

<210> SEQ ID NO 10
<211> LENGTH: 32
<212> TYPE: DNA
<213> ORGANISM: Artificial sequence
<220> FEATURE:
<223> OTHER INFORMATION: Synthetic primer - Nested Light Chain

<400> SEQUENCE: 10
caagaagcac acgactgagg cacctccaga tg                                       32

<210> SEQ ID NO 11
<211> LENGTH: 36
<212> TYPE: DNA
<213> ORGANISM: Artificial sequence
<220> FEATURE:
<223> OTHER INFORMATION: Synthetic primer - Race Abridged Anchor Primer
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
```

```
<400> SEQUENCE: 11
ggccacgcgt cgactagtac gggnngggnn gggnng                              36

<210> SEQ ID NO 12
<211> LENGTH: 20
<212> TYPE: DNA
<213> ORGANISM: Artificial sequence
<220> FEATURE:
<223> OTHER INFORMATION: Synthetic primer - T7 primer

<400> SEQUENCE: 12
gtaatacgac tcactatagg                                                20

<210> SEQ ID NO 13
<211> LENGTH: 18
<212> TYPE: DNA
<213> ORGANISM: Artificial sequence
<220> FEATURE:
<223> OTHER INFORMATION: Synthetic primer - M13 reverse primer

<400> SEQUENCE: 13
caggaaacag ctatgacc                                                  18

<210> SEQ ID NO 14
<211> LENGTH: 15
<212> TYPE: PRT
<213> ORGANISM: Homo sapiens
<220> FEATURE:
<223> OTHER INFORMATION: human IgG1 hinge domain

<400> SEQUENCE: 14

Glu Pro Lys Ser Cys Asp Lys Thr His Thr Cys Pro Pro Cys Pro
1               5                   10                  15

<210> SEQ ID NO 15
<211> LENGTH: 46
<212> TYPE: DNA
<213> ORGANISM: Homo sapiens
<220> FEATURE:
<223> OTHER INFORMATION: hVK3L-F3H3

<400> SEQUENCE: 15
gcgataaagc ttgccgccat ggaagcacca gcgcagcttc tcttcc                   46

<210> SEQ ID NO 16
<211> LENGTH: 50
<212> TYPE: DNA
<213> ORGANISM: Homo sapiens
<220> FEATURE:
<223> OTHER INFORMATION: hVK3LF2

<400> SEQUENCE: 16
accagcgcag cttctcttcc tcctgctact ctggctccca gataccaccg               50

<210> SEQ ID NO 17
<211> LENGTH: 45
<212> TYPE: DNA
<213> ORGANISM: Homo sapiens
<220> FEATURE:
<223> OTHER INFORMATION: hVK3LF12HVL

<400> SEQUENCE: 17
ggctcccaga taccaccggt caaattgttc tctcccagtc tccag                    45

<210> SEQ ID NO 18
```

```
<211> LENGTH: 35
<212> TYPE: DNA
<213> ORGANISM: Artificial sequence
<220> FEATURE:
<223> OTHER INFORMATION: Synthetic primer - 2H7VHNheF

<400> SEQUENCE: 18
gcgatagcta gccaggctta tctacagcag tctgg                              35

<210> SEQ ID NO 19
<211> LENGTH: 43
<212> TYPE: DNA
<213> ORGANISM: Artificial sequence
<220> FEATURE:
<223> OTHER INFORMATION: Synthetic primer - G4SNheR

<400> SEQUENCE: 19
gcgatagcta gccccacctc ctccagatcc accaccgccc gag                     43

<210> SEQ ID NO 20
<211> LENGTH: 35
<212> TYPE: DNA
<213> ORGANISM: Artificial sequence
<220> FEATURE:
<223> OTHER INFORMATION: Synthetic primer - O15VHXhoR

<400> SEQUENCE: 20
gcgtactcga ggagacggtg accgtggtcc ctgtg                              35

<210> SEQ ID NO 21
<211> LENGTH: 37
<212> TYPE: DNA
<213> ORGANISM: Artificial sequence
<220> FEATURE:
<223> OTHER INFORMATION: Synthetic primer - G1HC-Xho

<400> SEQUENCE: 21
gcagtctcga gcgagcccaa atcttgtgac aaaactc                            37

<210> SEQ ID NO 22
<211> LENGTH: 37
<212> TYPE: DNA
<213> ORGANISM: Artificial sequence
<220> FEATURE:
<223> OTHER INFORMATION: Synthetic primer - G1H-S-Xho

<400> SEQUENCE: 22
gcagtctcga gcgagcccaa atcttctgac aaaactc                            37

<210> SEQ ID NO 23
<211> LENGTH: 36
<212> TYPE: DNA
<213> ORGANISM: Artificial sequence
<220> FEATURE:
<223> OTHER INFORMATION: Synthetic primer - CH3REcoR1

<400> SEQUENCE: 23
gcgtgagaat tcttacccgg agacagggag aggctc                             36

<210> SEQ ID NO 24
<211> LENGTH: 32
<212> TYPE: DNA
<213> ORGANISM: Artificial sequence
<220> FEATURE:
<223> OTHER INFORMATION: Synthetic primer - G1 XBZ-R

<400> SEQUENCE: 24
```
gcgacgtcta gagtcattta cccggagaca gg                          32

<210> SEQ ID NO 25
<211> LENGTH: 54
<212> TYPE: DNA
<213> ORGANISM: Artificial sequence
<220> FEATURE:
<223> OTHER INFORMATION: Synthetic primer - G4SLinkR1-S

<400> SEQUENCE: 25
aattatggtg gcggtggctc gggcggtggt ggatctggag gaggtgggag tggg    54

<210> SEQ ID NO 26
<211> LENGTH: 54
<212> TYPE: DNA
<213> ORGANISM: Artificial sequence
<220> FEATURE:
<223> OTHER INFORMATION: Synthetic primer - G4SLinkR1-AS

<400> SEQUENCE: 26
aattcccact cccacctcct ccagatccac caccgcccga gccaccgcca ccat    54

<210> SEQ ID NO 27
<211> LENGTH: 36
<212> TYPE: DNA
<213> ORGANISM: Artificial sequence
<220> FEATURE:
<223> OTHER INFORMATION: Synthetic primer - 2E12VLXbaR

<400> SEQUENCE: 27
gcgtgtctag attaacgttt gatttccagc ttggtg                      36

<210> SEQ ID NO 28
<211> LENGTH: 35
<212> TYPE: DNA
<213> ORGANISM: Artificial sequence
<220> FEATURE:
<223> OTHER INFORMATION: Synthetic primer - 2E12VLR1F

<400> SEQUENCE: 28
gcgatgaatt ctgacattgt gctcacccaa tctcc                       35

<210> SEQ ID NO 29
<211> LENGTH: 34
<212> TYPE: DNA
<213> ORGANISM: Artificial sequence
<220> FEATURE:
<223> OTHER INFORMATION: Synthetic primer - 2E12VHR1F

<400> SEQUENCE: 29
gcgatgaatt ctcaggtgca gctgaaggag tcag                        34

<210> SEQ ID NO 30
<211> LENGTH: 37
<212> TYPE: DNA
<213> ORGANISM: Artificial sequence
<220> FEATURE:
<223> OTHER INFORMATION: Synthetic primer - 2E12VHXbaR

<400> SEQUENCE: 30
gcgagtctag attaagagga gacggtgact gaggttc                     37

<210> SEQ ID NO 31
<211> LENGTH: 27
<212> TYPE: DNA
<213> ORGANISM: Artificial sequence
<220> FEATURE:

-continued

<223> OTHER INFORMATION: Synthetic primer - 2e12VHdXbaF1

<400> SEQUENCE: 31
gggtctggag tggctgggaa tgatatg                                27

<210> SEQ ID NO 32
<211> LENGTH: 28
<212> TYPE: DNA
<213> ORGANISM: Artificial sequence
<220> FEATURE:
<223> OTHER INFORMATION: Synthetic primer - 2e12VHdXbaR1

<400> SEQUENCE: 32
attcccagcc actccagacc ctttcctg                               28

<210> SEQ ID NO 33
<211> LENGTH: 23
<212> TYPE: DNA
<213> ORGANISM: Artificial sequence
<220> FEATURE:
<223> OTHER INFORMATION: Synthetic primer - IgBsrG1F

<400> SEQUENCE: 33
gagaaccaca ggtgtacacc ctg                                    23

<210> SEQ ID NO 34
<211> LENGTH: 25
<212> TYPE: DNA
<213> ORGANISM: Artificial sequence
<220> FEATURE:
<223> OTHER INFORMATION: Synthetic primer - IgBsrG1R

<400> SEQUENCE: 34
gcagggtgta cacctgtggt tctcg                                  25

<210> SEQ ID NO 35
<211> LENGTH: 17
<212> TYPE: DNA
<213> ORGANISM: Artificial sequence
<220> FEATURE:
<223> OTHER INFORMATION: Synthetic primer - M13R

<400> SEQUENCE: 35
caggaaacag ctatgac                                           17

<210> SEQ ID NO 36
<211> LENGTH: 18
<212> TYPE: DNA
<213> ORGANISM: Artificial sequence
<220> FEATURE:
<223> OTHER INFORMATION: Synthetic primer - M13F

<400> SEQUENCE: 36
gtaaaacgac ggccagtg                                          18

<210> SEQ ID NO 37
<211> LENGTH: 20
<212> TYPE: DNA
<213> ORGANISM: Artificial sequence
<220> FEATURE:
<223> OTHER INFORMATION: Synthetic primer - T7

<400> SEQUENCE: 37
gtaatacgac tcactatagg                                        20

<210> SEQ ID NO 38

```
<211> LENGTH: 17
<212> TYPE: DNA
<213> ORGANISM: Artificial sequence
<220> FEATURE:
<223> OTHER INFORMATION: Synthetic primer - pD18F-17

<400> SEQUENCE: 38
aactagagaa cccactg                                                    17

<210> SEQ ID NO 39
<211> LENGTH: 20
<212> TYPE: DNA
<213> ORGANISM: Artificial sequence
<220> FEATURE:
<223> OTHER INFORMATION: Synthetic primer - pD18F-20

<400> SEQUENCE: 39
gctaactaga gaacccactg                                                 20

<210> SEQ ID NO 40
<211> LENGTH: 18
<212> TYPE: DNA
<213> ORGANISM: Artificial sequence
<220> FEATURE:
<223> OTHER INFORMATION: Synthetic primer - pD18F-1

<400> SEQUENCE: 40
atacgactca ctataggg                                                   18

<210> SEQ ID NO 41
<211> LENGTH: 19
<212> TYPE: DNA
<213> ORGANISM: Artificial sequence
<220> FEATURE:
<223> OTHER INFORMATION: Synthetic primer - pD18R-s

<400> SEQUENCE: 41
gctctagcat ttaggtgac                                                  19

<210> SEQ ID NO 42
<211> LENGTH: 18
<212> TYPE: DNA
<213> ORGANISM: Artificial sequence
<220> FEATURE:
<223> OTHER INFORMATION: Synthetic primer - CH3seqF1

<400> SEQUENCE: 42
catgaggctc tgcacaac                                                   18

<210> SEQ ID NO 43
<211> LENGTH: 18
<212> TYPE: DNA
<213> ORGANISM: Artificial sequence
<220> FEATURE:
<223> OTHER INFORMATION: Synthetic primer - CH3seqF2

<400> SEQUENCE: 43
cctctacagc aagctcac                                                   18

<210> SEQ ID NO 44
<211> LENGTH: 19
<212> TYPE: DNA
<213> ORGANISM: Artificial sequence
<220> FEATURE:
<223> OTHER INFORMATION: Synthetic primer - CH3seqR1

<400> SEQUENCE: 44
```

-continued

```
ggttcttggt cagctcatc                                                   19

<210> SEQ ID NO 45
<211> LENGTH: 18
<212> TYPE: DNA
<213> ORGANISM: Artificial sequence
<220> FEATURE:
<223> OTHER INFORMATION: Synthetic primer - CH3seqR2

<400> SEQUENCE: 45
gtgagcttgc tgtagagg                                                    18

<210> SEQ ID NO 46
<211> LENGTH: 51
<212> TYPE: DNA
<213> ORGANISM: Artificial sequence
<220> FEATURE:
<223> OTHER INFORMATION: Synthetic primer - L1-11R

<400> SEQUENCE: 46
gcgatagaat cccagatcc accaccgccc gagccaccgc caccataatt c                51

<210> SEQ ID NO 47
<211> LENGTH: 36
<212> TYPE: DNA
<213> ORGANISM: Artificial sequence
<220> FEATURE:
<223> OTHER INFORMATION: Synthetic primer - L1-6R

<400> SEQUENCE: 47
gcgatagaat cccagagcc accgccacca taattc                                 36

<210> SEQ ID NO 48
<211> LENGTH: 45
<212> TYPE: DNA
<213> ORGANISM: Artificial sequence
<220> FEATURE:
<223> OTHER INFORMATION: Synthetic primer - L3R

<400> SEQUENCE: 48
gcgtatgaat tccccgagcc accgccaccc ttacccggag acagg                      45

<210> SEQ ID NO 49
<211> LENGTH: 49
<212> TYPE: DNA
<213> ORGANISM: Artificial sequence
<220> FEATURE:
<223> OTHER INFORMATION: Synthetic primer - L4R

<400> SEQUENCE: 49
gcgtatgaat tcccagatcc accaccgccc gagccaccgc cacccttac                  49

<210> SEQ ID NO 50
<211> LENGTH: 44
<212> TYPE: DNA
<213> ORGANISM: Artificial sequence
<220> FEATURE:
<223> OTHER INFORMATION: Synthetic primer - L5R

<400> SEQUENCE: 50
gcgtatgaat tcccgctgcc tcctccccca gatccaccac cgcc                       44

<210> SEQ ID NO 51
<211> LENGTH: 23
<212> TYPE: DNA
<213> ORGANISM: Artificial sequence
<220> FEATURE:
```

<223> OTHER INFORMATION: Synthetic primer - IgBsrG1F

<400> SEQUENCE: 51
gagaaccaca ggtgtacacc ctg                                           23

<210> SEQ ID NO 52
<211> LENGTH: 50
<212> TYPE: DNA
<213> ORGANISM: Artificial sequence
<220> FEATURE:
<223> OTHER INFORMATION: Synthetic primer - L-CPPCPR

<400> SEQUENCE: 52
gcgatagaat tcggacaagg tggacacccc ttacccggag acagggagag              50

<210> SEQ ID NO 53
<211> LENGTH: 41
<212> TYPE: DNA
<213> ORGANISM: Artificial sequence
<220> FEATURE:
<223> OTHER INFORMATION: Synthetic primer - G281LH-NheR

<400> SEQUENCE: 53
actgctgcag ctggaccgcg ctagctccgc cgccacccga c                       41

<210> SEQ ID NO 54
<211> LENGTH: 40
<212> TYPE: DNA
<213> ORGANISM: Artificial sequence
<220> FEATURE:
<223> OTHER INFORMATION: Synthetic primer - G281LH-NheF

<400> SEQUENCE: 54
ggcggagcta gcgcggtcca gctgcagcag tctggacctg                         40

<210> SEQ ID NO 55
<211> LENGTH: 37
<212> TYPE: DNA
<213> ORGANISM: Artificial sequence
<220> FEATURE:
<223> OTHER INFORMATION: Synthetic primer - G281-LH-LPinF

<400> SEQUENCE: 55
gcgatcaccg gtgacatcca gatgactcag tctccag                            37

<210> SEQ ID NO 56
<211> LENGTH: 37
<212> TYPE: DNA
<213> ORGANISM: Artificial sequence
<220> FEATURE:
<223> OTHER INFORMATION: Synthetic primer - G281-LH-HXhoR

<400> SEQUENCE: 56
gcgatactcg aggagacggt gactgaggtt ccttgac                            37

<210> SEQ ID NO 57
<211> LENGTH: 38
<212> TYPE: DNA
<213> ORGANISM: Artificial sequence
<220> FEATURE:
<223> OTHER INFORMATION: Synthetic primer - G281-LH-LEcoF

<400> SEQUENCE: 57
gcgatcgaat tcagacatcc agatgactca gtctccag                           38

<210> SEQ ID NO 58

```
<211> LENGTH: 43
<212> TYPE: DNA
<213> ORGANISM: Artificial sequence
<220> FEATURE:
<223> OTHER INFORMATION: Synthetic primer - G281-LH-HXbaR

<400> SEQUENCE: 58
gcgattctag attaggaaga cacggtgact gaggttcctt gac                          43

<210> SEQ ID NO 59
<211> LENGTH: 37
<212> TYPE: DNA
<213> ORGANISM: Artificial sequence
<220> FEATURE:
<223> OTHER INFORMATION: Synthetic primer - G281-HL-HF

<400> SEQUENCE: 59
gcgataaccg gtgcggtcca gctgcagcag tctggac                                 37

<210> SEQ ID NO 60
<211> LENGTH: 52
<212> TYPE: DNA
<213> ORGANISM: Artificial sequence
<220> FEATURE:
<223> OTHER INFORMATION: Synthetic primer - G281-HL-HR3

<400> SEQUENCE: 60
gacccaccac cgcccgagcc accgccacca gaagagacgg tgactgaggt tc                52

<210> SEQ ID NO 61
<211> LENGTH: 49
<212> TYPE: DNA
<213> ORGANISM: Artificial sequence
<220> FEATURE:
<223> OTHER INFORMATION: Synthetic primer - G281-HL-HR2

<400> SEQUENCE: 61
actcccgcct cctcctgatc cgccgccacc cgacccacca ccgcccgag                    49

<210> SEQ ID NO 62
<211> LENGTH: 42
<212> TYPE: DNA
<213> ORGANISM: Artificial sequence
<220> FEATURE:
<223> OTHER INFORMATION: Synthetic primer - G281-HL-HNheR

<400> SEQUENCE: 62
gagtcatctg gatgtcgcta gcactcccgc ctcctcctga tc                           42

<210> SEQ ID NO 63
<211> LENGTH: 45
<212> TYPE: DNA
<213> ORGANISM: Artificial sequence
<220> FEATURE:
<223> OTHER INFORMATION: Synthetic primer - G281-HL-LNheF

<400> SEQUENCE: 63
atcaggagga ggcgggagtg ctagcgacat ccagatgact cagtc                        45

<210> SEQ ID NO 64
<211> LENGTH: 37
<212> TYPE: DNA
<213> ORGANISM: Artificial sequence
<220> FEATURE:
<223> OTHER INFORMATION: Synthetic primer - G281-HL-LXhoR

<400> SEQUENCE: 64
```
gcgatactcg agcctttgat ctccagttcg gtgcctc    37

<210> SEQ ID NO 65
<211> LENGTH: 42
<212> TYPE: DNA
<213> ORGANISM: Artificial sequence
<220> FEATURE:
<223> OTHER INFORMATION: Synthetic primer - G281-HL-LXhoR

<400> SEQUENCE: 65
gcgatatcta gactcaacct ttgatctcca gttcggtgcc tc    42

<210> SEQ ID NO 66
<211> LENGTH: 37
<212> TYPE: DNA
<213> ORGANISM: Artificial sequence
<220> FEATURE:
<223> OTHER INFORMATION: Synthetic primer - G281-HL-EcoF

<400> SEQUENCE: 66
gcgatagaat tcgcggtcca gctgcagcag tctggac    37

<210> SEQ ID NO 67
<211> LENGTH: 40
<212> TYPE: DNA
<213> ORGANISM: Artificial sequence
<220> FEATURE:
<223> OTHER INFORMATION: Synthetic primer - 194-LH-LF1

<400> SEQUENCE: 67
gcgtatgaac cggtgacatc cagatgacac agactacatc    40

<210> SEQ ID NO 68
<211> LENGTH: 50
<212> TYPE: DNA
<213> ORGANISM: Artificial sequence
<220> FEATURE:
<223> OTHER INFORMATION: Synthetic primer - 194-LF2

<400> SEQUENCE: 68
atccagatga cacagactac atcctccctg tctgcctctc tgggagacag    50

<210> SEQ ID NO 69
<211> LENGTH: 52
<212> TYPE: DNA
<213> ORGANISM: Artificial sequence
<220> FEATURE:
<223> OTHER INFORMATION: Synthetic primer - 194-LF3

<400> SEQUENCE: 69
gtctgcctct ctgggagaca gagtcaccat cagttgcagg gcaagtcagg ac    52

<210> SEQ ID NO 70
<211> LENGTH: 50
<212> TYPE: DNA
<213> ORGANISM: Artificial sequence
<220> FEATURE:
<223> OTHER INFORMATION: Synthetic primer - 194-LF4

<400> SEQUENCE: 70
gttgcagggc aagtcaggac attcgcaatt atttaaactg gtatcagcag    50

<210> SEQ ID NO 71
<211> LENGTH: 50
<212> TYPE: DNA
<213> ORGANISM: Artificial sequence
<220> FEATURE:

<223> OTHER INFORMATION: Synthetic primer - 194-LF5

<400> SEQUENCE: 71
atttaaactg gtatcagcag aaaccagatg gaactgttaa actcctgatc                50

<210> SEQ ID NO 72
<211> LENGTH: 50
<212> TYPE: DNA
<213> ORGANISM: Artificial sequence
<220> FEATURE:
<223> OTHER INFORMATION: Synthetic primer - 194-LF6

<400> SEQUENCE: 72
gaactgttaa actcctgatc tactacacat caagattaca ctcaggagtc                50

<210> SEQ ID NO 73
<211> LENGTH: 52
<212> TYPE: DNA
<213> ORGANISM: Artificial sequence
<220> FEATURE:
<223> OTHER INFORMATION: Synthetic primer - 194-LF7

<400> SEQUENCE: 73
caagattaca ctcaggagtc ccatcaaggt tcagtggcag tgggtctgga ac             52

<210> SEQ ID NO 74
<211> LENGTH: 52
<212> TYPE: DNA
<213> ORGANISM: Artificial sequence
<220> FEATURE:
<223> OTHER INFORMATION: Synthetic primer - 194-LR7

<400> SEQUENCE: 74
caggttggca atggtgagag aataatctgt tccagaccca ctgccactga ac             52

<210> SEQ ID NO 75
<211> LENGTH: 50
<212> TYPE: DNA
<213> ORGANISM: Artificial sequence
<220> FEATURE:
<223> OTHER INFORMATION: Synthetic primer - 194-LR6

<400> SEQUENCE: 75
gcaaaagtaa gtggcaatat cttctggttg caggttggca atggtgagag                50

<210> SEQ ID NO 76
<211> LENGTH: 51
<212> TYPE: DNA
<213> ORGANISM: Artificial sequence
<220> FEATURE:
<223> OTHER INFORMATION: Synthetic primer - 194-LR5

<400> SEQUENCE: 76
gaacgtccac ggaagcgtat taccctgttg gcaaaagtaa gtggcaatat c              51

<210> SEQ ID NO 77
<211> LENGTH: 52
<212> TYPE: DNA
<213> ORGANISM: Artificial sequence
<220> FEATURE:
<223> OTHER INFORMATION: Synthetic primer - 194-LR4

<400> SEQUENCE: 77
cgtttggtta ccagtttggt gcctccaccg aacgtccacg gaagcgtatt ac             52

<210> SEQ ID NO 78

```
<211> LENGTH: 46
<212> TYPE: DNA
<213> ORGANISM: Artificial sequence
<220> FEATURE:
<223> OTHER INFORMATION: Synthetic primer - 194-LR3

<400> SEQUENCE: 78
accaccgccc gagccaccgc caccccgttt ggttaccagt ttggtg          46

<210> SEQ ID NO 79
<211> LENGTH: 50
<212> TYPE: DNA
<213> ORGANISM: Artificial sequence
<220> FEATURE:
<223> OTHER INFORMATION: Synthetic primer - 194-LR2

<400> SEQUENCE: 79
gctagcgctc ccacctcctc cagatccacc accgcccgag ccaccgccac          50

<210> SEQ ID NO 80
<211> LENGTH: 42
<212> TYPE: DNA
<213> ORGANISM: Artificial sequence
<220> FEATURE:
<223> OTHER INFORMATION: Synthetic primer - 194-LH-LR1

<400> SEQUENCE: 80
gttgcagctg gacctcgcta gcgctcccac ctcctcagat tc          42

<210> SEQ ID NO 81
<211> LENGTH: 54
<212> TYPE: DNA
<213> ORGANISM: Artificial sequence
<220> FEATURE:
<223> OTHER INFORMATION: Synthetic primer - 194-LH-HF1

<400> SEQUENCE: 81
gatctggagg aggtgggagc gctagcgagg tccagctgca acagtctgga cctg          54

<210> SEQ ID NO 82
<211> LENGTH: 50
<212> TYPE: DNA
<213> ORGANISM: Artificial sequence
<220> FEATURE:
<223> OTHER INFORMATION: Synthetic primer - 194-HF2

<400> SEQUENCE: 82
agctgcaaca gtctggacct gaactggtga agcctggagc ttcaatgaag          50

<210> SEQ ID NO 83
<211> LENGTH: 50
<212> TYPE: DNA
<213> ORGANISM: Artificial sequence
<220> FEATURE:
<223> OTHER INFORMATION: Synthetic primer - 194-HF3

<400> SEQUENCE: 83
agcctggagc ttcaatgaag atttcctgca aggcctctgg ttactcattc          50

<210> SEQ ID NO 84
<211> LENGTH: 53
<212> TYPE: DNA
<213> ORGANISM: Artificial sequence
<220> FEATURE:
<223> OTHER INFORMATION: Synthetic primer - 194-HF4

<400> SEQUENCE: 84
```
gcaaggcctc tggttactca ttcactggct acatcgtgaa ctggctgaag cag        53

<210> SEQ ID NO 85
<211> LENGTH: 52
<212> TYPE: DNA
<213> ORGANISM: Artificial sequence
<220> FEATURE:
<223> OTHER INFORMATION: Synthetic primer - 194-HF5

<400> SEQUENCE: 85
atcgtgaact ggctgaagca gagccatgga aagaaccttg agtggattgg ac         52

<210> SEQ ID NO 86
<211> LENGTH: 52
<212> TYPE: DNA
<213> ORGANISM: Artificial sequence
<220> FEATURE:
<223> OTHER INFORMATION: Synthetic primer - 194-HF6

<400> SEQUENCE: 86
gaaccttgag tggattggac ttattaatcc atacaaaggt cttactacct ac         52

<210> SEQ ID NO 87
<211> LENGTH: 52
<212> TYPE: DNA
<213> ORGANISM: Artificial sequence
<220> FEATURE:
<223> OTHER INFORMATION: Synthetic primer - 194-HR6

<400> SEQUENCE: 87
aatgtggcct tgcccttgaa tttctggttg taggtagtaa gacctttgta tg         52

<210> SEQ ID NO 88
<211> LENGTH: 52
<212> TYPE: DNA
<213> ORGANISM: Artificial sequence
<220> FEATURE:
<223> OTHER INFORMATION: Synthetic primer - 194-HR5

<400> SEQUENCE: 88
catgtaggct gtgctggatg acttgtctac agttaatgtg gccttgccct tg         52

<210> SEQ ID NO 89
<211> LENGTH: 55
<212> TYPE: DNA
<213> ORGANISM: Artificial sequence
<220> FEATURE:
<223> OTHER INFORMATION: Synthetic primer - 194-HR4

<400> SEQUENCE: 89
actgcagagt cttcagatgt cagactgagg agctccatgt aggctgtgct ggatg      55

<210> SEQ ID NO 90
<211> LENGTH: 52
<212> TYPE: DNA
<213> ORGANISM: Artificial sequence
<220> FEATURE:
<223> OTHER INFORMATION: Synthetic primer - 194-HR3

<400> SEQUENCE: 90
accatagtac ccagatcttg cacagtaata gactgcagag tcttcagatg tc         52

<210> SEQ ID NO 91
<211> LENGTH: 52
<212> TYPE: DNA
<213> ORGANISM: Artificial sequence
<220> FEATURE:

<223> OTHER INFORMATION: Synthetic primer - 194-HR2

<400> SEQUENCE: 91
gcgccccaga catcgaagta ccagtccgag tcaccatagt acccagatct tg      52

<210> SEQ ID NO 92
<211> LENGTH: 52
<212> TYPE: DNA
<213> ORGANISM: Artificial sequence
<220> FEATURE:
<223> OTHER INFORMATION: Synthetic primer - 194-LH-HR1

<400> SEQUENCE: 92
gcgaatactc gaggagacgg tgaccgtggt ccctgcgccc agacatcga ag      52

<210> SEQ ID NO 93
<211> LENGTH: 42
<212> TYPE: DNA
<213> ORGANISM: Artificial sequence
<220> FEATURE:
<223> OTHER INFORMATION: Synthetic primer - 194-HL-HF1

<400> SEQUENCE: 93
gcgtatgaac cggtgaggtc cagctgcaac agtctggacc tg      42

<210> SEQ ID NO 94
<211> LENGTH: 55
<212> TYPE: DNA
<213> ORGANISM: Artificial sequence
<220> FEATURE:
<223> OTHER INFORMATION: Synthetic primer - 194-HL-HR1

<400> SEQUENCE: 94
accgccacca gaggagacgg tgaccgtggt ccctgcgccc agacatcga agtac      55

<210> SEQ ID NO 95
<211> LENGTH: 52
<212> TYPE: DNA
<213> ORGANISM: Artificial sequence
<220> FEATURE:
<223> OTHER INFORMATION: Synthetic primer - 194-HL-HR0

<400> SEQUENCE: 95
acctcctcca gatccaccac cgcccgagcc accgccacca gaggagacgg tg      52

<210> SEQ ID NO 96
<211> LENGTH: 49
<212> TYPE: DNA
<213> ORGANISM: Artificial sequence
<220> FEATURE:
<223> OTHER INFORMATION: Synthetic primer - 194-HL-LF1

<400> SEQUENCE: 96
gcgggggagg tggcagtgct agcgacatcc agatgacaca gactacatc      49

<210> SEQ ID NO 97
<211> LENGTH: 34
<212> TYPE: DNA
<213> ORGANISM: Artificial sequence
<220> FEATURE:
<223> OTHER INFORMATION: Synthetic primer - 194-HL-LR3Xho

<400> SEQUENCE: 97
gcgaatactc gagcgtttgg ttaccagttt ggtg      34

<210> SEQ ID NO 98

<210> SEQ ID NO 98
<211> LENGTH: 37
<212> TYPE: DNA
<213> ORGANISM: Artificial sequence
<220> FEATURE:
<223> OTHER INFORMATION: Synthetic primer - 194-HL-LR3Xba

<400> SEQUENCE: 98
gcgatatcta gattaccgtt tggttaccag tttggtg                        37

<210> SEQ ID NO 99
<211> LENGTH: 43
<212> TYPE: DNA
<213> ORGANISM: Artificial sequence
<220> FEATURE:
<223> OTHER INFORMATION: Synthetic primer - 194-HL-HF1R1

<400> SEQUENCE: 99
gcgtatgaga attcagaggt ccagctgcaa cagtctggac ctg                 43

<210> SEQ ID NO 100
<211> LENGTH: 41
<212> TYPE: DNA
<213> ORGANISM: Artificial sequence
<220> FEATURE:
<223> OTHER INFORMATION: Synthetic primer - 194-LH-LF1R1

<400> SEQUENCE: 100
gcgtatgaga attctgacat ccagatgaca cagactacat c                   41

<210> SEQ ID NO 101
<211> LENGTH: 54
<212> TYPE: DNA
<213> ORGANISM: Artificial sequence
<220> FEATURE:
<223> OTHER INFORMATION: Synthetic primer - 194-LH-HR1Xba

<400> SEQUENCE: 101
gcgtatctag attaggagac ggtgaccgtg gtccctgcgc cccagacatc gaag     54

<210> SEQ ID NO 102
<211> LENGTH: 725
<212> TYPE: DNA
<213> ORGANISM: Artificial sequence
<220> FEATURE:
<223> OTHER INFORMATION: Synthetic polynucleotide - G28-1 VLVH (DNA)

<400> SEQUENCE: 102
accggtgaca tccagatgac tcagtctcca gcctccctat ctgcatctgt gggagagact    60
gtcaccatca catgtcgaac aagtgaaaat gtttacagtt atttggcttg gtatcagcag   120
aaacagggaa atctcctcag ctcctggtc tcttttgcaa aaaccttagc agaaggtgtg   180
ccatcaaggt tcagtggcag tggatcaggc acacagtttt ctctgaagat cagcagcctg   240
cagcctgaag attctggaag ttatttctgt caacatcatt ccgataatcc gtggacgttc   300
ggtggaggca ccgaactgga gatcaaaggt ggcggtggct cggcggtgg tgggtcgggt   360
ggcggcggat ctgctagcgc agtccagctg cagcagtctg acctgagct ggaaaagcct   420
ggcgcttcag tgaagatttc ctgcaaggct tctggttact cattcactgg ctacaatatg   480
aactgggtga agcagaataa tggaaagagc cttgagtgga ttggaaatat tgatccttat   540
tatggtggta ctacctacaa ccggaagttc aagggcaagg ccacattgac tgtagacaaa   600
tcctccagca cagcctacat gcagctcaag agtctgacat ctgaggactc tgcagtctat   660
tactgtgcaa gatcggtcgg ccctatggac tactggggtc aaggaacctc agtcaccgtc   720

-continued

```
                                                                              725
tcgag
```

<210> SEQ ID NO 103
<211> LENGTH: 239
<212> TYPE: PRT
<213> ORGANISM: Artificial sequence
<220> FEATURE:
<223> OTHER INFORMATION: Synthetic polypeptide - G-28-1 VLVH (AA)
<220> FEATURE:
<221> NAME/KEY: misc_feature
<222> LOCATION: (1)..(107)
<223> OTHER INFORMATION: VL
<220> FEATURE:
<221> NAME/KEY: misc_feature
<222> LOCATION: (108)..(124)
<223> OTHER INFORMATION: Linker
<220> FEATURE:
<221> NAME/KEY: misc_feature
<222> LOCATION: (125)..(239)
<223> OTHER INFORMATION: VH

<400> SEQUENCE: 103

```
Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Val Tyr Ser Tyr
            20                  25                  30

Leu Ala Trp Tyr Gln Gln Lys Gln Gly Lys Ser Pro Gln Leu Leu Val
        35                  40                  45

Ser Phe Ala Lys Thr Leu Ala Glu Gly Val Pro Ser Arg Phe Ser Gly
    50                  55                  60

Ser Gly Ser Gly Thr Gln Phe Ser Leu Lys Ile Ser Ser Leu Gln Pro
65                  70                  75                  80

Glu Asp Ser Gly Ser Tyr Phe Cys Gln His His Ser Asp Asn Pro Trp
                85                  90                  95

Thr Phe Gly Gly Gly Thr Glu Leu Glu Ile Lys Gly Gly Gly Gly Ser
            100                 105                 110

Gly Gly Gly Gly Ser Gly Gly Gly Ser Ala Ser Ala Val Gln Leu
        115                 120                 125

Gln Gln Ser Gly Pro Glu Leu Glu Lys Pro Gly Ala Ser Val Lys Ile
    130                 135                 140

Ser Cys Lys Ala Ser Gly Tyr Ser Phe Thr Gly Tyr Asn Met Asn Trp
145                 150                 155                 160

Val Lys Gln Asn Asn Gly Lys Ser Leu Glu Trp Ile Gly Asn Ile Asp
                165                 170                 175

Pro Tyr Tyr Gly Gly Thr Thr Tyr Asn Arg Lys Phe Lys Gly Lys Ala
            180                 185                 190

Thr Leu Thr Val Asp Lys Ser Ser Ser Thr Ala Tyr Met Gln Leu Lys
        195                 200                 205

Ser Leu Thr Ser Glu Asp Ser Ala Val Tyr Tyr Cys Ala Arg Ser Val
    210                 215                 220

Gly Pro Met Asp Tyr Trp Gly Gln Gly Thr Ser Val Thr Val Ser
225                 230                 235
```

<210> SEQ ID NO 104
<211> LENGTH: 767
<212> TYPE: DNA
<213> ORGANISM: Artificial sequence
<220> FEATURE:
<223> OTHER INFORMATION: Synthetic polynucleotide - G28-1 VHVL (DNA)

<400> SEQUENCE: 104

```
accggtgagg tccagctgca acagtctgga cctgaactgg tgaagcctgg agcttcaatg      60
```

```
aagatttcct gcaaggcctc tggttactca ttcactggct acatcgtgaa ctggctgaag      120
cagagccatg gaaagaacct tgagtggatt ggacttatta atccatacaa aggtcttact      180
acctacaacc agaaattcaa gggcaaggcc acattaactg tagacaagtc atccagcaca      240
gcctacatgg agctcctcag tctgacatct gaagactctg cagtctatta ctgtgcaaga      300
tctgggtact atggtgactc ggactggtac ttcgatgtct ggggcgcagg gaccacggtc      360
accgtctcct ctggtggcgg tggctcgggc ggtggtggat ctggaggagg tgggagcggg      420
ggaggtggca gtgctagcga catccagatg acacagacta catcctccct gtctgcctct      480
ctgggagaca gagtcaccat cagttgcagg gcaagtcagg acattcgcaa ttatttaaac      540
tggtatcagc agaaaccaga tggaactgtt aaactcctga tctactacac atcaagatta      600
cactcaggag tcccatcaag gttcagtggc agtgggtctg gaacagatta ttctctcacc      660
attgccaacc tgcaaccaga agatattgcc acttactttt gccaacaggg taatacgctt      720
ccgtggacgt tcggtggagg caccaaactg gtaaccaaac gctcgag                   767
```

<210> SEQ ID NO 105
<211> LENGTH: 253
<212> TYPE: PRT
<213> ORGANISM: Artificial sequence
<220> FEATURE:
<223> OTHER INFORMATION: Synthetic polypeptide - G28-1 VHVL (AA)
<220> FEATURE:
<221> NAME/KEY: misc_feature
<222> LOCATION: (1)..(121)
<223> OTHER INFORMATION: VH
<220> FEATURE:
<221> NAME/KEY: misc_feature
<222> LOCATION: (122)..(144)
<223> OTHER INFORMATION: Linker
<220> FEATURE:
<221> NAME/KEY: misc_feature
<222> LOCATION: (145)..(253)
<223> OTHER INFORMATION: VL

<400> SEQUENCE: 105

```
Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Ile Val Asn Trp Leu Lys Gln Ser His Gly Lys Asn Leu Glu Trp Ile
        35                  40                  45

Gly Leu Ile Asn Pro Tyr Lys Gly Leu Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Ala Gly Thr Thr Val Thr Val Ser Ser Gly Gly Gly Gly Ser Gly
        115                 120                 125

Gly Gly Ser Gly Gly Gly Ser Gly Gly Gly Ser Ala Ser
    130                 135                 140

Asp Ile Gln Met Thr Gln Thr Thr Ser Ser Leu Ser Ala Ser Leu Gly
145                 150                 155                 160

Asp Arg Val Thr Ile Ser Cys Arg Ala Ser Gln Asp Ile Arg Asn Tyr
                165                 170                 175
```

```
Leu Asn Trp Tyr Gln Gln Lys Pro Asp Gly Thr Val Lys Leu Leu Ile
            180                 185                 190

Tyr Tyr Thr Ser Arg Leu His Ser Gly Val Pro Ser Arg Phe Ser Gly
        195                 200                 205

Ser Gly Ser Gly Thr Asp Tyr Ser Leu Thr Ile Ala Asn Leu Gln Pro
    210                 215                 220

Glu Asp Ile Ala Thr Tyr Phe Cys Gln Gln Gly Asn Thr Leu Pro Trp
225                 230                 235                 240

Thr Phe Gly Gly Gly Thr Lys Leu Val Thr Lys Arg Ser
                245                 250

<210> SEQ ID NO 106
<211> LENGTH: 749
<212> TYPE: DNA
<213> ORGANISM: Artificial sequence
<220> FEATURE:
<223> OTHER INFORMATION: Synthetic polynucleotide - G19-4 VLVH (DNA)

<400> SEQUENCE: 106
accggtgaca tccagatgac acagactaca tcctccctgt ctgcctctct gggagacaga      60
gtcaccatca gttgcagggc aagtcaggac attcgcaatt atttaaactg gtatcagcag     120
aaaccagatg gaactgttaa actcctgatc tactacacat caagattaca ctcaggagtc     180
ccatcaaggt tcagtggcag tgggtctgga acagattatt ctctcaccat tgccaacctg     240
caaccagaag atattgccac ttactttgc caacagggta atacgcttcc gtggacgttc      300
ggtggaggca ccaaactggt aaccaaacgg ggtggcggtg gctcgggcgg tggtggatct     360
ggaggaggtg ggagcgctag cgaggtccag ctgcaacagt ctggacctga actggtgaag     420
cctggagctt caatgaagat ttcctgcaag gcctctggtt actcattcac tggctacatc     480
gtgaactggc tgaagcagag ccatggaaag aaccttgagt ggattggact tattaatcca     540
tacaaaggtc ttactaccta caaccagaaa ttcaagggca aggccacatt aactgtagac     600
aagtcatcca gcacagccta catggagctc ctcagtctga catctgaaga ctctgcagtc     660
tattactgtg caagatctgg gtactatggt gactcggact ggtacttcga tgtctggggc     720
gcagggacca cggtcaccgt ctcctcgag                                       749

<210> SEQ ID NO 107
<211> LENGTH: 247
<212> TYPE: PRT
<213> ORGANISM: Artificial sequence
<220> FEATURE:
<223> OTHER INFORMATION: Synthetic polypeptide - G-19-4 VLVH (AA)
<220> FEATURE:
<221> NAME/KEY: misc_feature
<222> LOCATION: (1)..(108)
<223> OTHER INFORMATION: VL
<220> FEATURE:
<221> NAME/KEY: misc_feature
<222> LOCATION: (109)..(125)
<223> OTHER INFORMATION: Linker
<220> FEATURE:
<221> NAME/KEY: misc_feature
<222> LOCATION: (126)..(247)
<223> OTHER INFORMATION: VH

<400> SEQUENCE: 107

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
```

```
                35                  40                  45
Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ala Asn Leu Gln Pro
 65                  70                  75                  80

Glu Asp Ile Ala Thr Tyr Phe Cys Gln Gln Gly Asn Thr Leu Pro Trp
                 85                  90                  95

Thr Phe Gly Gly Gly Thr Lys Leu Val Thr Lys Arg Gly Gly Gly Gly
                100                 105                 110

Ser Gly Gly Gly Ser Gly Gly Gly Ser Ala Ser Glu Val Gln
                115                 120                 125

Leu Gln Gln Ser Gly Pro Glu Leu Val Lys Pro Gly Ala Ser Met Lys
130                 135                 140

Ile Ser Cys Lys Ala Ser Gly Tyr Ser Phe Thr Gly Tyr Ile Val Asn
145                 150                 155                 160

Trp Leu Lys Gln Ser His Gly Lys Asn Leu Glu Trp Ile Gly Leu Ile
                165                 170                 175

Asn Pro Tyr Lys Gly Leu Thr Thr Tyr Asn Gln Lys Phe Lys Gly Lys
                180                 185                 190

Ala Thr Leu Thr Val Asp Lys Ser Ser Thr Ala Tyr Met Glu Leu
                195                 200                 205

Leu Ser Leu Thr Ser Glu Asp Ser Ala Val Tyr Cys Ala Arg Ser
210                 215                 220

Gly Tyr Tyr Gly Asp Ser Asp Trp Tyr Phe Asp Val Trp Gly Ala Gly
225                 230                 235                 240

Thr Thr Val Thr Val Ser Ser
                245

<210> SEQ ID NO 108
<211> LENGTH: 752
<212> TYPE: DNA
<213> ORGANISM: Artificial sequence
<220> FEATURE:
<223> OTHER INFORMATION: Synthetic polynucleotide - G19-4 VHVL (DNA)

<400> SEQUENCE: 108
accggtgagg tccagctgca acagtctgga cctgaactgg tgaagcctgg agcttcaatg    60
aagatttcct gcaaggcctc tggttactca ttcactggct acatcgtgaa ctggctgaag    120
cagagccatg gaaagaacct tgagtggatt ggacttatta tccatacaa aggtcttact    180 acctacaacc agaaattcaa gggcaaggcc acattaactg tagacaagtc atccagcaca    240
gcctacatgg agctcctcag tctgacatct gaagactctg cagtctatta ctgtgcaaga    300
tctgggtact atggtgactc ggactggtac ttcgatgtct ggggcgcagg gaccacggtc    360
accgtctcct ctggtggcgg tggctcgggc ggtggtggat ctggaggagg tgggagcgct    420
agcgacatcc agatgacaca gactacatcc tccctgtctg cctctctggg agacagagtc    480
accatcagtt gcagggcaag tcaggacatt cgcaattatt taaactggta tcagcagaaa    540
ccagatggaa ctgttaaact cctgatctac tacacatcaa gattacactc aggagtccca    600
tcaaggttca gtggcagtgg gtctggaaca gattattctc tcaccattgc caacctgcaa    660
ccagaagata ttgccactta cttttgccaa cagggtaata cgcttccgtg gacgttcggt    720
ggaggcacca aactggtaac caaacgctcg ag                                  752

<210> SEQ ID NO 109
<211> LENGTH: 248
```

```
<212> TYPE: PRT
<213> ORGANISM: Artificial sequence
<220> FEATURE:
<223> OTHER INFORMATION: Synthetic polypeptide - G19-4 VHVL (AA)
<220> FEATURE:
<221> NAME/KEY: misc_feature
<222> LOCATION: (1)..(122)
<223> OTHER INFORMATION: VH
<220> FEATURE:
<221> NAME/KEY: misc_feature
<222> LOCATION: (123)..(139)
<223> OTHER INFORMATION: Linker
<220> FEATURE:
<221> NAME/KEY: misc_feature
<222> LOCATION: (140)..(248)
<223> OTHER INFORMATION: VL

<400> SEQUENCE: 109
```

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Ile Val Asn Trp Leu Lys Gln Ser His Gly Lys Asn Leu Glu Trp Ile
        35                  40                  45

Gly Leu Ile Asn Pro Tyr Lys Gly Leu Thr Thr Tyr Asn Gln Lys Phe
50                  55                  60

Lys Gly Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Ala Gly Thr Thr Val Thr Val Ser Gly Gly Gly Gly Ser Gly
            115                 120                 125

Gly Gly Gly Ser Gly Gly Gly Ser Ala Ser Asp Ile Gln Met Thr
    130                 135                 140

Gln Thr Thr Ser Ser Leu Ser Ala Ser Leu Gly Asp Arg Val Thr Ile
145                 150                 155                 160

Ser Cys Arg Ala Ser Gln Asp Ile Arg Asn Tyr Leu Asn Trp Tyr Gln
                165                 170                 175

Gln Lys Pro Asp Gly Thr Val Lys Leu Leu Ile Tyr Tyr Thr Ser Arg
            180                 185                 190

Leu His Ser Gly Val Pro Ser Arg Phe Ser Gly Ser Gly Ser Gly Thr
        195                 200                 205

Asp Tyr Ser Leu Thr Ile Ala Asn Leu Gln Pro Glu Asp Ile Ala Thr
210                 215                 220

Tyr Phe Cys Gln Gln Gly Asn Thr Leu Pro Trp Thr Phe Gly Gly Gly
225                 230                 235                 240

Thr Lys Leu Val Thr Lys Arg Ser
                245

```
<210> SEQ ID NO 110
<211> LENGTH: 45
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<223> OTHER INFORMATION: ssc(s)-hIgG1 (DNA)

<400> SEQUENCE: 110
```
gagcccaaat cttctgacaa aactcacaca tctccaccgt gctca                    45

<210> SEQ ID NO 111
<211> LENGTH: 15
<212> TYPE: PRT
<213> ORGANISM: Artificial sequence
<220> FEATURE:
<223> OTHER INFORMATION: Synthetic peptide - ssc(s)-hIgG1 (AA)

<400> SEQUENCE: 111

Glu Pro Lys Ser Ser Asp Lys Thr His Thr Ser Pro Pro Cys Ser
1               5                   10                  15

<210> SEQ ID NO 112
<211> LENGTH: 45
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<223> OTHER INFORMATION: scc(s)-hIgG1 (DNA)

<400> SEQUENCE: 112
gagcccaaat cttctgacaa aactcacaca tgtccaccgt gctca                    45

<210> SEQ ID NO 113
<211> LENGTH: 15
<212> TYPE: PRT
<213> ORGANISM: Artificial sequence
<220> FEATURE:
<223> OTHER INFORMATION: Synthetic peptide - scc(s)-hIgG1 (AA)

<400> SEQUENCE: 113

Glu Pro Lys Ser Ser Asp Lys Thr His Thr Cys Pro Pro Cys Ser
1               5                   10                  15

<210> SEQ ID NO 114
<211> LENGTH: 45
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<223> OTHER INFORMATION: css(s)-hIgG1 (DNA)

<400> SEQUENCE: 114
gagcccaaat cttgtgacaa aactcacaca tctccaccga gctca                    45

<210> SEQ ID NO 115
<211> LENGTH: 15
<212> TYPE: PRT
<213> ORGANISM: Artificial sequence
<220> FEATURE:
<223> OTHER INFORMATION: Synthetic peptide - css(s)-hIgG1 (AA)

<400> SEQUENCE: 115

Glu Pro Lys Ser Cys Asp Lys Thr His Thr Ser Pro Pro Ser Ser
1               5                   10                  15

<210> SEQ ID NO 116
<211> LENGTH: 45
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature

```
<223> OTHER INFORMATION: scs(s)-hIgG1 (DNA)

<400> SEQUENCE: 116
gagcccaaat cttgtgacaa aactcacaca tgtccaccga gctca          45

<210> SEQ ID NO 117
<211> LENGTH: 15
<212> TYPE: PRT
<213> ORGANISM: Artificial sequence
<220> FEATURE:
<223> OTHER INFORMATION: Synthetic peptide - scs(s)-hIgG1 (AA)

<400> SEQUENCE: 117

Glu Pro Lys Ser Ser Asp Lys Thr His Thr Cys Pro Pro Ser Ser
1               5                   10                  15

<210> SEQ ID NO 118
<211> LENGTH: 45
<212> TYPE: DNA
<213> ORGANISM: Artificial sequence
<220> FEATURE:
<223> OTHER INFORMATION: Synthetic primer

<400> SEQUENCE: 118
gagcccaaat cttgtgacaa aactcacaca tgtccaccgt gctca          45

<210> SEQ ID NO 119
<211> LENGTH: 15
<212> TYPE: PRT
<213> ORGANISM: Artificial sequence
<220> FEATURE:
<223> OTHER INFORMATION: Scorpion linker region

<400> SEQUENCE: 119

Glu Pro Lys Ser Cys Asp Lys Thr His Thr Cys Pro Pro Cys Ser
1               5                   10                  15

<210> SEQ ID NO 120
<211> LENGTH: 45
<212> TYPE: DNA
<213> ORGANISM: Artificial sequence
<220> FEATURE:
<223> OTHER INFORMATION: Synthetic primer

<400> SEQUENCE: 120
gagcccaaat cttgtgacaa aactcacaca tgtccaccgt gccca          45

<210> SEQ ID NO 121
<211> LENGTH: 15
<212> TYPE: PRT
<213> ORGANISM: Artificial sequence
<220> FEATURE:
<223> OTHER INFORMATION: Scorpion linker region

<400> SEQUENCE: 121

Glu Pro Lys Ser Cys Asp Lys Thr His Thr Cys Pro Pro Cys Pro
1               5                   10                  15

<210> SEQ ID NO 122
<211> LENGTH: 45
<212> TYPE: DNA
<213> ORGANISM: Artificial sequence
<220> FEATURE:
<223> OTHER INFORMATION: Synthetic primer

<400> SEQUENCE: 122
gagcccaaat cttctgacaa aactcacaca tctccaccga gccca          45
```

```
<210> SEQ ID NO 123
<211> LENGTH: 15
<212> TYPE: PRT
<213> ORGANISM: Artificial sequence
<220> FEATURE:
<223> OTHER INFORMATION: Scorpion linker region

<400> SEQUENCE: 123

Glu Pro Lys Ser Ser Asp Lys Thr His Thr Ser Pro Pro Ser Pro
1               5                   10                  15

<210> SEQ ID NO 124
<211> LENGTH: 45
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<223> OTHER INFORMATION: csc(p)-hIgG1 (DNA)

<400> SEQUENCE: 124
gagcccaaat cttgtgacaa aactcacaca tctccaccgt gccca                45

<210> SEQ ID NO 125
<211> LENGTH: 15
<212> TYPE: PRT
<213> ORGANISM: Artificial sequence
<220> FEATURE:
<223> OTHER INFORMATION: Scorpion linker region
<220> FEATURE:
<221> NAME/KEY: misc_feature
<223> OTHER INFORMATION: csc(p)-hIgG1 (AA)

<400> SEQUENCE: 125

Glu Pro Lys Ser Cys Asp Lys Thr His Thr Ser Pro Pro Cys Pro
1               5                   10                  15

<210> SEQ ID NO 126
<211> LENGTH: 45
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<223> OTHER INFORMATION: ssc(p)-hIgG1 (DNA)

<400> SEQUENCE: 126
gagcccaaat cttctgacaa aactcacaca tctccaccgt gccca                45

<210> SEQ ID NO 127
<211> LENGTH: 15
<212> TYPE: PRT
<213> ORGANISM: Artificial sequence
<220> FEATURE:
<223> OTHER INFORMATION: Scorpion linker region
<220> FEATURE:
<221> NAME/KEY: misc_feature
<223> OTHER INFORMATION: ssc(p)-hIgG1 (AA)

<400> SEQUENCE: 127

Glu Pro Lys Ser Ser Asp Lys Thr His Thr Ser Pro Pro Cys Pro
1               5                   10                  15

<210> SEQ ID NO 128
<211> LENGTH: 45
<212> TYPE: DNA
```

```
<213> ORGANISM: Artificial sequence
<220> FEATURE:
<223> OTHER INFORMATION: Synthetic primer
<220> FEATURE:
<221> NAME/KEY: misc_feature
<223> OTHER INFORMATION: scc(p)-hIgG1 (DNA)

<400> SEQUENCE: 128
gagcccaaat cttctgacaa aactcacaca tgtccaccgt gccca            45

<210> SEQ ID NO 129
<211> LENGTH: 15
<212> TYPE: PRT
<213> ORGANISM: Artificial sequence
<220> FEATURE:
<223> OTHER INFORMATION: Scorpion linker region
<220> FEATURE:
<221> NAME/KEY: misc_feature
<223> OTHER INFORMATION: scc(p)-hIgG1 (AA)

<400> SEQUENCE: 129

Glu Pro Lys Ser Ser Asp Lys Thr His Thr Cys Pro Pro Cys Pro
 1               5                  10                  15

<210> SEQ ID NO 130
<211> LENGTH: 45
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<223> OTHER INFORMATION: css(p)-hIgG1 (DNA)

<400> SEQUENCE: 130
gagcccaaat cttgtgacaa aactcacaca tctccaccga gccca            45

<210> SEQ ID NO 131
<211> LENGTH: 15
<212> TYPE: PRT
<213> ORGANISM: Artificial sequence
<220> FEATURE:
<223> OTHER INFORMATION: Scorpion linker region
<220> FEATURE:
<221> NAME/KEY: misc_feature
<223> OTHER INFORMATION: css(p)-hIgG1 (AA)

<400> SEQUENCE: 131

Glu Pro Lys Ser Cys Asp Lys Thr His Thr Ser Pro Pro Ser Pro
 1               5                  10                  15

<210> SEQ ID NO 132
<211> LENGTH: 45
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<223> OTHER INFORMATION: ssc(p)-hIgG1 (DNA)

<400> SEQUENCE: 132
gagcccaaat cttgtgacaa aactcacaca tgtccaccga gccca            45

<210> SEQ ID NO 133
<211> LENGTH: 15
<212> TYPE: PRT
<213> ORGANISM: Artificial sequence
<220> FEATURE:
<223> OTHER INFORMATION: Scorpion linker region
```

```
<220> FEATURE:
<221> NAME/KEY: misc_feature
<223> OTHER INFORMATION: ssc(p)-hIgG1 (DNA)

<400> SEQUENCE: 133

Glu Pro Lys Ser Ser Asp Lys Thr His Thr Cys Pro Pro Ser Pro
1               5                   10                  15

<210> SEQ ID NO 134
<211> LENGTH: 18
<212> TYPE: DNA
<213> ORGANISM: Artificial sequence
<220> FEATURE:
<221> NAME/KEY: misc_feature
<223> OTHER INFORMATION: ssc(p) (DNA)
<220> FEATURE:
<223> OTHER INFORMATION: Synthetic primer

<400> SEQUENCE: 134
agttgtccac cgtgccca                                              18

<210> SEQ ID NO 135
<211> LENGTH: 6
<212> TYPE: PRT
<213> ORGANISM: Artificial sequence
<220> FEATURE:
<223> OTHER INFORMATION: Scorpion linker region

<400> SEQUENCE: 135

Ser Cys Pro Pro Cys Pro
1               5

<210> SEQ ID NO 136
<211> LENGTH: 7
<212> TYPE: DNA
<213> ORGANISM: Artificial sequence
<220> FEATURE:
<223> OTHER INFORMATION: Synthetic primer

<400> SEQUENCE: 136 tgatcag                                                           7

<210> SEQ ID NO 137
<211> LENGTH: 2
<212> TYPE: PRT
<213> ORGANISM: Artificial sequence
<220> FEATURE:
<223> OTHER INFORMATION: Synthetic peptide

<400> SEQUENCE: 137

Asp Gln
1

<210> SEQ ID NO 138
<211> LENGTH: 7
<212> TYPE: DNA
<213> ORGANISM: Artificial sequence
<220> FEATURE:
<223> OTHER INFORMATION: Synthetic primer

<400> SEQUENCE: 138 ctcgagt                                                           7

<210> SEQ ID NO 139
<211> LENGTH: 2
<212> TYPE: PRT
<213> ORGANISM: Artificial sequence
<220> FEATURE:
```

<223> OTHER INFORMATION: Synthetic peptide

<400> SEQUENCE: 139

Ser Ser
1

<210> SEQ ID NO 140
<211> LENGTH: 654
<212> TYPE: DNA
<213> ORGANISM: Homo sapiens
<220> FEATURE:
<223> OTHER INFORMATION: hIgG1 wild type

<400> SEQUENCE: 140

```
gcacctgaac tcctgggtgg accgtcagtc ttcctcttcc ccccaaaacc caaggacacc    60
ctcatgatct cccggacccc tgaggtcaca tgcgtggtgg tggacgtgag ccacgaagac   120
cctgaggtca agttcaactg gtacgtggac ggcgtggagg tgcataatgc caagacaaag   180
ccgcgggagg agcagtacaa cagcacgtac cgtgtggtca gcgtcctcac cgtcctgcac   240
caggactggc tgaatggcaa ggagtacaag tgcaaggtct ccaacaaagc cctcccagcc   300
cccatcgaga aaacaatctc caaagccaaa gggcagcccc gagaaccaca ggtgtacacc   360
ctgcccccat cccgggatga gctgaccaag aaccaggtca gcctgacctg cctggtcaaa   420
ggcttctatc ccagcgacat cgccgtggag tgggagagca atgggcagcc ggagaacaac   480
tacaagacca cgcctcccgt gctggactcc gacggctcct tcttcctcta cagcaagctc   540
accgtggaca agagcaggtg gcagcagggg aacgtcttct catgctccgt gatgcatgag   600
gctctgcaca accactacac gcagaagagc ctctccctgt ctccgggtaa atga         654
```

<210> SEQ ID NO 141
<211> LENGTH: 217
<212> TYPE: PRT
<213> ORGANISM: Homo sapiens
<220> FEATURE:
<223> OTHER INFORMATION: hIgG1 wild type

<400> SEQUENCE: 141

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
```

```
                   165              170                175
Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215
```

<210> SEQ ID NO 142
<211> LENGTH: 654
<212> TYPE: DNA
<213> ORGANISM: Homo sapiens
<220> FEATURE:
<223> OTHER INFORMATION: hIgG1 (P238S)

<400> SEQUENCE: 142

```
gcacctgaac tcctgggtgg atcgtcagtc ttcctcttcc ccccaaaacc caaggacacc      60
ctcatgatct cccggacccc tgaggtcaca tgcgtggtgg tggacgtgag ccacgaagac     120
cctgaggtca agttcaactg gtacgtggac ggcgtggagg tgcataatgc caagacaaag     180
ccgcgggagg agcagtacaa cagcacgtac cgtgtggtca gcgtcctcac cgtcctgcac     240
caggactggc tgaatggcaa ggagtacaag tgcaaggtct ccaacaaagc cctcccagcc     300
cccatcgaga aaacaatctc caaagccaaa gggcagcccc gagaaccaca ggtgtacacc     360
ctgcccccat cccgggatga gctgaccaag aaccaggtca gcctgacctg cctggtcaaa     420
ggcttctatc ccagcgacat cgccgtggag tgggagagca atgggcagcc ggagaacaac     480
tacaagacca cgcctcccgt gctggactcc gacggctcct tcttcctcta cagcaagctc     540
accgtggaca agagcaggtg gcagcagggg aacgtcttct catgctccgt gatgcatgag     600
gctctgcaca accactacac gcagaagagc ctctccctgt ctccgggtaa atga           654
```

<210> SEQ ID NO 143
<211> LENGTH: 217
<212> TYPE: PRT
<213> ORGANISM: Homo sapiens
<220> FEATURE:
<223> OTHER INFORMATION: hIgG1 (P238S)

<400> SEQUENCE: 143

```
Ala Pro Glu Leu Leu Gly Gly Ser Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140
```

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 144
<211> LENGTH: 654
<212> TYPE: DNA
<213> ORGANISM: Homo sapiens
<220> FEATURE:
<223> OTHER INFORMATION: hIgG1 (P331S)

<400> SEQUENCE: 144
gcacctgaac tcctgggtgg accgtcagtc ttcctcttcc ccccaaaacc caaggacacc      60
ctcatgatct cccggacccc tgaggtcaca tgcgtggtgg tggacgtgag ccacgaagac     120
cctgaggtca agttcaactg gtacgtggac ggcgtggagg tgcataatgc caagacaaag     180
ccgcgggagg agcagtacaa cagcacgtac cgtgtggtca gcgtcctcac cgtcctgcac     240
caggactggc tgaatggcaa ggagtacaag tgcaaggtct ccaacaaagc cctcccagcc     300
tccatcgaga aaacaatctc caaagccaaa gggcagcccc gagaaccaca ggtgtacacc     360
ctgcccccat cccgggatga gctgaccaag aaccaggtca gcctgacctg cctggtcaaa     420
ggcttctatc ccagcgacat cgccgtggag tgggagagca atgggcagcc ggagaacaac     480
tacaagacca cgcctcccgt gctggactcc gacggctcct tcttcctcta cagcaagctc     540
accgtggaca agagcaggtg gcagcagggg aacgtcttct catgctccgt gatgcatgag     600
gctctgcaca accactacac gcagaagagc ctctccctgt ctccgggtaa atga           654

<210> SEQ ID NO 145
<211> LENGTH: 217
<212> TYPE: PRT
<213> ORGANISM: Homo sapiens
<220> FEATURE:
<223> OTHER INFORMATION: hIgG1 (P331S)

<400> SEQUENCE: 145

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Ser Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

```
Thr Lys Asn Gln Val Ser Leu Thr Cys Leu Val Lys Gly Phe Tyr Pro
        130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Tyr Ser Lys Leu Thr Val Asp Lys Ser Arg Trp Gln Gln Gly Asn Val
            180                 185                 190
Phe Ser Cys Ser Val Met His Glu Ala Leu His Asn His Tyr Thr Gln
        195                 200                 205
Lys Ser Leu Ser Leu Ser Pro Gly Lys
    210                 215
```

<210> SEQ ID NO 146
<211> LENGTH: 654
<212> TYPE: DNA
<213> ORGANISM: Homo sapiens
<220> FEATURE:
<223> OTHER INFORMATION: hIgG1 (P238S/P331S)

<400> SEQUENCE: 146

```
gcacctgaac tcctgggtgg atcgtcagtc ttcctcttcc ccccaaaacc caaggacacc    60
ctcatgatct cccggacccc tgaggtcaca tgcgtggtgg tggacgtgag ccacgaagac   120
cctgaggtca agttcaactg gtacgtggac ggcgtggagg tgcataatgc caagacaaag   180
ccgcgggagg agcagtacaa cagcacgtac cgtgtggtca gcgtcctcac cgtcctgcac   240
caggactggc tgaatggcaa ggagtacaag tgcaaggtct ccaacaaagc cctcccagcc   300
tccatcgaga aaacaatctc aaagccaaa gggcagcccc gagaaccaca ggtgtacacc   360
ctgcccccat cccgggatga gctgaccaag aaccaggtca gcctgacctg cctggtcaaa   420
ggcttctatc ccagcgacat cgccgtggag tgggagagca atgggcagcc ggagaacaac   480
tacaagacca cgcctcccgt gctggactcc gacggctcct tcttcctcta cagcaagctc   540
accgtggaca agagcaggtg gcagcagggg aacgtcttct catgctccgt gatgcatgag   600
gctctgcaca accactacac gcagaagagc ctctccctgt ctccgggtaa atga          654
```

<210> SEQ ID NO 147
<211> LENGTH: 217
<212> TYPE: PRT
<213> ORGANISM: Homo sapiens
<220> FEATURE:
<223> OTHER INFORMATION: hIgG1 (P238S/P331S)

<400> SEQUENCE: 147

```
Ala Pro Glu Leu Leu Gly Gly Ser Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Ser Ile Glu Lys Thr Ile Ser Lys Ala Lys Gly Gln
```

```
                    100                 105                 110
Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 148
<211> LENGTH: 60
<212> TYPE: DNA
<213> ORGANISM: Artificial sequence
<220> FEATURE:
<223> OTHER INFORMATION: Synthetic primer
<220> FEATURE:
<223> OTHER INFORMATION: STD1 (DNA)

<400> SEQUENCE: 148
aattatggtg gcggtggctc gggcggtggt ggatctggag gaggtgggag tgggaattct      60

<210> SEQ ID NO 149
<211> LENGTH: 20
<212> TYPE: PRT
<213> ORGANISM: Artificial sequence
<220> FEATURE:
<223> OTHER INFORMATION: Scorpion linker region
<220> FEATURE:
<223> OTHER INFORMATION: STD1 (AA)

<400> SEQUENCE: 149

Asn Tyr Gly Gly Gly Gly Ser Gly Gly Gly Gly Ser Gly Gly Gly Gly
1               5                   10                  15

Ser Gly Asn Ser
            20

<210> SEQ ID NO 150
<211> LENGTH: 114
<212> TYPE: DNA
<213> ORGANISM: Artificial sequence
<220> FEATURE:
<223> OTHER INFORMATION: Synthetic primer
<220> FEATURE:
<223> OTHER INFORMATION: STD2 (DNA)

<400> SEQUENCE: 150
aattatggtg gcggtggctc gggcggtggt ggatctggag gaggtgggag tgggaattat      60
ggtggcggtg gctcgggcgg tggtggatct ggaggaggtg ggagtgggaa ttct           114

<210> SEQ ID NO 151
<211> LENGTH: 38
<212> TYPE: PRT
<213> ORGANISM: Artificial sequence
<220> FEATURE:
<223> OTHER INFORMATION: Scorpion linker region
<220> FEATURE:
<223> OTHER INFORMATION: STD2 (AA)
```

<400> SEQUENCE: 151

Asn Tyr Gly Gly Gly Ser Gly Gly Gly Ser Gly Gly Gly
1               5                   10                  15

Ser Gly Asn Tyr Gly Gly Gly Ser Gly Gly Gly Ser Gly Gly
            20                  25                  30

Gly Gly Ser Gly Asn Ser
        35

<210> SEQ ID NO 152
<211> LENGTH: 6
<212> TYPE: DNA
<213> ORGANISM: Artificial sequence
<220> FEATURE:
<223> OTHER INFORMATION: Synthetic primer
<220> FEATURE:
<223> OTHER INFORMATION: Linker H1 (PN)

<400> SEQUENCE: 152 aattct                                                                    6

<210> SEQ ID NO 153
<211> LENGTH: 2
<212> TYPE: PRT
<213> ORGANISM: Artificial sequence
<220> FEATURE:
<223> OTHER INFORMATION: Scorpion linker region
<220> FEATURE:
<223> OTHER INFORMATION: Linker H1 (AA)

<400> SEQUENCE: 153

Asn Ser
1

<210> SEQ ID NO 154
<211> LENGTH: 24
<212> TYPE: DNA
<213> ORGANISM: Artificial sequence
<220> FEATURE:
<223> OTHER INFORMATION: Synthetic primer
<220> FEATURE:
<223> OTHER INFORMATION: Linker H2 (PN)

<400> SEQUENCE: 154
ggtggcggtg gctcggggaa ttct                                               24

<210> SEQ ID NO 155
<211> LENGTH: 8
<212> TYPE: PRT
<213> ORGANISM: Artificial sequence
<220> FEATURE:
<223> OTHER INFORMATION: Scorpion linker region
<220> FEATURE:
<223> OTHER INFORMATION: Linker H2 (AA)

<400> SEQUENCE: 155

Gly Gly Gly Gly Ser Gly Asn Ser
1               5

<210> SEQ ID NO 156
<211> LENGTH: 30
<212> TYPE: DNA
<213> ORGANISM: Artificial sequence
<220> FEATURE:
<223> OTHER INFORMATION: Synthetic primer
<220> FEATURE:
<223> OTHER INFORMATION: Linker H3 (PN)

-continued

<400> SEQUENCE: 156
aattatggtg gcggtggctc tgggaattct                                30

<210> SEQ ID NO 157
<211> LENGTH: 10
<212> TYPE: PRT
<213> ORGANISM: Artificial sequence
<220> FEATURE:
<223> OTHER INFORMATION: Scorpion linker region
<220> FEATURE:
<223> OTHER INFORMATION: Linker H3 (AA)

<400> SEQUENCE: 157

Asn Tyr Gly Gly Gly Gly Ser Gly Asn Ser
1               5                   10

<210> SEQ ID NO 158
<211> LENGTH: 39
<212> TYPE: DNA
<213> ORGANISM: Artificial sequence
<220> FEATURE:
<223> OTHER INFORMATION: Synthetic primer
<220> FEATURE:
<223> OTHER INFORMATION: Linker H4 (PN)

<400> SEQUENCE: 158
ggtggcggtg gctcgggcgg tggtggatct gggaattct                      39

<210> SEQ ID NO 159
<211> LENGTH: 13
<212> TYPE: PRT
<213> ORGANISM: Artificial sequence
<220> FEATURE:
<223> OTHER INFORMATION: Scorpion linker region
<220> FEATURE:
<223> OTHER INFORMATION: Linker H4 (AA)

<400> SEQUENCE: 159

Gly Gly Gly Gly Ser Gly Gly Gly Ser Gly Asn Ser
1               5                   10

<210> SEQ ID NO 160
<211> LENGTH: 45
<212> TYPE: DNA
<213> ORGANISM: Artificial sequence
<220> FEATURE:
<223> OTHER INFORMATION: Synthetic primer
<220> FEATURE:
<223> OTHER INFORMATION: Linker H5 (PN)

<400> SEQUENCE: 160
aattatggtg gcggtggctc gggcggtggt ggatctggga attct              45

<210> SEQ ID NO 161
<211> LENGTH: 15
<212> TYPE: PRT
<213> ORGANISM: Artificial sequence
<220> FEATURE:
<223> OTHER INFORMATION: Scorpion linker region
<220> FEATURE:
<223> OTHER INFORMATION: Linker H5 (AA)

<400> SEQUENCE: 161

Asn Tyr Gly Gly Gly Gly Ser Gly Gly Gly Ser Gly Asn Ser
1               5                   10                  15

<210> SEQ ID NO 162
<211> LENGTH: 54

```
<212> TYPE: DNA
<213> ORGANISM: Artificial sequence
<220> FEATURE:
<223> OTHER INFORMATION: Synthetic primer
<220> FEATURE:
<223> OTHER INFORMATION: Linker H6 (PN)

<400> SEQUENCE: 162
ggtggcggtg gctcgggcgg tggtggatct gggggaggag gcagcgggaa ttct          54

<210> SEQ ID NO 163
<211> LENGTH: 18
<212> TYPE: PRT
<213> ORGANISM: Artificial sequence
<220> FEATURE:
<223> OTHER INFORMATION: Scorpion linker region
<220> FEATURE:
<223> OTHER INFORMATION: Linker H6 (AA)

<400> SEQUENCE: 163

Gly Gly Gly Gly Ser Gly Gly Gly Gly Ser Gly Gly Gly Gly Ser Gly
1               5                   10                  15

Asn Ser

<210> SEQ ID NO 164
<211> LENGTH: 24
<212> TYPE: DNA
<213> ORGANISM: Artificial sequence
<220> FEATURE:
<223> OTHER INFORMATION: Synthetic primer
<220> FEATURE:
<223> OTHER INFORMATION: Linker H7 (PN)

<400> SEQUENCE: 164
gggtgtccac cttgtccgaa ttct                                           24

<210> SEQ ID NO 165
<211> LENGTH: 8
<212> TYPE: PRT
<213> ORGANISM: Artificial sequence
<220> FEATURE:
<223> OTHER INFORMATION: Scorpion linker region
<220> FEATURE:
<223> OTHER INFORMATION: Linker H7 (AA)

<400> SEQUENCE: 165

Gly Cys Pro Pro Cys Pro Asn Ser
1               5

<210> SEQ ID NO 166
<211> LENGTH: 45
<212> TYPE: DNA
<213> ORGANISM: Artificial sequence
<220> FEATURE:
<223> OTHER INFORMATION: Synthetic primer
<220> FEATURE:
<223> OTHER INFORMATION: Linker(G4S)3

<400> SEQUENCE: 166
ggtggcggtg gatccggcgg aggtgggtcg ggtggcggcg gatct                    45

<210> SEQ ID NO 167
<211> LENGTH: 12
<212> TYPE: PRT
<213> ORGANISM: Artificial sequence
<220> FEATURE:
<223> OTHER INFORMATION: Scorpion linker region
<220> FEATURE:
<223> OTHER INFORMATION: Linker(G4S)3
```

<400> SEQUENCE: 167

Gly Gly Gly Ser Gly Gly Gly Ser Gly Gly Gly Ser
1               5                   10

<210> SEQ ID NO 168
<211> LENGTH: 60
<212> TYPE: DNA
<213> ORGANISM: Artificial sequence
<220> FEATURE:
<223> OTHER INFORMATION: Synthetic primer
<220> FEATURE:
<223> OTHER INFORMATION: Linker(G4S)4

<400> SEQUENCE: 168

```
ggtggcggtg gctcgggcgg tggtggatct ggaggaggtg ggagcggggg aggtggcagt    60
```

<210> SEQ ID NO 169
<211> LENGTH: 17
<212> TYPE: PRT
<213> ORGANISM: Artificial sequence
<220> FEATURE:
<223> OTHER INFORMATION: Scorpion linker region
<220> FEATURE:
<223> OTHER INFORMATION: Linker(G4S)4

<400> SEQUENCE: 169

Gly Gly Gly Ser Gly Gly Gly Ser Gly Gly Gly Ser Gly Gly Gly Gly
1               5                   10                  15

Ser

<210> SEQ ID NO 170
<211> LENGTH: 2337
<212> TYPE: DNA
<213> ORGANISM: Artificial sequence
<220> FEATURE:
<223> OTHER INFORMATION: 2H7sssIgG1-STD1-2e12HL (DNA)

<400> SEQUENCE: 170

```
aagcttgccg ccatggattt tcaagtgcag attttcagct tcctgctaat cagtgcttca     60
gtcataatgt ccagaggaca aattgttctc tcccagtctc cagcaatcct gtctgcatct    120
ccaggggaga aggtcacaat gacttgcagg gccagctcaa gtgtaagtta catgcactgg    180
taccagcaga agccaggatc ctcccccaaa ccctggattt atgccccatc caacctggct    240
tctggagtcc ctgctcgctt cagtggcagt gggtctggga cctcttactc tctcacaatc    300
agcagagtgg aggctgaaga tgctgccact tattactgcc agcagtggag ttttaaccca    360
cccacgttcg gtgctgggac caagctggag ctgaaagatg cggtggctc gggcggtggt    420
ggatctggag gagtgggag ctctcaggct tatctacagc agtctggggc tgagtcggtg    480
aggcctgggg cctcagtgaa gatgtcctgc aaggcttctg gctacacatt taccagttac    540
aatatgcact gggtaaagca gacacctaga cagggcctgg aatggattgg agctatttat    600
ccaggaaatg gtgatacttc ctacaatcag aagttcaagg gcaaggccac actgactgta    660
gacaaatcct ccagcacagc ctacatgcag ctcagcagcc tgacatctga agactctgcg    720
gtctatttct gtgcaagagt ggtgtactat agtaactctt actggtactt cgatgtctgg    780
ggcacaggga ccacggtcac cgtctctgat caggagccca atcttctga caaaactcac    840
acatccccac cgagctcagc acctgaactc ctggggggac cgtcagtctt cctcttcccc    900
ccaaaaccca aggacaccct catgatctcc cggacccctg aggtcacatg cgtggtggtg    960
gacgtgagcc acgaagaccc tgaggtcaag ttcaactggt acgtggacgg cgtggaggtg   1020
```

-continued

```
cataatgcca agacaaagcc gcgggaggag cagtacaaca gcacgtaccg tgtggtcagc    1080
gtcctcaccg tcctgcacca ggactggctg aatggcaagg agtacaagtg caaggtctcc    1140
aacaaagccc tcccagcccc catcgagaaa acaatctcca aagccaaagg gcagccccga    1200
gaaccacagg tgtacaccct gccccatcc cgggatgagc tgaccaagaa ccaggtcagc    1260
ctgacctgcc tggtcaaagg cttctatccc agcgacatcg ccgtggagtg ggagagcaat    1320
gggcagccgg agaacaacta caagaccacg cctcccgtgc tggactccga cggctccttc    1380
ttcctctaca gcaagctcac cgtggacaag agcaggtggc agcaggggaa cgtcttctca    1440
tgctccgtga tgcatgaggc tctgcacaac cactacacgc agaagagcct ctccctgtct    1500
ccgggtaaga attatggtgg cgtggctcg ggcggtggtg gatctggagg aggtgggagt    1560
gggaattctc aggtgcagct gaaggagtca ggacctggcc tggtggcgcc ctcacagagc    1620
ctgtccatca catgcaccgt ctcagggttc tcattaaccg gctatggtgt aaactgggtt    1680
cgccagcctc caggaaaggg tctggagtgg ctgggaatga tatggggtga tggaagcaca    1740
gactataatt cagctctcaa atccagacta tcgatcacca aggacaactc caagagccaa    1800
gttttcttaa aaatgaacag tctgcaaact gatgacacag ccagatacta ctgtgctcga    1860
gatggttata gtaactttca ttactatgtt atggactact ggggtcaagg aacctcagtc    1920
accgtctcct ctggggtgg aggctctggt ggcggtggat ccggcggagg tgggtcgggt    1980
ggcggcggat ctgacattgt gctcacccaa tctccagctt cttggctgt gtctctaggt    2040 cagagagcca ccatctcctg cagagccagt gaaagtgttg aatattatgt cacaagttta    2100
atgcagtggt accaacagaa accaggacag ccacccaaac tcctcatctc tgctgctagc    2160
aacgtagaat ctggggtccc tgccaggttt agtggcagtg gtctgggac agactttagc    2220 ctcaacatcc atcctgtgga ggaggatgat attgcaatgt atttctgtca gcaaagtagg    2280
aaggttccat ggacgttcgg tggaggcacc aagctggaaa tcaaacgtta atctaga       2337
```

```
<210> SEQ ID NO 171
<211> LENGTH: 772
<212> TYPE: PRT
<213> ORGANISM: Artificial sequence
<220> FEATURE:
<223> OTHER INFORMATION: 2H7sssIgG1-STD1-2e12HL (AA)
<220> FEATURE:
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (23)..(128)
<223> OTHER INFORMATION: VL
<220> FEATURE:
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(281)
<223> OTHER INFORMATION: Hinge
<220> FEATURE:
<221> NAME/KEY: misc_feature
<222> LOCATION: (500)..(519)
<223> OTHER INFORMATION: EFD-BD2 linker
<220> FEATURE:
<221> NAME/KEY: misc_feature
<222> LOCATION: (520)..(640)
<223> OTHER INFORMATION: VH2
```

```
<220> FEATURE:
<221> NAME/KEY: misc_feature
<222> LOCATION: (641)..(660)
<223> OTHER INFORMATION: Linker2
<220> FEATURE:
<221> NAME/KEY: misc_feature
<222> LOCATION: (661)..(772)
<223> OTHER INFORMATION: VL2

<400> SEQUENCE: 171
```

| | | | | | | | | | | | | | | | |
|---|---|---|---|---|---|---|---|---|---|---|---|---|---|---|---|
| Met | Asp | Phe | Gln | Val | Gln | Ile | Phe | Ser | Phe | Leu | Leu | Ile | Ser | Ala | Ser |
| 1 | | | | 5 | | | | | 10 | | | | | 15 | |
| Val | Ile | Met | Ser | Arg | Gly | Gln | Ile | Val | Leu | Ser | Gln | Ser | Pro | Ala | Ile |
| | | | 20 | | | | | 25 | | | | | 30 | | |
| Leu | Ser | Ala | Ser | Pro | Gly | Glu | Lys | Val | Thr | Met | Thr | Cys | Arg | Ala | Ser |
| | | | 35 | | | | | 40 | | | | 45 | | | |
| Ser | Ser | Val | Ser | Tyr | Met | His | Trp | Tyr | Gln | Gln | Lys | Pro | Gly | Ser | Ser |
| | 50 | | | | | 55 | | | | | 60 | | | | |
| Pro | Lys | Pro | Trp | Ile | Tyr | Ala | Pro | Ser | Asn | Leu | Ala | Ser | Gly | Val | Pro |
| 65 | | | | | 70 | | | | | 75 | | | | | 80 |
| Ala | Arg | Phe | Ser | Gly | Ser | Gly | Ser | Gly | Thr | Ser | Tyr | Ser | Leu | Thr | Ile |
| | | | | 85 | | | | | 90 | | | | | 95 | |
| Ser | Arg | Val | Glu | Ala | Glu | Asp | Ala | Ala | Thr | Tyr | Tyr | Cys | Gln | Gln | Trp |
| | | | 100 | | | | | 105 | | | | | 110 | | |
| Ser | Phe | Asn | Pro | Pro | Thr | Phe | Gly | Ala | Gly | Thr | Lys | Leu | Glu | Leu | Lys |
| | | | 115 | | | | | 120 | | | | 125 | | | |
| Asp | Gly | Gly | Gly | Ser | Gly | Gly | Gly | Gly | Ser | Gly | Gly | Gly | Ser | Ser | Ser |
| | 130 | | | | | 135 | | | | | 140 | | | | |
| Gln | Ala | Tyr | Leu | Gln | Gln | Ser | Gly | Ala | Glu | Ser | Val | Arg | Pro | Gly | Ala |
| 145 | | | | | 150 | | | | | 155 | | | | | 160 |
| Ser | Val | Lys | Met | Ser | Cys | Lys | Ala | Ser | Gly | Tyr | Thr | Phe | Thr | Ser | Tyr |
| | | | | 165 | | | | | 170 | | | | | 175 | |
| Asn | Met | His | Trp | Val | Lys | Gln | Thr | Pro | Arg | Gln | Gly | Leu | Glu | Trp | Ile |
| | | | 180 | | | | | 185 | | | | | 190 | | |
| Gly | Ala | Ile | Tyr | Pro | Gly | Asn | Gly | Asp | Thr | Ser | Tyr | Asn | Gln | Lys | Phe |
| | | | 195 | | | | | 200 | | | | 205 | | | |
| Lys | Gly | Lys | Ala | Thr | Leu | Thr | Val | Asp | Lys | Ser | Ser | Ser | Thr | Ala | Tyr |
| | 210 | | | | | 215 | | | | | 220 | | | | |
| Met | Gln | Leu | Ser | Ser | Leu | Thr | Ser | Glu | Asp | Ser | Ala | Val | Tyr | Phe | Cys |
| 225 | | | | | 230 | | | | | 235 | | | | | 240 |
| Ala | Arg | Val | Val | Tyr | Tyr | Ser | Asn | Ser | Tyr | Trp | Tyr | Phe | Asp | Val | Trp |
| | | | | 245 | | | | | 250 | | | | | 255 | |
| Gly | Thr | Gly | Thr | Thr | Val | Thr | Val | Ser | Asp | Gln | Glu | Pro | Lys | Ser | Ser |
| | | | 260 | | | | | 265 | | | | | 270 | | |
| Asp | Lys | Thr | His | Thr | Ser | Pro | Pro | Ser | Ser | Ala | Pro | Glu | Leu | Leu | Gly |
| | | | 275 | | | | | 280 | | | | 285 | | | |
| Gly | Pro | Ser | Val | Phe | Leu | Phe | Pro | Pro | Lys | Pro | Lys | Asp | Thr | Leu | Met |
| | 290 | | | | | 295 | | | | | 300 | | | | |
| Ile | Ser | Arg | Thr | Pro | Glu | Val | Thr | Cys | Val | Val | Val | Asp | Val | Ser | His |
| 305 | | | | | 310 | | | | | 315 | | | | | 320 |
| Glu | Asp | Pro | Glu | Val | Lys | Phe | Asn | Trp | Tyr | Val | Asp | Gly | Val | Glu | Val |
| | | | | 325 | | | | | 330 | | | | | 335 | |
| His | Asn | Ala | Lys | Thr | Lys | Pro | Arg | Glu | Glu | Gln | Tyr | Asn | Ser | Thr | Tyr |
| | | | 340 | | | | | 345 | | | | | 350 | | |
| Arg | Val | Val | Ser | Val | Leu | Thr | Val | Leu | His | Gln | Asp | Trp | Leu | Asn | Gly |
| | | | 355 | | | | | 360 | | | | 365 | | | |

```
Lys Glu Tyr Lys Cys Lys Val Ser Asn Lys Ala Leu Pro Ala Pro Ile
            370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
                435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Asn Tyr Gly Gly Gly Ser Gly Gly Gly Ser Gly
                500                 505                 510

Gly Gly Gly Ser Gly Asn Ser Gln Val Gln Leu Lys Glu Ser Gly Pro
            515                 520                 525

Gly Leu Val Ala Pro Ser Gln Ser Leu Ser Ile Thr Cys Thr Val Ser
    530                 535                 540

Gly Phe Ser Leu Thr Gly Tyr Gly Val Asn Trp Val Arg Gln Pro Pro
545                 550                 555                 560

Gly Lys Gly Leu Glu Trp Leu Gly Met Ile Trp Gly Asp Gly Ser Thr
                565                 570                 575

Asp Tyr Asn Ser Ala Leu Lys Ser Arg Leu Ser Ile Thr Lys Asp Asn
                580                 585                 590

Ser Lys Ser Gln Val Phe Leu Lys Met Asn Ser Leu Gln Thr Asp Asp
            595                 600                 605

Thr Ala Arg Tyr Tyr Cys Ala Arg Asp Gly Tyr Ser Asn Phe His Tyr
    610                 615                 620

Tyr Val Met Asp Tyr Trp Gly Gln Gly Thr Ser Val Thr Val Ser Ser
625                 630                 635                 640

Gly Gly Gly Gly Ser Gly Gly Gly Gly Ser Gly Gly Gly Gly Ser Gly
                645                 650                 655

Gly Gly Gly Ser Asp Ile Val Leu Thr Gln Ser Pro Ala Ser Leu Ala
                660                 665                 670

Val Ser Leu Gly Gln Arg Ala Thr Ile Ser Cys Arg Ala Ser Glu Ser
            675                 680                 685

Val Glu Tyr Tyr Val Thr Ser Leu Met Gln Trp Tyr Gln Gln Lys Pro
    690                 695                 700

Gly Gln Pro Pro Lys Leu Leu Ile Ser Ala Ala Ser Asn Val Glu Ser
705                 710                 715                 720

Gly Val Pro Ala Arg Phe Ser Gly Ser Gly Ser Gly Thr Asp Phe Ser
                725                 730                 735

Leu Asn Ile His Pro Val Glu Glu Asp Asp Ile Ala Met Tyr Phe Cys
            740                 745                 750

Gln Gln Ser Arg Lys Val Pro Trp Thr Phe Gly Gly Gly Thr Lys Leu
    755                 760                 765

Glu Ile Lys Arg
770

<210> SEQ ID NO 172
```

```
<211> LENGTH: 772
<212> TYPE: PRT
<213> ORGANISM: Artificial sequence
<220> FEATURE:
<223> OTHER INFORMATION: 2H7sssIgG1(P238S/P331S)-STD1-2e12HL (w/2e12
      leader) (AA)
<220> FEATURE:
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (23)..(128)
<223> OTHER INFORMATION: VL
<220> FEATURE:
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(282)
<223> OTHER INFORMATION: Hinge
<220> FEATURE:
<221> NAME/KEY: misc_feature
<222> LOCATION: (500)..(519)
<223> OTHER INFORMATION: EFD-BD2 linker
<220> FEATURE:
<221> NAME/KEY: misc_feature
<222> LOCATION: (520)..(640)
<223> OTHER INFORMATION: VH2
<220> FEATURE:
<221> NAME/KEY: misc_feature
<222> LOCATION: (641)..(660)
<223> OTHER INFORMATION: Linker2
<220> FEATURE:
<221> NAME/KEY: misc_feature
<222> LOCATION: (661)..(772)
<223> OTHER INFORMATION: VL2

<400> SEQUENCE: 172

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Ser Gly Gly Gly Ser Gly Ser Ser
    130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190
```

-continued

```
Gly Ala Ile Tyr Pro Gly Asn Gly Asp Thr Ser Tyr Asn Gln Lys Phe
            195                 200                 205
Lys Gly Lys Ala Thr Leu Thr Val Asp Lys Ser Ser Thr Ala Tyr
        210                 215                 220
Met Gln Leu Ser Ser Leu Thr Ser Glu Asp Ser Ala Val Tyr Phe Cys
225                 230                 235                 240
Ala Arg Val Val Tyr Tyr Ser Asn Ser Tyr Trp Tyr Phe Asp Val Trp
                245                 250                 255
Gly Thr Gly Thr Thr Val Thr Val Ser Asp Gln Pro Lys Ser Ser
            260                 265                 270
Asp Lys Thr His Thr Ser Pro Pro Ser Ser Ala Pro Glu Leu Leu Gly
        275                 280                 285
Gly Ser Ser Val Phe Leu Phe Pro Pro Lys Pro Lys Asp Thr Leu Met
    290                 295                 300
Ile Ser Arg Thr Pro Glu Val Thr Cys Val Val Val Asp Val Ser His
305                 310                 315                 320
Glu Asp Pro Glu Val Lys Phe Asn Trp Tyr Val Asp Gly Val Glu Val
                325                 330                 335
His Asn Ala Lys Thr Lys Pro Arg Glu Glu Gln Tyr Asn Ser Thr Tyr
            340                 345                 350
Arg Val Val Ser Val Leu Thr Val Leu His Gln Asp Trp Leu Asn Gly
        355                 360                 365
Lys Glu Tyr Lys Cys Lys Val Ser Asn Lys Ala Leu Pro Ala Ser Ile
    370                 375                 380
Glu Lys Thr Ile Ser Lys Ala Lys Gly Gln Pro Arg Glu Pro Gln Val
385                 390                 395                 400
Tyr Thr Leu Pro Pro Ser Arg Asp Glu Leu Thr Lys Asn Gln Val Ser
                405                 410                 415
Leu Thr Cys Leu Val Lys Gly Phe Tyr Pro Ser Asp Ile Ala Val Glu
            420                 425                 430
Trp Glu Ser Asn Gly Gln Pro Glu Asn Asn Tyr Lys Thr Thr Pro Pro
        435                 440                 445
Val Leu Asp Ser Asp Gly Ser Phe Phe Leu Tyr Ser Lys Leu Thr Val
    450                 455                 460
Asp Lys Ser Arg Trp Gln Gln Gly Asn Val Phe Ser Cys Ser Val Met
465                 470                 475                 480
His Glu Ala Leu His Asn His Tyr Thr Gln Lys Ser Leu Ser Leu Ser
                485                 490                 495
Pro Gly Lys Asn Tyr Gly Gly Gly Ser Gly Gly Gly Ser Gly
            500                 505                 510
Gly Gly Gly Ser Gly Asn Ser Gln Val Gln Leu Lys Glu Ser Gly Pro
        515                 520                 525
Gly Leu Val Ala Pro Ser Gln Ser Leu Ser Ile Thr Cys Thr Val Ser
    530                 535                 540
Gly Phe Ser Leu Thr Gly Tyr Gly Val Asn Trp Val Arg Gln Pro Pro
545                 550                 555                 560
Gly Lys Gly Leu Glu Trp Leu Gly Met Ile Trp Gly Asp Gly Ser Thr
                565                 570                 575
Asp Tyr Asn Ser Ala Leu Lys Ser Arg Leu Ser Ile Thr Lys Asp Asn
            580                 585                 590
Ser Lys Ser Gln Val Phe Leu Lys Met Asn Ser Leu Gln Thr Asp Asp
        595                 600                 605
Thr Ala Arg Tyr Tyr Cys Ala Arg Asp Gly Tyr Ser Asn Phe His Tyr
```

```
                610                615                620
Tyr Val Met Asp Tyr Trp Gly Gln Gly Thr Ser Val Thr Val Ser Ser
625                 630                635                 640

Gly Gly Gly Gly Ser Gly Gly Gly Ser Gly Gly Gly Ser Gly
                645                650                655

Gly Gly Gly Ser Asp Ile Val Leu Thr Gln Ser Pro Ala Ser Leu Ala
                660                665                670

Val Ser Leu Gly Gln Arg Ala Thr Ile Ser Cys Arg Ala Ser Glu Ser
                675                680                685

Val Glu Tyr Tyr Val Thr Ser Leu Met Gln Trp Tyr Gln Gln Lys Pro
                690                695                700

Gly Gln Pro Pro Lys Leu Leu Ile Ser Ala Ala Ser Asn Val Glu Ser
705                 710                715                 720

Gly Val Pro Ala Arg Phe Ser Gly Ser Gly Ser Gly Thr Asp Phe Ser
                725                730                735

Leu Asn Ile His Pro Val Glu Asp Asp Ile Ala Met Tyr Phe Cys
                740                745                750

Gln Gln Ser Arg Lys Val Pro Trp Thr Phe Gly Gly Gly Thr Lys Leu
                755                760                765

Glu Ile Lys Arg
770

<210> SEQ ID NO 173
<211> LENGTH: 2322
<212> TYPE: DNA
<213> ORGANISM: Artificial sequence
<220> FEATURE:
<223> OTHER INFORMATION: 2H7sssIgG1-STD1-2e12LH (DNA)

<400> SEQUENCE: 173
aagcttgccg ccatggattt tcaagtgcag attttcagct tcctgctaat cagtgcttca      60
gtcataatgt ccagaggaca aattgttctc tcccagtctc cagcaatcct gtctgcatct     120
ccagggagag aggtcacaat gacttgcagg gccagctcaa gtgtaagtta catgcactgg     180
taccagcaga agccaggatc ctcccccaaa ccctggattt atgccccatc caacctggct     240
tctggagtcc ctgctcgctt cagtggcagt gggtctggga cctcttactc tctcacaatc     300
agcagagtgg aggctgaaga tgctgccact tattactgcc agcagtggag ttttaaccca     360
cccacgttcg gtgctgggac caagctggag ctgaaagatg cggtggctc gggcggtggt      420
ggatctggag gaggtgggag ctctcaggct tatctacagc agtctgggc tgagtcggtg      480
aggcctgggg cctcagtgaa gatgtcctgc aaggcttctg gctacacatt taccagttac     540
aatatgcact gggtaaagca gacacctaga cagggcctgg aatggattgg agctatttat     600
ccaggaaatg gtgatacttc ctacaatcag aagttcaagg gcaaggccac actgactgta     660
gacaaatcct ccagcacagc ctacatgcag ctcagcagcc tgacatctga agactctgcg     720
gtctatttct gtgcaagagt ggtgtactat agtaactctt actggtactt cgatgtctgg     780
ggcacaggga ccacggtcac cgtctctgat caggagccca atcttctga caaaactcac     840
acatccccac cgagcccagc acctgaactc ctggggggac cgtcagtctt cctcttcccc     900
ccaaaaccca aggacaccct catgatctcc cggacccctg aggtcacatg cgtggtggtg     960
gacgtgagcc acgaagaccc tgaggtcaag ttcaactggt acgtggacgg cgtggaggtg    1020
cataatgcca agacaaagcc gcgggaggag cagtacaaca gcacgtaccg tgtggtcagc    1080
gtcctcaccg tcctgcacca ggactggctg aatggcaagg agtacaagtg caaggtctcc    1140
```

-continued

```
aacaaagccc tcccagcccc catcgagaaa acaatctcca aagccaaagg gcagccccga    1200
gaaccacagg tgtacaccct gcccccatcc cgggatgagc tgaccaagaa ccaggtcagc    1260
ctgacctgcc tggtcaaagg cttctatccc agcgacatcg ccgtggagtg ggagagcaat    1320
gggcagccgg agaacaacta caagaccacg cctcccgtgc tggactccga cggctccttc    1380
ttcctctaca gcaagctcac cgtggacaag agcaggtggc agcagggaa cgtcttctca    1440 tgctccgtga tgcatgaggc tctgcacaac cactacacgc agaagagcct ctccctgtct    1500
ccgggtaaga attatggtgg cggtggctcg ggcggtggtg gatctggagg aggtgggagt    1560
gggaattctg acattgtgct cacccaatct ccagcttctt tggctgtgtc tctaggtcag    1620
agagccacca tctcctgcag agccagtgaa agtgttgaat attatgtcac aagtttaatg    1680
cagtggtacc aacagaaacc aggacagcca cccaaactcc tcatctctgc tgctagcaac    1740
gtagaatctg gggtccctgc caggtttagt ggcagtgggt ctgggacaga ctttagcctc    1800
aacatccatc ctgtggagga ggatgatatt gcaatgtatt tctgtcagca aagtaggaag    1860
gttccatgga cgttcggtgg aggcaccaag ctggaaatca acgggtgg cggtggatcc     1920 ggcggaggtg ggtcgggtgg cggcggatct caggtgcagc tgaaggagtc aggacctggc    1980
ctggtggcgc cctcacagag cctgtccatc acatgcaccg tctcagggtt ctcattaacc    2040
ggctatggta taaactgggt tcgccagcct ccaggaaagg gtctggagtg gctgggaatg    2100 atatgggtg atggaagcac agactataat tcagctctca atccagact atcgatcacc      2160 aaggacaact ccaagagcca gttttctta aaaatgaaca gtctgcaaac tgatgacaca     2220
gccagatact actgtgctcg agatggttat agtaactttc attactatgt tatggactac    2280
tggggtcaag gaacctcagt caccgtctcc tcttaatcta ga                        2322
```

<210> SEQ ID NO 174
<211> LENGTH: 767
<212> TYPE: PRT
<213> ORGANISM: Artificial sequence
<220> FEATURE:
<223> OTHER INFORMATION: 2H7sssIgG1-STD1-2e12LH (w/2e12 leader) (AA)
<220> FEATURE:
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (23)..(128)
<223> OTHER INFORMATION: VL
<220> FEATURE:
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(282)
<223> OTHER INFORMATION: Hinge
<220> FEATURE:
<221> NAME/KEY: misc_feature
<222> LOCATION: (500)..(519)
<223> OTHER INFORMATION: EFD-BD2 linker
<220> FEATURE:
<221> NAME/KEY: misc_feature
<222> LOCATION: (520)..(631)
<223> OTHER INFORMATION: VL2
<220> FEATURE:
<221> NAME/KEY: misc_feature
<222> LOCATION: (632)..(646)
<223> OTHER INFORMATION: Linker2
<220> FEATURE:

<221> NAME/KEY: misc_feature
<222> LOCATION: (647)..(767)
<223> OTHER INFORMATION: VH2

<400> SEQUENCE: 174

```
Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Ser Gly Gly Gly Ser Ser
130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Val Asp Lys Ser Ser Ser Thr Ala Tyr
    210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
                245                 250                 255

Gly Thr Gly Thr Thr Val Thr Val Ser Asp Gln Pro Lys Ser Ser
            260                 265                 270

Asp Lys Thr His Thr Ser Pro Pro Ser Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400
```

Tyr Thr Leu Pro Pro Ser Arg Asp Glu Leu Thr Lys Asn Gln Val Ser
            405                 410                 415

Leu Thr Cys Leu Val Lys Gly Phe Tyr Pro Ser Asp Ile Ala Val Glu
        420                 425                 430

Trp Glu Ser Asn Gly Gln Pro Glu Asn Asn Tyr Lys Thr Thr Pro Pro
            435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Asn Tyr Gly Gly Gly Ser Gly Gly Gly Ser Gly
            500                 505                 510

Gly Gly Gly Ser Gly Asn Ser Asp Ile Val Leu Thr Gln Ser Pro Ala
        515                 520                 525

Ser Leu Ala Val Ser Leu Gly Gln Arg Ala Thr Ile Ser Cys Arg Ala
    530                 535                 540

Ser Glu Ser Val Glu Tyr Tyr Val Thr Ser Leu Met Gln Trp Tyr Gln
545                 550                 555                 560

Gln Lys Pro Gly Gln Pro Pro Lys Leu Leu Ile Ser Ala Ala Ser Asn
                565                 570                 575

Val Glu Ser Gly Val Pro Ala Arg Phe Ser Gly Ser Gly Ser Gly Thr
            580                 585                 590

Asp Phe Ser Leu Asn Ile His Pro Val Glu Glu Asp Asp Ile Ala Met
        595                 600                 605

Tyr Phe Cys Gln Gln Ser Arg Lys Val Pro Trp Thr Phe Gly Gly Gly
    610                 615                 620

Thr Lys Leu Glu Ile Lys Arg Gly Gly Gly Gly Ser Gly Gly Gly Gly
625                 630                 635                 640

Ser Gly Gly Gly Gly Ser Gln Val Gln Leu Lys Glu Ser Gly Pro Gly
                645                 650                 655

Leu Val Ala Pro Ser Gln Ser Leu Ser Ile Thr Cys Thr Val Ser Gly
            660                 665                 670

Phe Ser Leu Thr Gly Tyr Gly Val Asn Trp Val Arg Gln Pro Pro Gly
        675                 680                 685

Lys Gly Leu Glu Trp Leu Gly Met Ile Trp Gly Asp Gly Ser Thr Asp
    690                 695                 700

Tyr Asn Ser Ala Leu Lys Ser Arg Leu Ser Ile Thr Lys Asp Asn Ser
705                 710                 715                 720

Lys Ser Gln Val Phe Leu Lys Met Asn Ser Leu Gln Thr Asp Asp Thr
                725                 730                 735

Ala Arg Tyr Tyr Cys Ala Arg Asp Gly Tyr Ser Asn Phe His Tyr Tyr
            740                 745                 750

Val Met Asp Tyr Trp Gly Gln Gly Thr Ser Val Thr Val Ser Ser
        755                 760                 765

```
<210> SEQ ID NO 175
<211> LENGTH: 767
<212> TYPE: PRT
<213> ORGANISM: Artificial sequence
<220> FEATURE:
<223> OTHER INFORMATION: 2H7sssIgG1(P238S/P331S)-STD1-2e12LH (w/2e12
      leader) (AA)
<220> FEATURE:
<221> NAME/KEY: misc_feature
```

```
<222> LOCATION: (1)..(22)
<223> OTHER INFORMATION: Leader
<220> FEATURE:
<221> NAME/KEY: misc_feature
<222> LOCATION: (23)..(128)
<223> OTHER INFORMATION: VL
<220> FEATURE:
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(282)
<223> OTHER INFORMATION: Hinge
<220> FEATURE:
<221> NAME/KEY: misc_feature
<222> LOCATION: (500)..(519)
<223> OTHER INFORMATION: EFD-BD2 Linker
<220> FEATURE:
<221> NAME/KEY: misc_feature
<222> LOCATION: (520)..(631)
<223> OTHER INFORMATION: VL2
<220> FEATURE:
<221> NAME/KEY: misc_feature
<222> LOCATION: (632)..(646)
<223> OTHER INFORMATION: Linker2
<220> FEATURE:
<221> NAME/KEY: misc_feature
<222> LOCATION: (647)..(767)
<223> OTHER INFORMATION: VH2

<400> SEQUENCE: 175

Met Asp Phe Gln Val Gln Ile Phe Ser Phe Leu Leu Ile Ser Ala Ser
 1               5                  10                  15

Val Ile Met Ser Arg Gly Gln Ile Val Leu Ser Gln Ser Pro Ala Ile
             20                  25                  30

Leu Ser Ala Ser Pro Gly Glu Lys Val Thr Met Thr Cys Arg Ala Ser
         35                  40                  45

Ser Ser Val Ser Tyr Met His Trp Tyr Gln Gln Lys Pro Gly Ser Ser
     50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                 85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Ser Gly Gly Gly Gly Ser Ser
    130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Val Asp Lys Ser Ser Ser Thr Ala Tyr
    210                 215                 220

Met Gln Leu Ser Ser Leu Thr Ser Glu Asp Ser Ala Val Tyr Phe Cys
```

```
                225                 230                 235                 240

Ala Arg Val Val Tyr Tyr Ser Asn Ser Tyr Trp Tyr Phe Asp Val Trp
                        245                 250                 255

Gly Thr Gly Thr Thr Val Thr Val Ser Asp Gln Glu Pro Lys Ser Ser
                        260                 265                 270

Asp Lys Thr His Thr Ser Pro Pro Ser Ser Ala Pro Glu Leu Leu Gly
                        275                 280                 285

Gly Ser Ser Val Phe Leu Phe Pro Pro Lys Pro Lys Asp Thr Leu Met
                290                 295                 300

Ile Ser Arg Thr Pro Glu Val Thr Cys Val Val Val Asp Val Ser His
        305                 310                 315                 320

Glu Asp Pro Glu Val Lys Phe Asn Trp Tyr Val Asp Gly Val Glu Val
                        325                 330                 335

His Asn Ala Lys Thr Lys Pro Arg Glu Glu Gln Tyr Asn Ser Thr Tyr
                        340                 345                 350

Arg Val Val Ser Val Leu Thr Val Leu His Gln Asp Trp Leu Asn Gly
                        355                 360                 365

Lys Glu Tyr Lys Cys Lys Val Ser Asn Lys Ala Leu Pro Ala Ser Ile
                370                 375                 380

Glu Lys Thr Ile Ser Lys Ala Lys Gly Gln Pro Arg Glu Pro Gln Val
        385                 390                 395                 400

Tyr Thr Leu Pro Pro Ser Arg Asp Glu Leu Thr Lys Asn Gln Val Ser
                        405                 410                 415

Leu Thr Cys Leu Val Lys Gly Phe Tyr Pro Ser Asp Ile Ala Val Glu
                        420                 425                 430

Trp Glu Ser Asn Gly Gln Pro Glu Asn Asn Tyr Lys Thr Thr Pro Pro
                        435                 440                 445

Val Leu Asp Ser Asp Gly Ser Phe Phe Leu Tyr Ser Lys Leu Thr Val
                450                 455                 460

Asp Lys Ser Arg Trp Gln Gln Gly Asn Val Phe Ser Cys Ser Val Met
        465                 470                 475                 480

His Glu Ala Leu His Asn His Tyr Thr Gln Lys Ser Leu Ser Leu Ser
                        485                 490                 495

Pro Gly Lys Asn Tyr Gly Gly Gly Ser Gly Gly Gly Ser Gly
                        500                 505                 510

Gly Gly Ser Gly Asn Ser Asp Ile Val Leu Thr Gln Ser Pro Ala
                        515                 520                 525

Ser Leu Ala Val Ser Leu Gly Gln Arg Ala Thr Ile Ser Cys Arg Ala
                530                 535                 540

Ser Glu Ser Val Glu Tyr Tyr Val Thr Ser Leu Met Gln Trp Tyr Gln
        545                 550                 555                 560

Gln Lys Pro Gly Gln Pro Pro Lys Leu Leu Ile Ser Ala Ala Ser Asn
                        565                 570                 575

Val Glu Ser Gly Val Pro Ala Arg Phe Ser Gly Ser Gly Ser Gly Thr
                        580                 585                 590

Asp Phe Ser Leu Asn Ile His Pro Val Glu Glu Asp Asp Ile Ala Met
                        595                 600                 605

Tyr Phe Cys Gln Gln Ser Arg Lys Val Pro Trp Thr Phe Gly Gly Gly
                        610                 615                 620

Thr Lys Leu Glu Ile Lys Arg Gly Gly Gly Ser Gly Gly Gly Gly
        625                 630                 635                 640

Ser Gly Gly Gly Gly Ser Gln Val Gln Leu Lys Glu Ser Gly Pro Gly
                        645                 650                 655
```

```
Leu Val Ala Pro Ser Gln Ser Leu Ser Ile Thr Cys Thr Val Ser Gly
            660                 665                 670
Phe Ser Leu Thr Gly Tyr Gly Val Asn Trp Val Arg Gln Pro Pro Gly
        675                 680                 685
Lys Gly Leu Glu Trp Leu Gly Met Ile Trp Gly Asp Gly Ser Thr Asp
    690                 695                 700
Tyr Asn Ser Ala Leu Lys Ser Arg Leu Ser Ile Thr Lys Asp Asn Ser
705                 710                 715                 720
Lys Ser Gln Val Phe Leu Lys Met Asn Ser Leu Gln Thr Asp Asp Thr
                725                 730                 735
Ala Arg Tyr Tyr Cys Ala Arg Asp Gly Tyr Ser Asn Phe His Tyr Tyr
            740                 745                 750
Val Met Asp Tyr Trp Gly Gln Gly Thr Ser Val Thr Val Ser Ser
        755                 760                 765

<210> SEQ ID NO 176
<211> LENGTH: 2376
<212> TYPE: DNA
<213> ORGANISM: Artificial sequence
<220> FEATURE:
<223> OTHER INFORMATION: 2H7sssIgG1-STD2-2e12LH (DNA)

<400> SEQUENCE: 176
aagcttgccg ccatggattt tcaagtgcag attttcagct tcctgctaat cagtgcttca      60
gtcataatgt ccagaggaca aattgttctc tcccagtctc cagcaatcct gtctgcatct     120
ccaggggaga aggtcacaat gacttgcagg gccagctcaa gtgtaagtta catgcactgg     180
taccagcaga agccaggatc ctcccccaaa ccctggattt atgccccatc caacctggct     240
tctggagtcc ctgctcgctt cagtggcagt gggtctggga cctcttactc tctcacaatc     300
agcagagtgg aggctgaaga tgctgccact tattactgcc agcagtggag ttttaaccca     360
cccacgttcg gtgctgggac caagctggag ctgaaagatg cggtggctc gggcggtggt     420
ggatctggag gaggtgggag ctctcaggct tatctacagc agtctggggc tgagtcggtg     480
aggcctgggg cctcagtgaa gatgtcctgc aaggcttctg gctacacatt taccagttac     540
aatatgcact gggtaaagca gacacctaga cagggcctgg aatggattgg agctatttat     600
ccaggaaatg gtgatacttc ctacaatcag aagttcaagg gcaaggccac actgactgta     660
gacaaatcct ccagcacagc ctacatgcag ctcagcagcc tgacatctga agactctgcg     720
gtctatttct gtgcaagagt ggtgtactat agtaactctt actggtactt cgatgtctgg     780
ggcacaggga ccacggtcac cgtctctgat caggagccca atcttctga caaaactcac     840
acatccccac cgagcccagc acctgaactc ctgggggac cgtcagtctt cctcttcccc      900
ccaaaaccca aggacaccct catgatctcc cggacccctg aggtcacatg cgtggtggtg     960
gacgtgagcc acgaagaccc tgaggtcaag ttcaactggt acgtggacgg cgtggaggtg    1020
cataatgcca agacaaagcc gcgggaggag cagtacaaca gcacgtaccg tgtggtcagc    1080
gtcctcaccg tcctgcacca ggactggctg aatggcaagg agtacaagtg caaggtctcc    1140
aacaaagccc tcccagcccc catcgagaaa acaatctcca agccaaagg gcagccccga    1200
gaaccacagg tgtacaccct gcccccatcc cgggatgagc tgaccaagaa ccaggtcagc    1260
ctgacctgcc tggtcaaagg cttctatccc agcgacatcg ccgtggagtg ggagagcaat    1320
gggcagccgg agaacaacta caagaccacg cctcccgtgc tggactccga cggctccttc    1380
ttcctctaca gcaagctcac cgtggacaag agcaggtggc agcaggggaa cgtcttctca    1440
tgctccgtga tgcatgaggc tctgcacaac cactacacgc agaagagcct ctccctgtct    1500
```

```
ccgggtaaga attatggtgg cggtggctcg ggcggtggtg gatctggagg aggtgggagt    1560
gggaattatg gtggcggtgg ctcgggcggt ggtggatctg gaggaggtgg gagtgggaat    1620
tctgacattg tgctcaccca atctccagct tctttggctg tgtctctagg tcagagagcc    1680
accatctcct gcagagccag tgaaagtgtt gaatattatg tcacaagttt aatgcagtgg    1740
taccaacaga aaccaggaca gccacccaaa ctcctcatct ctgctgctag caacgtagaa    1800 tctgggtcc ctgccaggtt tagtggcagt gggtctggga cagactttag cctcaacatc    1860
catcctgtgg aggaggatga tattgcaatg tatttctgtc agcaaagtag gaaggttcca    1920
tggacgttcg gtggaggcac caagctggaa atcaaacggg gtggcggtgg atccggcgga    1980
ggtgggtcgg gtggcggcgg atctcaggtg cagctgaagg agtcaggacc tggcctggtg    2040
gcgccctcac agagcctgtc catcacatgc accgtctcag ggttctcatt aaccggctat    2100
ggtgtaaact gggttcgcca gcctccagga aagggtctgg agtggctggg aatgatatgg    2160
ggtgatggaa gcacagacta taattcagct ctcaaatcca gactatcgat caccaaggac    2220
aactccaaga gccaagtttt cttaaaaatg aacagtctgc aaactgatga cacagccaga    2280
tactactgtg ctcgagatgg ttatagtaac tttcattact atgttatgga ctactgggt     2340 caaggaacct cagtcaccgt ctcctcttaa tctaga                              2376
```

<210> SEQ ID NO 177
<211> LENGTH: 785
<212> TYPE: PRT
<213> ORGANISM: Artificial sequence
<220> FEATURE:
<223> OTHER INFORMATION: 2H7sssIgG1-STD2-2e12LH (w/2e12 leader)
<220> FEATURE:
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (23)..(129)
<223> OTHER INFORMATION: VL
<220> FEATURE:
<221> NAME/KEY: misc_feature
<222> LOCATION: (130)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(282)
<223> OTHER INFORMATION: Hinge
<220> FEATURE:
<221> NAME/KEY: misc_feature
<222> LOCATION: (500)..(537)
<223> OTHER INFORMATION: EFD-BD2 Linker
<220> FEATURE:
<221> NAME/KEY: misc_feature
<222> LOCATION: (538)..(649)
<223> OTHER INFORMATION: VL2
<220> FEATURE:
<221> NAME/KEY: misc_feature
<222> LOCATION: (650)..(664)
<223> OTHER INFORMATION: Linker2
<220> FEATURE:
<221> NAME/KEY: misc_feature
<222> LOCATION: (665)..(785)
<223> OTHER INFORMATION: VH2

<400> SEQUENCE: 177

```
Met Asp Phe Gln Val Gln Ile Phe Ser Phe Leu Leu Ile Ser Ala Ser
1               5                   10                  15
```

-continued

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Gly Ser Gly Gly Gly Gly Ser Ser
    130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Val Asp Lys Ser Ser Ser Thr Ala Tyr
    210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
                245                 250                 255

Gly Thr Gly Thr Thr Val Thr Val Ser Asp Gln Glu Pro Lys Ser Ser
            260                 265                 270

Asp Lys Thr His Thr Ser Pro Pro Ser Ser Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
450 455 460

Asp Lys Ser Arg Trp Gln Gln Gly Asn Val Phe Ser Cys Ser Val Met
465 470 475 480

His Glu Ala Leu His Asn His Tyr Thr Gln Lys Ser Leu Ser Leu Ser
485 490 495

Pro Gly Lys Asn Tyr Gly Gly Gly Ser Gly Gly Gly Ser Gly
500 505 510

Gly Gly Gly Ser Gly Asn Tyr Gly Gly Gly Ser Gly Gly Gly Gly
515 520 525

Ser Gly Gly Gly Gly Ser Gly Asn Ser Asp Ile Val Leu Thr Gln Ser
530 535 540

Pro Ala Ser Leu Ala Val Ser Leu Gly Gln Arg Ala Thr Ile Ser Cys
545 550 555 560

Arg Ala Ser Glu Ser Val Glu Tyr Tyr Val Thr Ser Leu Met Gln Trp
565 570 575

Tyr Gln Gln Lys Pro Gly Gln Pro Pro Lys Leu Leu Ile Ser Ala Ala
580 585 590

Ser Asn Val Glu Ser Gly Val Pro Ala Arg Phe Ser Gly Ser Gly Ser
595 600 605

Gly Thr Asp Phe Ser Leu Asn Ile His Pro Val Glu Glu Asp Asp Ile
610 615 620

Ala Met Tyr Phe Cys Gln Gln Ser Arg Lys Val Pro Trp Thr Phe Gly
625 630 635 640

Gly Gly Thr Lys Leu Glu Ile Lys Arg Gly Gly Gly Gly Ser Gly Gly
645 650 655

Gly Gly Ser Gly Gly Gly Gly Ser Gln Val Gln Leu Lys Glu Ser Gly
660 665 670

Pro Gly Leu Val Ala Pro Ser Gln Ser Leu Ser Ile Thr Cys Thr Val
675 680 685

Ser Gly Phe Ser Leu Thr Gly Tyr Gly Val Asn Trp Val Arg Gln Pro
690 695 700

Pro Gly Lys Gly Leu Glu Trp Leu Gly Met Ile Trp Gly Asp Gly Ser
705 710 715 720

Thr Asp Tyr Asn Ser Ala Leu Lys Ser Arg Leu Ser Ile Thr Lys Asp
725 730 735

Asn Ser Lys Ser Gln Val Phe Leu Lys Met Asn Ser Leu Gln Thr Asp
740 745 750

Asp Thr Ala Arg Tyr Tyr Cys Ala Arg Asp Gly Tyr Ser Asn Phe His
755 760 765

Tyr Tyr Val Met Asp Tyr Trp Gly Gln Gly Thr Ser Val Thr Val Ser
770 775 780

Ser
785

<210> SEQ ID NO 178
<211> LENGTH: 785
<212> TYPE: PRT
<213> ORGANISM: Artificial sequence
<220> FEATURE:
<223> OTHER INFORMATION: 2H7sssIgG1(P238S/P331S)-STD2-2e12LH (w/2e12
      leader) (AA)
<220> FEATURE:
<221> NAME/KEY: misc_feature
<222> LOCATION: (1)..(22)
<223> OTHER INFORMATION: Leader
<220> FEATURE:

```
<221> NAME/KEY: misc_feature
<222> LOCATION: (23)..(128)
<223> OTHER INFORMATION: VL
<220> FEATURE:
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(281)
<223> OTHER INFORMATION: Hinge
<220> FEATURE:
<221> NAME/KEY: misc_feature
<222> LOCATION: (500)..(537)
<223> OTHER INFORMATION: EFD-BD2 Linker
<220> FEATURE:
<221> NAME/KEY: misc_feature
<222> LOCATION: (538)..(649)
<223> OTHER INFORMATION: VL2
<220> FEATURE:
<221> NAME/KEY: misc_feature
<222> LOCATION: (650)..(664)
<223> OTHER INFORMATION: Linker2
<220> FEATURE:
<221> NAME/KEY: misc_feature
<222> LOCATION: (665)..(785)
<223> OTHER INFORMATION: VH2

<400> SEQUENCE: 178

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
                20                  25                  30

Leu Ser Ala Ser Pro Gly Glu Lys Val Thr Met Thr Cys Arg Ala Ser
            35                  40                  45

Ser Ser Val Ser Tyr Met His Trp Tyr Gln Gln Lys Pro Gly Ser Ser
        50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Gly Ser Gly Gly Gly Gly Ser Ser
130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Val Asp Lys Ser Ser Ser Thr Ala Tyr
            210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
```

```
                245                 250                 255
Gly Thr Gly Thr Thr Val Thr Val Ser Asp Gln Glu Pro Lys Ser Ser
            260                 265                 270

Asp Lys Thr His Thr Ser Pro Pro Ser Ser Ala Pro Glu Leu Leu Gly
            275                 280                 285

Gly Ser Ser Val Phe Leu Phe Pro Pro Lys Pro Lys Asp Thr Leu Met
            290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
            325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
            355                 360                 365

Lys Glu Tyr Lys Cys Lys Val Ser Asn Lys Ala Leu Pro Ala Ser Ile
            370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
            405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
            435                 440                 445

Val Leu Asp Ser Asp Gly Ser Phe Phe Leu Tyr Ser Lys Leu Thr Val
            450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
            485                 490                 495

Pro Gly Lys Asn Tyr Gly Gly Gly Ser Gly Gly Gly Ser Gly
            500                 505                 510

Gly Gly Gly Ser Gly Asn Tyr Gly Gly Gly Ser Gly Gly Gly
            515                 520                 525

Ser Gly Gly Gly Gly Ser Gly Asn Ser Asp Ile Val Leu Thr Gln Ser
            530                 535                 540

Pro Ala Ser Leu Ala Val Ser Leu Gly Gln Arg Ala Thr Ile Ser Cys
545                 550                 555                 560

Arg Ala Ser Glu Ser Val Glu Tyr Tyr Val Thr Ser Leu Met Gln Trp
            565                 570                 575

Tyr Gln Gln Lys Pro Gly Gln Pro Pro Lys Leu Leu Ile Ser Ala Ala
            580                 585                 590

Ser Asn Val Glu Ser Gly Val Pro Ala Arg Phe Ser Gly Ser Gly Ser
            595                 600                 605

Gly Thr Asp Phe Ser Leu Asn Ile His Pro Val Glu Glu Asp Asp Ile
            610                 615                 620

Ala Met Tyr Phe Cys Gln Gln Ser Arg Lys Val Pro Trp Thr Phe Gly
625                 630                 635                 640

Gly Gly Thr Lys Leu Glu Ile Lys Arg Gly Gly Gly Ser Gly Gly
            645                 650                 655

Gly Gly Ser Gly Gly Gly Ser Gln Val Gln Leu Lys Glu Ser Gly
            660                 665                 670
```

-continued

```
Pro Gly Leu Val Ala Pro Ser Gln Ser Leu Ser Ile Thr Cys Thr Val
            675                 680                 685

Ser Gly Phe Ser Leu Thr Gly Tyr Gly Val Asn Trp Val Arg Gln Pro
    690                 695                 700

Pro Gly Lys Gly Leu Glu Trp Leu Gly Met Ile Trp Gly Asp Gly Ser
705                 710                 715                 720

Thr Asp Tyr Asn Ser Ala Leu Lys Ser Arg Leu Ser Ile Thr Lys Asp
                725                 730                 735

Asn Ser Lys Ser Gln Val Phe Leu Lys Met Asn Ser Leu Gln Thr Asp
            740                 745                 750

Asp Thr Ala Arg Tyr Tyr Cys Ala Arg Asp Gly Tyr Ser Asn Phe His
        755                 760                 765

Tyr Tyr Val Met Asp Tyr Trp Gly Gln Gly Thr Ser Val Thr Val Ser
    770                 775                 780

Ser
785
```

<210> SEQ ID NO 179
<211> LENGTH: 2391
<212> TYPE: DNA
<213> ORGANISM: Artificial sequence
<220> FEATURE:
<223> OTHER INFORMATION: 2H7sssIgG1-STD2-2e12HL (DNA)

<400> SEQUENCE: 179

```
aagcttgccg ccatggattt tcaagtgcag atttcagct tcctgctaat cagtgcttca      60
gtcataatgt ccagaggaca aattgttctc tcccagtctc cagcaatcct gtctgcatct    120
ccaggggaga aggtcacaat gacttgcagg gccagctcaa gtgtaagtta catgcactgg    180
taccagcaga agccaggatc ctcccccaaa ccctggattt atgccccatc caacctggct    240
tctggagtcc ctgctcgctt cagtggcagt gggtctggga cctcttactc tctcacaatc    300
agcagagtgg aggctgaaga tgctgccact tattactgcc agcagtggag ttttaaccca    360
cccacgttcg gtgctgggac caagctggag ctgaaagatg cggtggctc gggcggtggt    420
ggatctggag gaggtgggag ctctcaggct tatctacagc agtctggggc tgagtcggtg    480
aggcctgggg cctcagtgaa gatgtcctgc aaggcttctg gctacacatt taccagttac    540
aatatgcact gggtaaagca gacacctaga cagggcctgg aatggattgg agctatttat    600
ccaggaaatg gtgatacttc ctacaatcag aagttcaagg gcaaggccac actgactgta    660
gacaaatcct ccagcacagc ctacatgcag ctcagcagcc tgacatctga agactctgcg    720
gtctattct gtgcaagagt ggtgtactat agtaactctt actggtactt cgatgtctgg    780
ggcacaggga ccacggtcac cgtctctgat caggagccca atcttctga caaaactcac    840
acatccccac cgagcccagc acctgaactc ctgggggac cgtcagtctt cctcttcccc    900
ccaaaaccca aggacaccct catgatctcc cggacccctg aggtcacatg cgtggtggtg    960
gacgtgagcc acgaagaccc tgaggtcaag ttcaactggt acgtggacgg cgtggaggtg   1020
cataatgcca agacaaagcc gcgggaggag cagtacaaca gcacgtaccg tgtggtcagc   1080
gtcctcaccg tcctgcacca ggactggctg aatggcaagg agtacaagtg caaggtctcc   1140
aacaaagccc tcccagcccc catcgagaaa acaatctcca aagccaaagg cagccccga   1200
gaaccacagg tgtacaccct gcccccatcc cgggatgagc tgaccaagaa ccaggtcagc   1260
ctgacctgcc tggtcaaagg cttctatccc agcgacatcg ccgtggagtg ggagagcaat   1320
gggcagccgg agaacaacta caagaccacg cctcccgtgc tggactccga cggctccttc   1380
```

-continued

```
ttcctctaca gcaagctcac cgtggacaag agcaggtggc agcaggggaa cgtcttctca    1440
tgctccgtga tgcatgaggc tctgcacaac cactacacgc agaagagcct ctccctgtct    1500
ccgggtaaga attatggtgg cggtggctcg ggcggtggtg gatctggagg aggtgggagt    1560
gggaattatg gtggcggtgg ctcgggcggt ggtggatctg gaggaggtgg gagtgggaat    1620
tctcaggtgc agctgaagga gtcaggacct ggcctggtgg cgccctcaca gagcctgtcc    1680
atcacatgca ccgtctcagg gttctcatta accggctatg gtgtaaactg ggttcgccag    1740
cctccaggaa agggtctgga gtggctggga atgatatggg gtgatggaag cacagactat    1800
aattcagctc tcaaatccag actatcgatc accaaggaca actccaagag ccaagttttc    1860
ttaaaaatga acagtctgca aactgatgac acagccagat actactgtgc tcgagatggt    1920
tatagtaact ttcattacta tgttatggac tactggggtc aaggaacctc agtcaccgtc    1980
tcctctgggg gtggaggctc tggtggcggt ggatccggcg gaggtgggtc gggtggcggc    2040
ggatctgaca ttgtgctcac ccaatctcca gcttctttgg ctgtgtctct aggtcagaga    2100
gccaccatct cctgcagagc cagtgaaagt gttgaatatt atgtcacaag tttaatgcag    2160
tggtaccaac agaaaccagg acagccaccc aaactcctca tctctgctgc tagcaacgta    2220
gaatctgggg tccctgccag gtttagtggc agtgggtctg gacagactt tagcctcaac    2280 atccatcctg tggaggagga tgatattgca atgtatttct gtcagcaaag taggaaggtt    2340
ccatggacgt tcggtggagg caccaagctg gaaatcaaac gttaatctag a             2391
```

<210> SEQ ID NO 180
<211> LENGTH: 790
<212> TYPE: PRT
<213> ORGANISM: Artificial sequence
<220> FEATURE:
<223> OTHER INFORMATION: 2H7sssIgG1-STD2-2e12HL (w/2e12 leader) (AA)
<220> FEATURE:
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (23)..(128)
<223> OTHER INFORMATION: VL
<220> FEATURE:
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(282)
<223> OTHER INFORMATION: Hinge
<220> FEATURE:
<221> NAME/KEY: misc_feature
<222> LOCATION: (500)..(537)
<223> OTHER INFORMATION: EFD-BD2 Linker
<220> FEATURE:
<221> NAME/KEY: misc_feature
<222> LOCATION: (538)..(658)
<223> OTHER INFORMATION: VH2
<220> FEATURE:
<221> NAME/KEY: misc_feature
<222> LOCATION: (659)..(678)
<223> OTHER INFORMATION: Linker2
<220> FEATURE:
<221> NAME/KEY: misc_feature
<222> LOCATION: (679)..(790)
<223> OTHER INFORMATION: VL2

<400> SEQUENCE: 180

```
Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Ser Gly Gly Gly Gly Ser Ser
    130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
        180                 185                 190

Gly Ala Ile Tyr Pro Gly Asn Gly Asp Thr Ser Tyr Asn Gln Lys Phe
            195                 200                 205

Lys Gly Lys Ala Thr Leu Thr Val Asp Lys Ser Ser Thr Ala Tyr
210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
                245                 250                 255

Gly Thr Gly Thr Thr Val Thr Val Ser Asp Gln Glu Pro Lys Ser Ser
        260                 265                 270

Asp Lys Thr His Thr Ser Pro Pro Ser Ser Ala Pro Glu Leu Leu Gly
    275                 280                 285

Gly Pro Ser Val Phe Leu Phe Pro Pro Lys Pro Lys Asp Thr Leu Met
290                 295                 300

Ile Ser Arg Thr Pro Glu Val Thr Cys Val Val Asp Val Ser His
305                 310                 315                 320

Glu Asp Pro Glu Val Lys Phe Asn Trp Tyr Val Asp Gly Val Glu Val
            325                 330                 335

His Asn Ala Lys Thr Lys Pro Arg Glu Glu Gln Tyr Asn Ser Thr Tyr
        340                 345                 350

Arg Val Val Ser Val Leu Thr Val Leu His Gln Asp Trp Leu Asn Gly
    355                 360                 365

Lys Glu Tyr Lys Cys Lys Val Ser Asn Lys Ala Leu Pro Ala Pro Ile
370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
            405                 410                 415

Leu Thr Cys Leu Val Lys Gly Phe Tyr Pro Ser Asp Ile Ala Val Glu
        420                 425                 430
```

```
Trp Glu Ser Asn Gly Gln Pro Glu Asn Asn Tyr Lys Thr Thr Pro Pro
            435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Asn Tyr Gly Gly Gly Ser Gly Gly Gly Gly Ser Gly
            500                 505                 510

Gly Gly Gly Ser Gly Asn Tyr Gly Gly Gly Ser Gly Gly Gly Gly
        515                 520                 525

Ser Gly Gly Gly Ser Gly Asn Ser Gln Val Gln Leu Lys Glu Ser
        530                 535                 540

Gly Pro Gly Leu Val Ala Pro Ser Gln Ser Leu Ser Ile Thr Cys Thr
545                 550                 555                 560

Val Ser Gly Phe Ser Leu Thr Gly Tyr Gly Val Asn Trp Val Arg Gln
                565                 570                 575

Pro Pro Gly Lys Gly Leu Glu Trp Leu Gly Met Ile Trp Gly Asp Gly
            580                 585                 590

Ser Thr Asp Tyr Asn Ser Ala Leu Lys Ser Arg Leu Ser Ile Thr Lys
            595                 600                 605

Asp Asn Ser Lys Ser Gln Val Phe Leu Lys Met Asn Ser Leu Gln Thr
610                 615                 620

Asp Asp Thr Ala Arg Tyr Tyr Cys Ala Arg Asp Gly Tyr Ser Asn Phe
625                 630                 635                 640

His Tyr Tyr Val Met Asp Tyr Trp Gly Gln Gly Thr Ser Val Thr Val
                645                 650                 655

Ser Ser Gly Gly Gly Gly Ser Gly Gly Gly Gly Ser Gly Gly Gly Gly
            660                 665                 670

Ser Gly Gly Gly Gly Ser Asp Ile Val Leu Thr Gln Ser Pro Ala Ser
            675                 680                 685

Leu Ala Val Ser Leu Gly Gln Arg Ala Thr Ile Ser Cys Arg Ala Ser
    690                 695                 700

Glu Ser Val Glu Tyr Tyr Val Thr Ser Leu Met Gln Trp Tyr Gln Gln
705                 710                 715                 720

Lys Pro Gly Gln Pro Pro Lys Leu Leu Ile Ser Ala Ala Ser Asn Val
            725                 730                 735

Glu Ser Gly Val Pro Ala Arg Phe Ser Gly Ser Gly Ser Gly Thr Asp
            740                 745                 750

Phe Ser Leu Asn Ile His Pro Val Glu Glu Asp Asp Ile Ala Met Tyr
            755                 760                 765

Phe Cys Gln Gln Ser Arg Lys Val Pro Trp Thr Phe Gly Gly Gly Thr
770                 775                 780

Lys Leu Glu Ile Lys Arg
785                 790

<210> SEQ ID NO 181
<211> LENGTH: 790
<212> TYPE: PRT
<213> ORGANISM: Artificial sequence
<220> FEATURE:
<223> OTHER INFORMATION: 2H7sssIgG1(P238S/P331S)-STD2-2e12HL (w/2e12
      leader) (AA)
<220> FEATURE:
<221> NAME/KEY: misc_feature
```

```
<222> LOCATION: (1)..(22)
<223> OTHER INFORMATION: Leader
<220> FEATURE:
<221> NAME/KEY: misc_feature
<222> LOCATION: (23)..(128)
<223> OTHER INFORMATION: VL
<220> FEATURE:
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(282)
<223> OTHER INFORMATION: Hinge
<220> FEATURE:
<221> NAME/KEY: misc_feature
<222> LOCATION: (500)..(537)
<223> OTHER INFORMATION: EFD-BD2 Linker
<220> FEATURE:
<221> NAME/KEY: misc_feature
<222> LOCATION: (538)..(658)
<223> OTHER INFORMATION: VH2
<220> FEATURE:
<221> NAME/KEY: misc_feature
<222> LOCATION: (659)..(678)
<223> OTHER INFORMATION: Linker2
<220> FEATURE:
<221> NAME/KEY: misc_feature
<222> LOCATION: (679)..(790)
<223> OTHER INFORMATION: VL2

<400> SEQUENCE: 181

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Gly Ser Gly Gly Gly Gly Ser Ser
    130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Val Asp Lys Ser Ser Ser Thr Ala Tyr
    210                 215                 220

Met Gln Leu Ser Ser Leu Thr Ser Glu Asp Ser Ala Val Tyr Phe Cys
```

```
                    225                 230                 235                 240
Ala Arg Val Val Tyr Tyr Ser Asn Ser Tyr Trp Tyr Phe Asp Val Trp
                245                 250                 255

Gly Thr Gly Thr Thr Val Thr Val Ser Asp Gln Glu Pro Lys Ser Ser
                260                 265                 270

Asp Lys Thr His Thr Ser Pro Pro Ser Ser Ala Pro Glu Leu Leu Gly
                275                 280                 285

Gly Ser Ser Val Phe Leu Phe Pro Pro Lys Pro Lys Asp Thr Leu Met
            290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
                340                 345                 350

Arg Val Val Ser Val Leu Thr Val Leu His Gln Asp Trp Leu Asn Gly
                355                 360                 365

Lys Glu Tyr Lys Cys Lys Val Ser Asn Lys Ala Leu Pro Ala Ser Ile
            370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
                420                 425                 430

Trp Glu Ser Asn Gly Gln Pro Glu Asn Asn Tyr Lys Thr Thr Pro Pro
                435                 440                 445

Val Leu Asp Ser Asp Gly Ser Phe Phe Leu Tyr Ser Lys Leu Thr Val
            450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Asn Tyr Gly Gly Gly Ser Gly Gly Gly Gly Ser Gly
                500                 505                 510

Gly Gly Ser Gly Asn Tyr Gly Gly Gly Ser Gly Gly Gly Gly
            515                 520                 525

Ser Gly Gly Gly Ser Gly Asn Ser Gln Val Gln Leu Lys Glu Ser
            530                 535                 540

Gly Pro Gly Leu Val Ala Pro Ser Gln Ser Leu Ser Ile Thr Cys Thr
545                 550                 555                 560

Val Ser Gly Phe Ser Leu Thr Gly Tyr Gly Val Asn Trp Val Arg Gln
                565                 570                 575

Pro Pro Gly Lys Gly Leu Glu Trp Leu Gly Met Ile Trp Gly Asp Gly
                580                 585                 590

Ser Thr Asp Tyr Asn Ser Ala Leu Lys Ser Arg Leu Ser Ile Thr Lys
            595                 600                 605

Asp Asn Ser Lys Ser Gln Val Phe Leu Lys Met Asn Ser Leu Gln Thr
            610                 615                 620

Asp Asp Thr Ala Arg Tyr Tyr Cys Ala Arg Asp Gly Tyr Ser Asn Phe
625                 630                 635                 640

His Tyr Tyr Val Met Asp Tyr Trp Gly Gln Gly Thr Ser Val Thr Val
                645                 650                 655
```

```
Ser Ser Gly Gly Gly Ser Gly Gly Gly Ser Gly Gly Gly
        660             665             670

Ser Gly Gly Gly Ser Asp Ile Val Leu Thr Gln Ser Pro Ala Ser
        675             680             685

Leu Ala Val Ser Leu Gly Gln Arg Ala Thr Ile Ser Cys Arg Ala Ser
    690             695             700

Glu Ser Val Glu Tyr Tyr Val Thr Ser Leu Met Gln Trp Tyr Gln Gln
705             710             715             720

Lys Pro Gly Gln Pro Pro Lys Leu Leu Ile Ser Ala Ala Ser Asn Val
            725             730             735

Glu Ser Gly Val Pro Ala Arg Phe Ser Gly Ser Gly Ser Gly Thr Asp
        740             745             750

Phe Ser Leu Asn Ile His Pro Val Glu Glu Asp Asp Ile Ala Met Tyr
        755             760             765

Phe Cys Gln Gln Ser Arg Lys Val Pro Trp Thr Phe Gly Gly Gly Thr
    770             775             780

Lys Leu Glu Ile Lys Arg
785             790

<210> SEQ ID NO 182
<211> LENGTH: 2283
<212> TYPE: DNA
<213> ORGANISM: Artificial sequence
<220> FEATURE:
<223> OTHER INFORMATION: 2H7sssIgG1-H1-2e12HL (DNA)

<400> SEQUENCE: 182
aagcttgccg ccatggattt tcaagtgcag attttcagct tcctgctaat cagtgcttca      60
gtcataatgt ccagaggaca aattgttctc tcccagtctc cagcaatcct gtctgcatct     120
ccaggggaga aggtcacaat gacttgcagg gccagctcaa gtgtaagtta catgcactgg     180
taccagcaga agccaggatc ctcccccaaa ccctggattt atgccccatc caacctggct     240
tctggagtcc ctgctcgctt cagtggcagt gggtctggga cctcttactc tctcacaatc     300
agcagagtgg aggctgaaga tgctgccact tattactgcc agcagtggag ttttaaccca     360
cccacgttcg gtgctgggac caagctggag ctgaaagatg gcggtggctc gggcggtggt     420
ggatctggag gaggtgggag ctctcaggct tatctacagc agtctggggc tgagtcggtg     480
aggcctgggg cctcagtgaa gatgtcctgc aaggcttctg gctacacatt taccagttac     540
aatatgcact gggtaaagca gacacctaga cagggcctgg aatggattgg agctatttat     600
ccaggaaatg gtgatacttc ctacaatcag aagttcaagg gcaaggccac actgactgta     660
gacaaatcct ccagcacagc ctacatgcag ctcagcagcc tgacatctga agactctgcg     720
gtctatttct gtgcaagagt ggtgtactat agtaactctt actggtactt cgatgtctgg     780
ggcacaggga ccacggtcac cgtctctgat caggagccca atcttctga caaaactcac     840 acatccccac cgagcccagc acctgaactc ctggggggac cgtcagtctt cctcttcccc     900
ccaaaaccca aggacaccct catgatctcc cggacccctg aggtcacatg cgtggtggtg     960
gacgtgagcc acgaagaccc tgaggtcaag ttcaactggt acgtggacgg cgtggaggtg    1020
cataatgcca agacaaagcc gcgggaggag cagtacaaca gcacgtaccg tgtggtcagc    1080
gtcctcaccg tcctgcacca ggactggctg aatggcaagg agtacaagtg caaggtctcc    1140
aacaaagccc tcccagcccc catcgagaaa acaatctcca agccaaagg gcagccccga    1200 gaaccacagg tgtacaccct gcccccatcc cgggatgagc tgaccaagaa ccaggtcagc    1260
ctgacctgcc tggtcaaagg cttctatccc agcgacatcg ccgtggagtg ggagagcaat    1320
```

```
gggcagccgg agaacaacta caagaccacg cctcccgtgc tggactccga cggctccttc    1380
ttcctctaca gcaagctcac cgtggacaag agcaggtggc agcagggaa cgtcttctca    1440 tgctccgtga tgcatgaggc tctgcacaac cactacacgc agaagagcct ctccctgtct    1500
ccgggtaaga attctcaggt gcagctgaag gagtcaggac ctggcctggt ggcgccctca    1560
cagagcctgt ccatcacatg caccgtctca gggttctcat taaccggcta tggtgtaaac    1620
tgggttcgcc agcctccagg aaagggtctg gagtggctgg aatgatatg gggtgatgga    1680 agcacagact ataattcagc tctcaaatcc agactatcga tcaccaagga caactccaag    1740
agccaagttt tcttaaaaat gaacagtctg caaactgatg acacagccag atactactgt    1800
gctcgagatg ttatagtaa ctttcattac tatgttatgg actactgggg tcaaggaacc    1860
tcagtcaccg tctcctctgg gggtggaggc tctggtggcg gtggatccgg cggaggtggg    1920
tcgggtggcg gcggatctga cattgtgctc acccaatctc cagcttcttt ggctgtgtct    1980
ctaggtcaga gagccaccat ctcctgcaga gccagtgaaa gtgttgaata ttatgtcaca    2040
agtttaatgc agtggtacca acagaaacca ggacagccac ccaaactcct catctctgct    2100
gctagcaacg tagaatctgg ggtccctgcc aggtttagtg gcagtgggtc tgggacagac    2160
tttagcctca acatccatcc tgtggaggag gatgatattg caatgtattt ctgtcagcaa    2220
agtaggaagg ttccatggac gttcggtgga ggcaccaagc tggaaatcaa acgttaatct    2280
aga                                                                  2283
```

<210> SEQ ID NO 183
<211> LENGTH: 754
<212> TYPE: PRT
<213> ORGANISM: Artificial sequence
<220> FEATURE:
<223> OTHER INFORMATION: 2H7sssIgG1-H1-2e12HL (w/2e12 leader) (AA)
<220> FEATURE:
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (23)..(128)
<223> OTHER INFORMATION: VL
<220> FEATURE:
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(281)
<223> OTHER INFORMATION: Hinge
<220> FEATURE:
<221> NAME/KEY: misc_feature
<222> LOCATION: (500)..(501)
<223> OTHER INFORMATION: EFD-BD2 Linker
<220> FEATURE:
<221> NAME/KEY: misc_feature
<222> LOCATION: (502)..(622)
<223> OTHER INFORMATION: VH2
<220> FEATURE:
<221> NAME/KEY: misc_feature
<222> LOCATION: (623)..(642)
<223> OTHER INFORMATION: Linker2
<220> FEATURE:
<221> NAME/KEY: misc_feature
<222> LOCATION: (643)..(754)
<223> OTHER INFORMATION: VL2

<400> SEQUENCE: 183

```
Met Asp Phe Gln Val Gln Ile Phe Ser Phe Leu Leu Ile Ser Ala Ser
 1               5                  10                  15

Val Ile Met Ser Arg Gly Gln Ile Val Leu Ser Gln Ser Pro Ala Ile
             20                  25                  30

Leu Ser Ala Ser Pro Gly Glu Lys Val Thr Met Thr Cys Arg Ala Ser
         35                  40                  45

Ser Ser Val Ser Tyr Met His Trp Tyr Gln Gln Lys Pro Gly Ser Ser
     50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                 85                  90                  95

Ser Arg Val Glu Ala Glu Asp Ala Ala Thr Tyr Tyr Cys Gln Gln Trp
             100                 105                 110

Ser Phe Asn Pro Pro Thr Phe Gly Ala Gly Thr Lys Leu Glu Leu Lys
         115                 120                 125

Asp Gly Gly Gly Ser Gly Gly Gly Ser Gly Gly Gly Ser Ser
    130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                 165                 170                 175

Asn Met His Trp Val Lys Gln Thr Pro Arg Gln Gly Leu Glu Trp Ile
             180                 185                 190

Gly Ala Ile Tyr Pro Gly Asn Gly Asp Thr Ser Tyr Asn Gln Lys Phe
         195                 200                 205

Lys Gly Lys Ala Thr Leu Thr Val Asp Lys Ser Ser Thr Ala Tyr
    210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
                 245                 250                 255

Gly Thr Gly Thr Thr Val Thr Val Ser Asp Gln Glu Pro Lys Ser Ser
             260                 265                 270

Asp Lys Thr His Thr Ser Pro Pro Ser Pro Ala Pro Glu Leu Leu Gly
         275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                 325                 330                 335

His Asn Ala Lys Thr Lys Pro Arg Glu Glu Gln Tyr Asn Ser Thr Tyr
             340                 345                 350

Arg Val Val Ser Val Leu Thr Val Leu His Gln Asp Trp Leu Asn Gly
         355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                 405                 410                 415

Leu Thr Cys Leu Val Lys Gly Phe Tyr Pro Ser Asp Ile Ala Val Glu
```

```
                    420             425             430
Trp Glu Ser Asn Gly Gln Pro Glu Asn Tyr Lys Thr Thr Pro Pro
            435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                    485                 490                 495

Pro Gly Lys Asn Ser Gln Val Gln Leu Lys Glu Ser Gly Pro Gly Leu
            500                 505                 510

Val Ala Pro Ser Gln Ser Leu Ser Ile Thr Cys Thr Val Ser Gly Phe
    515                 520                 525

Ser Leu Thr Gly Tyr Gly Val Asn Trp Val Arg Gln Pro Pro Gly Lys
    530                 535                 540

Gly Leu Glu Trp Leu Gly Met Ile Trp Gly Asp Gly Ser Thr Asp Tyr
545                 550                 555                 560

Asn Ser Ala Leu Lys Ser Arg Leu Ser Ile Thr Lys Asp Asn Ser Lys
                565                 570                 575

Ser Gln Val Phe Leu Lys Met Asn Ser Leu Gln Thr Asp Asp Thr Ala
            580                 585                 590

Arg Tyr Tyr Cys Ala Arg Asp Gly Tyr Ser Asn Phe His Tyr Tyr Val
    595                 600                 605

Met Asp Tyr Trp Gly Gln Gly Thr Ser Val Thr Val Ser Ser Gly Gly
610                 615                 620

Gly Gly Ser Gly Gly Gly Gly Ser Gly Gly Gly Gly Ser Gly Gly Gly
625                 630                 635                 640

Gly Ser Asp Ile Val Leu Thr Gln Ser Pro Ala Ser Leu Ala Val Ser
                645                 650                 655

Leu Gly Gln Arg Ala Thr Ile Ser Cys Arg Ala Ser Glu Ser Val Glu
            660                 665                 670

Tyr Tyr Val Thr Ser Leu Met Gln Trp Tyr Gln Gln Lys Pro Gly Gln
    675                 680                 685

Pro Pro Lys Leu Leu Ile Ser Ala Ala Ser Asn Val Glu Ser Gly Val
    690                 695                 700

Pro Ala Arg Phe Ser Gly Ser Gly Ser Gly Thr Asp Phe Ser Leu Asn
705                 710                 715                 720

Ile His Pro Val Glu Glu Asp Asp Ile Ala Met Tyr Phe Cys Gln Gln
                725                 730                 735

Ser Arg Lys Val Pro Trp Thr Phe Gly Gly Gly Thr Lys Leu Glu Ile
            740                 745                 750

Lys Arg

<210> SEQ ID NO 184
<211> LENGTH: 2301
<212> TYPE: DNA
<213> ORGANISM: Artificial sequence
<220> FEATURE:
<223> OTHER INFORMATION: 2H7sssIgG1-H2-2e12HL (DNA)

<400> SEQUENCE: 184
aagcttgccg ccatggattt tcaagtgcag attttcagct tcctgctaat cagtgcttca     60
gtcataatgt ccagaggaca aattgttctc tcccagtctc cagcaatcct gtctgcatct    120
ccaggggaga aggtcacaat gacttgcagg gccagctcaa gtgtaagtta catgcactgg    180
```

| | |
|---|---|
| taccagcaga agccaggatc ctcccccaaa ccctggattt atgccccatc caacctggct | 240 |
| tctggagtcc ctgctcgctt cagtggcagt gggtctggga cctcttactc tctcacaatc | 300 |
| agcagagtgg aggctgaaga tgctgccact tattactgcc agcagtggag ttttaaccca | 360 |
| cccacgttcg gtgctgggac caagctggag ctgaaagatg cggtggctc gggcggtggt | 420 |
| ggatctggag gaggtgggag ctctcaggct tatctacagc agtctggggc tgagtcggtg | 480 |
| aggcctgggg cctcagtgaa gatgtcctgc aaggcttctg gctacacatt taccagttac | 540 |
| aatatgcact gggtaaagca gacacctaga cagggcctgg aatggattgg agctatttat | 600 |
| ccaggaaatg gtgatacttc ctacaatcag aagttcaagg gcaaggccac actgactgta | 660 |
| gacaaatcct ccagcacagc ctacatgcag ctcagcagcc tgacatctga agactctgcg | 720 |
| gtctatttct gtgcaagagt ggtgtactat agtaactctt actggtactt cgatgtctgg | 780 |
| ggcacaggga ccacggtcac cgtctctgat caggagccca atcttctga caaaactcac | 840 |
| acatccccac cgagcccagc acctgaactc ctgggggac cgtcagtctt cctcttcccc | 900 |
| ccaaaaccca aggacaccct catgatctcc cggaccctg aggtcacatg cgtggtggtg | 960 |
| gacgtgagcc acgaagaccc tgaggtcaag ttcaactggt acgtggacgg cgtggaggtg | 1020 |
| cataatgcca agacaaagcc gcgggaggag cagtacaaca gcacgtaccg tgtggtcagc | 1080 |
| gtcctcaccg tcctgcacca ggactggctg aatggcaagg agtacaagtg caaggtctcc | 1140 |
| aacaaagccc tcccagcccc catcgagaaa acaatctcca agccaaagg gcagccccga | 1200 |
| gaaccacagg tgtacaccct gcccccatcc cgggatgagc tgaccaagaa ccaggtcagc | 1260 |
| ctgacctgcc tggtcaaagg cttctatccc agcgacatcg ccgtggagtg ggagagcaat | 1320 |
| gggcagccgg agaacaacta caagaccacg cctcccgtgc tggactccga cggctccttc | 1380 |
| ttcctctaca gcaagctcac cgtggacaag agcaggtggc agcaggggaa cgtcttctca | 1440 |
| tgctccgtga tgcatgaggc tctgcacaac cactacacgc agaagagcct ctccctgtct | 1500 |
| ccgggtaagg gtggcggtgg ctcggggaat tctcaggtgc agctgaagga gtcaggacct | 1560 |
| ggcctggtgg cgccctcaca gagcctgtcc atcacatgca ccgtctcagg gttctcatta | 1620 |
| accggctatg gtgtaaactg ggttcgccag cctccaggaa agggtctgga gtggctggga | 1680 |
| atgatatggg gtgatggaag cacagactat aattcagctc tcaaatccag actatcgatc | 1740 |
| accaaggaca actccaagag ccaagttttc ttaaaaatga cagtctgca aactgatgac | 1800 |
| acagccagat actactgtgc tcgagatggt tatagtaact ttcattacta tgttatggac | 1860 |
| tactggggtc aaggaacctc agtcaccgtc tcctctgggg gtggaggctc tggtggcggt | 1920 |
| ggatccggcg gaggtgggtc gggtggcggc ggatctgaca ttgtgctcac ccaatctcca | 1980 |
| gcttctttgg ctgtgtctct aggtcagaga gccaccatct cctgcagagc cagtgaaagt | 2040 |
| gttgaatatt atgtcacaag tttaatgcag tggtaccaac agaaaccagg acagccaccc | 2100 |
| aaactcctca tctctgctgc tagcaacgta gaatctgggg tccctgccag gtttagtggc | 2160 |
| agtgggtctg gacagactt tagcctcaac atccatcctg tggaggagga tgatattgca | 2220 |
| atgtatttct gtcagcaaag taggaaggtt ccatggacgt tcggtggagg caccaagctg | 2280 |
| gaaatcaaac gttaatctag a | 2301 |

<210> SEQ ID NO 185
<211> LENGTH: 760
<212> TYPE: PRT
<213> ORGANISM: Artificial sequence
<220> FEATURE:
<223> OTHER INFORMATION: 2H7sssIgG1-H2-2e12HL (w/2e12 leader) (AA)
<220> FEATURE:

-continued

```
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (23)..(127)
<223> OTHER INFORMATION: VL
<220> FEATURE:
<221> NAME/KEY: misc_feature
<222> LOCATION: (128)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(282)
<223> OTHER INFORMATION: Hinge
<220> FEATURE:
<221> NAME/KEY: misc_feature
<222> LOCATION: (500)..(507)
<223> OTHER INFORMATION: EFD-BD2 Linker
<220> FEATURE:
<221> NAME/KEY: misc_feature
<222> LOCATION: (508)..(628)
<223> OTHER INFORMATION: VH2
<220> FEATURE:
<221> NAME/KEY: misc_feature
<222> LOCATION: (629)..(648)
<223> OTHER INFORMATION: Linker2
<220> FEATURE:
<221> NAME/KEY: misc_feature
<222> LOCATION: (649)..(760)
<223> OTHER INFORMATION: VL2

<400> SEQUENCE: 185

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Gly Ser Gly Gly Gly Gly Ser Ser
    130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Val Asp Lys Ser Ser Ser Thr Ala Tyr
    210                 215                 220
```

-continued

```
Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
            245                 250                 255

Gly Thr Gly Thr Thr Val Thr Val Ser Asp Gln Glu Pro Lys Ser Ser
        260                 265                 270

Asp Lys Thr His Thr Ser Pro Pro Ser Pro Ala Pro Glu Leu Leu Gly
    275                 280                 285

Gly Pro Ser Val Phe Leu Phe Pro Pro Lys Pro Lys Asp Thr Leu Met
290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Gly Gly Gly Gly Ser Gly Asn Ser Gln Val Gln Leu Lys
            500                 505                 510

Glu Ser Gly Pro Gly Leu Val Ala Pro Ser Gln Ser Leu Ser Ile Thr
        515                 520                 525

Cys Thr Val Ser Gly Phe Ser Leu Thr Gly Tyr Gly Val Asn Trp Val
530                 535                 540

Arg Gln Pro Pro Gly Lys Gly Leu Glu Trp Leu Gly Met Ile Trp Gly
545                 550                 555                 560

Asp Gly Ser Thr Asp Tyr Asn Ser Ala Leu Lys Ser Arg Leu Ser Ile
                565                 570                 575

Thr Lys Asp Asn Ser Lys Ser Gln Val Phe Leu Lys Met Asn Ser Leu
            580                 585                 590

Gln Thr Asp Asp Thr Ala Arg Tyr Tyr Cys Ala Arg Asp Gly Tyr Ser
        595                 600                 605

Asn Phe His Tyr Tyr Val Met Asp Tyr Trp Gly Gln Gly Thr Ser Val
610                 615                 620

Thr Val Ser Ser Gly Gly Gly Ser Gly Gly Gly Ser Gly
625                 630                 635                 640

Gly Gly Ser Gly Gly Gly Gly Ser Asp Ile Val Leu Thr Gln Ser Pro
                645                 650                 655
```

```
Ala Ser Leu Ala Val Ser Leu Gly Gln Arg Ala Thr Ile Ser Cys Arg
            660                 665                 670

Ala Ser Glu Ser Val Glu Tyr Tyr Val Thr Ser Leu Met Gln Trp Tyr
        675                 680                 685

Gln Gln Lys Pro Gly Gln Pro Pro Lys Leu Leu Ile Ser Ala Ala Ser
    690                 695                 700

Asn Val Glu Ser Gly Val Pro Ala Arg Phe Ser Gly Ser Gly Ser Gly
705                 710                 715                 720

Thr Asp Phe Ser Leu Asn Ile His Pro Val Glu Glu Asp Asp Ile Ala
                725                 730                 735

Met Tyr Phe Cys Gln Gln Ser Arg Lys Val Pro Trp Thr Phe Gly Gly
        740                 745                 750

Gly Thr Lys Leu Glu Ile Lys Arg
    755                 760

<210> SEQ ID NO 186
<211> LENGTH: 2307
<212> TYPE: DNA
<213> ORGANISM: Artificial sequence
<220> FEATURE:
<223> OTHER INFORMATION: 2H7sssIgG1-H3-2e12HL (DNA)

<400> SEQUENCE: 186
```

| | | | | | |
|---|---|---|---|---|---|
| aagcttgccg | ccatggattt | tcaagtgcag | attttcagct | tcctgctaat | cagtgcttca | 60 |
| gtcataatgt | ccagaggaca | aattgttctc | tcccagtctc | cagcaatcct | gtctgcatct | 120 |
| ccaggggaga | aggtcacaat | gacttgcagg | gccagctcaa | gtgtaagtta | catgcactgg | 180 |
| taccagcaga | agccaggatc | ctcccccaaa | ccctggattt | atgccccatc | caacctggct | 240 |
| tctggagtcc | ctgctcgctt | cagtggcagt | gggtctggga | cctcttactc | tctcacaatc | 300 |
| agcagagtgg | aggctgaaga | tgctgccact | tattactgcc | agcagtggag | ttttaaccca | 360 |
| cccacgttcg | gtgctgggac | caagctggag | ctgaaagatg | cggtggctc | gggcggtggt | 420 |
| ggatctggag | gaggtgggag | ctctcaggct | tatctacagc | agtctggggc | tgagtcggtg | 480 |
| aggcctgggg | cctcagtgaa | gatgtcctgc | aaggcttctg | gctacacatt | taccagttac | 540 |
| aatatgcact | gggtaaagca | gacacctaga | cagggcctgg | aatggattgg | agctatttat | 600 |
| ccaggaaatg | gtgatacttc | ctacaatcag | aagttcaagg | gcaaggccac | actgactgta | 660 |
| gacaaatcct | ccagcacagc | ctacatgcag | ctcagcagcc | tgacatctga | agactctgcg | 720 |
| gtctatttct | gtgcaagagt | ggtgtactat | agtaactctt | actggtactt | cgatgtctgg | 780 |
| ggcacaggga | ccacggtcac | cgtctctgat | caggagccca | aatcttctga | caaaactcac | 840 |
| acatccccac | cgagcccagc | acctgaactc | ctggggggac | cgtcagtctt | cctcttcccc | 900 |
| ccaaaaccca | aggacaccct | catgatctcc | cggacccctg | aggtcacatg | cgtggtggtg | 960 |
| gacgtgagcc | acgaagaccc | tgaggtcaag | ttcaactggt | acgtggacgg | cgtggaggtg | 1020 |
| cataatgcca | agacaaagcc | gcgggaggag | cagtacaaca | gcacgtaccg | tgtggtcagc | 1080 |
| gtcctcaccg | tcctgcacca | ggactggctg | aatggcaagg | agtacaagtg | caaggtctcc | 1140 |
| aacaaagccc | tcccagcccc | catcgagaaa | acaatctcca | aagccaaagg | gcagccccga | 1200 |
| gaaccacagg | tgtacaccct | gcccccatcc | cgggatgagc | tgaccaagaa | ccaggtcagc | 1260 |
| ctgacctgcc | tggtcaaagg | cttctatccc | agcgacatcg | ccgtggagtg | ggagagcaat | 1320 |
| gggcagccgg | agaacaacta | caagaccacg | cctcccgtgc | tggactccga | cggctccttc | 1380 |
| ttcctctaca | gcaagctcac | cgtggacaag | agcaggtggc | agcaggggaa | cgtcttctca | 1440 |

```
tgctccgtga tgcatgaggc tctgcacaac cactacacgc agaagagcct ctccctgtct    1500
ccgggtaaga attatggtgg cggtggctct gggaattctc aggtgcagct gaaggagtca    1560
ggacctggcc tggtggcgcc ctcacagagc ctgtccatca catgcaccgt ctcagggttc    1620
tcattaaccg gctatggtgt aaactgggtt cgccagcctc caggaaaggg tctggagtgg    1680
ctgggaatga tatggggtga tggaagcaca gactataatt cagctctcaa atccagacta    1740
tcgatcacca aggacaactc caagagccaa gttttcttaa aaatgaacag tctgcaaact    1800
gatgacacag ccagatacta ctgtgctcga gatggttata gtaactttca ttactatgtt    1860
atggactact ggggtcaagg aacctcagtc accgtctcct ctgggggtgg aggctctggt    1920
ggcggtggat ccggcggagg tgggtcgggt ggcggcggat ctgacattgt gctcacccaa    1980
tctccagctt ctttggctgt gtctctaggt cagagagcca ccatctcctg cagagccagt    2040
gaaagtgttg aatattatgt cacaagttta atgcagtggt accaacagaa accaggacag    2100
ccacccaaac tcctcatctc tgctgctagc aacgtagaat ctgggggtccc tgccaggttt    2160 agtggcagtg ggtctgggac agactttagc ctcaacatcc atcctgtgga ggaggatgat    2220
attgcaatgt atttctgtca gcaaagtagg aaggttccat ggacgttcgg tggaggcacc    2280
aagctggaaa tcaaacgtta atctaga                                          2307

<210> SEQ ID NO 187
<211> LENGTH: 762
<212> TYPE: PRT
<213> ORGANISM: Artificial sequence
<220> FEATURE:
<223> OTHER INFORMATION: 2H7sssIgG1-H3-2e12HL (w/2e12 leader) (AA)
<220> FEATURE:
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (23)..(128)
<223> OTHER INFORMATION: VL
<220> FEATURE:
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(282)
<223> OTHER INFORMATION: Hinge
<220> FEATURE:
<221> NAME/KEY: misc_feature
<222> LOCATION: (500)..(509)
<223> OTHER INFORMATION: EFD-BD2 Linker
<220> FEATURE:
<221> NAME/KEY: misc_feature
<222> LOCATION: (510)..(630)
<223> OTHER INFORMATION: VH2
<220> FEATURE:
<221> NAME/KEY: misc_feature
<222> LOCATION: (631)..(650)
<223> OTHER INFORMATION: Linker2
<220> FEATURE:
<221> NAME/KEY: misc_feature
<222> LOCATION: (651)..(762)
<223> OTHER INFORMATION: VL2

<400> SEQUENCE: 187

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
```

-continued

```
                    20                  25                  30
Leu Ser Ala Ser Pro Gly Glu Lys Val Thr Met Thr Cys Arg Ala Ser
            35                  40                  45
Ser Ser Val Ser Tyr Met His Trp Tyr Gln Gln Lys Pro Gly Ser Ser
        50                  55                  60
Pro Lys Pro Trp Ile Tyr Ala Pro Ser Asn Leu Ala Ser Gly Val Pro
65                  70                  75                  80
Ala Arg Phe Ser Gly Ser Gly Ser Gly Thr Ser Tyr Ser Leu Thr Ile
                85                  90                  95
Ser Arg Val Glu Ala Glu Asp Ala Ala Thr Tyr Tyr Cys Gln Gln Trp
            100                 105                 110
Ser Phe Asn Pro Pro Thr Phe Gly Ala Gly Thr Lys Leu Glu Leu Lys
        115                 120                 125
Asp Gly Gly Gly Ser Gly Gly Gly Gly Ser Gly Gly Gly Gly Ser Ser
130                 135                 140
Gln Ala Tyr Leu Gln Gln Ser Gly Ala Glu Ser Val Arg Pro Gly Ala
145                 150                 155                 160
Ser Val Lys Met Ser Cys Lys Ala Ser Gly Tyr Thr Phe Thr Ser Tyr
                165                 170                 175
Asn Met His Trp Val Lys Gln Thr Pro Arg Gln Gly Leu Glu Trp Ile
            180                 185                 190
Gly Ala Ile Tyr Pro Gly Asn Gly Asp Thr Ser Tyr Asn Gln Lys Phe
        195                 200                 205
Lys Gly Lys Ala Thr Leu Thr Val Asp Lys Ser Ser Thr Ala Tyr
210                 215                 220
Met Gln Leu Ser Ser Leu Thr Ser Glu Asp Ser Ala Val Tyr Phe Cys
225                 230                 235                 240
Ala Arg Val Val Tyr Tyr Ser Asn Ser Tyr Trp Tyr Phe Asp Val Trp
                245                 250                 255
Gly Thr Gly Thr Thr Val Thr Val Ser Asp Gln Glu Pro Lys Ser Ser
            260                 265                 270
Asp Lys Thr His Thr Ser Pro Pro Ser Pro Ala Pro Glu Leu Leu Gly
        275                 280                 285
Gly Pro Ser Val Phe Leu Phe Pro Pro Lys Pro Lys Asp Thr Leu Met
290                 295                 300
Ile Ser Arg Thr Pro Glu Val Thr Cys Val Val Val Asp Val Ser His
305                 310                 315                 320
Glu Asp Pro Glu Val Lys Phe Asn Trp Tyr Val Asp Gly Val Glu Val
                325                 330                 335
His Asn Ala Lys Thr Lys Pro Arg Glu Glu Gln Tyr Asn Ser Thr Tyr
            340                 345                 350
Arg Val Val Ser Val Leu Thr Val Leu His Gln Asp Trp Leu Asn Gly
        355                 360                 365
Lys Glu Tyr Lys Cys Lys Val Ser Asn Lys Ala Leu Pro Ala Pro Ile
            370                 375                 380
Glu Lys Thr Ile Ser Lys Ala Lys Gly Gln Pro Arg Glu Pro Gln Val
385                 390                 395                 400
Tyr Thr Leu Pro Pro Ser Arg Asp Glu Leu Thr Lys Asn Gln Val Ser
                405                 410                 415
Leu Thr Cys Leu Val Lys Gly Phe Tyr Pro Ser Asp Ile Ala Val Glu
            420                 425                 430
Trp Glu Ser Asn Gly Gln Pro Glu Asn Asn Tyr Lys Thr Thr Pro Pro
        435                 440                 445
```

```
Val Leu Asp Ser Asp Gly Ser Phe Phe Leu Tyr Ser Lys Leu Thr Val
    450                 455                 460
Asp Lys Ser Arg Trp Gln Gln Gly Asn Val Phe Ser Cys Ser Val Met
465                 470                 475                 480
His Glu Ala Leu His Asn His Tyr Thr Gln Lys Ser Leu Ser Leu Ser
                485                 490                 495
Pro Gly Lys Asn Tyr Gly Gly Gly Ser Gly Asn Ser Gln Val Gln
            500                 505                 510
Leu Lys Glu Ser Gly Pro Gly Leu Val Ala Pro Ser Gln Ser Leu Ser
        515                 520                 525
Ile Thr Cys Thr Val Ser Gly Phe Ser Leu Thr Gly Tyr Gly Val Asn
    530                 535                 540
Trp Val Arg Gln Pro Pro Gly Lys Gly Leu Glu Trp Leu Gly Met Ile
545                 550                 555                 560
Trp Gly Asp Gly Ser Thr Asp Tyr Asn Ser Ala Leu Lys Ser Arg Leu
                565                 570                 575
Ser Ile Thr Lys Asp Asn Ser Lys Ser Gln Val Phe Leu Lys Met Asn
            580                 585                 590
Ser Leu Gln Thr Asp Asp Thr Ala Arg Tyr Tyr Cys Ala Arg Asp Gly
        595                 600                 605
Tyr Ser Asn Phe His Tyr Tyr Val Met Asp Tyr Trp Gly Gln Gly Thr
    610                 615                 620
Ser Val Thr Val Ser Ser Gly Gly Gly Ser Gly Gly Gly Gly Ser
625                 630                 635                 640
Gly Gly Gly Gly Ser Gly Gly Gly Ser Asp Ile Val Leu Thr Gln
                645                 650                 655
Ser Pro Ala Ser Leu Ala Val Ser Leu Gly Gln Arg Ala Thr Ile Ser
            660                 665                 670
Cys Arg Ala Ser Glu Ser Val Glu Tyr Tyr Val Thr Ser Leu Met Gln
    675                 680                 685
Trp Tyr Gln Gln Lys Pro Gly Gln Pro Pro Lys Leu Leu Ile Ser Ala
690                 695                 700
Ala Ser Asn Val Glu Ser Gly Val Pro Ala Arg Phe Ser Gly Ser Gly
705                 710                 715                 720
Ser Gly Thr Asp Phe Ser Leu Asn Ile His Pro Val Glu Glu Asp Asp
                725                 730                 735
Ile Ala Met Tyr Phe Cys Gln Gln Ser Arg Lys Val Pro Trp Thr Phe
            740                 745                 750
Gly Gly Gly Thr Lys Leu Glu Ile Lys Arg
        755                 760

<210> SEQ ID NO 188
<211> LENGTH: 2316
<212> TYPE: DNA
<213> ORGANISM: Artificial sequence
<220> FEATURE:
<223> OTHER INFORMATION: 2H7sssIgG1-H4-2e12HL (DNA)

<400> SEQUENCE: 188
aagcttgccg ccatggattt tcaagtgcag attttcagct tcctgctaat cagtgcttca     60
gtcataatgt ccagaggaca aattgttctc tcccagtctc cagcaatcct gtctgcatct    120
ccaggggaga aggtcacaat gacttgcagg gccagctcaa gtgtaagtta catgcactgg    180
taccagcaga agccaggatc ctcccccaaa ccctggattt atgccccatc caacctggct    240
tctggagtcc ctgctcgctt cagtggcagt gggtctggga cctcttactc tctcacaatc    300
```

```
agcagagtgg aggctgaaga tgctgccact tattactgcc agcagtggag tttaaccca       360
cccacgttcg gtgctgggac caagctggag ctgaaagatg gcggtggctc gggcggtggt       420
ggatctggag gaggtgggag ctctcaggct tatctacagc agtctggggc tgagtcggtg       480
aggcctgggg cctcagtgaa gatgtcctgc aaggcttctg gctacacatt taccagttac       540
aatatgcact gggtaaagca gacacctaga cagggcctgg aatggattgg agctatttat       600
ccaggaaatg gtgatacttc ctacaatcag aagttcaagg gcaaggccac actgactgta       660
gacaaatcct ccagcacagc ctacatgcag ctcagcagcc tgacatctga agactctgcg       720
gtctatttct gtgcaagagt ggtgtactat agtaactctt actggtactt cgatgtctgg       780
ggcacaggga ccacggtcac cgtctctgat caggagccca atcttctga caaaactcac        840
acatccccac cgagcccagc acctgaactc ctggggggac cgtcagtctt cctcttcccc       900
ccaaaaccca aggacaccct catgatctcc cggacccctg aggtcacatg cgtggtggtg       960
gacgtgagcc acgaagaccc tgaggtcaag ttcaactggt acgtggacgg cgtggaggtg      1020
cataatgcca agacaaagcc gcgggaggag cagtacaaca gcacgtaccg tgtggtcagc      1080
gtcctcaccg tcctgcacca ggactggctg aatggcaagg agtacaagtg caaggtctcc      1140
aacaaagccc tcccagcccc catcgagaaa acaatctcca aagccaaagg cagcccccga      1200
gaaccacagg tgtacaccct gcccccatcc cgggatgagc tgaccaagaa ccaggtcagc      1260
ctgacctgcc tggtcaaagg cttctatccc agcgacatcg ccgtggagtg ggagagcaat      1320
gggcagccgg agaacaacta caagaccacg cctcccgtgc tggactccga cggctccttc      1380
ttcctctaca gcaagctcac cgtggacaag agcaggtggc agcaggggaa cgtcttctca      1440
tgctccgtga tgcatgaggc tctgcacaac cactacacgc agaagagcct ctccctgtct      1500
ccgggtaagg gtggcggtgg ctcgggcggt ggtggatctg ggaattctca ggtgcagctg      1560
aaggagtcag gacctggcct ggtggcgccc tcacagagcc tgtccatcac atgcaccgtc      1620
tcagggttct cattaaccgg ctatggtgta aactgggttc gccagcctcc aggaaagggt      1680
ctggagtggc tgggaatgat atggggtgat ggaagcacag actataattc agctctcaaa      1740
tccagactat cgatcaccaa ggacaactcc aagagccaag ttttcttaaa aatgaacagt      1800
ctgcaaactg atgacacagc cagatactac tgtgctcgag atggttatag taactttcat      1860
tactatgtta tggactactg gggtcaagga acctcagtca ccgtctcctc tggggggtgga      1920
ggctctggtg gcggtggatc cggcggaggt gggtcgggtg gcggcggatc tgacattgtg      1980
ctcacccaat ctccagcttc tttggctgtg tctctaggtc agagagccac catctcctgc      2040
agagccagtg aaagtgttga atattatgtc acaagtttaa tgcagtggta ccaacagaaa      2100
ccaggacagc cacccaaact cctcatctct gctgctagca cgtagaatc tggggtccct      2160
gccaggttta gtggcagtgg gtctgggaca gactttagcc tcaacatcca tcctgtggag      2220
gaggatgata ttgcaatgta tttctgtcag caaagtagga aggttccatg gacgttcggt      2280
ggaggcacca agctggaaat caaacgttaa tctaga                                2316
```

<210> SEQ ID NO 189
<211> LENGTH: 765
<212> TYPE: PRT
<213> ORGANISM: Artificial sequence
<220> FEATURE:
<223> OTHER INFORMATION: 2H7sssIgG1-H4-2e12HL (AA)
<220> FEATURE:
<221> NAME/KEY: misc_feature
<222> LOCATION: (1)..(22)
<223> OTHER INFORMATION: Leader
<220> FEATURE:

```
<221> NAME/KEY: misc_feature
<222> LOCATION: (23)..(128)
<223> OTHER INFORMATION: VL
<220> FEATURE:
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(282)
<223> OTHER INFORMATION: Hinge
<220> FEATURE:
<221> NAME/KEY: misc_feature
<222> LOCATION: (500)..(512)
<223> OTHER INFORMATION: EFD-BD2 Linker
<220> FEATURE:
<221> NAME/KEY: misc_feature
<222> LOCATION: (513)..(633)
<223> OTHER INFORMATION: VH2
<220> FEATURE:
<221> NAME/KEY: misc_feature
<222> LOCATION: (634)..(653)
<223> OTHER INFORMATION: Linker2
<220> FEATURE:
<221> NAME/KEY: misc_feature
<222> LOCATION: (654)..(765)
<223> OTHER INFORMATION: VL2

<400> SEQUENCE: 189

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Ser Gly Gly Gly Gly Ser Ser
    130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Val Asp Lys Ser Ser Ser Thr Ala Tyr
    210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
```

```
                    245                 250                 255
Gly Thr Gly Thr Thr Val Thr Val Ser Asp Gln Glu Pro Lys Ser Ser
                260                 265                 270

Asp Lys Thr His Thr Ser Pro Pro Ser Pro Ala Pro Glu Leu Leu Gly
            275                 280                 285

Gly Pro Ser Val Phe Leu Phe Pro Pro Lys Pro Lys Asp Thr Leu Met
        290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Gly Gly Gly Gly Ser Gly Gly Gly Gly Ser Gly Asn Ser
            500                 505                 510

Gln Val Gln Leu Lys Glu Ser Gly Pro Gly Leu Val Ala Pro Ser Gln
        515                 520                 525

Ser Leu Ser Ile Thr Cys Thr Val Ser Gly Phe Ser Leu Thr Gly Tyr
    530                 535                 540

Gly Val Asn Trp Val Arg Gln Pro Pro Gly Lys Gly Leu Glu Trp Leu
545                 550                 555                 560

Gly Met Ile Trp Gly Asp Gly Ser Thr Asp Tyr Asn Ser Ala Leu Lys
                565                 570                 575

Ser Arg Leu Ser Ile Thr Lys Asp Asn Ser Lys Ser Gln Val Phe Leu
            580                 585                 590

Lys Met Asn Ser Leu Gln Thr Asp Thr Ala Arg Tyr Tyr Cys Ala
        595                 600                 605

Arg Asp Gly Tyr Ser Asn Phe His Tyr Tyr Val Met Asp Tyr Trp Gly
610                 615                 620

Gln Gly Thr Ser Val Thr Val Ser Ser Gly Gly Gly Ser Gly Gly
625                 630                 635                 640

Gly Gly Ser Gly Gly Gly Gly Ser Gly Gly Gly Gly Ser Asp Ile Val
                645                 650                 655

Leu Thr Gln Ser Pro Ala Ser Leu Ala Val Ser Leu Gly Gln Arg Ala
            660                 665                 670
```

```
                Thr Ile Ser Cys Arg Ala Ser Glu Ser Val Glu Tyr Tyr Val Thr Ser
                    675                 680                 685

Leu Met Gln Trp Tyr Gln Gln Lys Pro Gly Gln Pro Pro Lys Leu Leu
                    690                 695                 700

Ile Ser Ala Ala Ser Asn Val Glu Ser Gly Val Pro Ala Arg Phe Ser
                705                 710                 715                 720

Gly Ser Gly Ser Gly Thr Asp Phe Ser Leu Asn Ile His Pro Val Glu
                                725                 730                 735

Glu Asp Asp Ile Ala Met Tyr Phe Cys Gln Gln Ser Arg Lys Val Pro
                                740                 745                 750

Trp Thr Phe Gly Gly Gly Thr Lys Leu Glu Ile Lys Arg
                                755                 760                 765

<210> SEQ ID NO 190
<211> LENGTH: 2322
<212> TYPE: DNA
<213> ORGANISM: Artificial sequence
<220> FEATURE:
<223> OTHER INFORMATION: 2H7sssIgG1-H5-2e12HL (DNA)

<400> SEQUENCE: 190
aagcttgccg ccatggattt tcaagtgcag attttcagct tcctgctaat cagtgcttca      60
gtcataatgt ccagaggaca aattgttctc tcccagtctc cagcaatcct gtctgcatct     120
ccaggggaga aggtcacaat gacttgcagg gccagctcaa gtgtaagtta catgcactgg     180
taccagcaga agccaggatc ctcccccaaa ccctggattt atgccccatc caacctggct     240
tctggagtcc ctgctcgctt cagtggcagt gggtctggga cctcttactc tctcacaatc     300
agcagagtgg aggctgaaga tgctgccact tattactgcc agcagtggag ttttaaccca     360
cccacgttcg gtgctgggac caagctggag ctgaaagatg cggtggctc gggcggtggt     420 ggatctggag gagtgggag ctctcaggct tatctacagc agtctgggc tgagtcggtg     480 aggcctgggg cctcagtgaa gatgtcctgc aaggcttctg gctacacatt taccagttac     540
aatatgcact gggtaaagca gacacctaga cagggcctgg aatggattgg agctatttat     600
ccaggaaatg gtgatacttc ctacaatcag aagttcaagg gcaaggccac actgactgta     660
gacaaatcct ccagcacagc ctacatgcag ctcagcagcc tgacatctga agactctgcg     720
gtctatttct gtgcaagagt ggtgtactat agtaactctt actggtactt cgatgtctgg     780
ggcacaggga ccacggtcac cgtctctgat caggagccca atcttctga caaaactcac     840 acatccccac cgagcccagc acctgaactc ctggggggac cgtcagtctt cctcttcccc     900
ccaaaaccca aggacaccct catgatctcc cggacccctg aggtcacatg cgtggtggtg     960
gacgtgagcc acgaagaccc tgaggtcaag ttcaactggt acgtggacgg cgtggaggtg    1020
cataatgcca agacaaagcc gcgggaggag cagtacaaca gcacgtaccg tgtggtcagc    1080
gtcctcaccg tcctgcacca ggactggctg aatggcaagg agtacaagtg caaggtctcc    1140
aacaaagccc tcccagcccc catcgagaaa acaatctcca agccaaagg gcagccccga    1200 gaaccacagg tgtacaccct gccccatcc cgggatgagc tgaccaagaa ccaggtcagc    1260
ctgacctgcc tggtcaaagg cttctatccc agcgacatcg ccgtggagtg ggagagcaat    1320
gggcagccgg agaacaacta caagaccacg cctcccgtgc tggactccga cggctccttc    1380
ttcctctaca gcaagctcac cgtggacaag agcaggtggc agcaggggaa cgtcttctca    1440
tgctccgtga tgcatgaggc tctgcacaac cactacacgc agaagagcct ctccctgtct    1500
ccgggtaaga attatggtgg cggtggctcg ggcggtggtg gatctgggaa ttctcaggtg    1560
```

```
cagctgaagg agtcaggacc tggcctggtg gcgccctcac agagcctgtc catcacatgc    1620
accgtctcag ggttctcatt aaccggctat ggtgtaaact gggttcgcca gcctccagga    1680
aagggtctgg agtggctggg aatgatatgg ggtgatggaa gcacagacta taattcagct    1740
ctcaaatcca gactatcgat caccaaggac aactccaaga gccaagtttt cttaaaaatg    1800
aacagtctgc aaactgatga cacagccaga tactactgtg ctcgagatgg ttatagtaac    1860
tttcattact atgttatgga ctactggggt caaggaacct cagtcaccgt ctcctctggg    1920
ggtggaggct ctggtggcgg tggatccggc ggaggtgggt cgggtggcgg cggatctgac    1980
attgtgctca cccaatctcc agcttctttg gctgtgtctc taggtcagag agccaccatc    2040
tcctgcagag ccagtgaaag tgttgaatat tatgtcacaa gtttaatgca gtggtaccaa    2100
cagaaaccag acagccacc caaactcctc atctctgctg ctagcaacgt agaatctggg    2160
gtccctgcca ggtttagtgg cagtgggtct gggacagact ttagcctcaa catccatcct    2220
gtggaggagg atgatattgc aatgtatttc tgtcagcaaa gtaggaaggt tccatggacg    2280
ttcggtggag gcaccaagct ggaaatcaaa cgttaatcta ga                       2322

<210> SEQ ID NO 191
<211> LENGTH: 767
<212> TYPE: PRT
<213> ORGANISM: Artificial sequence
<220> FEATURE:
<223> OTHER INFORMATION: 2H7sssIgG1-H5-2e12HL (w/2e12 leader) (AA)
<220> FEATURE:
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (23)..(128)
<223> OTHER INFORMATION: VL
<220> FEATURE:
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(282)
<223> OTHER INFORMATION: Hinge
<220> FEATURE:
<221> NAME/KEY: misc_feature
<222> LOCATION: (500)..(514)
<223> OTHER INFORMATION: EFD-BD2 Linker
<220> FEATURE:
<221> NAME/KEY: misc_feature
<222> LOCATION: (515)..(635)
<223> OTHER INFORMATION: VH2
<220> FEATURE:
<221> NAME/KEY: misc_feature
<222> LOCATION: (636)..(655)
<223> OTHER INFORMATION: Linker2
<220> FEATURE:
<221> NAME/KEY: misc_feature
<222> LOCATION: (656)..(767)
<223> OTHER INFORMATION: VL2

<400> SEQUENCE: 191

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45
```

```
Ser Ser Val Ser Tyr Met His Trp Tyr Gln Gln Lys Pro Gly Ser Ser
     50                  55                  60

Pro Lys Pro Trp Ile Tyr Ala Pro Ser Asn Leu Ala Ser Gly Val Pro
 65                  70                  75                  80

Ala Arg Phe Ser Gly Ser Gly Ser Gly Thr Ser Tyr Ser Leu Thr Ile
                 85                  90                  95

Ser Arg Val Glu Ala Glu Asp Ala Ala Thr Tyr Tyr Cys Gln Gln Trp
                100                 105                 110

Ser Phe Asn Pro Pro Thr Phe Gly Ala Gly Thr Lys Leu Glu Leu Lys
            115                 120                 125

Asp Gly Gly Gly Ser Gly Gly Gly Gly Ser Gly Gly Gly Gly Ser Ser
            130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
            195                 200                 205

Lys Gly Lys Ala Thr Leu Thr Val Asp Lys Ser Ser Thr Ala Tyr
210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
                245                 250                 255

Gly Thr Gly Thr Thr Val Thr Val Ser Asp Gln Glu Pro Lys Ser Ser
            260                 265                 270

Asp Lys Thr His Thr Ser Pro Pro Ser Pro Ala Pro Glu Leu Leu Gly
            275                 280                 285

Gly Pro Ser Val Phe Leu Phe Pro Pro Lys Pro Lys Asp Thr Leu Met
290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
            355                 360                 365

Lys Glu Tyr Lys Cys Lys Val Ser Asn Lys Ala Leu Pro Ala Pro Ile
370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Tyr Lys Thr Thr Pro Pro
            435                 440                 445

Val Leu Asp Ser Asp Gly Ser Phe Phe Leu Tyr Ser Lys Leu Thr Val
450                 455                 460

Asp Lys Ser Arg Trp Gln Gln Gly Asn Val Phe Ser Cys Ser Val Met
```

```
                465                 470                 475                 480
His Glu Ala Leu His Asn His Tyr Thr Gln Lys Ser Leu Ser Leu Ser
                    485                 490                 495

Pro Gly Lys Asn Tyr Gly Gly Gly Ser Gly Gly Gly Ser Gly
                500                 505                 510

Asn Ser Gln Val Gln Leu Lys Glu Ser Gly Pro Gly Leu Val Ala Pro
                515                 520                 525

Ser Gln Ser Leu Ser Ile Thr Cys Thr Val Ser Gly Phe Ser Leu Thr
                530                 535                 540

Gly Tyr Gly Val Asn Trp Val Arg Gln Pro Pro Gly Lys Gly Leu Glu
545                 550                 555                 560

Trp Leu Gly Met Ile Trp Gly Asp Gly Ser Thr Asp Tyr Asn Ser Ala
                    565                 570                 575

Leu Lys Ser Arg Leu Ser Ile Thr Lys Asp Asn Ser Lys Ser Gln Val
                580                 585                 590

Phe Leu Lys Met Asn Ser Leu Gln Thr Asp Asp Thr Ala Arg Tyr Tyr
                595                 600                 605

Cys Ala Arg Asp Gly Tyr Ser Asn Phe His Tyr Tyr Val Met Asp Tyr
                    610                 615                 620

Trp Gly Gln Gly Thr Ser Val Thr Val Ser Ser Gly Gly Gly Gly Ser
625                 630                 635                 640

Gly Gly Gly Gly Ser Gly Gly Gly Ser Gly Gly Gly Gly Ser Asp
                    645                 650                 655

Ile Val Leu Thr Gln Ser Pro Ala Ser Leu Ala Val Ser Leu Gly Gln
                660                 665                 670

Arg Ala Thr Ile Ser Cys Arg Ala Ser Glu Ser Val Glu Tyr Tyr Val
                675                 680                 685

Thr Ser Leu Met Gln Trp Tyr Gln Gln Lys Pro Gly Gln Pro Pro Lys
                690                 695                 700

Leu Leu Ile Ser Ala Ala Ser Asn Val Glu Ser Gly Val Pro Ala Arg
705                 710                 715                 720

Phe Ser Gly Ser Gly Ser Gly Thr Asp Phe Ser Leu Asn Ile His Pro
                    725                 730                 735

Val Glu Glu Asp Asp Ile Ala Met Tyr Phe Cys Gln Gln Ser Arg Lys
                740                 745                 750

Val Pro Trp Thr Phe Gly Gly Gly Thr Lys Leu Glu Ile Lys Arg
                    755                 760                 765

<210> SEQ ID NO 192
<211> LENGTH: 2331
<212> TYPE: DNA
<213> ORGANISM: Artificial sequence
<220> FEATURE:
<223> OTHER INFORMATION: 2H7sssIgG1-H6-2e12HL (DNA)

<400> SEQUENCE: 192
aagcttgccg ccatggattt tcaagtgcag attttcagct tcctgctaat cagtgcttca    60
gtcataatgt ccagaggaca aattgttctc tcccagtctc cagcaatcct gtctgcatct   120
ccaggggaga aggtcacaat gacttgcagg gccagctcaa gtgtaagtta catgcactgg   180
taccagcaga agccaggatc ctcccccaaa ccctggattt atgccccatc caacctggct   240
tctggagtcc ctgctcgctt cagtggcagt gggtctggga cctcttactc tctcacaatc   300
agcagagtgg aggctgaaga tgctgccact tattactgcc agcagtggag ttttaaccca   360
cccacgttcg gtgctgggac caagctggag ctgaaagatg cggtggctc gggcggtggt   420
```

```
ggatctggag gaggtgggag ctctcaggct tatctacagc agtctggggc tgagtcggtg      480
aggcctgggg cctcagtgaa gatgtcctgc aaggcttctg gctacacatt taccagttac      540
aatatgcact gggtaaagca gacacctaga cagggcctgg aatggattgg agctatttat      600
ccaggaaatg gtgatacttc ctacaatcag aagttcaagg gcaaggccac actgactgta      660
gacaaatcct ccagcacagc ctacatgcag ctcagcagcc tgacatctga agactctgcg      720
gtctatttct gtgcaagagt ggtgtactat agtaactctt actggtactt cgatgtctgg      780
ggcacaggga ccacggtcac cgtctctgat caggagccca atcttctga caaaactcac       840
acatccccac cgagcccagc acctgaactc ctggggggac cgtcagtctt cctcttcccc      900
ccaaaaccca aggacaccct catgatctcc cggacccctg aggtcacatg cgtggtggtg      960
gacgtgagcc acgaagaccc tgaggtcaag ttcaactggt acgtggacgg cgtggaggtg     1020
cataatgcca agacaaagcc gcgggaggag cagtacaaca gcacgtaccg tgtggtcagc     1080
gtcctcaccg tcctgcacca ggactggctg aatggcaagg agtacaagtg caaggtctcc     1140
aacaaagccc tcccagcccc catcgagaaa acaatctcca aagccaaagg cagccccga      1200
gaaccacagg tgtacaccct gcccccatcc cgggatgagc tgaccaagaa ccaggtcagc     1260
ctgacctgcc tggtcaaagg cttctatccc agcgacatcg ccgtggagtg ggagagcaat     1320
gggcagccgg agaacaacta caagaccacg cctcccgtgc tggactccga cggctccttc     1380
ttcctctaca gcaagctcac cgtggacaag agcaggtggc agcaggggaa cgtcttctca     1440
tgctccgtga tgcatgaggc tctgcacaac cactacacgc agaagagcct ctccctgtct     1500
ccgggtaagg gtggcggtgg ctcgggcggt ggtggatctg ggggaggagg cagcgggaat     1560
tctcaggtgc agctgaagga gtcaggacct ggcctggtgg cgccctcaca gagcctgtcc     1620
atcacatgca ccgtctcagg gttctcatta accggctatg gtgtaaactg ggttcgccag     1680
cctccaggaa agggtctgga gtggctggga atgatatggg gtgatggaag cacagactat     1740
aattcagctc tcaaatccag actatcgatc accaaggaca ctccaagag ccaagttttc      1800
ttaaaaatga acagtctgca aactgatgac acagccagat actactgtgc tcgagatggt     1860
tatagtaact tcattacta tgttatggac tactggggtc aaggaacctc agtcaccgtc     1920
tcctctgggg gtggaggctc tggtggcggt ggatccggcg gaggtgggtc gggtggcggc     1980
ggatctgaca ttgtgctcac ccaatctcca gcttctttgg ctgtgtctct aggtcagaga     2040
gccaccatct cctgcagagc cagtgaaagt gttgaatatt atgtcacaag tttaatgcag     2100
tggtaccaac agaaaccagg acagccaccc aaactcctca tctctgctgc tagcaacgta     2160
gaatctgggg tccctgccag gtttagtggc agtgggtctg gacagactt tagcctcaac     2220
atccatcctg tggaggagga tgatattgca atgtatttct gtcagcaaag taggaaggtt     2280
ccatggacgt tcggtggagg caccaagctg gaaatcaaac gttaatctag a              2331
```

<210> SEQ ID NO 193
<211> LENGTH: 770
<212> TYPE: PRT
<213> ORGANISM: Artificial sequence
<220> FEATURE:
<223> OTHER INFORMATION: 2H7sssIgG1-H6-2e12HL (w/2e12 leader) (AA)
<220> FEATURE:
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (23)..(128)
<223> OTHER INFORMATION: VL
<220> FEATURE:

```
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(282)
<223> OTHER INFORMATION: Hinge
<220> FEATURE:
<221> NAME/KEY: misc_feature
<222> LOCATION: (500)..(517)
<223> OTHER INFORMATION: EFD-BD2 Linker
<220> FEATURE:
<221> NAME/KEY: misc_feature
<222> LOCATION: (518)..(638)
<223> OTHER INFORMATION: VH2
<220> FEATURE:
<221> NAME/KEY: misc_feature
<222> LOCATION: (639)..(658)
<223> OTHER INFORMATION: Linker2
<220> FEATURE:
<221> NAME/KEY: misc_feature
<222> LOCATION: (659)..(770)
<223> OTHER INFORMATION: VL2

<400> SEQUENCE: 193

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Gly Ser Gly Gly Gly Gly Ser Ser
130                 135                 140

Gln Ala Tyr Leu Gln Gln Ser Gly Ala Glu Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Val Asp Lys Ser Ser Ser Thr Ala Tyr
210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
                245                 250                 255

Gly Thr Gly Thr Thr Val Thr Val Ser Asp Gln Glu Pro Lys Ser Ser
            260                 265                 270
```

```
Asp Lys Thr His Thr Ser Pro Pro Ser Pro Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Gly Gly Gly Gly Ser Gly Gly Gly Gly Ser Gly Gly Gly
            500                 505                 510

Gly Ser Gly Asn Ser Gln Val Gln Leu Lys Glu Ser Gly Pro Gly Leu
        515                 520                 525

Val Ala Pro Ser Gln Ser Leu Ser Ile Thr Cys Thr Val Ser Gly Phe
    530                 535                 540

Ser Leu Thr Gly Tyr Gly Val Asn Trp Val Arg Gln Pro Pro Gly Lys
545                 550                 555                 560

Gly Leu Glu Trp Leu Gly Met Ile Trp Gly Asp Gly Ser Thr Asp Tyr
                565                 570                 575

Asn Ser Ala Leu Lys Ser Arg Leu Ser Ile Thr Lys Asp Asn Ser Lys
            580                 585                 590

Ser Gln Val Phe Leu Lys Met Asn Ser Leu Gln Thr Asp Asp Thr Ala
        595                 600                 605

Arg Tyr Tyr Cys Ala Arg Asp Gly Tyr Ser Asn Phe His Tyr Tyr Val
    610                 615                 620

Met Asp Tyr Trp Gly Gln Gly Thr Ser Val Thr Val Ser Ser Gly Gly
625                 630                 635                 640

Gly Gly Ser Gly Gly Gly Gly Ser Gly Gly Gly Gly Ser Gly Gly Gly
                645                 650                 655

Gly Ser Asp Ile Val Leu Thr Gln Ser Pro Ala Ser Leu Ala Val Ser
            660                 665                 670

Leu Gly Gln Arg Ala Thr Ile Ser Cys Arg Ala Ser Glu Ser Val Glu
        675                 680                 685

Tyr Tyr Val Thr Ser Leu Met Gln Trp Tyr Gln Gln Lys Pro Gly Gln
```

```
              690              695              700
Pro Pro Lys Leu Leu Ile Ser Ala Ala Ser Asn Val Glu Ser Gly Val
705              710              715              720

Pro Ala Arg Phe Ser Gly Ser Gly Ser Gly Thr Asp Phe Ser Leu Asn
                725              730              735

Ile His Pro Val Glu Glu Asp Asp Ile Ala Met Tyr Phe Cys Gln Gln
            740              745              750

Ser Arg Lys Val Pro Trp Thr Phe Gly Gly Gly Thr Lys Leu Glu Ile
        755              760              765

Lys Arg
    770

<210> SEQ ID NO 194
<211> LENGTH: 2301
<212> TYPE: DNA
<213> ORGANISM: Artificial sequence
<220> FEATURE:
<223> OTHER INFORMATION: 2H7sscIgG1-H7-2e12HL (DNA)

<400> SEQUENCE: 194
aagcttgccg ccatggattt tcaagtgcag attttcagct tcctgctaat cagtgcttca      60
gtcataatgt ccagaggaca aattgttctc tcccagtctc cagcaatcct gtctgcatct    120
ccaggggaga aggtcacaat gacttgcagg gccagctcaa gtgtaagtta catgcactgg    180
taccagcaga agccaggatc ctcccccaaa ccctggattt atgccccatc caacctggct    240
tctggagtcc ctgctcgctt cagtggcagt gggtctggga cctcttactc tctcacaatc    300
agcagagtgg aggctgaaga tgctgccact tattactgcc agcagtggag ttttaaccca    360
cccacgttcg gtgctgggac caagctggag ctgaaagatg cggtggctc gggcggtggt    420 ggatctggag gaggtgggag ctctcaggct tatctacagc agtctggggc tgagtcggtg    480
aggcctgggg cctcagtgaa gatgtcctgc aaggcttctg gctacacatt taccagttac    540
aatatgcact gggtaaagca gacacctaga cagggcctgg aatggattgg agctatttat    600
ccaggaaatg gtgatacttc ctacaatcag aagttcaagg gcaaggccac actgactgta    660
gacaaatcct ccagcacagc ctacatgcag ctcagcagcc tgacatctga agactctgcg    720
gtctatttct gtgcaagagt ggtgtactat agtaactctt actggtactt cgatgtctgg    780
ggcacaggga ccacggtcac cgtctctgat caggagccca atcttctga caaaactcac    840 acatccccac cgtgcccagc acctgaactc ctggggggat cgtcagtctt cctcttcccc    900
ccaaaaccca aggacaccct catgatctcc cggacccctg aggtcacatg cgtggtggtg    960
gacgtgagcc acgaagaccc tgaggtcaag ttcaactggt acgtggacgg cgtggaggtg   1020
cataatgcca agacaaagcc gcgggaggag cagtacaaca gcacgtaccg tgtggtcagc   1080
gtcctcaccg tcctgcacca ggactggctg aatggcaagg agtacaagtg caaggtctcc   1140
aacaaagccc tcccagcccc catcgagaaa accatctcca agccaaagg gcagcccga    1200 gaaccacagg tgtacaccct gcccccatcc cggatgagc tgaccaagaa ccaggtcagc   1260
ctgacctgcc tggtcaaagg cttctatcca agcgacatcg ccgtggagtg ggagagcaat   1320
gggcagccgg agaacaacta caagaccacg cctcccgtgc tggactccga cggctccttc   1380
ttcctctaca gcaagctcac cgtggacaag agcaggtgg agcaggggaa cgtcttctca   1440
tgctccgtga tgcatgaggc tctgcacaac cactacacgc agaagagcct ctccctgtct   1500
ccgggtaagg ggtgtccacc ttgtccgaat tctcaggtgc agctgaagga gtcagggcct   1560
ggcagcgtgg cgccctcaca gagcctgtcc atcacatgca ccgtctcagg gttctcatta   1620
```

```
accggctatg gtgtaaactg ggttcgccag cctccaggaa agggtctgga gtggctggga    1680
atgatatggg gtgatggaag cacagactat aattcagctc tcaaatccag actatcgatc    1740
accaaggaca actccaagag ccaagttttc ttaaaaatga acagtctgca aactgatgac    1800
acagccagat actactgtgc tcgagatggt tatagtaact tcattacta tgttatggac    1860 tactggggtc aaggaacctc agtcaccgtc tcctctgggg gtggaggctc tggtggcggt    1920
ggatccggcg gaggtgggtc gggtggcggc ggatctgaca ttgtgctcac ccaatctcca    1980
gcttctttgg ctgtgtctct aggtcagaga gccaccatct cctgcagagc cagtgaaagt    2040
gttgaatatt atgtcacaag tttaatgcag tggtaccaac agaaaccagg acagccaccc    2100
aagctcctca tctctgctgc tagcaacgta aatctggggg tccctgccag gtttagtggc    2160
agtgggtctg ggacagactt tagcctcaac atccatcctg tggaggagga tgatattgca    2220
atgtatttct gtcagcaaag taggaaggtt ccatggacgt tcggtggagg caccaagctg    2280
gaaatcaaac gttaatctag a                                              2301
```

```
<210> SEQ ID NO 195
<211> LENGTH: 760
<212> TYPE: PRT
<213> ORGANISM: Artificial sequence
<220> FEATURE:
<223> OTHER INFORMATION: 2H7sscIgG1-H7-2e12HL (w/2e12 linker ) (AA)
<220> FEATURE:
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (23)..(128)
<223> OTHER INFORMATION: VL
<220> FEATURE:
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(282)
<223> OTHER INFORMATION: Hinge
<220> FEATURE:
<221> NAME/KEY: misc_feature
<222> LOCATION: (500)..(507)
<223> OTHER INFORMATION: EFD-BD2 Linker
<220> FEATURE:
<221> NAME/KEY: misc_feature
<222> LOCATION: (508)..(628)
<223> OTHER INFORMATION: VH2
<220> FEATURE:
<221> NAME/KEY: misc_feature
<222> LOCATION: (629)..(648)
<223> OTHER INFORMATION: Linker2
<220> FEATURE:
<221> NAME/KEY: misc_feature
<222> LOCATION: (649)..(760)
<223> OTHER INFORMATION: VL2

<400> SEQUENCE: 195

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
                20                  25                  30

Leu Ser Ala Ser Pro Gly Glu Lys Val Thr Met Thr Cys Arg Ala Ser
            35                  40                  45
```

```
Ser Ser Val Ser Tyr Met His Trp Tyr Gln Gln Lys Pro Gly Ser Ser
 50                  55                  60
Pro Lys Pro Trp Ile Tyr Ala Pro Ser Asn Leu Ala Ser Gly Val Pro
 65                  70                  75                  80
Ala Arg Phe Ser Gly Ser Gly Ser Gly Thr Ser Tyr Ser Leu Thr Ile
                 85                  90                  95
Ser Arg Val Glu Ala Glu Asp Ala Ala Thr Tyr Tyr Cys Gln Gln Trp
            100                 105                 110
Ser Phe Asn Pro Pro Thr Phe Gly Ala Gly Thr Lys Leu Glu Leu Lys
        115                 120                 125
Asp Gly Gly Gly Ser Gly Gly Gly Ser Gly Gly Gly Ser
130                 135                 140
Gln Ala Tyr Leu Gln Gln Ser Gly Ala Glu Ser Val Arg Pro Gly Ala
145                 150                 155                 160
Ser Val Lys Met Ser Cys Lys Ala Ser Gly Tyr Thr Phe Thr Ser Tyr
                165                 170                 175
Asn Met His Trp Val Lys Gln Thr Pro Arg Gln Gly Leu Glu Trp Ile
            180                 185                 190
Gly Ala Ile Tyr Pro Gly Asn Gly Asp Thr Ser Tyr Asn Gln Lys Phe
        195                 200                 205
Lys Gly Lys Ala Thr Leu Thr Val Asp Lys Ser Ser Thr Ala Tyr
210                 215                 220
Met Gln Leu Ser Ser Leu Thr Ser Glu Asp Ser Ala Val Tyr Phe Cys
225                 230                 235                 240
Ala Arg Val Val Tyr Tyr Ser Asn Ser Tyr Trp Tyr Phe Asp Val Trp
                245                 250                 255
Gly Thr Gly Thr Thr Val Thr Val Ser Asp Gln Glu Pro Lys Ser Ser
            260                 265                 270
Asp Lys Thr His Thr Ser Pro Pro Cys Pro Ala Pro Glu Leu Leu Gly
        275                 280                 285
Gly Ser Ser Val Phe Leu Phe Pro Pro Lys Pro Lys Asp Thr Leu Met
290                 295                 300
Ile Ser Arg Thr Pro Glu Val Thr Cys Val Val Val Asp Val Ser His
305                 310                 315                 320
Glu Asp Pro Glu Val Lys Phe Asn Trp Tyr Val Asp Gly Val Glu Val
                325                 330                 335
His Asn Ala Lys Thr Lys Pro Arg Glu Glu Gln Tyr Asn Ser Thr Tyr
            340                 345                 350
Arg Val Val Ser Val Leu Thr Val Leu His Gln Asp Trp Leu Asn Gly
        355                 360                 365
Lys Glu Tyr Lys Cys Lys Val Ser Asn Lys Ala Leu Pro Ala Pro Ile
370                 375                 380
Glu Lys Thr Ile Ser Lys Ala Lys Gly Gln Pro Arg Glu Pro Gln Val
385                 390                 395                 400
Tyr Thr Leu Pro Pro Ser Arg Asp Glu Leu Thr Lys Asn Gln Val Ser
                405                 410                 415
Leu Thr Cys Leu Val Lys Gly Phe Tyr Pro Ser Asp Ile Ala Val Glu
            420                 425                 430
Trp Glu Ser Asn Gly Gln Pro Glu Asn Asn Tyr Lys Thr Thr Pro Pro
        435                 440                 445
Val Leu Asp Ser Asp Gly Ser Phe Phe Leu Tyr Ser Lys Leu Thr Val
450                 455                 460
Asp Lys Ser Arg Trp Gln Gln Gly Asn Val Phe Ser Cys Ser Val Met
465                 470                 475                 480
```

His Glu Ala Leu His Asn His Tyr Thr Gln Lys Ser Leu Ser Leu Ser
            485                 490                 495

Pro Gly Lys Gly Cys Pro Cys Pro Asn Ser Gln Val Gln Leu Lys
        500                 505                 510

Glu Ser Gly Pro Gly Ser Val Ala Pro Ser Gln Ser Leu Ser Ile Thr
    515                 520                 525

Cys Thr Val Ser Gly Phe Ser Leu Thr Gly Tyr Gly Val Asn Trp Val
530                 535                 540

Arg Gln Pro Pro Gly Lys Gly Leu Glu Trp Leu Gly Met Ile Trp Gly
545                 550                 555                 560

Asp Gly Ser Thr Asp Tyr Asn Ser Ala Leu Lys Ser Arg Leu Ser Ile
                565                 570                 575

Thr Lys Asp Asn Ser Lys Ser Gln Val Phe Leu Lys Met Asn Ser Leu
            580                 585                 590

Gln Thr Asp Asp Thr Ala Arg Tyr Tyr Cys Ala Arg Asp Gly Tyr Ser
        595                 600                 605

Asn Phe His Tyr Tyr Val Met Asp Tyr Trp Gly Gln Gly Thr Ser Val
    610                 615                 620

Thr Val Ser Ser Gly Gly Gly Gly Ser Gly Gly Gly Gly Ser Gly Gly
625                 630                 635                 640

Gly Gly Ser Gly Gly Gly Gly Ser Asp Ile Val Leu Thr Gln Ser Pro
                645                 650                 655

Ala Ser Leu Ala Val Ser Leu Gly Gln Arg Ala Thr Ile Ser Cys Arg
            660                 665                 670

Ala Ser Glu Ser Val Glu Tyr Tyr Val Thr Ser Leu Met Gln Trp Tyr
        675                 680                 685

Gln Gln Lys Pro Gly Gln Pro Pro Lys Leu Leu Ile Ser Ala Ala Ser
    690                 695                 700

Asn Val Glu Ser Gly Val Pro Ala Arg Phe Ser Gly Ser Gly Ser Gly
705                 710                 715                 720

Thr Asp Phe Ser Leu Asn Ile His Pro Val Glu Glu Asp Asp Ile Ala
                725                 730                 735

Met Tyr Phe Cys Gln Gln Ser Arg Lys Val Pro Trp Thr Phe Gly Gly
            740                 745                 750

Gly Thr Lys Leu Glu Ile Lys Arg
        755                 760

<210> SEQ ID NO 196
<211> LENGTH: 2283
<212> TYPE: DNA
<213> ORGANISM: Artificial sequence
<220> FEATURE:
<223> OTHER INFORMATION: 2H7sssIgG1-H7-G194 HL (DNA)

<400> SEQUENCE: 196
aagcttgccg ccatggattt tcaagtgcag attttcagct tcctgctaat cagtgcttca      60
gtcataatgt ccagaggaca aattgttctc tcccagtctc cagcaatcct gtctgcatct     120
ccaggggaga aggtcacaat gacttgcagg gccagctcaa gtgtaagtta catgcactgg     180
taccagcaga agccaggatc ctcccccaaa ccctggattt atgccccatc caacctggct     240
tctggagtcc ctgctcgctt cagtggcagt gggtctggga cctcttactc tctcacaatc     300
agcagagtgg aggctgaaga tgctgccact tattactgcc agcagtggag ttttaaccca     360
cccacgttcg gtgctgggac caagctggag ctgaaagatg cggtggctc gggcggtggt     420 ggatctggag gaggtgggag ctctcaggct tatctacagc agtctggggc tgagtcggtg     480

```
aggcctgggg cctcagtgaa gatgtcctgc aaggcttctg gctacacatt taccagttac      540
aatatgcact gggtaaagca gacacctaga cagggcctgg aatggattgg agctatttat      600
ccaggaaatg gtgatacttc ctacaatcag aagttcaagg gcaaggccac actgactgta      660
gacaaatcct ccagcacagc ctacatgcag ctcagcagcc tgacatctga agactctgcg      720
gtctatttct gtgcaagagt ggtgtactat agtaactctt actggtactt cgatgtctgg      780
ggcacaggga ccacggtcac cgtctctgat caggagccca atcttctga caaaactcac      840 acatccccac cgtgcccagc acctgaactc ctggggggat cgtcagtctt cctcttcccc      900
ccaaaaccca aggacaccct catgatctcc cggacccctg aggtcacatg cgtggtggtg      960
gacgtgagcc acgaagaccc tgaggtcaag ttcaactggt acgtggacgg cgtggaggtg     1020
cataatgcca agacaaagcc gcgggaggag cagtacaaca gcacgtaccg tgtggtcagc     1080
gtcctcaccg tcctgcacca ggactggctg aatggcaagg agtacaagtg caaggtctcc     1140
aacaaagccc tcccagcccc catcgagaaa accatctcca agccaaagg gcagcccga     1200 gaaccacagg tgtacaccct gcccccatcc cgggatgagc tgaccaagaa ccaggtcagc     1260
ctgacctgcc tggtcaaagg cttctatcca agcgacatcg ccgtggagtg ggagagcaat     1320
gggcagccgg agaacaacta caagaccacg cctcccgtgc tggactccga cggctccttc     1380
ttcctctaca gcaagctcac cgtggacaag agcaggtggc agcaggggaa cgtcttctca     1440
tgctccgtga tgcatgaggc tctgcacaac cactacacgc agaagagcct ctccctgtct     1500
ccgggtaagg ggtgtccacc ttgtccgaat tctgaggtcc agctgcaaca gtctggacct     1560
gaactggtga agcctggagc ttcaatgaag atttcctgca aggcctctgg ttactcattc     1620
actggctaca tcgtgaactg gctgaagcag agccatggaa agaaccttga gtggattgga     1680
cttattaatc catacaaagg tcttactacc tacaaccaga aattcaaggg caaggccaca     1740
ttaactgtag acaagtcatc cagcacagcc tacatggagc tcctcagtct gacatctgaa     1800
gactctgcag tctattactg tgcaagatct gggtactatg gtgactcgga ctggtacttc     1860
gatgtctggg gcgcagggac cacggtcacc gtctcctctg gtggcggtgg ctcgggcggt     1920
ggtggatctg gaggaggtgg gagcgctagc gacatccaga tgacacagac tacatcctcc     1980
ctgtctgcct ctctgggaga cagagtcacc atcagttgca gggcaagtca ggacattcgc     2040
aattatttaa actggtatca gcagaaacca gatggaactg ttaaactcct gatctactac     2100
acatcaagat tacactcagg agtcccatca aggttcagtg gcagtgggtc tggaacagat     2160
tattctctca ccattgccaa cctgcaacca gaagatattg ccacttactt tgccaacag      2220 ggtaatacgc ttccgtggac gttcggtgga ggcaccaaac tggtaaccaa acggtaatct     2280
aga                                                                    2283
```

<210> SEQ ID NO 197
<211> LENGTH: 754
<212> TYPE: PRT
<213> ORGANISM: Artificial sequence
<220> FEATURE:
<223> OTHER INFORMATION: 2H7sssIgG1-H7-G194 HL (w/2e12 leader) (AA)
<220> FEATURE:
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (23)..(128)
<223> OTHER INFORMATION: VL
<220> FEATURE:
<221> NAME/KEY: misc_feature

```
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH1
<220> FEATURE:
<221> NAME/KEY: misc_feature
<222> LOCATION: (268)..(282)
<223> OTHER INFORMATION: Hinge
<220> FEATURE:
<221> NAME/KEY: misc_feature
<222> LOCATION: (500)..(507)
<223> OTHER INFORMATION: EFD-BD2 Linker
<220> FEATURE:
<221> NAME/KEY: misc_feature
<222> LOCATION: (508)..(629)
<223> OTHER INFORMATION: VH2
<220> FEATURE:
<221> NAME/KEY: misc_feature
<222> LOCATION: (630)..(646)
<223> OTHER INFORMATION: Linker2
<220> FEATURE:
<221> NAME/KEY: misc_feature
<222> LOCATION: (647)..(754)
<223> OTHER INFORMATION: VL2

<400> SEQUENCE: 197
```

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Ser Gly Gly Gly Ser Ser
    130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Val Asp Lys Ser Ser Thr Ala Tyr
    210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
                245                 250                 255

Gly Thr Gly Thr Thr Val Thr Val Ser Asp Gln Glu Pro Lys Ser Ser
            260                 265                 270

-continued

```
Asp Lys Thr His Thr Ser Pro Pro Cys Pro Ala Pro Glu Leu Leu Gly
        275                 280                 285

Gly Ser Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Gly Cys Pro Pro Cys Pro Asn Ser Glu Val Gln Leu Gln
            500                 505                 510

Gln Ser Gly Pro Glu Leu Val Lys Pro Gly Ala Ser Met Lys Ile Ser
        515                 520                 525

Cys Lys Ala Ser Gly Tyr Ser Phe Thr Gly Tyr Ile Val Asn Trp Leu
    530                 535                 540

Lys Gln Ser His Gly Lys Asn Leu Glu Trp Ile Gly Leu Ile Asn Pro
545                 550                 555                 560

Tyr Lys Gly Leu Thr Thr Tyr Asn Gln Lys Phe Lys Gly Lys Ala Thr
                565                 570                 575

Leu Thr Val Asp Lys Ser Ser Thr Ala Tyr Met Glu Leu Leu Ser
            580                 585                 590

Leu Thr Ser Glu Asp Ser Ala Val Tyr Tyr Cys Ala Arg Ser Gly Tyr
        595                 600                 605

Tyr Gly Asp Ser Asp Trp Tyr Phe Asp Val Trp Gly Ala Gly Thr Thr
    610                 615                 620

Val Thr Val Ser Ser Gly Gly Gly Ser Gly Gly Gly Ser Gly
625                 630                 635                 640

Gly Gly Gly Ser Ala Ser Asp Ile Gln Met Thr Gln Thr Thr Ser Ser
                645                 650                 655

Leu Ser Ala Ser Leu Gly Asp Arg Val Thr Ile Ser Cys Arg Ala Ser
            660                 665                 670

Gln Asp Ile Arg Asn Tyr Leu Asn Trp Tyr Gln Gln Lys Pro Asp Gly
        675                 680                 685

Thr Val Lys Leu Leu Ile Tyr Tyr Thr Ser Arg Leu His Ser Gly Val
    690                 695                 700
```

```
Pro Ser Arg Phe Ser Gly Ser Gly Ser Gly Thr Asp Tyr Ser Leu Thr
705                 710                 715                 720

Ile Ala Asn Leu Gln Pro Glu Asp Ile Ala Thr Tyr Phe Cys Gln Gln
                725                 730                 735

Gly Asn Thr Leu Pro Trp Thr Phe Gly Gly Gly Thr Lys Leu Val Thr
            740                 745                 750

Lys Arg

<210> SEQ ID NO 198
<211> LENGTH: 2298
<212> TYPE: DNA
<213> ORGANISM: Artificial sequence
<220> FEATURE:
<223> OTHER INFORMATION: 2H7sssIgG1-H7-G281 HL (DNA)

<400> SEQUENCE: 198
aagcttgccg ccatggattt tcaagtgcag attttcagct tcctgctaat cagtgcttca      60
gtcataatgt ccagaggaca aattgttctc tcccagtctc cagcaatcct gtctgcatct    120
ccaggggaga aggtcacaat gacttgcagg gccagctcaa gtgtaagtta catgcactgg    180
taccagcaga agccaggatc ctcccccaaa ccctggattt atgccccatc caacctggct    240
tctggagtcc ctgctcgctt cagtggcagt gggtctggga cctcttactc tctcacaatc    300
agcagagtgg aggctgaaga tgctgccact tattactgcc agcagtggag ttttaaccca    360
cccacgttcg gtgctgggac caagctggag ctgaaagatg cggtggctc gggcggtggt    420 ggatctggag gaggtgggag ctctcaggct tatctacagc agtctggggc tgagtcggtg    480
aggcctgggg cctcagtgaa gatgtcctgc aaggcttctg gctacacatt taccagttac    540
aatatgcact gggtaaagca gacacctaga cagggcctgg aatggattgg agctatttat    600
ccaggaaatg gtgatacttc ctacaatcag aagttcaagg gcaaggccac actgactgta    660
gacaaatcct ccagcacagc ctacatgcag ctcagcagcc tgacatctga agactctgcg    720
gtctatttct gtgcaagagt ggtgtactat agtaactctt actggtactt cgatgtctgg    780
ggcacaggga ccacggtcac cgtctctgat caggagccca atcttctga caaaactcac    840 acatccccac cgtgcccagc acctgaactc ctggggggat cgtcagtctt cctcttcccc    900
ccaaaaccca aggacaccct catgatctcc cggacccctg aggtcacatg cgtggtggtg    960
gacgtgagcc acgaagaccc tgaggtcaag ttcaactggt acgtggacgg cgtggaggtg   1020
cataatgcca agacaaagcc gcgggaggag cagtacaaca gcacgtaccg tgtggtcagc   1080
gtcctcaccg tcctgcacca ggactggctg aatggcaagg agtacaagtg caaggtctcc   1140
aacaaagccc tcccagcccc catcgagaaa accatctcca agccaaagg gcagccccga   1200 gaaccacagg tgtacaccct gccccatcc cgggatgagc tgaccaagaa ccaggtcagc   1260
ctgacctgcc tggtcaaagg cttctatcca agcgacatcg ccgtggagtg ggagagcaat   1320
gggcagccgg agaacaacta caagaccacg cctcccgtgc tggactccga cggctccttc   1380
ttcctctaca gcaagctcac cgtggacaag agcaggtggc agcagggaa cgtcttctca   1440 tgctccgtga tgcatgaggc tctgcacaac cactacacgc agaagagcct ctccctgtct   1500
ccgggtaagg ggtgtccacc ttgtccgaat tctgaggtcc agctgcaaca gtctggacct   1560
gaactggtga gcctggagc ttcaatgaag atttcctgca aggcctctgg ttactcattc   1620
actggctaca tcgtgaactg gctgaagcag agccatggaa agaaccttga gtggattgga   1680
cttattaatc catacaaagg tcttactacc tacaaccaga aattcaaggg caaggccaca   1740
```

```
ttaactgtag acaagtcatc cagcacagcc tacatggagc tcctcagtct gacatctgaa    1800
gactctgcag tctattactg tgcaagatct gggtactatg gtgactcgga ctggtacttc    1860
gatgtctggg gcgcaggga cacggtcacc gtctcctctg gtggcggtgg ctcgggcggt    1920
ggtggatctg gaggaggtgg gagcggggga ggtggcagtg ctagcgacat ccagatgaca    1980
cagactacat cctccctgtc tgcctctctg ggagacagag tcaccatcag ttgcagggca    2040
agtcaggaca ttcgcaatta tttaaactgg tatcagcaga accagatgg aactgttaaa    2100 ctcctgatct actacacatc aagattacac tcaggagtcc catcaaggtt cagtggcagt    2160
gggtctggaa cagattattc tctcaccatt gccaacctgc aaccagaaga tattgccact    2220 tactttgcc aacagggtaa tacgcttccg tggacgttcg gtggaggcac caaactggta    2280
accaaacggt aatctaga                                                  2298
```

```
<210> SEQ ID NO 199
<211> LENGTH: 759
<212> TYPE: PRT
<213> ORGANISM: Artificial sequence
<220> FEATURE:
<223> OTHER INFORMATION: 2H7sssIgG1-H7-G281 HL (w/2e12 leader) (AA)
<220> FEATURE:
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (23)..(128)
<223> OTHER INFORMATION: VL1
<220> FEATURE:
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH1
<220> FEATURE:
<221> NAME/KEY: misc_feature
<222> LOCATION: (268)..(282)
<223> OTHER INFORMATION: Hinge
<220> FEATURE:
<221> NAME/KEY: misc_feature
<222> LOCATION: (500)..(507)
<223> OTHER INFORMATION: EFD-BD2 Linker
<220> FEATURE:
<221> NAME/KEY: misc_feature
<222> LOCATION: (508)..(629)
<223> OTHER INFORMATION: VH2
<220> FEATURE:
<221> NAME/KEY: misc_feature
<222> LOCATION: (630)..(651)
<223> OTHER INFORMATION: Linker2
<220> FEATURE:
<221> NAME/KEY: misc_feature
<222> LOCATION: (652)..(759)
<223> OTHER INFORMATION: VL2

<400> SEQUENCE: 199

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80
```

```
Ala Arg Phe Ser Gly Ser Gly Ser Gly Thr Ser Tyr Ser Leu Thr Ile
            85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
            115                 120                 125

Asp Gly Gly Gly Ser Gly Gly Gly Gly Ser Gly Gly Gly Gly Ser Ser
            130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
            195                 200                 205

Lys Gly Lys Ala Thr Leu Thr Val Asp Lys Ser Ser Thr Ala Tyr
            210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
            245                 250                 255

Gly Thr Gly Thr Thr Val Thr Val Ser Asp Gln Glu Pro Lys Ser Ser
            260                 265                 270

Asp Lys Thr His Thr Ser Pro Pro Cys Pro Ala Pro Glu Leu Leu Gly
            275                 280                 285

Gly Ser Ser Val Phe Leu Phe Pro Pro Lys Pro Lys Asp Thr Leu Met
            290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
            325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
            355                 360                 365

Lys Glu Tyr Lys Cys Lys Val Ser Asn Lys Ala Leu Pro Ala Pro Ile
            370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
            405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
            435                 440                 445

Val Leu Asp Ser Asp Gly Ser Phe Phe Leu Tyr Ser Lys Leu Thr Val
            450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
            485                 490                 495

Pro Gly Lys Gly Cys Pro Pro Cys Pro Asn Ser Glu Val Gln Leu Gln
```

500             505             510
Gln Ser Gly Pro Glu Leu Val Lys Pro Gly Ala Ser Met Lys Ile Ser
            515                 520                 525

Cys Lys Ala Ser Gly Tyr Ser Phe Thr Gly Tyr Ile Val Asn Trp Leu
        530                 535                 540

Lys Gln Ser His Gly Lys Asn Leu Glu Trp Ile Gly Leu Ile Asn Pro
545                 550                 555                 560

Tyr Lys Gly Leu Thr Thr Tyr Asn Gln Lys Phe Lys Gly Lys Ala Thr
                565                 570                 575

Leu Thr Val Asp Lys Ser Ser Thr Ala Tyr Met Glu Leu Leu Ser
            580                 585                 590

Leu Thr Ser Glu Asp Ser Ala Val Tyr Tyr Cys Ala Arg Ser Gly Tyr
        595                 600                 605

Tyr Gly Asp Ser Asp Trp Tyr Phe Asp Val Trp Gly Ala Gly Thr Thr
        610                 615                 620

Val Thr Val Ser Ser Gly Gly Gly Gly Ser Gly Gly Gly Gly Ser Gly
625                 630                 635                 640

Gly Gly Ser Gly Gly Gly Gly Ser Ala Ser Asp Ile Gln Met Thr
            645                 650                 655

Gln Thr Thr Ser Ser Leu Ser Ala Ser Leu Gly Asp Arg Val Thr Ile
            660                 665                 670

Ser Cys Arg Ala Ser Gln Asp Ile Arg Asn Tyr Leu Asn Trp Tyr Gln
        675                 680                 685

Gln Lys Pro Asp Gly Thr Val Lys Leu Leu Ile Tyr Tyr Thr Ser Arg
690                 695                 700

Leu His Ser Gly Val Pro Ser Arg Phe Ser Gly Ser Gly Ser Gly Thr
705                 710                 715                 720

Asp Tyr Ser Leu Thr Ile Ala Asn Leu Gln Pro Glu Asp Ile Ala Thr
                725                 730                 735

Tyr Phe Cys Gln Gln Gly Asn Thr Leu Pro Trp Thr Phe Gly Gly Gly
            740                 745                 750

Thr Lys Leu Val Thr Lys Arg
        755

<210> SEQ ID NO 200
<211> LENGTH: 1533
<212> TYPE: DNA
<213> ORGANISM: Artificial sequence
<220> FEATURE:
<223> OTHER INFORMATION: 2e12-sss-IgG1 HL SMIP (DNA)

<400> SEQUENCE: 200 atggatttc aagtgcagat tttcagcttc ctgctaatca gtgcttcagt cataatgtcc      60
agaggagtcc aggtgcagct gaaggagtca ggacctggcc tggtggcgcc ctcacagagc    120
ctgtccatca catgcaccgt ctcagggttc tcattaaccg ctatggtgt aaactgggtt     180 cgccagcctc caggaaaggg tctagagtgg ctggaatga tatgggtga tggaagcaca     240 gactataatt cagctctcaa atccagacta tcgatcacca aggacaactc caagagccaa    300
gttttcttaa aaatgaacag tctgcaaact gatgacacag ccagatacta ctgtgctcga    360
gatggttata gtaactttca ttactatgtt atggactact ggggtcaagg aacctcagtc    420
accgtctcct ctgggggtgg aggctctggt ggcggtggat ccggcggagg tgggtcgggt    480
ggcggcggat ctgacattgt gctcacccaa tctccagctt ctttggctgt gtctctaggt    540
cagagagcca ccatctcctg cagagccagt gaaagtgttg aatattatgt cacaagttta    600

| | |
|---|---|
| atgcagtggt accaacagaa accaggacag ccacccaaac tcctcatctc tgctgctagc | 660 |
| aacgtagaat ctggggtccc tgccaggttt agtggcagtg ggtctgggac agactttagc | 720 |
| ctcaacatcc atcctgtgga ggaggatgat attgcaatgt atttctgtca gcaaagtagg | 780 |
| aaggttccat ggacgttcgg tggaggcacc aagctggaaa tcaaacgtga tcaggagccc | 840 |
| aaatcttctg acaaaactca cacatcccca ccgtcccag cacctgaact cctgggggga | 900 |
| tcgtcagtct tcctcttccc cccaaaaccc aaggacaccc tcatgatctc ccggaccct | 960 |
| gaggtcacat gcgtggtggt ggacgtgagc cacgaagacc ctgaggtcaa gttcaactgg | 1020 |
| tacgtggacg gcgtggaggt gcataatgcc aagacaaagc cgcggagga gcagtacaac | 1080 |
| agcacgtacc gtgtggtcag cgtcctcacc gtcctgcacc aggactggct gaatggcaag | 1140 |
| gagtacaagt gcaaggtctc caacaaagcc ctcccagcct ccatcgagaa aacaatctcc | 1200 |
| aaagccaaag gcagccccg agaaccacag gtgtacaccc tgcccccatc ccgggatgag | 1260 |
| ctgaccaaga accaggtcag cctgacctgc ctggtcaaag gcttctatcc cagcgacatc | 1320 |
| gccgtggagt gggagagcaa tgggcagccg gagaacaact acaagaccac gcctcccgtg | 1380 |
| ctggactccg acggctcctt cttcctctac agcaagctca ccgtggacaa gagcaggtgg | 1440 |
| cagcagggga acgtcttctc atgctccgtg atgcatgagg ctctgcacaa ccactacacg | 1500 |
| cagaagagcc tctccctgtc tccgggtaaa tga | 1533 |

<210> SEQ ID NO 201
<211> LENGTH: 510
<212> TYPE: PRT
<213> ORGANISM: Artificial sequence
<220> FEATURE:
<223> OTHER INFORMATION: 2e12-sss-IgG1 HL SMIP (AA)
<220> FEATURE:
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (24)..(144)
<223> OTHER INFORMATION: VH
<220> FEATURE:
<221> NAME/KEY: misc_feature
<222> LOCATION: (145)..(164)
<223> OTHER INFORMATION: Linker
<220> FEATURE:
<221> NAME/KEY: misc_feature
<222> LOCATION: (165)..(276)
<223> OTHER INFORMATION: VL
<220> FEATURE:
<221> NAME/KEY: misc_feature
<222> LOCATION: (279)..(293)
<223> OTHER INFORMATION: Hinge

<400> SEQUENCE: 201

```
Met Asp Phe Gln Val Gln Ile Phe Ser Phe Leu Leu Ile Ser Ala Ser
1               5                   10                  15

Val Ile Met Ser Arg Gly Val Gln Val Gln Leu Lys Glu Ser Gly Pro
            20                  25                  30

Gly Leu Val Ala Pro Ser Gln Ser Leu Ser Ile Thr Cys Thr Val Ser
        35                  40                  45

Gly Phe Ser Leu Thr Gly Tyr Gly Val Asn Trp Val Arg Gln Pro Pro
    50                  55                  60

Gly Lys Gly Leu Glu Trp Leu Gly Met Ile Trp Gly Asp Gly Ser Thr
65                  70                  75                  80

Asp Tyr Asn Ser Ala Leu Lys Ser Arg Leu Ser Ile Thr Lys Asp Asn
                85                  90                  95
```

```
Ser Lys Ser Gln Val Phe Leu Lys Met Asn Ser Leu Gln Thr Asp Asp
            100                 105                 110

Thr Ala Arg Tyr Tyr Cys Ala Arg Asp Gly Tyr Ser Asn Phe His Tyr
        115                 120                 125

Tyr Val Met Asp Tyr Trp Gly Gln Gly Thr Ser Val Thr Val Ser Ser
    130                 135                 140

Gly Gly Gly Gly Ser Gly Gly Gly Ser Gly Gly Gly Ser Gly
145                 150                 155                 160

Gly Gly Gly Ser Asp Ile Val Leu Thr Gln Ser Pro Ala Ser Leu Ala
            165                 170                 175

Val Ser Leu Gly Gln Arg Ala Thr Ile Ser Cys Arg Ala Ser Glu Ser
        180                 185                 190

Val Glu Tyr Tyr Val Thr Ser Leu Met Gln Trp Tyr Gln Gln Lys Pro
    195                 200                 205

Gly Gln Pro Pro Lys Leu Leu Ile Ser Ala Ala Ser Asn Val Glu Ser
        210                 215                 220

Gly Val Pro Ala Arg Phe Ser Gly Ser Gly Ser Gly Thr Asp Phe Ser
225                 230                 235                 240

Leu Asn Ile His Pro Val Glu Asp Asp Ile Ala Met Tyr Phe Cys
            245                 250                 255

Gln Gln Ser Arg Lys Val Pro Trp Thr Phe Gly Gly Gly Thr Lys Leu
        260                 265                 270

Glu Ile Lys Arg Asp Gln Glu Pro Lys Ser Ser Asp Lys Thr His Thr
    275                 280                 285

Ser Pro Pro Ser Pro Ala Pro Glu Leu Leu Gly Gly Ser Ser Val Phe
        290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
            325                 330                 335

Lys Phe Asn Trp Tyr Val Asp Gly Val Glu Val His Asn Ala Lys Thr
        340                 345                 350

Lys Pro Arg Glu Glu Gln Tyr Asn Ser Thr Tyr Arg Val Val Ser Val
    355                 360                 365

Leu Thr Val Leu His Gln Asp Trp Leu Asn Gly Lys Glu Tyr Lys Cys
370                 375                 380

Lys Val Ser Asn Lys Ala Leu Pro Ala Ser Ile Glu Lys Thr Ile Ser
385                 390                 395                 400

Lys Ala Lys Gly Gln Pro Arg Glu Pro Gln Val Tyr Thr Leu Pro Pro
            405                 410                 415

Ser Arg Asp Glu Leu Thr Lys Asn Gln Val Ser Leu Thr Cys Leu Val
        420                 425                 430

Lys Gly Phe Tyr Pro Ser Asp Ile Ala Val Glu Trp Glu Ser Asn Gly
    435                 440                 445

Gln Pro Glu Asn Asn Tyr Lys Thr Thr Pro Pro Val Leu Asp Ser Asp
        450                 455                 460

Gly Ser Phe Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
            485                 490                 495

Asn His Tyr Thr Gln Lys Ser Leu Ser Leu Ser Pro Gly Lys
        500                 505                 510

<210> SEQ ID NO 202
```

<211> LENGTH: 1518
<212> TYPE: DNA
<213> ORGANISM: Artificial sequence
<220> FEATURE:
<223> OTHER INFORMATION: 2e12-sss-IgG1 LH SMIP (DNA)

<400> SEQUENCE: 202

```
atggattttc aagtgcagat tttcagcttc ctgctaatca gtgcttcagt cataatgtcc      60
agaggagtcg acattgtgct cacccaatct ccagcttctt tggctgtgtc tctaggtcag     120
agagccacca tctcctgcag agccagtgaa agtgttgaat attatgtcac aagtttaatg     180
cagtggtacc aacagaaacc aggacagcca cccaaactcc tcatctctgc tgctagcaac     240
gtagaatctg ggtccctgc caggtttagt ggcagtgggt ctgggacaga ctttagcctc      300
aacatccatc ctgtggagga ggatgatatt gcaatgtatt tctgtcagca aagtaggaag     360
gttccatgga cgttcggtgg aggcaccaag ctggaaatca acggggtgg cggtggatcc      420
ggcggaggtg ggtcggtgg cggcggatct caggtgcagc tgaaggagtc aggacctggc     480
ctggtggcgc cctcacagag cctgtccatc acatgcaccg tctcagggtt ctcattaacc     540
ggctatggtg taaactgggt tcgccagcct ccaggaaagg gtctagagtg ctgggaatg      600
atatggggtg atggaagcac agactataat tcagctctca atccagact atcgatcacc     660
aaggacaact ccaagagcca agttttctta aaaatgaaca gtctgcaaac tgatgacaca     720
gccagatact actgtgctcg agatggttat agtaactttc attactatgt tatggactac     780
tggggtcaag gaacctcagt caccgtctcc tctgatcagg cccaaatc ttctgacaaa      840
actcacacat ccccaccgtc cccagcacct gaactcctgg ggggaccgtc agtcttcctc     900
ttccccccaa acccaagga cacccctcatg atctcccgga cccctgaggt cacatgcgtg     960
gtggtggacg tgagccacga agaccctgag gtcaagttca actggtacgt ggacggcgtg    1020
gaggtgcata atgccaagac aaagccgcgg gaggagcagt acaacagcac gtaccgtgtg    1080
gtcagcgtcc tcaccgtcct gcaccaggac tggctgaatg caaggagta caagtgcaag    1140
gtctccaaca aagccctccc agcccccatc gagaaaacaa tctccaaagc caagggcag   1200
ccccgagaac acaggtgta caccctgccc ccatcccggg atgagctgac caagaaccag    1260
gtcagcctga cctgcctggt caaaggcttc tatcccagcg acatcgccgt ggagtgggag    1320
agcaatgggc agccggagaa caactacaag accacgcctc ccgtgctgga ctccgacggc    1380
tccttcttcc tctacagcaa gctcaccgtg gacaagagca ggtggcagca ggggaacgtc    1440
ttctcatgct ccgtgatgca tgaggctctg cacaaccact acacgcagaa gagcctctcc    1500
ctgtctccgg gtaaatga                                                  1518
```

<210> SEQ ID NO 203
<211> LENGTH: 505
<212> TYPE: PRT
<213> ORGANISM: Artificial sequence
<220> FEATURE:
<223> OTHER INFORMATION: 2e12-sss-IgG1 LH SMIP (AA)
<220> FEATURE:
<221> NAME/KEY: misc_feature
<222> LOCATION: (1)..(23)
<223> OTHER INFORMATION: Leader
<220> FEATURE:
<221> NAME/KEY: misc_feature
<222> LOCATION: (24)..(135)
<223> OTHER INFORMATION: VL
<220> FEATURE:
<221> NAME/KEY: misc_feature
<222> LOCATION: (136)..(150)
<223> OTHER INFORMATION: Linker
<220> FEATURE:

```
<221> NAME/KEY: misc_feature
<222> LOCATION: (151)..(271)
<223> OTHER INFORMATION: VH
<220> FEATURE:
<221> NAME/KEY: misc_feature
<222> LOCATION: (274)..(288)
<223> OTHER INFORMATION: Hinge

<400> SEQUENCE: 203
```

Met Asp Phe Gln Val Gln Ile Phe Ser Phe Leu Leu Ile Ser Ala Ser
1               5                   10                  15

Val Ile Met Ser Arg Gly Val Asp Ile Val Leu Thr Gln Ser Pro Ala
            20                  25                  30

Ser Leu Ala Val Ser Leu Gly Gln Arg Ala Thr Ile Ser Cys Arg Ala
        35                  40                  45

Ser Glu Ser Val Glu Tyr Tyr Val Thr Ser Leu Met Gln Trp Tyr Gln
    50                  55                  60

Gln Lys Pro Gly Gln Pro Pro Lys Leu Leu Ile Ser Ala Ala Ser Asn
65                  70                  75                  80

Val Glu Ser Gly Val Pro Ala Arg Phe Ser Gly Ser Gly Ser Gly Thr
                85                  90                  95

Asp Phe Ser Leu Asn Ile His Pro Val Glu Asp Asp Ile Ala Met
            100                 105                 110

Tyr Phe Cys Gln Gln Ser Arg Lys Val Pro Trp Thr Phe Gly Gly Gly
        115                 120                 125

Thr Lys Leu Glu Ile Lys Arg Gly Gly Gly Ser Gly Gly Gly Gly
    130                 135                 140

Ser Gly Gly Gly Gly Ser Gln Val Gln Leu Lys Glu Ser Gly Pro Gly
145                 150                 155                 160

Leu Val Ala Pro Ser Gln Ser Leu Ser Ile Thr Cys Thr Val Ser Gly
                165                 170                 175

Phe Ser Leu Thr Gly Tyr Gly Val Asn Trp Val Arg Gln Pro Pro Gly
            180                 185                 190

Lys Gly Leu Glu Trp Leu Gly Met Ile Trp Gly Asp Gly Ser Thr Asp
        195                 200                 205

Tyr Asn Ser Ala Leu Lys Ser Arg Leu Ser Ile Thr Lys Asp Asn Ser
    210                 215                 220

Lys Ser Gln Val Phe Leu Lys Met Asn Ser Leu Gln Thr Asp Asp Thr
225                 230                 235                 240

Ala Arg Tyr Tyr Cys Ala Arg Asp Gly Tyr Ser Asn Phe His Tyr Tyr
                245                 250                 255

Val Met Asp Tyr Trp Gly Gln Gly Thr Ser Val Thr Val Ser Ser Asp
            260                 265                 270

Gln Glu Pro Lys Ser Ser Asp Lys Thr His Thr Ser Pro Pro Ser Pro
        275                 280                 285

Ala Pro Glu Leu Leu Gly Gly Pro Ser Val Phe Leu Phe Pro Pro Lys
    290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys

```
                370             375             380
Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Asp Glu Leu
                405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
                435                 440                 445

Tyr Lys Thr Thr Pro Pro Val Leu Asp Ser Asp Gly Ser Phe Phe Leu
            450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys
            500                 505

<210> SEQ ID NO 204
<211> LENGTH: 1498
<212> TYPE: DNA
<213> ORGANISM: Artificial sequence
<220> FEATURE:
<223> OTHER INFORMATION: G28-1 LH SMIP (DNA)

<400> SEQUENCE: 204
aagcttgccg ccatggaagc accagcgcag cttctcttcc tcctgctact ctggctccca      60
gataccaccg tgacatccca gatgactcag tctccagcct ccctatctgc atctgtggga    120
gagactgtca ccatcacatg tcgaacaagt gaaaatgttt acagttattt ggcttggtat    180
cagcagaaac agggaaaatc tcctcagctc ctggtctctt ttgcaaaaac cttagcagaa    240
ggtgtgccat caaggttcag tggcagtgga tcaggcacac agtttctctc tgaagatcagc   300 agcctgcagc ctgaagattc tggaagttat ttctgtcaac atcattccga taatccgtgg    360
acgttcggtg gaggcaccga actggagatc aaaggtggcg gtggctcggg cggtggtggg    420
tcgggtggcg gcggatctgc tagcgcagtc cagctgcagc agtctggacc tgagctggaa    480
aagcctggcg cttcagtgaa gatttcctgc aaggcttctg gttactcatt cactggctac    540
aatatgaact gggtgaagca gaataatgga agagccttg agtggattgg aaatattgat    600
ccttattatg gtggtactac ctacaaccgg aagttcaagg gcaaggccac attgactgta    660
gacaaatcct ccagcacagc ctacatgcag ctcaagagtc tgacatctga ggactctgca    720
gtctattact gtgcaagatc ggtcggccct atggactact ggggtcaagg aacctcagtc    780
accgtctcga gcgagcccaa atcttctgac aaaactcaca catgcccacc gtgcccagca    840
cctgaactcc tggtggaccc gtcagtcttc ctcttccccc caaaacccaa ggacaccctc    900
atgatctccc ggacccctga ggtcacatgc gtggtggtgg acgtgagcca cgaagaccct    960
gaggtcaagt tcaactggta cgtggacggc gtggaggtgc ataatgccaa gacaaagccg   1020
cgggaggagc agtacaacag cacgtaccgt gtggtcagcg tcctcaccgt cctgcaccag   1080
gactggctga atggcaagga gtacaagtgc aaggtctcca acaaagccct cccagccccc   1140
atcgagaaaa ccatctccaa agccaaaggg cagccccgag aaccacaggt gtacaccctg   1200
cccccatccc gggatgagct gaccaagaac caggtcagcc tgacctgcct ggtcaaaggc   1260
ttctatccaa gcgacatcgc cgtggagtgg gagagcaatg ggcagccgga gaacaactac   1320
```

-continued

```
aagaccacgc ctcccgtgct ggactccgac ggctccttct tcctctacag caagctcacc    1380
gtggacaaga gcaggtggca gcagggaac gtcttctcat gctccgtgat gcatgaggct    1440
ctgcacaacc actacacgca gaagagcctc tccctgtctc cgggtaagtg actctaga     1498
```

<210> SEQ ID NO 205
<211> LENGTH: 492
<212> TYPE: PRT
<213> ORGANISM: Artificial sequence
<220> FEATURE:
<223> OTHER INFORMATION: G28-1 LH SMIP (AA)
<220> FEATURE:
<221> NAME/KEY: misc_feature
<222> LOCATION: (1)..(20)
<223> OTHER INFORMATION: Leader
<220> FEATURE:
<221> NAME/KEY: misc_feature
<222> LOCATION: (21)..(127)
<223> OTHER INFORMATION: VL
<220> FEATURE:
<221> NAME/KEY: misc_feature
<222> LOCATION: (128)..(144)
<223> OTHER INFORMATION: Linker
<220> FEATURE:
<221> NAME/KEY: misc_feature
<222> LOCATION: (145)..(260)
<223> OTHER INFORMATION: VH
<220> FEATURE:
<221> NAME/KEY: misc_feature
<222> LOCATION: (261)..(275)
<223> OTHER INFORMATION: Hinge

<400> SEQUENCE: 205

```
Met Glu Ala Pro Ala Gln Leu Leu Phe Leu Leu Leu Leu Trp Leu Pro
1               5                   10                  15

Asp Thr Thr Gly Asp Ile Gln Met Thr Gln Ser Pro Ala Ser Leu Ser
            20                  25                  30

Ala Ser Val Gly Glu Thr Val Thr Ile Thr Cys Arg Thr Ser Glu Asn
        35                  40                  45

Val Tyr Ser Tyr Leu Ala Trp Tyr Gln Gln Lys Gln Gly Lys Ser Pro
    50                  55                  60

Gln Leu Leu Val Ser Phe Ala Lys Thr Leu Ala Glu Gly Val Pro Ser
65                  70                  75                  80

Arg Phe Ser Gly Ser Gly Ser Gly Thr Gln Phe Ser Leu Lys Ile Ser
                85                  90                  95

Ser Leu Gln Pro Glu Asp Ser Gly Ser Tyr Phe Cys Gln His His Ser
            100                 105                 110

Asp Asn Pro Trp Thr Phe Gly Gly Gly Thr Glu Leu Glu Ile Lys Gly
        115                 120                 125

Gly Gly Gly Ser Gly Gly Gly Gly Ser Gly Gly Gly Gly Ser Ala Ser
    130                 135                 140

Ala Val Gln Leu Gln Gln Ser Gly Pro Glu Leu Glu Lys Pro Gly Ala
145                 150                 155                 160

Ser Val Lys Ile Ser Cys Lys Ala Ser Gly Tyr Ser Phe Thr Gly Tyr
                165                 170                 175

Asn Met Asn Trp Val Lys Gln Asn Asn Gly Lys Ser Leu Glu Trp Ile
            180                 185                 190

Gly Asn Ile Asp Pro Tyr Tyr Gly Gly Thr Thr Tyr Asn Arg Lys Phe
        195                 200                 205

Lys Gly Lys Ala Thr Leu Thr Val Asp Lys Ser Ser Ser Thr Ala Tyr
    210                 215                 220

Met Gln Leu Lys Ser Leu Thr Ser Glu Asp Ser Ala Val Tyr Tyr Cys
225                 230                 235                 240
```

```
Ala Arg Ser Val Gly Pro Met Asp Tyr Trp Gly Gln Gly Thr Ser Val
            245                 250                 255

Thr Val Ser Ser Glu Pro Lys Ser Ser Asp Lys Thr His Thr Cys Pro
            260                 265                 270

Pro Cys Pro Ala Pro Glu Leu Leu Gly Gly Pro Ser Val Phe Leu Phe
            275                 280                 285

Pro Pro Lys Pro Lys Asp Thr Leu Met Ile Ser Arg Thr Pro Glu Val
            290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
            325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
            355                 360                 365

Ser Asn Lys Ala Leu Pro Ala Pro Ile Glu Lys Thr Ile Ser Lys Ala
            370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
            405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
            435                 440                 445

Phe Phe Leu Tyr Ser Lys Leu Thr Val Asp Lys Ser Arg Trp Gln Gln
            450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
            485                 490

<210> SEQ ID NO 206
<211> LENGTH: 1522
<212> TYPE: DNA
<213> ORGANISM: Artificial sequence
<220> FEATURE:
<223> OTHER INFORMATION: G28-1 HL SMIP (DNA)

<400> SEQUENCE: 206
aagcttgccg ccatggaagc accagcgcag cttctcttcc tcctgctact ctggctccca      60
gataccaccg gtgcggtcca gctgcagcag tctggacctg agtcggaaaa gcctggcgct     120
tcagtgaaga tttcctgcaa ggcttctggt tactcattca ctggctacaa tatgaactgg     180
gtgaagcaga ataatggaaa gagccttgag tggattggaa atattgatcc ttattatggt     240
ggtactacct acaaccggaa gttcaagggc aaggccacat tgactgtaga caaatcctcc     300
ggcacagcct acatgcagct caagagtctg acatctgagg actctgcagt ctattactgt     360
gcaagatcgg tcggcccta t ggactactgg ggtcaaggaa cctcagtcac cgtctcttct     420
ggtggcggtg gctcgggcgg tggtgggtcg ggtggcggcg gatcaggagg aggcgggagt     480
gctagcgaca tccagatgac tcagtctcca gcctccctat ctgcatctgt gggagagact     540
gtcaccatca catgtcgaac aagtgaaaat gtttacagtt atttggcttg gtatcagcag     600
aaacagggaa aatctcctca gctcctggtc tcttttgcaa aaaccttagc agaaggtgtg     660
```

```
ccatcaaggt tcagtggcag tggatcaggc acacagtttt ctctgaagat cagcagcctg    720
cagcctgaag attctggaag ttatttctgt caacatcatt ccgataatcc gtggacgttc    780
ggtggaggca ccgaactgga gatcaaaggc tcgagcgagc ccaaatcttc tgacaaaact    840
cacacatgcc caccgtgccc agcacctgaa ctcctgggtg gaccgtcagt cttcctcttc    900
cccccaaaac ccaaggacac cctcatgatc tcccggaccc ctgaggtcac atgcgtggtg    960
gtggacgtga gccacgaaga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggagtacaa gtgcaaggtc   1140
tccaacaaag ccctcccagc ccccatcgag aaaaccatct ccaaagccaa agggcagccc   1200
cgagaaccac aggtgtacac cctgccccca tcccgggatg agctgaccaa gaaccaggtc   1260
agcctgacct gcctggtcaa aggcttctat cccagcgaca tcgccgtgga gtgggagagc   1320
aatgggcagc cggagaacaa ctacaagacc acgcctcccg tgctggactc cgacggctcc   1380
ttcttcctct acagcaagct caccgtggac aagagcaggt ggcagcaggg gaacgtcttc   1440
tcatgctccg tgatgcatga ggctctgcac aaccactaca cgcagaagag cctctccctg   1500
tctccgggta agtgactcta ga                                           1522
```

<210> SEQ ID NO 207
<211> LENGTH: 500
<212> TYPE: PRT
<213> ORGANISM: Artificial sequence
<220> FEATURE:
<223> OTHER INFORMATION: G28-1 HL SMIP (AA)
<220> FEATURE:
<221> NAME/KEY: misc_feature
<222> LOCATION: (1)..(20)
<223> OTHER INFORMATION: Leader
<220> FEATURE:
<221> NAME/KEY: misc_feature
<222> LOCATION: (21)..(136)
<223> OTHER INFORMATION: VH
<220> FEATURE:
<221> NAME/KEY: misc_feature
<222> LOCATION: (137)..(158)
<223> OTHER INFORMATION: Linker
<220> FEATURE:
<221> NAME/KEY: misc_feature
<222> LOCATION: (159)..(266)
<223> OTHER INFORMATION: VL
<220> FEATURE:
<221> NAME/KEY: misc_feature
<222> LOCATION: (268)..(283)
<223> OTHER INFORMATION: Hinge

<400> SEQUENCE: 207

Met Glu Ala Pro Ala Gln Leu Leu Phe Leu Leu Leu Leu Trp Leu Pro
1               5                   10                  15

Asp Thr Thr Gly Ala Val Gln Leu Gln Gln Ser Gly Pro Glu Ser Glu
            20                  25                  30

Lys Pro Gly Ala Ser Val Lys Ile Ser Cys Lys Ala Ser Gly Tyr Ser
        35                  40                  45

Phe Thr Gly Tyr Asn Met Asn Trp Val Lys Gln Asn Gly Lys Ser
    50                  55                  60

Leu Glu Trp Ile Gly Asn Ile Asp Pro Tyr Tyr Gly Gly Thr Thr Tyr
65                  70                  75                  80

Asn Arg Lys Phe Lys Gly Lys Ala Thr Leu Thr Val Asp Lys Ser Ser
                85                  90                  95

Gly Thr Ala Tyr Met Gln Leu Lys Ser Leu Thr Ser Glu Asp Ser Ala

-continued

```
                100                 105                 110
Val Tyr Tyr Cys Ala Arg Ser Val Gly Pro Met Asp Tyr Trp Gly Gln
            115                 120                 125
Gly Thr Ser Val Thr Val Ser Ser Gly Gly Gly Gly Ser Gly Gly Gly
        130                 135                 140
Gly Ser Gly Gly Gly Ser Gly Gly Gly Ser Ala Ser Asp Ile
145                 150                 155                 160
Gln Met Thr Gln Ser Pro Ala Ser Leu Ser Ala Ser Val Gly Glu Thr
                165                 170                 175
Val Thr Ile Thr Cys Arg Thr Ser Glu Asn Val Tyr Ser Tyr Leu Ala
            180                 185                 190
Trp Tyr Gln Gln Lys Gln Gly Lys Ser Pro Gln Leu Leu Val Ser Phe
        195                 200                 205
Ala Lys Thr Leu Ala Glu Gly Val Pro Ser Arg Phe Ser Gly Ser Gly
    210                 215                 220
Ser Gly Thr Gln Phe Ser Leu Lys Ile Ser Ser Leu Gln Pro Glu Asp
225                 230                 235                 240
Ser Gly Ser Tyr Phe Cys Gln His His Ser Asp Asn Pro Trp Thr Phe
                245                 250                 255
Gly Gly Gly Thr Glu Leu Glu Ile Lys Gly Ser Ser Glu Pro Lys Ser
            260                 265                 270
Ser Asp Lys Thr His Thr Cys Pro Pro Cys Pro Ala Pro Glu Leu Leu
        275                 280                 285
Gly Gly Pro Ser Val Phe Leu Phe Pro Pro Lys Pro Lys Asp Thr Leu
    290                 295                 300
Met Ile Ser Arg Thr Pro Glu Val Thr Cys Val Val Val Asp Val Ser
305                 310                 315                 320
His Glu Asp Pro Glu Val Lys Phe Asn Trp Tyr Val Asp Gly Val Glu
                325                 330                 335
Val His Asn Ala Lys Thr Lys Pro Arg Glu Glu Gln Tyr Asn Ser Thr
            340                 345                 350
Tyr Arg Val Val Ser Val Leu Thr Val Leu His Gln Asp Trp Leu Asn
        355                 360                 365
Gly Lys Glu Tyr Lys Cys Lys Val Ser Asn Lys Ala Leu Pro Ala Pro
    370                 375                 380
Ile Glu Lys Thr Ile Ser Lys Ala Lys Gly Gln Pro Arg Glu Pro Gln
385                 390                 395                 400
Val Tyr Thr Leu Pro Pro Ser Arg Asp Glu Leu Thr Lys Asn Gln Val
                405                 410                 415
Ser Leu Thr Cys Leu Val Lys Gly Phe Tyr Pro Ser Asp Ile Ala Val
            420                 425                 430
Glu Trp Glu Ser Asn Gly Gln Pro Glu Asn Asn Tyr Lys Thr Thr Pro
        435                 440                 445
Pro Val Leu Asp Ser Asp Gly Ser Phe Phe Leu Tyr Ser Lys Leu Thr
    450                 455                 460
Val Asp Lys Ser Arg Trp Gln Gln Gly Asn Val Phe Ser Cys Ser Val
465                 470                 475                 480
Met His Glu Ala Leu His Asn His Tyr Thr Gln Lys Ser Leu Ser Leu
                485                 490                 495
Ser Pro Gly Lys
            500
```

<210> SEQ ID NO 208
<211> LENGTH: 1522

```
<212> TYPE: DNA
<213> ORGANISM: Artificial sequence
<220> FEATURE:
<223> OTHER INFORMATION: G19-4 LH SMIP (DNA)

<400> SEQUENCE: 208
aagcttgccg ccatggaagc accagcgcag cttctcttcc tcctgctact ctggctccca      60
gataccaccg gtgacatcca gatgacacag actacatcct ccctgtctgc ctctctggga     120
gacagagtca ccatcagttg cagggcaagt caggacattc gcaattattt aaactggtat     180
cagcagaaac cagatggaac tgttaaactc ctgatctact acacatcaag attacactca     240
ggagtcccat caaggttcag tggcagtggg tctggaacag attattctct caccattgcc     300
aacctgcaac cagaagatat tgccacttac ttttgccaac aggtaataca gcttccgtgg     360
acgttcggtg gaggcaccaa actggtaacc aaacggggtg gcgtggctc gggcggtggt      420
ggatctggag gaggtgggag cgctagcgag gtccagctgc aacagtctgg acctgaactg     480
gtgaagcctg gagcttcaat gaagatttcc tgcaaggcct ctggttactc attcactggc     540
tacatcgtga actggctgaa gcagagccat ggaagaacc ttgagtggat tggacttatt      600
aatccataca aggtcttac tacctacaac cagaaattca gggcaaggc cacattaact        660
gtagacaagt catccagcac agcctacatg gagctcctca gtctgacatc tgaagactct     720
gcagtctatt actgtgcaag atctgggtac tatggtgact cggactggta cttcgatgtc     780
tggggcgcag ggaccacggt caccgtctcc tcgagcgagc ccaaatcttc tgacaaaact     840
cacacatgcc caccgtgccc agcacctgaa ctcctgggtg gaccgtcagt cttcctcttc     900
cccccaaaac ccaaggacac cctcatgatc tcccggaccc ctgaggtcac atgcgtggtg     960
gtggacgtga gccacgaaga ccctgaggtc aagttcaact ggtacgtgga cggcgtggag    1020
gtgcataatg ccaagacaaa gccgcgggag gagcagtaca acagcacgta ccgtgtggtc    1080
agcgtcctca ccgtcctgca ccaggactgg ctgaatggca aggagtacaa gtgcaaggtc    1140
tccaacaaag ccctcccagc ccccatcgag aaaaccatct ccaaagccaa agggcagccc    1200
cgagaaccac aggtgtacac cctgccccca tcccgggatg agctgaccaa gaaccaggtc    1260
agcctgacct gcctggtcaa aggcttctat ccaagcgaca tcgccgtgga gtgggagagc    1320
aatgggcagc cggagaacaa ctacaagacc acgcctcccg tgctggactc cgacggctcc    1380
ttcttcctct acagcaagct caccgtggac aagagcaggt ggcagcaggg gaacgtcttc    1440
tcatgctccg tgatgcatga ggctctgcac aaccactaca cgcagaagag cctctccctg    1500
tctccgggta agtgactcta ga                                             1522

<210> SEQ ID NO 209
<211> LENGTH: 500
<212> TYPE: PRT
<213> ORGANISM: Artificial sequence
<220> FEATURE:
<223> OTHER INFORMATION: G19-4 LH SMIP (AA)
<220> FEATURE:
<221> NAME/KEY: misc_feature
<222> LOCATION: (1)..(20)
<223> OTHER INFORMATION: Leader
<220> FEATURE:
<221> NAME/KEY: misc_feature
<222> LOCATION: (21)..(128)
<223> OTHER INFORMATION: VL
<220> FEATURE:
<221> NAME/KEY: misc_feature
<222> LOCATION: (129)..(145)
<223> OTHER INFORMATION: Linker
<220> FEATURE:
<221> NAME/KEY: misc_feature
```

```
<222> LOCATION: (146)..(267)
<223> OTHER INFORMATION: VH
<220> FEATURE:
<221> NAME/KEY: misc_feature
<222> LOCATION: (268)..(282)
<223> OTHER INFORMATION: Hinge

<400> SEQUENCE: 209
```

| Met | Glu | Ala | Pro | Ala | Gln | Leu | Leu | Phe | Leu | Leu | Leu | Trp | Leu | Pro |
|---|---|---|---|---|---|---|---|---|---|---|---|---|---|---|
| 1 | | | | 5 | | | | | 10 | | | | | 15 |

| Asp | Thr | Thr | Gly | Asp | Ile | Gln | Met | Thr | Gln | Thr | Ser | Ser | Leu | Ser |
|---|---|---|---|---|---|---|---|---|---|---|---|---|---|---|
| | | | 20 | | | | | 25 | | | | | 30 | |

| Ala | Ser | Leu | Gly | Asp | Arg | Val | Thr | Ile | Ser | Cys | Arg | Ala | Ser | Gln | Asp |
|---|---|---|---|---|---|---|---|---|---|---|---|---|---|---|---|
| | | 35 | | | | | 40 | | | | | 45 | | | |

| Ile | Arg | Asn | Tyr | Leu | Asn | Trp | Tyr | Gln | Gln | Lys | Pro | Asp | Gly | Thr | Val |
|---|---|---|---|---|---|---|---|---|---|---|---|---|---|---|---|
| 50 | | | | | 55 | | | | | 60 | | | | | |

| Lys | Leu | Leu | Ile | Tyr | Tyr | Thr | Ser | Arg | Leu | His | Ser | Gly | Val | Pro | Ser |
|---|---|---|---|---|---|---|---|---|---|---|---|---|---|---|---|
| 65 | | | | | 70 | | | | | 75 | | | | | 80 |

| Arg | Phe | Ser | Gly | Ser | Gly | Ser | Gly | Thr | Asp | Tyr | Ser | Leu | Thr | Ile | Ala |
|---|---|---|---|---|---|---|---|---|---|---|---|---|---|---|---|
| | | | | 85 | | | | | 90 | | | | | 95 | |

| Asn | Leu | Gln | Pro | Glu | Asp | Ile | Ala | Thr | Tyr | Phe | Cys | Gln | Gln | Gly | Asn |
|---|---|---|---|---|---|---|---|---|---|---|---|---|---|---|---|
| | | | 100 | | | | | 105 | | | | | 110 | | |

| Thr | Leu | Pro | Trp | Thr | Phe | Gly | Gly | Gly | Thr | Lys | Leu | Val | Thr | Lys | Arg |
|---|---|---|---|---|---|---|---|---|---|---|---|---|---|---|---|
| | | 115 | | | | | 120 | | | | | 125 | | | |

| Gly | Gly | Gly | Gly | Ser | Gly | Gly | Gly | Gly | Ser | Gly | Gly | Gly | Ser | Ala |
|---|---|---|---|---|---|---|---|---|---|---|---|---|---|---|
| 130 | | | | | 135 | | | | | 140 | | | | |

| Ser | Glu | Val | Gln | Leu | Gln | Gln | Ser | Gly | Pro | Glu | Leu | Val | Lys | Pro | Gly |
|---|---|---|---|---|---|---|---|---|---|---|---|---|---|---|---|
| 145 | | | | | 150 | | | | | 155 | | | | | 160 |

| Ala | Ser | Met | Lys | Ile | Ser | Cys | Lys | Ala | Ser | Gly | Tyr | Ser | Phe | Thr | Gly |
|---|---|---|---|---|---|---|---|---|---|---|---|---|---|---|---|
| | | | 165 | | | | | 170 | | | | | 175 | | |

| Tyr | Ile | Val | Asn | Trp | Leu | Lys | Gln | Ser | His | Gly | Lys | Asn | Leu | Glu | Trp |
|---|---|---|---|---|---|---|---|---|---|---|---|---|---|---|---|
| | | | 180 | | | | | 185 | | | | | 190 | | |

| Ile | Gly | Leu | Ile | Asn | Pro | Tyr | Lys | Gly | Leu | Thr | Thr | Tyr | Asn | Gln | Lys |
|---|---|---|---|---|---|---|---|---|---|---|---|---|---|---|---|
| | | | 195 | | | | | 200 | | | | | 205 | | |

| Phe | Lys | Gly | Lys | Ala | Thr | Leu | Thr | Val | Asp | Lys | Ser | Ser | Ser | Thr | Ala |
|---|---|---|---|---|---|---|---|---|---|---|---|---|---|---|---|
| 210 | | | | | 215 | | | | | 220 | | | | | |

| Tyr | Met | Glu | Leu | Leu | Ser | Leu | Thr | Ser | Glu | Asp | Ser | Ala | Val | Tyr | Tyr |
|---|---|---|---|---|---|---|---|---|---|---|---|---|---|---|---|
| 225 | | | | | 230 | | | | | 235 | | | | | 240 |

| Cys | Ala | Arg | Ser | Gly | Tyr | Tyr | Gly | Asp | Ser | Asp | Trp | Tyr | Phe | Asp | Val |
|---|---|---|---|---|---|---|---|---|---|---|---|---|---|---|---|
| | | | 245 | | | | | 250 | | | | | 255 | | |

| Trp | Gly | Ala | Gly | Thr | Thr | Val | Thr | Val | Ser | Ser | Ser | Glu | Pro | Lys | Ser |
|---|---|---|---|---|---|---|---|---|---|---|---|---|---|---|---|
| | | | 260 | | | | | 265 | | | | | 270 | | |

| Ser | Asp | Lys | Thr | His | Thr | Cys | Pro | Pro | Cys | Pro | Ala | Pro | Glu | Leu | Leu |
|---|---|---|---|---|---|---|---|---|---|---|---|---|---|---|---|
| | 275 | | | | | 280 | | | | | 285 | | | | |

| Gly | Gly | Pro | Ser | Val | Phe | Leu | Phe | Pro | Pro | Lys | Pro | Lys | Asp | Thr | Leu |
|---|---|---|---|---|---|---|---|---|---|---|---|---|---|---|---|
| | 290 | | | | | 295 | | | | | 300 | | | | |

| Met | Ile | Ser | Arg | Thr | Pro | Glu | Val | Thr | Cys | Val | Val | Val | Asp | Val | Ser |
|---|---|---|---|---|---|---|---|---|---|---|---|---|---|---|---|
| 305 | | | | | 310 | | | | | 315 | | | | | 320 |

| His | Glu | Asp | Pro | Glu | Val | Lys | Phe | Asn | Trp | Tyr | Val | Asp | Gly | Val | Glu |
|---|---|---|---|---|---|---|---|---|---|---|---|---|---|---|---|
| | | | 325 | | | | | 330 | | | | | 335 | | |

| Val | His | Asn | Ala | Lys | Thr | Lys | Pro | Arg | Glu | Glu | Gln | Tyr | Asn | Ser | Thr |
|---|---|---|---|---|---|---|---|---|---|---|---|---|---|---|---|
| | | | 340 | | | | | 345 | | | | | 350 | | |

| Tyr | Arg | Val | Val | Ser | Val | Leu | Thr | Val | Leu | His | Gln | Asp | Trp | Leu | Asn |
|---|---|---|---|---|---|---|---|---|---|---|---|---|---|---|---|
| | | 355 | | | | | 360 | | | | | 365 | | | |

| Gly | Lys | Glu | Tyr | Lys | Cys | Lys | Val | Ser | Asn | Lys | Ala | Leu | Pro | Ala | Pro |
|---|---|---|---|---|---|---|---|---|---|---|---|---|---|---|---|
| | 370 | | | | | 375 | | | | | 380 | | | | |

```
Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
            405                 410                 415

Ser Leu Thr Cys Leu Val Lys Gly Phe Tyr Pro Ser Asp Ile Ala Val
        420                 425                 430

Glu Trp Glu Ser Asn Gly Gln Pro Glu Asn Asn Tyr Lys Thr Thr Pro
            435                 440                 445

Pro Val Leu Asp Ser Asp Gly Ser Phe Phe Leu Tyr Ser Lys Leu Thr
        450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
            485                 490                 495

Ser Pro Gly Lys
            500

<210> SEQ ID NO 210
<211> LENGTH: 1525
<212> TYPE: DNA
<213> ORGANISM: Artificial sequence
<220> FEATURE:
<223> OTHER INFORMATION: G19-4 HL SMIP (DNA)

<400> SEQUENCE: 210
aagcttgccg ccatggaagc accagcgcag cttctcttcc tcctgctact ctggctccca     60
gataccaccg gtgaggtcca gctgcaacag tctggacctg aactggtgaa gcctggagct    120
tcaatgaaga tttcctgcaa ggcctctggt tactcattca ctggctacat cgtgaactgg    180
ctgaagcaga gccatggaaa gaaccttgag tggattggac ttattaatcc atacaaaggt    240
cttactacct acaaccagaa attcaagggc aaggccacat tgactgtaga caagtcatcc    300
agcacagcct acatggagct cctcagtctg acatctgaag actctgcagt ctattactgt    360
gcaagatctg gtactatgg tgactcagac tggtacttcg atgtctgggg cgcagggacc    420
acagtcaccg tctcctctgg cggcggtggc tcgggcggtg gtggatctgg aggaggtggg    480
agcgctagcg acatccagat gacacagact acatcctccc tgtctgcctc tctgggagac    540
agagtcacca tcagttgcag ggcaagtcag gacattcgca attatttgaa ctggtatcag    600
cagaaaccag atggaactgt taaactcctg atctactaca tcaagactt acactcagga    660 gtcccatcaa ggttcagtgg cagtgggtct ggaacagatt attctctcac cattgccaac    720
ctgcaaccag aagatattgc cacttacttt tgccaacagg gtaatacact tcccctggacg    780 ttcggtggag ggaccaaact ggtgaccaaa cgctcgagcg agcccaaatc ttctgacaaa    840
actcacacat gcccaccgtg cccagcacct gaactcctgg gtggaccgtc agtcttcctc    900
ttccccccaa aacccaagga caccctcatg atctcccgga cccctgaggt cacatgcgtg    960
gtggtggacg tgagccacga agaccctgag gtcaagttca actggtacgt ggacggcgtg   1020
gaggtgcata atgccaagac aaagccgcgg gaggagcagt acaacagcac gtaccgtgtg   1080
gtcagcgtcc tcaccgtcct gcaccaggac tggctgaatg gcaaggagta caagtgcaag   1140
gtctccaaca aagccctccc agcccccatc gagaaaacca tctccaaagc caagggcag    1200 ccccgagaac cacaggtgta caccctgccc ccatcccggg atgagctgac caagaaccag   1260
gtcagcctga cctgcctggt caaaggcttc tatccaagcg acatcgccgt ggagtgggag   1320
agcaatgggc agccggagaa caactacaag accacgcctc ccgtgctgga ctccgacggc   1380
```

-continued

```
tccttcttcc tctacagcaa gctcaccgtg gacaagagca ggtggcagca ggggaacgtc    1440
ttctcatgct ccgtgatgca tgaggctctg cacaaccact acacgcagaa gagcctctcc    1500
ctgtctccgg gtaagtgact ctaga                                         1525

<210> SEQ ID NO 211
<211> LENGTH: 501
<212> TYPE: PRT
<213> ORGANISM: Artificial sequence
<220> FEATURE:
<223> OTHER INFORMATION: G19-4 HL SMIP (AA)
<220> FEATURE:
<221> NAME/KEY: misc_feature
<222> LOCATION: (1)..(20)
<223> OTHER INFORMATION: Leader
<220> FEATURE:
<221> NAME/KEY: misc_feature
<222> LOCATION: (21)..(142)
<223> OTHER INFORMATION: VH
<220> FEATURE:
<221> NAME/KEY: misc_feature
<222> LOCATION: (143)..(159)
<223> OTHER INFORMATION: Linker
<220> FEATURE:
<221> NAME/KEY: misc_feature
<222> LOCATION: (160)..(267)
<223> OTHER INFORMATION: VL
<220> FEATURE:
<221> NAME/KEY: misc_feature
<222> LOCATION: (270)..(284)
<223> OTHER INFORMATION: Hinge

<400> SEQUENCE: 211

Met Glu Ala Pro Ala Gln Leu Leu Phe Leu Leu Leu Leu Trp Leu Pro
1               5                   10                  15

Asp Thr Thr Gly Glu Val Gln Leu Gln Gln Ser Gly Pro Glu Leu Val
            20                  25                  30

Lys Pro Gly Ala Ser Met Lys Ile Ser Cys Lys Ala Ser Gly Tyr Ser
        35                  40                  45

Phe Thr Gly Tyr Ile Val Asn Trp Leu Lys Gln Ser His Gly Lys Asn
    50                  55                  60

Leu Glu Trp Ile Gly Leu Ile Asn Pro Tyr Lys Gly Leu Thr Thr Tyr
65                  70                  75                  80

Asn Gln Lys Phe Lys Gly Lys Ala Thr Leu Thr Val Asp Lys Ser Ser
                85                  90                  95

Ser Thr Ala Tyr Met Glu Leu Leu Ser Leu Thr Ser Glu Asp Ser Ala
            100                 105                 110

Val Tyr Tyr Cys Ala Arg Ser Gly Tyr Tyr Gly Asp Ser Asp Trp Tyr
        115                 120                 125

Phe Asp Val Trp Gly Ala Gly Thr Thr Val Thr Val Ser Ser Gly Gly
    130                 135                 140

Gly Gly Ser Gly Gly Gly Gly Ser Gly Gly Gly Ser Ala Ser Asp
145                 150                 155                 160

Ile Gln Met Thr Gln Thr Thr Ser Ser Leu Ser Ala Ser Leu Gly Asp
                165                 170                 175

Arg Val Thr Ile Ser Cys Arg Ala Ser Gln Asp Ile Arg Asn Tyr Leu
            180                 185                 190

Asn Trp Tyr Gln Gln Lys Pro Asp Gly Thr Val Lys Leu Leu Ile Tyr
        195                 200                 205

Tyr Thr Ser Arg Leu His Ser Gly Val Pro Ser Arg Phe Ser Gly Ser
    210                 215                 220

Gly Ser Gly Thr Asp Tyr Ser Leu Thr Ile Ala Asn Leu Gln Pro Glu
```

```
                225                 230                 235                 240
Asp Ile Ala Thr Tyr Phe Cys Gln Gln Gly Asn Thr Leu Pro Trp Thr
                    245                 250                 255
Phe Gly Gly Gly Thr Lys Leu Val Thr Lys Arg Ser Ser Glu Pro Lys
                    260                 265                 270
Ser Ser Asp Lys Thr His Thr Cys Pro Pro Cys Pro Ala Pro Glu Leu
                275                 280                 285
Leu Gly Gly Pro Ser Val Phe Leu Phe Pro Pro Lys Pro Lys Asp Thr
            290                 295                 300
Leu Met Ile Ser Arg Thr Pro Glu Val Thr Cys Val Val Val Asp Val
305                 310                 315                 320
Ser His Glu Asp Pro Glu Val Lys Phe Asn Trp Tyr Val Asp Gly Val
                325                 330                 335
Glu Val His Asn Ala Lys Thr Lys Pro Arg Glu Glu Gln Tyr Asn Ser
                340                 345                 350
Thr Tyr Arg Val Val Ser Val Leu Thr Val Leu His Gln Asp Trp Leu
            355                 360                 365
Asn Gly Lys Glu Tyr Lys Cys Lys Val Ser Asn Lys Ala Leu Pro Ala
        370                 375                 380
Pro Ile Glu Lys Thr Ile Ser Lys Ala Lys Gly Gln Pro Arg Glu Pro
385                 390                 395                 400
Gln Val Tyr Thr Leu Pro Pro Ser Arg Asp Glu Leu Thr Lys Asn Gln
                405                 410                 415
Val Ser Leu Thr Cys Leu Val Lys Gly Phe Tyr Pro Ser Asp Ile Ala
                420                 425                 430
Val Glu Trp Glu Ser Asn Gly Gln Pro Glu Asn Asn Tyr Lys Thr Thr
            435                 440                 445
Pro Pro Val Leu Asp Ser Asp Gly Ser Phe Phe Leu Tyr Ser Lys Leu
        450                 455                 460
Thr Val Asp Lys Ser Arg Trp Gln Gln Gly Asn Val Phe Ser Cys Ser
465                 470                 475                 480
Val Met His Glu Ala Leu His Asn His Tyr Thr Gln Lys Ser Leu Ser
                485                 490                 495
Leu Ser Pro Gly Lys
            500

<210> SEQ ID NO 212
<211> LENGTH: 2328
<212> TYPE: DNA
<213> ORGANISM: Artificial sequence
<220> FEATURE:
<223> OTHER INFORMATION: n2H7sssIgG1-STD1-2e12HL (DNA)

<400> SEQUENCE: 212
aagcttgccg ccatggaagc accagcgcag cttctcttcc tcctgctact ctggctccca      60
gataccaccg gtcaaattgt tctctcccag tctccagcaa tcctgtctgc atctccaggg     120
gagaaggtca caatgacttg cagggccagc tcaagtgtaa gttacatgca ctggtaccag     180
cagaagccag atcctccccc aaaccctgga tttatgccc  atccaacct ggcttctgga     240 gtccctgctc gcttcagtgg cagtgggtct gggacctctt actctctcac aatcagcaga     300
gtggaggctg aagatgctgc cacttattac tgccagcagt ggagtttaa cccacccacg     360 ttcggtgctg ggaccaagct ggagctgaaa gatggcggtg gctcgggcgg tggtggatct     420
ggaggaggtg gagctagcca ggcttatcta cagcagtctg ggctgagct ggtgaggcct     480 ggggcctcag tgaagatgtc ctgcaaggct tctggctaca catttaccag ttacaatatg     540
```

```
cactgggtaa agcagacacc tagacagggc ctggaatgga ttggagctat ttatccagga      600
aatggtgata cttcctacaa tcagaagttc aagggcaagg ccacactgac tgtagacaaa      660
tcctccagca cagcctacat gcagctcagc agcctgacat ctgaagactc tgcggtctat      720
ttctgtgcaa gagtggtgta ctatagtaac tcttactggt acttcgatgt ctggggcaca      780
gggaccacgg tcaccgtctc gagcgagccc aaatcttctg acaaaactca cacatcccca      840
ccgagcccag cacctgaact cctgggggga ccgtcagtct tcctcttccc cccaaaaccc      900
aaggacaccc tcatgatctc ccggacccct gaggtcacat gcgtggtggt ggacgtgagc      960
cacgaagacc ctgaggtcaa gttcaactgg tacgtggacg gcgtggaggt gcataatgcc     1020
aagacaaagc cgcgggagga gcagtacaac agcacgtacc gtgtggtcag cgtcctcacc     1080
gtcctgcacc aggactggct gaatggcaag gagtacaagt gcaaggtctc caacaaagcc     1140
ctcccagccc ccatcgagaa aacaatctcc aaagccaaag ggcagccccg agaaccacag     1200
gtgtacaccc tgcccccatc ccgggatgag ctgaccaaga accaggtcag cctgacctgc     1260
ctggtcaaag gcttctatcc cagcgacatc gccgtggagt gggagagcaa tgggcagccg     1320
gagaacaact acaagaccac gcctcccgtg ctggactccg acggctcctt cttcctctac     1380
agcaagctca ccgtggacaa gagcaggtgg cagcagggga acgtcttctc atgctccgtg     1440
atgcatgagg ctctgcacaa ccactacacg cagaagagcc tctccctgtc tccgggtaag     1500
aattatggtg gcggtggctc gggcggtggt ggatctggag gaggtgggag tgggaattct     1560
caggtgcagc tgaaggagtc aggacctggc ctggtggcgc cctcacagag cctgtccatc     1620
acatgcaccg tctcagggtt ctcattaacc ggctatggtg taaactgggt tcgccagcct     1680
ccaggaaagg gtctggagtg gctgggaatg atatggggtg atggaagcac agactataat     1740
tcagctctca atccagact atcgatcacc aaggacaact ccaagagcca gttttcttta     1800
aaaatgaaca gtctgcaaac tgatgacaca gccagatact actgtgctcg agatggttat     1860
agtaactttc attactatgt tatggactac tggggtcaag gaacctcagt caccgtctcc     1920 tctggggtg gaggctctgg tggcggtgga tccggcggag gtgggtcggg tggcggcgga     1980
tctgacattg tgctcaccca atctccagct tctttggctg tgtctctagg tcagagagcc     2040
accatctcct gcagagccag tgaaagtgtt gaatattatg tcacaagttt aatgcagtgg     2100
taccaacaga aaccaggaca gccacccaaa ctcctcatct ctgctgctag caacgtagaa     2160
tctggggtcc ctgccaggtt tagtggcagt gggtctggga cagactttag cctcaacatc     2220
catcctgtgg aggaggatga tattgcaatg tatttctgtc agcaaagtag gaaggttcca     2280
tggacgttcg gtggaggcac caagctggaa atcaaacgtt aatctaga                 2328
```

```
<210> SEQ ID NO 213
<211> LENGTH: 769
<212> TYPE: PRT
<213> ORGANISM: Artificial sequence
<220> FEATURE:
<223> OTHER INFORMATION: n2H7sssIgG1-STD1-2e12HL (AA)
<220> FEATURE:
<221> NAME/KEY: misc_feature
<222> LOCATION: (1)..(20)
<223> OTHER INFORMATION: Leader
<220> FEATURE:
<221> NAME/KEY: misc_feature
<222> LOCATION: (21)..(127)
<223> OTHER INFORMATION: VL
<220> FEATURE:
<221> NAME/KEY: misc_feature
<222> LOCATION: (128)..(142)
<223> OTHER INFORMATION: Linker
```

-continued

```
<220> FEATURE:
<221> NAME/KEY: misc_feature
<222> LOCATION: (143)..(264)
<223> OTHER INFORMATION: VH
<220> FEATURE:
<221> NAME/KEY: misc_feature
<222> LOCATION: (265)..(279)
<223> OTHER INFORMATION: Hinge
<220> FEATURE:
<221> NAME/KEY: misc_feature
<222> LOCATION: (497)..(516)
<223> OTHER INFORMATION: EFD-BD2 Linker
<220> FEATURE:
<221> NAME/KEY: misc_feature
<222> LOCATION: (517)..(637)
<223> OTHER INFORMATION: VH2
<220> FEATURE:
<221> NAME/KEY: misc_feature
<222> LOCATION: (638)..(657)
<223> OTHER INFORMATION: Linker2
<220> FEATURE:
<221> NAME/KEY: misc_feature
<222> LOCATION: (658)..(769)
<223> OTHER INFORMATION: VL2

<400> SEQUENCE: 213

Met Glu Ala Pro Ala Gln Leu Leu Phe Leu Leu Leu Trp Leu Pro
1               5                   10                  15

Asp Thr Thr Gly Gln Ile Val Leu Ser Gln Ser Pro Ala Ile Leu Ser
            20                  25                  30

Ala Ser Pro Gly Glu Lys Val Thr Met Thr Cys Arg Ala Ser Ser Ser
        35                  40                  45

Val Ser Tyr Met His Trp Tyr Gln Gln Lys Pro Gly Ser Ser Pro Lys
    50                  55                  60

Pro Trp Ile Tyr Ala Pro Ser Asn Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

Val Glu Ala Glu Asp Ala Ala Thr Tyr Tyr Cys Gln Gln Trp Ser Phe
            100                 105                 110

Asn Pro Pro Thr Phe Gly Ala Gly Thr Lys Leu Glu Leu Lys Asp Gly
        115                 120                 125

Gly Gly Ser Gly Gly Gly Ser Gly Gly Gly Ala Ser Gln Ala
    130                 135                 140

Tyr Leu Gln Gln Ser Gly Ala Glu Leu Val Arg Pro Gly Ala Ser Val
145                 150                 155                 160

Lys Met Ser Cys Lys Ala Ser Gly Tyr Thr Phe Thr Ser Tyr Asn Met
                165                 170                 175

His Trp Val Lys Gln Thr Pro Arg Gln Gly Leu Glu Trp Ile Gly Ala
            180                 185                 190

Ile Tyr Pro Gly Asn Gly Asp Thr Ser Tyr Asn Gln Lys Phe Lys Gly
        195                 200                 205

Lys Ala Thr Leu Thr Val Asp Lys Ser Ser Ser Thr Ala Tyr Met Gln
    210                 215                 220

Leu Ser Ser Leu Thr Ser Glu Asp Ser Ala Val Tyr Phe Cys Ala Arg
225                 230                 235                 240

Val Val Tyr Tyr Ser Asn Ser Tyr Trp Tyr Phe Asp Val Trp Gly Thr
                245                 250                 255

Gly Thr Thr Val Thr Val Ser Ser Glu Pro Lys Ser Ser Asp Lys Thr
            260                 265                 270

His Thr Ser Pro Pro Ser Pro Ala Pro Glu Leu Leu Gly Gly Pro Ser
        275                 280                 285
```

```
Val Phe Leu Phe Pro Pro Lys Pro Lys Asp Thr Leu Met Ile Ser Arg
    290                 295                 300
Thr Pro Glu Val Thr Cys Val Val Val Asp Val Ser His Glu Asp Pro
305                 310                 315                 320
Glu Val Lys Phe Asn Trp Tyr Val Asp Gly Val Glu Val His Asn Ala
                325                 330                 335
Lys Thr Lys Pro Arg Glu Glu Gln Tyr Asn Ser Thr Tyr Arg Val Val
                340                 345                 350
Ser Val Leu Thr Val Leu His Gln Asp Trp Leu Asn Gly Lys Glu Tyr
                355                 360                 365
Lys Cys Lys Val Ser Asn Lys Ala Leu Pro Ala Pro Ile Glu Lys Thr
    370                 375                 380
Ile Ser Lys Ala Lys Gly Gln Pro Arg Glu Pro Gln Val Tyr Thr Leu
385                 390                 395                 400
Pro Pro Ser Arg Asp Glu Leu Thr Lys Asn Gln Val Ser Leu Thr Cys
                405                 410                 415
Leu Val Lys Gly Phe Tyr Pro Ser Asp Ile Ala Val Glu Trp Glu Ser
                420                 425                 430
Asn Gly Gln Pro Glu Asn Asn Tyr Lys Thr Thr Pro Pro Val Leu Asp
    435                 440                 445
Ser Asp Gly Ser Phe Phe Leu Tyr Ser Lys Leu Thr Val Asp Lys Ser
450                 455                 460
Arg Trp Gln Gln Gly Asn Val Phe Ser Cys Ser Val Met His Glu Ala
465                 470                 475                 480
Leu His Asn His Tyr Thr Gln Lys Ser Leu Ser Leu Ser Pro Gly Lys
                485                 490                 495
Asn Tyr Gly Gly Gly Ser Gly Gly Gly Ser Gly Gly Gly Gly Gly Gly
                500                 505                 510
Ser Gly Asn Ser Gln Val Gln Leu Lys Glu Ser Gly Pro Gly Leu Val
    515                 520                 525
Ala Pro Ser Gln Ser Leu Ser Ile Thr Cys Thr Val Ser Gly Phe Ser
530                 535                 540
Leu Thr Gly Tyr Gly Val Asn Trp Val Arg Gln Pro Pro Gly Lys Gly
545                 550                 555                 560
Leu Glu Trp Leu Gly Met Ile Trp Gly Asp Gly Ser Thr Asp Tyr Asn
                565                 570                 575
Ser Ala Leu Lys Ser Arg Leu Ser Ile Thr Lys Asp Asn Ser Lys Ser
                580                 585                 590
Gln Val Phe Leu Lys Met Asn Ser Leu Gln Thr Asp Asp Thr Ala Arg
    595                 600                 605
Tyr Tyr Cys Ala Arg Asp Gly Tyr Ser Asn Phe His Tyr Tyr Val Met
    610                 615                 620
Asp Tyr Trp Gly Gln Gly Thr Ser Val Thr Val Ser Ser Gly Gly Gly
625                 630                 635                 640
Gly Ser Gly Gly Gly Gly Ser Gly Gly Gly Gly Ser Gly Gly Gly Gly
                645                 650                 655
Ser Asp Ile Val Leu Thr Gln Ser Pro Ala Ser Leu Ala Val Ser Leu
                660                 665                 670
Gly Gln Arg Ala Thr Ile Ser Cys Arg Ala Ser Glu Ser Val Glu Tyr
    675                 680                 685
Tyr Val Thr Ser Leu Met Gln Trp Tyr Gln Gln Lys Pro Gly Gln Pro
    690                 695                 700
Pro Lys Leu Leu Ile Ser Ala Ala Ser Asn Val Glu Ser Gly Val Pro
```

```
                705                 710                 715                 720
Ala Arg Phe Ser Gly Ser Gly Ser Gly Thr Asp Phe Ser Leu Asn Ile
                    725                 730                 735

His Pro Val Glu Glu Asp Asp Ile Ala Met Tyr Phe Cys Gln Gln Ser
                740                 745                 750

Arg Lys Val Pro Trp Thr Phe Gly Gly Gly Thr Lys Leu Glu Ile Lys
            755                 760                 765

Arg

<210> SEQ ID NO 214
<211> LENGTH: 2313
<212> TYPE: DNA
<213> ORGANISM: Artificial sequence
<220> FEATURE:
<223> OTHER INFORMATION: n2H7sssIgG1-STD2-2e12LH (DNA)

<400> SEQUENCE: 214
```

| | | | | |
|---|---|---|---|---|
| aagcttgccg | ccatggaagc | accagcgcag | cttctcttcc | tcctgctact | ctggctccca |   60 |
| gataccaccg | gtcaaattgt | tctctcccag | tctccagcaa | tcctgtctgc | atctccaggg |  120 |
| gagaaggtca | atgacttg | cagggccagc | tcaagtgtaa | gttacatgca | ctggtaccag |  180 |
| cagaagccag | gatcctcccc | caaaccctgg | atttatgccc | atccaacct | ggcttctgga |  240 |
| gtccctgctc | gcttcagtgg | cagtgggtct | gggacctctt | actctctcac | aatcagcaga |  300 |
| gtggaggctg | aagatgctgc | cacttattac | tgccagcagt | ggagttttaa | cccacccacg |  360 |
| ttcggtgctg | ggaccaagct | ggagctgaaa | gatggcggtg | gctcgggcgg | tggtggatct |  420 |
| ggaggaggtg | gagctagcca | ggcttatcta | cagcagtctg | ggctgagct | ggtgaggcct |  480 |
| ggggcctcag | tgaagatgtc | ctgcaaggct | tctggctaca | catttaccag | ttacaatatg |  540 |
| cactgggtaa | agcagacacc | tagacagggc | ctggaatgga | ttggagctat | ttatccagga |  600 |
| aatggtgata | cttcctacaa | tcagaagttc | aagggcaagg | ccacactgac | tgtagacaaa |  660 |
| tcctccagca | cagcctacat | gcagctcagc | agcctgacat | ctgaagactc | tgcggtctat |  720 |
| ttctgtgcaa | gagtggtgta | ctatagtaac | tcttactggt | acttcgatgt | ctggggcaca |  780 |
| gggaccacgg | tcaccgtctc | gagcgagccc | aaatcttctg | acaaaactca | cacatcccca |  840 |
| ccgagcccag | cacctgaact | cctgggggga | ccgtcagtct | tcctcttccc | cccaaaaccc |  900 |
| aaggacaccc | tcatgatctc | ccggaccct | gaggtcacat | gcgtggtggt | ggacgtgagc |  960 |
| cacgaagacc | ctgaggtcaa | gttcaactgg | tacgtggacg | gcgtggaggt | gcataatgcc | 1020 |
| aagacaaagc | cgcgggagga | gcagtacaac | agcacgtacc | gtgtggtcag | cgtcctcacc | 1080 |
| gtcctgcacc | aggactggct | gaatggcaag | gagtacaagt | gcaaggtctc | caacaaagcc | 1140 |
| ctcccagccc | ccatcgagaa | aacaatctcc | aaagccaaag | ggcagccccg | agaaccacag | 1200 |
| gtgtacaccc | tgcccccatc | ccgggatgag | ctgaccaaga | accaggtcag | cctgacctgc | 1260 |
| ctggtcaaag | gcttctatcc | cagcgacatc | gccgtggagt | gggagagcaa | tgggcagccg | 1320 |
| gagaacaact | acaagaccac | gcctcccgtg | ctggactccg | acggctcctt | cttcctctac | 1380 |
| agcaagctca | ccgtggacaa | gagcaggtgg | cagcagggga | acgtcttctc | atgctccgtg | 1440 |
| atgcatgagg | ctctgcacaa | ccactacacg | cagaagagcc | tctccctgtc | tccgggtaag | 1500 |
| aattatggtg | gcggtggctc | gggcggtggt | ggatctggag | gaggtgggag | tgggaattct | 1560 |
| gacattgtgc | tcacccaatc | tccagcttct | ttggctgtgt | ctctaggtca | gagagccacc | 1620 |
| atctcctgca | gagccagtga | aagtgttgaa | tattatgtca | caagttttaat | gcagtggtac | 1680 |
| caacagaaac | caggacagcc | acccaaactc | ctcatctctg | ctgctagcaa | cgtagaatct | 1740 |

-continued

```
ggggtccctg ccaggtttag tggcagtggg tctgggacag actttagcct caacatccat   1800
cctgtggagg aggatgatat tgcaatgtat ttctgtcagc aaagtaggaa ggttccatgg   1860
acgttcggtg gaggcaccaa gctgaaaatc aaacggggtg gcggtggatc cggcggaggt   1920
gggtcgggtg gcggcggatc tcaggtgcag ctgaaggagt caggacctgg cctggtggcg   1980
ccctcacaga gcctgtccat cacatgcacc gtctcaggtt tctcattaac cggctatggt   2040
gtaaactggg ttcgccagcc tccaggaaag gtctggagt ggctgggaat gatatggggt    2100
gatggaagca cagactataa ttcagctctc aaatccagac tatcgatcac caaggacaac   2160
tccaagagcc aagttttctt aaaaatgaac agtctgcaaa ctgatgacac agccagatac   2220
tactgtgctc gagatggtta tagtaacttt cattactatg ttatggacta ctggggtcaa   2280
ggaacctcag tcaccgtctc ctcttaatct aga                                2313
```

<210> SEQ ID NO 215
<211> LENGTH: 764
<212> TYPE: PRT
<213> ORGANISM: Artificial sequence
<220> FEATURE:
<223> OTHER INFORMATION: n2H7sssIgG1-STD2-2e12LH (AA)
<220> FEATURE:
<221> NAME/KEY: misc_feature
<222> LOCATION: (1)..(20)
<223> OTHER INFORMATION: Leader
<220> FEATURE:
<221> NAME/KEY: misc_feature
<222> LOCATION: (21)..(126)
<223> OTHER INFORMATION: VL
<220> FEATURE:
<221> NAME/KEY: misc_feature
<222> LOCATION: (127)..(142)
<223> OTHER INFORMATION: Linker
<220> FEATURE:
<221> NAME/KEY: misc_feature
<222> LOCATION: (143)..(264)
<223> OTHER INFORMATION: VH
<220> FEATURE:
<221> NAME/KEY: misc_feature
<222> LOCATION: (265)..(279)
<223> OTHER INFORMATION: Hinge
<220> FEATURE:
<221> NAME/KEY: misc_feature
<222> LOCATION: (497)..(516)
<223> OTHER INFORMATION: EFD-BD2 Linker
<220> FEATURE:
<221> NAME/KEY: misc_feature
<222> LOCATION: (517)..(628)
<223> OTHER INFORMATION: VL2
<220> FEATURE:
<221> NAME/KEY: misc_feature
<222> LOCATION: (629)..(643)
<223> OTHER INFORMATION: Linker
<220> FEATURE:
<221> NAME/KEY: misc_feature
<222> LOCATION: (644)..(764)
<223> OTHER INFORMATION: VH2

<400> SEQUENCE: 215

```
Met Glu Ala Pro Ala Gln Leu Leu Phe Leu Leu Leu Leu Trp Leu Pro
1               5                   10                  15

Asp Thr Thr Gly Gln Ile Val Leu Ser Gln Ser Pro Ala Ile Leu Ser
                20                  25                  30

Ala Ser Pro Gly Glu Lys Val Thr Met Thr Cys Arg Ala Ser Ser Ser
            35                  40                  45

Val Ser Tyr Met His Trp Tyr Gln Gln Lys Pro Gly Ser Ser Pro Lys
        50                  55                  60

Pro Trp Ile Tyr Ala Pro Ser Asn Leu Ala Ser Gly Val Pro Ala Arg
```

-continued

```
                65                  70                  75                  80
            Phe Ser Gly Ser Gly Ser Gly Thr Ser Tyr Ser Leu Thr Ile Ser Arg
                            85                  90                  95

Val Glu Ala Glu Asp Ala Ala Thr Tyr Tyr Cys Gln Gln Trp Ser Phe
                        100                 105                 110

Asn Pro Pro Thr Phe Gly Ala Gly Thr Lys Leu Glu Leu Lys Asp Gly
                        115                 120                 125

Gly Gly Ser Gly Gly Gly Ser Gly Gly Gly Ala Ser Gln Ala
                        130                 135                 140

Tyr Leu Gln Gln Ser Gly Ala Glu Leu Val Arg Pro Gly Ala Ser Val
            145                 150                 155                 160

Lys Met Ser Cys Lys Ala Ser Gly Tyr Thr Phe Thr Ser Tyr Asn Met
                            165                 170                 175

His Trp Val Lys Gln Thr Pro Arg Gln Gly Leu Glu Trp Ile Gly Ala
                        180                 185                 190

Ile Tyr Pro Gly Asn Gly Asp Thr Ser Tyr Asn Gln Lys Phe Lys Gly
                        195                 200                 205

Lys Ala Thr Leu Thr Val Asp Lys Ser Ser Thr Ala Tyr Met Gln
            210                 215                 220

Leu Ser Ser Leu Thr Ser Glu Asp Ser Ala Val Tyr Phe Cys Ala Arg
            225                 230                 235                 240

Val Val Tyr Tyr Ser Asn Ser Tyr Trp Tyr Phe Asp Val Trp Gly Thr
                            245                 250                 255

Gly Thr Thr Val Thr Val Ser Ser Glu Pro Lys Ser Ser Asp Lys Thr
                        260                 265                 270

His Thr Ser Pro Pro Ser Pro Ala Pro Glu Leu Leu Gly Gly Pro Ser
                        275                 280                 285

Val Phe Leu Phe Pro Pro Lys Pro Lys Asp Thr Leu Met Ile Ser Arg
                        290                 295                 300

Thr Pro Glu Val Thr Cys Val Val Val Asp Val Ser His Glu Asp Pro
            305                 310                 315                 320

Glu Val Lys Phe Asn Trp Tyr Val Asp Gly Val Glu Val His Asn Ala
                            325                 330                 335

Lys Thr Lys Pro Arg Glu Glu Gln Tyr Asn Ser Thr Tyr Arg Val Val
                        340                 345                 350

Ser Val Leu Thr Val Leu His Gln Asp Trp Leu Asn Gly Lys Glu Tyr
                        355                 360                 365

Lys Cys Lys Val Ser Asn Lys Ala Leu Pro Ala Pro Ile Glu Lys Thr
                        370                 375                 380

Ile Ser Lys Ala Lys Gly Gln Pro Arg Glu Pro Gln Val Tyr Thr Leu
            385                 390                 395                 400

Pro Pro Ser Arg Asp Glu Leu Thr Lys Asn Gln Val Ser Leu Thr Cys
                            405                 410                 415

Leu Val Lys Gly Phe Tyr Pro Ser Asp Ile Ala Val Glu Trp Glu Ser
                        420                 425                 430

Asn Gly Gln Pro Glu Asn Asn Tyr Lys Thr Thr Pro Pro Val Leu Asp
                        435                 440                 445

Ser Asp Gly Ser Phe Phe Leu Tyr Ser Lys Leu Thr Val Asp Lys Ser
                        450                 455                 460

Arg Trp Gln Gln Gly Asn Val Phe Ser Cys Ser Val Met His Glu Ala
            465                 470                 475                 480

Leu His Asn His Tyr Thr Gln Lys Ser Leu Ser Leu Ser Pro Gly Lys
                            485                 490                 495
```

-continued

Asn Tyr Gly Gly Gly Ser Gly Gly Gly Ser Gly Gly Gly
            500                 505                 510
Ser Gly Asn Ser Asp Ile Val Leu Thr Gln Ser Pro Ala Ser Leu Ala
        515                 520                 525
Val Ser Leu Gly Gln Arg Ala Thr Ile Ser Cys Arg Ala Ser Glu Ser
    530                 535                 540
Val Glu Tyr Tyr Val Thr Ser Leu Met Gln Trp Tyr Gln Gln Lys Pro
545                 550                 555                 560
Gly Gln Pro Pro Lys Leu Leu Ile Ser Ala Ala Ser Asn Val Glu Ser
                565                 570                 575
Gly Val Pro Ala Arg Phe Ser Gly Ser Gly Ser Gly Thr Asp Phe Ser
            580                 585                 590
Leu Asn Ile His Pro Val Glu Glu Asp Asp Ile Ala Met Tyr Phe Cys
        595                 600                 605
Gln Gln Ser Arg Lys Val Pro Trp Thr Phe Gly Gly Gly Thr Lys Leu
    610                 615                 620
Glu Ile Lys Arg Gly Gly Gly Gly Ser Gly Gly Gly Gly Ser Gly Gly
625                 630                 635                 640
Gly Gly Ser Gln Val Gln Leu Lys Glu Ser Gly Pro Gly Leu Val Ala
                645                 650                 655
Pro Ser Gln Ser Leu Ser Ile Thr Cys Thr Val Ser Gly Phe Ser Leu
            660                 665                 670
Thr Gly Tyr Gly Val Asn Trp Val Arg Gln Pro Pro Gly Lys Gly Leu
        675                 680                 685
Glu Trp Leu Gly Met Ile Trp Gly Asp Gly Ser Thr Asp Tyr Asn Ser
    690                 695                 700
Ala Leu Lys Ser Arg Leu Ser Ile Thr Lys Asp Asn Ser Lys Ser Gln
705                 710                 715                 720
Val Phe Leu Lys Met Asn Ser Leu Gln Thr Asp Asp Thr Ala Arg Tyr
                725                 730                 735
Tyr Cys Ala Arg Asp Gly Tyr Ser Asn Phe His Tyr Tyr Val Met Asp
            740                 745                 750
Tyr Trp Gly Gln Gly Thr Ser Val Thr Val Ser Ser
        755                 760

<210> SEQ ID NO 216
<211> LENGTH: 2048
<212> TYPE: DNA
<213> ORGANISM: Artificial sequence
<220> FEATURE:
<223> OTHER INFORMATION: n2H7sssIgG1-H1-2e12HL (DNA)

<400> SEQUENCE: 216
aagcttgccg ccatggaagc accagcgcag cttctcttcc tcctgctact ctggctccca    60
gataccaccg tcaaattgt tctctcccag tctccagcaa tcctgtctgc atctccaggg    120
gagaaggtca caatgacttg cagggccagc tcaagtgtaa gttacatgca ctggtaccag    180
cagaagccag gatcctcccc caaaccctgg atttatgccc catccaacct ggcttctgga    240
gtccctgctc gcttcagtgg cagtgggtct gggacctctt actctctcac aatcagcaga    300
gtggaggctg aagatgctgc cacttattac tgccagcagt ggagttttaa cccacccacg    360
ttcggtgctg ggaccaagct ggagctgaaa atggcggtg ctcgggcgg tggtggatct    420 ggaggaggtg gagctagcca ggcttatcta cagcagtctg ggctgagct ggtgaggcct    480 ggggcctcag tgaagatgtc ctgcaaggct tctggctaca catttaccag ttacaatatg    540
cactgggtaa agcagacacc tagacagggc ctggaatgga ttggagctat ttatccagga    600

```
aatggtgata cttcctacaa tcagaagttc aagggcaagg ccacactgac tgtagacaaa    660
tcctccagca cagcctacat gcagctcagc agcctgacat ctgaagactc tgcggtctat    720
ttctgtgcaa gagtggtgta ctatagtaac tcttactggt acttcgatgt ctggggcaca    780
gggaccacgg tcaccgtctc gagcgagccc aaatcttctg acaaaactca cacatcccca    840
ccgagcccag cacctgaact cctgggggga ccgtcagtct tcctcttccc cccaaaaccc    900
aaggacaccc tcatgatctc ccggacccct gaggtcacat gcgtggtggt ggacgtgagc    960
cacgaagacc ctgaggtcaa gttcaactgg tacgtggacg gcgtggaggt gcataatgcc   1020
aagacaaagc cgcgggagga gcagtacaac agcacgtacc gtgtggtcag cgtcctcacc   1080
gtcctgcacc aggactggct gaatggcaag gagtacaagt gcaaggtctc caacaaagcc   1140
ctcccagccc ccatcgagaa aacaatctcc aaagccaaag gcagccccg agaaccacag    1200 gtgtacaccc tgcccccatc ccgggatgag ctgaccaaga accaggtcag cctgacctgc   1260
ctggtcaaag gcttctatcc cagcgacatc gccgtggagt gggagagcaa tgggcagccg   1320
gagaacaact acaagaccac gcctcccgtg ctggactccg acggctcctt cttcctctac   1380
agcaagctca ccgtggacaa gagcaggtgg cagcagggga acgtcttctc atgctccgtg   1440
atgcatgagg ctctgcacaa ccactacacg cagaagagcc tctccctgtc tccgggtaag   1500
aattctcagg tgcagctgaa ggagtcagga cctggcctgg tggcgccctc acagagcctg   1560
tccatcacat gcaccgtctc agggttctca ttaaccggct atggtgtaaa ctgggttcgc   1620
cagcctccag gaaagggtct ggagtggctg gaatgatat ggggtgatgg aagcacagac   1680
tataattcag ctctcaaatc cagactatcg atcaccaagg acaactccaa gagccaagtt   1740
ttcttaaaaa tgaacagtct gcaaactgat gacacagcca gatactactg tgctcgagat   1800
ggttatagta actttcatta ctatgttatg gactactggg gtcaaggaac ctcagtcacc   1860
gtctcctctg ggggtggagg ctctggtggc ggtggatccg gcggaggtgg gtcgggtggc   1920
ggcggatctg acattgtgct cacccaatct ccagcttctt tggctgtgtc tctaggtcag   1980
agagccacca tctcctgcag agccagtgaa agtgttgaat attatgtcac aagtttaatg   2040
cagtggta                                                          2048
```

<210> SEQ ID NO 217
<211> LENGTH: 751
<212> TYPE: PRT
<213> ORGANISM: Artificial sequence
<220> FEATURE:
<223> OTHER INFORMATION: n2H7sssIgG1-H1-2e12HL (AA)
<220> FEATURE:
<221> NAME/KEY: misc_feature
<222> LOCATION: (1)..(20)
<223> OTHER INFORMATION: Leader
<220> FEATURE:
<221> NAME/KEY: misc_feature
<222> LOCATION: (21)..(126)
<223> OTHER INFORMATION: VL
<220> FEATURE:
<221> NAME/KEY: misc_feature
<222> LOCATION: (127)..(142)
<223> OTHER INFORMATION: Linker
<220> FEATURE:
<221> NAME/KEY: misc_feature
<222> LOCATION: (143)..(264)
<223> OTHER INFORMATION: VH
<220> FEATURE:
<221> NAME/KEY: misc_feature
<222> LOCATION: (265)..(279)
<223> OTHER INFORMATION: Hinge
<220> FEATURE:
<221> NAME/KEY: misc_feature

```
<222> LOCATION: (497)..(498)
<223> OTHER INFORMATION: EFD-BD2 Linker
<220> FEATURE:
<221> NAME/KEY: misc_feature
<222> LOCATION: (499)..(619)
<223> OTHER INFORMATION: VH2
<220> FEATURE:
<221> NAME/KEY: misc_feature
<222> LOCATION: (620)..(639)
<223> OTHER INFORMATION: Linker2
<220> FEATURE:
<221> NAME/KEY: misc_feature
<222> LOCATION: (640)..(751)
<223> OTHER INFORMATION: VL2

<400> SEQUENCE: 217
```

| | | | | | | | | | | | | | | |
|---|---|---|---|---|---|---|---|---|---|---|---|---|---|---|
| Met | Glu | Ala | Pro | Ala | Gln | Leu | Leu | Phe | Leu | Leu | Leu | Trp | Leu | Pro |
| 1 | | | | 5 | | | | | 10 | | | | | 15 |
| Asp | Thr | Thr | Gly | Gln | Ile | Val | Leu | Ser | Gln | Ser | Pro | Ala | Ile | Leu | Ser |
| | | | 20 | | | | | 25 | | | | | 30 | | |
| Ala | Ser | Pro | Gly | Glu | Lys | Val | Thr | Met | Thr | Cys | Arg | Ala | Ser | Ser | Ser |
| | | 35 | | | | | 40 | | | | | 45 | | | |
| Val | Ser | Tyr | Met | His | Trp | Tyr | Gln | Gln | Lys | Pro | Gly | Ser | Ser | Pro | Lys |
| | 50 | | | | | 55 | | | | | 60 | | | | |
| Pro | Trp | Ile | Tyr | Ala | Pro | Ser | Asn | Leu | Ala | Ser | Gly | Val | Pro | Ala | Arg |
| 65 | | | | | 70 | | | | | 75 | | | | | 80 |
| Phe | Ser | Gly | Ser | Gly | Ser | Gly | Thr | Ser | Tyr | Ser | Leu | Thr | Ile | Ser | Arg |
| | | | | 85 | | | | | 90 | | | | | 95 | |
| Val | Glu | Ala | Glu | Asp | Ala | Ala | Thr | Tyr | Tyr | Cys | Gln | Gln | Trp | Ser | Phe |
| | | | 100 | | | | | 105 | | | | | 110 | | |
| Asn | Pro | Pro | Thr | Phe | Gly | Ala | Gly | Thr | Lys | Leu | Glu | Leu | Lys | Asp | Gly |
| | | 115 | | | | | 120 | | | | | 125 | | | |
| Gly | Gly | Ser | Gly | Gly | Gly | Ser | Gly | Gly | Gly | Ala | Ser | Gln | Ala |
| | 130 | | | | | 135 | | | | | 140 | | | |
| Tyr | Leu | Gln | Gln | Ser | Gly | Ala | Glu | Leu | Val | Arg | Pro | Gly | Ala | Ser | Val |
| 145 | | | | | 150 | | | | | 155 | | | | | 160 |
| Lys | Met | Ser | Cys | Lys | Ala | Ser | Gly | Tyr | Thr | Phe | Thr | Ser | Tyr | Asn | Met |
| | | | | 165 | | | | | 170 | | | | | 175 | |
| His | Trp | Val | Lys | Gln | Thr | Pro | Arg | Gln | Gly | Leu | Glu | Trp | Ile | Gly | Ala |
| | | | 180 | | | | | 185 | | | | | 190 | | |
| Ile | Tyr | Pro | Gly | Asn | Gly | Asp | Thr | Ser | Tyr | Asn | Gln | Lys | Phe | Lys | Gly |
| | | 195 | | | | | 200 | | | | | 205 | | | |
| Lys | Ala | Thr | Leu | Thr | Val | Asp | Lys | Ser | Ser | Thr | Ala | Tyr | Met | Gln |
| | 210 | | | | | 215 | | | | | 220 | | | |
| Leu | Ser | Ser | Leu | Thr | Ser | Glu | Asp | Ser | Ala | Val | Tyr | Phe | Cys | Ala | Arg |
| 225 | | | | | 230 | | | | | 235 | | | | | 240 |
| Val | Val | Tyr | Tyr | Ser | Asn | Ser | Tyr | Trp | Tyr | Phe | Asp | Val | Trp | Gly | Thr |
| | | | | 245 | | | | | 250 | | | | | 255 | |
| Gly | Thr | Thr | Val | Thr | Val | Ser | Ser | Glu | Pro | Lys | Ser | Ser | Asp | Lys | Thr |
| | | | 260 | | | | | 265 | | | | | 270 | | |
| His | Thr | Ser | Pro | Pro | Ser | Pro | Ala | Pro | Glu | Leu | Leu | Gly | Gly | Pro | Ser |
| | | 275 | | | | | 280 | | | | | 285 | | | |
| Val | Phe | Leu | Phe | Pro | Pro | Lys | Pro | Lys | Asp | Thr | Leu | Met | Ile | Ser | Arg |
| | 290 | | | | | 295 | | | | | 300 | | | | |
| Thr | Pro | Glu | Val | Thr | Cys | Val | Val | Val | Asp | Val | Ser | His | Glu | Asp | Pro |
| 305 | | | | | 310 | | | | | 315 | | | | | 320 |
| Glu | Val | Lys | Phe | Asn | Trp | Tyr | Val | Asp | Gly | Val | Glu | Val | His | Asn | Ala |
| | | | | 325 | | | | | 330 | | | | | 335 | |

-continued

Lys Thr Lys Pro Arg Glu Glu Gln Tyr Asn Ser Thr Tyr Arg Val Val
                340                 345                 350

Ser Val Leu Thr Val Leu His Gln Asp Trp Leu Asn Gly Lys Glu Tyr
                355                 360                 365

Lys Cys Lys Val Ser Asn Lys Ala Leu Pro Ala Pro Ile Glu Lys Thr
                370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
                420                 425                 430

Asn Gly Gln Pro Glu Asn Asn Tyr Lys Thr Thr Pro Pro Val Leu Asp
                435                 440                 445

Ser Asp Gly Ser Phe Phe Leu Tyr Ser Lys Leu Thr Val Asp Lys Ser
                450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

Asn Ser Gln Val Gln Leu Lys Glu Ser Gly Pro Gly Leu Val Ala Pro
                500                 505                 510

Ser Gln Ser Leu Ser Ile Thr Cys Thr Val Ser Gly Phe Ser Leu Thr
                515                 520                 525

Gly Tyr Gly Val Asn Trp Val Arg Gln Pro Pro Gly Lys Gly Leu Glu
                530                 535                 540

Trp Leu Gly Met Ile Trp Gly Asp Gly Ser Thr Asp Tyr Asn Ser Ala
545                 550                 555                 560

Leu Lys Ser Arg Leu Ser Ile Thr Lys Asp Asn Ser Lys Ser Gln Val
                565                 570                 575

Phe Leu Lys Met Asn Ser Leu Gln Thr Asp Asp Thr Ala Arg Tyr Tyr
                580                 585                 590

Cys Ala Arg Asp Gly Tyr Ser Asn Phe His Tyr Tyr Val Met Asp Tyr
                595                 600                 605

Trp Gly Gln Gly Thr Ser Val Thr Val Ser Ser Gly Gly Gly Gly Ser
610                 615                 620

Gly Gly Gly Gly Ser Gly Gly Gly Ser Gly Gly Gly Gly Ser Asp
625                 630                 635                 640

Ile Val Leu Thr Gln Ser Pro Ala Ser Leu Ala Val Ser Leu Gly Gln
                645                 650                 655

Arg Ala Thr Ile Ser Cys Arg Ala Ser Glu Ser Val Glu Tyr Tyr Val
                660                 665                 670

Thr Ser Leu Met Gln Trp Tyr Gln Gln Lys Pro Gly Gln Pro Pro Lys
                675                 680                 685

Leu Leu Ile Ser Ala Ala Ser Asn Val Glu Ser Gly Val Pro Ala Arg
                690                 695                 700

Phe Ser Gly Ser Gly Ser Gly Thr Asp Phe Ser Leu Asn Ile His Pro
705                 710                 715                 720

Val Glu Glu Asp Asp Ile Ala Met Tyr Phe Cys Gln Gln Ser Arg Lys
                725                 730                 735

Val Pro Trp Thr Phe Gly Gly Gly Thr Lys Leu Glu Ile Lys Arg
                740                 745                 750

<210> SEQ ID NO 218

<211> LENGTH: 2292
<212> TYPE: DNA
<213> ORGANISM: Artificial sequence
<220> FEATURE:
<223> OTHER INFORMATION: n2H7sssIgG1-H2-2e12HL (DNA)

<400> SEQUENCE: 218

```
aagcttgccg ccatggaagc accagcgcag cttctcttcc tcctgctact ctggctccca      60
gataccaccg gtcaaattgt tctctcccag tctccagcaa tcctgtctgc atctccaggg     120
gagaaggtca caatgacttg cagggccagc tcaagtgtaa gttacatgca ctggtaccag     180
cagaagccag gatcctcccc caaaccctgg atttatgccc atccaacct ggcttctgga      240
gtccctgctc gcttcagtgg cagtgggtct gggacctctt actctctcac aatcagcaga     300
gtggaggctg aagatgctgc cacttattac tgccagcagt ggagttttaa cccacccacg     360
ttcggtgctg ggaccaagct ggagctgaaa gatggcggtg gctcgggcgg tggtggatct     420
ggaggaggtg gagctagcca ggcttatcta cagcagtctg ggctgagct ggtgaggcct      480
ggggcctcag tgaagatgtc ctgcaaggct tctggctaca catttaccag ttacaatatg     540
cactgggtaa agcagacacc tagacagggc ctggaatgga ttggagctat ttatccagga     600
aatggtgata cttcctacaa tcagaagttc aagggcaagg ccacactgac tgtagacaaa     660
tcctccagca cagcctacat gcagctcagc agcctgacat ctgaagactc tgcggtctat     720
ttctgtgcaa gagtggtgta ctatagtaac tcttactggt acttcgatgt ctggggcaca     780
gggaccacgg tcaccgtctc gagcgagccc aaatcttctg acaaaactca cacatcccca     840
ccgagcccag cacctgaact cctgggggga ccgtcagtct tcctcttccc cccaaaaccc     900
aaggacaccc tcatgatctc ccggaccct gaggtcacat gcgtggtggt ggacgtgagc      960
cacgaagacc ctgaggtcaa gttcaactgg tacgtggacg gcgtggaggt gcataatgcc    1020
aagacaaagc cgcgggagga gcagtacaac agcacgtacc gtgtggtcag cgtcctcacc    1080
gtcctgcacc aggactggct gaatggcaag gagtacaagt gcaaggtctc caacaaagcc    1140
ctcccagccc ccatcgagaa aacaatctcc aaagccaaag gcagccccg agaaccacag     1200
gtgtacaccc tgcccccatc ccgggatgag ctgaccaaga accaggtcag cctgacctgc    1260
ctggtcaaag gcttctatcc cagcgacatc gccgtggagt gggagagcaa tgggcagccg    1320
gagaacaact acaagaccac gcctcccgtg ctggactccg acggctcctt cttcctctac    1380
agcaagctca ccgtggacaa gagcaggtgg cagcagggga acgtcttctc atgctccgtg    1440
atgcatgagg ctctgcacaa ccactacacg cagaagagcc tctccctgtc tccgggtaag    1500
ggtggcggtg gctcggggaa ttctcaggtg cagctgaagg agtcaggacc tggcctggtg    1560
gcgcccTcac agagcctgtc catcacatgc accgtctcag ggtctcatt aaccggctat    1620
ggtgtaaact gggttcgcca gcctccagga aagggtctgg agtggctggg aatgatatgg    1680
ggtgatggaa gcacagacta taattcagct ctcaaatcca gactatcgat caccaaggac    1740
aactccaaga gccaagtttt cttaaaaatg aacagtctgc aaactgatga cacagccaga    1800
tactactgtg ctcgagatgg ttatagtaac tttcattact atgttatgga ctactgggt    1860
caaggaacct cagtcaccgt ctcctctggg ggtggaggct ctggtggcgg tggatccggc    1920
ggaggtgggt cgggtggcgg cggatctgac attgtgctca cccaatctcc agcttctttg    1980
gctgtgtctc taggtcagag agccaccatc tcctgcagag ccagtgaaag tgttgaatat    2040
tatgtcacaa gtttaatgca gtggtaccaa cagaaaccag acagccacc caaactcctc    2100
atctctgctg ctagcaacgt agaatctggg gtccctgcca ggtttagtgg cagtgggtct    2160
```

-continued

```
gggacagact ttagcctcaa catccatcct gtggaggagg atgatattgc aatgtatttc    2220
tgtcagcaaa gtaggaaggt tccatggacg ttcggtggag gcaccaagct ggaaatcaaa    2280
cgttaatcta ga                                                        2292
```

```
<210> SEQ ID NO 219
<211> LENGTH: 757
<212> TYPE: PRT
<213> ORGANISM: Artificial sequence
<220> FEATURE:
<223> OTHER INFORMATION: n2H7sssIgG1-H2-2e12HL (AA)
<220> FEATURE:
<221> NAME/KEY: misc_feature
<222> LOCATION: (1)..(20)
<223> OTHER INFORMATION: Leader
<220> FEATURE:
<221> NAME/KEY: misc_feature
<222> LOCATION: (21)..(126)
<223> OTHER INFORMATION: VL
<220> FEATURE:
<221> NAME/KEY: misc_feature
<222> LOCATION: (127)..(142)
<223> OTHER INFORMATION: Linker
<220> FEATURE:
<221> NAME/KEY: misc_feature
<222> LOCATION: (143)..(264)
<223> OTHER INFORMATION: VH
<220> FEATURE:
<221> NAME/KEY: misc_feature
<222> LOCATION: (265)..(279)
<223> OTHER INFORMATION: Hinge
<220> FEATURE:
<221> NAME/KEY: misc_feature
<222> LOCATION: (497)..(504)
<223> OTHER INFORMATION: EFD-BD2 Linker
<220> FEATURE:
<221> NAME/KEY: misc_feature
<222> LOCATION: (505)..(625)
<223> OTHER INFORMATION: VH2
<220> FEATURE:
<221> NAME/KEY: misc_feature
<222> LOCATION: (626)..(645)
<223> OTHER INFORMATION: Linker2
<220> FEATURE:
<221> NAME/KEY: misc_feature
<222> LOCATION: (646)..(757)
<223> OTHER INFORMATION: VL2

<400> SEQUENCE: 219
```

```
Met Glu Ala Pro Ala Gln Leu Leu Phe Leu Leu Leu Leu Trp Leu Pro
1               5                   10                  15

Asp Thr Thr Gly Gln Ile Val Leu Ser Gln Ser Pro Ala Ile Leu Ser
            20                  25                  30

Ala Ser Pro Gly Glu Lys Val Thr Met Thr Cys Arg Ala Ser Ser Ser
        35                  40                  45

Val Ser Tyr Met His Trp Tyr Gln Gln Lys Pro Gly Ser Ser Pro Lys
    50                  55                  60

Pro Trp Ile Tyr Ala Pro Ser Asn Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

Val Glu Ala Glu Asp Ala Ala Thr Tyr Tyr Cys Gln Gln Trp Ser Phe
            100                 105                 110

Asn Pro Pro Thr Phe Gly Ala Gly Thr Lys Leu Glu Leu Lys Asp Gly
        115                 120                 125

Gly Gly Ser Gly Gly Gly Gly Ser Gly Gly Gly Gly Ala Ser Gln Ala
    130                 135                 140

Tyr Leu Gln Gln Ser Gly Ala Glu Leu Val Arg Pro Gly Ala Ser Val
```

```
                145                 150                 155                 160
        Lys Met Ser Cys Lys Ala Ser Gly Tyr Thr Phe Thr Ser Tyr Asn Met
                        165                 170                 175

His Trp Val Lys Gln Thr Pro Arg Gln Gly Leu Glu Trp Ile Gly Ala
                        180                 185                 190

Ile Tyr Pro Gly Asn Gly Asp Thr Ser Tyr Asn Gln Lys Phe Lys Gly
                        195                 200                 205

Lys Ala Thr Leu Thr Val Asp Lys Ser Ser Thr Ala Tyr Met Gln
        210                 215                 220

Leu Ser Ser Leu Thr Ser Glu Asp Ser Ala Val Tyr Phe Cys Ala Arg
        225                 230                 235                 240

Val Val Tyr Tyr Ser Asn Ser Tyr Trp Tyr Phe Asp Val Trp Gly Thr
                        245                 250                 255

Gly Thr Thr Val Thr Val Ser Ser Glu Pro Lys Ser Ser Asp Lys Thr
                        260                 265                 270

His Thr Ser Pro Pro Ser Pro Ala Pro Glu Leu Leu Gly Gly Pro Ser
                        275                 280                 285

Val Phe Leu Phe Pro Pro Lys Pro Lys Asp Thr Leu Met Ile Ser Arg
        290                 295                 300

Thr Pro Glu Val Thr Cys Val Val Val Asp Val Ser His Glu Asp Pro
        305                 310                 315                 320

Glu Val Lys Phe Asn Trp Tyr Val Asp Gly Val Glu Val His Asn Ala
                        325                 330                 335

Lys Thr Lys Pro Arg Glu Glu Gln Tyr Asn Ser Thr Tyr Arg Val Val
                        340                 345                 350

Ser Val Leu Thr Val Leu His Gln Asp Trp Leu Asn Gly Lys Glu Tyr
                        355                 360                 365

Lys Cys Lys Val Ser Asn Lys Ala Leu Pro Ala Pro Ile Glu Lys Thr
        370                 375                 380

Ile Ser Lys Ala Lys Gly Gln Pro Arg Glu Pro Gln Val Tyr Thr Leu
        385                 390                 395                 400

Pro Pro Ser Arg Asp Glu Leu Thr Lys Asn Gln Val Ser Leu Thr Cys
                        405                 410                 415

Leu Val Lys Gly Phe Tyr Pro Ser Asp Ile Ala Val Glu Trp Glu Ser
                        420                 425                 430

Asn Gly Gln Pro Glu Asn Asn Tyr Lys Thr Thr Pro Pro Val Leu Asp
                        435                 440                 445

Ser Asp Gly Ser Phe Phe Leu Tyr Ser Lys Leu Thr Val Asp Lys Ser
        450                 455                 460

Arg Trp Gln Gln Gly Asn Val Phe Ser Cys Ser Val Met His Glu Ala
        465                 470                 475                 480

Leu His Asn His Tyr Thr Gln Lys Ser Leu Ser Leu Ser Pro Gly Lys
                        485                 490                 495

Gly Gly Gly Gly Ser Asn Ser Gln Val Gln Leu Lys Glu Ser Gly
                        500                 505                 510

Pro Gly Leu Val Ala Pro Ser Gln Ser Leu Ser Ile Thr Cys Thr Val
                        515                 520                 525

Ser Gly Phe Ser Leu Thr Gly Tyr Gly Val Asn Trp Val Arg Gln Pro
        530                 535                 540

Pro Gly Lys Gly Leu Glu Trp Leu Gly Met Ile Trp Gly Asp Gly Ser
        545                 550                 555                 560

Thr Asp Tyr Asn Ser Ala Leu Lys Ser Arg Leu Ser Ile Thr Lys Asp
                        565                 570                 575
```

```
Asn Ser Lys Ser Gln Val Phe Leu Lys Met Asn Ser Leu Gln Thr Asp
            580                 585                 590
Asp Thr Ala Arg Tyr Tyr Cys Ala Arg Asp Gly Tyr Ser Asn Phe His
        595                 600                 605
Tyr Tyr Val Met Asp Tyr Trp Gly Gln Gly Thr Ser Val Thr Val Ser
    610                 615                 620
Ser Gly Gly Gly Ser Gly Gly Gly Ser Gly Gly Gly Ser
625                 630                 635                 640
Gly Gly Gly Gly Ser Asp Ile Val Leu Thr Gln Ser Pro Ala Ser Leu
                645                 650                 655
Ala Val Ser Leu Gly Gln Arg Ala Thr Ile Ser Cys Arg Ala Ser Glu
            660                 665                 670
Ser Val Glu Tyr Tyr Val Thr Ser Leu Met Gln Trp Tyr Gln Gln Lys
        675                 680                 685
Pro Gly Gln Pro Pro Lys Leu Leu Ile Ser Ala Ser Asn Val Glu
    690                 695                 700
Ser Gly Val Pro Ala Arg Phe Ser Gly Ser Gly Ser Gly Thr Asp Phe
705                 710                 715                 720
Ser Leu Asn Ile His Pro Val Glu Glu Asp Asp Ile Ala Met Tyr Phe
                725                 730                 735
Cys Gln Gln Ser Arg Lys Val Pro Trp Thr Phe Gly Gly Gly Thr Lys
            740                 745                 750
Leu Glu Ile Lys Arg
        755
```

<210> SEQ ID NO 220
<211> LENGTH: 2298
<212> TYPE: DNA
<213> ORGANISM: Artificial sequence
<220> FEATURE:
<223> OTHER INFORMATION: n2H7sssIgG1-H3-2e12HL (DNA)

<400> SEQUENCE: 220

```
aagcttgccg ccatggaagc accagcgcag cttctcttcc tcctgctact ctggctccca    60
gataccaccg gtcaaattgt tctctcccag tctccagcaa tcctgtctgc atctccaggg   120
gagaaggtca caatgacttg cagggccagc tcaagtgtaa gttacatgca ctggtaccag   180
cagaagccag gatcctcccc caaaccctgg atttatgccc atccaacct ggcttctgga   240
gtccctgctc gcttcagtgg cagtgggtct gggacctctt actctctcac aatcagcaga   300
gtggaggctg aagatgctgc cacttattac tgccagcagt ggagttttaa cccacccacg   360
ttcggtgctg ggaccaagct ggagctgaaa gatggcggtg gctcgggcgg tggtggatct   420
ggaggaggtg gagctagcca ggcttatcta cagcagtctg ggctgagct ggtgaggcct   480
ggggcctcag tgaagatgtc ctgcaaggct tctggctaca catttaccag ttacaatatg   540
cactgggtaa agcagacacc tagacagggc ctggaatgga ttggagctat ttatccagga   600
aatggtgata cttcctacaa tcagaagttc aagggcaagg ccacactgac tgtagacaaa   660
tcctccagca cagcctacat gcagctcagc agcctgacat ctgaagactc tgcggtctat   720
ttctgtgcaa gagtggtgta ctatagtaac tcttactggt acttcgatgt ctggggcaca   780
gggaccacgg tcaccgtctc gagcgagccc aaatcttctg acaaaactca cacatcccca   840
ccgagcccag cacctgaact cctgggggga ccgtcagtct tcctcttccc cccaaaaccc   900
aaggacaccc tcatgatctc ccggacccct gaggtcacat gcgtggtggt ggacgtgagc   960
cacgaagacc ctgaggtcaa gttcaactgg tacgtggacg gcgtggaggt gcataatgcc  1020
```

-continued

```
aagacaaagc cgcgggagga gcagtacaac agcacgtacc gtgtggtcag cgtcctcacc    1080
gtcctgcacc aggactggct gaatggcaag gagtacaagt gcaaggtctc caacaaagcc    1140
ctcccagccc ccatcgagaa aacaatctcc aaagccaaag gcagccccg agaaccacag     1200 gtgtacaccc tgcccccatc ccgggatgag ctgaccaaga accaggtcag cctgacctgc    1260
ctggtcaaag gcttctatcc cagcgacatc gccgtggagt gggagagcaa tgggcagccg    1320
gagaacaact acaagaccac gcctcccgtg ctggactccg acggctcctt cttcctctac    1380
agcaagctca ccgtggacaa gagcaggtgg cagcagggga acgtcttctc atgctccgtg    1440
atgcatgagg ctctgcacaa ccactacacg cagaagagcc tctccctgtc tccgggtaag    1500
aattatggtg gcggtggctc tgggaattct caggtgcagc tgaaggagtc aggacctggc    1560
ctggtggcgc cctcacagag cctgtccatc acatgcaccg tctcagggtt ctcattaacc    1620
ggctatggtg taaactgggt tcgccagcct ccaggaaagg gtctggagtg gctgggaatg    1680
atatggggtg atggaagcac agactataat tcagctctca aatccagact atcgatcacc    1740
aaggacaact ccaagagcca agttttctta aaaatgaaca gtctgcaaac tgatgacaca    1800
gccagatact actgtgctcg agatggttat agtaactttc attactatgt tatggactac    1860
tggggtcaag gaacctcagt caccgtctcc tctgggggtg gaggctctgg tggcggtgga    1920
tccggcggag gtgggtcggg tggcggcgga tctgacattg tgctcaccca atctccagct    1980
tctttggctg tgtctctagg tcagagagcc accatctcct gcagagccag tgaaagtgtt    2040
gaatattatg tcacaagttt aatgcagtgg taccaacaga aaccaggaca gccacccaaa    2100
ctcctcatct ctgctgctag caacgtagaa tctggggtcc ctgccaggtt tagtggcagt    2160
gggtctggga cagactttag cctcaacatc catcctgtgg aggaggatga tattgcaatg    2220
tatttctgtc agcaaagtag gaaggttcca tggacgttcg gtggaggcac caagctggaa    2280
atcaaacgtt aatctaga                                                  2298
```

<210> SEQ ID NO 221
<211> LENGTH: 759
<212> TYPE: PRT
<213> ORGANISM: Artificial sequence
<220> FEATURE:
<223> OTHER INFORMATION: n2H7sssIgG1-H3-2e12HL (AA)
<220> FEATURE:
<221> NAME/KEY: misc_feature
<222> LOCATION: (1)..(20)
<223> OTHER INFORMATION: Leader
<220> FEATURE:
<221> NAME/KEY: misc_feature
<222> LOCATION: (21)..(126)
<223> OTHER INFORMATION: VL
<220> FEATURE:
<221> NAME/KEY: misc_feature
<222> LOCATION: (127)..(142)
<223> OTHER INFORMATION: Linker
<220> FEATURE:
<221> NAME/KEY: misc_feature
<222> LOCATION: (143)..(264)
<223> OTHER INFORMATION: VH
<220> FEATURE:
<221> NAME/KEY: misc_feature
<222> LOCATION: (265)..(279)
<223> OTHER INFORMATION: Hinge
<220> FEATURE:
<221> NAME/KEY: misc_feature
<222> LOCATION: (497)..(506)
<223> OTHER INFORMATION: EFD-BD2 Linker
<220> FEATURE:
<221> NAME/KEY: misc_feature
<222> LOCATION: (507)..(627)
<223> OTHER INFORMATION: VH2
<220> FEATURE:

```
<221> NAME/KEY: misc_feature
<222> LOCATION: (628)..(647)
<223> OTHER INFORMATION: Linker2
<220> FEATURE:
<221> NAME/KEY: misc_feature
<222> LOCATION: (648)..(759)
<223> OTHER INFORMATION: VL2

<400> SEQUENCE: 221
```

Met Glu Ala Pro Ala Gln Leu Leu Phe Leu Leu Leu Trp Leu Pro
1               5                   10                  15

Asp Thr Thr Gly Gln Ile Val Leu Ser Gln Ser Pro Ala Ile Leu Ser
            20                  25                  30

Ala Ser Pro Gly Glu Lys Val Thr Met Thr Cys Arg Ala Ser Ser Ser
        35                  40                  45

Val Ser Tyr Met His Trp Tyr Gln Gln Lys Pro Gly Ser Ser Pro Lys
    50                  55                  60

Pro Trp Ile Tyr Ala Pro Ser Asn Leu Ala Ser Gly Val Pro Ala Arg
65              70                  75                  80

Phe Ser Gly Ser Gly Ser Gly Thr Ser Tyr Ser Leu Thr Ile Ser Arg
                85                  90                  95

Val Glu Ala Glu Asp Ala Ala Thr Tyr Tyr Cys Gln Gln Trp Ser Phe
            100                 105                 110

Asn Pro Pro Thr Phe Gly Ala Gly Thr Lys Leu Glu Leu Lys Asp Gly
        115                 120                 125

Gly Gly Ser Gly Gly Gly Ser Gly Gly Gly Ala Ser Gln Ala
    130                 135                 140

Tyr Leu Gln Gln Ser Gly Ala Glu Leu Val Arg Pro Gly Ala Ser Val
145                 150                 155                 160

Lys Met Ser Cys Lys Ala Ser Gly Tyr Thr Phe Thr Ser Tyr Asn Met
                165                 170                 175

His Trp Val Lys Gln Thr Pro Arg Gln Gly Leu Glu Trp Ile Gly Ala
            180                 185                 190

Ile Tyr Pro Gly Asn Gly Asp Thr Ser Tyr Asn Gln Lys Phe Lys Gly
        195                 200                 205

Lys Ala Thr Leu Thr Val Asp Lys Ser Ser Ser Thr Ala Tyr Met Gln
    210                 215                 220

Leu Ser Ser Leu Thr Ser Glu Asp Ser Ala Val Tyr Phe Cys Ala Arg
225                 230                 235                 240

Val Val Tyr Tyr Ser Asn Ser Tyr Trp Tyr Phe Asp Val Trp Gly Thr
                245                 250                 255

Gly Thr Thr Val Thr Val Ser Ser Glu Pro Lys Ser Ser Asp Lys Thr
            260                 265                 270

His Thr Ser Pro Pro Ser Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr

```
                370             375             380
Ile Ser Lys Ala Lys Gly Gln Pro Arg Glu Pro Gln Val Tyr Thr Leu
385             390             395             400

Pro Pro Ser Arg Asp Glu Leu Thr Lys Asn Gln Val Ser Leu Thr Cys
            405             410             415

Leu Val Lys Gly Phe Tyr Pro Ser Asp Ile Ala Val Glu Trp Glu Ser
            420             425             430

Asn Gly Gln Pro Glu Asn Asn Tyr Lys Thr Thr Pro Pro Val Leu Asp
        435             440             445

Ser Asp Gly Ser Phe Phe Leu Tyr Ser Lys Leu Thr Val Asp Lys Ser
    450             455             460

Arg Trp Gln Gln Gly Asn Val Phe Ser Cys Ser Val Met His Glu Ala
465             470             475             480

Leu His Asn His Tyr Thr Gln Lys Ser Leu Ser Leu Ser Pro Gly Lys
                485             490             495

Asn Tyr Gly Gly Gly Ser Gly Asn Ser Gln Val Gln Leu Lys Glu
            500             505             510

Ser Gly Pro Gly Leu Val Ala Pro Ser Gln Ser Leu Ser Ile Thr Cys
    515             520             525

Thr Val Ser Gly Phe Ser Leu Thr Gly Tyr Gly Val Asn Trp Val Arg
530             535             540

Gln Pro Pro Gly Lys Gly Leu Glu Trp Leu Gly Met Ile Trp Gly Asp
545             550             555             560

Gly Ser Thr Asp Tyr Asn Ser Ala Leu Lys Ser Arg Leu Ser Ile Thr
            565             570             575

Lys Asp Asn Ser Lys Ser Gln Val Phe Leu Lys Met Asn Ser Leu Gln
        580             585             590

Thr Asp Asp Thr Ala Arg Tyr Tyr Cys Ala Arg Asp Gly Tyr Ser Asn
    595             600             605

Phe His Tyr Tyr Val Met Asp Tyr Trp Gly Gln Gly Thr Ser Val Thr
610             615             620

Val Ser Ser Gly Gly Gly Gly Ser Gly Gly Gly Gly Ser Gly Gly Gly
625             630             635             640

Gly Ser Gly Gly Gly Gly Ser Asp Ile Val Leu Thr Gln Ser Pro Ala
            645             650             655

Ser Leu Ala Val Ser Leu Gly Gln Arg Ala Thr Ile Ser Cys Arg Ala
        660             665             670

Ser Glu Ser Val Glu Tyr Tyr Val Thr Ser Leu Met Gln Trp Tyr Gln
    675             680             685

Gln Lys Pro Gly Gln Pro Pro Lys Leu Leu Ile Ser Ala Ala Ser Asn
690             695             700

Val Glu Ser Gly Val Pro Ala Arg Phe Ser Gly Ser Gly Ser Gly Thr
705             710             715             720

Asp Phe Ser Leu Asn Ile His Pro Val Glu Glu Asp Asp Ile Ala Met
            725             730             735

Tyr Phe Cys Gln Gln Ser Arg Lys Val Pro Trp Thr Phe Gly Gly Gly
        740             745             750

Thr Lys Leu Glu Ile Lys Arg
    755

<210> SEQ ID NO 222
<211> LENGTH: 2307
<212> TYPE: DNA
<213> ORGANISM: Artificial sequence
<220> FEATURE:
```

<223> OTHER INFORMATION: n2H7sssIgG1-H4-2e12HL (DNA)

<400> SEQUENCE: 222

| | |
|---|---|
| aagcttgccg ccatggaagc accagcgcag cttctcttcc tcctgctact ctggctccca | 60 |
| gataccaccg gtcaaattgt tctctcccag tctccagcaa tcctgtctgc atctccaggg | 120 |
| gagaaggtca caatgacttg cagggccagc tcaagtgtaa gttacatgca ctggtaccag | 180 |
| cagaagccag gatcctcccc caaaccctgg atttatgccc atccaacctg gcttctgga | 240 |
| gtccctgctc gcttcagtgg cagtgggtct gggacctctt actctctcac aatcagcaga | 300 |
| gtggaggctg aagatgctgc cacttattac tgccagcagt ggagttttaa cccacccacg | 360 |
| ttcggtgctg ggaccaagct ggagctgaaa gatggcggtg gctcgggcgg tggtggatct | 420 |
| ggaggaggtg gagctagcca ggcttatcta cagcagtctg ggctgagct ggtgaggcct | 480 |
| ggggcctcag tgaagatgtc ctgcaaggct tctggctaca catttaccag ttacaatatg | 540 |
| cactgggtaa agcagacacc tagacagggc ctggaatgga ttggagctat ttatccagga | 600 |
| aatggtgata cttcctacaa tcagaagttc aagggcaagg ccacactgac tgtagacaaa | 660 |
| tcctccagca cagcctacat gcagctcagc agcctgacat ctgaagactc tgcggtctat | 720 |
| ttctgtgcaa gagtggtgta ctatagtaac tcttactggt acttcgatgt ctggggcaca | 780 |
| gggaccacgg tcaccgtctc gagcgagccc aaatcttctg acaaaactca cacatcccca | 840 |
| ccgagcccag cacctgaact cctgggggga ccgtcagtct tcctcttccc cccaaaaccc | 900 |
| aaggacaccc tcatgatctc ccggacccct gaggtcacat gcgtggtggt ggacgtgagc | 960 |
| cacgaagacc ctgaggtcaa gttcaactgg tacgtggacg gcgtggaggt gcataatgcc | 1020 |
| aagacaaagc cgcgggagga gcagtacaac agcacgtacc gtgtggtcag cgtcctcacc | 1080 |
| gtcctgcacc aggactggct gaatggcaag gagtacaagt gcaaggtctc caacaaagcc | 1140 |
| ctcccagccc ccatcgagaa aacaatctcc aaagccaaag gcagccccg agaaccacag | 1200 |
| gtgtacaccc tgcccccatc ccgggatgag ctgaccaaga accaggtcag cctgacctgc | 1260 |
| ctggtcaaag gcttctatcc cagcgacatc gccgtggagt gggagagcaa tgggcagccg | 1320 |
| gagaacaact acaagaccac gcctcccgtg ctggactccg acggctcctt cttcctctac | 1380 |
| agcaagctca ccgtggacaa gagcaggtgg cagcagggga acgtcttctc atgctccgtg | 1440 |
| atgcatgagg ctctgcacaa ccactacacg cagaagagcc tctccctgtc tccgggtaag | 1500 |
| ggtggcggtg gctcgggcgg tggtggatct gggaattctc aggtgcagct gaaggagtca | 1560 |
| ggacctggcc tggtggcgcc ctcacagagc ctgtccatca catgcaccgt ctcagggttc | 1620 |
| tcattaaccg gctatggtgt aaactggtt cgccagcctc caggaaaggg tctggagtgg | 1680 |
| ctgggaatga tatggggtga tggaagcaca gactataatt cagctctcaa atccagacta | 1740 |
| tcgatcacca aggacaactc caagagccaa gttttcttaa aaatgaacag tctgcaaact | 1800 |
| gatgacacag ccagatacta ctgtgctcga atggttata gtaactttca ttactatgtt | 1860 |
| atggactact ggggtcaagg aacctcagtc accgtctcct ctggggggtgg aggctctggt | 1920 |
| ggcggtggat ccgcggagg tgggtcgggt ggcggcggat ctgacattgt gctcacccaa | 1980 |
| tctccagctt cttggctgt gtctctaggt cagagagcca ccatctcctg cagagccagt | 2040 |
| gaaagtgttg aatattatgt cacaagttta atgcagtggt accaacagaa accaggacag | 2100 |
| ccacccaaac tcctcatctc tgctgctagc aacgtagaat ctggggtccc tgccaggttt | 2160 |
| agtggcagtg ggtctgggac agactttagc ctcaacatcc atcctgtgga ggaggatgat | 2220 |
| attgcaatgt atttctgtca gcaaagtagg aaggttccat ggacgttcgg tggaggcacc | 2280 | aagctggaaa tcaaacgtta atctaga 2307

<210> SEQ ID NO 223
<211> LENGTH: 762
<212> TYPE: PRT
<213> ORGANISM: Artificial sequence
<220> FEATURE:
<223> OTHER INFORMATION: n2H7sssIgG1-H4-2e12HL (AA)
<220> FEATURE:
<221> NAME/KEY: misc_feature
<222> LOCATION: (1)..(20)
<223> OTHER INFORMATION: Leader
<220> FEATURE:
<221> NAME/KEY: misc_feature
<222> LOCATION: (21)..(126)
<223> OTHER INFORMATION: VL
<220> FEATURE:
<221> NAME/KEY: misc_feature
<222> LOCATION: (127)..(142)
<223> OTHER INFORMATION: Linker
<220> FEATURE:
<221> NAME/KEY: misc_feature
<222> LOCATION: (143)..(264)
<223> OTHER INFORMATION: VH
<220> FEATURE:
<221> NAME/KEY: misc_feature
<222> LOCATION: (265)..(279)
<223> OTHER INFORMATION: Hinge
<220> FEATURE:
<221> NAME/KEY: misc_feature
<222> LOCATION: (497)..(509)
<223> OTHER INFORMATION: EFD-BD2 Linker
<220> FEATURE:
<221> NAME/KEY: misc_feature
<222> LOCATION: (510)..(630)
<223> OTHER INFORMATION: VH2
<220> FEATURE:
<221> NAME/KEY: misc_feature
<222> LOCATION: (631)..(650)
<223> OTHER INFORMATION: Linker2
<220> FEATURE:
<221> NAME/KEY: misc_feature
<222> LOCATION: (651)..(762)
<223> OTHER INFORMATION: VL2

<400> SEQUENCE: 223

Met Glu Ala Pro Ala Gln Leu Leu Phe Leu Leu Leu Leu Trp Leu Pro
1               5                   10                  15

Asp Thr Thr Gly Gln Ile Val Leu Ser Gln Ser Pro Ala Ile Leu Ser
            20                  25                  30

Ala Ser Pro Gly Glu Lys Val Thr Met Thr Cys Arg Ala Ser Ser Ser
        35                  40                  45

Val Ser Tyr Met His Trp Tyr Gln Gln Lys Pro Gly Ser Ser Pro Lys
    50                  55                  60

Pro Trp Ile Tyr Ala Pro Ser Asn Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

Val Glu Ala Glu Asp Ala Ala Thr Tyr Tyr Cys Gln Gln Trp Ser Phe
            100                 105                 110

Asn Pro Pro Thr Phe Gly Ala Gly Thr Lys Leu Glu Leu Lys Asp Gly
        115                 120                 125

Gly Gly Ser Gly Gly Gly Gly Ser Gly Gly Gly Gly Ala Ser Gln Ala
    130                 135                 140

Tyr Leu Gln Gln Ser Gly Ala Glu Leu Val Arg Pro Gly Ala Ser Val
145                 150                 155                 160

Lys Met Ser Cys Lys Ala Ser Gly Tyr Thr Phe Thr Ser Tyr Asn Met
                165                 170                 175

His Trp Val Lys Gln Thr Pro Arg Gln Gly Leu Glu Trp Ile Gly Ala
            180                 185                 190
Ile Tyr Pro Gly Asn Gly Asp Thr Ser Tyr Asn Gln Lys Phe Lys Gly
            195                 200                 205
Lys Ala Thr Leu Thr Val Asp Lys Ser Ser Thr Ala Tyr Met Gln
210                 215                 220
Leu Ser Ser Leu Thr Ser Glu Asp Ser Ala Val Tyr Phe Cys Ala Arg
225                 230                 235                 240
Val Val Tyr Tyr Ser Asn Ser Tyr Trp Tyr Phe Asp Val Trp Gly Thr
            245                 250                 255
Gly Thr Thr Val Thr Val Ser Ser Glu Pro Lys Ser Ser Asp Lys Thr
            260                 265                 270
His Thr Ser Pro Pro Ser Pro Ala Pro Glu Leu Leu Gly Gly Pro Ser
            275                 280                 285
Val Phe Leu Phe Pro Pro Lys Pro Lys Asp Thr Leu Met Ile Ser Arg
            290                 295                 300
Thr Pro Glu Val Thr Cys Val Val Asp Val Ser His Glu Asp Pro
305                 310                 315                 320
Glu Val Lys Phe Asn Trp Tyr Val Asp Gly Val Glu Val His Asn Ala
            325                 330                 335
Lys Thr Lys Pro Arg Glu Glu Gln Tyr Asn Ser Thr Tyr Arg Val Val
            340                 345                 350
Ser Val Leu Thr Val Leu His Gln Asp Trp Leu Asn Gly Lys Glu Tyr
            355                 360                 365
Lys Cys Lys Val Ser Asn Lys Ala Leu Pro Ala Pro Ile Glu Lys Thr
            370                 375                 380
Ile Ser Lys Ala Lys Gly Gln Pro Arg Glu Pro Gln Val Tyr Thr Leu
385                 390                 395                 400
Pro Pro Ser Arg Asp Glu Leu Thr Lys Asn Gln Val Ser Leu Thr Cys
            405                 410                 415
Leu Val Lys Gly Phe Tyr Pro Ser Asp Ile Ala Val Glu Trp Glu Ser
            420                 425                 430
Asn Gly Gln Pro Glu Asn Asn Tyr Lys Thr Thr Pro Pro Val Leu Asp
            435                 440                 445
Ser Asp Gly Ser Phe Phe Leu Tyr Ser Lys Leu Thr Val Asp Lys Ser
450                 455                 460
Arg Trp Gln Gln Gly Asn Val Phe Ser Cys Ser Val Met His Glu Ala
465                 470                 475                 480
Leu His Asn His Tyr Thr Gln Lys Ser Leu Ser Leu Ser Pro Gly Lys
            485                 490                 495
Gly Gly Gly Gly Ser Gly Gly Gly Ser Gly Asn Ser Gln Val Gln
            500                 505                 510
Leu Lys Glu Ser Gly Pro Gly Leu Val Ala Pro Ser Gln Ser Leu Ser
            515                 520                 525
Ile Thr Cys Thr Val Ser Gly Phe Ser Leu Thr Gly Tyr Gly Val Asn
            530                 535                 540
Trp Val Arg Gln Pro Pro Gly Lys Gly Leu Glu Trp Leu Gly Met Ile
545                 550                 555                 560
Trp Gly Asp Gly Ser Thr Asp Tyr Asn Ser Ala Leu Lys Ser Arg Leu
            565                 570                 575
Ser Ile Thr Lys Asp Asn Ser Lys Ser Gln Val Phe Leu Lys Met Asn
            580                 585                 590
Ser Leu Gln Thr Asp Asp Thr Ala Arg Tyr Tyr Cys Ala Arg Asp Gly

|                |          |     |     |     |     |     |     |     |     |     |     |
|----------------|----------|-----|-----|-----|-----|-----|-----|-----|-----|-----|-----|
|                | 595      |     |     |     | 600 |     |     |     | 605 |     |     |

Tyr Ser Asn Phe His Tyr Tyr Val Met Asp Tyr Trp Gly Gln Gly Thr
    610             615                 620

Ser Val Thr Val Ser Ser Gly Gly Gly Ser Gly Gly Gly Gly Ser
625             630              635             640

Gly Gly Gly Gly Ser Gly Gly Gly Ser Asp Ile Val Leu Thr Gln
                645             650              655

Ser Pro Ala Ser Leu Ala Val Ser Leu Gly Gln Arg Ala Thr Ile Ser
        660             665                 670

Cys Arg Ala Ser Glu Ser Val Glu Tyr Tyr Val Thr Ser Leu Met Gln
        675             680                 685

Trp Tyr Gln Gln Lys Pro Gly Gln Pro Pro Lys Leu Leu Ile Ser Ala
    690             695             700

Ala Ser Asn Val Glu Ser Gly Val Pro Ala Arg Phe Ser Gly Ser Gly
705             710             715             720

Ser Gly Thr Asp Phe Ser Leu Asn Ile His Pro Val Glu Glu Asp Asp
                725             730             735

Ile Ala Met Tyr Phe Cys Gln Gln Ser Arg Lys Val Pro Trp Thr Phe
            740             745             750

Gly Gly Gly Thr Lys Leu Glu Ile Lys Arg
        755             760

```
<210> SEQ ID NO 224
<211> LENGTH: 2313
<212> TYPE: DNA
<213> ORGANISM: Artificial sequence
<220> FEATURE:
<223> OTHER INFORMATION: n2H7sssIgG1-H5-2e12HL (DNA)

<400> SEQUENCE: 224
aagcttgccg ccatggaagc accagcgcag cttctcttcc tcctgctact ctggctccca      60
gataccaccg gtcaaattgt tctctcccag tctccagcaa tcctgtctgc atctccaggg     120
gagaaggtca caatgacttg cagggccagc tcaagtgtaa gttacatgca ctggtaccag     180
cagaagccag gatcctcccc caaaccctgg atttatgccc atccaacct ggcttctgga      240
gtccctgctc gcttcagtgg cagtgggtct gggacctctt actctctcac aatcagcaga     300
gtggaggctg aagatgctgc cacttattac tgccagcagt ggagttttaa cccacccacg     360
ttcggtgctg ggaccaagct ggagctgaaa gatggcggtg gctcgggcgg tggtggatct     420
ggaggaggtg gagctagcca ggcttatcta cagcagtctg ggctgagct ggtgaggcct      480
ggggcctcag tgaagatgtc ctgcaaggct tctggctaca catttaccag ttacaatatg     540
cactgggtaa agcagacacc tagacagggc ctggaatgga ttggagctat ttatccagga     600
aatggtgata cttcctacaa tcagaagttc aagggcaagg ccacactgac tgtagacaaa     660
tcctccagca cagcctacat gcagctcagc agcctgacat ctgaagactc tgcggtctat     720
ttctgtgcaa gagtggtgta ctatagtaac tcttactggt acttcgatgt ctggggcaca     780
gggaccacgg tcaccgtctc gagcgagccc aaatcttctg acaaaactca cacatcccca     840
ccgagcccag cacctgaact cctgggggga ccgtcagtct tcctcttccc cccaaaaccc     900
aaggacaccc tcatgatctc ccggacccct gaggtcacat gcgtggtggt ggacgtgagc     960
cacgaagacc ctgaggtcaa gttcaactgg tacgtggacg gcgtggaggt gcataatgcc    1020
aagacaaagc cgcgggagga gcagtacaac agcacgtacc gtgtggtcag cgtcctcacc    1080
gtcctgcacc aggactggct gaatggcaag gagtacaagt gcaaggtctc caacaaagcc    1140
```

-continued

```
ctcccagccc ccatcgagaa acaatctcc aaagccaaag ggcagccccg agaaccacag   1200
gtgtacaccc tgcccccatc ccgggatgag ctgaccaaga accaggtcag cctgacctgc   1260
ctggtcaaag gcttctatcc cagcgacatc gccgtggagt gggagagcaa tgggcagccg   1320
gagaacaact acaagaccac gcctcccgtg ctggactccg acggctcctt cttcctctac   1380
agcaagctca ccgtggacaa gagcaggtgg cagcagggga cgtcttctc atgctccgtg   1440 atgcatgagg ctctgcacaa ccactacacg cagaagagcc tctccctgtc tccgggtaag   1500
aattatggtg gcggtggctc gggcggtggt ggatctggga attctcaggt gcagctgaag   1560
gagtcaggac ctggcctggt ggcgccctca cagagcctgt ccatcacatg caccgtctca   1620
gggttctcat taaccggcta tggtgtaaac tggggttcgcc agcctccagg aaagggtctg   1680
gagtggctgg gaatgatatg gggtgatgga agcacagact ataattcagc tctcaaatcc   1740
agactatcga tcaccaagga caactccaag agccaagttt tcttaaaaat gaacagtctg   1800
caaactgatg acacagccag atactactgt gctcgagatg gttatagtaa ctttcattac   1860
tatgttatgg actactgggg tcaaggaacc tcagtcaccg tctcctctgg gggtggaggc   1920
tctggtggcg gtggatccgg cggaggtggg tcgggtggcg gcggatctga cattgtgctc   1980
acccaatctc cagcttcttt ggctgtgtct ctaggtcaga gagccaccat ctcctgcaga   2040
gccagtgaaa gtgttgaata ttatgtcaca agtttaatgc agtggtacca acagaaacca   2100
ggacagccac ccaaactcct catctctgct gctagcaacg tagaatctgg ggtccctgcc   2160
aggtttagtg gcagtgggtc tgggacagac tttagcctca acatccatcc tgtgaggag   2220 gatgatattg caatgtattt ctgtcagcaa agtaggaagg ttccatggac gttcggtgga   2280
ggcaccaagc tggaaatcaa acgttaatct aga                                 2313
```

<210> SEQ ID NO 225
<211> LENGTH: 764
<212> TYPE: PRT
<213> ORGANISM: Artificial sequence
<220> FEATURE:
<223> OTHER INFORMATION: n2H7sssIgG1-H5-2e12HL (AA)
<220> FEATURE:
<221> NAME/KEY: misc_feature
<222> LOCATION: (1)..(20)
<223> OTHER INFORMATION: Leader
<220> FEATURE:
<221> NAME/KEY: misc_feature
<222> LOCATION: (21)..(126)
<223> OTHER INFORMATION: VL
<220> FEATURE:
<221> NAME/KEY: misc_feature
<222> LOCATION: (127)..(142)
<223> OTHER INFORMATION: Linker
<220> FEATURE:
<221> NAME/KEY: misc_feature
<222> LOCATION: (143)..(264)
<223> OTHER INFORMATION: VH
<220> FEATURE:
<221> NAME/KEY: misc_feature
<222> LOCATION: (265)..(279)
<223> OTHER INFORMATION: Hinge
<220> FEATURE:
<221> NAME/KEY: misc_feature
<222> LOCATION: (497)..(511)
<223> OTHER INFORMATION: EFD-BD2 Linker
<220> FEATURE:
<221> NAME/KEY: misc_feature
<222> LOCATION: (512)..(632)
<223> OTHER INFORMATION: VH2
<220> FEATURE:
<221> NAME/KEY: misc_feature
<222> LOCATION: (633)..(652)
<223> OTHER INFORMATION: Linker2
<220> FEATURE:

```
<221> NAME/KEY: misc_feature
<222> LOCATION: (653)..(764)
<223> OTHER INFORMATION: VL2

<400> SEQUENCE: 225
```

| | | | | | | | | | | | | | | |
|---|---|---|---|---|---|---|---|---|---|---|---|---|---|---|
| Met | Glu | Ala | Pro | Ala | Gln | Leu | Leu | Phe | Leu | Leu | Leu | Trp | Leu | Pro |
| 1 | | | | 5 | | | | | 10 | | | | | 15 |
| Asp | Thr | Thr | Gly | Gln | Ile | Val | Leu | Ser | Gln | Ser | Pro | Ala | Ile | Leu | Ser |
| | | | 20 | | | | | 25 | | | | | 30 | | |
| Ala | Ser | Pro | Gly | Glu | Lys | Val | Thr | Met | Thr | Cys | Arg | Ala | Ser | Ser |
| | | 35 | | | | | 40 | | | | | 45 | | |
| Val | Ser | Tyr | Met | His | Trp | Tyr | Gln | Gln | Lys | Pro | Gly | Ser | Ser | Pro | Lys |
| 50 | | | | | | 55 | | | | | 60 | | | | |
| Pro | Trp | Ile | Tyr | Ala | Pro | Ser | Asn | Leu | Ala | Ser | Gly | Val | Pro | Ala | Arg |
| 65 | | | | | 70 | | | | | 75 | | | | | 80 |
| Phe | Ser | Gly | Ser | Gly | Ser | Gly | Thr | Ser | Tyr | Ser | Leu | Thr | Ile | Ser | Arg |
| | | | | 85 | | | | | 90 | | | | | 95 | |
| Val | Glu | Ala | Glu | Asp | Ala | Ala | Thr | Tyr | Tyr | Cys | Gln | Gln | Trp | Ser | Phe |
| | | | 100 | | | | | 105 | | | | | 110 | | |
| Asn | Pro | Pro | Thr | Phe | Gly | Ala | Gly | Thr | Lys | Leu | Glu | Leu | Lys | Asp | Gly |
| | | 115 | | | | | 120 | | | | | 125 | | | |
| Gly | Gly | Ser | Gly | Gly | Gly | Ser | Gly | Gly | Gly | Ala | Ser | Gln | Ala |
| | 130 | | | | | 135 | | | | | 140 | | |
| Tyr | Leu | Gln | Gln | Ser | Gly | Ala | Glu | Leu | Val | Arg | Pro | Gly | Ala | Ser | Val |
| 145 | | | | | 150 | | | | | 155 | | | | | 160 |
| Lys | Met | Ser | Cys | Lys | Ala | Ser | Gly | Tyr | Thr | Phe | Thr | Ser | Tyr | Asn | Met |
| | | | | 165 | | | | | 170 | | | | | 175 | |
| His | Trp | Val | Lys | Gln | Thr | Pro | Arg | Gln | Gly | Leu | Glu | Trp | Ile | Gly | Ala |
| | | | 180 | | | | | 185 | | | | | 190 | | |
| Ile | Tyr | Pro | Gly | Asn | Gly | Asp | Thr | Ser | Tyr | Asn | Gln | Lys | Phe | Lys | Gly |
| | | 195 | | | | | 200 | | | | | 205 | | | |
| Lys | Ala | Thr | Leu | Thr | Val | Asp | Lys | Ser | Ser | Ser | Thr | Ala | Tyr | Met | Gln |
| | 210 | | | | | 215 | | | | | 220 | | | | |
| Leu | Ser | Ser | Leu | Thr | Ser | Glu | Asp | Ser | Ala | Val | Tyr | Phe | Cys | Ala | Arg |
| 225 | | | | | 230 | | | | | 235 | | | | | 240 |
| Val | Val | Tyr | Tyr | Ser | Asn | Ser | Tyr | Trp | Tyr | Phe | Asp | Val | Trp | Gly | Thr |
| | | | | 245 | | | | | 250 | | | | | 255 | |
| Gly | Thr | Thr | Val | Thr | Val | Ser | Ser | Glu | Pro | Lys | Ser | Ser | Asp | Lys | Thr |
| | | | 260 | | | | | 265 | | | | | 270 | | |
| His | Thr | Ser | Pro | Pro | Ser | Pro | Ala | Pro | Glu | Leu | Leu | Gly | Gly | Pro | Ser |
| | | 275 | | | | | 280 | | | | | 285 | | | |
| Val | Phe | Leu | Phe | Pro | Pro | Lys | Pro | Lys | Asp | Thr | Leu | Met | Ile | Ser | Arg |
| | 290 | | | | | 295 | | | | | 300 | | | | |
| Thr | Pro | Glu | Val | Thr | Cys | Val | Val | Asp | Val | Ser | His | Glu | Asp | Pro |
| 305 | | | | | 310 | | | | | 315 | | | | | 320 |
| Glu | Val | Lys | Phe | Asn | Trp | Tyr | Val | Asp | Gly | Val | Glu | Val | His | Asn | Ala |
| | | | | 325 | | | | | 330 | | | | | 335 | |
| Lys | Thr | Lys | Pro | Arg | Glu | Glu | Gln | Tyr | Asn | Ser | Thr | Tyr | Arg | Val | Val |
| | | | 340 | | | | | 345 | | | | | 350 | | |
| Ser | Val | Leu | Thr | Val | Leu | His | Gln | Asp | Trp | Leu | Asn | Gly | Lys | Glu | Tyr |
| | | 355 | | | | | 360 | | | | | 365 | | | |
| Lys | Cys | Lys | Val | Ser | Asn | Lys | Ala | Leu | Pro | Ala | Pro | Ile | Glu | Lys | Thr |
| | 370 | | | | | 375 | | | | | 380 | | | | |
| Ile | Ser | Lys | Ala | Lys | Gly | Gln | Pro | Arg | Glu | Pro | Gln | Val | Tyr | Thr | Leu |
| 385 | | | | | 390 | | | | | 395 | | | | | 400 |

Pro Pro Ser Arg Asp Glu Leu Thr Lys Asn Gln Val Ser Leu Thr Cys
            405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

Asn Tyr Gly Gly Gly Ser Gly Gly Gly Ser Gly Asn Ser Gln
            500                 505                 510

Val Gln Leu Lys Glu Ser Gly Pro Gly Leu Val Ala Pro Ser Gln Ser
            515                 520                 525

Leu Ser Ile Thr Cys Thr Val Ser Gly Phe Ser Leu Thr Gly Tyr Gly
530                 535                 540

Val Asn Trp Val Arg Gln Pro Pro Gly Lys Gly Leu Glu Trp Leu Gly
545                 550                 555                 560

Met Ile Trp Gly Asp Gly Ser Thr Asp Tyr Asn Ser Ala Leu Lys Ser
                565                 570                 575

Arg Leu Ser Ile Thr Lys Asp Asn Ser Lys Ser Gln Val Phe Leu Lys
            580                 585                 590

Met Asn Ser Leu Gln Thr Asp Asp Thr Ala Arg Tyr Tyr Cys Ala Arg
            595                 600                 605

Asp Gly Tyr Ser Asn Phe His Tyr Tyr Val Met Asp Tyr Trp Gly Gln
610                 615                 620

Gly Thr Ser Val Thr Val Ser Ser Gly Gly Gly Gly Ser Gly Gly Gly
625                 630                 635                 640

Gly Ser Gly Gly Gly Gly Ser Gly Gly Gly Gly Ser Asp Ile Val Leu
                645                 650                 655

Thr Gln Ser Pro Ala Ser Leu Ala Val Ser Leu Gly Gln Arg Ala Thr
            660                 665                 670

Ile Ser Cys Arg Ala Ser Glu Ser Val Glu Tyr Tyr Val Thr Ser Leu
            675                 680                 685

Met Gln Trp Tyr Gln Gln Lys Pro Gly Gln Pro Pro Lys Leu Leu Ile
690                 695                 700

Ser Ala Ala Ser Asn Val Glu Ser Gly Val Pro Ala Arg Phe Ser Gly
705                 710                 715                 720

Ser Gly Ser Gly Thr Asp Phe Ser Leu Asn Ile His Pro Val Glu Glu
                725                 730                 735

Asp Asp Ile Ala Met Tyr Phe Cys Gln Gln Ser Arg Lys Val Pro Trp
            740                 745                 750

Thr Phe Gly Gly Gly Thr Lys Leu Glu Ile Lys Arg
            755                 760

<210> SEQ ID NO 226
<211> LENGTH: 2322
<212> TYPE: DNA
<213> ORGANISM: Artificial sequence
<220> FEATURE:
<223> OTHER INFORMATION: n2H7sssIgG1-H6-2e12HL (DNA)

<400> SEQUENCE: 226

```
aagcttgccg ccatggaagc accagcgcag cttctcttcc tcctgctact ctggctccca    60
gataccaccg gtcaaattgt tctctcccag tctccagcaa tcctgtctgc atctccaggg   120
gagaaggtca caatgacttg cagggccagc tcaagtgtaa gttacatgca ctggtaccag   180
cagaagccag gatcctcccc caaaccctgg atttatgccc catccaacct ggcttctgga   240
gtccctgctc gcttcagtgg cagtgggtct gggacctctt actctctcac aatcagcaga   300
gtggaggctg aagatgctgc cacttattac tgccagcagt ggagttttaa cccacccacg   360
ttcggtgctg ggaccaagct ggagctgaaa gatggcggtg gctcgggcgg tggtggatct   420
ggaggaggtg gagctagcca ggcttatcta cagcagtctg ggctgagct ggtgaggcct   480
ggggcctcag tgaagatgtc ctgcaaggct tctggctaca catttaccag ttacaatatg   540
cactgggtaa agcagacacc tagacagggc ctggaatgga ttggagctat ttatccagga   600
aatggtgata cttcctacaa tcagaagttc aagggcaagg ccacactgac tgtagacaaa   660
tcctccagca cagcctacat gcagctcagc agcctgacat ctgaagactc tgcggtctat   720
ttctgtgcaa gagtggtgta ctatagtaac tcttactggt acttcgatgt ctggggcaca   780
gggaccacgg tcaccgtctc gagcgagccc aaatcttctg acaaaactca cacatcccca   840
ccgagcccag cacctgaact cctgggggga ccgtcagtct tcctcttccc cccaaaaccc   900
aaggacaccc tcatgatctc ccggacccct gaggtcacat gcgtggtggt ggacgtgagc   960
cacgaagacc ctgaggtcaa gttcaactgg tacgtggacg gcgtggaggt gcataatgcc  1020
aagacaaagc cgcgggagga gcagtacaac agcacgtacc gtgtggtcag cgtcctcacc  1080
gtcctgcacc aggactggct gaatggcaag gagtacaagt gcaaggtctc caacaaagcc  1140
ctcccagccc ccatcgagaa aacaatctcc aaagccaaag gcagccccg agaaccacag  1200
gtgtacaccc tgcccccatc ccgggatgag ctgaccaaga accaggtcag cctgacctgc  1260
ctggtcaaag gcttctatcc cagcgacatc gccgtggagt gggagagcaa tgggcagccg  1320
gagaacaact acaagaccac gcctcccgtg ctggactccg acggctcctt cttcctctac  1380
agcaagctca ccgtggacaa gagcaggtgg cagcagggga acgtcttctc atgctccgtg  1440
atgcatgagg ctctgcacaa ccactacacg cagaagagcc tctccctgtc tccgggtaag  1500
ggtggcggtg gctcgggcgg tggtggatct ggggaggag gcagcgggaa ttctcaggtg  1560
cagctgaagg agtcaggacc tggcctggtg gcgccctcac agagcctgtc catcacatgc  1620
accgtctcag ggttctcatt aaccggctat ggtgtaaact gggttcgcca gcctccagga  1680
aagggtctgg agtggctggg aatgatatgg ggtgatggaa gcacagacta taattcagct  1740
ctcaaatcca gactatcgat caccaaggac aactccaaga gccaagtttt cttaaaaatg  1800
aacagtctgc aaactgatga cacagccaga tactactgtg ctcgagatgg ttatagtaac  1860
tttcattact atgttatgga ctactggggt caaggaacct cagtcaccgt ctcctctggg  1920
ggtggaggct ctggtggcgg tggatccggc ggaggtgggg cggtggcgg cggatctgac  1980
attgtgctca cccaatctcc agcttctttg gctgtgtctc taggtcagag agccaccatc  2040
tcctgcagag ccagtgaaag tgttgaatat tatgtcacaa gtttaatgca gtggtaccaa  2100
cagaaaccag gacagccacc caaactcctc atctctgctg ctagcaacgt agaatctggg  2160
gtccctgcca ggtttagtgg cagtgggtct gggacagact ttagcctcaa catccatcct  2220
gtggaggagg atgatattgc aatgtatttc tgtcagcaaa gtaggaaggt tccatggacg  2280
ttcggtggag gcaccaagct ggaaatcaaa cgttaatcta ga                     2322
```

<210> SEQ ID NO 227

```
<211> LENGTH: 767
<212> TYPE: PRT
<213> ORGANISM: Artificial sequence
<220> FEATURE:
<223> OTHER INFORMATION: n2H7sssIgG1-H6-2e12HL (AA)
<220> FEATURE:
<221> NAME/KEY: misc_feature
<222> LOCATION: (1)..(20)
<223> OTHER INFORMATION: Leader
<220> FEATURE:
<221> NAME/KEY: misc_feature
<222> LOCATION: (21)..(126)
<223> OTHER INFORMATION: VL
<220> FEATURE:
<221> NAME/KEY: misc_feature
<222> LOCATION: (127)..(142)
<223> OTHER INFORMATION: Linker
<220> FEATURE:
<221> NAME/KEY: misc_feature
<222> LOCATION: (143)..(264)
<223> OTHER INFORMATION: VH
<220> FEATURE:
<221> NAME/KEY: misc_feature
<222> LOCATION: (265)..(279)
<223> OTHER INFORMATION: Hinge
<220> FEATURE:
<221> NAME/KEY: misc_feature
<222> LOCATION: (497)..(514)
<223> OTHER INFORMATION: EFD-BD2 Linker
<220> FEATURE:
<221> NAME/KEY: misc_feature
<222> LOCATION: (515)..(635)
<223> OTHER INFORMATION: VH2
<220> FEATURE:
<221> NAME/KEY: misc_feature
<222> LOCATION: (636)..(655)
<223> OTHER INFORMATION: Linker2
<220> FEATURE:
<221> NAME/KEY: misc_feature
<222> LOCATION: (656)..(767)
<223> OTHER INFORMATION: VL2

<400> SEQUENCE: 227

Met Glu Ala Pro Ala Gln Leu Leu Phe Leu Leu Leu Leu Trp Leu Pro
1               5                   10                  15

Asp Thr Thr Gly Gln Ile Val Leu Ser Gln Ser Pro Ala Ile Leu Ser
            20                  25                  30

Ala Ser Pro Gly Glu Lys Val Thr Met Thr Cys Arg Ala Ser Ser Ser
        35                  40                  45

Val Ser Tyr Met His Trp Tyr Gln Gln Lys Pro Gly Ser Ser Pro Lys
    50                  55                  60

Pro Trp Ile Tyr Ala Pro Ser Asn Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

Val Glu Ala Glu Asp Ala Ala Thr Tyr Tyr Cys Gln Gln Trp Ser Phe
            100                 105                 110

Asn Pro Pro Thr Phe Gly Ala Gly Thr Lys Leu Glu Leu Lys Asp Gly
        115                 120                 125

Gly Gly Ser Gly Gly Gly Gly Ser Gly Gly Gly Gly Ala Ser Gln Ala
    130                 135                 140

Tyr Leu Gln Gln Ser Gly Ala Glu Leu Val Arg Pro Gly Ala Ser Val
145                 150                 155                 160

Lys Met Ser Cys Lys Ala Ser Gly Tyr Thr Phe Thr Ser Tyr Asn Met
                165                 170                 175

His Trp Val Lys Gln Thr Pro Arg Gln Gly Leu Glu Trp Ile Gly Ala
            180                 185                 190
```

-continued

```
Ile Tyr Pro Gly Asn Gly Asp Thr Ser Tyr Asn Gln Lys Phe Lys Gly
            195                 200                 205

Lys Ala Thr Leu Thr Val Asp Lys Ser Ser Ser Thr Ala Tyr Met Gln
        210                 215                 220

Leu Ser Ser Leu Thr Ser Glu Asp Ser Ala Val Tyr Phe Cys Ala Arg
225                 230                 235                 240

Val Val Tyr Tyr Ser Asn Ser Tyr Trp Tyr Phe Asp Val Trp Gly Thr
                245                 250                 255

Gly Thr Thr Val Thr Val Ser Ser Glu Pro Lys Ser Ser Asp Lys Thr
            260                 265                 270

His Thr Ser Pro Pro Ser Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

Gly Gly Gly Gly Ser Gly Gly Gly Ser Gly Gly Gly Ser Gly
            500                 505                 510

Asn Ser Gln Val Gln Leu Lys Glu Ser Gly Pro Gly Leu Val Ala Pro
        515                 520                 525

Ser Gln Ser Leu Ser Ile Thr Cys Thr Val Ser Gly Phe Ser Leu Thr
    530                 535                 540

Gly Tyr Gly Val Asn Trp Val Arg Gln Pro Pro Gly Lys Gly Leu Glu
545                 550                 555                 560

Trp Leu Gly Met Ile Trp Gly Asp Gly Ser Thr Asp Tyr Asn Ser Ala
                565                 570                 575

Leu Lys Ser Arg Leu Ser Ile Thr Lys Asp Asn Ser Lys Ser Gln Val
            580                 585                 590

Phe Leu Lys Met Asn Ser Leu Gln Thr Asp Asp Thr Ala Arg Tyr Tyr
        595                 600                 605

Cys Ala Arg Asp Gly Tyr Ser Asn Phe His Tyr Tyr Val Met Asp Tyr
    610                 615                 620
```

```
Trp Gly Gln Gly Thr Ser Val Thr Val Ser Ser Gly Gly Gly Ser
625                 630                 635                 640

Gly Gly Gly Gly Ser Gly Gly Gly Ser Gly Gly Gly Ser Asp
            645                 650                 655

Ile Val Leu Thr Gln Ser Pro Ala Ser Leu Ala Val Ser Leu Gly Gln
            660                 665                 670

Arg Ala Thr Ile Ser Cys Arg Ala Ser Glu Ser Val Glu Tyr Tyr Val
            675                 680                 685

Thr Ser Leu Met Gln Trp Tyr Gln Gln Lys Pro Gly Gln Pro Pro Lys
690                 695                 700

Leu Leu Ile Ser Ala Ala Ser Asn Val Glu Ser Gly Val Pro Ala Arg
705                 710                 715                 720

Phe Ser Gly Ser Gly Ser Gly Thr Asp Phe Ser Leu Asn Ile His Pro
                725                 730                 735

Val Glu Glu Asp Asp Ile Ala Met Tyr Phe Cys Gln Gln Ser Arg Lys
            740                 745                 750

Val Pro Trp Thr Phe Gly Gly Gly Thr Lys Leu Glu Ile Lys Arg
            755                 760                 765

<210> SEQ ID NO 228
<211> LENGTH: 2337
<212> TYPE: DNA
<213> ORGANISM: Artificial sequence
<220> FEATURE:
<223> OTHER INFORMATION: 2H7sssIgG1-H7-G281 HL (DNA)

<400> SEQUENCE: 228
aagcttgccg ccatggattt tcaagtgcag attttcagct tcctgctaat cagtgcttca      60
gtcataatgt ccagaggaca aattgttctc tcccagtctc cagcaatcct gtctgcatct     120
ccagggagag aggtcacaat gacttgcagg gccagctcaa gtgtaagtta catgcactgg     180
taccagcaga agccaggatc ctcccccaaa ccctggattt atgccccatc caacctggct     240
tctggagtcc ctgctcgctt cagtggcagt gggtctggga cctcttactc tctcacaatc     300
agcagagtgg aggctgaaga tgctgccact tattactgcc agcagtggag ttttaaccca     360
cccacgttcg gtgctgggac caagctggag ctgaaagatg cggtggctc gggcggtggt     420 ggatctggag gaggtgggag ctctcaggct tatctacagc agtctggggc tgagtcggtg     480
aggcctgggg cctcagtgaa gatgtcctgc aaggcttctg gctacacatt taccagttac     540
aatatgcact gggtaaagca gacacctaga cagggcctgg aatggattgg agctatttat     600
ccaggaaatg gtgatacttc ctacaatcag aagttcaagg gcaaggccac actgactgta     660
gacaaatcct ccagcacagc ctacatgcag ctcagcagcc tgacatctga agactctgcg     720
gtctatttct gtgcaagagt ggtgtactat agtaactctt actggtactt cgatgtctgg     780
ggcacaggga ccacggtcac cgtctctgat caggagccca atcttgtga caaaactcac     840 acatccccac cgtgctcagc acctgaactc ctggggggac cgtcagtctt cctcttcccc     900
ccaaaaccca aggacaccct catgatctcc cggaccctg aggtcacatg cgtggtggtg     960
gacgtgagcc acgaagaccc tgaggtcaag ttcaactggt acgtggacgg cgtggaggtg    1020
cataatgcca agacaaagcc gcgggaggag cagtacaaca gcacgtaccg tgtggtcagc    1080
gtcctcaccg tcctgcacca ggactggctg aatggcaagg agtacaagtg caaggtctcc    1140
aacaaagccc tccagcccc catcgagaaa acaatctcca agccaaagg gcagccccga    1200 gaaccacagg tgtacaccct gcccccatcc cgggatgagc tgaccaagaa ccaggtcagc    1260
```

```
ctgacctgcc tggtcaaagg cttctatccc agcgacatcg ccgtggagtg ggagagcaat    1320
gggcagccgg agaacaacta caagaccacg cctcccgtgc tggactccga cggctccttc    1380
ttcctctaca gcaagctcac cgtggacaag agcaggtggc agcaggggaa cgtcttctca    1440
tgctccgtga tgcatgaggc tctgcacaac cactacacgc agaagagcct ctccctgtct    1500
ccgggtaaga attatggtgg cggtggctcg ggcggtggtg gatctggagg aggtgggagt    1560
gggaattctc aggtgcagct gaaggagtca ggacctggcc tggtggcgcc ctcacagagc    1620
ctgtccatca catgcaccgt ctcagggttc tcattaaccg gctatggtgt aaactgggtt    1680
cgccagcctc caggaaaggg tctggagtgg ctgggaatga tatggggtga tggaagcaca    1740
gactataatt cagctctcaa atccagacta tcgatcacca aggacaactc caagagccaa    1800
gttttcttaa aaatgaacag tctgcaaact gatgacacag ccagatacta ctgtgctcga    1860
gatggttata gtaactttca ttactatgtt atggactact ggggtcaagg aacctcagtc    1920
accgtctcct ctgggggtgg aggctctggt ggcggtggat ccggcggagg tgggtcgggt    1980
ggcggcggat ctgacattgt gctcacccaa tctccagctt ctttggctgt gtctctaggt    2040
cagagagcca ccatctcctg cagagccagt gaaagtgttg aatattatgt cacaagttta    2100
atgcagtggt accaacagaa accaggacag ccacccaaac tcctcatctc tgctgctagc    2160
aacgtagaat ctggggtccc tgccaggttt agtggcagtg ggtctgggac agactttagc    2220
ctcaacatcc atcctgtgga ggaggatgat attgcaatgt atttctgtca gcaaagtagg    2280
aaggttccat ggacgttcgg tggaggcacc aagctggaaa tcaaacgtta atctaga      2337
```

```
<210> SEQ ID NO 229
<211> LENGTH: 772
<212> TYPE: PRT
<213> ORGANISM: Artificial sequence
<220> FEATURE:
<223> OTHER INFORMATION: 2H7cscIgG1-STD1-2e12HL (w/2E12 leader) (AA)
<220> FEATURE:
<221> NAME/KEY: misc_feature
<222> LOCATION: (1)..(22)
<223> OTHER INFORMATION: Leader
<220> FEATURE:
<221> NAME/KEY: misc_feature
<222> LOCATION: (23)..(128)
<223> OTHER INFORMATION: VL
<220> FEATURE:
<221> NAME/KEY: misc_feature
<222> LOCATION: (129)..(144)
<223> OTHER INFORMATION: Linker
<220> FEATURE:
<221> NAME/KEY: misc_feature
<222> LOCATION: (145)..(265)
<223> OTHER INFORMATION: VH
<220> FEATURE:
<221> NAME/KEY: misc_feature
<222> LOCATION: (268)..(282)
<223> OTHER INFORMATION: Hinge
<220> FEATURE:
<221> NAME/KEY: misc_feature
<222> LOCATION: (500)..(519)
<223> OTHER INFORMATION: EFD-BD2 Linker
<220> FEATURE:
<221> NAME/KEY: misc_feature
<222> LOCATION: (520)..(640)
<223> OTHER INFORMATION: VH2
<220> FEATURE:
<221> NAME/KEY: misc_feature
<222> LOCATION: (641)..(660)
<223> OTHER INFORMATION: Linker2
<220> FEATURE:
<221> NAME/KEY: misc_feature
<222> LOCATION: (661)..(772)
<223> OTHER INFORMATION: VL2
```

-continued

```
<400> SEQUENCE: 229

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Ser Gly Gly Gly Ser Ser
130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Val Asp Lys Ser Ser Ser Thr Ala Tyr
    210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
                245                 250                 255

Gly Thr Gly Thr Thr Val Thr Val Ser Asp Gln Glu Pro Lys Ser Cys
            260                 265                 270

Asp Lys Thr His Thr Ser Pro Pro Cys Ser Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415
```

```
Leu Thr Cys Leu Val Lys Gly Phe Tyr Pro Ser Asp Ile Ala Val Glu
            420                 425                 430
Trp Glu Ser Asn Gly Gln Pro Glu Asn Asn Tyr Lys Thr Thr Pro Pro
                435                 440                 445
Val Leu Asp Ser Asp Gly Ser Phe Phe Leu Tyr Ser Lys Leu Thr Val
        450                 455                 460
Asp Lys Ser Arg Trp Gln Gln Gly Asn Val Phe Ser Cys Ser Val Met
465                 470                 475                 480
His Glu Ala Leu His Asn His Tyr Thr Gln Lys Ser Leu Ser Leu Ser
                485                 490                 495
Pro Gly Lys Asn Tyr Gly Gly Gly Ser Gly Gly Gly Gly Ser Gly Gly
                500                 505                 510
Gly Gly Ser Gly Asn Ser Gln Val Gln Leu Lys Glu Ser Gly Pro Gly
        515                 520                 525
Gly Leu Val Ala Pro Ser Gln Ser Leu Ser Ile Thr Cys Thr Val Ser
530                 535                 540
Gly Phe Ser Leu Thr Gly Tyr Gly Val Asn Trp Val Arg Gln Pro Pro
545                 550                 555                 560
Gly Lys Gly Leu Glu Trp Leu Gly Met Ile Trp Gly Asp Gly Ser Thr
                565                 570                 575
Asp Tyr Asn Ser Ala Leu Lys Ser Arg Leu Ser Ile Thr Lys Asp Asn
            580                 585                 590
Ser Lys Ser Gln Val Phe Leu Lys Met Asn Ser Leu Gln Thr Asp Asp
        595                 600                 605
Thr Ala Arg Tyr Tyr Cys Ala Arg Asp Gly Tyr Ser Asn Phe His Tyr
610                 615                 620
Tyr Val Met Asp Tyr Trp Gly Gln Gly Thr Ser Val Thr Val Ser Ser
625                 630                 635                 640
Gly Gly Gly Gly Ser Gly Gly Gly Ser Gly Gly Gly Ser Gly
                645                 650                 655
Gly Gly Gly Ser Asp Ile Val Leu Thr Gln Ser Pro Ala Ser Leu Ala
            660                 665                 670
Val Ser Leu Gly Gln Arg Ala Thr Ile Ser Cys Arg Ala Ser Glu Ser
        675                 680                 685
Val Glu Tyr Tyr Val Thr Ser Leu Met Gln Trp Tyr Gln Gln Lys Pro
690                 695                 700
Gly Gln Pro Pro Lys Leu Leu Ile Ser Ala Ala Ser Asn Val Glu Ser
705                 710                 715                 720
Gly Val Pro Ala Arg Phe Ser Gly Ser Gly Ser Gly Thr Asp Phe Ser
                725                 730                 735
Leu Asn Ile His Pro Val Glu Glu Asp Asp Ile Ala Met Tyr Phe Cys
            740                 745                 750
Gln Gln Ser Arg Lys Val Pro Trp Thr Phe Gly Gly Gly Thr Lys Leu
        755                 760                 765
Glu Ile Lys Arg
    770

<210> SEQ ID NO 230
<211> LENGTH: 45
<212> TYPE: DNA
<213> ORGANISM: Artificial sequence
<220> FEATURE:
<223> OTHER INFORMATION: scs(s)-hIgG1 (DNA)

<400> SEQUENCE: 230
gagcccaaat cttctgacaa aactcacaca tctccaccga gctca                         45
```

<210> SEQ ID NO 231
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: scs(s) -hIgG1 (AA)

<400> SEQUENCE: 231

Glu Pro Lys Ser Ser Asp Lys Thr His Thr Ser Pro Pro Ser Ser
1               5                   10                  15

<210> SEQ ID NO 232
<211> LENGTH: 45
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: ccc(s) (DNA)

<400> SEQUENCE: 232
gagcccaaat cttgtgacaa aactcacaca tctccaccgt gctca                    45

<210> SEQ ID NO 233
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: ccc(s) (AA)

<400> SEQUENCE: 233

Glu Pro Lys Ser Cys Asp Lys Thr His Thr Ser Pro Pro Cys Ser
1               5                   10                  15

<210> SEQ ID NO 234
<211> LENGTH: 24
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H8 (PN)

<400> SEQUENCE: 234
gggtctccac cttctccgaa ttct                                           24

<210> SEQ ID NO 235
<211> LENGTH: 8
<212> TYPE: PRT
<213> ORGANISM: Artificial sequence
<220> FEATURE:
<223> OTHER INFORMATION: Scorpion region linker

<400> SEQUENCE: 235

Gly Ser Pro Pro Ser Pro Asn Ser
1               5

<210> SEQ ID NO 236
<211> LENGTH: 21
<212> TYPE: DNA
<213> ORGANISM: Artificial sequence
<220> FEATURE:
<223> OTHER INFORMATION: Scorpion region linker polynucleotide
<220> FEATURE:

```
<223> OTHER INFORMATION: Linker H9 (PN)

<400> SEQUENCE: 236
tctccacctt ctccgaattc t                                              21

<210> SEQ ID NO 237
<211> LENGTH: 7
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H9 (AA)

<400> SEQUENCE: 237

Ser Pro Pro Ser Pro Asn Ser
1               5

<210> SEQ ID NO 238

<400> SEQUENCE: 238

000

<210> SEQ ID NO 239

<400> SEQUENCE: 239

000

<210> SEQ ID NO 240
<211> LENGTH: 51
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H11 (PN)

<400> SEQUENCE: 240
gagcccacat ctaccgacaa aactcacaca tctccaccca gcccgaattc t              51

<210> SEQ ID NO 241
<211> LENGTH: 17
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H11 (AA)

<400> SEQUENCE: 241

Glu Pro Thr Ser Thr Asp Lys Thr His Thr Ser Pro Pro Ser Pro Asn
1               5                   10                  15
Ser

<210> SEQ ID NO 242
<211> LENGTH: 51
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H12 (PN)

<400> SEQUENCE: 242
gagcccacat ctaccgacaa aactcacaca tctccaccca gcccgaattc t              51
```

<210> SEQ ID NO 243
<211> LENGTH: 17
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H12 (AA)

<400> SEQUENCE: 243

Glu Pro Thr Ser Thr Asp Lys Thr His Thr Cys Pro Pro Cys Pro Asn
1               5                   10                  15

Ser

<210> SEQ ID NO 244
<211> LENGTH: 51
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H13 (PN)

<400> SEQUENCE: 244
gagcccacat ctaccgacaa aactcacaca tctccaccca gcccgaattc t         51

<210> SEQ ID NO 245
<211> LENGTH: 17
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H13 (AA)

<400> SEQUENCE: 245

Glu Pro Lys Ser Ser Asp Lys Thr His Thr Cys Pro Pro Cys Pro Asn
1               5                   10                  15

Ser

<210> SEQ ID NO 246
<211> LENGTH: 36
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H15 (PN)

<400> SEQUENCE: 246
ggcggtggtg gctcctgtcc accttgtccg aattct                          36

<210> SEQ ID NO 247
<211> LENGTH: 12
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H15 (AA)

<400> SEQUENCE: 247

Gly Gly Gly Gly Ser Cys Pro Pro Cys Pro Asn Ser
1               5                   10

<210> SEQ ID NO 248
<211> LENGTH: 45

```
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H16 (PN)

<400> SEQUENCE: 248
ctgtctgtga aagctgactt cctcactcca tccatcggga attct            45

<210> SEQ ID NO 249
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H16 (AA)

<400> SEQUENCE: 249

Leu Ser Val Lys Ala Asp Phe Leu Thr Pro Ser Ile Gly Asn Ser
1               5                   10                  15

<210> SEQ ID NO 250
<211> LENGTH: 60
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H17 (PN)

<400> SEQUENCE: 250
ctgtctgtga aagctgactt cctcactcca tccatctcct gtccaccttg cccgaattct      60

<210> SEQ ID NO 251
<211> LENGTH: 20
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H17 (AA)

<400> SEQUENCE: 251

Leu Ser Val Lys Ala Asp Phe Leu Thr Pro Ser Ile Ser Cys Pro Pro
1               5                   10                  15

Cys Pro Asn Ser
            20

<210> SEQ ID NO 252
<211> LENGTH: 45
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker  H18 (PN)

<400> SEQUENCE: 252
ctgtctgtgc tcgctaactt cagtcagcca gagatcggga attct            45

<210> SEQ ID NO 253
<211> LENGTH: 15
<212> TYPE: PRT
<213> ORGANISM: Artificial sequence
<220> FEATURE:
<223> OTHER INFORMATION: Scorpion region linker
<220> FEATURE:
```

<223> OTHER INFORMATION: Linker H18 (AA)

<400> SEQUENCE: 253

Leu Ser Val Leu Ala Asn Phe Ser Gln Pro Glu Ile Gly Asn Ser
1               5                   10                  15

<210> SEQ ID NO 254
<211> LENGTH: 60
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H19 (PN)

<400> SEQUENCE: 254
ctgtctgtgc tcgctaactt cagtcagcca gagatctcct gtccaccttg cccgaattct    60

<210> SEQ ID NO 255
<211> LENGTH: 20
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H19 (AA)

<400> SEQUENCE: 255

Leu Ser Val Leu Ala Asn Phe Ser Gln Pro Glu Ile Ser Cys Pro Pro
1               5                   10                  15

Cys Pro Asn Ser
            20

<210> SEQ ID NO 256
<211> LENGTH: 45
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H20 (PN)

<400> SEQUENCE: 256
ctgaaaatcc aggagagggt cagtaagcca aagatctcga attct    45

<210> SEQ ID NO 257
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H20 (AA)

<400> SEQUENCE: 257

Leu Lys Ile Gln Glu Arg Val Ser Lys Pro Lys Ile Ser Asn Ser
1               5                   10                  15

<210> SEQ ID NO 258
<211> LENGTH: 60
<212> TYPE: DNA
<213> ORGANISM: Artificial sequence
<220> FEATURE:
<223> OTHER INFORMATION: Scorpion region linker polypeptide
<220> FEATURE:
<223> OTHER INFORMATION: Linker H21 (PN)

<400> SEQUENCE: 258

```
ctgaaaatcc aggagagggt cagtaagcca aagatctcct gtccaccttg cccgaattct    60
```

<210> SEQ ID NO 259
<211> LENGTH: 20
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H21 (AA)

<400> SEQUENCE: 259

Leu Lys Ile Gln Glu Arg Val Ser Lys Pro Lys Ile Ser Cys Pro Pro
1               5                   10                  15

Cys Pro Asn Ser
            20

<210> SEQ ID NO 260
<211> LENGTH: 45
<212> TYPE: DNA
<213> ORGANISM: Artificial sequence
<220> FEATURE:
<223> OTHER INFORMATION: Scorpion region linker polypeptide
<220> FEATURE:
<223> OTHER INFORMATION: Linker H22 (PN)

<400> SEQUENCE: 260

```
ctggatgtga gtgagaggcc ttttcctcca cacatccaga attct                    45
```

<210> SEQ ID NO 261
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H22 (AA)

<400> SEQUENCE: 261

Leu Asp Val Ser Glu Arg Pro Phe Pro Pro His Ile Gln Asn Ser
1               5                   10                  15

<210> SEQ ID NO 262
<211> LENGTH: 63
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H23 (PN)

<400> SEQUENCE: 262

```
ctggatgtga gtgagaggcc ttttcctcca cacatccagt cctgtccacc ttgcccgaat    60
tct                                                                  63
```

<210> SEQ ID NO 263
<211> LENGTH: 21
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H23 (AA)

<400> SEQUENCE: 263

Leu Asp Val Ser Glu Arg Pro Phe Pro Pro His Ile Gln Ser Cys Pro
1               5                   10                  15

Pro Cys Pro Asn Ser
            20

<210> SEQ ID NO 264
<211> LENGTH: 45
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H24 (DNA)

<400> SEQUENCE: 264
cgggaacagc tggcagaggt cactttgagc ttgaaagcga attct                45

<210> SEQ ID NO 265
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H24 (AA)

<400> SEQUENCE: 265

Arg Glu Gln Leu Ala Glu Val Thr Leu Ser Leu Lys Ala Asn Ser
1               5                   10                  15

<210> SEQ ID NO 266
<211> LENGTH: 60
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H25 (PN)

<400> SEQUENCE: 266
cgggaacagc tggcagaggt cactttgagc gtgaaagctt gtccaccctg cccgaattct    60

<210> SEQ ID NO 267
<211> LENGTH: 20
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H25 (AA)

<400> SEQUENCE: 267

Arg Glu Gln Leu Ala Glu Val Thr Leu Ser Leu Lys Ala Cys Pro Pro
1               5                   10                  15

Cys Pro Asn Ser
            20

<210> SEQ ID NO 268
<211> LENGTH: 45
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H26 (PN)

<400> SEQUENCE: 268
cggattcacc agatgaactc cgagttgagc gtgctcgcga attct                45

<210> SEQ ID NO 269

```
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H26 (AA)

<400> SEQUENCE: 269

Arg Ile His Gln Met Asn Ser Glu Leu Ser Val Leu Ala Asn Ser
1               5                   10                  15

<210> SEQ ID NO 270
<211> LENGTH: 60
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H27 (PN)

<400> SEQUENCE: 270
cggattcacc agatgaactc cgagttgagc gtgctcgctt gtccaccctg cccgaattct    60

<210> SEQ ID NO 271
<211> LENGTH: 20
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H27 (AA)

<400> SEQUENCE: 271

Arg Ile His Gln Met Asn Ser Glu Leu Ser Val Leu Ala Cys Pro Pro
1               5                   10                  15

Cys Pro Asn Ser
            20

<210> SEQ ID NO 272
<211> LENGTH: 45
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker  H28 (PN)

<400> SEQUENCE: 272
gataccaaag ggaagaacgt cctcgagaag atcttctcga attct                    45

<210> SEQ ID NO 273
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H28 (AA)

<400> SEQUENCE: 273

Asp Thr Lys Gly Lys Asn Val Leu Glu Lys Ile Phe Ser Asn Ser
1               5                   10                  15

<210> SEQ ID NO 274
<211> LENGTH: 63
<212> TYPE: DNA
<213> ORGANISM: Artificial sequence
<220> FEATURE:
```

<223> OTHER INFORMATION: Scorpion region linker polynucleotide
<220> FEATURE:
<223> OTHER INFORMATION: Linker H29 (PN)

<400> SEQUENCE: 274

```
gataccaaag ggaagaacgt cctcgagaag atcttcgact cctgtccacc ttgcccgaat    60
tct                                                                  63
```

<210> SEQ ID NO 275
<211> LENGTH: 21
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H29 (AA)

<400> SEQUENCE: 275

Asp Thr Lys Gly Lys Asn Val Leu Glu Lys Ile Phe Asp Ser Cys Pro
1               5                   10                  15

Pro Cys Pro Asn Ser
            20

<210> SEQ ID NO 276
<211> LENGTH: 45
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H30 (PN)

<400> SEQUENCE: 276

```
ctgccacctg agacacagga gagtcaagaa gtcaccctga attct                    45
```

<210> SEQ ID NO 277
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H30 (AA)

<400> SEQUENCE: 277

Leu Pro Pro Glu Thr Gln Glu Ser Gln Glu Val Thr Leu Asn Ser
1               5                   10                  15

<210> SEQ ID NO 278
<211> LENGTH: 63
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H31 (PN)

<400> SEQUENCE: 278

```
ctgccacctg agacacagga gagtcaagaa gtcaccctgt cctgtccacc ttgcccgaat    60
tct                                                                  63
```

<210> SEQ ID NO 279
<211> LENGTH: 21
<212> TYPE: PRT
<213> ORGANISM: Artificial sequence
<220> FEATURE:
<223> OTHER INFORMATION: Scorpion region linker

```
<220> FEATURE:
<223> OTHER INFORMATION: Linker H31 (AA)

<400> SEQUENCE: 279

Leu Pro Pro Glu Thr Gln Glu Ser Gln Glu Val Thr Leu Ser Cys Pro
1               5                   10                  15

Pro Cys Pro Asn Ser
            20

<210> SEQ ID NO 280
<211> LENGTH: 45
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H32 (PN)

<400> SEQUENCE: 280
cggattcacc tgaacgtgtc cgagaggccc tttcctccga attct                45

<210> SEQ ID NO 281
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H32 (AA)

<400> SEQUENCE: 281

Arg Ile His Leu Asn Val Ser Glu Arg Pro Phe Pro Pro Asn Ser
1               5                   10                  15

<210> SEQ ID NO 282
<211> LENGTH: 60
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker  H33 (PN)

<400> SEQUENCE: 282
cggattcacc tgaacgtgtc cgagaggccc tttcctccct gtccaccctg cccgaattct    60

<210> SEQ ID NO 283
<211> LENGTH: 20
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H33 (AA)

<400> SEQUENCE: 283

Arg Ile His Leu Asn Val Ser Glu Arg Pro Phe Pro Pro Cys Pro Pro
1               5                   10                  15

Cys Pro Asn Ser
            20

<210> SEQ ID NO 284

<400> SEQUENCE: 284

000
```

```
<210> SEQ ID NO 285
<400> SEQUENCE: 285

000

<210> SEQ ID NO 286
<400> SEQUENCE: 286

000

<210> SEQ ID NO 287
<400> SEQUENCE: 287

000

<210> SEQ ID NO 288
<211> LENGTH: 39
<212> TYPE: DNA
<213> ORGANISM: Artificial sequence
<220> FEATURE:
<223> OTHER INFORMATION: Scorpion region linker
<220> FEATURE:
<223> OTHER INFORMATION: Linker H36 (PN)

<400> SEQUENCE: 288
gggtgtccac cttgtccagg cggtggtgga tcgaattct                    39

<210> SEQ ID NO 289
<211> LENGTH: 13
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H36 (AA)

<400> SEQUENCE: 289

Gly Cys Pro Pro Cys Pro Gly Gly Gly Gly Ser Asn Ser
1               5                   10

<210> SEQ ID NO 290
<400> SEQUENCE: 290

000

<210> SEQ ID NO 291
<400> SEQUENCE: 291

000

<210> SEQ ID NO 292
<400> SEQUENCE: 292

000

<210> SEQ ID NO 293
<400> SEQUENCE: 293

000

<210> SEQ ID NO 294
```

```
<400> SEQUENCE: 294

000

<210> SEQ ID NO 295

<400> SEQUENCE: 295

000

<210> SEQ ID NO 296
<211> LENGTH: 27
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H40 (PN)

<400> SEQUENCE: 296
ggatgtccac cttgtcccgc gaattct                                         27

<210> SEQ ID NO 297
<211> LENGTH: 9
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H40 (AA)

<400> SEQUENCE: 297

Gly Cys Pro Pro Cys Pro Ala Asn Ser
1               5

<210> SEQ ID NO 298

<400> SEQUENCE: 298

000

<210> SEQ ID NO 299
<211> LENGTH: 9
<212> TYPE: PRT
<213> ORGANISM: Artificial sequence
<220> FEATURE:
<223> OTHER INFORMATION: Scorpion region linker
<220> FEATURE:
<221> NAME/KEY: misc_feature
<223> OTHER INFORMATION: Linker H41

<400> SEQUENCE: 299

Gly Cys Pro Pro Cys Pro Ala Asn Ser
1               5

<210> SEQ ID NO 300

<400> SEQUENCE: 300

000

<210> SEQ ID NO 301
<211> LENGTH: 8
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H42(AA)
```

```
<400> SEQUENCE: 301

Gly Cys Pro Pro Cys Pro Asn Ser
1               5

<210> SEQ ID NO 302

<400> SEQUENCE: 302

000

<210> SEQ ID NO 303

<400> SEQUENCE: 303

000

<210> SEQ ID NO 304
<211> LENGTH: 36
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H44 (PN)

<400> SEQUENCE: 304
ggaggagcta gttgtccacc ttgtcccggg aattct                              36

<210> SEQ ID NO 305
<211> LENGTH: 12
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H44 (AA)

<400> SEQUENCE: 305

Gly Gly Ala Ser Cys Pro Pro Cys Pro Gly Asn Ser
1               5                   10

<210> SEQ ID NO 306
<211> LENGTH: 36
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H45 (PN)

<400> SEQUENCE: 306
ggaggagcca gttgtccacc ttgtgccggg aattct                              36

<210> SEQ ID NO 307
<211> LENGTH: 12
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H45 (AA)

<400> SEQUENCE: 307

Gly Gly Ala Ser Cys Pro Pro Cys Ala Gly Asn Ser
1               5                   10

<210> SEQ ID NO 308
<211> LENGTH: 33
```

```
<212> TYPE: DNA
<213> ORGANISM: Artificial sequence
<220> FEATURE:
<223> OTHER INFORMATION: Scorpion region linker polynucleotide
<220> FEATURE:
<223> OTHER INFORMATION: Linker H46

<400> SEQUENCE: 308
ggaggagcca gttgtccacc ttgtgcgaat tct                                33

<210> SEQ ID NO 309
<211> LENGTH: 11
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H46

<400> SEQUENCE: 309

Gly Gly Ala Ser Cys Pro Pro Cys Ala Asn Ser
1               5                   10

<210> SEQ ID NO 310
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H47

<400> SEQUENCE: 310

Leu Ser Val Lys Ala Asp Phe Leu Thr Pro Ser Ile Gly Asn Ser
1               5                   10                  15

<210> SEQ ID NO 311
<211> LENGTH: 12
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H48

<400> SEQUENCE: 311

Lys Ala Asp Phe Leu Thr Pro Ser Ile Gly Asn Ser
1               5                   10

<210> SEQ ID NO 312

<400> SEQUENCE: 312

000

<210> SEQ ID NO 313
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H50

<400> SEQUENCE: 313

Leu Ser Val Leu Ala Asn Phe Ser Gln Pro Glu Ile Gly Asn Ser
1               5                   10                  15

<210> SEQ ID NO 314
```

```
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H51

<400> SEQUENCE: 314

Leu Ser Val Leu Ala Asn Phe Ser Gln Pro Glu Ile Gly Asn Ser
1               5                   10                  15

<210> SEQ ID NO 315
<211> LENGTH: 11
<212> TYPE: PRT
<213> ORGANISM: Artificial sequence
<220> FEATURE:
<223> OTHER INFORMATION: Synthetic peptide
<220> FEATURE:
<223> OTHER INFORMATION: Scorpion region linker

<400> SEQUENCE: 315

Ser Gln Pro Glu Ile Val Pro Ile Ser Asn Ser
1               5                   10

<210> SEQ ID NO 316
<211> LENGTH: 16
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H53

<400> SEQUENCE: 316

Ser Gln Pro Glu Ile Val Pro Ile Ser Cys Pro Pro Cys Pro Asn Ser
1               5                   10                  15

<210> SEQ ID NO 317
<211> LENGTH: 19
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H54

<400> SEQUENCE: 317

Ser Val Leu Ala Asn Phe Ser Gln Pro Glu Ile Ser Cys Pro Pro Cys
1               5                   10                  15

Pro Asn Ser

<210> SEQ ID NO 318
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H55

<400> SEQUENCE: 318

Arg Ile His Gln Met Asn Ser Glu Leu Ser Val Leu Ala Asn Ser
1               5                   10                  15

<210> SEQ ID NO 319
<211> LENGTH: 12
<212> TYPE: PRT
<213> ORGANISM: Artificial sequence
```

```
<220> FEATURE:
<223> OTHER INFORMATION: Scorpion region linker
<220> FEATURE:
<223> OTHER INFORMATION: Linker H56

<400> SEQUENCE: 319

Gln Met Asn Ser Glu Leu Ser Val Leu Ala Asn Ser
1               5                   10

<210> SEQ ID NO 320
<211> LENGTH: 10
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H57

<400> SEQUENCE: 320

Val Ser Glu Arg Pro Phe Pro Pro Asn Ser
1               5                   10

<210> SEQ ID NO 321
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H58

<400> SEQUENCE: 321

Lys Pro Phe Phe Thr Cys Gly Ser Ala Asp Thr Cys Pro Asn Ser
1               5                   10                  15

<210> SEQ ID NO 322
<211> LENGTH: 15
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H59

<400> SEQUENCE: 322

Lys Pro Phe Phe Thr Cys Gly Ser Ala Asp Thr Cys Pro Asn Ser
1               5                   10                  15

<210> SEQ ID NO 323
<211> LENGTH: 14
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H60

<400> SEQUENCE: 323

Gln Tyr Asn Cys Pro Gly Gln Tyr Thr Phe Ser Met Asn Ser
1               5                   10

<210> SEQ ID NO 324
<211> LENGTH: 21
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H61
```

<400> SEQUENCE: 324

Glu Pro Ala Phe Thr Pro Gly Pro Asn Ile Glu Leu Gln Lys Asp Ser
1               5                   10                  15

Asp Cys Pro Asn Ser
            20

<210> SEQ ID NO 325
<211> LENGTH: 21
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H62

<400> SEQUENCE: 325

Gln Arg His Asn Asn Ser Ser Leu Asn Thr Arg Thr Gln Lys Ala Arg
1               5                   10                  15

His Cys Pro Asn Ser
            20

<210> SEQ ID NO 326
<211> LENGTH: 19
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H63

<400> SEQUENCE: 326

Asn Ser Leu Phe Asn Gln Glu Val Gln Ile Pro Leu Thr Glu Ser Tyr
1               5                   10                  15

Cys Asn Ser

<210> SEQ ID NO 327
<211> LENGTH: 21
<212> TYPE: PRT
<213> ORGANISM: Artificial sequence
<220> FEATURE:
<223> OTHER INFORMATION: Scorpion region linker

<400> SEQUENCE: 327

Gln Arg His Asn Asn Ser Ser Leu Asn Thr Arg Thr Gln Lys Ala Arg
1               5                   10                  15

His Cys Pro Asn Ser
            20

<210> SEQ ID NO 328
<211> LENGTH: 21
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H65

<400> SEQUENCE: 328

Glu Pro Ala Phe Thr Pro Gly Pro Asn Ile Glu Leu Gln Lys Asp Ser
1               5                   10                  15

Asp Cys Pro Asn Ser
            20

<210> SEQ ID NO 329
<211> LENGTH: 21

```
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H66

<400> SEQUENCE: 329

Glu Pro Ala Phe Thr Pro Gly Pro Asn Ile Glu Leu Gln Lys Asp Ser
1               5                   10                  15

Asp Cys Pro Asn Ser
            20

<210> SEQ ID NO 330
<211> LENGTH: 21
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H67

<400> SEQUENCE: 330

Glu Pro Ala Phe Thr Pro Gly Pro Asn Ile Glu Leu Gln Lys Asp Ser
1               5                   10                  15

Asp Cys Pro Asn Ser
            20

<210> SEQ ID NO 331
<211> LENGTH: 118
<212> TYPE: PRT
<213> ORGANISM: Artificial sequence
<220> FEATURE:
<223> OTHER INFORMATION: Scorpion region linker
<220> FEATURE:
<223> OTHER INFORMATION: Linker H68

<400> SEQUENCE: 331

Arg Thr Arg Tyr Leu Gln Val Ser Gln Gln Leu Gln Gln Thr Asn Arg
1               5                   10                  15

Val Leu Glu Val Thr Asn Ser Ser Leu Arg Gln Gln Leu Arg Leu Lys
            20                  25                  30

Ile Thr Gln Leu Gly Gln Ser Ala Glu Asp Leu Gln Gly Ser Arg Arg
        35                  40                  45

Glu Leu Ala Gln Ser Gln Glu Ala Leu Gln Val Glu Gln Arg Ala His
    50                  55                  60

Gln Ala Ala Glu Gly Gln Leu Gln Ala Cys Gln Ala Asp Arg Gln Lys
65                  70                  75                  80

Thr Lys Glu Thr Leu Gln Ser Glu Glu Gln Gln Arg Arg Ala Leu Glu
                85                  90                  95

Gln Lys Leu Ser Asn Met Glu Asn Arg Leu Lys Pro Phe Phe Thr Cys
            100                 105                 110

Gly Ser Ala Asp Thr Cys
        115

<210> SEQ ID NO 332
<211> LENGTH: 10
<212> TYPE: PRT
<213> ORGANISM: Artificial sequence
<220> FEATURE:
<223> OTHER INFORMATION: anti-CD-20 VL CDR1

<400> SEQUENCE: 332

Arg Ala Ser Ser Ser Val Ser Tyr Ile His
```

<210> SEQ ID NO 333
<211> LENGTH: 10
<212> TYPE: PRT
<213> ORGANISM: Artificial sequence
<220> FEATURE:
<223> OTHER INFORMATION: anti-CD-20 VL CDR1

<400> SEQUENCE: 333

Arg Ala Ser Ser Ser Val Ser Tyr Ile Val
1               5                   10

<210> SEQ ID NO 334
<211> LENGTH: 9
<212> TYPE: PRT
<213> ORGANISM: Artificial sequence
<220> FEATURE:
<223> OTHER INFORMATION: anti-CD-20 VL CDR3

<400> SEQUENCE: 334

Gln Gln Trp Ser Phe Asn Pro Pro Thr
1               5

<210> SEQ ID NO 335
<211> LENGTH: 9
<212> TYPE: PRT
<213> ORGANISM: Artificial sequence
<220> FEATURE:
<223> OTHER INFORMATION: anti-CD-20 VL CDR3

<400> SEQUENCE: 335

Gln Gln Tyr Ser Phe Asn Pro Pro Thr
1               5

<210> SEQ ID NO 336
<211> LENGTH: 17
<212> TYPE: PRT
<213> ORGANISM: Artificial sequence
<220> FEATURE:
<223> OTHER INFORMATION: anti-CD-20 VH CDR2

<400> SEQUENCE: 336

Ala Ile Tyr Pro Gly Asn Gly Asp Thr Ser Tyr Asn Gln Lys Phe Lys
1               5                   10                  15

Gly

<210> SEQ ID NO 337
<211> LENGTH: 17
<212> TYPE: PRT
<213> ORGANISM: Artificial sequence
<220> FEATURE:
<223> OTHER INFORMATION: anti-CD-20 VH CDR2

<400> SEQUENCE: 337

Ala Ile Tyr Pro Gly Asn Gly Glu Thr Ser Tyr Asn Gln Lys Phe Lys
1               5                   10                  15

Gly

<210> SEQ ID NO 338
<211> LENGTH: 12
<212> TYPE: PRT
<213> ORGANISM: Artificial sequence
<220> FEATURE:
<223> OTHER INFORMATION: anti-CD20 VH CDR3

<400> SEQUENCE: 338

```
Ser Val Tyr Tyr Ser Asn Tyr Trp Tyr Phe Asp Leu
1               5                   10
```

<210> SEQ ID NO 339
<211> LENGTH: 12
<212> TYPE: PRT
<213> ORGANISM: Artificial sequence
<220> FEATURE:
<223> OTHER INFORMATION: anti-CD20 VH CDR3

<400> SEQUENCE: 339

```
Ser Val Tyr Tyr Gly Gly Tyr Trp Tyr Phe Asp Leu
1               5                   10
```

<210> SEQ ID NO 340
<211> LENGTH: 12
<212> TYPE: PRT
<213> ORGANISM: Artificial sequence
<220> FEATURE:
<223> OTHER INFORMATION: anti-CD20 VH CDR3

<400> SEQUENCE: 340

```
Ser Tyr Tyr Ser Asn Ser Asp Trp Tyr Phe Asp Leu
1               5                   10
```

<210> SEQ ID NO 341
<211> LENGTH: 12
<212> TYPE: PRT
<213> ORGANISM: Artificial sequence
<220> FEATURE:
<223> OTHER INFORMATION: anti-CD20 VH CDR3

<400> SEQUENCE: 341

```
Ser Tyr Tyr Ser Gly Gly Asp Trp Tyr Phe Asp Leu
1               5                   10
```

<210> SEQ ID NO 342
<211> LENGTH: 12
<212> TYPE: PRT
<213> ORGANISM: Artificial sequence
<220> FEATURE:
<223> OTHER INFORMATION: anti-CD20 VH CDR3

<400> SEQUENCE: 342

```
Ser Tyr Lys Ser Asn Ser Tyr Trp Tyr Phe Asp Leu
1               5                   10
```

<210> SEQ ID NO 343
<211> LENGTH: 12
<212> TYPE: PRT
<213> ORGANISM: Artificial sequence
<220> FEATURE:
<223> OTHER INFORMATION: anti-CD20 VH CDR3

<400> SEQUENCE: 343

```
Ser Tyr Tyr Ser Asn Ser Tyr Trp Tyr Phe Asp Leu
1               5                   10
```

<210> SEQ ID NO 344
<211> LENGTH: 12
<212> TYPE: PRT
<213> ORGANISM: Artificial sequence
<220> FEATURE:
<223> OTHER INFORMATION: anti-CD-20 VH CDR3

<400> SEQUENCE: 344

```
Ser Tyr Lys Ser Asn Ser Asp Trp Tyr Phe Asp Leu
```

```
1               5                   10
```

<210> SEQ ID NO 345
<211> LENGTH: 12
<212> TYPE: PRT
<213> ORGANISM: Artificial sequence
<220> FEATURE:
<223> OTHER INFORMATION: anti-CD20 VH CDR3

<400> SEQUENCE: 345

```
Ser Tyr Lys Ser Gly Gly Asp Trp Tyr Phe Asp Leu
1               5                   10
```

<210> SEQ ID NO 346
<211> LENGTH: 8
<212> TYPE: PRT
<213> ORGANISM: Artificial sequence
<220> FEATURE:
<223> OTHER INFORMATION: Scorpion linker core (2H7) sequence

<400> SEQUENCE: 346

```
Gly Cys Pro Pro Cys Pro Asn Ser
1               5
```

<210> SEQ ID NO 347
<211> LENGTH: 4
<212> TYPE: PRT
<213> ORGANISM: Artificial sequence
<220> FEATURE:
<223> OTHER INFORMATION: Extension sequence

<400> SEQUENCE: 347

```
Ala Pro Glu Leu
1
```

<210> SEQ ID NO 348
<211> LENGTH: 9
<212> TYPE: PRT
<213> ORGANISM: Artificial sequence
<220> FEATURE:
<223> OTHER INFORMATION: Synthetic peptide
<220> FEATURE:
<223> OTHER INFORMATION: Extension sequence

<400> SEQUENCE: 348

```
Ala Pro Glu Leu Gly Gly Gly Gly Ser
1               5
```

<210> SEQ ID NO 349
<211> LENGTH: 14
<212> TYPE: PRT
<213> ORGANISM: Artificial sequence
<220> FEATURE:
<223> OTHER INFORMATION: Extension sequence

<400> SEQUENCE: 349

```
Ala Pro Glu Leu Gly Gly Gly Gly Ser Gly Gly Gly Gly Ser
1               5                   10
```

<210> SEQ ID NO 350
<211> LENGTH: 19
<212> TYPE: PRT
<213> ORGANISM: Artificial sequence
<220> FEATURE:
<223> OTHER INFORMATION: Extension sequence

<400> SEQUENCE: 350

```
Ala Pro Glu Leu Gly Gly Gly Gly Ser Gly Gly Gly Gly Ser Gly Gly
```

Gly Gly Ser

<210> SEQ ID NO 351
<211> LENGTH: 12
<212> TYPE: PRT
<213> ORGANISM: Artificial sequence
<220> FEATURE:
<223> OTHER INFORMATION: Extended scorpion linker

<400> SEQUENCE: 351

Gly Cys Pro Pro Cys Pro Asn Ser Ala Pro Glu Leu
1               5                   10

<210> SEQ ID NO 352
<211> LENGTH: 17
<212> TYPE: PRT
<213> ORGANISM: Artificial sequence
<220> FEATURE:
<223> OTHER INFORMATION: Extended scorpion linker

<400> SEQUENCE: 352

Gly Cys Pro Pro Cys Pro Asn Ser Ala Pro Glu Leu Gly Gly Gly Gly
1               5                   10                  15

Ser

<210> SEQ ID NO 353
<211> LENGTH: 22
<212> TYPE: PRT
<213> ORGANISM: Artificial sequence
<220> FEATURE:
<223> OTHER INFORMATION: Extended scorpion linker

<400> SEQUENCE: 353

Gly Cys Pro Pro Cys Pro Asn Ser Ala Pro Glu Leu Gly Gly Gly Gly
1               5                   10                  15

Ser Gly Gly Gly Gly Ser
            20

<210> SEQ ID NO 354
<211> LENGTH: 27
<212> TYPE: PRT
<213> ORGANISM: Artificial sequence
<220> FEATURE:
<223> OTHER INFORMATION: Extended scorpion linker

<400> SEQUENCE: 354

Gly Cys Pro Pro Cys Pro Asn Ser Ala Pro Glu Leu Gly Gly Gly Gly
1               5                   10                  15

Ser Gly Gly Gly Gly Ser Gly Gly Gly Gly Ser
            20                  25

<210> SEQ ID NO 355

<400> SEQUENCE: 355

000

<210> SEQ ID NO 356

<400> SEQUENCE: 356

000

<210> SEQ ID NO 357

```
<400> SEQUENCE: 357

000

<210> SEQ ID NO 358
<400> SEQUENCE: 358

000

<210> SEQ ID NO 359
<400> SEQUENCE: 359

000

<210> SEQ ID NO 360
<400> SEQUENCE: 360

000

<210> SEQ ID NO 361
<400> SEQUENCE: 361

000

<210> SEQ ID NO 362
<400> SEQUENCE: 362

000

<210> SEQ ID NO 363
<400> SEQUENCE: 363

000

<210> SEQ ID NO 364
<400> SEQUENCE: 364

000

<210> SEQ ID NO 365
<400> SEQUENCE: 365

000

<210> SEQ ID NO 366
<211> LENGTH: 10
<212> TYPE: PRT
<213> ORGANISM: Artificial sequence
<220> FEATURE:
<223> OTHER INFORMATION: partial CH3 sequence

<400> SEQUENCE: 366

Gln Lys Ser Leu Ser Leu Ser Pro Gly Lys
 1               5                  10

<210> SEQ ID NO 367
<211> LENGTH: 9
<212> TYPE: PRT
<213> ORGANISM: Artificial sequence
<220> FEATURE:
```

<223> OTHER INFORMATION: Partial CH3 sequence

<400> SEQUENCE: 367

Gln Lys Ser Leu Ser Leu Ser Pro Gly
1               5

<210> SEQ ID NO 368
<211> LENGTH: 1
<212> TYPE: PRT
<213> ORGANISM: Artificial sequence
<220> FEATURE:
<223> OTHER INFORMATION: Partial CH3 sequence

<400> SEQUENCE: 368

Gln
1

<210> SEQ ID NO 369
<211> LENGTH: 3
<212> TYPE: PRT
<213> ORGANISM: Artificial sequence
<220> FEATURE:
<223> OTHER INFORMATION: Partial CH3 sequence

<400> SEQUENCE: 369

Gln Lys Ser
1

<210> SEQ ID NO 370
<211> LENGTH: 6
<212> TYPE: PRT
<213> ORGANISM: Artificial sequence
<220> FEATURE:
<223> OTHER INFORMATION: Partial CH3 sequence

<400> SEQUENCE: 370

Gln Lys Ser Leu Ser Leu
1               5

<210> SEQ ID NO 371
<211> LENGTH: 5
<212> TYPE: PRT
<213> ORGANISM: Artificial sequence
<220> FEATURE:
<223> OTHER INFORMATION: Partial CH3 sequence

<400> SEQUENCE: 371

Gln Lys Ser Leu Ser
1               5

<210> SEQ ID NO 372
<211> LENGTH: 5
<212> TYPE: PRT
<213> ORGANISM: Artificial sequence
<220> FEATURE:
<223> OTHER INFORMATION: Scorpion linker

<400> SEQUENCE: 372

Gly Cys Pro Pro Cys
1               5

<210> SEQ ID NO 373
<211> LENGTH: 12
<212> TYPE: PRT
<213> ORGANISM: Artificial sequence
<220> FEATURE:
<223> OTHER INFORMATION: Scorpion linker

```
<400> SEQUENCE: 373

Gln Tyr Asn Cys Pro Gly Gln Tyr Thr Phe Ser Met
1               5                   10

<210> SEQ ID NO 374
<211> LENGTH: 11
<212> TYPE: PRT
<213> ORGANISM: Artificial sequence
<220> FEATURE:
<223> OTHER INFORMATION: Scorpion linker

<400> SEQUENCE: 374

Pro Phe Phe Thr Cys Gly Ser Ala Asp Thr Cys
1               5                   10

<210> SEQ ID NO 375
<211> LENGTH: 18
<212> TYPE: PRT
<213> ORGANISM: Artificial sequence
<220> FEATURE:
<223> OTHER INFORMATION: Scorpion linker

<400> SEQUENCE: 375

Glu Pro Ala Phe Thr Pro Gly Pro Asn Ile Glu Leu Gln Lys Asp Ser
1               5                   10                  15

Asp Cys

<210> SEQ ID NO 376
<211> LENGTH: 18
<212> TYPE: PRT
<213> ORGANISM: Artificial sequence
<220> FEATURE:
<223> OTHER INFORMATION: Scorpion linker

<400> SEQUENCE: 376

Gln Arg His Asn Asn Ser Ser Leu Asn Thr Arg Thr Gln Lys Ala Arg
1               5                   10                  15

His Cys

<210> SEQ ID NO 377
<211> LENGTH: 17
<212> TYPE: PRT
<213> ORGANISM: Artificial sequence
<220> FEATURE:
<223> OTHER INFORMATION: Scorpion linker

<400> SEQUENCE: 377

Asn Ser Leu Phe Asn Gln Glu Val Gln Ile Pro Leu Thr Glu Ser Tyr
1               5                   10                  15

Cys

<210> SEQ ID NO 378
<211> LENGTH: 10
<212> TYPE: PRT
<213> ORGANISM: Artificial sequence
<220> FEATURE:
<223> OTHER INFORMATION: anti-CD20 VL CDR1 (TRU-015)

<400> SEQUENCE: 378

Arg Ala Ser Ser Ser Val Ser Tyr Met His
1               5                   10

<210> SEQ ID NO 379
<211> LENGTH: 13
<212> TYPE: PRT
```

```
<213> ORGANISM: Artificial sequence
<220> FEATURE:
<223> OTHER INFORMATION: anti-CD20 VH CDR3 (TRU-015)

<400> SEQUENCE: 379

Val Val Tyr Tyr Ser Asn Ser Tyr Trp Tyr Phe Asp Val
1               5                   10
```